US012596118B2

(12) United States Patent
Costa et al.

(10) Patent No.: US 12,596,118 B2
(45) Date of Patent: Apr. 7, 2026

(54) OLIGONUCLEOTIDES FOR INDUCING PATERNAL UBE3A EXPRESSION

(71) Applicant: Hoffmann-La Roche Inc., Little Falls, NJ (US)

(72) Inventors: Veronica Costa, Basel (CH); Maj Hedtjärn, Hørsholm (DK); Marius Hoener, Basel (CH); Ravi Jagasia, Basel (CH); Mads Aaboe Jensen, Hørsholm (DK); Christoph Patsch, Basel (CH); Lykke Pedersen, Hørsholm (DK); Søren Vestergaard Rasmussen, Hørsholm (DK)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 19/258,035

(22) Filed: Jul. 2, 2025

(65) Prior Publication Data

US 2025/0389713 A1 Dec. 25, 2025

Related U.S. Application Data

(63) Continuation of application No. 18/491,513, filed on Oct. 20, 2023, which is a continuation of application
(Continued)

(30) Foreign Application Priority Data

Nov. 12, 2015 (EP) .................................... 15194367
Sep. 19, 2016 (EP) .................................... 16189502

(51) Int. Cl.
*C12N 15/11* (2006.01)
*C12N 5/00* (2006.01)
(Continued)

(52) U.S. Cl.
CPC ....... *G01N 33/5014* (2013.01); *C12N 5/0018* (2013.01); *C12N 5/0619* (2013.01);
(Continued)

(58) Field of Classification Search
CPC ..... C12N 15/11; C12N 15/111; C12N 15/113; C12N 15/1137; C12N 2310/11;
(Continued)

(56) References Cited

U.S. PATENT DOCUMENTS 4,373,084 A 2/1983 Robinson
6,184,212 B1 2/2001 Miraglia et al.
(Continued)

FOREIGN PATENT DOCUMENTS

EP 2864479 B1 4/2015
EP 2640853 B1 12/2018
(Continued)

OTHER PUBLICATIONS

Owais et al. (Cancers 2020, 12(8), 2108, pp. 1-19).*
(Continued)

*Primary Examiner* — Terra C Gibbs
(74) *Attorney, Agent, or Firm* — Clark & Elbing LLP; Thomas J. Takara

(57) ABSTRACT

The present invention relates to oligonucleotides that are capable of inducing expression of ubiquitin-protein ligase E3A (UBE3A) from the paternal allele in animal or human neurons. The oligonucleotides target the suppressor of the UBE3A paternal allele by hybridization to SNHG14 long non-coding RNA downstream of SNORD109B. The present invention further relates to pharmaceutical compositions and methods for treatment of Angelman syndrome.

30 Claims, 2 Drawing Sheets

Specification includes a Sequence Listing.

Related U.S. Application Data

No. 17/581,089, filed on Jan. 21, 2022, now Pat. No. 11,852,627, which is a continuation of application No. 16/933,445, filed on Jul. 20, 2020, now Pat. No. 11,320,421, which is a continuation of application No. 16/663,024, filed on Oct. 24, 2019, now Pat. No. 10,718,753, which is a continuation of application No. 16/388,714, filed on Apr. 18, 2019, now Pat. No. 10,739,332, which is a continuation of application No. 15/351,113, filed on Nov. 14, 2016, now Pat. No. 10,494,633, which is a continuation of application No. PCT/EP2016/077383, filed on Nov. 11, 2016.

(51) Int. Cl.
*C12N 5/074* (2010.01)
*C12N 5/0793* (2010.01)
*C12N 5/0797* (2010.01)
*C12N 15/113* (2010.01)
*G01N 33/50* (2006.01)

(52) U.S. Cl.
CPC ......... *C12N 5/0623* (2013.01); *C12N 5/0696* (2013.01); *C12N 15/11* (2013.01); *C12N 15/111* (2013.01); *C12N 15/113* (2013.01); *C12N 15/1137* (2013.01); *G01N 33/5058* (2013.01); *C12N 2310/11* (2013.01); *C12N 2310/20* (2017.05); *C12N 2310/315* (2013.01); *C12N 2310/321* (2013.01); *C12N 2310/322* (2013.01); *C12N 2310/3231* (2013.01); *C12N 2310/33* (2013.01); *C12N 2310/3341* (2013.01); *C12N 2310/341* (2013.01); *C12N 2310/346* (2013.01); *C12N 2310/351* (2013.01); *C12N 2320/34* (2013.01); *C12N 2500/38* (2013.01); *C12N 2500/44* (2013.01); *C12N 2501/01* (2013.01); *C12N 2501/11* (2013.01); *C12N 2501/115* (2013.01); *C12N 2501/119* (2013.01); *C12N 2501/13* (2013.01); *C12N 2501/41* (2013.01); *C12N 2501/60* (2013.01); *C12N 2501/727* (2013.01); *C12N 2501/999* (2013.01); *C12N 2503/02* (2013.01); *C12N 2506/45* (2013.01); *C12N 2533/52* (2013.01)

(58) Field of Classification Search
CPC ........ C12N 2310/315; C12N 2310/321; C12N 2310/322; C12N 2310/3231; C12N 2310/3341; C12N 2310/341; C12N 2310/346; A61K 31/7088
See application file for complete search history.

(56) References Cited

U.S. PATENT DOCUMENTS

| | | | |
|---|---|---|---|
| 6,300,132 B1 | 10/2001 | Monia et al. | |
| 6,617,162 B2 | 9/2003 | Dobie et al. | |
| 8,067,173 B2 | 11/2011 | Liew | |
| 9,617,539 B2 | 4/2017 | Rigo et al. | |
| 10,494,633 B2 | 12/2019 | Costa et al. | |
| 10,718,753 B2 | 7/2020 | Costa et al. | |
| 10,739,332 B2 | 8/2020 | Costa et al. | |
| 11,261,446 B2 * | 3/2022 | Jafar-Nejad | C12N 15/113 |
| 11,320,421 B2 | 5/2022 | Costa et al. | |
| 11,852,627 B2 | 12/2023 | Costa et al. | |
| 12,259,380 B2 | 3/2025 | Costa et al. | |
| 2002/0098511 A1 | 7/2002 | Heichman et al. | |
| 2003/0087855 A1 | 5/2003 | Ward et al. | |
| 2013/0225659 A1 | 8/2013 | Bennett | |
| 2015/0191723 A1 | 7/2015 | Rigo et al. | |
| 2017/0191064 A1 | 7/2017 | Costa et al. | |
| 2019/0310244 A1 | 10/2019 | Costa et al. | |
| 2020/0057052 A1 | 2/2020 | Costa et al. | |
| 2020/0348286 A1 | 11/2020 | Costa et al. | |
| 2022/0146496 A1 | 5/2022 | Costa et al. | |
| 2023/0296587 A1 | 9/2023 | Costa et al. | |
| 2024/0085402 A1 | 3/2024 | Costa et al. | |
| 2025/0116656 A2 | 4/2025 | Costa et al. | |

FOREIGN PATENT DOCUMENTS

| | | | |
|---|---|---|---|
| EP | 3374509 B1 | | 12/2020 |
| WO | WO-93/07883 | A1 | 4/1993 |
| WO | WO-98/039352 | A1 | 9/1998 |
| WO | WO-99/14226 | A2 | 3/1999 |
| WO | WO-00/47599 | A1 | 8/2000 |
| WO | WO-00/66604 | A2 | 11/2000 |
| WO | WO-01/23613 | A1 | 4/2001 |
| WO | WO-2001/092582 | A1 | 12/2001 |
| WO | WO-2004/016754 | A2 | 2/2004 |
| WO | WO-2004/046160 | A2 | 6/2004 |
| WO | WO-2007/031091 | A2 | 3/2007 |
| WO | WO-2007/087113 | A2 | 8/2007 |
| WO | WO-2007/090071 | A2 | 8/2007 |
| WO | WO-2007/134181 | A2 | 11/2007 |
| WO | WO-2007/146511 | A2 | 12/2007 |
| WO | WO-2008/113832 | A2 | 9/2008 |
| WO | WO-2008/116860 | A2 | 10/2008 |
| WO | WO-2008/150729 | A2 | 12/2008 |
| WO | WO-2008/154401 | A2 | 12/2008 |
| WO | WO-2009/006478 | A2 | 1/2009 |
| WO | WO-2009/067647 | A1 | 5/2009 |
| WO | WO-2009/090182 | A1 | 7/2009 |
| WO | WO-2009/124238 | A1 | 10/2009 |
| WO | WO-2010/036698 | A1 | 4/2010 |
| WO | WO-2010/077578 | A1 | 7/2010 |
| WO | WO-2011/017521 | A2 | 2/2011 |
| WO | WO-2011/079261 | A2 | 6/2011 |
| WO | WO-2011/156202 | A1 | 12/2011 |
| WO | WO-2012/009402 | A2 | 1/2012 |
| WO | WO-2012/012467 | A2 | 1/2012 |
| WO | WO-2012/064806 | A2 | 5/2012 |
| WO | WO-2012/143379 | A1 | 10/2012 |
| WO | WO-2013/033230 | A1 | 3/2013 |
| WO | WO-2013/036868 | A1 | 3/2013 |
| WO | WO-2013/154798 | A1 | 10/2013 |
| WO | WO-2014/004572 | A2 | 1/2014 |
| WO | WO-2014/076195 | A1 | 5/2014 |
| WO | WO-2014/077693 | A1 | 5/2014 |
| WO | WO-2017/081223 | A1 | 5/2017 |
| WO | WO-2017/081250 | A1 | 5/2017 |
| WO | WO-2017/081254 | A1 | 5/2017 |
| WO | WO-2019/006107 | A1 | 1/2019 |
| WO | WO-2019/109001 | A1 | 6/2019 |
| WO | WO-2019/145384 | A1 | 8/2019 |
| WO | WO-2020/205463 | A1 | 10/2020 |

OTHER PUBLICATIONS

Ganesan et al. (Cancers Feb. 13, 2025;17(4):626, pp. 1-25).*
"Angelman Syndrome," Cleveland Clinic, <https://my.clevelandclinic.org/health/diseases/17978-angelman-syndrome>, Last reviewed on Dec. 11, 2018, Retrieved on Mar. 31, 2021 (7 pages).
"Angelman Syndrome," Natural Living Center. Retrieved from <http://www.naturallivingcenter.net/ns/DisplayMonograph.asp?StoreID=b571dewxvcs92j200akhmccqa7w8v75&DocID=condition-angelman#PREVENTION> on Feb. 11, 2019 (1 page).
Abaturov et al., "Angelman Syndrome. part 3, (Differential diagnosis and treatment)," Child's Health, Nov. 2015, 7(67):86-92 (English Abstract).
Bauman, "Uconn Stem Cell Lines Go Global," Health and Wellness Research, dated Feb. 2014 [ retrieved Mar. 31, 2021], retreived from URL <https://today .uconn.edu/2014/02/uconn-stem-cell-lines-go-global/#>, 6 pages.
Beaudet, "Drugs to awaken a paternal gene," Nature, 2012, 481(7380):150-152.
Bergstrom, "Unnatural Nucleosides with Unusual Base Pairing Properties," Current Protocols in Nucleic Acid Chemistry. 1:Unit 1.4-Unit 1.4.32(Supplement 37) (Jun. 2009) (32 pages).

(56) References Cited

OTHER PUBLICATIONS

Biological Material transfer agreements relating to the iPSC cells in 029, retrieved on Aug. 11, 2022, 8 pages (2011).
Blaydes et al., "Analysis of murine Snrpn and human SNRPN gene imprinting in transgenic mice," Mamm Genome. 10(6):549-55 (1999).
Boissart et al., "Differentiation from human pluripotent stem cells of cortical neurons of the superficial layers amenable to psychiatric disease modeling and high-throughput drug screening," Transl Psychiatry. 3(e294): 11 pages (2013).
Caruthers et al, "[15] Chemical synthesis of deoxyoligonucleotides by the phosphoramidite method," Methods in Enzvmology, 1987, 154:287-313.
Cavaillé et al., "Identification of brain-specific and imprinted small nucleolar RNA genes exhibiting an unusual genomic organization," Proc Natl Acad Sci U S A. 97(26):14311-6 (Dec. 19, 2000).
Cellbank.mcgill.ca, [ online] "The Repository for Mutant Human Cell Strains," available on or before Apr. 2008, Wayback Machine URL <Cellbank.mcgill.ca/?Topic=Order>, 2 pages.
Chamberlain et al., "Angelman Syndrome, A genomic Imprinting Disorder of the Brain," The Journal of Neuroscience, 2010, 30(30):9958-9963.
Chamberlain et al., "Induced pluripotent stem cell models of the genomic imprinting disorders Angelman and Prader-Willi syndromes," Proc Natl Academy Science USA, 2010, 107(41):17668-17673.
Chamberlain, "Declaration of Dr Stormy J. Chamberlain," dated Apr. 8, 2021, 9 pages.
Chung et al., "Prader-Willi syndrome: reflections on seminal studies and future therapies," Open Bioi., 2020, 10(9):2300195 (17 pages).
Cleveland Clinic, "Angelman Syndrome Prevention," [retrieved on Feb. 11, 2019] retrieved from URL<https://my.clevelandclinic.org/health/diseases/17978-angelman-syndrome/prevention> (1 page).
Cleveland Clinic, "Angelman Syndrome: What It Is, Symptoms & Treatment," <https://my.clevelandclinic.org/health/diseases/17978-angelman-syndrome>, last reviewed on Apr. 7, 2022, retrieved on Jan. 10, 2025 (17 pages).
Conference program for Keystone Symposium on MicroRNAs and Huma Disease, Banff, Alberta, Feb. 11-16, 2011, retrieved on Oct. 5, 2019, retrieved from URL <http://www.keystonesymposia.org/11J6>, 7 pages.
Connecticut Stem Cell Research program grant agreement, Dec. 2008, 4 pages.
Crooke, "Basic Principles of Antisense Technology," Antisense Drug Technology: Principles, Strategies and Applications, Jan. 2001: 1-18.
CV of Dr Stormy J. Chamberlain, No Date, 9 pages.
Danckwardt et al., "3' end mRNA processing; molecular mechanisms and implications for health and disease," The EMBO Journal, Feb. 6, 2008, 27:482-498.
Declaration of Dr Frank Rigo, Apr. 10, 2019, 21 pages.
Declaration of Lykke Pedersen, Jun. 8, 2020, 24 pages.
Declaration of Professor Claes Wahlestedt, May 10, 2019, 45 pages.
Deleavey et al., "Designing Chemically Modified Oligonucleotides for Targeted Gene Silencing," Chemistry & Biology. 19(8):937-54 (2012).
Devos et al., "Antisense Oligonucleotides: Treating Neurodegeneration at the Level of RNA," Neurotherapeutics. 10(3):486-97 (2013).
Dunkley et al., "Characterization of a human pluripotent stem cell-derived model of neuronal development using multiplexed targeted proteomics," Proteomics Clin Appl., Aug. 2015, 9(7-8):684-694.
Efthymiou et al., "Functional Screening Assays with Neurons Generated from Pluripotent Stem Cell-Derived Neural Stem Cells," J. Biomol. Screen, 2014, 19(1):32-43.
Entrez gene summary for SNORD109B, dated Mar. 29, 2020, retrieved from URL <https://www.ncbi.nlm.nih.gov/gene?cmd=Retrieve&dopt=full_report&list_uids=338429>, 1 page.
Extracts of information from US20030087855 Sequence ID No. 87, May 8, 2003, 1 page.
Extracts of information from U.S. Pat. No. 6,184,212 Sequence ID No. 261, Feb. 6, 2001, 2 pages.
Extracts of information from U.S. Pat. No. 6,300,132 Sequence ID No. 71, Oct. 9, 2001, 1 page.
Extracts of information from U.S. Pat. No. 6,617,162 Sequence ID No. 43, Sep. 9, 2003, 1 page.
Extracts of information from WO2004016754 Sequence ID No. 7124, Feb. 26, 2004, 1 page.
Faghihi et al., "Regulatory roles of natural antisense transcripts," Nature Rev Mol Cell Biol., 2009, 10(9):637-643.
Faghihi, "RNAi Screen Indicates Widespread Biological Function for Human Natural Antisense Transcripts," PLoS One, 2010, 5:e13177 10 pages.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol BioSyst. 5(8):838-43 (2009).
Freier et al., "Methods of Selecting Sites in RNA for Antisense Targeting," Antisense Drug Technology: Principles, Strategies and Applications, May 2001: 107-119.
Freier et al., "The ups and downs of nucleic acid duplex stability: structure-stability studies on chemically-modified DNA:RNA duplexes," Nucleic Acids Res. 25(22):4429-43 (1997).
GenBank entry NM_130838.1 "*Homo sapiens* ubiquitin protein ligase E3A (UBE3A), Transcript variant 1, mRNA," dated Jul. 2, 2017, 7 pages.
Germain et al., "Antisense oligonucleotides targeting UBE3A-ATS restore expression of UBE3A by relieving transcriptional interference," bioRxiv preprint, https://doi.org/10.1101/2021.07.09.451826, (2021) (33 pages).
Hagedorn et al., "Locked nucleic acid: Modality, diversity, and drug discovery," Drug Discovery Todav, 2018, 23(1):101-114.
Hansen et al., "Entropy titration. A calorimetric method for the determination of deltaG°(K), deltaH° and deltaS°," Chem Comm., 1965, 3:36-38.
Hélène C, et al., "Specific regulation of gene expression by antisense, sense and antigene nucleic acids," Biochimica et Biophysica Acta, 1049, pp. 99-125, (1990).
Hirao et al., "Natural versus Artificial Creation of Base Pairs in DNA: Origin of Nucleobases from the Perspectives of Unnatural Base Pair Studies," Accounts of Chemical Research, Dec. 18, 2012, 45(12):2055-2065.
Holdgate et al., "Measurements of binding thermodynamics in drug discovery," Drug Discov Today., Nov. 15, 2005, 10(22):1543-1550.
Huang et al., "Topoisomerase inhibitors unsilence the dormant allele of Ube3a in neurons," Nature, 2012, 481(7380):185-189.
Ionis, "Ionis Announces Pivotal Phase 3 Trial Design for ION582 in Angelman Syndrome", Ionis Pharmaceuticals, Inc., Nov. 6, 2024 (2 pages).
Johnstone et al., "A human imprinting centre demonstrates conserved acquisition but diverged maintenance of imprinting in a mouse model for Angelman syndrome imprinting defects," Human Molecular Genetics. 15(3):393-404 (2006).
King et al., "Topoisomerases facilitate transcription of long genes linked to autism," Nature, 2013, 501(7456):58-62.
Koch et al., "Quantum Mechanical Studies on DNA and LNA, Nucleic Acid Therapeutics," 2014, 24(2):139-148.
Landers et al., "Regulation of the large (~1000 kb) imprinted murine Ube3a antisense transcript by alternative exons upstream of Snurf/Snrpn," Nucleic Acids Res. 32(11):3480-92 (2004).
Luo et al., "A Ribonucleolytic Rat Torpedoes RNA Polymerase II," Cell, Dec. 29, 2004, 119(7):911-914.
Mangos et al., "Efficient RNase H-Directed Cleavage of RNA Promoted by Antisense DNA or 2'F-ANA Constructs Containing Acyclic Nucleotide Inserts" J Am Chem Soc. 125(3):654-61 (2003).
Manoharan, "Chapter 16: Oligonucleotide Conjugates in Antisense Technology." Antisense Drug Technology: Principles, Strategies, and Applications. Marcel Dekker, Inc., 391-469 (2001) (85 pages).
Manoharan, "Oligonucleotide Conjugates as Potential Antisense Drugs with Improved Uptake, Biodistribution, Targeted Delivery, and Mechanism of Action," Antisense and Nucleic Acid Drug Development, Jul. 2004, 12(2):103-128.

(56) References Cited

OTHER PUBLICATIONS

Mayo Clinic, "Angelman syndrome" Diagnosis and treatment, Mayo Clinic. Apr. 22, 2025.
McTigue et al., "Sequence-dependent thermodynamic parameters for locked nucleic acid (LNA)-DNA duplex formation," Biochemistry, May 11, 2004, 43(18):5388-5405.
Meng et al., "Ube3a-ATS is an atypical RNA polymerase II transcript that represses the paternal expression of Ube3a," Human Molecular Genetics, 2012, 21(13):3001-3012.
Meng et al., "Towards a therapy for Angelman syndrome by reduction of a long non-coding RNA," Nature. 518(7539):409-12 (Feb. 2015).
Mergny et al., "Analysis of thermal melting curves," Oligonucleotides. 13(6):515-537 (Dec. 2003) (23 pages).
Milazzo et al., "Antisense oligonucleotide treatment rescues UBE3A expression and multiple phenotypes of an Angelman syndrome mouse model," JCI Insight. 6(15):1-12 (Aug. 2021) (13 pages).
Mitsuoka et al., "A bridged nucleic acid, 2',4'-BNACOC: synthesis of fully modified oligonucleotides bearing thymine, 5-methylcytocine, adenine and guanine 2',4'-BNACOC monomers and RNA-selective nucleic-acid recognition," Nucleic Acids Research. 37(4):1225-38 (2009).
Modarresi et al., "Inhibition of natural antisense transcripts in vivo results in gene-specific transcriptional upregulation," Nature Biotechnology, 2012, vol. 30(5):Supporting Online Material: 33 pages.
Modarresi et al., "Inhibition of natural antisense transcripts in vivo results in gene-specific transcriptional upregulation," Nature Biotechnology, Mar. 25, 2012, 30(5):453-459.
Morita et al., "2'-O,4'-C-ethylene-bridged nucleic acids (ENA): highly nuclease-resistant and thermodynamically stable oligonucleotides for antisense drug," Bioorganic & Med Chem Lett. 12(1):73-76 (2002) (4 pages).
Morris et al., "Bidirectional Transcription Directs Both Transcriptional Gene Activation and Suppression in Human Cells," PLoS Genetics, Nov. 2008, 4(11):e1000258 9 pages.
NCBI.nlm.nih.gov Gene ID: 338429, "SNORD109B small nucleolar RNA, C/D box 109B [*Homo sapiens* (human)]," <https://ncbi.nlm.nih.gov/gene/338429>, Last updated on Apr. 8, 2022, Retrieved on Apr. 28, 2022 (5 pages).
NCBI.nlm.nih.gov, "SNORD109A small nucleolar RNA, C/D box 109A [*Homo sapiens* (human)]," Mar. 2, 2021, retrieved from URL <https://ncbi.nlm.nih.gov/gene?Dbgene&Cmd=DetailsSearch&Term=338428>, 1 page.
Papargyri et al., "Chemical Diversity of Locked Nucelic Acid-Modified Antisense Oligonucleotides allos Optimization of Pharmaceutical Properties," Molecular Therapy Nucleic Acids., Mar. 2020, (19):706-717.
Petrov, "Chemistry Guide for Schoolchildren," M List, 1998, p. 321.
Phillips M., et al., "In vivo applications of antisense oligonucleotides for peptide research," Regulatory Peptides 59 pp. 131-141 (1995).
Philpot et al., "Angelman syndrome: advancing the research frontier of neurodevelopmental disorders," J Neurodevelop Disord, Mar. 2011:50-56.
PNAS, "Information for Authors," revised Jan. 2020, 117 :xi-xviii.
Rougelle et al., "The Angelman syndrome candidate gene, UBE3A/E6-AP, is imprinted in brain," Nature Genetics, 1997, 17:14-15.
Rougeulle et al., "An imprinted antisense RNA overlaps UBE3A and a second maternally expressed transcript," Nature Genetics, 1998, 19:15-16.
Santalucia, John Jr., "A unified view of polymer, dumbbell, and oligonucleotide DNA nearest-neighbor thermodynamics," Proc Natl Acad Sci. 95:1460-5 (1998).
Second Declaration of Claes Wahlestedt, dated Jun. 15, 2020, 50 pages.
Seth at al., "Synthesis and Biophysical Evaluation of 2',4'-Constrained 2' O-Methoxyethyl and 2',4'-Constrained 2' O-Ethyl Nucleic Acid Analogues," J Org Chem. 75(5):1569-81 (2010) (13 pages).
Sharma et al., "Antisense oligonucleotides: modifications and clinical trials," MedChemComm. 5(10):1454-1471 (2014).
Shi et al., "In situ entry of oligonucleotides into brain cells can occur through a nucleic acid channel," Oligonucleotides, 2007, 17(1):122-133.
Smith et al., "Transcription is required to establish maternal imprinting at the Prader-Willi syndrome and Angelman syndrome locus," PLoS Genetics, 2011, 7(12):e1002422 10 pages.
Sugimoto et al., "Thermodynamic Parameters To Predict Stability of RNA/DNA Hybrid Duplexes," Biochemistry. 34(35): 11211-11216 (Sep. 1995) (6 pages).
Swayze et al., "The Medicinal Chemistry of Oligonucleotides," Antisense Drug Technology, CRC Press, 2nd edition, chapter 6, 23 pages (Jul. 24, 2007).
UCSC Genome Browser on Human Dec. 2013 (GRCh38/hg38) Assembly, Dec. 2013, 1 page.
Uhlmann, "Recent Advances in the medicinal chemistry of antisense oligonucleotides," Current Opinion in Drug Development, 2000, 3(2):203-213.
U.S. Appl. No. 61/664,083, Rigo et al., filed Jun. 25, 2012, 90 pages.
U.S. Appl. No. 61/738,959, Rigo et al., filed Dec. 18, 2012, 102 pages.
U.S. Appl. No. 61/750,939, Rigo et al., filed Jan. 10, 2013, 105 pages.
U.S. Appl. No. 61/755,617, Rigo et al., filed Jan. 23, 2013, 108 pages.
U.S. Appl. No. 61/772,925, Rigo et al., filed Mar. 5, 2013, 109 pages.
Vester et al., "Chemically modified oligonucleotides with efficient RNase H response," Bioorg Med Chem Lett., Apr. 1, 2008, 18(7):2296-2300.
Wahlestedt , "Natural antisense and noncoding RNA transcripts as potential drug targets," Drug Discovery Today, 2006, 11(11/12):503-508.
Wahlestedt et al., "Presentation: Regulatory Natural Antisense Transcripts," Keystone Symposium on MicroRNAs and Human Disease, Banff, Alberta, Feb. 11-16, 2011, 41 pages.
Www.uniprot.org, "UniProtKB—Q05086," Last updated Dec. 11, 2019, retrieved on Feb. 4, 2020, retrieved from URL <httos://www.uniprot.org/uniprot/Q05086>, 23 pages.
Yang D. et al., "Gene targets of antisense therapies in breast cancer," Expert Opinion on Therapeutic Targets, 6:3, pp. 375-385, (2005) (12 pages).
Boards of Appeal of the European Patent Office, Datasheet for the decision of Apr. 2, 2020 for European Application No. 06772386.6 (14 pages).
Brief Communication for European Patent Application No. 11840796.4, dated Oct. 18, 2021 (11 pages).
Colombian Office Action with Colombian Application No. NC20180004550, dated Apr. 14, 2020, 23 pages.
European Grounds of Appeal for European Patent No. 2864479, dated Apr. 29, 2022 (69 pages).
European Opposition in European Patent No. 2864479, dated Jun. 17, 2020, 17 pages.
European Revision of the EPC: Article 54(5), CA/PL4/00, dated Jan. 24, 2000, 4 pages.
European Revision of the European Patent Convention: CA/100/00, dated Aug. 9, 2000, 5 pages.
European Search Report for European Patent Application No. 23152543, dated Jul. 26, 2023 (7 pages).
Interlocutory decision in Opposition proceedings for European Patent Application No. 11840796.4, dated Jun. 21, 2022 (22 pages).
International Search Report and Written Opinion for International Patent Application No. PCT/EP2016/077383, dated Feb. 23, 2017 (12 pages).
Search overview of documents teaching the targeting of non-overlapping regions, Feb. 17, 2020, 29 pages.

* cited by examiner

OLIGONUCLEOTIDES FOR INDUCING PATERNAL UBE3A EXPRESSION

CROSS-REFERENCE TO RELATED APPLICATIONS

This application is a continuation of application Ser. No. 18/491,513, filed Oct. 20, 2023, which is a continuation of application Ser. No. 17/581,089, filed Jan. 21, 2022, which is a continuation of application Ser. No. 16/933,445, filed Jul. 20, 2020, which is a continuation of application Ser. No. 16/663,024, filed Oct. 24, 2019, which is a continuation of application Ser. No. 16/388,714, filed Apr. 18, 2019, which is a continuation of application Ser. No. 15/351,113, filed Nov. 14, 2016, which is a continuation of PCT/EP2016/077383, filed Nov. 11, 2016, which claims priority to EP15194367.7, filed Nov. 12, 2015 and EP16189502.4, filed Sep. 19, 2016, the contents of which are hereby incorporated by reference.

SEQUENCE LISTING

The instant application contains a Sequence Listing which has been submitted electronically in XML format and is hereby incorporated by reference in its entirety. Said XML copy, created on Jul. 1, 2025, is named 51551-014008_Sequence_Listing_7_1_25 and is 1,507,829 bytes in size.

FIELD OF INVENTION

The present invention relates to oligonucleotides (oligomers) that are complementary to and hybridize to SNHG14 downstream of SNORD109B, leading to induction of paternal expression of Ubiquitin-protein ligase E3A (UBE3A) in an animal or human. The present invention further relates to pharmaceutical compositions and methods for treatment of Angelman syndrome.

BACKGROUND

Angelman syndrome is neuro-genetic disorder caused by deletion or inactivation of the UBE3A genes on the maternally inherited chromosome 15q11.2. The paternal copy of the UBE3A gene is subject to genomic imprinting and silencing in neurons by an endogenous antisense transcript of UBE3A, termed SNHG14 (also known as UBE3A-ATS) (Meng et al. 2012 Hum Mol Genet. Vol. 21 pp. 3001-12). Other cell types than neurons seem to express the UBE3A gene from both the maternal and paternal allele.

Angelman syndrome is characterized by severe intellectual and developmental disability, sleep disturbance, seizures, jerky movements, EEG abnormalities, frequent laughter or smiling, and profound language impairments.

WO 2012/064806 discloses a method of inducing UBE3A expression in a cell by using a topoisomerase inhibitor. The method can be used to treat Angelman syndrome. There is no disclosure of antisense oligonucleotides.

WO 2014/004572 discloses oligonucleotides with 2'-O-methoxyethyl-RNA (MOE) modifications targeting mouse UBE3A-ATS. The oligonucleotides are only tested in mice related assays. In the region downstream of MBII-52 snoRNA (also known as SNORD115) and upstream of the UBE3A pre-mRNA there is no conservation between mouse and human. Oligonucleotides targeting mouse UBE3A-ATS can therefore not be translated into oligonucleotides that will function in a human. There is no disclosure of oligonucleotides targeting human UBE3A-ATS.

OBJECTIVE OF THE INVENTION

The present invention identifies novel oligonucleotides which induce human paternal UBE3A expression in neuronal without affection expression of the paternal SNORD115, SNORD116 and SNRPN transcripts significantly.

SUMMARY OF INVENTION

The present invention relates to oligonucleotides targeting a nucleic acid capable of supressing the expression of UBE3A and to treat or prevent diseases related to decreased activity of UBE3A, in particular in neuronal cells.

Accordingly, in a first aspect the invention provides oligonucleotides which comprise a contiguous nucleotide sequence of 10 to 30 nucleotides in length with at least 98% complementarity to the part of human SNHG14 long non-coding RNA corresponding to position 25278410 to 25419462 on human chromosome 15 version GRCh38.p2. This region is also resembled by SEQ ID NO: 1. The oligonucleotide can be an antisense oligonucleotide, preferably with a gapmer design. Preferably, the oligonucleotide is capable of inducing the expression of UBE3A, in particular paternal UBE3A expression in a neuron, by degradation, reduction or removal of the UBE3A suppressor, in particular by reduction of the SNHG14 long non-coding RNA transcript downstream of SNORD109B. The UBE3A re-expression is achieved, without significantly affecting the expression of SNORD115. The degradation of the target nucleic acid is preferably achieved via nuclease recruitment.

In a further aspect, the invention provides pharmaceutical compositions comprising the oligonucleotides of the invention and pharmaceutically acceptable diluents, carriers, salts and/or adjuvants.

In a further aspect, the invention provides methods for in vivo or in vitro induction of UBE3A expression in a target cell where expression of paternal UBE3A is suppressed, by administering an oligonucleotide or composition of the invention in an effective amount to said cell.

In a further aspect the invention provides methods for treating or preventing a disease, disorder or dysfunction associated with in vivo activity of UBE3A comprising administering a therapeutically or prophylactically effective amount of the oligonucleotide of the invention to a subject suffering from or susceptible to the disease, disorder or dysfunction.

In a further aspect the oligonucleotide or composition of the invention is used for the treatment or prevention of Angelman syndrome.

DEFINITIONS

Oligonucleotide

Figure 1:
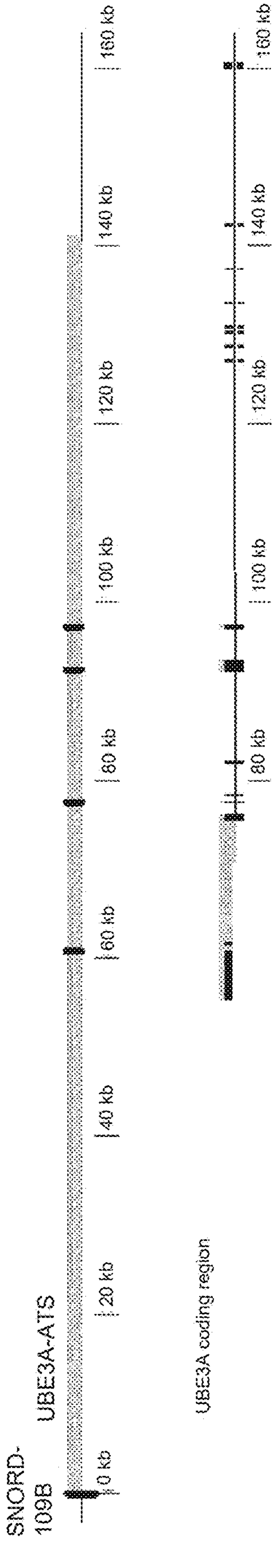
FIG. 1: The upper strand illustrates the region of the SNHG14 transcript downstream of SNORD109B (UBE3A-ATS) where the black boxes indicate the location of the tested mouse oligonucleotides. The lower strand illustrates the UBE3A coding region, where the black boxes indicate exons. Exon 1 is located around 160 kb. The oligonucleotides are placed in the antisense region of Exon 9 (positioned at ~97 kb), Exon 10 (positioned at ~92 kb), Exon 13 (positioned at ~77 kb) and the 5' end of Exon 16 (positioned at ~60 kb).

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs. Preferably, the antisense oligonucleotides of the present invention are single stranded.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide are present in the contiguous nucleotide sequence. In some embodiments the oligonucleotide comprises the contiguous nucleotide sequence and may, optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprises a modified sugar moiety. The term modified nucleoside may also be used herein interchangeably with the term "nucleoside analogue" or modified "units" or modified "monomers".

Modified Internucleoside Linkage

The term "modified internucleoside linkage" is defined as generally understood by the skilled person as linkages other than phosphodiester (PO) linkages, that covalently couples two nucleosides together. Nucleotides with modified internucleoside linkage are also termed "modified nucleotides". In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region of a gapmer oligonucleotide, as well as in regions of modified nucleosides.

In an embodiment, the oligonucleotide comprises one or more internucleoside linkages modified from the natural phosphodiester to a linkage that is for example more resistant to nuclease attack. Nuclease resistance may be determined by incubating the oligonucleotide in blood serum or by using a nuclease resistance assay (e.g. snake venom phosphodiesterase (SVPD)), both are well known in the art. Internucleoside linkages which are capable of enhancing the nuclease resistance of an oligonucleotide are referred to as nuclease resistant internucleoside linkages. In preferred embodiments at least 50% of the internucleoside linkages in the oligonucleotide, or contiguous nucleotide sequence thereof, are modified, such as at least 60%, such as at least 70%, such as at least 80 or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

Modified internucleoside linkages may be selected from the group comprising phosphorothioate, diphosphorothioate and boranophosphate. In preferred embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage.

A phosphorothioate internucleoside linkage is particularly useful due to nuclease resistance, beneficial pharmakokinetics and ease of manufacture. In preferred embodiments at least 50% of the internucleoside linkages in the oligonucleotide, or contiguous nucleotide sequence thereof, are phosphorothioate, such as at least 60%, such as at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide comprises one or more neutral internucleoside linkage, particularly a internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—$P(O)_2$—O—, —O—P(O,S)—O—, —O—$P(S)_2$—O—, —S—$P(O)_2$—O—, —S—P(O,S)—O—, —S—$P(S)_2$—O—, —O—$P(O)_2$—S—, —O—P(O,S)—S—, —S—$P(O)_2$—S—, —O—PO($R^H$)—O—, 0-PO($OCH_3$)—O—, —O—PO($NR^H$)—O—, —O—PO($OCH_2CH_2S$—R)—O—, —O—PO($BH_3$)—O—, —O—PO(NHRH)—O—, —O—$P(O)_2$—$NR^H$—, —$NR^H$—$P(O)_2$—O—, —$NR^H$—CO—O—, —$NR^H$—CO—$NR^H$—, and/or the internucleoside linker may be selected form the group consisting of: —O—CO—O—, —O—CO—$NR^H$—, —$NR^H$—CO—$CH_2$—, —O—$CH_2$—CO—$NR^H$—, —O—$CH_2$—$CH_2$—$NR^H$—, —CO—$NR^H$—$CH_2$—, —$CH_2$—$NR^H$CO—, —O—$CH_2$—$CH_2$—S—, —S—$CH_2$—$CH_2$—O—, —S—$CH_2$—$CH_2$—S—, —$CH_2$—$SO_2$—$CH_2$—, —$CH_2$—CO—$NR^H$—, —O—$CH_2$—$CH_2$—$NR^H$—CO—, —$CH_2$—$NCH_3$—O—$CH_2$—, where $R^H$ is selected from hydrogen and C1-4-alkyl.

Nuclease resistant linkages, such as phosphothioate linkages, are particularly useful in oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the oligonucleotide are phosphorothioate and/or boranophosphate linkages. Preferably, all the internucleoside linkages in the oligonucleotide are phosphorothioate linkages.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Complementarity

The term complementarity describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the number of nucleotides in percent of a contiguous nucleotide sequence in a nucleic acid molecule (e.g. oligonucleotide) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences, dividing by the total number of nucleotides in the oligonucleotide and multiplying by 100. In such a comparison a nucleobase/nucleotide which does not align (form a base pair) is termed a mismatch.

The term "fully complementary", refers to 100% complementarity.

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy ΔG° is a more accurate representation of binding affinity and is related to the dissociation constant ($K_d$) of the reaction by $\Delta G°=-RT \ln(K_d)$, where R is the gas constant and T is the absolute temperature. Therefore, a very low ΔG° of the reaction between an oligonucleotide and the target nucleic acid reflects a strong hybridization between the oligonucleotide and target nucleic acid. ΔG° is the energy associated with a reaction where aqueous concentrations are 1 M, the pH is 7, and the temperature is 37° C. The hybridization of oligonucleotides to a target nucleic acid is a spontaneous reaction and for spontaneous reactions ΔG° is less than zero. ΔG° can be measured experimentally, for example, by use of the isothermal titration calorimetry (ITC) method as described in Hansen et al., 1965, *Chem. Comm.* 36-38 and Holdgate et al., 2005, *Drug Discov Today*. The skilled person will know that commercial equipment is available for ΔG° measurements. ΔG° can also be estimated numerically by using the nearest neighbor model as described by SantaLucia, 1998, *Proc Natl Acad Sci USA*. 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated ΔG° values below −10 kcal for oligonucleotides that are 10-30 nucleotides in length. In some embodiments the degree or strength of hybridization is measured by the standard state Gibbs free energy ΔG°. The oligonucleotides may hybridize to a target nucleic acid with estimated ΔG° values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

The Target

The target refers to the protein which it is desired to modulate.

Target Nucleic Acid

A target nucleic acid is the intended target which the oligonucleotide of the invention hybridizes to, and may for example be a gene, a RNA, a non-coding RNA, a long non-coding RNA, a mRNA, and pre-mRNA, a mature mRNA or a cDNA sequence. In some embodiments the target nucleic acid is a non-coding RNA or a long non-coding RNA, or a subsequence thereof. For in vivo or in vitro application, the oligonucleotide of the invention is capable of decreasing the level of the SNHG14 transcript downstream of SNORD109B of and thereby relieving the suppression of the paternal UBE3A transcript in the intended target cell. The contiguous sequence of nucleobases of the oligonucleotide of the invention is complementary to the target nucleic acid, as measured across the length of the oligonucleotide, optionally with the exception of one or two mismatches, and optionally excluding nucleotide based linker regions which may link the oligonucleotide to an optional functional group such as a conjugate.

Target Sequence

The oligonucleotide comprises a contiguous nucleotide sequence which is complementary to or hybridizes to a sub-sequence of the target nucleic acid molecule. The term "target sequence" as used herein refers to a sequence of nucleotides present in the target nucleic acid which comprises the nucleobase sequence which is complementary to the oligonucleotide of the invention. In some embodiments, the target sequence consists of a region on the target nucleic acid which is complementary to the contiguous nucleotide sequence of the oligonucleotide of the invention. In some embodiments the target sequence is longer than the complementary sequence of a single oligonucleotide, and may, for example represent a preferred region of the target nucleic acid which may be targeted by several oligonucleotides of the invention.

The oligonucleotide of the invention comprises a contiguous nucleotide sequence which is complementary to the target nucleic acid, such as a target sequence.

The oligonucleotide comprises a contiguous nucleotide sequence of at least 8 nucleotides which is complementary to or hybridizes to a target sequence present in the target nucleic acid molecule. The contiguous nucleotide sequence (and therefore the target sequence) comprises of at least 8 contiguous nucleotides, such as 9, 10, 11, 12, 13, 14, 15, 16, 17, 18, 19, 20, 21, 22, 23, 24, 25, 26, 27, 28, 29 or 30 contiguous nucleotides, such as from 12-25, such as from 14-18 contiguous nucleotides.

Target Cell

The term a target cell as used herein refers to a cell which is expressing the target nucleic acid. In some embodiments the target cell may be in vivo or in vitro. In some embodiments the target cell is a mammalian cell such as a rodent cell, such as a mouse cell or a rat cell, or a primate cell such as a monkey cell or a human cell. In preferred embodiments the target cell is a neuronal cell.

Naturally Occurring Variant

The term "naturally occurring variant" refers to variants of SNHG14 transcript downstream of SNORD109B gene or transcripts which originate from the same genetic loci as the target nucleic acid, but may differ for example, by virtue of degeneracy of the genetic code causing a multiplicity of codons in the long non-coding RNA. The oligonucleotide of the invention may therefore be designed to target the target nucleic acid and naturally occurring variants thereof.

Modulation of Expression

The term "modulation of expression" as used herein is to be understood as an overall term for an oligonucleotide's ability to alter the amount of UBE3A protein when compared to the amount of UBE3A before administration of the oligonucleotide. Alternatively modulation of expression may be determined by reference to a control experiment where the oligonucleotide of the invention is not administered. The modulation effected by the oligonucleotide is related to it's ability to reduce, remove, prevent, lessen, lower or terminate the suppression of the paternal UBE3A transcript, e.g. by degradation or removal of the non-coding SNHG14 transcript downstream of SNORD109B or by blockage or prevention of polymerase activity associated with the SNHG14 transcript downstream of SNORD109B. The modulation can also be viewed as the oligonucleotide's ability to restore, increase or enhance expression of paternal UBE3A, e.g. by removal or blockage of inhibitory mechanisms affected by the non-coding SNHG14 transcript downstream of SNORD109B.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T_m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into oligonucleotides, such as enhanced nucleoside resistance and enhanced affinity.

2' Modified Nucleosides.

A 2' sugar modified nucleoside is a nucleoside which has a substituent other than H or —OH at the 2' position (2' substituted nucleoside) or comprises a 2' linked biradicle, and includes 2' substituted nucleosides and LNA (2'-4' biradicle bridged) nucleosides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-fluoro-ANA (F-ANA). For further examples, please see e.g. Freier & Altmann; Nucl. Acid Res., 1997, 25, 4429-4443 and Uhlmann; Curr. Opinion in Drug Development, 2000, 3(2), 293-213; and Deleavey and Damha, Chemistry and Biology 2012, 19, 937. Below are illustrations of some 2' substituted modified nucleosides.

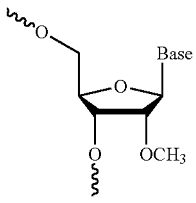

2'-O-Me

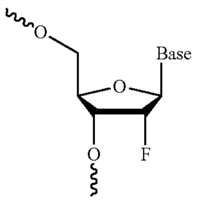

2'F-RNA

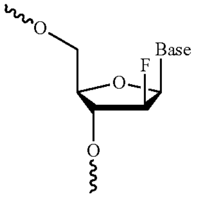

2'F-ANA

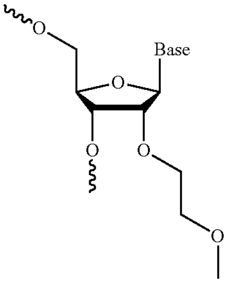

2'-O-MOE

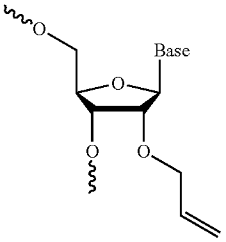

2'-O-Allyl

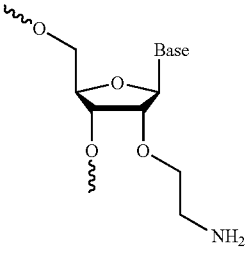

2'-O-Ethylamine

Locked Nucleic Acid Nucleosides (LNA).

LNA nucleosides are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

In some embodiments, the modified nucleoside or the LNA nucleosides of the oligomer of the invention has a general structure of the formula I or II:

Formula I

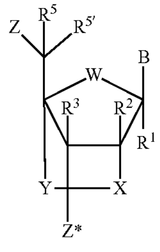

or

β-D

Formula II

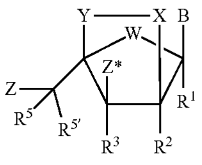

α-L wherein W is selected from —O—, —S—, —N($R^a$)—, —C($R^aR^b$)—, such as, in some embodiments —O—;

B designates a nucleobase or modified nucleobase moiety;

Z designates an internucleoside linkage to an adjacent nucleoside, or a 5'-terminal group;

Z* designates an internucleoside linkage to an adjacent nucleoside, or a 3'-terminal group;

X designates a group selected from the list consisting of —C($R^aR^b$)—, —C($R^a$)═C($R^b$)—, —C($R^a$)═N—, —O—, —Si($R^a$)$_2$—, —S—, —$SO_2$—, —N($R^a$)—, and >C═Z In some embodiments, X is selected from the group consisting of: —O—, —S—, NH—, $NR^aR^b$, —$CH_2$—, $CR^aR^b$, —C(═$CH_2$)—, and —C(═$CR^aR^b$)—

In some embodiments, X is —O—

Y designates a group selected from the group consisting of —C($R^aR^b$)—, —C($R^a$)═C($R^b$)—, —C($R^a$)═N—, —O—, —Si($R^a$)$_2$—, —S—, —$SO_2$—, —N($R^a$)—, and >C═Z In some embodiments, Y is selected from the group consisting of: —$CH_2$—, —C($R^aR^b$)—, —$CH_2CH_2$—, —C($R^aR^b$)—C($R^aR^b$)—, —$CH_2CH_2CH_2$—, —C($R^aR^b$)C($R^aR^b$)C($R^aR^b$)—, —C($R^a$)═C($R^b$)—, and —C($R^a$)═N—

In some embodiments, Y is selected from the group consisting of: —$CH_2$—, —$CHR^a$—, —$CHCH_3$—, $CR^aR^b$— or —X—Y— together designate a bivalent linker group (also referred to as a radicle) together designate a bivalent linker group consisting of 1, 2, 3 or 4 groups/atoms selected from the group consisting of —C($R^aR^b$)—, —C($R^a$)═C($R^b$)—, —C($R^a$)═N—, —O—, —Si($R^a$)$_2$—, —S—, —$SO_2$—, —N($R^a$)—, and >C═Z, In some embodiments, —X—Y— designates a biradicle selected from the groups consisting of: —X—$CH_2$—, —X—$CR^aR^b$—, —X—$CHR^a$—, —X—C($HCH_3$)$^-$, —O—Y—, —O—$CH_2$—, —S—$CH_2$—, —NH—$CH_2$—, —O—$CHCH_3$—, —$CH_2$—O—$CH_2$, —O—CH($CH_3CH_3$)—, —O—$CH_2$—$CH_2$—, $OCH_2$—$CH_2$—$CH_2$—, —O—$CH_2OCH_2$—, —O—$NCH_2$—, —C(═$CH_2$)—$CH_2$—, —$NR^a$—$CH_2$—, N—O—$CH_2$, —S—$CR^aR^b$— and —S—$CHR^a$—.

In some embodiments —X—Y— designates —O—$CH_2$— or —O—CH($CH_3$)—.

wherein Z is selected from —O—, —S—, and —N($R^a$)—, and $R^a$ and, when present $R^b$, each is independently selected from hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl) amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted and where two geminal substituents $R^a$ and $R^b$ together may designate optionally substituted methylene (═$CH_2$), wherein for all chiral centers, asymmetric groups may be found in either R or S orientation, wherein $R^1$, $R^2$, $R^3$, $R^5$ and $R^{5*}$ are independently selected from the group consisting of: hydrogen, optionally substituted $C_{1-6}$-alkyl, optionally substituted $C_{2-6}$-alkenyl, optionally substituted $C_{2-6}$-alkynyl, hydroxy, $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl) amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted, and where two geminal substituents together may designate oxo, thioxo, imino, or optionally substituted methylene.

In some embodiments $R^1$, $R^2$, $R^3$, $R^5$ and $R^{5*}$ are independently selected from $C_{1-6}$ alkyl, such as methyl, and hydrogen.

In some embodiments $R^1$, $R^2$, $R^3$, $R^5$ and $R^{5*}$ are all hydrogen.

In some embodiments $R^1$, $R^2$, $R^3$, are all hydrogen, and either $R^5$ and $R^{5*}$ is also hydrogen and the other of $R^5$ and $R^{5*}$ is other than hydrogen, such as $C_{1-6}$ alkyl such as methyl.

In some embodiments, $R^a$ is either hydrogen or methyl. In some embodiments, when present, $R^b$ is either hydrogen or methyl.

In some embodiments, one or both of $R^a$ and $R^b$ is hydrogen

In some embodiments, one of $R^a$ and $R^b$ is hydrogen and the other is other than hydrogen In some embodiments, one of $R^a$ and $R^b$ is methyl and the other is hydrogen In some embodiments, both of $R^a$ and $R^b$ are methyl.

In some embodiments, the biradicle —X—Y— is —O—$CH_2$—, W is O, and all of $R^1$, $R^2$, $R^3$, $R^5$ and $R^{5*}$ are all hydrogen. Such LNA nucleosides are disclosed in WO99/014226, WO00/66604, WO98/039352 and WO2004/046160 which are all hereby incorporated by reference, and include what are commonly known as beta-D-oxy LNA and alpha-L-oxy LNA nucleosides.

In some embodiments, the biradicle —X—Y— is —S—$CH_2$—, W is O, and all of $R^1$, $R^2$, $R^3$, $R^5$ and $R^{5*}$ are all hydrogen. Such thio LNA nucleosides are disclosed in WO99/014226 and WO2004/046160 which are hereby incorporated by reference.

In some embodiments, the biradicle —X—Y— is —NH—$CH_2$—, W is O, and all of $R^1$, $R^2$, $R^3$, $R^5$ and $R^{5*}$ are all hydrogen. Such amino LNA nucleosides are disclosed in WO99/014226 and WO2004/046160 which are hereby incorporated by reference.

In some embodiments, the biradicle —X—Y— is —O—$CH_2$—$CH_2$— or —O—$CH_2$—$CH_2$— $CH_2$—, W is O, and all of $R^1$, $R^2$, $R^3$, $R^5$ and $R^{5*}$ are all hydrogen. Such LNA nucleosides are disclosed in WO00/047599 and Morita et al, Bioorganic & Med. Chem. Lett. 12 73-76, which are hereby incorporated by reference, and include what are commonly known as 2'-O-4'C-ethylene bridged nucleic acids (ENA).

In some embodiments, the biradicle —X—Y— is —O—$CH_2$—, W is O, and all of $R^1$, $R^2$, $R^3$, and one of $R^5$ and $R^{5*}$ are hydrogen, and the other of $R^5$ and $R^{5*}$ is other than hydrogen such as $C_{1-6}$ alkyl, such as methyl. Such 5' substituted LNA nucleosides are disclosed in WO2007/134181 which is hereby incorporated by reference.

In some embodiments, the biradicle —X—Y— is —O—$CR^aR^b$—, wherein one or both of $R^a$ and $R^b$ are other than hydrogen, such as methyl, W is O, and all of $R^1$, $R^2$, $R^3$, and one of $R^5$ and $R^{5*}$ are hydrogen, and the other of $R^5$ and $R^{5*}$ is other than hydrogen such as $C_{1-6}$ alkyl, such as methyl. Such bis modified LNA nucleosides are disclosed in WO2010/077578 which is hereby incorporated by reference.

In some embodiments, the biradicle —X—Y— designate the bivalent linker group —O—$CH(CH_2OCH_3)$— (2' O-methoxyethyl bicyclic nucleic acid—Seth at al., 2010, J. Org. Chem. Vol 75(5) pp. 1569-81). In some embodiments, the biradicle —X—Y— designate the bivalent linker group —O—$CH(CH_2CH_3)$— (2'O-ethyl bicyclic nucleic acid—Seth at al., 2010, J. Org. Chem. Vol 75(5) pp. 1569-81). In some embodiments, the biradicle —X—Y— is —O—$CHR^a$—, W is O, and all of $R^1$, $R^2$, $R^3$, $R^5$ and $R^{5*}$ are all hydrogen. Such 6' substituted LNA nucleosides are disclosed in WO10036698 and WO07090071 which are both hereby incorporated by reference.

In some embodiments, the biradicle —X—Y— is —O—$CH(CH_2OCH_3)$—, W is O, and all of $R^1$, $R^2$, $R^3$, $R^5$ and $R^{5*}$ are all hydrogen. Such LNA nucleosides are also known as cyclic MOEs in the art (cMOE) and are disclosed in WO07090071.

In some embodiments, the biradicle —X—Y— designate the bivalent linker group —O—$CH(CH_3)$—.—in either the R- or S-configuration. In some embodiments, the biradicle —X—Y— together designate the bivalent linker group —O—$CH_2$—O—$CH_2$— (Seth at al., 2010, J. Org. Chem). In some embodiments, the biradicle —X—Y— is —O—CH ($CH_3$)—, W is O, and all of $R^1$, $R^2$, $R^3$, $R^5$ and $R^{5*}$ are all hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L) which are both hereby incorporated by reference).

In some embodiments, the biradicle —X—Y— is —O—$CR^aR^b$—, wherein in neither $R^a$ or $R^b$ is hydrogen, W is O, and all of $R^1$, $R^2$, $R^3$, $R^5$ and $R^{5*}$ are all hydrogen. In some embodiments, $R^a$ and $R^b$ are both methyl. Such 6' di-substituted LNA nucleosides are disclosed in WO 2009006478 which is hereby incorporated by reference.

In some embodiments, the biradicle —X—Y— is —S—$CHR^a$—, W is O, and all of $R^1$, $R^2$, $R^3$, $R^5$ and $R^{5*}$ are all hydrogen. Such 6' substituted thio LNA nucleosides are disclosed in WO11156202 which is hereby incorporated by reference. In some 6' substituted thio LNA embodiments $R^a$ is methyl.

In some embodiments, the biradicle —X—Y— is —C(=$CH_2$)—C($R^aR^b$)—, such as —C(=$CH_2$)—$CH_2$—, or —C(=$CH_2$)—$CH(CH_3)$—W is O, and all of $R^1$, $R^2$, $R^3$, $R^5$ and $R^{5*}$ are all hydrogen. Such vinyl carbo LNA nucleosides are disclosed in WO08154401 and WO09067647 which are both hereby incorporated by reference.

In some embodiments the biradicle —X—Y— is —N(—$OR^a$)—, W is O, and all of $R^1$, $R^2$, $R^3$, $R^5$ and $R^{5*}$ are all hydrogen. In some embodiments $R^a$ is $C_{1-6}$ alkyl such as methyl. Such LNA nucleosides are also known as N substituted LNAs and are disclosed in WO2008/150729 which is hereby incorporated by reference.

In some embodiments, the biradicle —X—Y— together designate the bivalent linker group —O—$NR^a$—$CH_3$— (Seth at al., 2010, J. Org. Chem). In some embodiments the biradicle —X—Y— is —N($R^a$)—, W is O, and all of $R^1$, $R^2$, $R^3$, $R^5$ and $R^{5*}$ are all hydrogen. In some embodiments $R^a$ is $C_{1-6}$ alkyl such as methyl.

In some embodiments, one or both of $R^5$ and $R^{5*}$ is hydrogen and, when substituted the other of $R^5$ and $R^{5*}$ is $C_{1-6}$ alkyl such as methyl. In such an embodiment, $R^1$, $R^2$, $R^3$, may all be hydrogen, and the biradicle —X—Y— may be selected from —O—$CH_2$— or —O—C($HCR^a$)—, such as —O—C(HCH3)-.

In some embodiments, the biradicle is —$CR^aR^b$—O—$CR^aR^b$—, such as $CH_2$—O—$CH_2$—, W is O and all of $R^1$, $R^2$, $R^3$, $R^5$ and $R^{5*}$ are all hydrogen. In some embodiments $R^a$ is $C_{1-6}$ alkyl such as methyl. Such LNA nucleosides are also known as conformationally restricted nucleotides (CRNs) and are disclosed in WO2013036868 which is hereby incorporated by reference.

In some embodiments, the biradicle is —O—$CR^aR^b$—O—$CR^aR^b$—, such as O—$CH_2$—O—$CH_2$—, W is O and all of $R^1$, $R^2$, $R^3$, $R^5$ and $R^{5*}$ are all hydrogen. In some embodiments $R^a$ is $C_{1-6}$ alkyl such as methyl. Such LNA nucleosides are also known as COC nucleotides and are disclosed in Mitsuoka et al., Nucleic Acids Research 2009 37(4), 1225-1238, which is hereby incorporated by reference.

It will be recognized than, unless specified, the LNA nucleosides may be in the beta-D or alpha-L stereoisoform.

Certain examples of LNA nucleosides are presented in Scheme 1.

Scheme 1

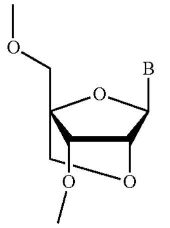
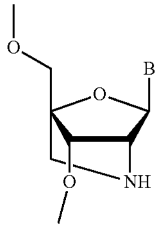
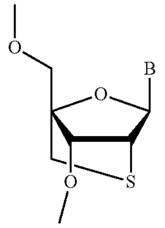

β-D-oxy LNA β-D-amino LNA β-D-thio LNA

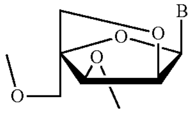
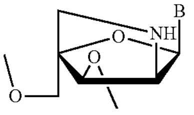

α-D-oxy LNA α-D-amino LNA

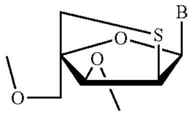
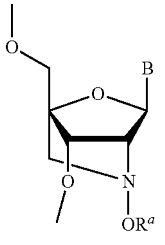

α-D-thio LNA β-D-amino substituted LNA

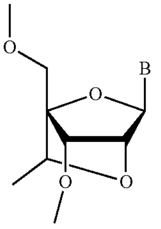
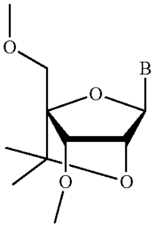

6'methyl β-D-oxy LNA 6'dimethylβ-D-oxy LNA

-continued

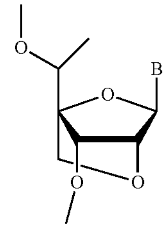

5′methyl β-D-oxy LNA

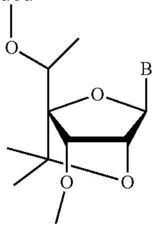

5′methyl, 6′dimethyl β-D-oxy LNA

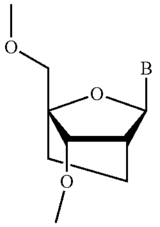

Carbocyclic(vinyl) β-D-oxy LNA

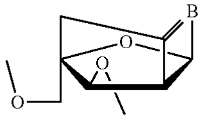

Carbocyclic(vinyl) α-L-LNA

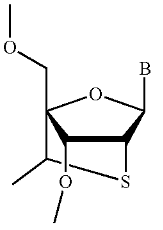

6′methyl thio β-D LNA

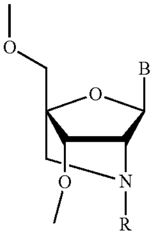

Substituted β-D amino LNA

As illustrated in the examples, in preferred embodiments of the invention the LNA nucleosides in the oligonucleotides are beta-D-oxy-LNA nucleosides.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 10% or more than 20% of the of the initial rate determined when using a oligonucleotide having the same base sequence as the modified oligonucleotide being tested, but containing only DNA monomers, with phosphorothioate linkages between all monomers in the oligonucleotide, and using the methodology provided by Example 91-95 of WO01/23613 (hereby incorporated by reference).

Gapmer

The term gapmer as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. Headmers and tailmers are oligonucleotides capable of recruiting RNase H where one of the flanks is missing, i.e. only one of the ends of the oligonucleotide comprises affinity enhancing modified nucleosides. For headmers the 3' flank is missing (i.e. the 5' flanc comprise affinity enhancing modified nucleosides) and for tailmers the 5' flank is missing (i.e. the 3' flank comprises affinity enhancing modified nucleosides).

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer refers to a LNA gapmer wherein the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside(s). In some embodiments the mixed wing gapmer has one flank which comprises LNA nucleosides (e.g. 5' or 3') and the other flank (3' or 5' respectfully) comprises 2' substituted modified nucleoside(s).

Conjugate

The term conjugate as used herein refers to an oligonucleotide which is covalently linked to a non-nucleotide moiety (conjugate moiety or region C or third region).

Conjugation of the oligonucleotide of the invention to one or more non-nucleotide moieties may improve the pharmacology of the oligonucleotide, e.g. by affecting the activity, cellular distribution, cellular uptake or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue or cell type and thereby enhance the effectiveness of the oligonucleotide in that organ, tissue or cell type. A the same time the conjugate may serve to reduce activity of the oligonucleotide in non-target cell types, tissues or organs, e.g. off target activity or activity in non-target cell types, tissues or organs. WO 93/07883 and WO 2013/033230 provides suitable conjugate moieties, which are hereby incorporated by reference. WO 2012/143379 provides a method of delivering a drug across the blood-brain-barrier by conjugation to an antibody fragment with affinity to the transferrin receptor, which are hereby incorporated by reference.

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103, each of which is incorporated herein by reference in its entirety.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof. In some embodiments the non-nucleotide moiety an antibody or antibody fragment, such as an antibody or antibody fragment that facilitates delivery across the blood-brain-barrier, in particular an antibody or antibody fragment targeting the transferrin receptor.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide (region A).

In some embodiments of the invention the conjugate or oligonucleotide conjugate of the invention may optionally, comprise a linker region (second region or region B and/or region Y) which is positioned between the oligonucleotide (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA. Phosphodiester containing biocleavable linkers are described in more detail in WO 2014/076195 (hereby incorporated by reference).

Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups The oligonucleotide conjugates of the present invention can be constructed of the following regional elements A-C, A-B-C, A-B-Y-C, A-Y-B-C or A-Y-C. In some embodiments the linker (region Y) is an amino alkyl, such as a C2-C36 amino alkyl group, including, for example C6 to C12 amino alkyl groups. In a preferred embodiment the linker (region Y) is a C6 amino alkyl group.

Control

By the term "control" when used in relation to measurements of the effect of an oligonucleotide it is generally understood that the control is an untreated individual or target cell or a individual or target cell treated with a non-targeting oligonucleotide (mock). It may however also be an individual treated with the standard of care.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

DETAILED DESCRIPTION OF THE INVENTION

The Target

An aspect of the invention is to modulate the level of pig, primate or human UBE3A protein expression, in particular to increase the expression of paternal UBE3A expression in neuronal cells, in particular in human neuronal cells. The human UBE3A protein exists in several isoforms which are listed under Uniprot nr. Q05086. Several mutations in the maternal UBE3A gene can results in Angelman syndrome.

The target nucleic acid for the oligonucleotides of the invention is RNA, in particular a long non-coding RNA. The long non-coding RNA which is targeted by the oligonucleotides of the present invention is human SNHG14 (also known as UBE3A-ATS with Ensembl entry number ENSG00000224078, version GRCh38.p2). In particular the target nucleic acid is the region downstream of SNORD109B corresponding to position 25278410 to 25419462 on chromosome 15 (SEQ ID NO: 1). In Rhesus monkey (*Macaca* mulatta) the UBE3A supressor is defined as region downstream of SNORD109A corresponding to position 4222848 to U.S. Pat. No. 4,373,084 (forward strand) on chromosome 7 using the Ensembl assembly MMUL 1.0 (SEQ ID NO: 2).

In some embodiments, the target nucleic acid is SEQ ID NO: 1, or naturally occurring variants thereof.

In certain embodiments the target nucleic acid correspond to regions which are conserved between human (SEQ ID NO: 1) and Rhesus monkey (SEQ ID NO: 2). In certain embodiments target nucleic acid correspond to regions which are conserved between human (SEQ ID NO:1), Rhesus monkey (SEQ ID NO: 2) and mouse (SEQ ID NO: 3).

In certain embodiments the target nucleic acid is the region that is antisense to the UBE3A pre-mRNA, this region corresponds to position 55319 to 141053 of SEQ ID NO: 1.

In certain embodiments the target nucleic acid is the region that is downstream of SNORD109B and upstream of the region that is antisense to the UBE3A pre-mRNA, this region corresponds to position 1 to 55319 of SEQ ID NO: 1.

In some embodiments, the target nucleic acid is present in a cell, such as a mammalian cell in particular a human cell in vitro or in vivo (the target cell). In certain embodiments the target cell is a neuron, preferably a human neuronal cell.

The target sequence may be a sub-sequence of the target nucleic acid. In some embodiments the oligonucleotide targets sub-sequence selected from the group consisting of the antisense region of exon 9, exon10, exon13, exon14, intron 14, exon 15, intron15 and exon 16 of UBE3A. In some embodiments the oligonucleotide or contiguous nucleotide sequence hybridize or is complementary to a single stranded nucleic acid molecule selected from the group consisting of positions: 55319-76274, 77483-77573, 92157-93403 and 97056-97354 of SEQ ID NO: 1. In some embodiments the oligonucleotide or contiguous nucleotide sequence hybridize or is complementary to a single stranded nucleic acid molecule selected from the group consisting of positions: 60821-60849, 77567-77583, 92323-92339 and 97156-97172 of SEQ ID NO: 1.

In some embodiments the target nucleic acid is a region corresponding to positions 9200-9250 of SEQ ID NO: 1.

In some embodiments the target nucleic acid is a region corresponding to positions 11505-11555 of SEQ ID NO: 1.

In some embodiments the target nucleic acid is a region corresponding to positions 15100-15150 of SEQ ID NO: 1.

In some embodiments the target nucleic acid is a region corresponding to positions 30590-30740 of SEQ ID NO: 1.

In some embodiments the target nucleic acid is a region corresponding to positions 46380-46430 of SEQ ID NO: 1.

The Oligonucleotides of the Invention

The invention relates to oligonucleotides capable of modulating expression of paternal UBE3A, in particular induction or up-regulation of paternally expressed UBE3A in neuronal cells. The modulation is achieved by hybridizing to a target nucleic acid located on the long non-coding RNA SNHG14 transcript downstream of SNORD109B. In certain embodiments the oligonucleotide of the invention hybridizes to a sub-sequence of the target nucleic acid of SEQ ID NO: 1 with a ΔG° below −10 kcal, such as with a ΔG° between −10 to −60 kcal, such as −12 to −40, such as from −15 to −30 kcal or −16 to −27 kcal such as −18 to −25 kcal.

The oligonucleotide of the invention is an antisense oligonucleotide which targets the pig, rhesus monkey and/or human SNHG14 transcript downstream of SNORD109B.

In some embodiments the antisense oligonucleotide of the invention is capable of modulating the expression of the target by removing, interfering with or decreasing the suppressor of the target. Preferably, the oligonucleotides of the invention induce UBE3A expression in a cell, in particular paternal UBE3A expression in a neuron, by degradation or removal of the SNHG14 transcript downstream of SNORD109B. In some embodiments the oligonucleotides of the invention are capable of increasing the expression of UBE3A by least 20% compared to the expression level of UBE3A in a neuronal cell treated with saline or a non-targeting oligonucleotide, more preferably by at least 30%, 35%, 40%, 45%, 50%, 55%, 60%, 80%, 100%, 120%, 150%, 160%, 170%, 180%, 190%, 200%, 210%, 220%, 230%, 240% or 250% compared to the expression level of UBE3A in a neuronal cell treated with saline or a non-targeting oligonucleotide. In additional embodiments the oligonucleotides of the invention are capable of decreasing the level of the SNHG14 transcript downstream of SNORD109B (in particular the part of the transcript that is antisense to the UBE3A pre-mRNA region) by at least 20% compared to the level of the SNHG14 transcript downstream of SNORD109B in a neuronal cell treated with saline or a non-targeting oligonucleotide, more preferably by at least 30%, 40%, 50%, 60%, 70%, 80%, 90% or 95% compared to the level of the SNHG14 transcript downstream of SNORD109B in a neuronal cell treated with saline or a non-targeting oligonucleotide, without reducing SNORD115 levels by more than 0%, 1%, 2%, 3%, 4%, 5%, 6%, 7%, 8%, 9%, 10%, 12%, 14%, 16%, 18%, 20%, 25% or 30% compared to the level of SNORD115 in a cell treated with saline or a non-targeting oligonucleotide. SNRPN and SNORD116 transcripts are located upstream from the SNORD115 transcript consequently if the SNORD115 transcript is not reduced by the oligonucleotide it is highly likely that the SNRPN and SNORD116 transcripts are also not reduced. In a further embodiment SNRPN and SNORD116 transcripts levels are not reduced by more than 0%, 1%, 2%, 3%, 4%, 5%, 6%, 7%, 8%, 9%, 10%, 12%, 14%, 16%, 18%, 20%, 25% or 30% compared to the level of SNRPN and SNORD116 in a cell treated with saline or a non-targeting oligonucleotide.

The target modulation is triggered by the hybridization between a contiguous nucleotide sequence of the oligonucleotide and the target nucleic acid. In some embodiments the oligonucleotide of the invention comprises mismatches between the oligonucleotide and the target nucleic acid. Despite mismatches hybridization to the target nucleic acid may still be sufficient to show a desired modulation of UBE3A expression. Reduced binding affinity resulting from mismatches may advantageously be compensated by increased number of nucleotides in the oligonucleotide and/or an increased number of modified nucleosides capable of increasing the binding affinity to the target, such as 2' modified nucleosides, including LNA, present within the oligonucleotide sequence.

An aspect of the present invention relates to an antisense oligonucleotide which comprises a contiguous nucleotide sequence of 10 to 30 nucleotides in length with at least 90%, such as 95%, such as 98% such as 100% complementarity to position 25278410 to 25419462 on human chromosome 15.

In some embodiments, the oligonucleotide comprises a contiguous sequence which is at least 90% complementary, such as at least 91%, such as at least 92%, such as at least 93%, such as at least 94%, such as at least 95%, such as at least 96%, such as at least 97%, such as at least 98%, or 100% complementary with a region of the target nucleic acid shown as SEQ ID NO: 1, 2 or 3.

In a preferred embodiment the oligonucleotide of the invention, or contiguous nucleotide sequence thereof is fully complementary (100% complementary) to a region of the target nucleic acid shown as SEQ ID NO: 1, or in some embodiments may comprise one or two mismatches between the oligonucleotide and the target nucleic acid.

In some embodiments the oligonucleotide sequence is 100% complementary to a corresponding target nucleic acid region present in SEQ ID NO: 1 and SEQ ID NO: 2. In some embodiments the oligonucleotide sequence is 100% complementary to a corresponding target nucleic acid region present SEQ ID NO: 1, 2 and 3.

In some embodiments, the oligonucleotide comprises a contiguous nucleotide sequence of 10 to 30 nucleotides in length with at least 90% complementary, such as 100% complementarity, to a corresponding target nucleic acid region present in SEQ ID NO: 1, wherein the target nucleic acid region is selected from the group consisting of region A1 to A3649 in table 1

TABLE 1

Regions of SEQ ID NO 1 which may be targeted using oligonucleotide of the invention

| Reg. A | Position in SEQ ID NO 1 from | to | Length |
|---|---|---|---|
| 1 | 10 | 75 | 66 |
| 2 | 77 | 91 | 15 |
| 3 | 93 | 108 | 16 |
| 4 | 168 | 213 | 46 |
| 5 | 217 | 282 | 66 |
| 6 | 284 | 299 | 16 |
| 7 | 301 | 328 | 28 |
| 8 | 330 | 344 | 15 |

TABLE 1-continued

Regions of SEQ ID NO 1 which may be targeted using oligonucleotide of the invention

| Reg. A | Position in SEQ ID NO 1 from | to | Length |
|---|---|---|---|
| 9 | 361 | 400 | 40 |
| 10 | 415 | 447 | 33 |
| 11 | 449 | 470 | 22 |
| 12 | 472 | 487 | 16 |
| 13 | 489 | 521 | 33 |
| 14 | 523 | 540 | 18 |
| 15 | 551 | 570 | 20 |
| 16 | 590 | 638 | 49 |
| 17 | 652 | 670 | 19 |
| 18 | 672 | 733 | 62 |
| 19 | 735 | 756 | 22 |
| 20 | 758 | 773 | 16 |
| 21 | 781 | 829 | 49 |
| 22 | 831 | 870 | 40 |
| 23 | 882 | 903 | 22 |
| 24 | 918 | 949 | 32 |
| 25 | 961 | 990 | 30 |
| 26 | 1007 | 1021 | 15 |
| 27 | 1019 | 1050 | 32 |
| 28 | 1052 | 1090 | 39 |
| 29 | 1092 | 1139 | 48 |
| 30 | 1147 | 1179 | 33 |
| 31 | 1175 | 1212 | 38 |
| 32 | 1220 | 1242 | 23 |
| 33 | 1245 | 1259 | 15 |
| 34 | 1265 | 1278 | 14 |
| 35 | 1285 | 1323 | 39 |
| 36 | 1317 | 1330 | 14 |
| 37 | 1337 | 1355 | 19 |
| 38 | 1357 | 1403 | 47 |
| 39 | 1405 | 1421 | 17 |
| 40 | 1423 | 1481 | 59 |
| 41 | 1486 | 1515 | 30 |
| 42 | 1521 | 1581 | 61 |
| 43 | 1611 | 1633 | 23 |
| 44 | 1631 | 1644 | 14 |
| 45 | 1635 | 1663 | 29 |
| 46 | 1669 | 1684 | 16 |
| 47 | 1685 | 1709 | 25 |
| 48 | 1711 | 1724 | 14 |
| 49 | 1726 | 1746 | 21 |
| 50 | 1754 | 1808 | 55 |
| 51 | 1819 | 1860 | 42 |
| 52 | 1862 | 1878 | 17 |
| 53 | 1896 | 1910 | 15 |
| 54 | 1923 | 1944 | 22 |
| 55 | 1946 | 1987 | 42 |
| 56 | 1985 | 2051 | 67 |
| 57 | 2053 | 2082 | 30 |
| 58 | 2088 | 2104 | 17 |
| 59 | 2106 | 2125 | 20 |
| 60 | 2132 | 2207 | 76 |
| 61 | 2209 | 2234 | 26 |
| 62 | 2247 | 2261 | 15 |
| 63 | 2263 | 2286 | 24 |
| 64 | 2290 | 2306 | 17 |
| 65 | 2308 | 2329 | 22 |
| 66 | 2347 | 2391 | 45 |
| 67 | 2398 | 2431 | 34 |
| 68 | 2447 | 2468 | 22 |
| 69 | 2470 | 2555 | 86 |
| 70 | 2565 | 2579 | 15 |
| 71 | 2579 | 2592 | 14 |
| 72 | 2589 | 2605 | 17 |
| 73 | 2594 | 2657 | 64 |
| 74 | 2672 | 2687 | 16 |
| 75 | 2692 | 2705 | 14 |
| 76 | 2703 | 2721 | 19 |
| 77 | 2770 | 2824 | 55 |
| 78 | 2826 | 2841 | 16 |
| 79 | 2838 | 2851 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 80 | 2843 | 2889 | 47 |
| 81 | 2896 | 2930 | 35 |
| 82 | 2930 | 2967 | 38 |
| 83 | 2965 | 2988 | 24 |
| 84 | 2984 | 3028 | 45 |
| 85 | 3024 | 3080 | 57 |
| 86 | 3081 | 3135 | 55 |
| 87 | 3140 | 3176 | 37 |
| 88 | 3168 | 3189 | 22 |
| 89 | 3197 | 3222 | 26 |
| 90 | 3212 | 3226 | 15 |
| 91 | 3221 | 3248 | 28 |
| 92 | 3243 | 3256 | 14 |
| 93 | 3250 | 3264 | 15 |
| 94 | 3266 | 3292 | 27 |
| 95 | 3326 | 3343 | 18 |
| 96 | 3345 | 3391 | 47 |
| 97 | 3400 | 3422 | 23 |
| 98 | 3424 | 3441 | 18 |
| 99 | 3434 | 3447 | 14 |
| 100 | 3443 | 3503 | 61 |
| 101 | 3495 | 3508 | 14 |
| 102 | 3505 | 3558 | 54 |
| 103 | 3589 | 3609 | 21 |
| 104 | 3611 | 3641 | 31 |
| 105 | 3662 | 3696 | 35 |
| 106 | 3698 | 3719 | 22 |
| 107 | 3723 | 3790 | 68 |
| 108 | 3810 | 3854 | 45 |
| 109 | 3858 | 3873 | 16 |
| 110 | 3902 | 3968 | 67 |
| 111 | 3971 | 4009 | 39 |
| 112 | 4005 | 4018 | 14 |
| 113 | 4011 | 4030 | 20 |
| 114 | 4032 | 4077 | 46 |
| 115 | 4082 | 4114 | 33 |
| 116 | 4123 | 4140 | 18 |
| 117 | 4150 | 4164 | 15 |
| 118 | 4166 | 4183 | 18 |
| 119 | 4185 | 4243 | 59 |
| 120 | 4248 | 4268 | 21 |
| 121 | 4284 | 4313 | 30 |
| 122 | 4317 | 4348 | 32 |
| 123 | 4364 | 4471 | 108 |
| 124 | 4473 | 4491 | 19 |
| 125 | 4494 | 4519 | 26 |
| 126 | 4521 | 4535 | 15 |
| 127 | 4545 | 4560 | 16 |
| 128 | 4567 | 4606 | 40 |
| 129 | 4616 | 4714 | 99 |
| 130 | 4725 | 4755 | 31 |
| 131 | 4757 | 4786 | 30 |
| 132 | 4788 | 4852 | 65 |
| 133 | 4856 | 4910 | 55 |
| 134 | 4912 | 4935 | 24 |
| 135 | 4937 | 4970 | 34 |
| 136 | 4972 | 5010 | 39 |
| 137 | 5058 | 5078 | 21 |
| 138 | 5080 | 5116 | 37 |
| 139 | 5110 | 5124 | 15 |
| 140 | 5135 | 5166 | 32 |
| 141 | 5168 | 5201 | 34 |
| 142 | 5203 | 5247 | 45 |
| 143 | 5261 | 5276 | 16 |
| 144 | 5278 | 5293 | 16 |
| 145 | 5314 | 5330 | 17 |
| 146 | 5332 | 5382 | 51 |
| 147 | 5398 | 5414 | 17 |
| 148 | 5427 | 5456 | 30 |
| 149 | 5458 | 5471 | 14 |
| 150 | 5487 | 5500 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 151 | 5506 | 5545 | 40 |
| 152 | 5561 | 5577 | 17 |
| 153 | 5580 | 5617 | 38 |
| 154 | 5607 | 5620 | 14 |
| 155 | 5619 | 5642 | 24 |
| 156 | 5644 | 5683 | 40 |
| 157 | 5685 | 5698 | 14 |
| 158 | 5713 | 5759 | 47 |
| 159 | 5756 | 5769 | 14 |
| 160 | 5784 | 5803 | 20 |
| 161 | 5801 | 5865 | 65 |
| 162 | 5873 | 5905 | 33 |
| 163 | 5907 | 5937 | 31 |
| 164 | 5939 | 5985 | 47 |
| 165 | 5987 | 6017 | 31 |
| 166 | 6016 | 6039 | 24 |
| 167 | 6028 | 6092 | 65 |
| 168 | 6102 | 6127 | 26 |
| 169 | 6127 | 6152 | 26 |
| 170 | 6151 | 6171 | 21 |
| 171 | 6178 | 6206 | 29 |
| 172 | 6217 | 6234 | 18 |
| 173 | 6224 | 6270 | 47 |
| 174 | 6272 | 6289 | 18 |
| 175 | 6291 | 6310 | 20 |
| 176 | 6312 | 6357 | 46 |
| 177 | 6367 | 6389 | 23 |
| 178 | 6396 | 6422 | 27 |
| 179 | 6440 | 6454 | 15 |
| 180 | 6456 | 6482 | 27 |
| 181 | 6484 | 6513 | 30 |
| 182 | 6505 | 6519 | 15 |
| 183 | 6518 | 6553 | 36 |
| 184 | 6552 | 6565 | 14 |
| 185 | 6557 | 6590 | 34 |
| 186 | 6596 | 6628 | 33 |
| 187 | 6640 | 6675 | 36 |
| 188 | 6686 | 6711 | 26 |
| 189 | 6714 | 6746 | 33 |
| 190 | 6781 | 6818 | 38 |
| 191 | 6832 | 6885 | 54 |
| 192 | 6889 | 6912 | 24 |
| 193 | 6920 | 6938 | 19 |
| 194 | 6940 | 6960 | 21 |
| 195 | 6954 | 6976 | 23 |
| 196 | 6998 | 7033 | 36 |
| 197 | 7035 | 7061 | 27 |
| 198 | 7071 | 7143 | 73 |
| 199 | 7159 | 7214 | 56 |
| 200 | 7253 | 7266 | 14 |
| 201 | 7268 | 7281 | 14 |
| 202 | 7283 | 7328 | 46 |
| 203 | 7329 | 7343 | 15 |
| 204 | 7338 | 7355 | 18 |
| 205 | 7345 | 7374 | 30 |
| 206 | 7374 | 7387 | 14 |
| 207 | 7383 | 7396 | 14 |
| 208 | 7389 | 7405 | 17 |
| 209 | 7399 | 7413 | 15 |
| 210 | 7420 | 7437 | 18 |
| 211 | 7427 | 7448 | 22 |
| 212 | 7450 | 7503 | 54 |
| 213 | 7495 | 7565 | 71 |
| 214 | 7561 | 7616 | 56 |
| 215 | 7618 | 7703 | 86 |
| 216 | 7717 | 7772 | 56 |
| 217 | 7776 | 7838 | 63 |
| 218 | 7852 | 7869 | 18 |
| 219 | 7882 | 7910 | 29 |
| 220 | 7919 | 7942 | 24 |
| 221 | 7944 | 7957 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 222 | 7959 | 7977 | 19 |
| 223 | 7979 | 7996 | 18 |
| 224 | 7998 | 8014 | 17 |
| 225 | 8030 | 8046 | 17 |
| 226 | 8059 | 8092 | 34 |
| 227 | 8100 | 8113 | 14 |
| 228 | 8115 | 8141 | 27 |
| 229 | 8143 | 8175 | 33 |
| 230 | 8179 | 8192 | 14 |
| 231 | 8187 | 8208 | 22 |
| 232 | 8205 | 8219 | 15 |
| 233 | 8210 | 8229 | 20 |
| 234 | 8231 | 8252 | 22 |
| 235 | 8254 | 8298 | 45 |
| 236 | 8302 | 8316 | 15 |
| 237 | 8306 | 8329 | 24 |
| 238 | 8331 | 8357 | 27 |
| 239 | 8400 | 8443 | 44 |
| 240 | 8443 | 8456 | 14 |
| 241 | 8445 | 8460 | 16 |
| 242 | 8472 | 8505 | 34 |
| 243 | 8494 | 8507 | 14 |
| 244 | 8554 | 8569 | 16 |
| 245 | 8571 | 8653 | 83 |
| 246 | 8659 | 8673 | 15 |
| 247 | 8675 | 8694 | 20 |
| 248 | 8696 | 8713 | 18 |
| 249 | 8736 | 8844 | 109 |
| 250 | 8847 | 8909 | 63 |
| 251 | 8915 | 8959 | 45 |
| 252 | 8961 | 8975 | 15 |
| 253 | 8993 | 9009 | 17 |
| 254 | 9024 | 9048 | 25 |
| 255 | 9050 | 9063 | 14 |
| 256 | 9089 | 9120 | 32 |
| 257 | 9127 | 9166 | 40 |
| 258 | 9191 | 9249 | 59 |
| 259 | 9257 | 9285 | 29 |
| 260 | 9288 | 9302 | 15 |
| 261 | 9331 | 9397 | 67 |
| 262 | 9399 | 9438 | 40 |
| 263 | 9437 | 9455 | 19 |
| 264 | 9483 | 9505 | 23 |
| 265 | 9507 | 9526 | 20 |
| 266 | 9583 | 9598 | 16 |
| 267 | 9600 | 9613 | 14 |
| 268 | 9628 | 9641 | 14 |
| 269 | 9653 | 9674 | 22 |
| 270 | 9676 | 9690 | 15 |
| 271 | 9745 | 9758 | 14 |
| 272 | 9752 | 9780 | 29 |
| 273 | 9796 | 9809 | 14 |
| 274 | 9811 | 9825 | 15 |
| 275 | 9832 | 9853 | 22 |
| 276 | 9877 | 9899 | 23 |
| 277 | 9901 | 9932 | 32 |
| 278 | 10000 | 10016 | 17 |
| 279 | 10029 | 10049 | 21 |
| 280 | 10051 | 10071 | 21 |
| 281 | 10089 | 10120 | 32 |
| 282 | 10111 | 10127 | 17 |
| 283 | 10122 | 10203 | 82 |
| 284 | 10211 | 10237 | 27 |
| 285 | 10239 | 10256 | 18 |
| 286 | 10258 | 10285 | 28 |
| 287 | 10287 | 10304 | 18 |
| 288 | 10306 | 10350 | 45 |
| 289 | 10352 | 10375 | 24 |
| 290 | 10381 | 10402 | 22 |
| 291 | 10412 | 10470 | 59 |
| 292 | 10474 | 10488 | 15 |

TABLE 1-continued

Regions of SEQ ID NO 1 which may be targeted using oligonucleotide of the invention

| Reg. A | Position in SEQ ID NO 1 from | to | Length |
|---|---|---|---|
| 293 | 10508 | 10557 | 50 |
| 294 | 10565 | 10630 | 66 |
| 295 | 10632 | 10674 | 43 |
| 296 | 10698 | 10711 | 14 |
| 297 | 10701 | 10714 | 14 |
| 298 | 10704 | 10718 | 15 |
| 299 | 10720 | 10740 | 21 |
| 300 | 10742 | 10785 | 44 |
| 301 | 10786 | 10809 | 24 |
| 302 | 10811 | 10829 | 19 |
| 303 | 10832 | 10867 | 36 |
| 304 | 10869 | 10930 | 62 |
| 305 | 10932 | 10950 | 19 |
| 306 | 10959 | 10996 | 38 |
| 307 | 10998 | 11028 | 31 |
| 308 | 11037 | 11077 | 41 |
| 309 | 11079 | 11105 | 27 |
| 310 | 11115 | 11132 | 18 |
| 311 | 11134 | 11154 | 21 |
| 312 | 11156 | 11196 | 41 |
| 313 | 11206 | 11239 | 34 |
| 314 | 11241 | 11255 | 15 |
| 315 | 11266 | 11287 | 22 |
| 316 | 11299 | 11329 | 31 |
| 317 | 11331 | 11352 | 22 |
| 318 | 11358 | 11403 | 46 |
| 319 | 11405 | 11432 | 28 |
| 320 | 11434 | 11480 | 47 |
| 321 | 11482 | 11535 | 54 |
| 322 | 11539 | 11573 | 35 |
| 323 | 11584 | 11732 | 149 |
| 324 | 11731 | 11763 | 33 |
| 325 | 11765 | 11782 | 18 |
| 326 | 11784 | 11813 | 30 |
| 327 | 11815 | 11829 | 15 |
| 328 | 11831 | 11852 | 22 |
| 329 | 11854 | 11871 | 18 |
| 330 | 11866 | 11895 | 30 |
| 331 | 11930 | 11943 | 14 |
| 332 | 11975 | 12007 | 33 |
| 333 | 11996 | 12012 | 17 |
| 334 | 12017 | 12040 | 24 |
| 335 | 12050 | 12083 | 34 |
| 336 | 12088 | 12111 | 24 |
| 337 | 12133 | 12151 | 19 |
| 338 | 12161 | 12174 | 14 |
| 339 | 12179 | 12225 | 47 |
| 340 | 12238 | 12256 | 19 |
| 341 | 12265 | 12278 | 14 |
| 342 | 12296 | 12360 | 65 |
| 343 | 12362 | 12381 | 20 |
| 344 | 12384 | 12399 | 16 |
| 345 | 12400 | 12475 | 76 |
| 346 | 12487 | 12502 | 16 |
| 347 | 12504 | 12531 | 28 |
| 348 | 12533 | 12562 | 30 |
| 349 | 12564 | 12602 | 39 |
| 350 | 12627 | 12646 | 20 |
| 351 | 12655 | 12679 | 25 |
| 352 | 12681 | 12698 | 18 |
| 353 | 12700 | 12812 | 113 |
| 354 | 12828 | 12876 | 49 |
| 355 | 12877 | 12913 | 37 |
| 356 | 12932 | 12945 | 14 |
| 357 | 12936 | 12967 | 32 |
| 358 | 12988 | 13002 | 15 |
| 359 | 12996 | 13009 | 14 |
| 360 | 13018 | 13035 | 18 |
| 361 | 13031 | 13049 | 19 |
| 362 | 13056 | 13093 | 38 |
| 363 | 13096 | 13126 | 31 |
| 364 | 13128 | 13142 | 15 |
| 365 | 13144 | 13193 | 50 |
| 366 | 13201 | 13221 | 21 |
| 367 | 13223 | 13280 | 58 |
| 368 | 13282 | 13298 | 17 |
| 369 | 13300 | 13315 | 16 |
| 370 | 13307 | 13320 | 14 |
| 371 | 13315 | 13331 | 17 |
| 372 | 13351 | 13411 | 61 |
| 373 | 13422 | 13437 | 16 |
| 374 | 13439 | 13456 | 18 |
| 375 | 13461 | 13483 | 23 |
| 376 | 13485 | 13541 | 57 |
| 377 | 13543 | 13560 | 18 |
| 378 | 13574 | 13606 | 33 |
| 379 | 13618 | 13646 | 29 |
| 380 | 13778 | 13801 | 24 |
| 381 | 13994 | 14009 | 16 |
| 382 | 14508 | 14521 | 14 |
| 383 | 15049 | 15067 | 19 |
| 384 | 15069 | 15090 | 22 |
| 385 | 15102 | 15139 | 38 |
| 386 | 15142 | 15180 | 39 |
| 387 | 15182 | 15205 | 24 |
| 388 | 15238 | 15252 | 15 |
| 389 | 15254 | 15277 | 24 |
| 390 | 15292 | 15320 | 29 |
| 391 | 15322 | 15348 | 27 |
| 392 | 15343 | 15358 | 16 |
| 393 | 15362 | 15387 | 26 |
| 394 | 15399 | 15414 | 16 |
| 395 | 15416 | 15445 | 30 |
| 396 | 15459 | 15528 | 70 |
| 397 | 15537 | 15592 | 56 |
| 398 | 15610 | 15638 | 29 |
| 399 | 15640 | 15653 | 14 |
| 400 | 15655 | 15717 | 63 |
| 401 | 15719 | 15738 | 20 |
| 402 | 15757 | 15778 | 22 |
| 403 | 15783 | 15801 | 19 |
| 404 | 15818 | 15838 | 21 |
| 405 | 15835 | 15849 | 15 |
| 406 | 15840 | 15857 | 18 |
| 407 | 15856 | 15898 | 43 |
| 408 | 15900 | 15916 | 17 |
| 409 | 15931 | 15972 | 42 |
| 410 | 15988 | 16028 | 41 |
| 411 | 16030 | 16075 | 46 |
| 412 | 16103 | 16164 | 62 |
| 413 | 16207 | 16243 | 37 |
| 414 | 16233 | 16246 | 14 |
| 415 | 16255 | 16329 | 75 |
| 416 | 16349 | 16376 | 28 |
| 417 | 16378 | 16404 | 27 |
| 418 | 16399 | 16419 | 21 |
| 419 | 16421 | 16461 | 41 |
| 420 | 16463 | 16479 | 17 |
| 421 | 16481 | 16503 | 23 |
| 422 | 16506 | 16579 | 74 |
| 423 | 16582 | 16620 | 39 |
| 424 | 16622 | 16698 | 77 |
| 425 | 16700 | 16716 | 17 |
| 426 | 16723 | 16771 | 49 |
| 427 | 16786 | 16816 | 31 |
| 428 | 16835 | 16864 | 30 |
| 429 | 16865 | 16878 | 14 |
| 430 | 16872 | 16888 | 17 |
| 431 | 16890 | 16906 | 17 |
| 432 | 16904 | 16938 | 35 |
| 433 | 16965 | 17052 | 88 |
| 434 | 17054 | 17069 | 16 |

TABLE 1-continued

Regions of SEQ ID NO 1
which may be targeted using
oligonucleotide of the invention

| Reg. | Position in SEQ ID NO 1 | | Length |
|------|------|------|--------|
| A | from | to | Length |
| 435 | 17071 | 17085 | 15 |
| 436 | 17083 | 17098 | 16 |
| 437 | 17088 | 17111 | 24 |
| 438 | 17124 | 17138 | 15 |
| 439 | 17140 | 17159 | 20 |
| 440 | 17181 | 17202 | 22 |
| 441 | 17202 | 17218 | 17 |
| 442 | 17229 | 17248 | 20 |
| 443 | 17250 | 17268 | 19 |
| 444 | 17332 | 17349 | 18 |
| 445 | 17363 | 17387 | 25 |
| 446 | 17389 | 17429 | 41 |
| 447 | 17450 | 17464 | 15 |
| 448 | 17482 | 17497 | 16 |
| 449 | 18104 | 18117 | 14 |
| 450 | 18418 | 18431 | 14 |
| 451 | 18613 | 18626 | 14 |
| 452 | 18620 | 18634 | 15 |
| 453 | 18707 | 18721 | 15 |
| 454 | 18841 | 18855 | 15 |
| 455 | 18875 | 18889 | 15 |
| 456 | 19282 | 19295 | 14 |
| 457 | 19310 | 19323 | 14 |
| 458 | 19454 | 19467 | 14 |
| 459 | 19774 | 19792 | 19 |
| 460 | 19794 | 19864 | 71 |
| 461 | 19862 | 19890 | 29 |
| 462 | 19892 | 19918 | 27 |
| 463 | 19907 | 19931 | 25 |
| 464 | 19927 | 19942 | 16 |
| 465 | 19932 | 19971 | 40 |
| 466 | 19973 | 20011 | 39 |
| 467 | 20022 | 20063 | 42 |
| 468 | 20080 | 20093 | 14 |
| 469 | 20131 | 20144 | 14 |
| 470 | 20240 | 20253 | 14 |
| 471 | 20448 | 20463 | 16 |
| 472 | 20495 | 20508 | 14 |
| 473 | 20532 | 20545 | 14 |
| 474 | 20600 | 20613 | 14 |
| 475 | 20617 | 20630 | 14 |
| 476 | 20960 | 20977 | 18 |
| 477 | 21412 | 21428 | 17 |
| 478 | 21465 | 21479 | 15 |
| 479 | 21489 | 21508 | 20 |
| 480 | 21797 | 21812 | 16 |
| 481 | 22015 | 22030 | 16 |
| 482 | 22144 | 22157 | 14 |
| 483 | 22153 | 22167 | 15 |
| 484 | 22265 | 22278 | 14 |
| 485 | 23110 | 23123 | 14 |
| 486 | 23114 | 23133 | 20 |
| 487 | 23286 | 23303 | 18 |
| 488 | 23364 | 23379 | 16 |
| 489 | 23478 | 23498 | 21 |
| 490 | 23544 | 23587 | 44 |
| 491 | 23589 | 23630 | 42 |
| 492 | 23658 | 23676 | 19 |
| 493 | 23678 | 23702 | 25 |
| 494 | 23704 | 23729 | 26 |
| 495 | 23731 | 23748 | 18 |
| 496 | 23740 | 23755 | 16 |
| 497 | 23744 | 23757 | 14 |
| 498 | 23750 | 23764 | 15 |
| 499 | 23767 | 23795 | 29 |
| 500 | 23802 | 23816 | 15 |
| 501 | 23818 | 23831 | 14 |
| 502 | 23855 | 23869 | 15 |
| 503 | 23906 | 23926 | 21 |
| 504 | 23928 | 23942 | 15 |
| 505 | 23994 | 24007 | 14 |

TABLE 1-continued

Regions of SEQ ID NO 1
which may be targeted using
oligonucleotide of the invention

| Reg. | Position in SEQ ID NO 1 | | Length |
|------|------|------|--------|
| A | from | to | Length |
| 506 | 24005 | 24018 | 14 |
| 507 | 24023 | 24056 | 34 |
| 508 | 24074 | 24088 | 15 |
| 509 | 24088 | 24104 | 17 |
| 510 | 24112 | 24163 | 52 |
| 511 | 24199 | 24212 | 14 |
| 512 | 24231 | 24244 | 14 |
| 513 | 24237 | 24252 | 16 |
| 514 | 24254 | 24267 | 14 |
| 515 | 24281 | 24325 | 45 |
| 516 | 24327 | 24353 | 27 |
| 517 | 24355 | 24374 | 20 |
| 518 | 24376 | 24399 | 24 |
| 519 | 24401 | 24416 | 16 |
| 520 | 24442 | 24489 | 48 |
| 521 | 24492 | 24506 | 15 |
| 522 | 24498 | 24511 | 14 |
| 523 | 24538 | 24556 | 19 |
| 524 | 24546 | 24562 | 17 |
| 525 | 24591 | 24618 | 28 |
| 526 | 24620 | 24633 | 14 |
| 527 | 24635 | 24650 | 16 |
| 528 | 24665 | 24681 | 17 |
| 529 | 24687 | 24706 | 20 |
| 530 | 24709 | 24729 | 21 |
| 531 | 24731 | 24752 | 22 |
| 532 | 24756 | 24771 | 16 |
| 533 | 24773 | 24788 | 16 |
| 534 | 24793 | 24821 | 29 |
| 535 | 24823 | 24854 | 32 |
| 536 | 24856 | 24870 | 15 |
| 537 | 24873 | 24922 | 50 |
| 538 | 24933 | 24954 | 22 |
| 539 | 24965 | 24984 | 20 |
| 540 | 25019 | 25052 | 34 |
| 541 | 25054 | 25099 | 46 |
| 542 | 25112 | 25125 | 14 |
| 543 | 25133 | 25169 | 37 |
| 544 | 25171 | 25184 | 14 |
| 545 | 25186 | 25221 | 36 |
| 546 | 25236 | 25253 | 18 |
| 547 | 25246 | 25296 | 51 |
| 548 | 25298 | 25336 | 39 |
| 549 | 25332 | 25348 | 17 |
| 550 | 25349 | 25363 | 15 |
| 551 | 25388 | 25432 | 45 |
| 552 | 25439 | 25462 | 24 |
| 553 | 25509 | 25523 | 15 |
| 554 | 25525 | 25547 | 23 |
| 555 | 25578 | 25593 | 16 |
| 556 | 25587 | 25601 | 15 |
| 557 | 25604 | 25617 | 14 |
| 558 | 25633 | 25655 | 23 |
| 559 | 25672 | 25716 | 45 |
| 560 | 25725 | 25738 | 14 |
| 561 | 25764 | 25800 | 37 |
| 562 | 25802 | 25828 | 27 |
| 563 | 25831 | 25846 | 16 |
| 564 | 25851 | 25872 | 22 |
| 565 | 25877 | 25904 | 28 |
| 566 | 25921 | 25946 | 26 |
| 567 | 25943 | 25970 | 28 |
| 568 | 25972 | 25986 | 15 |
| 569 | 26051 | 26064 | 14 |
| 570 | 26068 | 26086 | 19 |
| 571 | 26113 | 26137 | 25 |
| 572 | 26139 | 26159 | 21 |
| 573 | 26182 | 26197 | 16 |
| 574 | 26243 | 26296 | 54 |
| 575 | 26298 | 26313 | 16 |
| 576 | 26327 | 26350 | 24 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 577 | 26366 | 26385 | 20 |
| 578 | 26387 | 26404 | 18 |
| 579 | 26397 | 26415 | 19 |
| 580 | 26416 | 26453 | 38 |
| 581 | 26447 | 26461 | 15 |
| 582 | 26457 | 26471 | 15 |
| 583 | 26481 | 26498 | 18 |
| 584 | 26502 | 26525 | 24 |
| 585 | 26528 | 26562 | 35 |
| 586 | 26564 | 26590 | 27 |
| 587 | 26590 | 26622 | 33 |
| 588 | 26624 | 26638 | 15 |
| 589 | 26687 | 26702 | 16 |
| 590 | 26706 | 26719 | 14 |
| 591 | 26717 | 26730 | 14 |
| 592 | 26729 | 26743 | 15 |
| 593 | 26767 | 26797 | 31 |
| 594 | 26796 | 26816 | 21 |
| 595 | 26831 | 26847 | 17 |
| 596 | 26837 | 26850 | 14 |
| 597 | 26877 | 26890 | 14 |
| 598 | 26900 | 26922 | 23 |
| 599 | 26911 | 26933 | 23 |
| 600 | 26933 | 26946 | 14 |
| 601 | 26938 | 26977 | 40 |
| 602 | 26979 | 26992 | 14 |
| 603 | 26981 | 27017 | 37 |
| 604 | 27023 | 27041 | 19 |
| 605 | 27039 | 27055 | 17 |
| 606 | 27075 | 27121 | 47 |
| 607 | 27138 | 27153 | 16 |
| 608 | 27163 | 27266 | 104 |
| 609 | 27270 | 27293 | 24 |
| 610 | 27325 | 27358 | 34 |
| 611 | 27363 | 27408 | 46 |
| 612 | 27419 | 27448 | 30 |
| 613 | 27450 | 27469 | 20 |
| 614 | 27471 | 27498 | 28 |
| 615 | 27510 | 27523 | 14 |
| 616 | 27535 | 27562 | 28 |
| 617 | 28098 | 28119 | 22 |
| 618 | 28136 | 28155 | 20 |
| 619 | 28169 | 28197 | 29 |
| 620 | 28199 | 28212 | 14 |
| 621 | 28221 | 28244 | 24 |
| 622 | 28271 | 28285 | 15 |
| 623 | 28400 | 28414 | 15 |
| 624 | 28441 | 28476 | 36 |
| 625 | 28490 | 28533 | 44 |
| 626 | 28535 | 28562 | 28 |
| 627 | 28575 | 28600 | 26 |
| 628 | 28621 | 28634 | 14 |
| 629 | 28650 | 28663 | 14 |
| 630 | 28674 | 28687 | 14 |
| 631 | 28681 | 28699 | 19 |
| 632 | 28713 | 28730 | 18 |
| 633 | 28736 | 28761 | 26 |
| 634 | 28763 | 28811 | 49 |
| 635 | 28821 | 28854 | 34 |
| 636 | 28856 | 28881 | 26 |
| 637 | 28883 | 28920 | 38 |
| 638 | 28922 | 28947 | 26 |
| 639 | 28979 | 29006 | 28 |
| 640 | 29008 | 29056 | 49 |
| 641 | 29078 | 29095 | 18 |
| 642 | 29098 | 29129 | 32 |
| 643 | 29122 | 29135 | 14 |
| 644 | 29131 | 29144 | 14 |
| 645 | 29144 | 29158 | 15 |
| 646 | 29160 | 29207 | 48 |
| 647 | 29209 | 29230 | 22 |
| 648 | 29234 | 29266 | 33 |
| 649 | 29268 | 29286 | 19 |
| 650 | 29301 | 29315 | 15 |
| 651 | 29304 | 29323 | 20 |
| 652 | 29330 | 29352 | 23 |
| 653 | 29344 | 29358 | 15 |
| 654 | 29347 | 29365 | 19 |
| 655 | 29377 | 29402 | 26 |
| 656 | 29402 | 29422 | 21 |
| 657 | 29424 | 29445 | 22 |
| 658 | 29443 | 29457 | 15 |
| 659 | 29447 | 29460 | 14 |
| 660 | 29462 | 29475 | 14 |
| 661 | 29491 | 29512 | 22 |
| 662 | 29514 | 29551 | 38 |
| 663 | 29547 | 29560 | 14 |
| 664 | 29553 | 29620 | 68 |
| 665 | 29625 | 29700 | 76 |
| 666 | 29714 | 29745 | 32 |
| 667 | 29774 | 29805 | 32 |
| 668 | 29816 | 29847 | 32 |
| 669 | 29875 | 29892 | 18 |
| 670 | 29894 | 29908 | 15 |
| 671 | 29897 | 29910 | 14 |
| 672 | 29917 | 29938 | 22 |
| 673 | 29939 | 29952 | 14 |
| 674 | 29961 | 29976 | 16 |
| 675 | 29974 | 29987 | 14 |
| 676 | 29978 | 30001 | 24 |
| 677 | 30006 | 30023 | 18 |
| 678 | 30025 | 30039 | 15 |
| 679 | 30043 | 30107 | 65 |
| 680 | 30145 | 30158 | 14 |
| 681 | 30149 | 30166 | 18 |
| 682 | 30173 | 30228 | 56 |
| 683 | 30230 | 30250 | 21 |
| 684 | 30251 | 30309 | 59 |
| 685 | 30321 | 30358 | 38 |
| 686 | 30359 | 30380 | 22 |
| 687 | 30382 | 30422 | 41 |
| 688 | 30428 | 30442 | 15 |
| 689 | 30455 | 30482 | 28 |
| 690 | 30484 | 30498 | 15 |
| 691 | 30516 | 30531 | 16 |
| 692 | 30533 | 30646 | 114 |
| 693 | 30654 | 30745 | 92 |
| 694 | 30745 | 30760 | 16 |
| 695 | 30752 | 30766 | 15 |
| 696 | 30788 | 30843 | 56 |
| 697 | 30845 | 30867 | 23 |
| 698 | 30869 | 30912 | 44 |
| 699 | 30906 | 30920 | 15 |
| 700 | 30934 | 30951 | 18 |
| 701 | 30962 | 30984 | 23 |
| 702 | 30989 | 31002 | 14 |
| 703 | 31010 | 31033 | 24 |
| 704 | 31036 | 31062 | 27 |
| 705 | 31092 | 31106 | 15 |
| 706 | 31128 | 31166 | 39 |
| 707 | 31168 | 31182 | 15 |
| 708 | 31189 | 31203 | 15 |
| 709 | 31205 | 31218 | 14 |
| 710 | 31224 | 31253 | 30 |
| 711 | 31256 | 31272 | 17 |
| 712 | 31274 | 31292 | 19 |
| 713 | 31294 | 31322 | 29 |
| 714 | 31324 | 31353 | 30 |
| 715 | 31357 | 31370 | 14 |
| 716 | 31373 | 31399 | 27 |
| 717 | 31403 | 31426 | 24 |
| 718 | 31445 | 31460 | 16 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 719 | 31463 | 31483 | 21 |
| 720 | 31485 | 31501 | 17 |
| 721 | 31494 | 31508 | 15 |
| 722 | 31507 | 31529 | 23 |
| 723 | 31531 | 31565 | 35 |
| 724 | 31567 | 31615 | 49 |
| 725 | 31630 | 31665 | 36 |
| 726 | 31675 | 31691 | 17 |
| 727 | 31703 | 31721 | 19 |
| 728 | 31729 | 31769 | 41 |
| 729 | 31770 | 31790 | 21 |
| 730 | 31795 | 31813 | 19 |
| 731 | 31815 | 31835 | 21 |
| 732 | 31837 | 31865 | 29 |
| 733 | 31876 | 31889 | 14 |
| 734 | 31920 | 31945 | 26 |
| 735 | 31962 | 31978 | 17 |
| 736 | 31983 | 32014 | 32 |
| 737 | 32029 | 32050 | 22 |
| 738 | 32058 | 32110 | 53 |
| 739 | 32129 | 32147 | 19 |
| 740 | 32166 | 32242 | 77 |
| 741 | 32244 | 32279 | 36 |
| 742 | 32296 | 32315 | 20 |
| 743 | 32334 | 32396 | 63 |
| 744 | 32398 | 32425 | 28 |
| 745 | 32427 | 32453 | 27 |
| 746 | 32459 | 32481 | 23 |
| 747 | 32475 | 32498 | 24 |
| 748 | 32490 | 32523 | 34 |
| 749 | 32519 | 32534 | 16 |
| 750 | 32525 | 32547 | 23 |
| 751 | 32542 | 32555 | 14 |
| 752 | 32559 | 32572 | 14 |
| 753 | 32574 | 32587 | 14 |
| 754 | 32595 | 32618 | 24 |
| 755 | 32613 | 32626 | 14 |
| 756 | 32627 | 32649 | 23 |
| 757 | 32651 | 32664 | 14 |
| 758 | 32655 | 32689 | 35 |
| 759 | 32693 | 32719 | 27 |
| 760 | 32721 | 32750 | 30 |
| 761 | 32752 | 32778 | 27 |
| 762 | 32780 | 32795 | 16 |
| 763 | 32797 | 32847 | 51 |
| 764 | 32881 | 32894 | 14 |
| 765 | 32891 | 32904 | 14 |
| 766 | 32896 | 32911 | 16 |
| 767 | 32927 | 32972 | 46 |
| 768 | 32986 | 33017 | 32 |
| 769 | 33019 | 33036 | 18 |
| 770 | 33038 | 33096 | 59 |
| 771 | 33102 | 33123 | 22 |
| 772 | 33132 | 33145 | 14 |
| 773 | 33150 | 33163 | 14 |
| 774 | 33166 | 33199 | 34 |
| 775 | 33214 | 33260 | 47 |
| 776 | 33262 | 33292 | 31 |
| 777 | 33294 | 33307 | 14 |
| 778 | 33316 | 33351 | 36 |
| 779 | 33360 | 33402 | 43 |
| 780 | 33412 | 33425 | 14 |
| 781 | 33427 | 33442 | 16 |
| 782 | 33439 | 33452 | 14 |
| 783 | 33443 | 33456 | 14 |
| 784 | 33460 | 33501 | 42 |
| 785 | 33503 | 33535 | 33 |
| 786 | 33542 | 33557 | 16 |
| 787 | 34168 | 34181 | 14 |
| 788 | 34370 | 34385 | 16 |
| 789 | 35422 | 35435 | 14 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 790 | 35627 | 35641 | 15 |
| 791 | 35685 | 35700 | 16 |
| 792 | 35837 | 35851 | 15 |
| 793 | 35849 | 35864 | 16 |
| 794 | 35866 | 35879 | 14 |
| 795 | 35974 | 35987 | 14 |
| 796 | 36009 | 36042 | 34 |
| 797 | 36044 | 36079 | 36 |
| 798 | 36081 | 36097 | 17 |
| 799 | 36099 | 36120 | 22 |
| 800 | 36119 | 36133 | 15 |
| 801 | 36147 | 36163 | 17 |
| 802 | 36171 | 36200 | 30 |
| 803 | 36216 | 36241 | 26 |
| 804 | 36245 | 36274 | 30 |
| 805 | 36265 | 36283 | 19 |
| 806 | 36295 | 36348 | 54 |
| 807 | 36352 | 36389 | 38 |
| 808 | 36383 | 36400 | 18 |
| 809 | 36402 | 36419 | 18 |
| 810 | 36475 | 36520 | 46 |
| 811 | 36522 | 36539 | 18 |
| 812 | 36541 | 36626 | 86 |
| 813 | 36652 | 36672 | 21 |
| 814 | 36675 | 36705 | 31 |
| 815 | 36707 | 36746 | 40 |
| 816 | 36780 | 36808 | 29 |
| 817 | 36810 | 36823 | 14 |
| 818 | 36825 | 36901 | 77 |
| 819 | 36903 | 36922 | 20 |
| 820 | 36924 | 36982 | 59 |
| 821 | 36999 | 37030 | 32 |
| 822 | 37056 | 37083 | 28 |
| 823 | 37091 | 37135 | 45 |
| 824 | 37194 | 37221 | 28 |
| 825 | 37238 | 37277 | 40 |
| 826 | 37280 | 37294 | 15 |
| 827 | 37298 | 37315 | 18 |
| 828 | 37325 | 37350 | 26 |
| 829 | 37363 | 37383 | 21 |
| 830 | 37377 | 37394 | 18 |
| 831 | 37384 | 37397 | 14 |
| 832 | 37390 | 37438 | 49 |
| 833 | 37456 | 37481 | 26 |
| 834 | 37478 | 37491 | 14 |
| 835 | 37481 | 37503 | 23 |
| 836 | 37506 | 37524 | 19 |
| 837 | 37526 | 37545 | 20 |
| 838 | 37540 | 37572 | 33 |
| 839 | 37574 | 37590 | 17 |
| 840 | 37601 | 37616 | 16 |
| 841 | 37621 | 37658 | 38 |
| 842 | 37673 | 37690 | 18 |
| 843 | 37703 | 37738 | 36 |
| 844 | 37740 | 37753 | 14 |
| 845 | 37764 | 37790 | 27 |
| 846 | 37800 | 37818 | 19 |
| 847 | 37820 | 37850 | 31 |
| 848 | 37888 | 37909 | 22 |
| 849 | 37911 | 37972 | 62 |
| 850 | 37986 | 38014 | 29 |
| 851 | 38016 | 38032 | 17 |
| 852 | 38034 | 38053 | 20 |
| 853 | 38055 | 38073 | 19 |
| 854 | 38075 | 38090 | 16 |
| 855 | 38092 | 38128 | 37 |
| 856 | 38141 | 38167 | 27 |
| 857 | 38171 | 38194 | 24 |
| 858 | 38213 | 38240 | 28 |
| 859 | 38264 | 38286 | 23 |
| 860 | 38288 | 38370 | 83 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 861 | 38394 | 38420 | 27 |
| 862 | 38452 | 38467 | 16 |
| 863 | 38471 | 38487 | 17 |
| 864 | 38477 | 38490 | 14 |
| 865 | 38494 | 38507 | 14 |
| 866 | 38536 | 38556 | 21 |
| 867 | 38580 | 38593 | 14 |
| 868 | 38602 | 38618 | 17 |
| 869 | 38628 | 38654 | 27 |
| 870 | 38693 | 38709 | 17 |
| 871 | 38709 | 38722 | 14 |
| 872 | 38711 | 38725 | 15 |
| 873 | 38740 | 38756 | 17 |
| 874 | 38749 | 38769 | 21 |
| 875 | 38772 | 38797 | 26 |
| 876 | 38827 | 38846 | 20 |
| 877 | 38860 | 38883 | 24 |
| 878 | 38885 | 38905 | 21 |
| 879 | 38911 | 38931 | 21 |
| 880 | 38933 | 38949 | 17 |
| 881 | 38962 | 39032 | 71 |
| 882 | 39034 | 39047 | 14 |
| 883 | 39049 | 39070 | 22 |
| 884 | 39075 | 39115 | 41 |
| 885 | 39127 | 39143 | 17 |
| 886 | 39148 | 39162 | 15 |
| 887 | 39164 | 39222 | 59 |
| 888 | 39218 | 39231 | 14 |
| 889 | 39224 | 39256 | 33 |
| 890 | 39265 | 39306 | 42 |
| 891 | 39297 | 39311 | 15 |
| 892 | 39308 | 39343 | 36 |
| 893 | 39345 | 39359 | 15 |
| 894 | 39361 | 39381 | 21 |
| 895 | 39370 | 39383 | 14 |
| 896 | 39383 | 39399 | 17 |
| 897 | 39417 | 39469 | 53 |
| 898 | 39490 | 39503 | 14 |
| 899 | 39500 | 39522 | 23 |
| 900 | 39535 | 39549 | 15 |
| 901 | 39551 | 39611 | 61 |
| 902 | 39628 | 39647 | 20 |
| 903 | 39649 | 39690 | 42 |
| 904 | 39707 | 39759 | 53 |
| 905 | 39773 | 39797 | 25 |
| 906 | 39799 | 39858 | 60 |
| 907 | 39872 | 39928 | 57 |
| 908 | 39930 | 39969 | 40 |
| 909 | 39973 | 39997 | 25 |
| 910 | 39998 | 40013 | 16 |
| 911 | 40015 | 40064 | 50 |
| 912 | 40067 | 40108 | 42 |
| 913 | 40110 | 40140 | 31 |
| 914 | 40147 | 40163 | 17 |
| 915 | 40154 | 40179 | 26 |
| 916 | 40181 | 40196 | 16 |
| 917 | 40232 | 40282 | 51 |
| 918 | 40284 | 40307 | 24 |
| 919 | 40309 | 40368 | 60 |
| 920 | 40381 | 40399 | 19 |
| 921 | 40431 | 40471 | 41 |
| 922 | 40479 | 40493 | 15 |
| 923 | 40484 | 40522 | 39 |
| 924 | 40524 | 40544 | 21 |
| 925 | 40547 | 40561 | 15 |
| 926 | 40577 | 40594 | 18 |
| 927 | 40586 | 40599 | 14 |
| 928 | 40616 | 40631 | 16 |
| 929 | 40634 | 40647 | 14 |
| 930 | 40674 | 40727 | 54 |
| 931 | 40738 | 40755 | 18 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 932 | 40749 | 40771 | 23 |
| 933 | 40780 | 40802 | 23 |
| 934 | 40811 | 40834 | 24 |
| 935 | 40847 | 40865 | 19 |
| 936 | 40861 | 40875 | 15 |
| 937 | 40869 | 40897 | 29 |
| 938 | 40899 | 40919 | 21 |
| 939 | 40921 | 40939 | 19 |
| 940 | 40942 | 40962 | 21 |
| 941 | 40967 | 40980 | 14 |
| 942 | 41008 | 41097 | 90 |
| 943 | 41099 | 41131 | 33 |
| 944 | 41133 | 41200 | 68 |
| 945 | 41202 | 41223 | 22 |
| 946 | 41225 | 41242 | 18 |
| 947 | 41266 | 41279 | 14 |
| 948 | 41275 | 41298 | 24 |
| 949 | 41300 | 41321 | 22 |
| 950 | 41325 | 41360 | 36 |
| 951 | 41367 | 41388 | 22 |
| 952 | 41403 | 41421 | 19 |
| 953 | 41439 | 41462 | 24 |
| 954 | 41481 | 41496 | 16 |
| 955 | 41508 | 41523 | 16 |
| 956 | 41531 | 41550 | 20 |
| 957 | 41552 | 41590 | 39 |
| 958 | 41590 | 41603 | 14 |
| 959 | 41612 | 41662 | 51 |
| 960 | 41664 | 41688 | 25 |
| 961 | 41685 | 41698 | 14 |
| 962 | 41691 | 41716 | 26 |
| 963 | 41718 | 41764 | 47 |
| 964 | 41761 | 41776 | 16 |
| 965 | 41778 | 41809 | 32 |
| 966 | 41798 | 41811 | 14 |
| 967 | 41838 | 41866 | 29 |
| 968 | 41872 | 41893 | 22 |
| 969 | 41885 | 41898 | 14 |
| 970 | 41912 | 41925 | 14 |
| 971 | 41914 | 41930 | 17 |
| 972 | 41923 | 41942 | 20 |
| 973 | 41933 | 41956 | 24 |
| 974 | 41962 | 41978 | 17 |
| 975 | 41997 | 42012 | 16 |
| 976 | 42026 | 42042 | 17 |
| 977 | 42035 | 42048 | 14 |
| 978 | 42037 | 42050 | 14 |
| 979 | 42048 | 42064 | 17 |
| 980 | 42056 | 42079 | 24 |
| 981 | 42081 | 42095 | 15 |
| 982 | 42096 | 42139 | 44 |
| 983 | 42141 | 42187 | 47 |
| 984 | 42190 | 42226 | 37 |
| 985 | 42232 | 42253 | 22 |
| 986 | 42255 | 42305 | 51 |
| 987 | 42307 | 42320 | 14 |
| 988 | 42347 | 42375 | 29 |
| 989 | 42389 | 42425 | 37 |
| 990 | 42427 | 42442 | 16 |
| 991 | 42452 | 42474 | 23 |
| 992 | 42482 | 42496 | 15 |
| 993 | 42495 | 42509 | 15 |
| 994 | 42536 | 42550 | 15 |
| 995 | 42566 | 42580 | 15 |
| 996 | 42590 | 42612 | 23 |
| 997 | 42646 | 42678 | 33 |
| 998 | 42683 | 42723 | 41 |
| 999 | 42735 | 42750 | 16 |
| 1000 | 42752 | 42817 | 66 |
| 1001 | 42843 | 42873 | 31 |
| 1002 | 42890 | 42939 | 50 |

TABLE 1-continued

Regions of SEQ ID NO 1 which may be targeted using oligonucleotide of the invention

| Reg. A | Position in SEQ ID NO 1 from | to | Length |
|---|---|---|---|
| 1003 | 42938 | 42989 | 52 |
| 1004 | 42991 | 43005 | 15 |
| 1005 | 43007 | 43020 | 14 |
| 1006 | 43036 | 43055 | 20 |
| 1007 | 43057 | 43102 | 46 |
| 1008 | 43113 | 43145 | 33 |
| 1009 | 43147 | 43180 | 34 |
| 1010 | 43204 | 43221 | 18 |
| 1011 | 43221 | 43265 | 45 |
| 1012 | 43267 | 43296 | 30 |
| 1013 | 43311 | 43334 | 24 |
| 1014 | 43336 | 43361 | 26 |
| 1015 | 43371 | 43395 | 25 |
| 1016 | 43399 | 43423 | 25 |
| 1017 | 43425 | 43453 | 29 |
| 1018 | 43452 | 43468 | 17 |
| 1019 | 43470 | 43488 | 19 |
| 1020 | 43495 | 43522 | 28 |
| 1021 | 43525 | 43559 | 35 |
| 1022 | 43561 | 43584 | 24 |
| 1023 | 43590 | 43611 | 22 |
| 1024 | 43618 | 43650 | 33 |
| 1025 | 43670 | 43685 | 16 |
| 1026 | 43722 | 43774 | 53 |
| 1027 | 43776 | 43791 | 16 |
| 1028 | 43808 | 43835 | 28 |
| 1029 | 43835 | 43851 | 17 |
| 1030 | 43853 | 43868 | 16 |
| 1031 | 43923 | 43937 | 15 |
| 1032 | 43952 | 43987 | 36 |
| 1033 | 44011 | 44029 | 19 |
| 1034 | 44028 | 44070 | 43 |
| 1035 | 44072 | 44094 | 23 |
| 1036 | 44101 | 44130 | 30 |
| 1037 | 44137 | 44205 | 69 |
| 1038 | 44224 | 44244 | 21 |
| 1039 | 44246 | 44265 | 20 |
| 1040 | 44267 | 44318 | 52 |
| 1041 | 44316 | 44336 | 21 |
| 1042 | 44338 | 44359 | 22 |
| 1043 | 44361 | 44424 | 64 |
| 1044 | 44439 | 44474 | 36 |
| 1045 | 44476 | 44500 | 25 |
| 1046 | 44502 | 44519 | 18 |
| 1047 | 44539 | 44553 | 15 |
| 1048 | 44563 | 44578 | 16 |
| 1049 | 44585 | 44599 | 15 |
| 1050 | 44601 | 44617 | 17 |
| 1051 | 44640 | 44701 | 62 |
| 1052 | 44704 | 44723 | 20 |
| 1053 | 44741 | 44763 | 23 |
| 1054 | 44766 | 44846 | 81 |
| 1055 | 44870 | 44889 | 20 |
| 1056 | 44887 | 44905 | 19 |
| 1057 | 44920 | 44947 | 28 |
| 1058 | 44949 | 44966 | 18 |
| 1059 | 44994 | 45022 | 29 |
| 1060 | 45042 | 45059 | 18 |
| 1061 | 45061 | 45087 | 27 |
| 1062 | 45116 | 45154 | 39 |
| 1063 | 45156 | 45182 | 27 |
| 1064 | 45183 | 45198 | 16 |
| 1065 | 45210 | 45243 | 34 |
| 1066 | 45245 | 45320 | 76 |
| 1067 | 45331 | 45367 | 37 |
| 1068 | 45380 | 45399 | 20 |
| 1069 | 45415 | 45428 | 14 |
| 1070 | 45421 | 45486 | 66 |
| 1071 | 45488 | 45545 | 58 |
| 1072 | 45556 | 45576 | 21 |
| 1073 | 45578 | 45597 | 20 |
| 1074 | 45603 | 45650 | 48 |
| 1075 | 45652 | 45665 | 14 |
| 1076 | 45675 | 45715 | 41 |
| 1077 | 45749 | 45763 | 15 |
| 1078 | 45804 | 45826 | 23 |
| 1079 | 45839 | 45861 | 23 |
| 1080 | 45878 | 45910 | 33 |
| 1081 | 45926 | 45954 | 29 |
| 1082 | 45956 | 45975 | 20 |
| 1083 | 45977 | 45997 | 21 |
| 1084 | 45999 | 46020 | 22 |
| 1085 | 46046 | 46063 | 18 |
| 1086 | 46065 | 46088 | 24 |
| 1087 | 46097 | 46118 | 22 |
| 1088 | 46120 | 46142 | 23 |
| 1089 | 46144 | 46160 | 17 |
| 1090 | 46162 | 46185 | 24 |
| 1091 | 46204 | 46280 | 77 |
| 1092 | 46302 | 46326 | 25 |
| 1093 | 46328 | 46355 | 28 |
| 1094 | 46358 | 46377 | 20 |
| 1095 | 46379 | 46436 | 58 |
| 1096 | 46457 | 46471 | 15 |
| 1097 | 46473 | 46492 | 20 |
| 1098 | 46501 | 46541 | 41 |
| 1099 | 46543 | 46572 | 30 |
| 1100 | 46584 | 46626 | 43 |
| 1101 | 46655 | 46683 | 29 |
| 1102 | 46685 | 46702 | 18 |
| 1103 | 46704 | 46722 | 19 |
| 1104 | 46724 | 46763 | 40 |
| 1105 | 46784 | 46800 | 17 |
| 1106 | 46802 | 46827 | 26 |
| 1107 | 46830 | 46867 | 38 |
| 1108 | 46869 | 46887 | 19 |
| 1109 | 46889 | 46920 | 32 |
| 1110 | 46922 | 46947 | 26 |
| 1111 | 46976 | 47009 | 34 |
| 1112 | 47011 | 47030 | 20 |
| 1113 | 47032 | 47064 | 33 |
| 1114 | 47066 | 47092 | 27 |
| 1115 | 47108 | 47130 | 23 |
| 1116 | 47132 | 47168 | 37 |
| 1117 | 47170 | 47199 | 30 |
| 1118 | 47201 | 47222 | 22 |
| 1119 | 47238 | 47277 | 40 |
| 1120 | 47296 | 47350 | 55 |
| 1121 | 47352 | 47391 | 40 |
| 1122 | 47416 | 47440 | 25 |
| 1123 | 47452 | 47466 | 15 |
| 1124 | 47468 | 47523 | 56 |
| 1125 | 47522 | 47546 | 25 |
| 1126 | 47548 | 47567 | 20 |
| 1127 | 47569 | 47595 | 27 |
| 1128 | 47597 | 47634 | 38 |
| 1129 | 47657 | 47693 | 37 |
| 1130 | 47712 | 47731 | 20 |
| 1131 | 47749 | 47762 | 14 |
| 1132 | 47771 | 47825 | 55 |
| 1133 | 47827 | 47846 | 20 |
| 1134 | 47848 | 47872 | 25 |
| 1135 | 47874 | 47888 | 15 |
| 1136 | 47890 | 47909 | 20 |
| 1137 | 47911 | 47925 | 15 |
| 1138 | 47927 | 47952 | 26 |
| 1139 | 47961 | 47993 | 33 |
| 1140 | 48001 | 48016 | 16 |
| 1141 | 48051 | 48083 | 33 |
| 1142 | 48096 | 48158 | 63 |
| 1143 | 48158 | 48176 | 19 |
| 1144 | 48186 | 48201 | 16 |

TABLE 1-continued

Regions of SEQ ID NO 1 which may be targeted using oligonucleotide of the invention

| Reg. A | Position in SEQ ID NO 1 from | to | Length |
|---|---|---|---|
| 1145 | 48213 | 48239 | 27 |
| 1146 | 48241 | 48256 | 16 |
| 1147 | 48258 | 48278 | 21 |
| 1148 | 48280 | 48339 | 60 |
| 1149 | 48341 | 48357 | 17 |
| 1150 | 48359 | 48377 | 19 |
| 1151 | 48379 | 48393 | 15 |
| 1152 | 48395 | 48488 | 94 |
| 1153 | 48492 | 48510 | 19 |
| 1154 | 48528 | 48549 | 22 |
| 1155 | 48550 | 48589 | 40 |
| 1156 | 48636 | 48658 | 23 |
| 1157 | 48683 | 48697 | 15 |
| 1158 | 48699 | 48762 | 64 |
| 1159 | 48762 | 48775 | 14 |
| 1160 | 48773 | 48832 | 60 |
| 1161 | 48873 | 48886 | 14 |
| 1162 | 48888 | 48914 | 27 |
| 1163 | 48916 | 48944 | 29 |
| 1164 | 48969 | 49008 | 40 |
| 1165 | 49010 | 49024 | 15 |
| 1166 | 49051 | 49110 | 60 |
| 1167 | 49116 | 49150 | 35 |
| 1168 | 49151 | 49184 | 34 |
| 1169 | 49187 | 49200 | 14 |
| 1170 | 49213 | 49230 | 18 |
| 1171 | 49233 | 49247 | 15 |
| 1172 | 49267 | 49284 | 18 |
| 1173 | 49297 | 49310 | 14 |
| 1174 | 49317 | 49369 | 53 |
| 1175 | 49371 | 49435 | 65 |
| 1176 | 49444 | 49458 | 15 |
| 1177 | 49467 | 49500 | 34 |
| 1178 | 49510 | 49538 | 29 |
| 1179 | 49540 | 49559 | 20 |
| 1180 | 49561 | 49584 | 24 |
| 1181 | 49591 | 49626 | 36 |
| 1182 | 49628 | 49646 | 19 |
| 1183 | 49653 | 49737 | 85 |
| 1184 | 49787 | 49802 | 16 |
| 1185 | 49817 | 49835 | 19 |
| 1186 | 49841 | 49860 | 20 |
| 1187 | 49862 | 49883 | 22 |
| 1188 | 49885 | 49905 | 21 |
| 1189 | 49921 | 49950 | 30 |
| 1190 | 49961 | 49979 | 19 |
| 1191 | 49995 | 50051 | 57 |
| 1192 | 50053 | 50071 | 19 |
| 1193 | 50073 | 50088 | 16 |
| 1194 | 50132 | 50158 | 27 |
| 1195 | 50167 | 50183 | 17 |
| 1196 | 50201 | 50226 | 26 |
| 1197 | 50226 | 50239 | 14 |
| 1198 | 50259 | 50313 | 55 |
| 1199 | 50323 | 50341 | 19 |
| 1200 | 50343 | 50396 | 54 |
| 1201 | 50390 | 50403 | 14 |
| 1202 | 50398 | 50448 | 51 |
| 1203 | 50451 | 50483 | 33 |
| 1204 | 50489 | 50507 | 19 |
| 1205 | 50526 | 50548 | 23 |
| 1206 | 50550 | 50569 | 20 |
| 1207 | 50575 | 50602 | 28 |
| 1208 | 50606 | 50621 | 16 |
| 1209 | 50617 | 50630 | 14 |
| 1210 | 50623 | 50641 | 19 |
| 1211 | 50634 | 50647 | 14 |
| 1212 | 50644 | 50663 | 20 |
| 1213 | 50665 | 50684 | 20 |
| 1214 | 50705 | 50730 | 26 |
| 1215 | 50732 | 50763 | 32 |
| 1216 | 50766 | 50799 | 34 |
| 1217 | 50797 | 50823 | 27 |
| 1218 | 50838 | 50864 | 27 |
| 1219 | 50870 | 50884 | 15 |
| 1220 | 50885 | 50911 | 27 |
| 1221 | 50924 | 50937 | 14 |
| 1222 | 50939 | 50974 | 36 |
| 1223 | 50980 | 51008 | 29 |
| 1224 | 51015 | 51030 | 16 |
| 1225 | 51034 | 51047 | 14 |
| 1226 | 51075 | 51089 | 15 |
| 1227 | 51109 | 51123 | 15 |
| 1228 | 51135 | 51172 | 38 |
| 1229 | 51189 | 51216 | 28 |
| 1230 | 51241 | 51260 | 20 |
| 1231 | 51273 | 51294 | 22 |
| 1232 | 51296 | 51312 | 17 |
| 1233 | 51337 | 51357 | 21 |
| 1234 | 51356 | 51381 | 26 |
| 1235 | 51393 | 51465 | 73 |
| 1236 | 51476 | 51494 | 19 |
| 1237 | 51496 | 51515 | 20 |
| 1238 | 51530 | 51544 | 15 |
| 1239 | 51546 | 51572 | 27 |
| 1240 | 51586 | 51600 | 15 |
| 1241 | 51602 | 51617 | 16 |
| 1242 | 51619 | 51677 | 59 |
| 1243 | 51679 | 51700 | 22 |
| 1244 | 51727 | 51741 | 15 |
| 1245 | 51743 | 51821 | 79 |
| 1246 | 51826 | 51859 | 34 |
| 1247 | 51884 | 51912 | 29 |
| 1248 | 51918 | 51936 | 19 |
| 1249 | 51947 | 51979 | 33 |
| 1250 | 52004 | 52017 | 14 |
| 1251 | 52023 | 52048 | 26 |
| 1252 | 52141 | 52167 | 27 |
| 1253 | 52169 | 52188 | 20 |
| 1254 | 52204 | 52225 | 22 |
| 1255 | 52246 | 52262 | 17 |
| 1256 | 52289 | 52306 | 18 |
| 1257 | 52321 | 52339 | 19 |
| 1258 | 52341 | 52360 | 20 |
| 1259 | 52360 | 52428 | 69 |
| 1260 | 52430 | 52504 | 75 |
| 1261 | 52506 | 52567 | 62 |
| 1262 | 52579 | 52594 | 16 |
| 1263 | 52591 | 52610 | 20 |
| 1264 | 52612 | 52642 | 31 |
| 1265 | 52644 | 52667 | 24 |
| 1266 | 52672 | 52686 | 15 |
| 1267 | 52688 | 52702 | 15 |
| 1268 | 52715 | 52753 | 39 |
| 1269 | 52770 | 52783 | 14 |
| 1270 | 52779 | 52792 | 14 |
| 1271 | 52814 | 52845 | 32 |
| 1272 | 52834 | 52857 | 24 |
| 1273 | 52858 | 52885 | 28 |
| 1274 | 52887 | 52943 | 57 |
| 1275 | 52945 | 52962 | 18 |
| 1276 | 52971 | 53019 | 49 |
| 1277 | 53011 | 53036 | 26 |
| 1278 | 53053 | 53066 | 14 |
| 1279 | 53092 | 53112 | 21 |
| 1280 | 53124 | 53151 | 28 |
| 1281 | 53161 | 53175 | 15 |
| 1282 | 53184 | 53220 | 37 |
| 1283 | 53222 | 53243 | 22 |
| 1284 | 53245 | 53260 | 16 |
| 1285 | 53278 | 53304 | 27 |
| 1286 | 53311 | 53346 | 36 |

TABLE 1-continued

Regions of SEQ ID NO 1 which may be targeted using oligonucleotide of the invention

| Reg. A | Position in SEQ ID NO 1 from | to | Length |
|---|---|---|---|
| 1287 | 53364 | 53386 | 23 |
| 1288 | 53388 | 53404 | 17 |
| 1289 | 53417 | 53431 | 15 |
| 1290 | 53449 | 53463 | 15 |
| 1291 | 53465 | 53484 | 20 |
| 1292 | 53514 | 53527 | 14 |
| 1293 | 53552 | 53567 | 16 |
| 1294 | 53570 | 53591 | 22 |
| 1295 | 53618 | 53644 | 27 |
| 1296 | 53645 | 53667 | 23 |
| 1297 | 53669 | 53684 | 16 |
| 1298 | 53714 | 53742 | 29 |
| 1299 | 53744 | 53764 | 21 |
| 1300 | 53818 | 53843 | 26 |
| 1301 | 53845 | 53860 | 16 |
| 1302 | 53875 | 53889 | 15 |
| 1303 | 53961 | 53991 | 31 |
| 1304 | 53991 | 54013 | 23 |
| 1305 | 54015 | 54055 | 41 |
| 1306 | 54057 | 54081 | 25 |
| 1307 | 54114 | 54135 | 22 |
| 1308 | 54163 | 54178 | 16 |
| 1309 | 54180 | 54193 | 14 |
| 1310 | 54195 | 54254 | 60 |
| 1311 | 54261 | 54290 | 30 |
| 1312 | 54292 | 54307 | 16 |
| 1313 | 54309 | 54327 | 19 |
| 1314 | 54357 | 54372 | 16 |
| 1315 | 54404 | 54420 | 17 |
| 1316 | 54418 | 54439 | 22 |
| 1317 | 54441 | 54466 | 26 |
| 1318 | 54468 | 54512 | 45 |
| 1319 | 54519 | 54532 | 14 |
| 1320 | 54555 | 54572 | 18 |
| 1321 | 54588 | 54601 | 14 |
| 1322 | 54609 | 54633 | 25 |
| 1323 | 54644 | 54688 | 45 |
| 1324 | 54690 | 54721 | 32 |
| 1325 | 54723 | 54761 | 39 |
| 1326 | 54786 | 54802 | 17 |
| 1327 | 54819 | 54835 | 17 |
| 1328 | 54837 | 54912 | 76 |
| 1329 | 54924 | 54941 | 18 |
| 1330 | 54999 | 55017 | 19 |
| 1331 | 55019 | 55035 | 17 |
| 1332 | 55060 | 55073 | 14 |
| 1333 | 55075 | 55100 | 26 |
| 1334 | 55129 | 55171 | 43 |
| 1335 | 55173 | 55188 | 16 |
| 1336 | 55190 | 55203 | 14 |
| 1337 | 55210 | 55230 | 21 |
| 1338 | 55233 | 55281 | 49 |
| 1339 | 55276 | 55289 | 14 |
| 1340 | 55283 | 55320 | 38 |
| 1341 | 55330 | 55379 | 50 |
| 1342 | 55381 | 55423 | 43 |
| 1343 | 55420 | 55441 | 22 |
| 1344 | 55486 | 55502 | 17 |
| 1345 | 55515 | 55533 | 19 |
| 1346 | 55535 | 55553 | 19 |
| 1347 | 55555 | 55569 | 15 |
| 1348 | 55569 | 55588 | 20 |
| 1349 | 55590 | 55611 | 22 |
| 1350 | 55615 | 55663 | 49 |
| 1351 | 55665 | 55678 | 14 |
| 1352 | 55696 | 55713 | 18 |
| 1353 | 55715 | 55738 | 24 |
| 1354 | 55744 | 55774 | 31 |
| 1355 | 55776 | 55794 | 19 |
| 1356 | 55801 | 55823 | 23 |
| 1357 | 55862 | 55906 | 45 |

TABLE 1-continued

Regions of SEQ ID NO 1 which may be targeted using oligonucleotide of the invention

| Reg. A | Position in SEQ ID NO 1 from | to | Length |
|---|---|---|---|
| 1358 | 55920 | 55933 | 14 |
| 1359 | 55922 | 55947 | 26 |
| 1360 | 55974 | 55993 | 20 |
| 1361 | 55990 | 56031 | 42 |
| 1362 | 56045 | 56073 | 29 |
| 1363 | 56082 | 56114 | 33 |
| 1364 | 56117 | 56140 | 24 |
| 1365 | 56183 | 56214 | 32 |
| 1366 | 56218 | 56236 | 19 |
| 1367 | 56261 | 56282 | 22 |
| 1368 | 56311 | 56336 | 26 |
| 1369 | 56331 | 56345 | 15 |
| 1370 | 56338 | 56358 | 21 |
| 1371 | 56369 | 56390 | 22 |
| 1372 | 56391 | 56431 | 41 |
| 1373 | 56433 | 56451 | 19 |
| 1374 | 56453 | 56473 | 21 |
| 1375 | 56475 | 56498 | 24 |
| 1376 | 56500 | 56546 | 47 |
| 1377 | 56558 | 56581 | 24 |
| 1378 | 56584 | 56597 | 14 |
| 1379 | 56611 | 56647 | 37 |
| 1380 | 56643 | 56657 | 15 |
| 1381 | 56667 | 56691 | 25 |
| 1382 | 56732 | 56759 | 28 |
| 1383 | 56788 | 56805 | 18 |
| 1384 | 56821 | 56845 | 25 |
| 1385 | 56850 | 56882 | 33 |
| 1386 | 56885 | 56906 | 22 |
| 1387 | 56928 | 56942 | 15 |
| 1388 | 56944 | 56959 | 16 |
| 1389 | 56961 | 56975 | 15 |
| 1390 | 56984 | 57002 | 19 |
| 1391 | 57004 | 57041 | 38 |
| 1392 | 57057 | 57082 | 26 |
| 1393 | 57084 | 57122 | 39 |
| 1394 | 57162 | 57222 | 61 |
| 1395 | 57224 | 57246 | 23 |
| 1396 | 57259 | 57284 | 26 |
| 1397 | 57317 | 57332 | 16 |
| 1398 | 57346 | 57369 | 24 |
| 1399 | 57388 | 57423 | 36 |
| 1400 | 57425 | 57440 | 16 |
| 1401 | 57442 | 57455 | 14 |
| 1402 | 57475 | 57492 | 18 |
| 1403 | 57508 | 57522 | 15 |
| 1404 | 57522 | 57546 | 25 |
| 1405 | 57548 | 57576 | 29 |
| 1406 | 57593 | 57634 | 42 |
| 1407 | 57658 | 57675 | 18 |
| 1408 | 57687 | 57771 | 85 |
| 1409 | 57786 | 57803 | 18 |
| 1410 | 57801 | 57819 | 19 |
| 1411 | 57830 | 57858 | 29 |
| 1412 | 57889 | 57911 | 23 |
| 1413 | 57926 | 57945 | 20 |
| 1414 | 57947 | 57972 | 26 |
| 1415 | 58009 | 58028 | 20 |
| 1416 | 58030 | 58060 | 31 |
| 1417 | 58063 | 58091 | 29 |
| 1418 | 58124 | 58146 | 23 |
| 1419 | 58147 | 58162 | 16 |
| 1420 | 58163 | 58198 | 36 |
| 1421 | 58214 | 58292 | 79 |
| 1422 | 58292 | 58309 | 18 |
| 1423 | 58336 | 58429 | 94 |
| 1424 | 58436 | 58457 | 22 |
| 1425 | 58453 | 58501 | 49 |
| 1426 | 58525 | 58553 | 29 |
| 1427 | 58566 | 58579 | 14 |
| 1428 | 58571 | 58584 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 1429 | 58586 | 58601 | 16 |
| 1430 | 58604 | 58630 | 27 |
| 1431 | 58656 | 58682 | 27 |
| 1432 | 58696 | 58713 | 18 |
| 1433 | 58722 | 58744 | 23 |
| 1434 | 58757 | 58771 | 15 |
| 1435 | 58805 | 58979 | 175 |
| 1436 | 58987 | 59073 | 87 |
| 1437 | 59072 | 59123 | 52 |
| 1438 | 59124 | 59150 | 27 |
| 1439 | 59154 | 59234 | 81 |
| 1440 | 59231 | 59276 | 46 |
| 1441 | 59291 | 59413 | 123 |
| 1442 | 59413 | 59458 | 46 |
| 1443 | 59466 | 59511 | 46 |
| 1444 | 59513 | 59533 | 21 |
| 1445 | 59549 | 59764 | 216 |
| 1446 | 59762 | 59825 | 64 |
| 1447 | 59824 | 59907 | 84 |
| 1448 | 59916 | 60004 | 89 |
| 1449 | 60006 | 60030 | 25 |
| 1450 | 60027 | 60040 | 14 |
| 1451 | 60032 | 60100 | 69 |
| 1452 | 60119 | 60188 | 70 |
| 1453 | 60191 | 60227 | 37 |
| 1454 | 60220 | 60287 | 68 |
| 1455 | 60289 | 60314 | 26 |
| 1456 | 60316 | 60554 | 239 |
| 1457 | 60556 | 60575 | 20 |
| 1458 | 60579 | 60593 | 15 |
| 1459 | 60595 | 60638 | 44 |
| 1460 | 60651 | 60690 | 40 |
| 1461 | 60692 | 60724 | 33 |
| 1462 | 60716 | 60799 | 84 |
| 1463 | 60801 | 60872 | 72 |
| 1464 | 60868 | 60881 | 14 |
| 1465 | 60885 | 60912 | 28 |
| 1466 | 60961 | 61009 | 49 |
| 1467 | 61014 | 61042 | 29 |
| 1468 | 61046 | 61059 | 14 |
| 1469 | 61053 | 61066 | 14 |
| 1470 | 61061 | 61084 | 24 |
| 1471 | 61134 | 61164 | 31 |
| 1472 | 61178 | 61199 | 22 |
| 1473 | 61201 | 61229 | 29 |
| 1474 | 61258 | 61284 | 27 |
| 1475 | 61286 | 61304 | 19 |
| 1476 | 61316 | 61332 | 17 |
| 1477 | 61341 | 61354 | 14 |
| 1478 | 61356 | 61383 | 28 |
| 1479 | 61407 | 61440 | 34 |
| 1480 | 61451 | 61468 | 18 |
| 1481 | 61470 | 61497 | 28 |
| 1482 | 61493 | 61506 | 14 |
| 1483 | 61499 | 61529 | 31 |
| 1484 | 61531 | 61558 | 28 |
| 1485 | 61590 | 61615 | 26 |
| 1486 | 61623 | 61640 | 18 |
| 1487 | 61673 | 61877 | 205 |
| 1488 | 61879 | 61898 | 20 |
| 1489 | 61900 | 61941 | 42 |
| 1490 | 61943 | 61962 | 20 |
| 1491 | 61964 | 61983 | 20 |
| 1492 | 62003 | 62017 | 15 |
| 1493 | 62015 | 62080 | 66 |
| 1494 | 62100 | 62124 | 25 |
| 1495 | 62133 | 62146 | 14 |
| 1496 | 62139 | 62175 | 37 |
| 1497 | 62191 | 62237 | 47 |
| 1498 | 62250 | 62270 | 21 |
| 1499 | 62283 | 62316 | 34 |
| 1500 | 62310 | 62358 | 49 |
| 1501 | 62357 | 62397 | 41 |
| 1502 | 62399 | 62413 | 15 |
| 1503 | 62415 | 62470 | 56 |
| 1504 | 62472 | 62501 | 30 |
| 1505 | 62503 | 62541 | 39 |
| 1506 | 62553 | 62609 | 57 |
| 1507 | 62611 | 62656 | 46 |
| 1508 | 62663 | 62690 | 28 |
| 1509 | 62703 | 62735 | 33 |
| 1510 | 62737 | 62759 | 23 |
| 1511 | 62765 | 62789 | 25 |
| 1512 | 62802 | 62816 | 15 |
| 1513 | 62810 | 62824 | 15 |
| 1514 | 62853 | 62868 | 16 |
| 1515 | 62864 | 62878 | 15 |
| 1516 | 62878 | 62907 | 30 |
| 1517 | 62905 | 62937 | 33 |
| 1518 | 62937 | 62951 | 15 |
| 1519 | 62943 | 62956 | 14 |
| 1520 | 62946 | 62960 | 15 |
| 1521 | 62961 | 62988 | 28 |
| 1522 | 62993 | 63006 | 14 |
| 1523 | 63005 | 63019 | 15 |
| 1524 | 63030 | 63049 | 20 |
| 1525 | 63057 | 63076 | 20 |
| 1526 | 63073 | 63088 | 16 |
| 1527 | 63078 | 63125 | 48 |
| 1528 | 63128 | 63152 | 25 |
| 1529 | 63154 | 63170 | 17 |
| 1530 | 63172 | 63196 | 25 |
| 1531 | 63185 | 63223 | 39 |
| 1532 | 63225 | 63245 | 21 |
| 1533 | 63236 | 63254 | 19 |
| 1534 | 63245 | 63261 | 17 |
| 1535 | 63263 | 63276 | 14 |
| 1536 | 63280 | 63295 | 16 |
| 1537 | 63292 | 63336 | 45 |
| 1538 | 63344 | 63368 | 25 |
| 1539 | 63369 | 63396 | 28 |
| 1540 | 63385 | 63398 | 14 |
| 1541 | 63395 | 63417 | 23 |
| 1542 | 63433 | 63451 | 19 |
| 1543 | 63440 | 63453 | 14 |
| 1544 | 63454 | 63470 | 17 |
| 1545 | 63472 | 63511 | 40 |
| 1546 | 63513 | 63539 | 27 |
| 1547 | 63547 | 63603 | 57 |
| 1548 | 63625 | 63651 | 27 |
| 1549 | 63676 | 63692 | 17 |
| 1550 | 63730 | 63746 | 17 |
| 1551 | 63759 | 63775 | 17 |
| 1552 | 63779 | 63833 | 55 |
| 1553 | 63844 | 63883 | 40 |
| 1554 | 63889 | 63907 | 19 |
| 1555 | 63910 | 63938 | 29 |
| 1556 | 63943 | 63962 | 20 |
| 1557 | 64004 | 64033 | 30 |
| 1558 | 64056 | 64087 | 32 |
| 1559 | 64112 | 64132 | 21 |
| 1560 | 64142 | 64158 | 17 |
| 1561 | 64160 | 64191 | 32 |
| 1562 | 64193 | 64209 | 17 |
| 1563 | 64214 | 64227 | 14 |
| 1564 | 64228 | 64241 | 14 |
| 1565 | 64254 | 64278 | 25 |
| 1566 | 64280 | 64298 | 19 |
| 1567 | 64300 | 64338 | 39 |
| 1568 | 64340 | 64355 | 16 |
| 1569 | 64357 | 64380 | 24 |
| 1570 | 64412 | 64434 | 23 |

TABLE 1-continued

Regions of SEQ ID NO 1 which may be targeted using oligonucleotide of the invention

| Reg. A | Position in SEQ ID NO 1 from | to | Length |
|---|---|---|---|
| 1571 | 64438 | 64456 | 19 |
| 1572 | 64458 | 64488 | 31 |
| 1573 | 64490 | 64517 | 28 |
| 1574 | 64519 | 64538 | 20 |
| 1575 | 64552 | 64572 | 21 |
| 1576 | 64585 | 64608 | 24 |
| 1577 | 64625 | 64642 | 18 |
| 1578 | 64631 | 64644 | 14 |
| 1579 | 64644 | 64683 | 40 |
| 1580 | 64703 | 64716 | 14 |
| 1581 | 64736 | 64751 | 16 |
| 1582 | 64759 | 64773 | 15 |
| 1583 | 64775 | 64806 | 32 |
| 1584 | 64815 | 64831 | 17 |
| 1585 | 64845 | 64878 | 34 |
| 1586 | 64880 | 64904 | 25 |
| 1587 | 64915 | 64937 | 23 |
| 1588 | 64948 | 64971 | 24 |
| 1589 | 64973 | 64994 | 22 |
| 1590 | 64996 | 65017 | 22 |
| 1591 | 65019 | 65055 | 37 |
| 1592 | 65062 | 65109 | 48 |
| 1593 | 65111 | 65138 | 28 |
| 1594 | 65140 | 65179 | 40 |
| 1595 | 65181 | 65195 | 15 |
| 1596 | 65210 | 65230 | 21 |
| 1597 | 65232 | 65248 | 17 |
| 1598 | 65271 | 65296 | 26 |
| 1599 | 65298 | 65319 | 22 |
| 1600 | 65321 | 65371 | 51 |
| 1601 | 65391 | 65413 | 23 |
| 1602 | 65415 | 65436 | 22 |
| 1603 | 65436 | 65454 | 19 |
| 1604 | 65477 | 65490 | 14 |
| 1605 | 65492 | 65520 | 29 |
| 1606 | 65522 | 65552 | 31 |
| 1607 | 65554 | 65579 | 26 |
| 1608 | 65581 | 65594 | 14 |
| 1609 | 65591 | 65606 | 16 |
| 1610 | 65595 | 65616 | 22 |
| 1611 | 65618 | 65632 | 15 |
| 1612 | 65634 | 65657 | 24 |
| 1613 | 65661 | 65716 | 56 |
| 1614 | 65730 | 65747 | 18 |
| 1615 | 65748 | 65807 | 60 |
| 1616 | 65809 | 65829 | 21 |
| 1617 | 65831 | 65844 | 14 |
| 1618 | 65846 | 65859 | 14 |
| 1619 | 65861 | 65891 | 31 |
| 1620 | 65898 | 65920 | 23 |
| 1621 | 65930 | 65963 | 34 |
| 1622 | 65980 | 66060 | 81 |
| 1623 | 66069 | 66085 | 17 |
| 1624 | 66095 | 66108 | 14 |
| 1625 | 66110 | 66126 | 17 |
| 1626 | 66139 | 66173 | 35 |
| 1627 | 66175 | 66191 | 17 |
| 1628 | 66204 | 66226 | 23 |
| 1629 | 66224 | 66263 | 40 |
| 1630 | 66265 | 66278 | 14 |
| 1631 | 66280 | 66320 | 41 |
| 1632 | 66322 | 66345 | 24 |
| 1633 | 66355 | 66371 | 17 |
| 1634 | 66375 | 66407 | 33 |
| 1635 | 66411 | 66424 | 14 |
| 1636 | 66421 | 66441 | 21 |
| 1637 | 66440 | 66460 | 21 |
| 1638 | 66463 | 66482 | 20 |
| 1639 | 66484 | 66501 | 18 |
| 1640 | 66509 | 66527 | 19 |
| 1641 | 66534 | 66548 | 15 |

TABLE 1-continued

Regions of SEQ ID NO 1 which may be targeted using oligonucleotide of the invention

| Reg. A | Position in SEQ ID NO 1 from | to | Length |
|---|---|---|---|
| 1642 | 66556 | 66569 | 14 |
| 1643 | 66562 | 66593 | 32 |
| 1644 | 66606 | 66637 | 32 |
| 1645 | 66639 | 66665 | 27 |
| 1646 | 66674 | 66690 | 17 |
| 1647 | 66692 | 66720 | 29 |
| 1648 | 66722 | 66742 | 21 |
| 1649 | 66758 | 66786 | 29 |
| 1650 | 66787 | 66802 | 16 |
| 1651 | 66812 | 66862 | 51 |
| 1652 | 66864 | 66885 | 22 |
| 1653 | 66940 | 66953 | 14 |
| 1654 | 66982 | 66997 | 16 |
| 1655 | 67024 | 67084 | 61 |
| 1656 | 67103 | 67118 | 16 |
| 1657 | 67156 | 67185 | 30 |
| 1658 | 67181 | 67195 | 15 |
| 1659 | 67193 | 67206 | 14 |
| 1660 | 67215 | 67229 | 15 |
| 1661 | 67231 | 67271 | 41 |
| 1662 | 67288 | 67301 | 14 |
| 1663 | 67294 | 67345 | 52 |
| 1664 | 67362 | 67379 | 18 |
| 1665 | 67381 | 67397 | 17 |
| 1666 | 67409 | 67448 | 40 |
| 1667 | 67468 | 67481 | 14 |
| 1668 | 67483 | 67510 | 28 |
| 1669 | 67540 | 67561 | 22 |
| 1670 | 67620 | 67640 | 21 |
| 1671 | 67656 | 67672 | 17 |
| 1672 | 67674 | 67749 | 76 |
| 1673 | 67751 | 67764 | 14 |
| 1674 | 67783 | 67801 | 19 |
| 1675 | 67803 | 67828 | 26 |
| 1676 | 67830 | 67848 | 19 |
| 1677 | 67850 | 67868 | 19 |
| 1678 | 67877 | 67918 | 42 |
| 1679 | 67933 | 67961 | 29 |
| 1680 | 67963 | 67978 | 16 |
| 1681 | 67998 | 68026 | 29 |
| 1682 | 68028 | 68046 | 19 |
| 1683 | 68048 | 68082 | 35 |
| 1684 | 68084 | 68112 | 29 |
| 1685 | 68114 | 68130 | 17 |
| 1686 | 68129 | 68155 | 27 |
| 1687 | 68170 | 68192 | 23 |
| 1688 | 68194 | 68237 | 44 |
| 1689 | 68239 | 68261 | 23 |
| 1690 | 68272 | 68286 | 15 |
| 1691 | 68290 | 68373 | 84 |
| 1692 | 68375 | 68419 | 45 |
| 1693 | 68442 | 68487 | 46 |
| 1694 | 68489 | 68547 | 59 |
| 1695 | 68549 | 68592 | 44 |
| 1696 | 68599 | 68614 | 16 |
| 1697 | 68617 | 68657 | 41 |
| 1698 | 68659 | 68686 | 28 |
| 1699 | 68688 | 68735 | 48 |
| 1700 | 68732 | 68747 | 16 |
| 1701 | 68749 | 68786 | 38 |
| 1702 | 68788 | 68830 | 43 |
| 1703 | 68837 | 68879 | 43 |
| 1704 | 68882 | 68899 | 18 |
| 1705 | 68918 | 68942 | 25 |
| 1706 | 68944 | 68968 | 25 |
| 1707 | 68983 | 69007 | 25 |
| 1708 | 69012 | 69027 | 16 |
| 1709 | 69020 | 69064 | 45 |
| 1710 | 69064 | 69077 | 14 |
| 1711 | 69079 | 69114 | 36 |
| 1712 | 69116 | 69196 | 81 |

TABLE 1-continued

Regions of SEQ ID NO 1 which may be targeted using oligonucleotide of the invention

| Reg. A | Position in SEQ ID NO 1 from | to | Length |
|---|---|---|---|
| 1713 | 69185 | 69198 | 14 |
| 1714 | 69202 | 69219 | 18 |
| 1715 | 69228 | 69246 | 19 |
| 1716 | 69240 | 69282 | 43 |
| 1717 | 69294 | 69317 | 24 |
| 1718 | 69306 | 69324 | 19 |
| 1719 | 69333 | 69346 | 14 |
| 1720 | 69352 | 69366 | 15 |
| 1721 | 69387 | 69431 | 45 |
| 1722 | 69433 | 69447 | 15 |
| 1723 | 69452 | 69480 | 29 |
| 1724 | 69482 | 69497 | 16 |
| 1725 | 69491 | 69504 | 14 |
| 1726 | 69511 | 69564 | 54 |
| 1727 | 69566 | 69628 | 63 |
| 1728 | 69628 | 69642 | 15 |
| 1729 | 69659 | 69681 | 23 |
| 1730 | 69684 | 69697 | 14 |
| 1731 | 69719 | 69744 | 26 |
| 1732 | 69746 | 69763 | 18 |
| 1733 | 69765 | 69792 | 28 |
| 1734 | 69801 | 69828 | 28 |
| 1735 | 69853 | 69901 | 49 |
| 1736 | 69933 | 69949 | 17 |
| 1737 | 69951 | 69966 | 16 |
| 1738 | 69968 | 69983 | 16 |
| 1739 | 69988 | 70061 | 74 |
| 1740 | 70083 | 70100 | 18 |
| 1741 | 70110 | 70154 | 45 |
| 1742 | 70161 | 70199 | 39 |
| 1743 | 70202 | 70225 | 24 |
| 1744 | 70231 | 70246 | 16 |
| 1745 | 70269 | 70295 | 27 |
| 1746 | 70292 | 70327 | 36 |
| 1747 | 70331 | 70349 | 19 |
| 1748 | 70351 | 70371 | 21 |
| 1749 | 70381 | 70403 | 23 |
| 1750 | 70405 | 70420 | 16 |
| 1751 | 70422 | 70483 | 62 |
| 1752 | 70496 | 70533 | 38 |
| 1753 | 70535 | 70578 | 44 |
| 1754 | 70577 | 70639 | 63 |
| 1755 | 70653 | 70667 | 15 |
| 1756 | 70661 | 70674 | 14 |
| 1757 | 70669 | 70695 | 27 |
| 1758 | 70687 | 70705 | 19 |
| 1759 | 70708 | 70744 | 37 |
| 1760 | 70746 | 70764 | 19 |
| 1761 | 70766 | 70779 | 14 |
| 1762 | 70781 | 70832 | 52 |
| 1763 | 70834 | 70851 | 18 |
| 1764 | 70858 | 70887 | 30 |
| 1765 | 70889 | 70902 | 14 |
| 1766 | 70920 | 70933 | 14 |
| 1767 | 70935 | 70964 | 30 |
| 1768 | 70974 | 70987 | 14 |
| 1769 | 71008 | 71028 | 21 |
| 1770 | 71030 | 71046 | 17 |
| 1771 | 71048 | 71073 | 26 |
| 1772 | 71075 | 71106 | 32 |
| 1773 | 71108 | 71133 | 26 |
| 1774 | 71137 | 71152 | 16 |
| 1775 | 71153 | 71170 | 18 |
| 1776 | 71179 | 71192 | 14 |
| 1777 | 71197 | 71224 | 28 |
| 1778 | 71235 | 71251 | 17 |
| 1779 | 71253 | 71311 | 59 |
| 1780 | 71310 | 71329 | 20 |
| 1781 | 71330 | 71364 | 35 |
| 1782 | 71366 | 71386 | 21 |
| 1783 | 71388 | 71410 | 23 |
| 1784 | 71412 | 71433 | 22 |
| 1785 | 71448 | 71472 | 25 |
| 1786 | 71475 | 71491 | 17 |
| 1787 | 71491 | 71553 | 63 |
| 1788 | 71555 | 71581 | 27 |
| 1789 | 71583 | 71624 | 42 |
| 1790 | 71634 | 71700 | 67 |
| 1791 | 71706 | 71725 | 20 |
| 1792 | 71732 | 71747 | 16 |
| 1793 | 71789 | 71804 | 16 |
| 1794 | 71810 | 71824 | 15 |
| 1795 | 71819 | 71834 | 16 |
| 1796 | 71839 | 71872 | 34 |
| 1797 | 71876 | 71889 | 14 |
| 1798 | 71886 | 71908 | 23 |
| 1799 | 71910 | 71924 | 15 |
| 1800 | 71985 | 71999 | 15 |
| 1801 | 72000 | 72021 | 22 |
| 1802 | 72023 | 72047 | 25 |
| 1803 | 72071 | 72158 | 88 |
| 1804 | 72165 | 72192 | 28 |
| 1805 | 72194 | 72234 | 41 |
| 1806 | 72236 | 72255 | 20 |
| 1807 | 72257 | 72281 | 25 |
| 1808 | 72283 | 72299 | 17 |
| 1809 | 72312 | 72329 | 18 |
| 1810 | 72323 | 72336 | 14 |
| 1811 | 72348 | 72395 | 48 |
| 1812 | 72398 | 72411 | 14 |
| 1813 | 72413 | 72455 | 43 |
| 1814 | 72470 | 72503 | 34 |
| 1815 | 72506 | 72541 | 36 |
| 1816 | 72545 | 72558 | 14 |
| 1817 | 72560 | 72586 | 27 |
| 1818 | 72583 | 72597 | 15 |
| 1819 | 72588 | 72602 | 15 |
| 1820 | 72611 | 72636 | 26 |
| 1821 | 72638 | 72688 | 51 |
| 1822 | 72696 | 72736 | 41 |
| 1823 | 72738 | 72761 | 24 |
| 1824 | 72774 | 72799 | 26 |
| 1825 | 72801 | 72886 | 86 |
| 1826 | 72888 | 72903 | 16 |
| 1827 | 72928 | 72958 | 31 |
| 1828 | 72962 | 72990 | 29 |
| 1829 | 73001 | 73014 | 14 |
| 1830 | 73017 | 73053 | 37 |
| 1831 | 73055 | 73078 | 24 |
| 1832 | 73077 | 73090 | 14 |
| 1833 | 73088 | 73121 | 34 |
| 1834 | 73124 | 73153 | 30 |
| 1835 | 73147 | 73172 | 26 |
| 1836 | 73164 | 73203 | 40 |
| 1837 | 73218 | 73257 | 40 |
| 1838 | 73260 | 73273 | 14 |
| 1839 | 73268 | 73281 | 14 |
| 1840 | 73278 | 73291 | 14 |
| 1841 | 73298 | 73313 | 16 |
| 1842 | 73451 | 73465 | 15 |
| 1843 | 73459 | 73472 | 14 |
| 1844 | 73512 | 73567 | 56 |
| 1845 | 73569 | 73611 | 43 |
| 1846 | 73614 | 73645 | 32 |
| 1847 | 73661 | 73713 | 53 |
| 1848 | 73712 | 73727 | 16 |
| 1849 | 73716 | 73731 | 16 |
| 1850 | 73735 | 73748 | 14 |
| 1851 | 73741 | 73760 | 20 |
| 1852 | 73764 | 73782 | 19 |
| 1853 | 73783 | 73801 | 19 |
| 1854 | 73795 | 73829 | 35 |

TABLE 1-continued

Regions of SEQ ID NO 1 which may be targeted using oligonucleotide of the invention

| Reg. A | Position in SEQ ID NO 1 from | to | Length |
|---|---|---|---|
| 1855 | 73860 | 73873 | 14 |
| 1856 | 73885 | 73904 | 20 |
| 1857 | 73906 | 73919 | 14 |
| 1858 | 73916 | 73945 | 30 |
| 1859 | 73947 | 73961 | 15 |
| 1860 | 73978 | 74018 | 41 |
| 1861 | 74020 | 74046 | 27 |
| 1862 | 74061 | 74082 | 22 |
| 1863 | 74092 | 74158 | 67 |
| 1864 | 74160 | 74177 | 18 |
| 1865 | 74179 | 74209 | 31 |
| 1866 | 74216 | 74245 | 30 |
| 1867 | 74270 | 74287 | 18 |
| 1868 | 74289 | 74305 | 17 |
| 1869 | 74307 | 74368 | 62 |
| 1870 | 74369 | 74411 | 43 |
| 1871 | 74416 | 74461 | 46 |
| 1872 | 74463 | 74479 | 17 |
| 1873 | 74506 | 74541 | 36 |
| 1874 | 74543 | 74636 | 94 |
| 1875 | 74647 | 74704 | 58 |
| 1876 | 74745 | 74770 | 26 |
| 1877 | 74789 | 74813 | 25 |
| 1878 | 74815 | 74838 | 24 |
| 1879 | 74850 | 74877 | 28 |
| 1880 | 74891 | 74923 | 33 |
| 1881 | 74925 | 74940 | 16 |
| 1882 | 74952 | 74969 | 18 |
| 1883 | 74979 | 75001 | 23 |
| 1884 | 75037 | 75066 | 30 |
| 1885 | 75068 | 75088 | 21 |
| 1886 | 75097 | 75123 | 27 |
| 1887 | 75131 | 75149 | 19 |
| 1888 | 75152 | 75189 | 38 |
| 1889 | 75210 | 75252 | 43 |
| 1890 | 75254 | 75276 | 23 |
| 1891 | 75288 | 75310 | 23 |
| 1892 | 75338 | 75357 | 20 |
| 1893 | 75359 | 75372 | 14 |
| 1894 | 75376 | 75397 | 22 |
| 1895 | 75405 | 75432 | 28 |
| 1896 | 75440 | 75470 | 31 |
| 1897 | 75482 | 75501 | 20 |
| 1898 | 75503 | 75540 | 38 |
| 1899 | 75544 | 75560 | 17 |
| 1900 | 75562 | 75576 | 15 |
| 1901 | 75589 | 75610 | 22 |
| 1902 | 75633 | 75646 | 14 |
| 1903 | 75648 | 75679 | 32 |
| 1904 | 75691 | 75709 | 19 |
| 1905 | 75711 | 75724 | 14 |
| 1906 | 75740 | 75764 | 25 |
| 1907 | 75763 | 75776 | 14 |
| 1908 | 75767 | 75790 | 24 |
| 1909 | 75780 | 75794 | 15 |
| 1910 | 75792 | 75808 | 17 |
| 1911 | 75810 | 75829 | 20 |
| 1912 | 75831 | 75863 | 33 |
| 1913 | 75865 | 75880 | 16 |
| 1914 | 75882 | 75922 | 41 |
| 1915 | 75932 | 75998 | 67 |
| 1916 | 76000 | 76026 | 27 |
| 1917 | 76028 | 76045 | 18 |
| 1918 | 76046 | 76082 | 37 |
| 1919 | 76098 | 76413 | 316 |
| 1920 | 76420 | 76442 | 23 |
| 1921 | 76456 | 76477 | 22 |
| 1922 | 76484 | 76558 | 75 |
| 1923 | 76573 | 76592 | 20 |
| 1924 | 76608 | 76622 | 15 |
| 1925 | 76627 | 76663 | 37 |
| 1926 | 76665 | 76683 | 19 |
| 1927 | 76685 | 76698 | 14 |
| 1928 | 76702 | 76716 | 15 |
| 1929 | 76725 | 76744 | 20 |
| 1930 | 76745 | 76761 | 17 |
| 1931 | 76780 | 76796 | 17 |
| 1932 | 76798 | 76812 | 15 |
| 1933 | 76814 | 76832 | 19 |
| 1934 | 76834 | 76859 | 26 |
| 1935 | 76871 | 76934 | 64 |
| 1936 | 77012 | 77034 | 23 |
| 1937 | 77039 | 77055 | 17 |
| 1938 | 77081 | 77094 | 14 |
| 1939 | 77121 | 77184 | 64 |
| 1940 | 77186 | 77200 | 15 |
| 1941 | 77202 | 77225 | 24 |
| 1942 | 77227 | 77247 | 21 |
| 1943 | 77261 | 77317 | 57 |
| 1944 | 77327 | 77340 | 14 |
| 1945 | 77342 | 77366 | 25 |
| 1946 | 77377 | 77394 | 18 |
| 1947 | 77396 | 77439 | 44 |
| 1948 | 77453 | 77468 | 16 |
| 1949 | 77462 | 77593 | 132 |
| 1950 | 77586 | 77599 | 14 |
| 1951 | 77595 | 77641 | 47 |
| 1952 | 77643 | 77728 | 86 |
| 1953 | 77730 | 77768 | 39 |
| 1954 | 77778 | 77816 | 39 |
| 1955 | 77818 | 77835 | 18 |
| 1956 | 77837 | 77855 | 19 |
| 1957 | 77861 | 77876 | 16 |
| 1958 | 77882 | 77898 | 17 |
| 1959 | 77900 | 77924 | 25 |
| 1960 | 77923 | 77936 | 14 |
| 1961 | 77957 | 77970 | 14 |
| 1962 | 77962 | 77985 | 24 |
| 1963 | 77994 | 78022 | 29 |
| 1964 | 78024 | 78056 | 33 |
| 1965 | 78079 | 78128 | 50 |
| 1966 | 78132 | 78158 | 27 |
| 1967 | 78173 | 78213 | 41 |
| 1968 | 78224 | 78265 | 42 |
| 1969 | 78275 | 78332 | 58 |
| 1970 | 78334 | 78440 | 107 |
| 1971 | 78442 | 78489 | 48 |
| 1972 | 78491 | 78505 | 15 |
| 1973 | 78501 | 78514 | 14 |
| 1974 | 78507 | 78537 | 31 |
| 1975 | 78557 | 78570 | 14 |
| 1976 | 78562 | 78623 | 62 |
| 1977 | 78625 | 78665 | 41 |
| 1978 | 78668 | 78684 | 17 |
| 1979 | 78686 | 78759 | 74 |
| 1980 | 78761 | 78787 | 27 |
| 1981 | 78793 | 78814 | 22 |
| 1982 | 78816 | 78854 | 39 |
| 1983 | 78847 | 78860 | 14 |
| 1984 | 78874 | 78909 | 36 |
| 1985 | 78917 | 78944 | 28 |
| 1986 | 78956 | 78978 | 23 |
| 1987 | 78991 | 79008 | 18 |
| 1988 | 79003 | 79032 | 30 |
| 1989 | 79026 | 79040 | 15 |
| 1990 | 79044 | 79072 | 29 |
| 1991 | 79098 | 79158 | 61 |
| 1992 | 79162 | 79182 | 21 |
| 1993 | 79184 | 79228 | 45 |
| 1994 | 79221 | 79235 | 15 |
| 1995 | 79230 | 79262 | 33 |
| 1996 | 79287 | 79333 | 47 |

TABLE 1-continued

Regions of SEQ ID NO 1 which may be targeted using oligonucleotide of the invention

| Reg. A | Position in SEQ ID NO 1 from | to | Length |
|---|---|---|---|
| 1997 | 79356 | 79392 | 37 |
| 1998 | 79441 | 79476 | 36 |
| 1999 | 79488 | 79522 | 35 |
| 2000 | 79522 | 79539 | 18 |
| 2001 | 79568 | 79583 | 16 |
| 2002 | 79574 | 79601 | 28 |
| 2003 | 79603 | 79618 | 16 |
| 2004 | 79617 | 79639 | 23 |
| 2005 | 79651 | 79683 | 33 |
| 2006 | 79685 | 79724 | 40 |
| 2007 | 79721 | 79736 | 16 |
| 2008 | 79727 | 79782 | 56 |
| 2009 | 79784 | 79812 | 29 |
| 2010 | 79809 | 79834 | 26 |
| 2011 | 79841 | 79861 | 21 |
| 2012 | 79873 | 79923 | 51 |
| 2013 | 79928 | 79948 | 21 |
| 2014 | 79950 | 79986 | 37 |
| 2015 | 79993 | 80019 | 27 |
| 2016 | 80019 | 80063 | 45 |
| 2017 | 80071 | 80088 | 18 |
| 2018 | 80114 | 80160 | 47 |
| 2019 | 80154 | 80183 | 30 |
| 2020 | 80185 | 80212 | 28 |
| 2021 | 80214 | 80232 | 19 |
| 2022 | 80240 | 80266 | 27 |
| 2023 | 80293 | 80312 | 20 |
| 2024 | 80344 | 80380 | 37 |
| 2025 | 80382 | 80420 | 39 |
| 2026 | 80410 | 80423 | 14 |
| 2027 | 80417 | 80438 | 22 |
| 2028 | 80440 | 80456 | 17 |
| 2029 | 80467 | 80499 | 33 |
| 2030 | 80501 | 80527 | 27 |
| 2031 | 80532 | 80561 | 30 |
| 2032 | 80563 | 80599 | 37 |
| 2033 | 80604 | 80692 | 89 |
| 2034 | 80702 | 80737 | 36 |
| 2035 | 80739 | 80795 | 57 |
| 2036 | 80796 | 80871 | 76 |
| 2037 | 80873 | 80891 | 19 |
| 2038 | 80925 | 80961 | 37 |
| 2039 | 80963 | 80992 | 30 |
| 2040 | 81009 | 81068 | 60 |
| 2041 | 81070 | 81150 | 81 |
| 2042 | 81156 | 81199 | 44 |
| 2043 | 81201 | 81225 | 25 |
| 2044 | 81237 | 81253 | 17 |
| 2045 | 81255 | 81271 | 17 |
| 2046 | 81292 | 81351 | 60 |
| 2047 | 81353 | 81371 | 19 |
| 2048 | 81392 | 81422 | 31 |
| 2049 | 81438 | 81483 | 46 |
| 2050 | 81485 | 81503 | 19 |
| 2051 | 81512 | 81526 | 15 |
| 2052 | 81532 | 81554 | 23 |
| 2053 | 81556 | 81593 | 38 |
| 2054 | 81606 | 81664 | 59 |
| 2055 | 81666 | 81698 | 33 |
| 2056 | 81701 | 81720 | 20 |
| 2057 | 81728 | 81776 | 49 |
| 2058 | 81781 | 81810 | 30 |
| 2059 | 81812 | 81847 | 36 |
| 2060 | 81849 | 81893 | 45 |
| 2061 | 81908 | 81934 | 27 |
| 2062 | 81943 | 81964 | 22 |
| 2063 | 81967 | 82034 | 68 |
| 2064 | 82036 | 82134 | 99 |
| 2065 | 82136 | 82154 | 19 |
| 2066 | 82176 | 82197 | 22 |
| 2067 | 82199 | 82250 | 52 |

TABLE 1-continued

Regions of SEQ ID NO 1 which may be targeted using oligonucleotide of the invention

| Reg. A | Position in SEQ ID NO 1 from | to | Length |
|---|---|---|---|
| 2068 | 82252 | 82269 | 18 |
| 2069 | 82271 | 82293 | 23 |
| 2070 | 82300 | 82314 | 15 |
| 2071 | 82329 | 82343 | 15 |
| 2072 | 82344 | 82357 | 14 |
| 2073 | 82378 | 82407 | 30 |
| 2074 | 82406 | 82422 | 17 |
| 2075 | 82421 | 82443 | 23 |
| 2076 | 82446 | 82469 | 24 |
| 2077 | 82490 | 82507 | 18 |
| 2078 | 82502 | 82523 | 22 |
| 2079 | 82547 | 82576 | 30 |
| 2080 | 82590 | 82603 | 14 |
| 2081 | 82628 | 82647 | 20 |
| 2082 | 82650 | 82666 | 17 |
| 2083 | 82669 | 82683 | 15 |
| 2084 | 82685 | 82716 | 32 |
| 2085 | 82715 | 82736 | 22 |
| 2086 | 82760 | 82785 | 26 |
| 2087 | 82778 | 82791 | 14 |
| 2088 | 82780 | 82818 | 39 |
| 2089 | 82811 | 82825 | 15 |
| 2090 | 82821 | 82864 | 44 |
| 2091 | 82883 | 82915 | 33 |
| 2092 | 82919 | 82935 | 17 |
| 2093 | 82930 | 82946 | 17 |
| 2094 | 82937 | 82957 | 21 |
| 2095 | 82959 | 82972 | 14 |
| 2096 | 82974 | 83000 | 27 |
| 2097 | 83020 | 83036 | 17 |
| 2098 | 83038 | 83088 | 51 |
| 2099 | 83090 | 83115 | 26 |
| 2100 | 83120 | 83140 | 21 |
| 2101 | 83142 | 83155 | 14 |
| 2102 | 83160 | 83186 | 27 |
| 2103 | 83198 | 83215 | 18 |
| 2104 | 83227 | 83246 | 20 |
| 2105 | 83273 | 83339 | 67 |
| 2106 | 83341 | 83385 | 45 |
| 2107 | 83387 | 83400 | 14 |
| 2108 | 83413 | 83426 | 14 |
| 2109 | 83417 | 83449 | 33 |
| 2110 | 83486 | 83520 | 35 |
| 2111 | 83522 | 83565 | 44 |
| 2112 | 83567 | 83581 | 15 |
| 2113 | 83576 | 83670 | 95 |
| 2114 | 83681 | 83701 | 21 |
| 2115 | 83703 | 83716 | 14 |
| 2116 | 83733 | 83817 | 85 |
| 2117 | 83817 | 83830 | 14 |
| 2118 | 83832 | 83853 | 22 |
| 2119 | 83855 | 83871 | 17 |
| 2120 | 83886 | 83926 | 41 |
| 2121 | 83958 | 83974 | 17 |
| 2122 | 83976 | 83991 | 16 |
| 2123 | 83993 | 84031 | 39 |
| 2124 | 84033 | 84067 | 35 |
| 2125 | 84069 | 84102 | 34 |
| 2126 | 84104 | 84121 | 18 |
| 2127 | 84143 | 84233 | 91 |
| 2128 | 84249 | 84281 | 33 |
| 2129 | 84283 | 84403 | 121 |
| 2130 | 84404 | 84432 | 29 |
| 2131 | 84431 | 84444 | 14 |
| 2132 | 84434 | 84490 | 57 |
| 2133 | 84503 | 84520 | 18 |
| 2134 | 84522 | 84555 | 34 |
| 2135 | 84557 | 84572 | 16 |
| 2136 | 84574 | 84597 | 24 |
| 2137 | 84607 | 84626 | 20 |
| 2138 | 84650 | 84675 | 26 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 2139 | 84677 | 84700 | 24 |
| 2140 | 84721 | 84753 | 33 |
| 2141 | 84755 | 84807 | 53 |
| 2142 | 84809 | 84826 | 18 |
| 2143 | 84831 | 84849 | 19 |
| 2144 | 84879 | 84893 | 15 |
| 2145 | 84895 | 84915 | 21 |
| 2146 | 84917 | 84961 | 45 |
| 2147 | 85234 | 85247 | 14 |
| 2148 | 85253 | 85267 | 15 |
| 2149 | 85256 | 85351 | 96 |
| 2150 | 85359 | 85374 | 16 |
| 2151 | 85363 | 85376 | 14 |
| 2152 | 85365 | 85381 | 17 |
| 2153 | 85380 | 85414 | 35 |
| 2154 | 85416 | 85454 | 39 |
| 2155 | 85456 | 85484 | 29 |
| 2156 | 85509 | 85545 | 37 |
| 2157 | 85535 | 85550 | 16 |
| 2158 | 85566 | 85584 | 19 |
| 2159 | 85586 | 85610 | 25 |
| 2160 | 85604 | 85627 | 24 |
| 2161 | 85628 | 85665 | 38 |
| 2162 | 85698 | 85723 | 26 |
| 2163 | 85713 | 85728 | 16 |
| 2164 | 85722 | 85735 | 14 |
| 2165 | 85770 | 85785 | 16 |
| 2166 | 85800 | 85813 | 14 |
| 2167 | 85875 | 85888 | 14 |
| 2168 | 85950 | 85963 | 14 |
| 2169 | 86097 | 86125 | 29 |
| 2170 | 86127 | 86142 | 16 |
| 2171 | 86175 | 86198 | 24 |
| 2172 | 86226 | 86242 | 17 |
| 2173 | 86237 | 86302 | 66 |
| 2174 | 86308 | 86327 | 20 |
| 2175 | 86321 | 86334 | 14 |
| 2176 | 86329 | 86382 | 54 |
| 2177 | 86384 | 86400 | 17 |
| 2178 | 86403 | 86417 | 15 |
| 2179 | 86414 | 86437 | 24 |
| 2180 | 86439 | 86455 | 17 |
| 2181 | 86461 | 86478 | 18 |
| 2182 | 86473 | 86487 | 15 |
| 2183 | 86480 | 86517 | 38 |
| 2184 | 86517 | 86531 | 15 |
| 2185 | 86565 | 86583 | 19 |
| 2186 | 86600 | 86632 | 33 |
| 2187 | 86634 | 86651 | 18 |
| 2188 | 86653 | 86678 | 26 |
| 2189 | 86697 | 86756 | 60 |
| 2190 | 86782 | 86796 | 15 |
| 2191 | 86786 | 86809 | 24 |
| 2192 | 86811 | 86855 | 45 |
| 2193 | 86857 | 86891 | 35 |
| 2194 | 86894 | 86908 | 15 |
| 2195 | 86916 | 86933 | 18 |
| 2196 | 86945 | 86959 | 15 |
| 2197 | 86951 | 86965 | 15 |
| 2198 | 86969 | 86990 | 22 |
| 2199 | 87017 | 87057 | 41 |
| 2200 | 87059 | 87073 | 15 |
| 2201 | 87062 | 87076 | 15 |
| 2202 | 87066 | 87089 | 24 |
| 2203 | 87097 | 87121 | 25 |
| 2204 | 87110 | 87134 | 25 |
| 2205 | 87130 | 87155 | 26 |
| 2206 | 87160 | 87194 | 35 |
| 2207 | 87185 | 87198 | 14 |
| 2208 | 87209 | 87260 | 52 |
| 2209 | 87257 | 87270 | 14 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 2210 | 87274 | 87287 | 14 |
| 2211 | 87276 | 87294 | 19 |
| 2212 | 87294 | 87328 | 35 |
| 2213 | 87317 | 87333 | 17 |
| 2214 | 87336 | 87360 | 25 |
| 2215 | 87368 | 87418 | 51 |
| 2216 | 87441 | 87460 | 20 |
| 2217 | 87462 | 87487 | 26 |
| 2218 | 87489 | 87518 | 30 |
| 2219 | 87520 | 87539 | 20 |
| 2220 | 87542 | 87570 | 29 |
| 2221 | 87572 | 87601 | 30 |
| 2222 | 87603 | 87644 | 42 |
| 2223 | 87642 | 87750 | 109 |
| 2224 | 87756 | 87776 | 21 |
| 2225 | 87778 | 87803 | 26 |
| 2226 | 87803 | 87837 | 35 |
| 2227 | 87872 | 87888 | 17 |
| 2228 | 87890 | 87917 | 28 |
| 2229 | 87949 | 87964 | 16 |
| 2230 | 87963 | 88008 | 46 |
| 2231 | 88010 | 88027 | 18 |
| 2232 | 88029 | 88046 | 18 |
| 2233 | 88048 | 88089 | 42 |
| 2234 | 88091 | 88108 | 18 |
| 2235 | 88110 | 88177 | 68 |
| 2236 | 88179 | 88192 | 14 |
| 2237 | 88194 | 88229 | 36 |
| 2238 | 88234 | 88259 | 26 |
| 2239 | 88261 | 88291 | 31 |
| 2240 | 88303 | 88328 | 26 |
| 2241 | 88328 | 88341 | 14 |
| 2242 | 88340 | 88354 | 15 |
| 2243 | 88356 | 88372 | 17 |
| 2244 | 88411 | 88446 | 36 |
| 2245 | 88448 | 88465 | 18 |
| 2246 | 88469 | 88511 | 43 |
| 2247 | 88518 | 88533 | 16 |
| 2248 | 88531 | 88557 | 27 |
| 2249 | 88547 | 88560 | 14 |
| 2250 | 88573 | 88593 | 21 |
| 2251 | 88597 | 88618 | 22 |
| 2252 | 88620 | 88690 | 71 |
| 2253 | 88692 | 88745 | 54 |
| 2254 | 88954 | 88973 | 20 |
| 2255 | 88988 | 89047 | 60 |
| 2256 | 89066 | 89091 | 26 |
| 2257 | 89098 | 89119 | 22 |
| 2258 | 89135 | 89149 | 15 |
| 2259 | 89151 | 89181 | 31 |
| 2260 | 89177 | 89193 | 17 |
| 2261 | 89223 | 89273 | 51 |
| 2262 | 89285 | 89300 | 16 |
| 2263 | 89315 | 89383 | 69 |
| 2264 | 89404 | 89442 | 39 |
| 2265 | 89444 | 89541 | 98 |
| 2266 | 89579 | 89639 | 61 |
| 2267 | 89660 | 89692 | 33 |
| 2268 | 89694 | 89741 | 48 |
| 2269 | 89773 | 89787 | 15 |
| 2270 | 89789 | 89817 | 29 |
| 2271 | 89826 | 89888 | 63 |
| 2272 | 89904 | 89922 | 19 |
| 2273 | 89937 | 89950 | 14 |
| 2274 | 89945 | 89958 | 14 |
| 2275 | 89956 | 89974 | 19 |
| 2276 | 89971 | 89985 | 15 |
| 2277 | 89979 | 89992 | 14 |
| 2278 | 89984 | 90000 | 17 |
| 2279 | 89999 | 90014 | 16 |
| 2280 | 90017 | 90041 | 25 |

TABLE 1-continued

Regions of SEQ ID NO 1 which may be targeted using oligonucleotide of the invention

| Reg. A | Position in SEQ ID NO 1 from | to | Length |
|---|---|---|---|
| 2281 | 90036 | 90049 | 14 |
| 2282 | 90077 | 90093 | 17 |
| 2283 | 90099 | 90128 | 30 |
| 2284 | 90130 | 90155 | 26 |
| 2285 | 90157 | 90200 | 44 |
| 2286 | 90225 | 90256 | 32 |
| 2287 | 90258 | 90293 | 36 |
| 2288 | 90305 | 90318 | 14 |
| 2289 | 90320 | 90352 | 33 |
| 2290 | 90356 | 90370 | 15 |
| 2291 | 90400 | 90421 | 22 |
| 2292 | 90423 | 90461 | 39 |
| 2293 | 90464 | 90507 | 44 |
| 2294 | 90509 | 90530 | 22 |
| 2295 | 90529 | 90542 | 14 |
| 2296 | 90531 | 90567 | 37 |
| 2297 | 90569 | 90612 | 44 |
| 2298 | 90614 | 90730 | 117 |
| 2299 | 90732 | 90758 | 27 |
| 2300 | 90760 | 90885 | 126 |
| 2301 | 90887 | 90918 | 32 |
| 2302 | 90920 | 90946 | 27 |
| 2303 | 90938 | 90955 | 18 |
| 2304 | 90960 | 90973 | 14 |
| 2305 | 90965 | 90981 | 17 |
| 2306 | 90973 | 91000 | 28 |
| 2307 | 90997 | 91011 | 15 |
| 2308 | 91002 | 91019 | 18 |
| 2309 | 91059 | 91140 | 82 |
| 2310 | 91142 | 91157 | 16 |
| 2311 | 91157 | 91194 | 38 |
| 2312 | 91196 | 91231 | 36 |
| 2313 | 91233 | 91251 | 19 |
| 2314 | 91253 | 91274 | 22 |
| 2315 | 91296 | 91310 | 15 |
| 2316 | 91335 | 91367 | 33 |
| 2317 | 91406 | 91442 | 37 |
| 2318 | 91447 | 91477 | 31 |
| 2319 | 91489 | 91509 | 21 |
| 2320 | 91520 | 91621 | 102 |
| 2321 | 91623 | 91674 | 52 |
| 2322 | 91680 | 91703 | 24 |
| 2323 | 91715 | 91731 | 17 |
| 2324 | 91733 | 91771 | 39 |
| 2325 | 91773 | 91788 | 16 |
| 2326 | 91790 | 91805 | 16 |
| 2327 | 91807 | 91823 | 17 |
| 2328 | 91825 | 91859 | 35 |
| 2329 | 91861 | 91900 | 40 |
| 2330 | 91907 | 91926 | 20 |
| 2331 | 91928 | 91943 | 16 |
| 2332 | 91950 | 91980 | 31 |
| 2333 | 91982 | 91996 | 15 |
| 2334 | 91998 | 92011 | 14 |
| 2335 | 92010 | 92027 | 18 |
| 2336 | 92027 | 92067 | 41 |
| 2337 | 92069 | 92126 | 58 |
| 2338 | 92128 | 92321 | 194 |
| 2339 | 92323 | 92540 | 218 |
| 2340 | 92542 | 92558 | 17 |
| 2341 | 92566 | 92684 | 119 |
| 2342 | 92686 | 92726 | 41 |
| 2343 | 92728 | 92837 | 110 |
| 2344 | 92839 | 93032 | 194 |
| 2345 | 93034 | 93094 | 61 |
| 2346 | 93100 | 93209 | 110 |
| 2347 | 93211 | 93254 | 44 |
| 2348 | 93256 | 93323 | 68 |
| 2349 | 93325 | 93448 | 124 |
| 2350 | 93459 | 93477 | 19 |
| 2351 | 93475 | 93497 | 23 |

TABLE 1-continued

Regions of SEQ ID NO 1 which may be targeted using oligonucleotide of the invention

| Reg. A | Position in SEQ ID NO 1 from | to | Length |
|---|---|---|---|
| 2352 | 93509 | 93530 | 22 |
| 2353 | 93532 | 93566 | 35 |
| 2354 | 93568 | 93601 | 34 |
| 2355 | 93606 | 93646 | 41 |
| 2356 | 93668 | 93716 | 49 |
| 2357 | 93718 | 93742 | 25 |
| 2358 | 93744 | 93788 | 45 |
| 2359 | 93790 | 93808 | 19 |
| 2360 | 93811 | 93832 | 22 |
| 2361 | 93874 | 93901 | 28 |
| 2362 | 93904 | 93986 | 83 |
| 2363 | 94021 | 94036 | 16 |
| 2364 | 94038 | 94079 | 42 |
| 2365 | 94073 | 94086 | 14 |
| 2366 | 94097 | 94116 | 20 |
| 2367 | 94118 | 94141 | 24 |
| 2368 | 94140 | 94219 | 80 |
| 2369 | 94242 | 94257 | 16 |
| 2370 | 94264 | 94335 | 72 |
| 2371 | 94337 | 94356 | 20 |
| 2372 | 94358 | 94378 | 21 |
| 2373 | 94373 | 94386 | 14 |
| 2374 | 94384 | 94403 | 20 |
| 2375 | 94405 | 94422 | 18 |
| 2376 | 94453 | 94497 | 45 |
| 2377 | 94497 | 94558 | 62 |
| 2378 | 94560 | 94605 | 46 |
| 2379 | 94630 | 94724 | 95 |
| 2380 | 94739 | 94752 | 14 |
| 2381 | 94755 | 94786 | 32 |
| 2382 | 94800 | 94815 | 16 |
| 2383 | 94872 | 94901 | 30 |
| 2384 | 94903 | 94953 | 51 |
| 2385 | 94955 | 95060 | 106 |
| 2386 | 95070 | 95085 | 16 |
| 2387 | 95093 | 95110 | 18 |
| 2388 | 95135 | 95149 | 15 |
| 2389 | 95154 | 95168 | 15 |
| 2390 | 95170 | 95210 | 41 |
| 2391 | 95227 | 95257 | 31 |
| 2392 | 95302 | 95318 | 17 |
| 2393 | 95311 | 95356 | 46 |
| 2394 | 95359 | 95401 | 43 |
| 2395 | 95403 | 95453 | 51 |
| 2396 | 95450 | 95463 | 14 |
| 2397 | 95475 | 95491 | 17 |
| 2398 | 95503 | 95553 | 51 |
| 2399 | 95555 | 95569 | 15 |
| 2400 | 95583 | 95609 | 27 |
| 2401 | 95634 | 95668 | 35 |
| 2402 | 95718 | 95738 | 21 |
| 2403 | 95727 | 95740 | 14 |
| 2404 | 95836 | 95849 | 14 |
| 2405 | 95851 | 95872 | 22 |
| 2406 | 95874 | 95888 | 15 |
| 2407 | 95890 | 95910 | 21 |
| 2408 | 95912 | 95925 | 14 |
| 2409 | 95938 | 95969 | 32 |
| 2410 | 95973 | 95990 | 18 |
| 2411 | 95992 | 96066 | 75 |
| 2412 | 96073 | 96087 | 15 |
| 2413 | 96103 | 96120 | 18 |
| 2414 | 96122 | 96167 | 46 |
| 2415 | 96169 | 96182 | 14 |
| 2416 | 96183 | 96211 | 29 |
| 2417 | 96213 | 96234 | 22 |
| 2418 | 96246 | 96279 | 34 |
| 2419 | 96300 | 96334 | 35 |
| 2420 | 96358 | 96375 | 18 |
| 2421 | 96377 | 96398 | 22 |
| 2422 | 96424 | 96467 | 44 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 2423 | 96496 | 96518 | 23 |
| 2424 | 96520 | 96535 | 16 |
| 2425 | 96540 | 96566 | 27 |
| 2426 | 96572 | 96592 | 21 |
| 2427 | 96604 | 96646 | 43 |
| 2428 | 96642 | 96655 | 14 |
| 2429 | 96648 | 96667 | 20 |
| 2430 | 96681 | 96728 | 48 |
| 2431 | 96730 | 96781 | 52 |
| 2432 | 96804 | 96829 | 26 |
| 2433 | 96831 | 96879 | 49 |
| 2434 | 96887 | 96916 | 30 |
| 2435 | 96928 | 96944 | 17 |
| 2436 | 96946 | 96959 | 14 |
| 2437 | 96970 | 96990 | 21 |
| 2438 | 96992 | 97021 | 30 |
| 2439 | 97023 | 97037 | 15 |
| 2440 | 97039 | 97073 | 35 |
| 2441 | 97075 | 97366 | 292 |
| 2442 | 97368 | 97393 | 26 |
| 2443 | 97420 | 97466 | 47 |
| 2444 | 97469 | 97507 | 39 |
| 2445 | 97513 | 97529 | 17 |
| 2446 | 97531 | 97583 | 53 |
| 2447 | 97585 | 97600 | 16 |
| 2448 | 97602 | 97631 | 30 |
| 2449 | 97633 | 97683 | 51 |
| 2450 | 97685 | 97703 | 19 |
| 2451 | 97705 | 97742 | 38 |
| 2452 | 97787 | 97803 | 17 |
| 2453 | 97805 | 97822 | 18 |
| 2454 | 97824 | 97876 | 53 |
| 2455 | 97878 | 97921 | 44 |
| 2456 | 97923 | 97943 | 21 |
| 2457 | 97945 | 97963 | 19 |
| 2458 | 97965 | 97994 | 30 |
| 2459 | 97995 | 98011 | 17 |
| 2460 | 98014 | 98044 | 31 |
| 2461 | 98039 | 98061 | 23 |
| 2462 | 98055 | 98076 | 22 |
| 2463 | 98077 | 98090 | 14 |
| 2464 | 98079 | 98092 | 14 |
| 2465 | 98085 | 98098 | 14 |
| 2466 | 98100 | 98115 | 16 |
| 2467 | 98113 | 98145 | 33 |
| 2468 | 98142 | 98160 | 19 |
| 2469 | 98162 | 98180 | 19 |
| 2470 | 98188 | 98219 | 32 |
| 2471 | 98215 | 98237 | 23 |
| 2472 | 98227 | 98240 | 14 |
| 2473 | 98232 | 98255 | 24 |
| 2474 | 98255 | 98268 | 14 |
| 2475 | 98264 | 98287 | 24 |
| 2476 | 98292 | 98326 | 35 |
| 2477 | 98373 | 98397 | 25 |
| 2478 | 98399 | 98428 | 30 |
| 2479 | 98442 | 98461 | 20 |
| 2480 | 98480 | 98501 | 22 |
| 2481 | 98499 | 98520 | 22 |
| 2482 | 98524 | 98538 | 15 |
| 2483 | 98537 | 98550 | 14 |
| 2484 | 98545 | 98585 | 41 |
| 2485 | 98595 | 98610 | 16 |
| 2486 | 98599 | 98624 | 26 |
| 2487 | 98644 | 98668 | 25 |
| 2488 | 98678 | 98704 | 27 |
| 2489 | 98703 | 98718 | 16 |
| 2490 | 98736 | 98754 | 19 |
| 2491 | 98778 | 98794 | 17 |
| 2492 | 98802 | 98821 | 20 |
| 2493 | 98845 | 98876 | 32 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 2494 | 98878 | 98900 | 23 |
| 2495 | 98900 | 98972 | 73 |
| 2496 | 98961 | 98976 | 16 |
| 2497 | 98974 | 98998 | 25 |
| 2498 | 99011 | 99029 | 19 |
| 2499 | 99033 | 99065 | 33 |
| 2500 | 99067 | 99107 | 41 |
| 2501 | 99151 | 99186 | 36 |
| 2502 | 99188 | 99219 | 32 |
| 2503 | 99222 | 99245 | 24 |
| 2504 | 99254 | 99276 | 23 |
| 2505 | 99288 | 99312 | 25 |
| 2506 | 99314 | 99338 | 25 |
| 2507 | 99367 | 99430 | 64 |
| 2508 | 99444 | 99491 | 48 |
| 2509 | 99496 | 99554 | 59 |
| 2510 | 99570 | 99585 | 16 |
| 2511 | 99587 | 99618 | 32 |
| 2512 | 99620 | 99669 | 50 |
| 2513 | 99679 | 99710 | 32 |
| 2514 | 99720 | 99748 | 29 |
| 2515 | 99750 | 99763 | 14 |
| 2516 | 99768 | 99805 | 38 |
| 2517 | 99818 | 99841 | 24 |
| 2518 | 99855 | 99879 | 25 |
| 2519 | 99881 | 99900 | 20 |
| 2520 | 99902 | 99932 | 31 |
| 2521 | 99934 | 99954 | 21 |
| 2522 | 99959 | 100011 | 53 |
| 2523 | 100011 | 100037 | 27 |
| 2524 | 100057 | 100071 | 15 |
| 2525 | 100073 | 100102 | 30 |
| 2526 | 100104 | 100118 | 15 |
| 2527 | 100131 | 100186 | 56 |
| 2528 | 100188 | 100201 | 14 |
| 2529 | 100194 | 100212 | 19 |
| 2530 | 100214 | 100277 | 64 |
| 2531 | 100279 | 100303 | 25 |
| 2532 | 100309 | 100355 | 47 |
| 2533 | 100349 | 100386 | 38 |
| 2534 | 100379 | 100393 | 15 |
| 2535 | 100388 | 100401 | 14 |
| 2536 | 100403 | 100423 | 21 |
| 2537 | 100452 | 100473 | 22 |
| 2538 | 100508 | 100542 | 35 |
| 2539 | 100548 | 100580 | 33 |
| 2540 | 100582 | 100612 | 31 |
| 2541 | 100614 | 100652 | 39 |
| 2542 | 100695 | 100714 | 20 |
| 2543 | 100736 | 100749 | 14 |
| 2544 | 100751 | 100790 | 40 |
| 2545 | 100808 | 100842 | 35 |
| 2546 | 100844 | 100860 | 17 |
| 2547 | 100862 | 100930 | 69 |
| 2548 | 100939 | 100953 | 15 |
| 2549 | 100955 | 100971 | 17 |
| 2550 | 100973 | 101003 | 31 |
| 2551 | 101021 | 101048 | 28 |
| 2552 | 101057 | 101093 | 37 |
| 2553 | 101109 | 101148 | 40 |
| 2554 | 101145 | 101189 | 45 |
| 2555 | 101194 | 101208 | 15 |
| 2556 | 101210 | 101244 | 35 |
| 2557 | 101256 | 101271 | 16 |
| 2558 | 101277 | 101300 | 24 |
| 2559 | 101310 | 101327 | 18 |
| 2560 | 101329 | 101345 | 17 |
| 2561 | 101374 | 101397 | 24 |
| 2562 | 101409 | 101426 | 18 |
| 2563 | 101453 | 101466 | 14 |
| 2564 | 101474 | 101487 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 2565 | 101481 | 101515 | 35 |
| 2566 | 101518 | 101541 | 24 |
| 2567 | 101542 | 101560 | 19 |
| 2568 | 101554 | 101591 | 38 |
| 2569 | 101593 | 101609 | 17 |
| 2570 | 101635 | 101695 | 61 |
| 2571 | 101707 | 101746 | 40 |
| 2572 | 101748 | 101763 | 16 |
| 2573 | 101774 | 101810 | 37 |
| 2574 | 101812 | 101828 | 17 |
| 2575 | 101819 | 101835 | 17 |
| 2576 | 101829 | 101842 | 14 |
| 2577 | 101842 | 101855 | 14 |
| 2578 | 101857 | 101878 | 22 |
| 2579 | 101880 | 101943 | 64 |
| 2580 | 101947 | 101981 | 35 |
| 2581 | 101988 | 102009 | 22 |
| 2582 | 102022 | 102066 | 45 |
| 2583 | 102068 | 102084 | 17 |
| 2584 | 102100 | 102113 | 14 |
| 2585 | 102115 | 102130 | 16 |
| 2586 | 102132 | 102145 | 14 |
| 2587 | 102192 | 102241 | 50 |
| 2588 | 102269 | 102285 | 17 |
| 2589 | 102312 | 102327 | 16 |
| 2590 | 102357 | 102392 | 36 |
| 2591 | 102407 | 102428 | 22 |
| 2592 | 102430 | 102444 | 15 |
| 2593 | 102460 | 102485 | 26 |
| 2594 | 102487 | 102508 | 22 |
| 2595 | 102532 | 102573 | 42 |
| 2596 | 102595 | 102642 | 48 |
| 2597 | 102653 | 102694 | 42 |
| 2598 | 102701 | 102718 | 18 |
| 2599 | 102720 | 102734 | 15 |
| 2600 | 102736 | 102757 | 22 |
| 2601 | 102799 | 102836 | 38 |
| 2602 | 102847 | 102882 | 36 |
| 2603 | 102890 | 102927 | 38 |
| 2604 | 102938 | 102971 | 34 |
| 2605 | 102982 | 103019 | 38 |
| 2606 | 103014 | 103027 | 14 |
| 2607 | 103027 | 103054 | 28 |
| 2608 | 103065 | 103088 | 24 |
| 2609 | 103090 | 103108 | 19 |
| 2610 | 103098 | 103112 | 15 |
| 2611 | 103117 | 103138 | 22 |
| 2612 | 103152 | 103170 | 19 |
| 2613 | 103174 | 103204 | 31 |
| 2614 | 103206 | 103234 | 29 |
| 2615 | 103240 | 103268 | 29 |
| 2616 | 103286 | 103325 | 40 |
| 2617 | 103327 | 103347 | 21 |
| 2618 | 103349 | 103384 | 36 |
| 2619 | 103386 | 103405 | 20 |
| 2620 | 103422 | 103449 | 28 |
| 2621 | 103451 | 103493 | 43 |
| 2622 | 103495 | 103509 | 15 |
| 2623 | 103511 | 103560 | 50 |
| 2624 | 103565 | 103582 | 18 |
| 2625 | 103585 | 103607 | 23 |
| 2626 | 103631 | 103645 | 15 |
| 2627 | 103653 | 103684 | 32 |
| 2628 | 103683 | 103696 | 14 |
| 2629 | 103691 | 103733 | 43 |
| 2630 | 103738 | 103762 | 25 |
| 2631 | 103752 | 103765 | 14 |
| 2632 | 103755 | 103768 | 14 |
| 2633 | 103758 | 103771 | 14 |
| 2634 | 103790 | 103814 | 25 |
| 2635 | 103803 | 103816 | 14 |
| 2636 | 103830 | 103865 | 36 |
| 2637 | 103900 | 103923 | 24 |
| 2638 | 103912 | 103933 | 22 |
| 2639 | 103945 | 103964 | 20 |
| 2640 | 103990 | 104005 | 16 |
| 2641 | 104024 | 104055 | 32 |
| 2642 | 104058 | 104077 | 20 |
| 2643 | 104086 | 104099 | 14 |
| 2644 | 104095 | 104122 | 28 |
| 2645 | 104124 | 104146 | 23 |
| 2646 | 104148 | 104168 | 21 |
| 2647 | 104162 | 104176 | 15 |
| 2648 | 104173 | 104187 | 15 |
| 2649 | 104201 | 104241 | 41 |
| 2650 | 104234 | 104266 | 33 |
| 2651 | 104268 | 104286 | 19 |
| 2652 | 104288 | 104302 | 15 |
| 2653 | 104304 | 104335 | 32 |
| 2654 | 104340 | 104354 | 15 |
| 2655 | 104356 | 104373 | 18 |
| 2656 | 104375 | 104391 | 17 |
| 2657 | 104393 | 104417 | 25 |
| 2658 | 104426 | 104439 | 14 |
| 2659 | 104448 | 104478 | 31 |
| 2660 | 104480 | 104504 | 25 |
| 2661 | 104519 | 104546 | 28 |
| 2662 | 104549 | 104580 | 32 |
| 2663 | 104604 | 104620 | 17 |
| 2664 | 104620 | 104646 | 27 |
| 2665 | 104654 | 104673 | 20 |
| 2666 | 104675 | 104691 | 17 |
| 2667 | 104689 | 104776 | 88 |
| 2668 | 104829 | 104842 | 14 |
| 2669 | 104838 | 104852 | 15 |
| 2670 | 104934 | 104952 | 19 |
| 2671 | 104956 | 104987 | 32 |
| 2672 | 104993 | 105045 | 53 |
| 2673 | 105041 | 105055 | 15 |
| 2674 | 105047 | 105078 | 32 |
| 2675 | 105090 | 105107 | 18 |
| 2676 | 105101 | 105115 | 15 |
| 2677 | 105109 | 105137 | 29 |
| 2678 | 105149 | 105167 | 19 |
| 2679 | 105163 | 105176 | 14 |
| 2680 | 105185 | 105237 | 53 |
| 2681 | 105230 | 105243 | 14 |
| 2682 | 105233 | 105250 | 18 |
| 2683 | 105260 | 105286 | 27 |
| 2684 | 105288 | 105340 | 53 |
| 2685 | 105345 | 105370 | 26 |
| 2686 | 105372 | 105402 | 31 |
| 2687 | 105441 | 105458 | 18 |
| 2688 | 105460 | 105521 | 62 |
| 2689 | 105526 | 105541 | 16 |
| 2690 | 105543 | 105560 | 18 |
| 2691 | 105562 | 105575 | 14 |
| 2692 | 105582 | 105606 | 25 |
| 2693 | 105616 | 105671 | 56 |
| 2694 | 105677 | 105704 | 28 |
| 2695 | 105703 | 105725 | 23 |
| 2696 | 105746 | 105759 | 14 |
| 2697 | 105750 | 105765 | 16 |
| 2698 | 105776 | 105796 | 21 |
| 2699 | 105798 | 105824 | 27 |
| 2700 | 105827 | 105907 | 81 |
| 2701 | 105924 | 105939 | 16 |
| 2702 | 105941 | 105963 | 23 |
| 2703 | 105990 | 106014 | 25 |
| 2704 | 106017 | 106048 | 32 |
| 2705 | 106039 | 106072 | 34 |
| 2706 | 106061 | 106074 | 14 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 2707 | 106073 | 106102 | 30 |
| 2708 | 106092 | 106107 | 16 |
| 2709 | 106114 | 106159 | 46 |
| 2710 | 106161 | 106180 | 20 |
| 2711 | 106197 | 106243 | 47 |
| 2712 | 106237 | 106250 | 14 |
| 2713 | 106243 | 106256 | 14 |
| 2714 | 106247 | 106267 | 21 |
| 2715 | 106273 | 106333 | 61 |
| 2716 | 106335 | 106367 | 33 |
| 2717 | 106369 | 106417 | 49 |
| 2718 | 106419 | 106471 | 53 |
| 2719 | 106486 | 106523 | 38 |
| 2720 | 106525 | 106538 | 14 |
| 2721 | 106552 | 106572 | 21 |
| 2722 | 106584 | 106598 | 15 |
| 2723 | 106609 | 106696 | 88 |
| 2724 | 106698 | 106723 | 26 |
| 2725 | 106725 | 106740 | 16 |
| 2726 | 106743 | 106781 | 39 |
| 2727 | 106783 | 106811 | 29 |
| 2728 | 106826 | 106866 | 41 |
| 2729 | 106875 | 106902 | 28 |
| 2730 | 106916 | 106935 | 20 |
| 2731 | 106942 | 106960 | 19 |
| 2732 | 106991 | 107010 | 20 |
| 2733 | 107019 | 107038 | 20 |
| 2734 | 107040 | 107072 | 33 |
| 2735 | 107079 | 107094 | 16 |
| 2736 | 107087 | 107101 | 15 |
| 2737 | 107090 | 107109 | 20 |
| 2738 | 107113 | 107127 | 15 |
| 2739 | 107129 | 107143 | 15 |
| 2740 | 107154 | 107172 | 19 |
| 2741 | 107174 | 107198 | 25 |
| 2742 | 107210 | 107226 | 17 |
| 2743 | 107226 | 107239 | 14 |
| 2744 | 107237 | 107274 | 38 |
| 2745 | 107296 | 107356 | 61 |
| 2746 | 107358 | 107381 | 24 |
| 2747 | 107383 | 107415 | 33 |
| 2748 | 107417 | 107433 | 17 |
| 2749 | 107435 | 107455 | 21 |
| 2750 | 107457 | 107508 | 52 |
| 2751 | 107510 | 107525 | 16 |
| 2752 | 107527 | 107546 | 20 |
| 2753 | 107559 | 107573 | 15 |
| 2754 | 107586 | 107617 | 32 |
| 2755 | 107643 | 107689 | 47 |
| 2756 | 107694 | 107716 | 23 |
| 2757 | 107744 | 107792 | 49 |
| 2758 | 107790 | 107832 | 43 |
| 2759 | 107834 | 107860 | 27 |
| 2760 | 107864 | 107896 | 33 |
| 2761 | 107898 | 107912 | 15 |
| 2762 | 107914 | 107953 | 40 |
| 2763 | 107967 | 107992 | 26 |
| 2764 | 107994 | 108008 | 15 |
| 2765 | 108010 | 108038 | 29 |
| 2766 | 108065 | 108084 | 20 |
| 2767 | 108113 | 108215 | 103 |
| 2768 | 108220 | 108249 | 30 |
| 2769 | 108253 | 108281 | 29 |
| 2770 | 108283 | 108304 | 22 |
| 2771 | 108317 | 108359 | 43 |
| 2772 | 108361 | 108375 | 15 |
| 2773 | 108386 | 108402 | 17 |
| 2774 | 108421 | 108440 | 20 |
| 2775 | 108538 | 108551 | 14 |
| 2776 | 108561 | 108575 | 15 |
| 2777 | 108577 | 108616 | 40 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 2778 | 108618 | 108665 | 48 |
| 2779 | 108677 | 108707 | 31 |
| 2780 | 108735 | 108768 | 34 |
| 2781 | 108762 | 108777 | 16 |
| 2782 | 108780 | 108824 | 45 |
| 2783 | 108842 | 108885 | 44 |
| 2784 | 108907 | 108970 | 64 |
| 2785 | 108983 | 109019 | 37 |
| 2786 | 109021 | 109053 | 33 |
| 2787 | 109055 | 109068 | 14 |
| 2788 | 109070 | 109099 | 30 |
| 2789 | 109097 | 109122 | 26 |
| 2790 | 109113 | 109132 | 20 |
| 2791 | 109125 | 109165 | 41 |
| 2792 | 109167 | 109181 | 15 |
| 2793 | 109183 | 109200 | 18 |
| 2794 | 109214 | 109248 | 35 |
| 2795 | 109256 | 109277 | 22 |
| 2796 | 109281 | 109298 | 18 |
| 2797 | 109298 | 109311 | 14 |
| 2798 | 109300 | 109318 | 19 |
| 2799 | 109324 | 109374 | 51 |
| 2800 | 109377 | 109397 | 21 |
| 2801 | 109399 | 109437 | 39 |
| 2802 | 109446 | 109461 | 16 |
| 2803 | 109463 | 109476 | 14 |
| 2804 | 109472 | 109485 | 14 |
| 2805 | 109478 | 109514 | 37 |
| 2806 | 109516 | 109540 | 25 |
| 2807 | 109556 | 109588 | 33 |
| 2808 | 109601 | 109644 | 44 |
| 2809 | 109661 | 109681 | 21 |
| 2810 | 109683 | 109709 | 27 |
| 2811 | 109707 | 109737 | 31 |
| 2812 | 109739 | 109754 | 16 |
| 2813 | 109754 | 109768 | 15 |
| 2814 | 109770 | 109798 | 29 |
| 2815 | 109810 | 109829 | 20 |
| 2816 | 109859 | 109877 | 19 |
| 2817 | 109879 | 109934 | 56 |
| 2818 | 109955 | 109975 | 21 |
| 2819 | 109975 | 109988 | 14 |
| 2820 | 109994 | 110096 | 103 |
| 2821 | 110103 | 110129 | 27 |
| 2822 | 110131 | 110152 | 22 |
| 2823 | 110153 | 110173 | 21 |
| 2824 | 110175 | 110195 | 21 |
| 2825 | 110192 | 110226 | 35 |
| 2826 | 110297 | 110312 | 16 |
| 2827 | 110301 | 110314 | 14 |
| 2828 | 110308 | 110333 | 26 |
| 2829 | 110335 | 110351 | 17 |
| 2830 | 110353 | 110368 | 16 |
| 2831 | 110376 | 110401 | 26 |
| 2832 | 110418 | 110462 | 45 |
| 2833 | 110464 | 110481 | 18 |
| 2834 | 110531 | 110558 | 28 |
| 2835 | 110571 | 110590 | 20 |
| 2836 | 110599 | 110639 | 41 |
| 2837 | 110630 | 110643 | 14 |
| 2838 | 110641 | 110661 | 21 |
| 2839 | 110668 | 110681 | 14 |
| 2840 | 110683 | 110709 | 27 |
| 2841 | 110717 | 110798 | 82 |
| 2842 | 110804 | 110849 | 46 |
| 2843 | 110853 | 110890 | 38 |
| 2844 | 110928 | 110966 | 39 |
| 2845 | 110971 | 111003 | 33 |
| 2846 | 111000 | 111013 | 14 |
| 2847 | 111015 | 111033 | 19 |
| 2848 | 111035 | 111050 | 16 |

TABLE 1-continued

Regions of SEQ ID NO 1 which may be targeted using oligonucleotide of the invention

| Reg. A | Position in SEQ ID NO 1 from | to | Length |
|---|---|---|---|
| 2849 | 111062 | 111094 | 33 |
| 2850 | 111092 | 111105 | 14 |
| 2851 | 111107 | 111140 | 34 |
| 2852 | 111161 | 111203 | 43 |
| 2853 | 111209 | 111223 | 15 |
| 2854 | 111224 | 111280 | 57 |
| 2855 | 111275 | 111290 | 16 |
| 2856 | 111283 | 111303 | 21 |
| 2857 | 111305 | 111320 | 16 |
| 2858 | 111311 | 111347 | 37 |
| 2859 | 111355 | 111368 | 14 |
| 2860 | 111357 | 111371 | 15 |
| 2861 | 111360 | 111381 | 22 |
| 2862 | 111373 | 111421 | 49 |
| 2863 | 111412 | 111426 | 15 |
| 2864 | 111451 | 111468 | 18 |
| 2865 | 111467 | 111480 | 14 |
| 2866 | 111482 | 111496 | 15 |
| 2867 | 111486 | 111500 | 15 |
| 2868 | 111497 | 111510 | 14 |
| 2869 | 111531 | 111564 | 34 |
| 2870 | 111580 | 111606 | 27 |
| 2871 | 111616 | 111637 | 22 |
| 2872 | 111658 | 111671 | 14 |
| 2873 | 111674 | 111688 | 15 |
| 2874 | 111692 | 111710 | 19 |
| 2875 | 111712 | 111725 | 14 |
| 2876 | 111727 | 111761 | 35 |
| 2877 | 111781 | 111804 | 24 |
| 2878 | 111811 | 111828 | 18 |
| 2879 | 111831 | 111849 | 19 |
| 2880 | 111856 | 111871 | 16 |
| 2881 | 111901 | 111917 | 17 |
| 2882 | 111919 | 111940 | 22 |
| 2883 | 111942 | 111987 | 46 |
| 2884 | 111984 | 112002 | 19 |
| 2885 | 112004 | 112069 | 66 |
| 2886 | 112070 | 112091 | 22 |
| 2887 | 112093 | 112116 | 24 |
| 2888 | 112118 | 112132 | 15 |
| 2889 | 112139 | 112170 | 32 |
| 2890 | 112180 | 112196 | 17 |
| 2891 | 112204 | 112223 | 20 |
| 2892 | 112236 | 112283 | 48 |
| 2893 | 112329 | 112343 | 15 |
| 2894 | 112345 | 112383 | 39 |
| 2895 | 112385 | 112401 | 17 |
| 2896 | 112404 | 112423 | 20 |
| 2897 | 112463 | 112477 | 15 |
| 2898 | 112485 | 112547 | 63 |
| 2899 | 112563 | 112581 | 19 |
| 2900 | 112583 | 112597 | 15 |
| 2901 | 112607 | 112638 | 32 |
| 2902 | 112640 | 112664 | 25 |
| 2903 | 112683 | 112721 | 39 |
| 2904 | 112730 | 112759 | 30 |
| 2905 | 112773 | 112811 | 39 |
| 2906 | 112811 | 112825 | 15 |
| 2907 | 112828 | 112862 | 35 |
| 2908 | 112882 | 112912 | 31 |
| 2909 | 112914 | 112967 | 54 |
| 2910 | 112968 | 112982 | 15 |
| 2911 | 112984 | 113016 | 33 |
| 2912 | 113044 | 113064 | 21 |
| 2913 | 113074 | 113097 | 24 |
| 2914 | 113111 | 113153 | 43 |
| 2915 | 113169 | 113194 | 26 |
| 2916 | 113198 | 113212 | 15 |
| 2917 | 113214 | 113230 | 17 |
| 2918 | 113232 | 113263 | 32 |
| 2919 | 113265 | 113284 | 20 |

TABLE 1-continued

Regions of SEQ ID NO 1 which may be targeted using oligonucleotide of the invention

| Reg. A | Position in SEQ ID NO 1 from | to | Length |
|---|---|---|---|
| 2920 | 113306 | 113328 | 23 |
| 2921 | 113330 | 113355 | 26 |
| 2922 | 113357 | 113371 | 15 |
| 2923 | 113404 | 113422 | 19 |
| 2924 | 113421 | 113489 | 69 |
| 2925 | 113533 | 113559 | 27 |
| 2926 | 113561 | 113574 | 14 |
| 2927 | 113595 | 113616 | 22 |
| 2928 | 113648 | 113700 | 53 |
| 2929 | 113702 | 113739 | 38 |
| 2930 | 113762 | 113823 | 62 |
| 2931 | 113825 | 113960 | 136 |
| 2932 | 113962 | 114015 | 54 |
| 2933 | 114017 | 114048 | 32 |
| 2934 | 114045 | 114124 | 80 |
| 2935 | 114151 | 114170 | 20 |
| 2936 | 114182 | 114218 | 37 |
| 2937 | 114230 | 114270 | 41 |
| 2938 | 114272 | 114292 | 21 |
| 2939 | 114296 | 114339 | 44 |
| 2940 | 114354 | 114433 | 80 |
| 2941 | 114440 | 114457 | 18 |
| 2942 | 114459 | 114484 | 26 |
| 2943 | 114478 | 114536 | 59 |
| 2944 | 114538 | 114559 | 22 |
| 2945 | 114567 | 114592 | 26 |
| 2946 | 114594 | 114610 | 17 |
| 2947 | 114612 | 114652 | 41 |
| 2948 | 114681 | 114752 | 72 |
| 2949 | 114775 | 114805 | 31 |
| 2950 | 114803 | 114816 | 14 |
| 2951 | 114807 | 114821 | 15 |
| 2952 | 114823 | 114847 | 25 |
| 2953 | 114868 | 114912 | 45 |
| 2954 | 114947 | 114961 | 15 |
| 2955 | 114974 | 114997 | 24 |
| 2956 | 115001 | 115015 | 15 |
| 2957 | 115004 | 115017 | 14 |
| 2958 | 115019 | 115069 | 51 |
| 2959 | 115060 | 115073 | 14 |
| 2960 | 115072 | 115085 | 14 |
| 2961 | 115087 | 115100 | 14 |
| 2962 | 115102 | 115124 | 23 |
| 2963 | 115132 | 115151 | 20 |
| 2964 | 115154 | 115168 | 15 |
| 2965 | 115188 | 115208 | 21 |
| 2966 | 115219 | 115256 | 38 |
| 2967 | 115258 | 115283 | 26 |
| 2968 | 115285 | 115300 | 16 |
| 2969 | 115331 | 115353 | 23 |
| 2970 | 115355 | 115372 | 18 |
| 2971 | 115380 | 115397 | 18 |
| 2972 | 115399 | 115412 | 14 |
| 2973 | 115426 | 115475 | 50 |
| 2974 | 115496 | 115510 | 15 |
| 2975 | 115521 | 115545 | 25 |
| 2976 | 115555 | 115580 | 26 |
| 2977 | 115582 | 115600 | 19 |
| 2978 | 115602 | 115621 | 20 |
| 2979 | 115653 | 115677 | 25 |
| 2980 | 115692 | 115720 | 29 |
| 2981 | 115722 | 115738 | 17 |
| 2982 | 115769 | 115783 | 15 |
| 2983 | 115792 | 115808 | 17 |
| 2984 | 115819 | 115837 | 19 |
| 2985 | 115846 | 115878 | 33 |
| 2986 | 115888 | 115901 | 14 |
| 2987 | 115916 | 115932 | 17 |
| 2988 | 115943 | 115956 | 14 |
| 2989 | 115967 | 115993 | 27 |
| 2990 | 115996 | 116014 | 19 |

TABLE 1-continued

Regions of SEQ ID NO 1 which may be targeted using oligonucleotide of the invention

| Reg. A | Position in SEQ ID NO 1 from | to | Length |
|---|---|---|---|
| 2991 | 116027 | 116045 | 19 |
| 2992 | 116105 | 116127 | 23 |
| 2993 | 116126 | 116139 | 14 |
| 2994 | 116141 | 116158 | 18 |
| 2995 | 116171 | 116186 | 16 |
| 2996 | 116194 | 116208 | 15 |
| 2997 | 116257 | 116279 | 23 |
| 2998 | 116318 | 116373 | 56 |
| 2999 | 116375 | 116437 | 63 |
| 3000 | 116439 | 116454 | 16 |
| 3001 | 116456 | 116496 | 41 |
| 3002 | 116500 | 116532 | 33 |
| 3003 | 116534 | 116554 | 21 |
| 3004 | 116556 | 116573 | 18 |
| 3005 | 116575 | 116592 | 18 |
| 3006 | 116596 | 116615 | 20 |
| 3007 | 116617 | 116650 | 34 |
| 3008 | 116650 | 116664 | 15 |
| 3009 | 116666 | 116694 | 29 |
| 3010 | 116775 | 116792 | 18 |
| 3011 | 116794 | 116811 | 18 |
| 3012 | 116813 | 116838 | 26 |
| 3013 | 116840 | 116872 | 33 |
| 3014 | 116890 | 116911 | 22 |
| 3015 | 116921 | 116948 | 28 |
| 3016 | 116952 | 116988 | 37 |
| 3017 | 116990 | 117006 | 17 |
| 3018 | 117008 | 117036 | 29 |
| 3019 | 117059 | 117133 | 75 |
| 3020 | 117187 | 117207 | 21 |
| 3021 | 117204 | 117217 | 14 |
| 3022 | 117209 | 117237 | 29 |
| 3023 | 117239 | 117252 | 14 |
| 3024 | 117255 | 117275 | 21 |
| 3025 | 117277 | 117300 | 24 |
| 3026 | 117337 | 117371 | 35 |
| 3027 | 117373 | 117416 | 44 |
| 3028 | 117418 | 117450 | 33 |
| 3029 | 117456 | 117507 | 52 |
| 3030 | 117518 | 117532 | 15 |
| 3031 | 117534 | 117590 | 57 |
| 3032 | 117582 | 117604 | 23 |
| 3033 | 117593 | 117617 | 25 |
| 3034 | 117621 | 117648 | 28 |
| 3035 | 117640 | 117662 | 23 |
| 3036 | 117664 | 117688 | 25 |
| 3037 | 117690 | 117711 | 22 |
| 3038 | 117728 | 117743 | 16 |
| 3039 | 117747 | 117781 | 35 |
| 3040 | 117784 | 117801 | 18 |
| 3041 | 117792 | 117822 | 31 |
| 3042 | 117824 | 117842 | 19 |
| 3043 | 117850 | 117869 | 20 |
| 3044 | 117890 | 117940 | 51 |
| 3045 | 117936 | 117968 | 33 |
| 3046 | 117970 | 117990 | 21 |
| 3047 | 117989 | 118034 | 46 |
| 3048 | 118034 | 118057 | 24 |
| 3049 | 118061 | 118083 | 23 |
| 3050 | 118086 | 118122 | 37 |
| 3051 | 118122 | 118182 | 61 |
| 3052 | 118172 | 118186 | 15 |
| 3053 | 118197 | 118211 | 15 |
| 3054 | 118216 | 118275 | 60 |
| 3055 | 118291 | 118316 | 26 |
| 3056 | 118318 | 118354 | 37 |
| 3057 | 118373 | 118388 | 16 |
| 3058 | 118391 | 118405 | 15 |
| 3059 | 118407 | 118423 | 17 |
| 3060 | 118425 | 118456 | 32 |
| 3061 | 118465 | 118492 | 28 |

TABLE 1-continued

Regions of SEQ ID NO 1 which may be targeted using oligonucleotide of the invention

| Reg. A | Position in SEQ ID NO 1 from | to | Length |
|---|---|---|---|
| 3062 | 118498 | 118521 | 24 |
| 3063 | 118533 | 118551 | 19 |
| 3064 | 118553 | 118581 | 29 |
| 3065 | 118587 | 118617 | 31 |
| 3066 | 118620 | 118679 | 60 |
| 3067 | 118687 | 118716 | 30 |
| 3068 | 118731 | 118771 | 41 |
| 3069 | 118779 | 118805 | 27 |
| 3070 | 118816 | 118830 | 15 |
| 3071 | 118832 | 118895 | 64 |
| 3072 | 118910 | 119065 | 156 |
| 3073 | 119067 | 119081 | 15 |
| 3074 | 119095 | 119140 | 46 |
| 3075 | 119170 | 119205 | 36 |
| 3076 | 119210 | 119232 | 23 |
| 3077 | 119230 | 119246 | 17 |
| 3078 | 119236 | 119252 | 17 |
| 3079 | 119255 | 119274 | 20 |
| 3080 | 119271 | 119284 | 14 |
| 3081 | 119290 | 119307 | 18 |
| 3082 | 119320 | 119335 | 16 |
| 3083 | 119357 | 119463 | 107 |
| 3084 | 119465 | 119483 | 19 |
| 3085 | 119485 | 119535 | 51 |
| 3086 | 119550 | 119571 | 22 |
| 3087 | 119577 | 119608 | 32 |
| 3088 | 119610 | 119646 | 37 |
| 3089 | 119648 | 119688 | 41 |
| 3090 | 119713 | 119752 | 40 |
| 3091 | 119743 | 119784 | 42 |
| 3092 | 119786 | 119800 | 15 |
| 3093 | 119822 | 119836 | 15 |
| 3094 | 119830 | 119847 | 18 |
| 3095 | 119849 | 119900 | 52 |
| 3096 | 119912 | 119925 | 14 |
| 3097 | 119960 | 119982 | 23 |
| 3098 | 119984 | 120013 | 30 |
| 3099 | 120038 | 120054 | 17 |
| 3100 | 120057 | 120090 | 34 |
| 3101 | 120092 | 120134 | 43 |
| 3102 | 120138 | 120154 | 17 |
| 3103 | 120157 | 120189 | 33 |
| 3104 | 120187 | 120200 | 14 |
| 3105 | 120191 | 120211 | 21 |
| 3106 | 120225 | 120239 | 15 |
| 3107 | 120242 | 120267 | 26 |
| 3108 | 120271 | 120301 | 31 |
| 3109 | 120320 | 120340 | 21 |
| 3110 | 120363 | 120406 | 44 |
| 3111 | 120406 | 120421 | 16 |
| 3112 | 120414 | 120468 | 55 |
| 3113 | 120457 | 120470 | 14 |
| 3114 | 120487 | 120518 | 32 |
| 3115 | 120545 | 120563 | 19 |
| 3116 | 120567 | 120587 | 21 |
| 3117 | 120589 | 120625 | 37 |
| 3118 | 120619 | 120633 | 15 |
| 3119 | 120650 | 120663 | 14 |
| 3120 | 120676 | 120694 | 19 |
| 3121 | 120703 | 120717 | 15 |
| 3122 | 120721 | 120737 | 17 |
| 3123 | 120755 | 120812 | 58 |
| 3124 | 120816 | 120838 | 23 |
| 3125 | 120843 | 120871 | 29 |
| 3126 | 120873 | 120899 | 27 |
| 3127 | 120903 | 120922 | 20 |
| 3128 | 120933 | 120946 | 14 |
| 3129 | 120936 | 120981 | 46 |
| 3130 | 120983 | 121004 | 22 |
| 3131 | 121006 | 121021 | 16 |
| 3132 | 121023 | 121036 | 14 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 3133 | 121035 | 121061 | 27 |
| 3134 | 121063 | 121079 | 17 |
| 3135 | 121081 | 121097 | 17 |
| 3136 | 121105 | 121134 | 30 |
| 3137 | 121138 | 121156 | 19 |
| 3138 | 121155 | 121168 | 14 |
| 3139 | 121158 | 121174 | 17 |
| 3140 | 121166 | 121189 | 24 |
| 3141 | 121194 | 121208 | 15 |
| 3142 | 121201 | 121218 | 18 |
| 3143 | 121213 | 121237 | 25 |
| 3144 | 121246 | 121271 | 26 |
| 3145 | 121298 | 121314 | 17 |
| 3146 | 121311 | 121324 | 14 |
| 3147 | 121327 | 121351 | 25 |
| 3148 | 121359 | 121388 | 30 |
| 3149 | 121390 | 121419 | 30 |
| 3150 | 121446 | 121462 | 17 |
| 3151 | 121468 | 121487 | 20 |
| 3152 | 121499 | 121515 | 17 |
| 3153 | 121517 | 121543 | 27 |
| 3154 | 121545 | 121564 | 20 |
| 3155 | 121575 | 121597 | 23 |
| 3156 | 121599 | 121617 | 19 |
| 3157 | 121619 | 121662 | 44 |
| 3158 | 121664 | 121681 | 18 |
| 3159 | 121683 | 121700 | 18 |
| 3160 | 121702 | 121751 | 50 |
| 3161 | 121773 | 121788 | 16 |
| 3162 | 121790 | 121805 | 16 |
| 3163 | 121807 | 121834 | 28 |
| 3164 | 121836 | 121857 | 22 |
| 3165 | 121859 | 121874 | 16 |
| 3166 | 121877 | 121925 | 49 |
| 3167 | 121923 | 121936 | 14 |
| 3168 | 121928 | 121943 | 16 |
| 3169 | 121962 | 121976 | 15 |
| 3170 | 121978 | 121992 | 15 |
| 3171 | 122004 | 122028 | 25 |
| 3172 | 122030 | 122056 | 27 |
| 3173 | 122046 | 122059 | 14 |
| 3174 | 122052 | 122072 | 21 |
| 3175 | 122080 | 122095 | 16 |
| 3176 | 122099 | 122122 | 24 |
| 3177 | 122143 | 122163 | 21 |
| 3178 | 122169 | 122189 | 21 |
| 3179 | 122258 | 122274 | 17 |
| 3180 | 122289 | 122309 | 21 |
| 3181 | 122311 | 122346 | 36 |
| 3182 | 122357 | 122395 | 39 |
| 3183 | 122446 | 122468 | 23 |
| 3184 | 122471 | 122489 | 19 |
| 3185 | 122491 | 122512 | 22 |
| 3186 | 122526 | 122541 | 16 |
| 3187 | 122543 | 122557 | 15 |
| 3188 | 122579 | 122592 | 14 |
| 3189 | 122606 | 122653 | 48 |
| 3190 | 122663 | 122690 | 28 |
| 3191 | 122728 | 122742 | 15 |
| 3192 | 122757 | 122770 | 14 |
| 3193 | 122779 | 122840 | 62 |
| 3194 | 122842 | 122857 | 16 |
| 3195 | 122900 | 122923 | 24 |
| 3196 | 122933 | 122955 | 23 |
| 3197 | 122968 | 123042 | 75 |
| 3198 | 123055 | 123076 | 22 |
| 3199 | 123094 | 123108 | 15 |
| 3200 | 123114 | 123134 | 21 |
| 3201 | 123143 | 123160 | 18 |
| 3202 | 123162 | 123180 | 19 |
| 3203 | 123184 | 123198 | 15 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 3204 | 123200 | 123235 | 36 |
| 3205 | 123237 | 123321 | 85 |
| 3206 | 123314 | 123329 | 16 |
| 3207 | 123342 | 123360 | 19 |
| 3208 | 123356 | 123389 | 34 |
| 3209 | 123391 | 123410 | 20 |
| 3210 | 123412 | 123453 | 42 |
| 3211 | 123455 | 123485 | 31 |
| 3212 | 123488 | 123503 | 16 |
| 3213 | 123506 | 123524 | 19 |
| 3214 | 123526 | 123543 | 18 |
| 3215 | 123545 | 123578 | 34 |
| 3216 | 123598 | 123634 | 37 |
| 3217 | 123654 | 123683 | 30 |
| 3218 | 123685 | 123706 | 22 |
| 3219 | 123710 | 123774 | 65 |
| 3220 | 123803 | 123816 | 14 |
| 3221 | 123818 | 123831 | 14 |
| 3222 | 123896 | 123939 | 44 |
| 3223 | 123941 | 123974 | 34 |
| 3224 | 123976 | 124021 | 46 |
| 3225 | 124026 | 124040 | 15 |
| 3226 | 124042 | 124079 | 38 |
| 3227 | 124091 | 124109 | 19 |
| 3228 | 124158 | 124185 | 28 |
| 3229 | 124238 | 124274 | 37 |
| 3230 | 124319 | 124332 | 14 |
| 3231 | 124335 | 124373 | 39 |
| 3232 | 124394 | 124412 | 19 |
| 3233 | 124419 | 124445 | 27 |
| 3234 | 124450 | 124470 | 21 |
| 3235 | 124472 | 124493 | 22 |
| 3236 | 124499 | 124520 | 22 |
| 3237 | 124522 | 124561 | 40 |
| 3238 | 124564 | 124595 | 32 |
| 3239 | 124607 | 124649 | 43 |
| 3240 | 124662 | 124729 | 68 |
| 3241 | 124750 | 124767 | 18 |
| 3242 | 124769 | 124793 | 25 |
| 3243 | 124812 | 124828 | 17 |
| 3244 | 124853 | 124906 | 54 |
| 3245 | 124923 | 124948 | 26 |
| 3246 | 124958 | 124986 | 29 |
| 3247 | 125023 | 125042 | 20 |
| 3248 | 125032 | 125046 | 15 |
| 3249 | 125065 | 125083 | 19 |
| 3250 | 125073 | 125091 | 19 |
| 3251 | 125093 | 125107 | 15 |
| 3252 | 125132 | 125149 | 18 |
| 3253 | 125139 | 125154 | 16 |
| 3254 | 125151 | 125200 | 50 |
| 3255 | 125201 | 125274 | 74 |
| 3256 | 125314 | 125329 | 16 |
| 3257 | 125331 | 125370 | 40 |
| 3258 | 125372 | 125386 | 15 |
| 3259 | 125411 | 125431 | 21 |
| 3260 | 125433 | 125462 | 30 |
| 3261 | 125475 | 125562 | 88 |
| 3262 | 125564 | 125589 | 26 |
| 3263 | 125605 | 125639 | 35 |
| 3264 | 125641 | 125699 | 59 |
| 3265 | 125719 | 125732 | 14 |
| 3266 | 125737 | 125769 | 33 |
| 3267 | 125815 | 125829 | 15 |
| 3268 | 125834 | 125848 | 15 |
| 3269 | 125850 | 125884 | 35 |
| 3270 | 125899 | 125966 | 68 |
| 3271 | 125967 | 125999 | 33 |
| 3272 | 126026 | 126080 | 55 |
| 3273 | 126097 | 126115 | 19 |
| 3274 | 126130 | 126149 | 20 |

TABLE 1-continued

Regions of SEQ ID NO 1 which may be targeted using oligonucleotide of the invention

| Reg. A | Position in SEQ ID NO 1 from | to | Length |
|---|---|---|---|
| 3275 | 126151 | 126179 | 29 |
| 3276 | 126186 | 126238 | 53 |
| 3277 | 126241 | 126279 | 39 |
| 3278 | 126275 | 126295 | 21 |
| 3279 | 126297 | 126312 | 16 |
| 3280 | 126320 | 126363 | 44 |
| 3281 | 126376 | 126395 | 20 |
| 3282 | 126406 | 126419 | 14 |
| 3283 | 126420 | 126442 | 23 |
| 3284 | 126467 | 126501 | 35 |
| 3285 | 126503 | 126538 | 36 |
| 3286 | 126566 | 126580 | 15 |
| 3287 | 126584 | 126597 | 14 |
| 3288 | 126620 | 126653 | 34 |
| 3289 | 126654 | 126694 | 41 |
| 3290 | 126697 | 126715 | 19 |
| 3291 | 126764 | 126777 | 14 |
| 3292 | 126792 | 126828 | 37 |
| 3293 | 126842 | 126862 | 21 |
| 3294 | 126866 | 126879 | 14 |
| 3295 | 126881 | 126897 | 17 |
| 3296 | 126906 | 126925 | 20 |
| 3297 | 126956 | 126987 | 32 |
| 3298 | 126989 | 127023 | 35 |
| 3299 | 127026 | 127135 | 110 |
| 3300 | 127142 | 127174 | 33 |
| 3301 | 127176 | 127191 | 16 |
| 3302 | 127193 | 127217 | 25 |
| 3303 | 127229 | 127253 | 25 |
| 3304 | 127255 | 127280 | 26 |
| 3305 | 127294 | 127394 | 101 |
| 3306 | 127396 | 127415 | 20 |
| 3307 | 127417 | 127478 | 62 |
| 3308 | 127491 | 127504 | 14 |
| 3309 | 127506 | 127530 | 25 |
| 3310 | 127542 | 127566 | 25 |
| 3311 | 127582 | 127628 | 47 |
| 3312 | 127654 | 127675 | 22 |
| 3313 | 127681 | 127706 | 26 |
| 3314 | 127706 | 127739 | 34 |
| 3315 | 127769 | 127792 | 24 |
| 3316 | 127808 | 127829 | 22 |
| 3317 | 127839 | 127888 | 50 |
| 3318 | 127900 | 127932 | 33 |
| 3319 | 127943 | 127975 | 33 |
| 3320 | 127988 | 128046 | 59 |
| 3321 | 128048 | 128069 | 22 |
| 3322 | 128068 | 128106 | 39 |
| 3323 | 128105 | 128118 | 14 |
| 3324 | 128121 | 128157 | 37 |
| 3325 | 128159 | 128188 | 30 |
| 3326 | 128190 | 128268 | 79 |
| 3327 | 128279 | 128317 | 39 |
| 3328 | 128321 | 128335 | 15 |
| 3329 | 128342 | 128368 | 27 |
| 3330 | 128374 | 128446 | 73 |
| 3331 | 128444 | 128540 | 97 |
| 3332 | 128546 | 128586 | 41 |
| 3333 | 128588 | 128640 | 53 |
| 3334 | 128642 | 128674 | 33 |
| 3335 | 128675 | 128879 | 205 |
| 3336 | 128881 | 128936 | 56 |
| 3337 | 128934 | 129000 | 67 |
| 3338 | 129002 | 129060 | 59 |
| 3339 | 129074 | 129100 | 27 |
| 3340 | 129107 | 129123 | 17 |
| 3341 | 129125 | 129163 | 39 |
| 3342 | 129168 | 129230 | 63 |
| 3343 | 129264 | 129277 | 14 |
| 3344 | 129284 | 129318 | 35 |
| 3345 | 129320 | 129346 | 27 |

TABLE 1-continued

Regions of SEQ ID NO 1 which may be targeted using oligonucleotide of the invention

| Reg. A | Position in SEQ ID NO 1 from | to | Length |
|---|---|---|---|
| 3346 | 129357 | 129391 | 35 |
| 3347 | 129393 | 129420 | 28 |
| 3348 | 129447 | 129485 | 39 |
| 3349 | 129489 | 129504 | 16 |
| 3350 | 129514 | 129540 | 27 |
| 3351 | 129550 | 129563 | 14 |
| 3352 | 129559 | 129595 | 37 |
| 3353 | 129606 | 129627 | 22 |
| 3354 | 129633 | 129681 | 49 |
| 3355 | 129683 | 129697 | 15 |
| 3356 | 129699 | 129716 | 18 |
| 3357 | 129706 | 129738 | 33 |
| 3358 | 129757 | 129790 | 34 |
| 3359 | 129792 | 129820 | 29 |
| 3360 | 129812 | 129846 | 35 |
| 3361 | 129851 | 129867 | 17 |
| 3362 | 129869 | 129883 | 15 |
| 3363 | 129885 | 129915 | 31 |
| 3364 | 129917 | 129955 | 39 |
| 3365 | 129957 | 130046 | 90 |
| 3366 | 130042 | 130070 | 29 |
| 3367 | 130110 | 130156 | 47 |
| 3368 | 130158 | 130309 | 152 |
| 3369 | 130311 | 130373 | 63 |
| 3370 | 130375 | 130391 | 17 |
| 3371 | 130407 | 130429 | 23 |
| 3372 | 130439 | 130461 | 23 |
| 3373 | 130475 | 130507 | 33 |
| 3374 | 130512 | 130550 | 39 |
| 3375 | 130552 | 130582 | 31 |
| 3376 | 130584 | 130614 | 31 |
| 3377 | 130616 | 130764 | 149 |
| 3378 | 130766 | 130869 | 104 |
| 3379 | 130871 | 131021 | 151 |
| 3380 | 131033 | 131051 | 19 |
| 3381 | 131092 | 131105 | 14 |
| 3382 | 131112 | 131188 | 77 |
| 3383 | 131194 | 131237 | 44 |
| 3384 | 131233 | 131247 | 15 |
| 3385 | 131236 | 131287 | 52 |
| 3386 | 131292 | 131307 | 16 |
| 3387 | 131314 | 131333 | 20 |
| 3388 | 131373 | 131386 | 14 |
| 3389 | 131396 | 131417 | 22 |
| 3390 | 131419 | 131439 | 21 |
| 3391 | 131429 | 131458 | 30 |
| 3392 | 131481 | 131499 | 19 |
| 3393 | 131676 | 131689 | 14 |
| 3394 | 131729 | 131743 | 15 |
| 3395 | 131745 | 131764 | 20 |
| 3396 | 131785 | 131807 | 23 |
| 3397 | 131809 | 131875 | 67 |
| 3398 | 131877 | 131953 | 77 |
| 3399 | 131955 | 131980 | 26 |
| 3400 | 132020 | 132068 | 49 |
| 3401 | 132086 | 132108 | 23 |
| 3402 | 132118 | 132138 | 21 |
| 3403 | 132152 | 132183 | 32 |
| 3404 | 132185 | 132205 | 21 |
| 3405 | 132219 | 132232 | 14 |
| 3406 | 132234 | 132252 | 19 |
| 3407 | 132261 | 132291 | 31 |
| 3408 | 132319 | 132337 | 19 |
| 3409 | 132345 | 132363 | 19 |
| 3410 | 132365 | 132378 | 14 |
| 3411 | 132414 | 132483 | 70 |
| 3412 | 132504 | 132547 | 44 |
| 3413 | 132549 | 132582 | 34 |
| 3414 | 132584 | 132602 | 19 |
| 3415 | 132616 | 132642 | 27 |
| 3416 | 132643 | 132681 | 39 |

TABLE 1-continued

Regions of SEQ ID NO 1 which may be targeted using oligonucleotide of the invention

| Reg. A | Position in SEQ ID NO 1 from | to | Length |
|---|---|---|---|
| 3417 | 132685 | 132714 | 30 |
| 3418 | 132736 | 132769 | 34 |
| 3419 | 132771 | 132793 | 23 |
| 3420 | 132809 | 132825 | 17 |
| 3421 | 132827 | 132841 | 15 |
| 3422 | 132861 | 132884 | 24 |
| 3423 | 132882 | 132900 | 19 |
| 3424 | 132899 | 132915 | 17 |
| 3425 | 132917 | 132951 | 35 |
| 3426 | 132940 | 132954 | 15 |
| 3427 | 132958 | 132983 | 26 |
| 3428 | 132985 | 133031 | 47 |
| 3429 | 133032 | 133051 | 20 |
| 3430 | 133042 | 133060 | 19 |
| 3431 | 133051 | 133071 | 21 |
| 3432 | 133073 | 133087 | 15 |
| 3433 | 133083 | 133104 | 22 |
| 3434 | 133097 | 133110 | 14 |
| 3435 | 133131 | 133199 | 69 |
| 3436 | 133198 | 133222 | 25 |
| 3437 | 133233 | 133249 | 17 |
| 3438 | 133251 | 133284 | 34 |
| 3439 | 133327 | 133429 | 103 |
| 3440 | 133431 | 133596 | 166 |
| 3441 | 133588 | 133602 | 15 |
| 3442 | 133598 | 133611 | 14 |
| 3443 | 133613 | 133628 | 16 |
| 3444 | 133628 | 133646 | 19 |
| 3445 | 133651 | 133670 | 20 |
| 3446 | 133666 | 133707 | 42 |
| 3447 | 133718 | 133742 | 25 |
| 3448 | 133743 | 133777 | 35 |
| 3449 | 133779 | 133794 | 16 |
| 3450 | 133821 | 133851 | 31 |
| 3451 | 133859 | 133880 | 22 |
| 3452 | 133890 | 133921 | 32 |
| 3453 | 133923 | 133974 | 52 |
| 3454 | 133982 | 133998 | 17 |
| 3455 | 134000 | 134036 | 37 |
| 3456 | 134065 | 134107 | 43 |
| 3457 | 134120 | 134173 | 54 |
| 3458 | 134165 | 134179 | 15 |
| 3459 | 134187 | 134200 | 14 |
| 3460 | 134207 | 134242 | 36 |
| 3461 | 134244 | 134258 | 15 |
| 3462 | 134260 | 134273 | 14 |
| 3463 | 134275 | 134299 | 25 |
| 3464 | 134314 | 134346 | 33 |
| 3465 | 134356 | 134371 | 16 |
| 3466 | 134365 | 134380 | 16 |
| 3467 | 134374 | 134420 | 47 |
| 3468 | 134445 | 134477 | 33 |
| 3469 | 134508 | 134523 | 16 |
| 3470 | 134531 | 134548 | 18 |
| 3471 | 134542 | 134555 | 14 |
| 3472 | 134568 | 134621 | 54 |
| 3473 | 134647 | 134667 | 21 |
| 3474 | 134679 | 134719 | 41 |
| 3475 | 134721 | 134824 | 104 |
| 3476 | 134826 | 134849 | 24 |
| 3477 | 134856 | 134869 | 14 |
| 3478 | 134877 | 134910 | 34 |
| 3479 | 134912 | 134966 | 55 |
| 3480 | 134960 | 134980 | 21 |
| 3481 | 134989 | 135012 | 24 |
| 3482 | 135014 | 135066 | 53 |
| 3483 | 135074 | 135093 | 20 |
| 3484 | 135108 | 135125 | 18 |
| 3485 | 135151 | 135260 | 110 |
| 3486 | 135264 | 135277 | 14 |
| 3487 | 135273 | 135310 | 38 |

TABLE 1-continued

Regions of SEQ ID NO 1 which may be targeted using oligonucleotide of the invention

| Reg. A | Position in SEQ ID NO 1 from | to | Length |
|---|---|---|---|
| 3488 | 135321 | 135337 | 17 |
| 3489 | 135340 | 135365 | 26 |
| 3490 | 135360 | 135374 | 15 |
| 3491 | 135364 | 135386 | 23 |
| 3492 | 135388 | 135430 | 43 |
| 3493 | 135432 | 135447 | 16 |
| 3494 | 135498 | 135521 | 24 |
| 3495 | 135519 | 135545 | 27 |
| 3496 | 135559 | 135622 | 64 |
| 3497 | 135624 | 135647 | 24 |
| 3498 | 135656 | 135673 | 18 |
| 3499 | 135675 | 135704 | 30 |
| 3500 | 135721 | 135742 | 22 |
| 3501 | 135753 | 135796 | 44 |
| 3502 | 135815 | 135858 | 44 |
| 3503 | 135860 | 135880 | 21 |
| 3504 | 135883 | 135915 | 33 |
| 3505 | 135922 | 135965 | 44 |
| 3506 | 135979 | 135993 | 15 |
| 3507 | 135995 | 136036 | 42 |
| 3508 | 136051 | 136065 | 15 |
| 3509 | 136108 | 136165 | 58 |
| 3510 | 136173 | 136190 | 18 |
| 3511 | 136192 | 136287 | 96 |
| 3512 | 136289 | 136303 | 15 |
| 3513 | 136317 | 136346 | 30 |
| 3514 | 136375 | 136415 | 41 |
| 3515 | 136429 | 136470 | 42 |
| 3516 | 136472 | 136496 | 25 |
| 3517 | 136498 | 136532 | 35 |
| 3518 | 136542 | 136565 | 24 |
| 3519 | 136643 | 136657 | 15 |
| 3520 | 136674 | 136701 | 28 |
| 3521 | 136704 | 136719 | 16 |
| 3522 | 136715 | 136728 | 14 |
| 3523 | 136721 | 136737 | 17 |
| 3524 | 136737 | 136750 | 14 |
| 3525 | 136783 | 136810 | 28 |
| 3526 | 136824 | 136849 | 26 |
| 3527 | 136859 | 136896 | 38 |
| 3528 | 136898 | 136927 | 30 |
| 3529 | 136949 | 136983 | 35 |
| 3530 | 136985 | 137000 | 16 |
| 3531 | 137053 | 137071 | 19 |
| 3532 | 137077 | 137097 | 21 |
| 3533 | 137108 | 137164 | 57 |
| 3534 | 137166 | 137196 | 31 |
| 3535 | 137198 | 137221 | 24 |
| 3536 | 137223 | 137267 | 45 |
| 3537 | 137276 | 137359 | 84 |
| 3538 | 137360 | 137385 | 26 |
| 3539 | 137393 | 137440 | 48 |
| 3540 | 137438 | 137496 | 59 |
| 3541 | 137498 | 137518 | 21 |
| 3542 | 137523 | 137536 | 14 |
| 3543 | 137539 | 137572 | 34 |
| 3544 | 137584 | 137612 | 29 |
| 3545 | 137614 | 137628 | 15 |
| 3546 | 137630 | 137644 | 15 |
| 3547 | 137646 | 137669 | 24 |
| 3548 | 137702 | 137727 | 26 |
| 3549 | 137731 | 137745 | 15 |
| 3550 | 137759 | 137772 | 14 |
| 3551 | 137784 | 137819 | 36 |
| 3552 | 137832 | 137858 | 27 |
| 3553 | 137861 | 137876 | 16 |
| 3554 | 137878 | 137900 | 23 |
| 3555 | 137909 | 137925 | 17 |
| 3556 | 137924 | 137961 | 38 |
| 3557 | 137968 | 137981 | 14 |
| 3558 | 138011 | 138033 | 23 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 3559 | 138035 | 138077 | 43 |
| 3560 | 138079 | 138097 | 19 |
| 3561 | 138224 | 138238 | 15 |
| 3562 | 138232 | 138252 | 21 |
| 3563 | 138242 | 138256 | 15 |
| 3564 | 138255 | 138284 | 30 |
| 3565 | 138295 | 138326 | 32 |
| 3566 | 138328 | 138357 | 30 |
| 3567 | 138359 | 138389 | 31 |
| 3568 | 138403 | 138449 | 47 |
| 3569 | 138451 | 138492 | 42 |
| 3570 | 138500 | 138515 | 16 |
| 3571 | 138524 | 138548 | 25 |
| 3572 | 138555 | 138568 | 14 |
| 3573 | 138571 | 138589 | 19 |
| 3574 | 138589 | 138629 | 41 |
| 3575 | 138644 | 138680 | 37 |
| 3576 | 138697 | 138710 | 14 |
| 3577 | 138712 | 138729 | 18 |
| 3578 | 138744 | 138761 | 18 |
| 3579 | 138776 | 138801 | 26 |
| 3580 | 138860 | 138896 | 37 |
| 3581 | 138898 | 138923 | 26 |
| 3582 | 138925 | 138965 | 41 |
| 3583 | 138967 | 139008 | 42 |
| 3584 | 139010 | 139031 | 22 |
| 3585 | 139029 | 139043 | 15 |
| 3586 | 139034 | 139048 | 15 |
| 3587 | 139041 | 139056 | 16 |
| 3588 | 139055 | 139074 | 20 |
| 3589 | 139078 | 139094 | 17 |
| 3590 | 139084 | 139098 | 15 |
| 3591 | 139092 | 139116 | 25 |
| 3592 | 139133 | 139147 | 15 |
| 3593 | 139154 | 139173 | 20 |
| 3594 | 139175 | 139192 | 18 |
| 3595 | 139204 | 139229 | 26 |
| 3596 | 139231 | 139255 | 25 |
| 3597 | 139257 | 139270 | 14 |
| 3598 | 139272 | 139303 | 32 |
| 3599 | 139315 | 139335 | 21 |
| 3600 | 139337 | 139372 | 36 |
| 3601 | 139383 | 139397 | 15 |
| 3602 | 139399 | 139419 | 21 |
| 3603 | 139423 | 139437 | 15 |
| 3604 | 139435 | 139492 | 58 |
| 3605 | 139501 | 139518 | 18 |
| 3606 | 139508 | 139521 | 14 |
| 3607 | 139571 | 139586 | 16 |
| 3608 | 139588 | 139622 | 35 |
| 3609 | 139636 | 139655 | 20 |
| 3610 | 139657 | 139673 | 17 |
| 3611 | 139685 | 139699 | 15 |
| 3612 | 139724 | 139795 | 72 |
| 3613 | 139796 | 139811 | 16 |
| 3614 | 139818 | 139834 | 17 |
| 3615 | 139836 | 139857 | 22 |
| 3616 | 139856 | 139869 | 14 |
| 3617 | 139859 | 139882 | 24 |
| 3618 | 139891 | 139920 | 30 |
| 3619 | 139930 | 139952 | 23 |
| 3620 | 139965 | 139980 | 16 |
| 3621 | 139982 | 140011 | 30 |
| 3622 | 140013 | 140031 | 19 |
| 3623 | 140047 | 140072 | 26 |
| 3624 | 140074 | 140099 | 26 |
| 3625 | 140101 | 140119 | 19 |
| 3626 | 140121 | 140135 | 15 |
| 3627 | 140144 | 140158 | 15 |
| 3628 | 140157 | 140183 | 27 |
| 3629 | 140185 | 140210 | 26 |

TABLE 1-continued

| Regions of SEQ ID NO 1 which may be targeted using oligonucleotide of the invention | | | |
|---|---|---|---|
| Reg. | Position in SEQ ID NO 1 | | |
| A | from | to | Length |
| 3630 | 140231 | 140262 | 32 |
| 3631 | 140258 | 140272 | 15 |
| 3632 | 140264 | 140288 | 25 |
| 3633 | 140290 | 140325 | 36 |
| 3634 | 140339 | 140364 | 26 |
| 3635 | 140369 | 140402 | 34 |
| 3636 | 140428 | 140451 | 24 |
| 3637 | 140453 | 140510 | 58 |
| 3638 | 140512 | 140541 | 30 |
| 3639 | 140556 | 140621 | 66 |
| 3640 | 140626 | 140651 | 26 |
| 3641 | 140653 | 140724 | 72 |
| 3642 | 140726 | 140789 | 64 |
| 3643 | 140802 | 140825 | 24 |
| 3644 | 140837 | 140861 | 25 |
| 3645 | 140863 | 140896 | 34 |
| 3646 | 140903 | 140927 | 25 |
| 3647 | 140958 | 140993 | 36 |
| 3648 | 141001 | 141014 | 14 |
| 3649 | 141022 | 141053 | 32 |

In some embodiments, the oligonucleotide comprises a contiguous nucleotide sequence of 10 to 30 nucleotides in length with at least 90% complementary, such as 100% complementarity, to a corresponding target nucleic acid region present in SEQ ID NO: 1, wherein the target nucleic acid region is selected from the group consisting of region B1 to B400 in table 2

TABLE 2

| Regions of SEQ ID NO 1 which may be targeted using oligonucleotide of the invention | | | |
|---|---|---|---|
| | Position in SEQ ID NO 1 | | |
| Reg. | To | From | Length |
| B1 | 225 | 238 | 14 |
| B2 | 1163 | 1178 | 16 |
| B3 | 2526 | 2539 | 14 |
| B4 | 2805 | 2820 | 16 |
| B5 | 3027 | 3040 | 14 |
| B6 | 3208 | 3222 | 15 |
| B7 | 3212 | 3225 | 14 |
| B8 | 3228 | 3241 | 14 |
| B9 | 3243 | 3256 | 14 |
| B10 | 3810 | 3854 | 45 |
| B11 | 4664 | 4680 | 17 |
| B12 | 5516 | 5529 | 14 |
| B13 | 5657 | 5671 | 15 |
| B14 | 5661 | 5676 | 16 |
| B15 | 5964 | 5977 | 14 |
| B16 | 6217 | 6234 | 18 |
| B17 | 6224 | 6237 | 14 |
| B18 | 6408 | 6422 | 15 |
| B19 | 7300 | 7313 | 14 |
| B20 | 7399 | 7412 | 14 |
| B21 | 7541 | 7564 | 24 |
| B22 | 7626 | 7640 | 15 |
| B23 | 7662 | 7694 | 33 |
| B24 | 7791 | 7806 | 16 |
| B25 | 7853 | 7868 | 16 |
| B26 | 8206 | 8219 | 14 |
| B27 | 8443 | 8456 | 14 |
| B28 | 8739 | 8752 | 14 |
| B29 | 9197 | 9212 | 16 |

TABLE 2-continued

| Regions of SEQ ID NO 1 which may be targeted using oligonucleotide of the invention | | | |
|---|---|---|---|
| | Position in SEQ ID NO 1 | | |
| Reg. | To | From | Length |
| B30 | 10189 | 10203 | 15 |
| B31 | 10754 | 10768 | 15 |
| B32 | 10758 | 10771 | 14 |
| B33 | 11790 | 11803 | 14 |
| B34 | 11870 | 11883 | 14 |
| B35 | 11993 | 12007 | 15 |
| B36 | B11996 | 12011 | 16 |
| B37 | 12017 | 12040 | 24 |
| B38 | 12095 | 12108 | 14 |
| B39 | 12345 | 12358 | 14 |
| B40 | 12721 | 12734 | 14 |
| B41 | 13372 | 13386 | 15 |
| B42 | 13489 | 13505 | 17 |
| B43 | 15576 | 15590 | 15 |
| B44 | 15617 | 15632 | 16 |
| B45 | 15840 | 15853 | 14 |
| B46 | 16041 | 16054 | 14 |
| B47 | 16207 | 16222 | 16 |
| B48 | 16308 | 16321 | 14 |
| B49 | 16349 | 16362 | 14 |
| B50 | 16463 | 16479 | 17 |
| B51 | 16528 | 16542 | 15 |
| B52 | 16543 | 16556 | 14 |
| B53 | 20495 | 20508 | 14 |
| B54 | 20617 | 20630 | 14 |
| B55 | 20960 | 20977 | 18 |
| B56 | 21465 | 21479 | 15 |
| B57 | 21491 | 21508 | 18 |
| B58 | 23479 | 23496 | 18 |
| B59 | 23741 | 23755 | 15 |
| B60 | 25236 | 25249 | 14 |
| B61 | 25323 | 25336 | 14 |
| B62 | 25447 | 25462 | 16 |
| B63 | 25588 | 25601 | 14 |
| B64 | 25853 | 25867 | 15 |
| B65 | 25885 | 25898 | 14 |
| B66 | 26280 | 26293 | 14 |
| B67 | 26388 | 26404 | 17 |
| B68 | 26416 | 26450 | 35 |
| B69 | 26687 | 26702 | 16 |
| B70 | 26706 | 26719 | 14 |
| B71 | 26783 | 26796 | 14 |
| B72 | 27039 | 27052 | 14 |
| B73 | 27251 | 27265 | 15 |
| B74 | 28683 | 28698 | 16 |
| B75 | 29302 | 29315 | 14 |
| B76 | 29304 | 29317 | 14 |
| B77 | 29308 | 29321 | 14 |
| B78 | 29532 | 29545 | 14 |
| B79 | 29974 | 29987 | 14 |
| B80 | 30054 | 30068 | 15 |
| B81 | 30267 | 30281 | 15 |
| B82 | 30623 | 30638 | 16 |
| B83 | 30628 | 30641 | 14 |
| B84 | 30814 | 30827 | 14 |
| B85 | 30881 | 30894 | 14 |
| B86 | 32459 | 32478 | 20 |
| B87 | 37299 | 37315 | 17 |
| B88 | 39083 | 39096 | 14 |
| B89 | 39370 | 39383 | 14 |
| B90 | 39659 | 39672 | 14 |
| B91 | 40814 | 40831 | 18 |
| B92 | 40851 | 40864 | 14 |
| B93 | 41782 | 41795 | 14 |
| B94 | 41873 | 41886 | 14 |
| B95 | 42037 | 42050 | 14 |
| B96 | 42048 | 42063 | 16 |
| B97 | 42096 | 42116 | 21 |
| B98 | 42959 | 42973 | 15 |
| B99 | 43165 | 43178 | 14 |
| B100 | 45926 | 45939 | 14 |
| B101 | 48163 | 48176 | 14 |

TABLE 2-continued

| Regions of SEQ ID NO 1 which may be targeted using oligonucleotide of the invention | | | |
|---|---|---|---|
| | Position in SEQ ID NO 1 | | |
| Reg. | To | From | Length |
| B102 | 52732 | 52745 | 14 |
| B103 | 52984 | 53015 | 32 |
| B104 | 54404 | 54420 | 17 |
| B105 | 55294 | 55320 | 27 |
| B106 | 55337 | 55350 | 14 |
| B107 | 55420 | 55434 | 15 |
| B108 | 55487 | 55501 | 15 |
| B109 | 55623 | 55638 | 16 |
| B110 | 56195 | 56214 | 20 |
| B111 | 56584 | 56597 | 14 |
| B112 | 57267 | 57282 | 16 |
| B113 | 58126 | 58139 | 14 |
| B114 | 58170 | 58183 | 14 |
| B115 | 58295 | 58309 | 15 |
| B116 | 58658 | 58671 | 14 |
| B117 | 58906 | 58921 | 16 |
| B118 | 58988 | 59005 | 18 |
| B119 | 59024 | 59045 | 22 |
| B120 | 59191 | 59207 | 17 |
| B121 | 59236 | 59251 | 16 |
| B122 | 59298 | 59312 | 15 |
| B123 | 59358 | 59378 | 21 |
| B124 | 59400 | 59413 | 14 |
| B125 | 59434 | 59447 | 14 |
| B126 | 59589 | 59602 | 14 |
| B127 | 59620 | 59642 | 23 |
| B128 | 59718 | 59743 | 26 |
| B129 | 59826 | 59841 | 16 |
| B130 | 59843 | 59864 | 22 |
| B131 | 59882 | 59906 | 25 |
| B132 | 59930 | 59958 | 29 |
| B133 | 59959 | 60004 | 46 |
| B134 | 60006 | 60029 | 24 |
| B135 | 60033 | 60071 | 39 |
| B136 | 60139 | 60171 | 33 |
| B137 | 60193 | 60215 | 23 |
| B138 | 60212 | 60225 | 14 |
| B139 | 60231 | 60244 | 14 |
| B140 | 60246 | 60265 | 20 |
| B141 | 60267 | 60282 | 16 |
| B142 | 60292 | 60309 | 18 |
| B143 | 60348 | 60361 | 14 |
| B144 | 60358 | 60429 | 72 |
| B145 | 60427 | 60517 | 91 |
| B146 | 60519 | 60545 | 27 |
| B147 | 60557 | 60575 | 19 |
| B148 | 60580 | 60593 | 14 |
| B149 | 60595 | 60622 | 28 |
| B150 | 60675 | 60690 | 16 |
| B151 | 60697 | 60713 | 17 |
| B152 | 60727 | 60754 | 28 |
| B153 | 60756 | 60799 | 44 |
| B154 | 60801 | 60817 | 17 |
| B155 | 60819 | 60855 | 37 |
| B156 | 61423 | 61436 | 14 |
| B157 | 61592 | 61605 | 14 |
| B158 | 61624 | 61637 | 14 |
| B159 | 61673 | 61713 | 41 |
| B160 | 61715 | 61731 | 17 |
| B161 | 61733 | 61752 | 20 |
| B162 | 61769 | 61794 | 26 |
| B163 | 61805 | 61825 | 21 |
| B164 | 62101 | 62114 | 14 |
| B165 | 62302 | 62315 | 14 |
| B166 | 62436 | 62449 | 14 |
| B167 | 62664 | 62679 | 16 |
| B168 | 62993 | 63006 | 14 |
| B169 | 63098 | 63111 | 14 |
| B170 | 63347 | 63367 | 21 |
| B171 | 63371 | 63396 | 26 |
| B172 | 63385 | 63398 | 14 |
| B173 | 63526 | 63539 | 14 |

TABLE 2-continued

Regions of SEQ ID NO 1 which may be targeted using oligonucleotide of the invention

| Reg. | Position in SEQ ID NO 1 To | From | Length |
|---|---|---|---|
| B174 | 65032 | 65045 | 14 |
| B175 | 66556 | 66569 | 14 |
| B176 | 67158 | 67183 | 26 |
| B177 | 67181 | 67194 | 14 |
| B178 | 68007 | 68021 | 15 |
| B179 | 68644 | 68657 | 14 |
| B180 | 69294 | 69317 | 24 |
| B181 | 69306 | 69323 | 18 |
| B182 | 69353 | 69366 | 14 |
| B183 | 70497 | 70511 | 15 |
| B184 | 71600 | 71613 | 14 |
| B185 | 71887 | 71905 | 19 |
| B186 | 72259 | 72272 | 14 |
| B187 | 72589 | 72602 | 14 |
| B188 | 72783 | 72796 | 14 |
| B189 | 73528 | 73541 | 14 |
| B190 | 73783 | 73800 | 18 |
| B191 | 74907 | 74920 | 14 |
| B192 | 75965 | 75981 | 17 |
| B193 | 75983 | 75998 | 16 |
| B194 | 76004 | 76020 | 17 |
| B195 | 76110 | 76166 | 57 |
| B196 | 76186 | 76205 | 20 |
| B197 | 76234 | 76253 | 20 |
| B198 | 76261 | 76280 | 20 |
| B199 | 76369 | 76382 | 14 |
| B200 | 77139 | 77152 | 14 |
| B201 | 77409 | 77422 | 14 |
| B203 | 77526 | 77590 | 65 |
| B202 | 77478 | 77524 | 47 |
| B204 | 77628 | 77641 | 14 |
| B205 | 77688 | 77701 | 14 |
| B206 | 78275 | 78308 | 34 |
| B207 | 78310 | 78332 | 23 |
| B208 | 78340 | 78356 | 17 |
| B209 | 78358 | 78371 | 14 |
| B210 | 78373 | 78395 | 23 |
| B211 | 78397 | 78440 | 44 |
| B212 | 78442 | 78455 | 14 |
| B213 | 78475 | 78489 | 15 |
| B214 | 78696 | 78709 | 14 |
| B215 | 78847 | 78860 | 14 |
| B216 | 79493 | 79516 | 24 |
| B217 | 79705 | 79718 | 14 |
| B218 | 81009 | 81054 | 46 |
| B219 | 81353 | 81367 | 15 |
| B220 | 81970 | 81986 | 17 |
| B221 | 81991 | 82006 | 16 |
| B222 | 82042 | 82106 | 65 |
| B223 | 82278 | 82291 | 14 |
| B224 | 82716 | 82735 | 20 |
| B225 | 84314 | 84328 | 15 |
| B226 | 85628 | 85665 | 38 |
| B227 | 86226 | 86239 | 14 |
| B228 | 86237 | 86253 | 17 |
| B229 | 86566 | 86579 | 14 |
| B230 | 86945 | 86959 | 15 |
| B231 | 87337 | 87358 | 22 |
| B232 | 87662 | 87675 | 14 |
| B233 | 89424 | 89439 | 16 |
| B234 | 89972 | 89985 | 14 |
| B235 | 90782 | 90795 | 14 |
| B236 | 90939 | 90953 | 15 |
| B237 | 90942 | 90955 | 14 |
| B238 | 90965 | 90981 | 17 |
| B239 | 91101 | 91115 | 15 |
| B240 | 92083 | 92096 | 14 |
| B241 | 92164 | 92177 | 14 |
| B242 | 92179 | 92192 | 14 |
| B243 | 92194 | 92210 | 17 |
| B244 | 92212 | 92236 | 25 |
| B245 | 92245 | 92260 | 16 |

TABLE 2-continued

Regions of SEQ ID NO 1 which may be targeted using oligonucleotide of the invention

| Reg. | Position in SEQ ID NO 1 To | From | Length |
|---|---|---|---|
| B246 | 92262 | 92302 | 41 |
| B247 | 92304 | 92321 | 18 |
| B248 | 92323 | 92366 | 44 |
| B249 | 92375 | 92389 | 15 |
| B250 | 92392 | 92405 | 14 |
| B251 | 92407 | 92426 | 20 |
| B252 | 92442 | 92459 | 18 |
| B253 | 92497 | 92516 | 20 |
| B254 | 92578 | 92591 | 14 |
| B255 | 92599 | 92612 | 14 |
| B256 | 92614 | 92651 | 38 |
| B257 | 92659 | 92684 | 26 |
| B258 | 92686 | 92699 | 14 |
| B259 | 92704 | 92726 | 23 |
| B260 | 92731 | 92750 | 20 |
| B261 | 92752 | 92774 | 23 |
| B262 | 92780 | 92795 | 16 |
| B263 | 92800 | 92813 | 14 |
| B264 | 92839 | 92858 | 20 |
| B265 | 92860 | 92891 | 32 |
| B266 | 92893 | 92906 | 14 |
| B267 | 92908 | 92921 | 14 |
| B268 | 92923 | 92941 | 19 |
| B269 | 92965 | 92986 | 22 |
| B270 | 92988 | 93002 | 15 |
| B271 | 93044 | 93059 | 16 |
| B272 | 93061 | 93076 | 16 |
| B273 | 93105 | 93122 | 18 |
| B274 | 93142 | 93209 | 68 |
| B275 | 93227 | 93241 | 15 |
| B276 | 93288 | 93305 | 18 |
| B277 | 93325 | 93344 | 20 |
| B278 | 93398 | 93412 | 15 |
| B279 | 93572 | 93586 | 15 |
| B280 | 94509 | 94522 | 14 |
| B281 | 95720 | 95738 | 19 |
| B282 | 97050 | 97065 | 16 |
| B283 | 97079 | 97098 | 20 |
| B284 | 97127 | 97194 | 68 |
| B285 | 97208 | 97230 | 23 |
| B286 | 97232 | 97284 | 53 |
| B287 | 97286 | 97311 | 26 |
| B288 | 97313 | 97362 | 50 |
| B289 | 97368 | 97383 | 16 |
| B290 | 97426 | 97439 | 14 |
| B291 | 98077 | 98090 | 14 |
| B292 | 98227 | 98240 | 14 |
| B293 | 98232 | 98255 | 24 |
| B294 | 99151 | 99164 | 14 |
| B295 | 99405 | 99418 | 14 |
| B296 | 99570 | 99583 | 14 |
| B297 | 99733 | 99748 | 16 |
| B298 | 101829 | 101842 | 14 |
| B299 | 101882 | 101895 | 14 |
| B300 | 101955 | 101968 | 14 |
| B301 | 102202 | 102215 | 14 |
| B302 | 103310 | 103325 | 16 |
| B303 | 103653 | 103666 | 14 |
| B304 | 103908 | 103923 | 16 |
| B305 | 103912 | 103928 | 17 |
| B306 | 103917 | 103933 | 17 |
| B307 | 104971 | 104984 | 14 |
| B308 | 105217 | 105230 | 14 |
| B309 | 105233 | 105250 | 18 |
| B310 | 105443 | 105457 | 15 |
| B311 | 105544 | 105559 | 16 |
| B312 | 106047 | 106071 | 25 |
| B313 | 106061 | 106074 | 14 |
| B314 | 106093 | 106107 | 15 |
| B315 | 106114 | 106130 | 17 |
| B316 | 106243 | 106256 | 14 |
| B317 | 106251 | 106264 | 14 |

TABLE 2-continued

Regions of SEQ ID NO 1 which may be targeted using oligonucleotide of the invention

| Reg. | Position in SEQ ID NO 1 To | From | Length |
|---|---|---|---|
| B318 | 106840 | 106855 | 16 |
| B319 | 108113 | 108130 | 18 |
| B320 | 108325 | 108338 | 14 |
| B321 | 108856 | 108869 | 14 |
| B322 | 109109 | 109122 | 14 |
| B323 | 109113 | 109127 | 15 |
| B324 | 109116 | 109132 | 17 |
| B325 | 110301 | 110314 | 14 |
| B326 | 110315 | 110328 | 14 |
| B327 | 110317 | 110330 | 14 |
| B328 | 112528 | 112546 | 19 |
| B329 | 112607 | 112620 | 14 |
| B330 | 114775 | 114788 | 14 |
| B331 | 116322 | 116335 | 14 |
| B332 | 116968 | 116981 | 14 |
| B333 | 117788 | 117801 | 14 |
| B334 | 118034 | 118057 | 24 |
| B335 | 118230 | 118246 | 17 |
| B336 | 118235 | 118248 | 14 |
| B337 | 118870 | 118883 | 14 |
| B338 | 119755 | 119784 | 30 |
| B339 | 119786 | 119800 | 15 |
| B340 | 120363 | 120406 | 44 |
| B341 | 120504 | 120517 | 14 |
| B342 | 121161 | 121174 | 14 |
| B343 | 121330 | 121347 | 18 |
| B344 | 121338 | 121351 | 14 |
| B345 | 123417 | 123430 | 14 |
| B346 | 123464 | 123481 | 18 |
| B347 | 125026 | 125042 | 17 |
| B348 | 127046 | 127071 | 26 |
| B349 | 127090 | 127103 | 14 |
| B350 | 127311 | 127324 | 14 |
| B351 | 127354 | 127367 | 14 |
| B352 | 127363 | 127379 | 17 |
| B353 | 127399 | 127412 | 14 |
| B354 | 127863 | 127876 | 14 |
| B355 | 128134 | 128148 | 15 |
| B356 | 128280 | 128310 | 31 |
| B357 | 128343 | 128368 | 26 |
| B358 | 128444 | 128457 | 14 |
| B359 | 128446 | 128469 | 24 |
| B360 | 128498 | 128511 | 14 |
| B361 | 128511 | 128524 | 14 |
| B362 | 129892 | 129905 | 14 |
| B363 | 130261 | 130283 | 23 |
| B364 | 130375 | 130388 | 14 |
| B365 | 130415 | 130428 | 14 |
| B366 | 130634 | 130650 | 17 |
| B367 | 130667 | 130717 | 51 |
| B368 | 130719 | 130764 | 46 |
| B369 | 130783 | 130796 | 14 |
| B370 | 130798 | 130820 | 23 |
| B371 | 130840 | 130861 | 22 |
| B372 | 130975 | 130994 | 20 |
| B373 | 131112 | 131132 | 21 |
| B374 | 131142 | 131161 | 20 |
| B375 | 131233 | 131246 | 14 |
| B376 | 131729 | 131743 | 15 |
| B377 | 132754 | 132767 | 14 |
| B378 | 132924 | 132937 | 14 |
| B379 | 133174 | 133190 | 17 |
| B380 | 133198 | 133212 | 15 |
| B381 | 133207 | 133222 | 16 |
| B382 | 133476 | 133489 | 14 |
| B383 | 133479 | 133492 | 14 |
| B384 | 133491 | 133531 | 41 |
| B385 | 133533 | 133550 | 18 |
| B386 | 133555 | 133594 | 40 |
| B387 | 134160 | 134173 | 14 |
| B388 | 134165 | 134178 | 14 |
| B389 | 134533 | 134546 | 14 |

TABLE 2-continued

Regions of SEQ ID NO 1 which may be targeted using oligonucleotide of the invention

| Reg. | Position in SEQ ID NO 1 To | From | Length |
|---|---|---|---|
| B390 | 136724 | 136737 | 14 |
| B391 | 137438 | 137463 | 26 |
| B392 | 137878 | 137891 | 14 |
| B393 | 138082 | 138097 | 16 |
| B394 | 138233 | 138252 | 20 |
| B395 | 138930 | 138943 | 14 |
| B396 | 138947 | 138960 | 14 |
| B397 | 138950 | 138963 | 14 |
| B398 | 139502 | 139518 | 17 |
| B399 | 139508 | 139521 | 14 |
| B400 | 140978 | 140991 | 14 |

In certain embodiments the oligonucleotide or contiguous nucleotide sequence is complementary to a region (or sub-sequence)(or sub-sequence) of the target nucleic acid, wherein the target nucleic acid region is selected from the group consisting of position 1589-10889, 46089-53989 and 60789-62489 of SEQ ID NO:1.

In one embodiment the oligonucleotide comprises a contiguous nucleotide sequence of 10 to 30 nucleotides in length with at least 90%, such as 100% complementary to a target nucleic acid sequence of position 55319 to 141053 of SEQ ID NO: 1.

In one embodiment the oligonucleotide comprises a contiguous nucleotide sequence of 10 to 30 nucleotides in length with at least 90%, such as 100% complementary to a target nucleic acid sequence of position 1 to 55318 of SEQ ID NO: 1.

In some embodiments, the oligonucleotide comprises a contiguous nucleotide sequence of 10 to 30 nucleotides in length with at least 90% complementary to a sub-sequence of the target nucleic acid selected from the group corresponding to positions: 55319-76274, 77483-77573, 92157-93403 and 97056-97354 of SEQ ID NO: 1.

In some embodiments the oligonucleotide a contiguous nucleotide sequence of 10 to 30 nucleotides in length with at least 90% complementary to a sub-sequence of the target nucleic acid selected from the group corresponding to positions: 60821-60849, 77567-77583, 92323-92339 and 97156-97172 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 5218-5240 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 5782-5803 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 8113-8139 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 9200-9250 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 11505-11555 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 13223-13242 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions 15100-15150 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions 15113-15180 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions 29635-29705 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions 30590-30740 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions 39800-39855 of SEQ ID NO: 1.

In some embodiments the oligonucleotide a contiguous nucleotide sequence of 10 to 30 nucleotides in length with at least 90% complementary to a sub-sequence of the target nucleic acid to positions 44435-44460 of SEQ ID NO: 1.

In some embodiments the oligonucleotide a contiguous nucleotide sequence of 10 to 30 nucleotides in length with at least 90% complementary to a sub-sequence of the target nucleic acid to positions 45245-45270 of SEQ ID NO: 1.

In some embodiments the oligonucleotide a contiguous nucleotide sequence of 10 to 30 nucleotides in length with at least 90% complementary to a sub-sequence of the target nucleic acid to positions 46380-46430 of SEQ ID NO: 1.

In some embodiments the oligonucleotide a contiguous nucleotide sequence of 10 to 30 nucleotides in length with at least 90% complementary to a sub-sequence of the target nucleic acid to positions 68915-68940 of SEQ ID NO: 1.

In some embodiments, the oligonucleotide comprises or consists of 8 to 35 nucleotides in length, such as from 10 to 30, such as 11 to 22, such as from 12 to 18, such as from 13 to 17 or 14 to 16 contiguous nucleotides in length. In a preferred embodiment, the oligonucleotide comprises or consists of 15 to 20 nucleotides in length.

In some embodiments, the oligonucleotide or contiguous nucleotide sequence thereof comprises or consists of 22 or less nucleotides, such as 20 or less nucleotides, such as 18 or less nucleotides, such as 14, 15, 16 or 17 nucleotides. It is to be understood that any range given herein includes the range endpoints. Accordingly, if an oligonucleotide is said to include from 10 to 30 nucleotides, both 10 and 30 nucleotides are included.

In some embodiments, the contiguous nucleotide sequence comprises or consists of 8, 9, 10, 11, 12, 13, 14, 15, 16, 17, 18, 19, 20, 21, 22, 23, 24, 25, 26, 27, 28, 29 or 30 contiguous nucleotides in length. In a preferred embodiment, the oligonucleotide comprises or consists of 16, 17, 18 or 19 nucleotides in length.

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 4 to 150 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 4 to 818 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 4 to 678 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 166, 167, 167 or 169 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 570, 571,572, 679, 680, 681, 682 and 683 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 34, 186, 187, 188, 573, 574, 575, 576, 572, 684, 685, 686, 687, 688, 689, 690, 691, 692, 963, 964, 965 and 696 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 35, 199, 200, 201, 202, 203, 204, 205, 206, 207, 209 and 210 or SEQ ID NO: 582, 583 and 584 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 221, 222, 223, 224, 225, 585, 586, 587, 588, 589, 698, 699,700, 701, 702, 703, 704, 705, 706, 707, 708, 709, 710, 711, 712, 713, 714, 715, 716, 717 and 718 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 236, 237, 238, 239, 240 and 590.

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 241, 591 and 719 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 46, 47, 48, 285, 286, 287, 288, 289, 290, 291, 292, 293, 294, 295, 296, 297, 298, 299, 300, 301, 302, 303, 304,305, 613, 614, 615, 616, 617, 618, 619, 620, 621, 622, 623, 624, 625, 626,627, 628, 629, 630, 631, 632, 721, 722, 723, 724, 725, 726, 727, 728, 729, 730, 731, 732, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 800, 800, 800, 800, 801, 801, 802, 803, 804, 805, 806 and 807 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 331, 332, 638, 639, 640, 808, 809, 810, 811, 812, 813, 814 and 815 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 409, 410, 411, 642, 643, 644, 645, 646, 816, 818 and 818 (see motif sequences listed in table 3 in the Examples section).

It is understood that the contiguous nucleobase sequences (motif sequence) can be modified to for example increase nuclease resistance and/or binding affinity to the target nucleic acid. Modifications are described in the definitions and in the "Oligonucleotide design" section. Table 3 lists preferred designs of each motif sequence.

Oligonucleotide Design

Oligonucleotide design refers to the pattern of nucleoside sugar modifications in the oligonucleotide sequence. The oligonucleotides of the invention comprise sugar-modified nucleosides and may also comprise DNA or RNA nucleosides. In some embodiments, the oligonucleotide comprises sugar-modified nucleosides and DNA nucleosides. Incorporation of modified nucleosides into the oligonucleotide of the invention may enhance the affinity of the oligonucleotide for the target nucleic acid. In that case, the modified nucleosides can be referred to as affinity enhancing modified nucleotides.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. In some embodiments, at least 1 of the modified nucleosides is a locked nucleic acid (LNA), such as at least 2, such as at least 3, at least 4, at least 5, at least 6, at least 7, or at least 8 of the modified nucleosides are LNA. In a still further embodiment all the modified nucleosides are LNA.

In an embodiment, the oligonucleotide of the invention may comprise modifications, which are independently selected from these three types of modifications (modified sugar, modified nucleobase and modified internucleoside linkage) or a combination thereof. Preferably the oligonucleotide comprises one or more sugar modified nucleosides, such as 2' sugar modified nucleosides. Preferably the oligonucleotide of the invention comprise the one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. Even more preferably the the one or more modified nucleoside is LNA.

In a further embodiment the oligonucleotide comprises at least one modified internucleoside linkage. In a preferred embodiment the the internucleoside linkages within the contiguous nucleotide sequence are phosphorothioate or boranophosphate internucleoside linkages.

In some embodiments, the oligonucleotide of the invention comprise at least one modified nucleoside which is a 2'-MOE-RNA, such as 2, 3, 4, 5, 6, 7, 8, 9 or 10 2'-MOE-RNA nucleoside units. In some embodiments, at least one of said modified nucleoside is 2'-fluoro DNA, such as 2, 3, 4, 5, 6, 7, 8, 9 or 10 2'-fluoro-DNA nucleoside units.

In some embodiments, the oligonucleotide of the invention comprises at least one LNA unit, such as 1, 2, 3, 4, 5, 6, 7, or 8 LNA units, such as from 2 to 6 LNA units, such as from 3 to 7 LNA units, 4 to 8 LNA units or 3, 4, 5, 6 or 7 LNA units. In some embodiments, all the modified nucleosides are LNA nucleosides. In a further embodiment, the oligonucleotide may comprise both beta-D-oxy-LNA, and one or more of the following LNA units: thio-LNA, amino-LNA, oxy-LNA, and/or ENA in either the beta-D or alpha-L configurations or combinations thereof. In a further embodiment, all LNA cytosine units are 5-methyl-cytosine. In a preferred embodiment the oligonucleotide or contiguous nucleotide sequence has at least 1 LNA unit at the 5' end and at least 2 LNA units at the 3' end of the nucleotide sequence.

In some embodiments, the oligonucleotide of the invention comprises at least one LNA unit and at least one 2' substituted modified nucleoside.

In some embodiments of the invention, the oligonucleotide comprise both 2' sugar modified nucleosides and DNA units. Preferably the oligonucleotide comprise both LNA and DNA units. Preferably, the combined total of LNA and DNA units is 8-30, such as 10-25, preferably 12-22, such as 12-18, even more preferably 11-16. In some embodiments of the invention, the nucleotide sequence of the oligonucleotide, such as the contiguous nucleotide sequence consists of at least one or two LNA units and the remaining nucleotide units are DNA units. In some embodiments the oligonucleotide comprises only LNA nucleosides and naturally occurring nucleosides (such as RNA or DNA, most preferably DNA nucleosides), optionally with modified internucleoside linkages such as phosphorothioate.

In an embodiment of the invention the oligonucleotide of the invention is capable of recruiting RNase H.

Gapmer Design

In a preferred embodiment the oligonucleotide of the invention has a gapmer design or structure also referred herein merely as "Gapmer". In a gapmer structure the oligonucleotide comprises at least three distinct structural regions a 5'-flank, a gap and a 3'-flank, F-G-F' in '5->3' orientation. In this design, flanking regions F and F' (also termed wing regions) comprise a contiguous stretch of modified nucleosides, which are complementary to the UBE3A target nucleic acid, while the gap region, G, comprises a contiguous stretch of nucleotides which are capable of recruiting a nuclease, preferably an endonuclease such as RNase, for example RNase H, when the oligonucleotide is in duplex with the target nucleic acid. Nucleosides which are capable of recruiting a nuclease, in particular RNase H, can be selected from the group consisting of DNA, alpha-L-oxy-LNA, 2'-Flouro-ANA and UNA. Regions F and F', flanking the 5' and 3' ends of region G, preferably comprise non-nuclease recruiting nucleosides (nucleosides with a 3' endo structure), more preferably one or more affinity enhancing modified nucleosides. In some embodiments, the 3' flank comprises at least one LNA nucleoside, preferably at least 2 LNA nucleosides. In some embodiments, the 5' flank comprises at least one LNA nucleoside. In some embodiments both the 5' and 3' flanking regions comprise a LNA nucleoside. In some embodiments all the nucleosides in the flanking regions are LNA nucleosides. In other embodiments, the flanking regions may comprise both LNA nucleosides and other nucleosides (mixed flanks), such as DNA nucleosides and/or non-LNA modified nucleosides, such as 2' substituted nucleosides. In this case the gap is defined as a contiguous sequence of at least 5 RNase H recruiting nucleosides (nucleosides with a 2' endo structure, preferably DNA) flanked at the 5' and 3' end by an affinity enhancing modified nucleoside, preferably LNA, such as beta-D-oxy-LNA. Consequently, the nucleosides of the 5' flanking region and the 3' flanking region which are adjacent to the gap region are modified nucleosides, preferably non-nuclease recruiting nucleosides. In oligonucleotides with mixed flanks where the flanks comprise DNA the 5' and 3' nucleosides are modified nucleosides.

Region F

Region F (5' flank or 5' wing) attached to the '5 end of region G comprises, contains or consists of at least one modified nucleoside such as at least 2, at least 3, at least 4, at least 5, at least 6, at least 7 modified nucleosides. In an embodiment region F comprises or consists of from 1 to 7 modified nucleosides, such as from 2 to 6 modified nucleosides, such as from 2 to 5 modified nucleosides, such as from 2 to 4 modified nucleosides, such as from 1 to 3 modified nucleosides, such as 1, 2, 3 or 4 modified nucleosides. In a further embodiment further additional nucleosides may be attached to the '5 end of region F, representing a region D preferably comprising 1, 2 or 3 nucleoside units, such as DNA nucleosides. Region D can take the function of a biocleavable (B) linker described in the definition of "Linkers".

In some embodiments, the modified nucleosides in region F have a 3' endo structure.

In an embodiment, one or more of the modified nucleosides in region F are 2' modified nucleosides.

In a further embodiment one or more of the 2' modified nucleosides in region F are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In one embodiment of the invention all the modified nucleosides in region F are LNA nucleosides. In a further embodiment the LNA nucleosides in region F are independently selected from the group consisting of oxy-LNA, thio-LNA, amino-LNA, cET, and/or ENA, in either the beta-D or alpha-L configurations or combinations thereof. In a preferred embodiment region F has at least 1 beta-D-oxy LNA unit, at the 5' end of the contiguous sequence.

Region G

Region G (gap region) preferably comprise, contain or consist of at least 4, such as at least 5, such as at least 6, at least 7, at least 8, at least 9, at least 10, at least 11, at least 12, at least 13, at least 14, at least 15 or at least 16 consecutive nucleosides capable of recruiting the aforementioned nuclease, in particular RNaseH. In a further embodiment region G comprise, contain or consist of from 5 to 12, or from 6 to 10 or from 7 to 9, such as 8 consecutive nucleotide units capable of recruiting aforementioned nuclease.

The nucleoside units in region G, which are capable of recruiting nuclease are in an embodiment selected from the group consisting of DNA, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked "sugar" residue.

In a still further embodiment at least one nucleoside unit in region G is a DNA nucleoside unit, such as from 1 to 16 DNA units, such as 2, 3, 4, 5, 6, 7, 8, 9, 10, 11, 12, 13, 14 or 15 DNA units, preferably from 2 to 13 DNA units, such as from 4 to 12 DNA units, more preferably from 5 to 11, or from 10 to 16, 11 to 15 or 12 to 14 DNA units. In some embodiments, region G consists of 100% DNA units. In a preferred embodiment G consists of, most preferably 10, 11, 12, 13, 14 or 15 DNA units.

In further embodiments the region G may consist of a mixture of DNA and other nucleosides capable of mediating RNase H cleavage. Region G may consist of at least 50% DNA, more preferably 60%, 70% or 80% DNA, and even more preferred 90% or 95% DNA.

In a still further embodiment at least one nucleoside unit in region G is an alpha-L-LNA nucleoside unit, such as at least one alpha-L-LNA unit, such as 2, 3, 4, 5, 6, 7, 8 or 9 alpha-L-LNA units. In a further embodiment, region G comprises the least one alpha-L-LNA is alpha-L-oxy-LNA unit. In a further embodiment region G comprises a combination of DNA and alpha-L-LNA nucleoside units.

In some embodiments the size of the contiguous sequence in region G may be longer, such as 15, 16, 17, 18, 19 or 20 nucleoside units.

In some embodiments, nucleosides in region G have a 2' endo structure.

Region F'

Region F' (3' flank or 3' wing) attached to the '3 end of region G comprises, contains or consists of at least one modified nucleoside such as at least 2, at least 3, at least 4, at least 5, at least 6, at least 7 modified nucleosides. In an embodiment region F' comprise or consist of from 1 to 7 modified nucleosides, such as from 2 to 6 modified nucleoside, such as from 2 to 4 modified nucleosides, such as from 1 to 3 modified nucleosides, such as 1, 2, 3 or 4 modified nucleosides. In a further embodiment further additional nucleosides attached to the '3 end of region F', representing a region D', preferably comprising 1, 2 or 3 nucleoside units, such as DNA nucleosides. Region D' can take the function of a biocleavable (B) linker described, in the section "Linkers".

In some embodiments, the modified nucleosides in region F' have a 3' endo structure.

In a preferred embodiment, modified nucleosides in region F' is LNA.

In a further embodiment modified nucleosides in region F' are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In one embodiment of the invention all the modified nucleosides in region F' are LNA nucleosides. In a further embodiment the LNA nucleosides in region F' are independently selected from the group consisting of oxy-LNA, thio-LNA, amino-LNA, cET and/or ENA, in either the beta-D or alpha-L configurations or combinations thereof. In a preferred embodiment region F' has at least 2 beta-D-oxy LNA unit, at the 3' end of the contiguous sequence.

Region D and D'

Region D and D' can be attached to the 5' end of region F or the 3' end of region F', respectively.

Region D or D' may independently comprise 1, 2, 3, 4 or 5 additional nucleotides, which may be complementary or non-complementary to the target nucleic acid. In this respect the oligonucleotide of the invention, may in some embodiments comprise a contiguous nucleotide sequence capable of modulating the target which is flanked at the 5' and/or 3' end by additional nucleotides. Such additional nucleotides may serve as a nuclease susceptible biocleavable linker (see definition of linkers). In some embodiments the additional 5' and/or 3' end nucleotides are linked with phosphodiester linkages, and may be DNA or RNA. In another embodiment, the additional 5' and/or 3' end nucleotides are modified nucleotides which may for example be included to enhance nuclease stability or for ease of synthesis. In an embodiment of the oligonucleotide of the invention, comprises a region D and/or D' in addition to the contiguous nucleotide sequence.

The gapmer oligonucleotide of the present invention can be represented by the following formulae:

F-G-F'; in particular $F_{1-7}$-$G_{4-12}$-$F'_{17}$

D-F-G-F', in particular $D_{1-3}$-$F_{17}$-$G_{4-12}$-$F'_{17}$

F-G-F'-D', in particular $F_{17}$-$G_{4-12}$-$F'_{1-7}$-$D'_{1-3}$

D-F-G-F'-D', in particular $D_{1-3}$-$F_{17}$-$G_{4-12}$-$F'_{1-7}$-$D'_{1-3}$

The preferred number and types of nucleosides in regions F, G and F', D and D' have been described above. The design of the individual oligonucleotide may also have profound impact on the properties of the oligonucleotide in its use for modulating expression of UBE3A.

In some embodiments the oligonucleotide is a gapmer consisting of 14, 15, 16, 17, 18, 19 or 20 nucleotides in length, wherein each of regions F and F' independently consists of 2, 3 or 4 modified nucleoside units complementary to a part of the human SNHG14 long non-coding RNA which is antisense to the UBE3A pre-mRNA (the target nucleic acid) and region G consists of 10, 11, 12, 13, 14 or 15 nucleoside units, capable of recruiting nuclease when in duplex with the target nucleic acid.

In a further embodiments, the oligonucleotide is a gapmer wherein each of regions F and F' independently consists of 2, 3, 4 or 5 modified nucleoside units, such as nucleoside units containing a 2'-O-methoxyethyl-ribose sugar (2'-MOE) or nucleoside units containing a 2'-fluoro-deoxyribose sugar and/or LNA units, and region G consists of 9, 10, 11, 12, 13, 14 or 15 nucleoside units, such as DNA units or other nuclease recruiting nucleosides such as alpha-L-LNA or a mixture of DNA and nuclease recruiting nucleosides.

In a further specific embodiment, the oligonucleotide is a gapmer wherein each of regions F and F' region consists of two LNA units each, and region G consists of 10, 11, 12, 13, 14 or 15 nucleoside units, preferably DNA units. Specific gapmer designs of this nature include 2-10-2, 2-11-2, 2-12-2, 2-13-2, 2-14-2 and 2-15-2.

In a further specific embodiment, the oligonucleotide is a gapmer wherein each of regions F and F' independently consists of three LNA units, and region G consists of 10, 11, 12, 13, 14 or 15 nucleoside units, preferably DNA units. Specific gapmer designs of this nature include 3-10-3, 3-11-3, 3-12-3, 3-13-3, 3-14-3 and 3-15-3.

In a further specific embodiment, the oligonucleotide is a gapmer wherein each of regions F and F' consists of four LNA units each, and region G consists of 10, 11, 12, 13, 14 or 15 nucleoside units, preferably DNA units. Specific gapmer designs of this nature include 4-10-4, 4-11-4, 4-12-4, 4-13-4, 4-14-4 and 4-15-4.

Specific gapmer designs of this nature include F-G-F' designs selected from a group consisting of a gap with 10 nucleosides and independently 1 to 4 modified nucleosides in the wings including 1-10-1, 2-10-1, 1-10-2, 1-10-3, 3-10-1, 1-10-4, 4-10-1, 2-10-2, 2-10-3, 3-10-2, 2-10-4, 4-10-2, 3-10-3, 3-10-4, 4-10-3 and 4-10-4 gapmers.

Specific gapmer designs of this nature include F-G-F' designs selected from a group consisting of a gap with 11 nucleosides and independently 1 to 4 modified nucleosides in the wings including, 1-11-1, 2-11-1, 1-11-2, 1-11-3, 3-11-1, 1-11-4, 4-11-1, 2-11-2, 2-11-3, 3-11-2, 2-11-4, 4-11-2, 3-11-3, 3-11-4, 4-11-3 and 4-11-4 gapmers.

Specific gapmer designs of this nature include F-G-F' designs selected from a group consisting of a gap with 12 nucleosides including, 1-12-1, 2-12-1, 1-12-2, 1-12-3, 3-12-1, 1-12-4, 4-12-1, 2-12-2, 2-12-3, 3-12-2, 2-12-4, 4-12-2, 3-12-3, 3-12-4, 4-12-3 and 4-12-4 gapmers.

Specific gapmer designs of this nature include F-G-F' designs selected from a group consisting of a gap with 13 nucleosides and independently 1 to 4 modified nucleosides in the wings including 1-13-1, 1-13-2, 1-13-3, 3-13-1, 1-13-4, 4-13-1, 2-13-1, 2-13-2, 2-13-3, 3-13-2, 2-13-4, 4-13-2, 3-13-3, 3-13-4, 4-13-3, and 4-13-4 gapmers.

Specific gapmer designs of this nature include F-G-F' designs selected from a group consisting of a gap with 14 nucleosides and independently 1 to 4 modified nucleosides in the wings including 1-14-1, 1-14-2, 2-14-1, 1-14-3, 3-14-1, 1-14-4, 4-14-1, 2-14-2, 2-14-3, 3-14-2 2-14-4, 4-14-2, 3-14-3, 3-14-4 and 4-14-3 gapmers.

Specific gapmer designs of this nature include F-G-F' designs selected from a group consisting of a gap with 15 nucleosides and independently 1 to 4 modified nucleosides in the wings including 1-15-1, 1-15-2, 2-15-1, 1-15-3, 3-15-1, 1-15-4, 4-15-1, 2-15-2, 2-15-3, 3-15-2 2-15-4, 4-15-2, 3-15-3, 3-15-4 and 4-15-3 gapmers.

Specific gapmer designs of this nature include F-G-F' designs selected from a group consisting of a gap with 16 nucleosides and independently 1 to 4 modified nucleosides in the wings including 1-16-1, 1-16-2, 2-16-1, 1-15-3, 3-16-1, 1-16-4, 4-16-1, 2-16-2, 2-16-3, 3-16-2 2-16-4, 4-16-2, 3-16-3, 3-16-4 and 4-16-3 gapmers.

In some embodiments the F-G-F' design is selected from 2-10-4, 3-10-3 and 4-10-2.

In some embodiments the F-G-F' design is selected from 2-11-4, 3-11-2, 3-11-3 and 4-11-2.

In some embodiments the F-G-F' design is selected from 2-12-2, 2-12-3, 2-12-4, 3-12-2, 3-12-3, and 4-12-2.

In some embodiments the F-G-F' design is selected from 2-13-2, 2-13-3, 2-13-4, 3-13-3 and 4-13-2.

In some embodiments the F-G-F' design is selected from 2-14-2, 2-14-4, 3-14-3 and 4-14-2.

In some embodiments the F-G-F' design is selected from 2-15-2 and 2-16-2.

In some embodiments the F-G-F' design is selected from the designs indicated in table 3.

In all instances the F-G-F' design may further include region D and/or D', which may have 1, 2 or 3 nucleoside units, such as DNA units. Preferably, the nucleosides in region F and F' are modified nucleosides, while nucleotides in region G are preferably unmodified nucleosides.

In each design, the preferred modified nucleoside is LNA.

In another embodiment all the internucleoside linkages in the gap in a gapmer are phosphorothioate and/or boranophosphate linkages. In another embodiment all the internucleoside linkages in the flanks (F and F' region) in a gapmer are phosphorothioate and/or boranophosphate linkages. In another preferred embodiment all the internucleoside linkages in the D and D' region in a gapmer are phosphodiester linkages.

For specific gapmers as disclosed herein, when the cytosine (C) residues are annotated as 5-methyl-cytosine, in various embodiments, one or more of the C's present in the oligonucleotide may be unmodified C residues.

Further gapmer designs are disclosed in WO2004/046160, WO2007/146511 and incorporated by reference.

For certain embodiments of the invention, the oligonucleotide is selected from the group of oligonucleotide compounds in table 3.

For certain embodiments of the invention, the oligonucleotide is selected from the group of oligonucleotide compounds with CMP-ID-NO: 4_1 to 150_2.

For certain embodiments of the invention, the oligonucleotide is selected from the group of oligonucleotide compounds with CMP-ID-NO: 4_1 to 678_1.

For certain embodiments of the invention, the oligonucleotide is selected from the group of oligonucleotide compounds with CMP-ID-NO: 4_1 to 818_1 (see oligonucleotide sequences listed in table 3 in the Examples section).

For certain embodiments of the invention, the oligonucleotide is an oligonucleotide compound with CMP-ID-NO: 155_1 or 165_1.

For certain embodiments of the invention, the oligonucleotide is selected from the group of oligonucleotide compounds with CMP-ID-NO: 169_52, 169_50 or 169_56.

For certain embodiments of the invention, the oligonucleotide is selected from the group of oligonucleotide compounds with CMP-ID-NO: 172_1, 272_1, 5727, 572_6 or 572_5.

For certain embodiments of the invention, the oligonucleotide is an oligonucleotide compound with CMP-ID-NO: 175_1.

For certain embodiments of the invention, the oligonucleotide is an oligonucleotide compound with CMP-ID-NO: 178_1.

For certain embodiments of the invention, the oligonucleotide is selected from the group of oligonucleotide compounds with CMP-ID-NO: 5738, 186_1 or 187_1.

For certain embodiments of the invention, the oligonucleotide is an oligonucleotide compound with CMP-ID-NO: 186_1.

For certain embodiments of the invention, the oligonucleotide is selected from the group of oligonucleotide compounds with CMP-ID-NO: 200_1, 204_1, 206_1, 35_2 or 209_1.

For certain embodiments of the invention, the oligonucleotide is selected from the group of oligonucleotide compounds with CMP-ID-NO: 585_1, 5858, 5869, 5865, 5868, 586_4 or 586_6.

For certain embodiments of the invention, the oligonucleotide is an oligonucleotide compound with CMP-ID-NO: 233_1.

For certain embodiments of the invention, the oligonucleotide is an oligonucleotide compound with CMP-ID-NO: 237_8 or 590_13.

For certain embodiments of the invention, the oligonucleotide is an oligonucleotide compound with CMP-ID-NO: 220_1.

For certain embodiments of the invention, the oligonucleotide is selected from the group of oligonucleotide compounds with CMP-ID-NO: 5911, 592_2, 592_4 or 241_9.

For certain embodiments of the invention, the oligonucleotide is selected from the group of oligonucleotide compounds with CMP-ID-NO: 5974, 598_4, 39_1 or 602_1.

For certain embodiments of the invention, the oligonucleotide is an oligonucleotide compound with CMP-ID-NO: 39_1.

For certain embodiments of the invention, the oligonucleotide is an oligonucleotide compound with CMP-ID-NO: 611_7.

For certain embodiments of the invention, the oligonucleotide is an oligonucleotide compound with CMP-ID-NO: 271_1 or 278_1.

For certain embodiments of the invention, the oligonucleotide is selected from the group of oligonucleotide compounds with CMP-ID-NO: 6164, 621_2, 6211, 622_3, 6225, 622_4, 624_3, 624_5, 287_1, 6256, 6267, 6268, 6269, 48_1, 6316, 631_1, 303_1, 304_6 or 304_10.

For certain embodiments of the invention, the oligonucleotide is an oligonucleotide compound with CMP-ID-NO: 636_8.

For certain embodiments of the invention, the oligonucleotide is selected from the group of oligonucleotide compounds with CMP-ID-NO: 6388, 6395, 331_1 or 640_4.

For certain embodiments of the invention, the oligonucleotide is selected from the group of oligonucleotide compounds with CMP-ID-NO: 359_1, 3611, 3615, 362_1 or 641_5.

For certain embodiments of the invention, the oligonucleotide is selected from the group of oligonucleotide compounds with CMP-ID-NO: 378_1, 379_1, 399_1.

For certain embodiments of the invention, the oligonucleotide is selected from the group of oligonucleotide compounds with CMP-ID-NO: 403_1, 405_1, 642_12, 642_13, 644_3 or 646_16.

For certain embodiments of the invention, the oligonucleotide is an oligonucleotide compound with CMP-ID-NO: 85_1 or 425_5.

For certain embodiments of the invention, the oligonucleotide is an oligonucleotide compound with CMP-ID-NO: 116_1.

For certain embodiments of the invention, the oligonucleotide is an oligonucleotide compound with CMP-ID-NO: 123_1 or 124_1.

For certain embodiments of the invention, the oligonucleotide is an oligonucleotide compound with CMP-ID-NO: 126_2.

Method of Manufacture

In a further aspect, the invention provides methods for manufacturing the oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand). In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Composition

In a further aspect, the invention provides pharmaceutical compositions comprising any of the aforementioned oligonucleotides and/or oligonucleotide conjugates and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts.

WO 2007/031091 provides suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

Oligonucleotides or oligonucleotide conjugates of the invention may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

In some embodiments, the oligonucleotide or oligonucleotide conjugate of the invention is a prodrug. In particular with respect to oligonucleotide conjugates the conjugate moiety is cleaved of the oligonucleotide once the prodrug is delivered to the site of action, e.g. the target cell.

Applications

The oligonucleotides of the invention may be utilized as research reagents for, for example, therapeutics and prophylaxis.

In research, such oligonucleotides may be used to specifically modulate the synthesis of UBE3A protein in cells (e.g. in vitro cell cultures) and experimental animals thereby facilitating functional analysis of the target or an appraisal of its usefulness as a target for therapeutic intervention. The target modulation is achieved by degrading or inhibiting a modulator of the gene or mRNA producing the protein.

For therapeutics, an animal or a human, suspected of having a disease or disorder, which can be treated by modulating the expression of UBE3A.

The invention provides methods for treating or preventing a disease, comprising administering a therapeutically or prophylactically effective amount of an oligonucleotide, an oligonucleotide conjugate or a pharmaceutical composition of the invention to a subject suffering from or susceptible to the disease.

The invention also relates to an oligonucleotide, a composition or a conjugate as defined herein for use as a medicament.

The oligonucleotide, oligonucleotide conjugate or a pharmaceutical composition according to the invention is typically administered in an effective amount.

The invention also provides for the use of the oligonucleotide or oligonucleotide conjugate of the invention as described for the manufacture of a medicament for the treatment of a disorder as referred to herein, or for a method of the treatment of as a disorder as referred to herein.

The disease or disorder, as referred to herein, is associated with expression of UBE3A. In some embodiments the disease or disorder may be associated with a mutation in the maternal UBE3A gene. In some embodiments, the target nucleic acid is a regulator of the paternal UBE3A gene.

The methods of the invention are preferably employed for treatment or prophylaxis against diseases caused by abnormal levels and/or activity of UBE3A. The disease may in particular be caused by reduced levels and/or activity of UBE3A protein.

The invention further relates to use of an oligonucleotide, oligonucleotide conjugate or a pharmaceutical composition as defined herein for the manufacture of a medicament for the treatment of abnormal levels and/or activity of UBE3A, in particular low levels and/or activity of UBE3A.

In one embodiment, the invention relates to oligonucleotides, oligonucleotide conjugates or pharmaceutical compositions for use in the treatment of Angelman syndrome.

Administration

The oligonucleotides or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, intra-muscular, intracerebral, intracerebroventricular or intrathecal).

In a preferred embodiment the oligonucleotide or pharmaceutical compositions of the present invention are administered by a parenteral route including intravenous, intraarterial, subcutaneous, intraperitoneal or intramuscular injection or infusion, intrathecal or intracranial, e.g., intracerebral or intraventricular, administration. In one embodiment the active oligonucleotide or oligonucleotide conjugate is administered intracerebral or intracerebroventricular. In another embodiment the active oligonucleotide or oligonucleotide conjugate is administered intrathecal.

The invention also provides for the use of the oligonucleotide or oligonucleotide conjugate of the invention as described for the manufacture of a medicament wherein the medicament is in a dosage form for intrathecal administration.

The invention also provides for the use of the oligonucleotide or oligonucleotide conjugate of the invention as described for the manufacture of a medicament wherein the medicament is in a dosage form for intracerebral or intraventricular administration.

The invention also provides for the use of the oligonucleotide or oligonucleotide conjugate of the invention as described for the manufacture of a medicament wherein the medicament is in a dosage form for intracerebroventricular administration.

Combination Therapies

In some embodiments the oligonucleotide, oligonucleotide conjugate or pharmaceutical composition of the invention is for use in a combination treatment with another therapeutic agent. The therapeutic agent can for example be anticonvulsant medication.

EMBODIMENTS

The following embodiments of the present invention may be used in combination with any other embodiments described herein.

1. An antisense oligonucleotide which comprises or consists of a contiguous nucleotide sequence of 10 to 30 nucleotides in length capable of inducing human paternal UBE3A expression, in particular in a neuronal cell.

2. The oligonucleotide of embodiment 1, wherein the contiguous nucleotide sequence is at least 95% complementarity to the part of human SNHG14 long non-coding RNA which is downstream of SNORD109B corresponding to position 25278410 to 25419462 on chromosome 15.
3. The oligonucleotide of embodiment 1 or 2, wherein the oligonucleotide is capable of hybridizing to a target nucleic acid of SEQ ID NO: 1 with a ΔG° below −10 kcal.
4. The oligonucleotide of embodiment 1-3, wherein the contiguous nucleotide sequence is at least 95%, such as 98%, such as 100% complementarity to region of the target nucleic acid of SEQ ID NO: 1 and/or 2.
5. The oligonucleotide of embodiment 1-3, wherein the contiguous nucleotide sequence is 100% complementary to a region of the target nucleic acid of position 1 to 55318 of SEQ ID NO: 1.
6. The oligonucleotide of embodiment 1-4, wherein the contiguous nucleotide sequence is complementary to a sub-sequence of the target nucleic acid, wherein the subsequence is selected from the group consisting of the regions indicated in table 1 or 2.
7. The oligonucleotide of embodiment 1-4, wherein the contiguous nucleotide sequence is at least 98% complementarity to the part of human SNHG14 long non-coding RNA which is antisense to the UBE3A pre-mRNA.
8. The oligonucleotide of embodiments 1-4 or 7, wherein the oligonucleotide is capable of hybridizing to a target nucleic acid corresponding to position 55319 to 141053 of SEQ ID NO: 1, with a ΔG° below −10 kcal.
9. The oligonucleotide of embodiments 1-4 or 7-8, wherein the contiguous nucleotide sequence is 100% complementary to a target nucleic acid of position 55319 to 141053 of SEQ ID NO: 1.
10. The oligonucleotide of embodiment 1-8, wherein the target nucleic acid is RNA.
11. The oligonucleotide of embodiment 10, wherein the RNA is a long non-coding RNA.
12. The oligonucleotide of embodiment 1-11, wherein the contiguous nucleotide sequence comprises or consists of at least 10 contiguous nucleotides, particularly 11, 12, 13, 14, 15, 16, 17, 18, 19, 20, 21, 22, 23, 24, 25, 26, 27, 28, or 29 contiguous nucleotides.
13. The oligonucleotide of embodiment 1-12, wherein the contiguous nucleotide sequence comprises or consists of from 12 to 22 nucleotides.
14. The oligonucleotide of embodiment 13, wherein the contiguous nucleotide sequence comprises or consists of from 15-20 nucleotides.
15. The oligonucleotide of embodiment 1-14, wherein the oligonucleotide comprises or consists of 10 to 35 nucleotides in length.
16. The oligonucleotide of embodiment 15, wherein the oligonucleotide comprises or consists of 15 to 24 nucleotides in length.
17. The oligonucleotide of embodiment 15 or 17, wherein the oligonucleotide comprises or consists of 17 to 22 nucleotides in length.
18. The oligonucleotide of embodiment 1-17, wherein the oligonucleotide or contiguous nucleotide sequence is single stranded.
19. The oligonucleotide of embodiment 1-18, wherein the contiguous nucleotide sequence is complementary to a sub-sequence of the target nucleic acid, selected from the group consisting of the regions indicated in table 1 or 2.
20. The oligonucleotide of embodiment 1-18, wherein the contiguous nucleotide sequence is complementary to a sub-sequence of the target nucleic acid selected from the group consisting of position 1589-10889, 46089-53989 and 60789-62489 of SEQ ID NO: 1.
21. The oligonucleotide of embodiment 1-18, wherein the contiguous nucleotide sequence is complementary to a sub-sequence of the target nucleic acid corresponding to positions 5218-5240 of SEQ ID NO: 1.
22. The oligonucleotide of embodiment 1-18, wherein the contiguous nucleotide sequence is complementary to a sub-sequence of the target nucleic acid corresponding to positions 5782-5803 of SEQ ID NO: 1.
23. The oligonucleotide of embodiment 1-18, wherein the contiguous nucleotide sequence is complementary to a sub-sequence of the target nucleic acid corresponding to positions 8113-8139 of SEQ ID NO: 1.
24. The oligonucleotide of embodiment 1-18, wherein the contiguous nucleotide sequence is complementary to a sub-sequence of the target nucleic acid corresponding to positions: 9200-9250 of SEQ ID NO: 1.
25. The oligonucleotide of embodiment 1-18, wherein the contiguous nucleotide sequence is complementary to a sub-sequence of the target nucleic acid corresponding to positions: 11505-11555 of SEQ ID NO: 1.
26. The oligonucleotide of embodiment 1-18, wherein the contiguous nucleotide sequence is complementary to a sub-sequence of the target nucleic acid corresponding to positions 13223-13242 of SEQ ID NO: 1.
27. The oligonucleotide of embodiment 1-18, wherein the contiguous nucleotide sequence is complementary to a sub-sequence of the target nucleic acid corresponding to positions 15100-15150 of SEQ ID NO: 1.
28. The oligonucleotide of embodiment 1-18, wherein the contiguous nucleotide sequence is complementary to a sub-sequence of the target nucleic acid corresponding to positions 15113-15180 of SEQ ID NO: 1.
29. The oligonucleotide of embodiment 1-18, wherein the contiguous nucleotide sequence is complementary to a sub-sequence of the target nucleic acid corresponding to positions 29635-29705 of SEQ ID NO: 1.
30. The oligonucleotide of embodiment 1-18, wherein the contiguous nucleotide sequence is complementary to a sub-sequence of the target nucleic acid corresponding to positions 30590-30740 of SEQ ID NO: 1.
31. The oligonucleotide of embodiment 1-18, wherein the contiguous nucleotide sequence is complementary to a sub-sequence of the target nucleic acid corresponding to positions 39800-39855 of SEQ ID NO: 1.
32. The oligonucleotide of embodiment 1-18, wherein the contiguous nucleotide sequence is complementary to a sub-sequence of the target nucleic acid corresponding to positions 44435-44460 of SEQ ID NO: 1.
33. The oligonucleotide of embodiment 1-18, wherein the contiguous nucleotide sequence is complementary to a sub-sequence of the target nucleic acid corresponding to positions 45245-45270 of SEQ ID NO: 1
34. The oligonucleotide of embodiment 1-18, wherein the contiguous nucleotide sequence is complementary to a sub-sequence of the target nucleic acid to positions 46380-46430 of SEQ ID NO: 1.
35. The oligonucleotide of embodiment 1-18, wherein the contiguous nucleotide sequence is complementary to a sub-sequence of the target nucleic acid corresponding to positions 68915-68940 of SEQ ID NO: 1.

36. The oligonucleotide of embodiment 1-35, wherein the oligonucleotide is neither siRNA nor self-complementary.

37. The oligonucleotide of embodiment 1-36, wherein the contiguous nucleotide sequence comprises or consists of a sequence selected from the group consisting of SEQ ID NO: 4, 5, 6, 7, 8, 9, 10, 11, 12, 13, 14, 15, 16, 17, 1819, 20, 21, 22, 23, 23, 24, 25, 26, 26, 27, 28, 29, 30, 31, 31, 32, 33, 34, 35, 36, 37, 38, 39, 40, 41, 42, 43, 44, 44, 45, 45, 46, 47, 48, 49, 50, 51, 52, 53, 53, 54, 54, 55, 56, 57, 58, 59, 60, 61, 62, 63, 64, 64, 65, 66, 67, 68, 69, 70, 71, 72, 73, 74, 75, 76, 77, 78, 79, 79, 80, 81, 8283, 84, 85, 86, 87, 88, 89, 90, 91, 92, 93, 94, 95, 95, 96, 96, 96, 97, 98, 99, 100, 101, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 702, 703, 704, 705, 706, 707, 708, 709, 710, 711, 712, 713, 714, 715, 716, 717, 718, 719, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 755, 756, 757, 758, 759, 760, 761, 762, 763, 764, 765, 766, 767, 768, 769, 770, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817 and 818.

38. The oligonucleotide of embodiment 1-36, wherein the contiguous nucleotide sequence comprises or consists of a sequence selected from the group consisting of SEQ ID NO: 166, 167, 167 or 169 (see motif sequences listed in table 3 in the Examples section).

39. The oligonucleotide of embodiment 1-36, wherein the contiguous nucleotide sequence comprises or consists of a sequence selected from the group consisting of SEQ ID NO: 570, 571,572, 679, 680, 681, 682 and 683 (see motif sequences listed in table 3 in the Examples section).

40. The oligonucleotide of embodiment 1-36, wherein the contiguous nucleotide sequence comprises or consists of a sequence selected from the group consisting of SEQ ID NO: 570, 571,572, 679, 680, 681, 682 and 683 (see motif sequences listed in table 3 in the Examples section).

41. The oligonucleotide of embodiment 1-36, wherein the contiguous nucleotide sequence comprises or consists of a sequence selected from the group consisting of SEQ ID NO: 35, 199 to 210 or SEQ ID NO: 582 to 584 (see motif sequences listed in table 3 in the Examples section).

42. The oligonucleotide of embodiment 1-36, wherein the contiguous nucleotide sequence comprises or consists of a sequence selected from the group consisting of SEQ ID NO: 236, 237, 238, 239, 240 and 590 (see motif sequences listed in table 3 in the Examples section).

43. The oligonucleotide of embodiment 1-36, wherein the contiguous nucleotide sequence comprises or consists of a sequence selected from the group consisting of SEQ ID NO: 221 to 225 or SEQ ID NO: 585 to 589 (see motif sequences listed in table 3 in the Examples section).

44. The oligonucleotide of embodiment 1-36, wherein the contiguous nucleotide sequence comprises or consists of a sequence selected from the group consisting of SEQ ID NO: 241 or 591 (see motif sequences listed in table 3 in the Examples section).

45. The oligonucleotide of embodiment 1-36, wherein the contiguous nucleotide sequence comprises or consists of a sequence selected from the group consisting of SEQ ID NO: 46-48, 285 to 305 or SEQ ID NO: 613 to 632 or SEQ ID NO: 721 to 807 (see motif sequences listed in table 3 in the Examples section).

46. The oligonucleotide of embodiment 1-36, wherein the contiguous nucleotide sequence comprises or consists of a sequence selected from the group consisting of of SEQ ID NO: 331, 332, 638, 639, 640, 808, 809, 810, 811, 812, 813, 814 and 815 (see motif sequences listed in table 3 in the Examples section).

47. The oligonucleotide of embodiment 1-36, wherein the contiguous nucleotide sequence comprises or consists of a sequence selected from the group consisting of SEQ ID NO: 409 to 411 or SEQ ID NO: 642 to 646 or SEQ ID NO: 816 to 818 (see motif sequences listed in table 3 in the Examples section).
48. The oligonucleotide of embodiment 1-47, wherein the contiguous nucleotide sequence has zero to three mismatches compared to the target nucleic acid it is complementary to.
49. The oligonucleotide of embodiment 48, wherein the contiguous nucleotide sequence has one mismatch compared to the target nucleic acid.
50. The oligonucleotide of embodiment 48, wherein the contiguous nucleotide sequence has two mismatches compared to the target nucleic acid.
51. The oligonucleotide of embodiment 48, wherein the contiguous nucleotide sequence is fully complementary to the target nucleic acid sequence.
52. The oligonucleotide of embodiment 1-51, comprising one or more modified nucleosides.
53. The oligonucleotide of embodiment 52, wherein the one or more modified nucleoside is a high-affinity modified nucleosides.
54. The oligonucleotide of embodiment 52 or 53, wherein the one or more modified nucleoside is a 2' sugar modified nucleoside.
55. The oligonucleotide of embodiment 54, wherein the one or more 2' sugar modified nucleoside is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, 2'-fluoro-ANA and LNA nucleosides.
56. The oligonucleotide of embodiment 54, wherein the one or more modified nucleoside is a LNA nucleoside.
57. The oligonucleotide of embodiment 56, wherein the modified LNA nucleoside is oxy-LNA.
58. The oligonucleotide of embodiment 57, wherein the modified nucleoside is beta-D-oxy-LNA.
59. The oligonucleotide of embodiment 57, wherein the modified nucleoside is alpha-L-oxy-LNA
60. The oligonucleotide of embodiment 56, wherein the modified nucleoside is thio-LNA.
61. The oligonucleotide of embodiment 56, wherein the modified nucleoside is amino-LNA.
62. The oligonucleotide of embodiment 56, wherein the modified nucleoside is cET.
63. The oligonucleotide of embodiment 56, wherein the modified nucleoside is ENA.
64. The oligonucleotide of embodiment 56, wherein the modified LNA nucleoside is selected from beta-D-oxy-LNA, alpha-L-oxy-LNA, beta-D-amino-LNA, alpha-L-amino-LNA, beta-D-thio-LNA, alpha-L-thio-LNA, (S)cET, (R)cET beta-D-ENA and alpha-L-ENA.
65. The oligonucleotide of any one of embodiments 1-64, wherein the oligonucleotide comprises at least one modified internucleoside linkage.
66. The oligonucleotide of embodiment 65, wherein the modified internucleoside linkage is nuclease resistant.
67. The oligonucleotide of embodiment 65 or 66, wherein at least 50% of the internucleoside linkages within the contiguous nucleotide sequence are phosphorothioate internucleoside linkages or boranophosphate internucleoside linkages.
68. The oligonucleotide of embodiment 65 or 66, wherein all the internucleoside linkages within the contiguous nucleotide sequence are phosphorothioate internucleoside linkages.
69. The oligonucleotide of embodiment 1-68, wherein the oligonucleotide is capable of recruiting RNase H.
70. The oligonucleotide of embodiment 69, wherein the oligonucleotide is a gapmer.
71. The oligonucleotide of embodiment 69 or 70, wherein the oligonucleotide is a gapmer of formula 5'-F-G-F'-3', where region F and F' independently comprise or consist of 1-7 modified nucleosides and G is a region between 6 and 16 nucleosides which are capable of recruiting RNaseH.
72. The oligonucleotide of embodiment 71, wherein the modified nucleoside is a 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.
73. The oligonucleotide of embodiment 71 or 72, wherein one or more of the modified nucleosides in region F and F' is a LNA nucleoside.
74. The oligonucleotide of embodiment 73, wherein all the modified nucleosides in region F and F' are LNA nucleosides.
75. The oligonucleotide of embodiment 74, wherein region F and F' consist of LNA nucleosides.
76. The oligonucleotide of embodiment 73-75, wherein all the modified nucleosides in region F and F' are oxy-LNA nucleosides.
77. The oligonucleotide of embodiment 73, wherein at least one of region F or F' further comprises at least one 2' substituted modified nucleoside independently selected from the group consisting of 2'-O-alkyl-RNA, 2'-O-methyl-RNA, 2'-alkoxy-RNA, 2'-O-methoxyethyl-RNA, 2'-amino-DNA and 2'-fluoro-DNA.
78. The oligonucleotide of embodiment 73-77, wherein the RNaseH recruiting nucleosides in region G are independently selected from DNA, alpha-L-LNA, C4' alkylated DNA, ANA and 2'F-ANA and UNA.
79. The oligonucleotide of embodiment 78, wherein the nucleosides in region G is DNA and/or alpha-L-LNA nucleosides.
80. The oligonucleotide of embodiment 78 or 79, wherein region G consists of at least 75% DNA nucleosides.
81. The oligonucleotide of embodiment 1-80, wherein the oligonucleotide is capable of increasing the expression of UBE3A by at least 30% compared to a control.
82. The oligonucleotide of embodiment 1-81, wherein the level of the SNHG14 transcript downstream of SNORD109B is reduced by at least 20% compared to a control.
83. The oligonucleotide of embodiment 1-82, wherein the expression of SNORD115 is not significantly affected compared to a control.
84. The oligonucleotide of embodiment 1-83, wherein the oligonucleotide is selected from CMP ID NO: 4_1 to 678_1.
85. The oligonucleotide of embodiment 1-83, wherein the oligonucleotide is selected from the group consisting of CMP ID NO: 4_1, 4_2, 5_1, 5_2, 6_1, 6_2, 7_1, 7_2, 8_1, 9_1, 10_1, 11_1, 11_2, 12_1, 12_2, 13_1, 13_2, 14_1, 15_1, 16_1, 17_1, 17_2, 18_1, 18_2, 19_1, 19_2, 20_1, 21_1, 22_1, 23_1, 23_2, 24_1, 25_1, 26_1, 26_2, 27_1, 28_1, 28_2, 29_1, 29_2, 30_1, 31_1, 31_2, 32_1, 33_1, 34_1, 34_2, 34_3, 34_4, 34_5, 34_6, 34_7, 35_1, 35_2, 36_1, 37_1, 38_1, 38_2, 38_3, 38_4, 38_5, 38_6, 39_1, 39_2, 39_3, 39_4, 39_5, 40_1, 40_2, 40_3, 40_4, 40_5, 40_6, 40_7, 40_8, 41_1, 42_1, 43_1, 44_1, 44_2, 45_1, 45_2, 46_1, 47_1, 48_1, 48_2, 48_3, 48_4, 48_5, 48_6, 48_7, 49_1, 50_1, 51_1, 52_1, 53_1, 53_2, 54_1, 54_2, 54_3, 55_1, 55_2, 56_1, 57_1, 58_1, 58_2, 58_3, 59_1, 59_2, 60_1, 60_2, 60_3, 61_1, 62_1, 63_1, 64_1, 64_2, 65_1, 66_1, 67_1, 68_1, 69_1, 69_2, 69_3, 70_1, 70_2, 70_3, 71_1, 72_1, 72_2, 73_1, 73_2, 73_3, 74_1, 74_2, 75_1, 75_2, 76_1, 77_1, 77_2, 77_3, 78_1, 79_1, 79_2, 79_3, 80_1, 80_2, 80_3, 81_1, 82_1, 82_2, 83_1, 83_2, 84_1, 84_2, 85_1, 85_2, 86_1, 87_1, 88_1, 88_2, 89_1, 90_1, 91_1, 92_1, 93_1, 94_1, 95_1, 95_2, 96_1, 96_2, 96_3, 97_1, 97_2, 97_3, 97_4, 98_1, 98_2, 98_3, 99_1, 99_2, 99_3, 99_4, 100_1, 100_2, 100_3, 101_1, 101_2, 101_3, 101_4, 102_1, 102_2, 102_3, 102_4, 103_1, 103_2, 103_3, 103_4, 104_1, 104_2, 104_3, 105_1, 105_2, 105_3, 105_4, 106_1, 106_2, 106_3, 106_4, 107_1, 107_2, 107_3, 107_4, 108_1, 108_2, 108_3, 108_4, 109_1, 109_2, 109_3, 109_4, 110_1, 110_2, 111_1, 111_2, 111_3, 112_1, 112_2, 113_1, 114_1, 115_1, 116_1, 117_1, 118_1, 119_1, 120_1, 120_2, 121_1, 122_1, 123_1, 124_1, 125_1, 126_1, 126_2, 127_1, 128_1, 128_2, 128_3, 128_4, 129_1, 129_2, 130_1, 131_1, 132_1, 132_2, 132_3, 133_1, 133_2, 133_3, 133_4, 134_1, 134_2, 135_1, 135_2, 136_1, 137_1, 138_1, 139_1, 140_1, 141_1, 142_1, 143_1, 144_1, 145_1, 145_2, 146_1, 146_2, 147_1, 148_1, 149_1, 150_1, 150_2, 151_1, 152_1, 153_1, 154_1, 155_1, 156_1, 157_1, 158_1, 159_1, 160_1, 161_1, 162_1, 163_1, 164_1, 165_1, 166_1, 167_1, 168_1, 169_1, 169_10, 169_11, 169_12, 169_13, 169_14, 169_15, 169_16, 169_17, 169_18, 169_19, 169_2, 169_20, 169_21, 169_22, 169_23, 169_24, 169_25, 169_26, 169_27, 169_28, 169_29, 169_3, 169_30, 169_31, 169_32, 169_33, 169_34, 169_35, 169_36, 169_37, 169_38, 169_39, 169_4, 169_40, 169_41, 169_42, 169_43, 169_44, 169_45, 169_46, 169_47, 169_48, 169_49, 169_5, 169_50, 169_51, 169_52, 169_53, 169_54, 169_55, 169_56, 169_57, 169_6, 169_7, 169_8, 169_9, 169_58, 169_59, 169_60, 169_61, 169_62, 170_1, 171_1, 172_1, 173_1, 174_1, 175_1, 176_1, 177_1, 178_1, 179_1, 180_1, 181_1, 182_1, 183_1, 184_1, 185_1, 186_1, 187_1, 188_1, 189_1, 190_1, 191_1, 192_1, 193_1, 194_1, 195_1, 196_1, 197_1, 198_1, 199_1, 200_1, 201_1, 202_1, 203_1, 204_1, 205_1, 206_1, 207_1, 208_1, 208_2, 208_3, 208_4, 208_5, 208_6, 208_7, 209_1, 209_10, 209_2, 209_3, 209_4, 209_5, 209_6, 209_7, 209_8, 209_9, 210_1, 211_1, 212_1, 213_1, 214_1, 215_1, 216_1, 217_1, 218_1, 219_1, 220_1, 221_1, 222_1, 223_1, 224_1, 225_1, 226_1, 227_1, 228_1, 229_1, 230_1, 231_1, 232_1, 233_1, 234_1, 235_1, 236_1, 236_10, 236_11, 236_12, 236_13, 236_14, 236_15, 236_16, 236_2, 236_3, 236_4, 236_5, 236_6, 236_7, 236_8, 236_9, 236_17, 236_18, 236_19, 236_20, 236_21, 237_1, 237_10, 237_11, 237_12, 237_13, 237_14, 237_15, 237_16, 237_2, 237_3, 237_4, 237_5, 237_6, 237_7, 237_8, 237_9, 237_17, 237_18, 237_19, 237_20, 237_21, 238_1, 239_1, 239_10, 239_11, 239_12, 239_13, 239_14, 239_15, 239_16, 239_2, 239_3, 239_4, 239_5, 239_6, 239_7, 239_8, 239_9, 239_17, 239_18, 239_19, 239_20, 239_21, 240_1, 241_1, 241_10, 241_2, 241_3, 241_4, 241_5, 241_6, 241_7, 241_8, 241_9, 241_11, 241_12, 241_13, 241_14, 241_15, 242_1, 243_1, 244_1, 244_2, 244_3, 244_4, 244_5, 245_1, 246_1, 247_1, 248_1, 249_1, 250_1, 251_1, 252_1, 253_1, 254_1, 255_1, 256_1, 257_1, 258_1, 259_1, 260_1, 261_1, 262_1, 263_1, 264_1, 265_1, 266_1, 267_1, 268_1, 269_1, 270_1, 271_1, 272_1, 273_1, 274_1, 275_1, 276_1, 277_1, 278_1, 279_1, 280_1, 281_1, 282_1, 283_1, 284_1, 285_1, 285_2, 285_3, 285_4, 285_5, 285_6, 285_7, 285_8, 285_9, 285_10, 285_11, 286_1, 287_1, 288_1, 289_1, 290_1, 291_1, 292_1, 293_1, 294_1, 295_1, 296_1, 297_1, 298_1, 299_1, 300_1, 301_1, 302_1, 303_1, 304_1, 304_10, 304_2, 304_3, 304_4, 304_5, 304_6, 304_7, 304_8, 304_9, 304_11, 304_12, 304_13, 304_14, 304_15, 305_1, 306_1, 307_1, 308_1, 309_1, 310_1, 311_1, 312_1, 313_1, 314_1, 315_1, 316_1, 317_1, 318_1, 319_1, 320_1, 321_1, 322_1, 323_1, 324_1, 325_1, 326_1, 327_1, 328_1, 329_1, 330_1, 331_1, 332_1, 333_1, 334_1, 335_1, 336_1, 337_1, 338_1, 339_1, 340_1, 341_1, 342_1, 343_1, 344_1, 345_1, 346_1, 347_1, 348_1, 349_1, 350_1, 351_1, 352_1, 353_1, 354_1, 355_1, 356_1, 357_1, 358_1, 359_1, 360_1, 361_1, 361_10, 361_2, 361_3, 361_4, 361_5, 361_6, 361_7, 361_8, 361_9, 362_1, 362_10, 362_2, 362_3, 362_4, 362_5, 362_6, 362_7, 362_8, 362_9, 363_1, 364_1, 365_1, 366_1, 367_1, 368_1, 369_1, 370_1, 371_1, 372_1, 373_1, 374_1, 375_1, 376_1, 377_1, 378_1, 379_1, 380_1, 381_1, 382_1, 383_1, 384_1, 385_1, 386_1, 387_1, 388_1, 389_1, 390_1, 391_1, 392_1, 393_1, 394_1, 395_1, 396_1, 397_1, 398_1, 399_1, 400_1, 401_1, 402_1, 403_1, 404_1, 405_1, 406_1, 407_1, 408_1, 409_1, 410_1, 411_1, 412_1, 413_1, 414_1, 415_1, 416_1, 417_1, 418_1, 419_1, 420_1, 421_1, 422_1, 423_1, 424_1, 425_1, 425_10, 425_2, 425_3, 425_4, 425_5, 425_6, 425_7, 425_8, 425_9, 426_1, 427_1, 428_1, 429_1, 430_1, 431_1, 432_1, 433_1, 434_1, 435_1, 436_1, 437_1, 438_1, 439_1, 440_1, 441_1, 442_1, 443_1, 444_1, 445_1, 446_1, 447_1, 448_1, 449_1, 450_1, 451_1, 452_1, 453_1, 454_1, 455_1, 456_1, 457_1, 458_1, 459_1, 460_1, 461_1, 462_1, 463_1, 464_1, 465_1, 466_1, 467_1, 468_1, 469_1, 470_1, 471_1, 472_1, 473_1, 474_1, 475_1, 476_1, 477_1, 478_1, 479_1, 480_1, 481_1, 482_1, 483_1, 484_1, 485_1, 486_1, 487_1, 488_1, 489_1, 490_1, 491_1, 492_1, 493_1, 494_1, 495_1, 496_1, 497_1, 498_1, 499_1, 500_1, 501_1, 502_1, 503_1, 504_1, 505_1, 506_1, 507_1, 508_1, 509_1, 510_1, 511_1, 512_1, 513_1, 514_1, 515_1, 516_1, 517_1, 518_1, 519_1, 520_1, 521_1, 522_1, 523_1, 524_1, 525_1, 526_1, 527_1, 528_1, 529_1, 530_1, 531_1, 532_1, 533_1, 534_1, 535_1, 536_1, 537_1, 538_1, 539_1, 540_1, 541_1, 542_1, 543_1, 544_1, 545_1, 546_1, 547_1, 548_1, 549_1, 550_1, 551_1, 552_1, 553_1, 554_1, 555_1, 556_1, 557_1, 558_1, 559_1, 560_1, 561_1, 562_1, 563_1, 564_1, 565_1, 566_1, 567_1, 568_1, 569_1, 570_1, 570_2, 570_3, 570_4, 570_5, 570_6, 570_7, 570_8, 570_9, 570_10, 570_11, 570_12, 570_13, 570_14, 571_1, 571_2, 571_3, 571_4, 571_5, 571_6, 571_7, 571_8, 571_9, 571_10, 571_11, 571_12, 571_13, 571_14, 572_1, 572_2, 572_3, 572_4, 572_5, 572_6, 572_7, 572_8, 572_9, 572_10, 572_11, 572_12, 572_13, 572_14, 573_1, 573_2, 573_3, 573_4, 573_5, 573_6, 573_7, 573_8, 573_9, 573_10, 573_11, 573_12, 573_13, 573_14, 574_1, 574_2, 574_3, 574_4, 574_5, 574_6, 574_7, 574_8, 574_9, 574_10, 574_11, 574_12, 574_13, 574_14, 575_1, 575_2, 575_3, 575_4, 575_5, 575_6, 575_7, 575_8, 575_9, 575_10, 575_11, 575_12, 575_13, 575_14, 576_1, 576_2, 576_3, 576_4, 576_5, 576_6, 576_7, 576_8, 576_9, 576_10, 576_11, 576_12, 576_13, 576_14, 577_1, 577_2, 577_3, 577_4, 577_5, 577_6, 577_7, 577_8, 577_9, 577_10, 577_11, 577_12, 577_13, 577_14, 578_1, 578_2, 578_3, 578_4, 578_5, 578_6, 578_7, 578_8, 578_9, 579_1, 579_2, 579_3, 579_4, 579_5, 579_6, 579_7, 579_8, 579_9, 580_1, 580_2, 580_3, 580_4, 580_5, 580_6, 580_7, 580_8, 580_9, 581_1, 581_2, 581_3, 581_4, 581_5, 581_6, 581_7, 581_8, 581_9, 582_1, 582_2, 582_3, 582_4, 582_5, 582_6, 582_7, 582_8, 582_9, 583_1, 583_2, 583_3, 583_4, 583_5, 583_6, 583_7, 583_8, 583_9, 584_1, 584_2, 584_3, 584_4, 584_5, 584_6, 584_7, 584_8, 585_1, 585_2, 585_3, 585_4, 585_5, 585_6, 585_7, 585_8, 585_9, 585_10, 585_11, 585_12, 585_13, 585_14, 586_1, 586_2, 586_3, 586_4, 586_5, 586_6, 586_7, 586_8, 586_9, 586_10, 586_11, 586_12, 586_13, 586_14, 587_1, 587_2, 587_3, 587_4, 587_5, 587_6, 587_7, 587_8, 587_9, 587_10, 587_11, 587_12, 587_13, 587_14, 588_1, 588_2, 588_3, 588_4, 588_5, 588_6, 588_7, 588_8, 588_9, 588_10, 588_11, 588_12, 588_13, 588_14, 589_1, 589_2, 589_3, 589_4, 589_5, 589_6, 589_7, 589_8, 589_9, 589_10, 589_11, 589_12, 589_13, 589_14, 590_1, 590_10, 590_11, 590_12, 590_13, 590_14, 590_15, 590_2, 590_3, 590_4, 590_5, 590_6, 590_7, 590_8, 590_9, 590_16, 590_17, 590_18, 590_19, 590_20, 591_1, 591_2, 592_1, 592_2, 592_3, 592_4, 592_5, 592_6, 592_7, 592_8, 592_9, 592_10, 592_11, 592_12, 592_13, 592_14, 593_1, 593_2, 593_3, 593_4, 594_1, 594_2, 594_3, 594_4, 595_1, 595_2, 595_3, 595_4, 596_1, 596_2, 596_3, 596_4, 597_1, 597_2, 597_3, 597_4, 598_1, 598_2, 598_3, 598_4, 599_1, 599_2, 599_3, 599_4, 600_1, 600_2, 600_3, 600_4, 601_1, 601_2, 601_3, 601_4, 602_1, 602_2, 602_3, 602_4, 603_1, 603_2, 603_3, 603_4, 604_1, 604_2, 604_3, 604_4, 605_1, 605_2, 605_3, 605_4, 606_1, 606_2, 606_3, 606_4, 607_1, 607_2, 607_3, 607_4, 608_1, 608_2, 608_3, 608_4, 608_5, 608_6, 608_7, 608_8, 608_9, 609_1, 609_2, 609_3, 609_4, 609_5, 609_6, 609_7, 609_8, 609_9, 610_1, 610_2, 610_3, 610_4, 610_5, 610_6, 610_7, 610_8, 610_9, 611_1, 611_2, 611_3, 611_4, 611_5, 611_6, 611_7, 611_8, 611_9, 612_1, 612_2, 612_3, 612_4, 612_5, 612_6, 612_7, 612_8, 612_9, 613_1, 613_2, 613_3, 613_4, 613_5, 613_6, 613_7, 613_8, 613_9, 613_10, 614_1, 614_2, 614_3, 614_4, 614_5, 614_6, 614_7, 614_8, 614_9, 614_10, 615_1, 615_2, 615_3, 615_4, 615_5, 615_6, 615_7, 615_8, 615_9, 615_10, 616_1, 616_2, 616_3, 616_4, 616_5, 616_6, 616_7, 616_8, 616_9, 616_10, 617_1, 617_2, 617_3, 617_4, 617_5, 617_6, 617_7, 617_8, 617_9, 617_10, 618_1, 618_2, 618_3, 618_4, 618_5, 618_6, 618_7, 618_8, 618_9, 618_10, 619_1, 619_2, 619_3, 619_4, 619_5, 619_6, 619_7, 619_8, 619_9, 619_10, 620_1, 620_2, 620_3, 620_4, 620_5, 620_6, 620_7, 620_8, 620_9, 620_10, 621_1, 621_2, 621_3, 621_4, 621_5, 621_6, 621_7, 621_8, 621_9, 621_10, 621_11, 622_1, 622_2, 622_3, 622_4, 622_5, 622_6, 622_7, 622_8, 622_9, 622_10, 623_1, 623_2, 623_3, 623_4, 623_5, 623_6, 623_7, 623_8, 623_9, 623_10, 624_1, 624_2, 624_3, 624_4, 624_5, 624_6, 624_7, 624_8, 624_9, 624_10, 625_1, 625_2, 625_3, 625_4, 625_5, 625_6, 625_7, 625_8, 625_9, 625_10, 625_11, 625_12, 625_13, 625_14, 626_1, 626_2, 626_3, 626_4, 626_5, 626_6, 626_7, 626_8, 626_9, 626_10, 626_11, 626_12, 626_13, 626_14, 627_1, 627_2, 627_3, 627_4, 627_5, 627_6, 627_7, 627_8, 627_9, 627_10, 627_11, 627_12, 627_13, 627_14, 628_1, 628_2, 628_3, 628_4, 628_5, 628_6, 628_7, 628_8, 628_9, 628_10, 628_11, 628_12, 628_13, 628_14, 629_1, 629_10, 629_11, 629_2, 629_3, 629_4, 629_5, 629_6, 629_7, 629_8, 629_9, 629_12, 629_13, 629_14, 629_15, 629_16, 630_1, 630_2,630_3,631_1,631_10, 631_2,631_3,631_4, 631_5,631_6, 631_7,631_8, 631_9, 631_11, 631_12, 631_13, 631_14, 631_15, 632_1, 632_2, 632_3, 632_4, 632_5, 632_6, 632_7, 632_8, 632_9, 632_10, 632_11, 632_12, 632_13, 632_14, 633_1, 633_2, 633_3, 633_4, 633_5, 633_6, 633_7, 633_8, 633_9, 634_1, 634_2, 634_3, 634_4, 634_5, 634_6, 634_7, 634_8, 634_9, 635_1, 635_2, 635_3, 635_4, 635_5, 635_6, 635_7, 635_8, 635_9, 636_1, 636_2, 636_3, 636_4, 636_5, 636_6, 636_7, 636_8, 636_9, 637_1, 637_2, 637_3, 637_4, 637_5, 637_6, 637_7, 637_8, 637_9, 638_1, 638_2, 638_3, 638_4, 638_5, 638_6, 638_7, 638_8, 638_9, 638_10, 638_11, 638_12, 638_13, 638_14, 639_1, 639_2, 639_3, 639_4, 639_5, 639_6, 639_7, 639_8, 639_9, 639_10, 639_11, 639_12, 639_13, 639_14, 640_1, 640_2, 640_3, 640_4, 640_5, 640_6, 640_7, 640_8, 640_9, 640_10, 640_11, 640_12, 640_13, 640_14, 641_1, 641_2, 641_3, 641_4, 641_5, 641_6, 641_7, 641_8, 641_9, 642_1, 642_10, 642_11, 642_12, 642_13, 642_14, 642_15, 642_16, 642_17, 642_2, 642_3, 642_4, 642_5, 642_6, 642_7, 642_8, 642_9, 642_18, 642_19, 642_20, 642_21, 642_22, 643_1, 644_1, 644_2, 644_3, 644_4, 644_5, 644_6, 645_1, 645_2, 645_3, 645_4, 645_5, 645_6, 645_7, 645_8, 645_9, 645_10, 646_1, 646_10, 646_11, 646_12, 646_13, 646_14, 646_15, 646_16, 646_17, 646_18, 646_19, 646_2, 646_3, 646_4, 646_5, 646_6, 646_7, 646_8, 646_9, 646_20, 646_21, 646_22, 646_23, 646_24, 647_1, 648_1, 649_1, 650_1, 651_1, 652_1, 653_1, 654_1, 655_1, 656_1, 657_1, 658_1, 659_1, 660_1, 661_1, 662_1, 663_1, 664_1, 665_1, 666_1, 667_1, 668_1, 669_1, 670_1, 671_1, 672_1, 673_1, 674_1, 675_1, 676_1, 677_1, 678_1, 679_1, 679_2, 679_3, 679_4, 679_5, 680_1, 680_2, 680_3, 680_4, 680_5, 681_1, 681_2, 681_3, 681_4, 681_5, 682_1, 682_2, 682_3, 682_4, 682_5, 683_1, 683_2, 683_3, 683_4, 683_5, 684_1, 684_2, 684_3, 684_4, 684_5, 685_1, 685_2, 685_3, 685_4, 685_5, 686_1, 686_2, 686_3, 686_4, 686_5, 687_1, 687_2, 687_3, 687_4, 687_5, 688_1, 688_2, 688_3, 688_4, 688_5, 689_1, 689_2, 689_3, 689_4, 689_5, 690_1, 690_2, 690_3, 690_4, 690_5, 691_1, 691_2, 692_1, 692_2, 692_3, 692_4, 692_5, 693_1, 693_2, 693_3, 693_4, 693_5, 694_1, 694_2, 694_3, 694_4, 694_5, 695_1, 695_2, 695_3, 695_4, 695_5, 696_1, 696_2, 696_3, 696_4, 696_5, 697_1, 697_2, 697_3, 697_4, 697_5, 698_1, 698_2, 698_3, 698_4, 698_5, 699_1, 699_2, 699_3, 699_4, 699_5, 700_1, 700_2, 700_3, 700_4, 700_5, 701_1, 701_2, 701_3, 701_4, 701_5, 702_1, 702_2, 702_3, 702_4, 702_5, 703_1, 703_2, 703_3, 703_4, 703_5, 704_1, 704_2, 704_3, 704_4, 704_5, 705_1, 705_2, 705_3, 705_4, 705_5, 706_1, 706_2, 706_3, 706_4, 706_5, 707_1, 707_2, 707_3, 707_4, 707_5, 708_1, 708_2, 708_3, 708_4, 708_5, 709_1, 709_2, 709_3, 709_4, 709_5, 710_1, 710_2, 710_3, 710_4, 710_5, 711_1, 711_2, 711_3, 711_4, 711_5, 712_1, 712_2, 712_3, 712_4, 712_5, 713_1, 713_2, 713_3, 713_4, 713_5, 714_1, 714_2, 714_3, 714_4, 714_5, 715_1, 715_2, 715_3, 715_4, 715_5, 716_1, 716_2, 716_3, 716_4, 716_5, 717_1, 717_2, 717_3, 717_4, 717_5, 718_1, 718_2, 719_1, 719_2, 719_3, 719_4, 719_5, 720_1, 720_2, 720_3, 720_4, 720_5, 721_1, 721_2, 721_3, 721_4, 721_5, 722_1, 722_2, 722_3, 722_4, 722_5, 723_1, 723_2, 723_3, 723_4, 723_5, 724_1, 724_2, 724_3, 724_4, 724_5, 725_1, 725_2, 725_3, 725_4, 725_5, 726_1, 726_2, 726_3, 726_4, 726_5, 727_1, 727_2, 727_3, 727_4, 727_5, 728_1, 728_2, 728_3, 728_4, 728_5, 729_1, 729_2, 729_3, 729_4, 729_5, 730_1, 730_2, 730_3, 730_4, 730_5, 731_1, 731_2, 731_3, 731_4, 731_5, 732_1, 732_2, 732_3, 732_4, 732_5, 733_1, 733_2, 733_3, 733_4, 733_5, 734_1, 734_2, 734_3, 734_4, 734_5, 735_1, 735_2, 735_3, 735_4, 735_5, 736_1, 736_2, 736_3, 736_4, 736_5, 737_1, 737_2, 737_3, 737_4, 737_5, 738_1, 738_2, 738_3, 738_4, 738_5, 738_6, 739_1, 739_2, 739_3, 739_4, 739_5, 740_1, 740_2, 740_3, 740_4, 740_5, 741_1, 741_2, 741_3, 741_4, 741_5, 742_1, 742_2, 742_3, 743_1, 743_2, 743_3, 743_4, 743_5, 744_1, 744_2, 744_3, 744_4, 744_5, 745_1, 745_2, 745_3, 745_4, 745_5, 746_1, 746_2, 746_3, 747_1, 747_2, 747_3, 747_4, 747_5, 748_1, 748_2, 748_3, 748_4, 748_5, 749_1, 749_2, 749_3, 749_4, 749_5, 750_1, 750_2, 750_3, 750_4, 751_1, 751_2, 751_3, 751_4, 751_5, 752_1, 752_2, 752_3, 752_4, 752_5, 753_1, 753_2, 753_3, 753_4, 753_5, 754_1, 754_2, 754_3, 754_4, 754_5, 755_1, 755_2, 755_3, 755_4, 755_5, 756_1, 756_2, 756_3, 756_4, 756_5, 757_1, 757_2, 757_3, 757_4, 757_5, 758_1, 758_2, 758_3, 758_4, 758_5, 759_1, 759_2, 759_3, 759_4, 759_5, 760_1, 760_2, 760_3, 760_4, 760_5, 761_1, 761_2, 761_3, 761_4, 761_5, 762_1, 762_2, 762_3, 762_4, 762_5, 763_1, 763_2, 763_3, 763_4, 763_5, 764_1, 764_2, 764_3, 764_4, 764_5, 765_1, 765_2, 765_3, 765_4, 765_5, 766_1, 766_2, 766_3, 766_4, 766_5, 767_1, 767_2, 767_3, 767_4, 767_5, 768_1, 768_2, 768_3, 768_4, 768_5, 769_1, 769_2, 769_3, 769_4, 769_5, 770_1, 770_2, 770_3, 770_4, 770_5, 771_1, 771_2, 771_3, 771_4, 771_5, 772_1, 772_2, 772_3, 772_4, 772_5, 773_1, 773_2, 773_3, 773_4, 773_5, 774_1, 774_2, 774_3, 774_4, 774_5, 775_1, 775_2, 775_3, 775_4, 775_5, 776_1, 776_2, 776_3, 776_4, 776_5, 777_1, 777_2, 777_3, 777_4, 777_5, 778_1, 778_2, 778_3, 778_4, 778_5, 779_1, 779_2, 779_3, 779_4, 779_5, 780_1, 780_2, 780_3, 780_4, 780_5, 781_1, 782_1, 782_2, 782_3, 782_4, 782_5, 783_1, 783_2, 783_3, 783_4, 783_5, 784_1, 784_2, 784_3, 784_4, 784_5, 785_1, 786_1, 786_2, 786_3, 786_4, 786_5, 787_1, 787_2, 787_3, 787_4, 787_5, 788_1, 788_2, 788_3, 788_4, 788_5, 789_1, 789_2, 789_3, 789_4, 789_5, 790_1, 790_2, 790_3, 790_4, 790_5, 791_1, 791_2, 791_3, 791_4, 791_5, 792_1, 792_2, 792_3, 792_4, 792_5, 793_1, 793_2, 793_3, 793_4, 793_5, 794_1, 794_2, 794_3, 794_4, 794_5, 795_1, 795_2, 795_3, 795_4, 795_5, 796_1, 796_2, 796_3, 796_4, 796_5, 797_1, 797_2, 797_3, 797_4, 797_5, 798_1, 798_2, 798_3, 798_4, 798_5, 799_1, 799_2, 799_3, 799_4, 799_5, 800_1, 800_2, 800_3, 800_4, 800_5, 801_1, 801_2, 801_3, 801_4, 801_5, 802_1, 802_2, 802_3, 802_4, 802_5, 803_1, 803_2, 803_3, 803_4, 803_5, 804_1, 804_2, 804_3, 804_4, 804_5, 805_1, 805_2, 805_3, 805_4, 805_5, 806_1, 806_2, 806_3, 806_4, 806_5, 807_1, 807_2, 807_3, 807_4, 807_5, 808_1, 808_2, 808_3, 808_4, 808_5, 809_1, 809_2, 809_3, 809_4, 809_5, 810_1, 810_2, 810_3, 810_4, 810_5, 811_1, 811_2, 811_3, 811_4, 811_5, 812_1, 812_2, 812_3, 812_4, 812_5, 813_1, 813_2, 813_3, 813_4, 813_5, 814_1, 814_2, 814_3, 814_4, 814_5, 815_1, 815_2, 815_3, 815_4, 815_5, 816_1, 816_2, 816_3, 816_4, 816_5, 816_6, 817_1 and 818_1.

86. The oligonucleotide of embodiment 85, wherein the oligonucleotide is selected from CMP-ID-NO: 155_1 or 165_1.

87. The oligonucleotide of embodiment 85, wherein the oligonucleotide is selected from the group consisting of CMP-ID-NO 169_52, 169_50 or 169_56.

88. The oligonucleotide of embodiment 85, wherein the oligonucleotide is selected from the group consisting of CMP-ID-NO: 172_1, 272_1, 572_7, 572_6 or 572_5.

89. The oligonucleotide of embodiment 85, wherein the oligonucleotide is selected from CMP-ID-NO: 175_1.

90. The oligonucleotide of embodiment 85, wherein the oligonucleotide is selected from CMP-ID-NO: 178_1.

91. The oligonucleotide of embodiment 85, wherein the oligonucleotide is selected from CMP-ID-NO: 573_8, 186_1 or 187_1.

92. The oligonucleotide of embodiment 85, wherein the oligonucleotide is selected from CMP-ID-NO: 186_1.

93. The oligonucleotide of embodiment 85, wherein the oligonucleotide is selected from the group consisting of CMP-ID-NO: 200_1, 204_1, 206_1, 35_2 or 209_1.

94. The oligonucleotide of embodiment 85, wherein the oligonucleotide is selected from the group consisting of CMP-ID-NO: 585_1, 585_8, 586_9, 586_5, 586_8, 586_4 or 586_6.

95. The oligonucleotide of embodiment 85, wherein the oligonucleotide is selected from CMP-ID-NO: 233_1.

96. The oligonucleotide of embodiment 85, wherein the oligonucleotide is selected from CMP-ID-NO: 237_8 or 590_13.

97. The oligonucleotide of embodiment 85, wherein the oligonucleotide is selected from CMP-ID-NO: 220_1.

98. The oligonucleotide of embodiment 85, wherein the oligonucleotide is selected from the group consisting of CMP-ID-NO: 591_1, 592_2, 592_4 or 241_9.

99. The oligonucleotide of embodiment 85, wherein the oligonucleotide is selected from the group consisting of CMP-ID-NO: 597_4, 598_4, 39_1 or 602_1.

100. The oligonucleotide of embodiment 85, wherein the oligonucleotide is selected from CMP-ID-NO: 39_1.

101. The oligonucleotide of embodiment 85, wherein the oligonucleotide is selected from CMP-ID-NO: 611_7.

102. The oligonucleotide of embodiment 85, wherein the oligonucleotide is selected from the group consisting of CMP-ID-NO: 271_1 or 278_1.

103. The oligonucleotide of embodiment 85, wherein the oligonucleotide is selected from the group consisting of CMP-ID-NO: 616_4, 621_2, 621_1, 622_3, 622_5, 622_4, 624_3, 624_5, 287_1, 625_6, 626_7, 626_8, 626_9, 48_1, 631_6, 631_1, 303_1, 304_6 or 304_10.

104. The oligonucleotide of embodiment 85, wherein the oligonucleotide is selected from CMP-ID-NO: 636_8.

105. The oligonucleotide of embodiment 85, wherein the oligonucleotide is selected from the group consisting of CMP-ID-NO: 638_8, 639_5, 331_1 or 640_4.

106. The oligonucleotide of embodiment 85, wherein the oligonucleotide is selected from the group consisting of CMP-ID-NO: 359_1, 361_1, 361_5, 362_1 or 641_5.

107. The oligonucleotide of embodiment 85, wherein the oligonucleotide is selected from the group consisting of CMP-ID-NO: 378_1, 379_1 or 399_1.

108. The oligonucleotide of embodiment 85, wherein the oligonucleotide is selected from the group consisting of CMP-ID-NO: 403_1, 405_1, 642_12, 642_13, 644_3 or 646_16.

109. The oligonucleotide of embodiment 85, wherein the oligonucleotide is selected from CMP-ID-NO: 85_1 or 425_5.
110. The oligonucleotide of embodiment 85, wherein the oligonucleotide is selected from CMP-ID-NO: 116_1.
111. The oligonucleotide of embodiment 85, wherein the oligonucleotide is selected from CMP-ID-NO: 123_1 or 124_1.
113. A conjugate comprising the oligonucleotide according to any one of embodiments 1-112, and at least one conjugate moiety covalently attached to said oligonucleotide.
114. The oligonucleotide conjugate of embodiment 113, wherein the conjugate moiety is selected from carbohydrates, cell surface receptor ligands, drug substances, hormones, lipophilic substances, polymers, proteins, peptides, toxins, vitamins, viral proteins or combinations thereof.
115. The oligonucleotide conjugate of embodiment 113 or 114, wherein the conjugate moiety is an antibody or antibody fragment.
116. The oligonucleotide conjugate of embodiment 115, wherein the antibody or antibody fragment has affinity to the transferrin receptor.
117. The oligonucleotide conjugate of embodiment 113-115, comprising a linker which is positioned between the oligonucleotide and the conjugate moiety.
118. The oligonucleotide conjugate of embodiment 117, wherein the linker is a physiologically labile linker.
119. The oligonucleotide conjugate of embodiment 118, wherein the physiologically labile linker is nuclease susceptible linker.
120. The oligonucleotide conjugate of embodiment 118 or 119, wherein the oligonucleotide has the formula D-F-G-F' or F-G-F'-D', wherein F, F' and G are as defined in embodiments 73-80 and D or D' comprises 1, 2 or 3 DNA nucleosides with phosphorothioate internucleoside linkages.
121. The oligonucleotide conjugate of embodiment 113-120, which display improved uptake into the brain of the conjugate oligonucleotide as compared to an unconjugated oligonucleotide.
122. A pharmaceutical composition comprising the oligonucleotide of embodiment 1-112 or a conjugate of embodiment 113-121 and a pharmaceutically acceptable diluent, carrier, salt and/or adjuvant.
123. A method for manufacturing the oligonucleotide of embodiment 1-112, comprising reacting nucleotide units thereby forming covalently linked contiguous nucleotide units comprised in the oligonucleotide.
124. The method of embodiment 123, further comprising reacting the contiguous nucleotide sequence with a non-nucleotide conjugation moiety.
125. A method for manufacturing the composition of embodiment 122, comprising mixing the oligonucleotide with a pharmaceutically acceptable diluent, carrier, salt and/or adjuvant.
126. An in vivo or in vitro method for inducing UBE3A expression in a target cell where expression of paternal UBE3A is suppressed, said method comprising administering an oligonucleotide of any one of embodiments 1-112 or a conjugate of embodiment 113-121 or the pharmaceutical composition of embodiment 122 in an effective amount to said cell.
127. The method of embodiment 126, wherein the expression of UBE3A is increased by at least 40% compared to a control.
128. The method of embodiment 126 or 127, wherein the level of the SNHG14 transcript downstream of SNORD109B is reduced by at least 30% compared to a control.
129. The method of embodiment 126-128, wherein the target cell is a neuronal cell.
130. The method of embodiment 126-129, wherein the expression of SNORD115 is not significantly affected compared to a control.
131. A method for treating or preventing a disease comprising administering a therapeutically or prophylactically effective amount of an oligonucleotide of embodiment 1-112 or a conjugate of embodiment 113-121 or the pharmaceutical composition of embodiment 122 to a subject suffering from or susceptible to the disease.
132. The oligonucleotide of embodiment 1-112 or a conjugate of embodiment 113-121 or the pharmaceutical composition of embodiment 122, for use as a medicament for treatment or prevention of a disease in a subject.
133. Use of the oligonucleotide of oligonucleotide of embodiment 1-112 or a conjugate of embodiment 113-121 for the preparation of a medicament for treatment or prevention of a disease in a subject.
134. The method, the oligonucleotide or the use of embodiments 131-133, wherein the disease is associated with in vivo activity of UBE3A.
135. The method, the oligonucleotide or the use of embodiments 131-134, wherein the disease is associated with reduced expression of UBE3A and/or reduced activity of UBE3A in neuronal cells.
136. The method, the oligonucleotide or the use of embodiment 135, wherein the reduced expression of UBE3A and/or reduced activity of UBE3A is due to mutations in the maternal allele of the UBE3A gene.
137. The method, the oligonucleotide or the use of embodiments 134-136, wherein the UBE3A expression is increased by at least 30%, or at least 50%, or at least 70%, or at least 90%, or at least 100%, or at least 150% or at least 200%, compared to the expression without the oligonucleotide of embodiment 1-112 or a conjugate of embodiment 113-121 or the pharmaceutical composition of embodiment 122.
138. The method, the oligonucleotide or the use of embodiments 131-137, wherein the disease is Angelman syndrome.
139. The method, the oligonucleotide or the use of embodiments 131-138, wherein the subject is a mammal.
140. The method, the oligonucleotide or the use of embodiment 139, wherein the mammal is human.
141. The method, the oligonucleotide or the use of embodiment 139 or 140, wherein the subject is an infant or a juvenile.

EXAMPLES

Materials and Methods

Table 3: List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

TABLE 3

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 4 | AACTTCATCAATATTTCCC | 3-13-3 | AACttcatcaatatttCCC | 4_1 | -23.36 | 1677 |
| 4 | AACTTCATCAATATTTCCC | 2-15-2 | AActtcatcaatatttcCC | 4_2 | -19.60 | 1677 |
| 5 | ACTTCATCAATATTTCCC | 3-12-3 | ACTtcatcaatatttCCC | 5_1 | -23.80 | 1677 |
| 5 | ACTTCATCAATATTTCCC | 2-14-2 | ACttcatcaatatttcCC | 5_2 | -20.24 | 1677 |
| 6 | CAACTTCATCAATATTTCCC | 2-14-4 | CAacttcatcaatattTCCC | 6_1 | -25.64 | 1677 |
| 6 | CAACTTCATCAATATTTCCC | 2-16-2 | CAacttcatcaatatttcCC | 6_2 | -22.28 | 1677 |
| 7 | CAACTTCATCAATATTTCC | 4-13-2 | CAACttcatcaatatttCC | 7_1 | -21.47 | 1678 |
| 7 | CAACTTCATCAATATTTCC | 2-15-2 | CAacttcatcaatatttCC | 7_2 | -19.46 | 1678 |
| 8 | CCAACTTCATCAATATTTCC | 3-14-3 | CCAacttcatcaatattTCC | 8_1 | -25.64 | 1678 |
| 9 | CCCAACTTCATCAATATTTC | 4-14-2 | CCCAacttcatcaatattTC | 9_1 | -25.64 | 1679 |
| 10 | ACCCAACTTCATCAATATTT | 2-16-2 | ACccaacttcatcaatatTT | 10_1 | -20.05 | 1680 |
| 11 | CCCAACTTCATCAATATTT | 4-13-2 | CCCAacttcatcaatatTT | 11_1 | -23.96 | 1680 |
| 11 | CCCAACTTCATCAATATTT | 2-15-2 | CCcaacttcatcaatatTT | 11_2 | -20.28 | 1680 |
| 12 | ACCCAACTTCATCAATATT | 4-13-2 | ACCCaacttcatcaataTT | 12_1 | -23.64 | 1681 |
| 12 | ACCCAACTTCATCAATATT | 2-15-2 | ACccaacttcatcaataTT | 12_2 | -19.18 | 1681 |
| 13 | CCCAACTTCATCAATATT | 4-12-2 | CCCAacttcatcaataTT | 13_1 | -23.09 | 1681 |
| 13 | CCCAACTTCATCAATATT | 2-14-2 | CCcaacttcatcaataTT | 13_2 | -19.41 | 1681 |
| 14 | TACCCAACTTCATCAATAT | 2-15-2 | TAcccaacttcatcaatAT | 14_1 | -19.31 | 1682 |
| 15 | TACCCAACTTCATCAATA | 2-14-2 | TAcccaacttcatcaaTA | 15_1 | -19.14 | 1683 |
| 16 | TTACCCAACTTCATCAATA | 2-15-2 | TTacccaacttcatcaaTA | 16_1 | -19.74 | 1683 |
| 17 | TTTACCCAACTTCATCAAT | 4-13-2 | TTTAcccaacttcatcaAT | 17_1 | -21.68 | 1684 |
| 17 | TTTACCCAACTTCATCAAT | 2-15-2 | TTtacccaacttcatcaAT | 17_2 | -19.22 | 1684 |
| 18 | ATACTTTACCCAACTTCAT | 3-13-3 | ATActttacccaacttCAT | 18_1 | -23.44 | 1688 |
| 18 | ATACTTTACCCAACTTCA T | 2-15-2 | ATactttacccaacttcAT | 18_2 | -20.13 | 1688 |
| 19 | TACTTTACCCAACTTCAT | 3-12-3 | TACtttacccaacttCAT | 19_1 | -22.78 | 1688 |
| 19 | TACTTTACCCAACTTCAT | 2-14-2 | TActttacccaacttcAT | 19_2 | -19.30 | 1688 |
| 20 | TTATACTTTACCCAACTTCA | 2-16-2 | TTatactttacccaacttCA | 20_1 | -21.40 | 1689 |
| 21 | TCACTGTTCTGACTTT | 3-10-3 | TCActgttctgacTTT | 21_1 | -19.11 | 1712 |
| 22 | TTCAATCTCTATCTCATCAT | 2-16-2 | TTcaatctctatctcatcAT | 22_1 | -19.42 | 4169 |
| 23 | CTTCAATCTCTATCTCATCA | 4-14-2 | CTTCaatctctatctcatCA | 23_1 | -24.21 | 4170 |
| 23 | CTTCAATCTCTATCTCATCA | 2-16-2 | CTtcaatctctatctcatCA | 23_2 | -22.04 | 4170 |
| 24 | TTCAATCTCTATCTCATCA | 2-15-2 | TTcaatctctatctcatCA | 24_1 | -19.44 | 4170 |
| 25 | CTTCAATCTCTATCTCATC | 2-15-2 | CTtcaatctctatctcaTC | 25_1 | -19.87 | 4171 |
| 26 | ACTTCAATCTCTATCTCAT | 3-13-3 | ACTtcaatctctatctCAT | 26_1 | -22.36 | 4172 |
| 26 | ACTTCAATCTCTATCTCAT | 2-15-2 | ACttcaatctctatctcAT | 26_2 | -19.08 | 4172 |
| 27 | CACTTCAATCTCTATCTCAT | 2-16-2 | CActtcaatctctatctcAT | 27_1 | -20.98 | 4172 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 28 | ACTTCAATCTCTATCTCA | 2-12-4 | ACttcaatctctatCTCA | 28_1 | -21.96 | 4173 |
| 28 | ACTTCAATCTCTATCTCA | 2-14-2 | ACttcaatctctatctCA | 28_2 | -19.10 | 4173 |
| 29 | CACTTCAATCTCTATCTCA | 2-13-4 | CActtcaatctctatCTCA | 29_1 | -23.86 | 4173 |
| 29 | CACTTCAATCTCTATCTCA | 2-15-2 | CActtcaatctctatctCA | 29_2 | -21.00 | 4173 |
| 30 | ACACTTCAATCTCTATCTC | 2-15-2 | ACacttcaatctctatcTC | 30_1 | -19.38 | 4174 |
| 31 | TACACTTCAATCTCTATCTC | 2-14-4 | TAcacttcaatctctaTCTC | 31_1 | -23.31 | 4174 |
| 31 | TACACTTCAATCTCTATCTC | 2-16-2 | TAcacttcaatctctatcTC | 31_2 | -20.53 | 4174 |
| 32 | TACACTTCAATCTCTATCT | 4-13-2 | TACActtcaatctctatCT | 32_1 | -22.34 | 4175 |
| 33 | CTTTGTCTCTCTTTACT | 2-13-2 | CTttgtctctctttaCT | 33_1 | -19.36 | 4374 |
| 34 | TATACCTTTCTTTAACCC | 3-12-3 | TATacctttctttaaCCC | 34_1 | -24.89 | 8118 |
| 34 | TATACCTTTCTTTAACCC | 2-14-2 | TAtacctttctttaacCC | 34_2 | -20.83 | 8118 |
| 34 | TATACCTTTCTTTAACCC | 1-3-1-7-1-1-1-1-2 | TataCctttcttTaAcCC | 34_3 | -21.63 | 8116 |
| 34 | TATACCTTTCTTTAACCC | 1-4-1-6-1-3-2 | TatacCtttcttTaacCC | 34_4 | -21.31 | 8116 |
| 34 | TATACCTTTCTTTAACCC | 1-2-1-1-1-7-2-1-2 | TatAcCtttctttAAcCC | 34_5 | -21.51 | 8116 |
| 34 | TATACCTTTCTTTAACCC | 2-3-1-7-1-2-2 | TAtacCtttctttAacCC | 34_6 | -21.84 | 8116 |
| 34 | TATACCTTTCTTTAACCC | 2-13-3 | TAtacctttctttaaCCC | 34_7 | -23.21 | 8116 |
| 35 | TGTTTATACCCTTTCC | 2-12-2 | TGtttataccctttCC | 35_1 | -20.33 | 9212 |
| 35 | TGTTTATACCCTTTCC | 4-10-2 | TGTTtataccctttCC | 35_2 | -22.69 | 9212 |
| 36 | TCTCCTTTATGACTCC | 2-10-4 | TCtcctttatgaCTCC | 36_1 | -23.29 | 10839 |
| 37 | CTTCTCCTTTATGACTC | 2-13-2 | CTtctcctttatgacTC | 37_1 | -19.26 | 10840 |
| 38 | CCATTTATTTCCATTTATT | 4-13-2 | CCATttatttccatttaTT | 38_1 | -22.32 | 15567 |
| 38 | CCATTTATTTCCATTTATT | 2-15-2 | CCatttatttccatttaTT | 38_2 | -19.61 | 15567 |
| 38 | CCATTTATTTCCATTTATT | 1-2-1-9-2-1-3 | CcaTttatttccaTTtATT | 38_3 | -20.02 | 15567 |
| 38 | CCATTTATTTCCATTTATT | 1-1-1-1-1-8-1-1-1-1-2 | CcAtTtatttccaTtTaTT | 38_4 | -18.95 | 15567 |
| 38 | CCATTTATTTCCATTTATT | 2-2-1-8-1-3-2 | CCatTtatttccaTttaTT | 38_5 | -20.35 | 15567 |
| 38 | CCATTTATTTCCATTTATT | 1-2-3-6-1-3-3 | CcaTTTatttccAtttATT | 38_6 | -20.87 | 15567 |
| 39 | CTTTCCATTTATTTCCATTT | 2-14-4 | CTttccatttatttccATTT | 39_1 | -23.14 | 15570 |
| 39 | CTTTCCATTTATTTCCATTT | 1-13-1-1-1-1-2 | CtttccatttatttCcAtTT | 39_2 | -20.96 | 15570 |
| 39 | CTTTCCATTTATTTCCATTT | 1-13-1-3-2 | CtttccatttatttCcatTT | 39_3 | -20.91 | 15570 |

TABLE 3-continued

List of oligonucleotides or contiguous nucleobase sequences complementary to SEQ ID NO: 1
(motif sequences indicated by SEQ ID NO), oligonucleotide designs made from these, as well as
specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 39 | CTTTCCATTTATTTCCATTT | 1-3-1-1-1-11-2 | CtttCcAtttatttccatTT | 39_4 | −20.96 | 15570 |
| 39 | CTTTCCATTTATTTCCATTT | 1-1-1-3-1-9-1-1-2 | CtTtccAtttatttccAtTT | 39_5 | −20.54 | 15570 |
| 40 | TCTTTCCATTTATTTCCATT | 2-14-4 | TCtttccatttatttcCATT | 40_1 | −24.62 | 15571 |
| 40 | TCTTTCCATTTATTTCCATT | 2-13-1-1-3 | TCtttccatttatttCcATT | 40_2 | −23.39 | 15571 |
| 40 | TCTTTCCATTTATTTCCATT | 2-13-1-2-2 | TCtttccatttatttCcaTT | 40_3 | −22.53 | 15571 |
| 40 | TCTTTCCATTTATTTCCATT | 2-14-1-1-2 | TCtttccatttatttcCaTT | 40_4 | −22.34 | 15571 |
| 40 | TCTTTCCATTTATTTCCATT | 2-3-1-11-3 | TCtttCcatttatttccATT | 40_5 | −23.39 | 15571 |
| 40 | TCTTTCCATTTATTTCCATT | 2-4-1-10-3 | TCtttcCatttatttccATT | 40_6 | −23.20 | 15571 |
| 40 | TCTTTCCATTTATTTCCATT | 2-3-1-12-2 | TCtttCcatttatttccaTT | 40_7 | −22.53 | 15571 |
| 40 | TCTTTCCATTTATTTCCATT | 2-4-1-11-2 | TCtttcCatttatttccaTT | 40_8 | −22.34 | 15571 |
| 41 | ATTACCCATCCGTTCT | 2-12-2 | ATtacccatccgttCT | 41_1 | −21.15 | 21965 |
| 42 | GCATTAGGCACATTACAT | 3-12-3 | GCAttaggcacattaCAT | 42_1 | −23.96 | 22211 |
| 43 | ATTATTATTTAACCTTCCTA | 2-16-2 | ATtattatttaaccttccTA | 43_1 | −19.28 | 30451 |
| 44 | ACATTATTATTTAACCTTCC | 4-14-2 | ACATta ttatttaaccttCC | 44_1 | −22.84 | 30453 |
| 44 | ACATTATTATTTAACCTTCC | 2-16-2 | ACattattatttaaccttCC | 44_2 | −20.13 | 30453 |
| 45 | CATTATTATTTAACCTTCC | 4-13-2 | CATTattatttaaccttCC | 45_1 | −22.04 | 30453 |
| 45 | CATTATTATTTAACCTTCC | 2-15-2 | CAttattatttaaccttCC | 45_2 | −19.55 | 30453 |
| 46 | CCTCTGCTTATAACTTT | 2-13-2 | CCtctgcttataactTT | 46_1 | −19.15 | 30699 |
| 47 | CTACTATACTTTCCTCT | 2-11-4 | CTactatacttccCTCT | 47_1 | −22.32 | 30711 |
| 48 | GTTCTACTATACTTTCC | 4-11-2 | GTTCtactatactttCC | 48_1 | −21.69 | 30714 |
| 48 | GTTCTACTATACTTTCC | 2-13-2 | GTtctactatactttCC | 48_2 | −19.21 | 30714 |
| 48 | GTTCTACTATACTTTCC | 1-2-1-7-2-2-2 | GttCtactataCTttCC | 48_3 | −20.83 | 30712 |
| 48 | GTTCTACTATACTTTCC | 2-9-1-3-2 | GTtctactataCtttCC | 48_4 | −20.20 | 30712 |
| 48 | GTTCTACTATACTTTCC | 1-2-1-9-1-1-2 | GttCtactatactTtCC | 48_5 | −18.95 | 30712 |
| 48 | GTTCTACTATACTTTCC | 2-1-1-10-3 | GTtCtactatacttTCC | 48_6 | −21.18 | 30712 |
| 48 | GTTCTACTATACTTTCC | 1-3-1-10-2 | GttcTactatactttCC | 48_7 | −18.61 | 30712 |
| 49 | CACCTGATAACAGACCCT | 3-12-3 | CACctgataacagacCCT | 49_1 | −26.38 | 36068 |
| 50 | CACCTGATAACAGACC | 3-10-3 | CACctgataacagACC | 50_1 | −21.10 | 36070 |

TABLE 3-continued

List of oligonucleotides or contiguous nucleobase sequences complementary to SEQ ID NO: 1
(motif sequences indicated by SEQ ID NO), oligonucleotide designs made from these, as well as
specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 51 | CCCACCAAAGGATATATT | 3-12-3 | CCCaccaaaggatatATT | 51_1 | -23.47 | 37208 |
| 52 | ACCAGCTACAGGAACCTC | 3-12-3 | ACCagctacaggaacCTC | 52_1 | -26.57 | 46132 |
| 53 | CTATATCTCACTCCTATTT | 4-13-2 | CTATatctcactcctatTT | 53_1 | -23.07 | 48143 |
| 53 | CTATATCTCACTCCTATTT | 2-13-4 | CTatatctcactcctATTT | 53_2 | -22.12 | 48143 |
| 54 | CTATATCTCACTCCTATT | 2-14-2 | CTatatctcactcctaTT | 54_1 | -19.40 | 48144 |
| 54 | CTATATCTCACTCCTATT | 2-12-4 | CTatatctcactccTATT | 54_2 | -22.28 | 48144 |
| 54 | CTATATCTCACTCCTATT | 3-12-3 | CTAtatctcactcctATT | 54_3 | -21.44 | 48144 |
| 55 | CTACTATATCTCACTCCTAT | 2-16-2 | CTactatatctcactcctAT | 55_1 | -22.00 | 48145 |
| 55 | CTACTATATCTCACTCCTAT | 2-14-4 | CTactatatctcactcCTAT | 55_2 | -25.54 | 48145 |
| 56 | TACTATATCTCACTCCTAT | 2-13-4 | TActatatctcactcCTAT | 56_1 | -23.29 | 48145 |
| 57 | CTACTATATCTCACTCCTA | 2-15-2 | CTactatatctcactccTA | 57_1 | -21.91 | 48146 |
| 58 | TACTATATCTCACTCCTA | 2-14-2 | TActatatctcactccTA | 58_1 | -19.66 | 48146 |
| 58 | TACTATATCTCACTCCTA | 2-12-4 | TActatatctcactCCTA | 58_2 | -23.59 | 48146 |
| 58 | TACTATATCTCACTCCTA | 3-12-3 | TACtatatctcactcCTA | 58_3 | -22.62 | 48146 |
| 59 | CTACTATATCTCACTCCT | 2-14-2 | CTactatatctcactcCT | 59_1 | -21.25 | 48147 |
| 59 | CTACTATATCTCACTCCT | 4-12-2 | CTACtatatctcactcCT | 59_2 | -23.87 | 48147 |
| 60 | CTACTATATCTCACTCC | 2-13-2 | CTactatatctcactCC | 60_1 | -20.13 | 48148 |
| 60 | CTACTATATCTCACTCC | 2-11-4 | CTactatatctcaCTCC | 60_2 | -23.00 | 48148 |
| 60 | CTACTATATCTCACTCC | 3-11-3 | CTActatatctcacTCC | 60_3 | -22.56 | 48148 |
| 61 | CCTACTATATCTCACTC | 2-11-4 | CCtactatatctcACTC | 61_1 | -21.93 | 48149 |
| 62 | CTCCTACTATATCTCACTC | 4-13-2 | CTCCtactatatctcacTC | 62_1 | -25.69 | 48149 |
| 63 | TCCTACTATATCTCACTC | 3-12-3 | TCCtactatatctcaCTC | 63_1 | -23.88 | 48149 |
| 64 | CTCCTACTATATCTCACT | 4-12-2 | CTCCtactatatctcaCT | 64_1 | -24.87 | 48150 |
| 64 | CTCCTACTATATCTCACT | 3-12-3 | CTCctactatatctcACT | 64_2 | -22.93 | 48150 |
| 65 | TTTCCTCTCCTACTATATC | 2-15-2 | TTtcctctcctactataTC | 65_1 | -21.23 | 48155 |
| 66 | ATCCATATCCTTTCCT | 3-10-3 | ATCcatatcctttCCT | 66_1 | -24.02 | 48168 |
| 67 | CATCCATATCCTTTCCT | 4-11-2 | CATCcatatcctttcCT | 67_1 | -24.94 | 48168 |
| 68 | ATCATCCATATCCTTTCC | 4-12-2 | ATCAtccatatcctttCC | 68_1 | -25.69 | 48169 |
| 69 | CATCATCCATATCCTTTC | 4-12-2 | CATCatccatatccttTC | 69_1 | -23.32 | 48170 |
| 69 | CATCATCCATATCCTTTC | 2-14-2 | CAtcatccatatccttTC | 69_2 | -20.72 | 48170 |
| 69 | CATCATCCATATCCTTTC | 2-12-4 | CAtcatccatatccTTTC | 69_3 | -22.56 | 48170 |
| 70 | TACATCATCCATATCCTTTC | 2-16-2 | TAcatcatccatatccttTC | 70_1 | -22.45 | 48170 |
| 70 | TACATCATCCATATCCTTTC | 4-14-2 | TACAtcatccatatccttTC | 70_2 | -25.00 | 48170 |
| 70 | TACATCATCCATATCCTTTC | 2-14-4 | TAcatcatccatatccTTTC | 70_3 | -24.29 | 48170 |
| 71 | ACATCATCCATATCCTTT | 3-12-3 | ACAtcatccatatccTTT | 71_1 | -22.11 | 48171 |
| 72 | CATCATCCATATCCTTT | 2-13-2 | CAtcatccatatcctTT | 72_1 | -19.04 | 48171 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 72 | CATCATCCATATCCTTT | 4-11-2 | CATCatccatatcctTT | 72_2 | -21.64 | 48171 |
| 73 | TACATCATCCATATCCTTT | 2-15-2 | TAcatcatccatatcctTT | 73_1 | -20.76 | 48171 |
| 73 | TACATCATCCATATCCTTT | 2-13-4 | TAcatcatccatatcCTTT | 73_2 | -23.36 | 48171 |
| 73 | TACATCATCCATATCCTTT | 3-13-3 | TACatcatccatatccTTT | 73_3 | -22.88 | 48171 |
| 74 | ATACATCATCCATATCCTT | 2-15-2 | ATacatcatccatatccTT | 74_1 | -20.80 | 48172 |
| 74 | ATACATCATCCATATCCTT | 4-13-2 | ATACatcatccatatccTT | 74_2 | -23.12 | 48172 |
| 75 | TACATCATCCATATCCTT | 2-14-2 | TAcatcatccatatccTT | 75_1 | -19.97 | 48172 |
| 75 | TACATCATCCATATCCTT | 4-12-2 | TACAtcatccatatccTT | 75_2 | -22.52 | 48172 |
| 76 | TATACATCATCCATATCCTT | 2-16-2 | TAtacatcatccatatccTT | 76_1 | -21.36 | 48172 |
| 77 | ATACATCATCCATATCCT | 3-12-3 | ATAcatcatccatatCCT | 77_1 | -24.15 | 48173 |
| 77 | ATACATCATCCATATCCT | 2-14-2 | ATacatcatccatatcCT | 77_2 | -20.55 | 48173 |
| 77 | ATACATCATCCATATCCT | 2-13-3 | ATacatcatccatatCCT | 77_3 | -22.92 | 48173 |
| 78 | ATATACATCATCCATATCCT | 2-16-2 | ATatacatcatccatatcCT | 78_1 | -22.04 | 48173 |
| 79 | TACATCATCCATATCCT | 2-11-4 | TAcatcatccataTCCT | 79_1 | -23.21 | 48173 |
| 79 | TACATCATCCATATCCT | 2-13-2 | TAcatcatccatatcCT | 79_2 | -19.71 | 48173 |
| 79 | TACATCATCCATATCCT | 4-11-2 | TACAtcatccatatcCT | 79_3 | -22.27 | 48173 |
| 80 | TATACATCATCCATATCCT | 2-15-2 | TAtacatcatccatatcCT | 80_1 | -21.11 | 48173 |
| 80 | TATACATCATCCATATCCT | 3-13-3 | TATacatcatccatatCCT | 80_2 | -25.15 | 48173 |
| 80 | TATACATCATCCATATCCT | 4-13-2 | TATAcatcatccatatcCT | 80_3 | -24.01 | 48173 |
| 81 | ATACATCATCCATATCC | 3-11-3 | ATAcatcatccataTCC | 81_1 | -21.79 | 48174 |
| 82 | ATATACATCATCCATATCC | 4-13-2 | ATATacatcatccatatCC | 82_1 | -23.73 | 48174 |
| 82 | ATATACATCATCCATATCC | 2-15-2 | ATatacatcatccatatCC | 82_2 | -20.93 | 48174 |
| 83 | TATACATCATCCATATCC | 2-14-2 | TAtacatcatccatatCC | 83_1 | -20.00 | 48174 |
| 83 | TATACATCATCCATATCC | 4-12-2 | TATAcatcatccatatCC | 83_2 | -22.90 | 48174 |
| 84 | TATATACATCATCCATATCC | 2-16-2 | TAtatacatcatccatatCC | 84_1 | -21.49 | 48174 |
| 84 | TATATACATCATCCATATCC | 4-14-2 | TATAtacatcatccatatCC | 84_2 | -24.29 | 48174 |
| 85 | GCTTCATATTTCTCCA | 2-12-2 | GCttcatatttctcCA | 85_1 | -20.44 | 49345 |
| 85 | GCTTCATATTTCTCCA | 2-11-3 | GCttcatatttctCCA | 85_2 | -22.81 | 49345 |
| 86 | CATCTTGTTCTTTACCT | 2-13-2 | CAtcttgttctttacCT | 86_1 | -19.67 | 49581 |
| 87 | TATATTCACCATTGCC | 2-10-4 | TAtattcaccatTGCC | 87_1 | -22.70 | 49724 |
| 88 | CCTTATATTCACCATTG | 2-13-2 | CCttatattcaccatTG | 88_1 | -19.44 | 49726 |
| 88 | CCTTATATTCACCATTG | 2-11-4 | CCttatattcaccATTG | 88_2 | -21.25 | 49726 |
| 89 | CCTCCTTATATTCACC | 4-10-2 | CCTCcttatattcaCC | 89_1 | -24.64 | 49730 |
| 90 | CCCTTCCTTTATTCAA | 3-10-3 | CCCttcctttattCAA | 90_1 | -23.86 | 50189 |
| 91 | CCTTACTGTTAAATCCT | 2-13-2 | CCttactgttaaatcCT | 91_1 | -19.81 | 50475 |
| 92 | CAGGCAGATAACCTCCAA | 3-12-3 | CAGgcagataacctcCAA | 92_1 | -25.31 | 52419 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 93 | CAGCAGGCAGATAACCTC | 3-12-3 | CAGcaggcagataacCTC | 93_1 | -25.88 | 52422 |
| 94 | CGAATCTTGACATACAGG | 3-12-3 | CGAatcttgacatacAGG | 94_1 | -21.47 | 53955 |
| 95 | CTCATACTTGCTTTAAT | 4-11-2 | CTCAtacttgctttaAT | 95_1 | -19.10 | 60821 |
| 95 | CTCATACTTGCTTTAAT | 2-13-2 | CTcatacttgctttaAT | 95_2 | -16.35 | 60821 |
| 96 | ACATCTCATACTTGCTT | 2-11-4 | ACatctcatacttGCTT | 96_1 | -21.31 | 60825 |
| 96 | ACATCTCATACTTGCTT | 2-13-2 | ACatctcatacttgcTT | 96_2 | -17.66 | 60825 |
| 96 | ACATCTCATACTTGCTT | 2-12-3 | ACatctcatacttgCTT | 96_3 | -19.52 | 60825 |
| 97 | ACATCTCATACTTGCT | 2-10-4 | ACatctcatactTGCT | 97_1 | -21.18 | 60826 |
| 97 | ACATCTCATACTTGCT | 2-12-2 | ACatctcatacttgCT | 97_2 | -17.70 | 60826 |
| 97 | ACATCTCATACTTGCT | 2-11-3 | ACatctcatacttGCT | 97_3 | -19.49 | 60826 |
| 97 | ACATCTCATACTTGCT | 4-10-2 | ACATctcatacttgCT | 97_4 | -20.48 | 60826 |
| 98 | TACATCTCATACTTGCT | 2-11-4 | TAcatctcatactTGCT | 98_1 | -22.33 | 60826 |
| 98 | TACATCTCATACTTGCT | 2-13-2 | TAcatctcatacttgCT | 98_2 | -18.85 | 60826 |
| 98 | TACATCTCATACTTGCT | 4-11-2 | TACAtctcatacttgCT | 98_3 | -21.40 | 60826 |
| 99 | CCTACATCTCATACTTGC | 3-12-3 | CCTacatctcatactTGC | 99_1 | -26.29 | 60827 |
| 99 | CCTACATCTCATACTTGC | 2-14-2 | CCtacatctcatacttGC | 99_2 | -22.98 | 60827 |
| 99 | CCTACATCTCATACTTGC | 2-13-3 | CCtacatctcatactTGC | 99_3 | -24.67 | 60827 |
| 99 | CCTACATCTCATACTTGC | 2-12-4 | CCtacatctcatacTTGC | 99_4 | -25.70 | 60827 |
| 100 | CTACATCTCATACTTGC | 3-11-3 | CTAcatctcatactTGC | 100_1 | -22.33 | 60827 |
| 100 | CTACATCTCATACTTGC | 2-13-2 | CTacatctcatacttGC | 100_2 | -19.41 | 60827 |
| 100 | CTACATCTCATACTTGC | 2-12-3 | CTacatctcatactTGC | 100_3 | -21.10 | 60827 |
| 101 | TACATCTCATACTTGC | 3-10-3 | TACatctcatactTGC | 101_1 | -19.94 | 60827 |
| 101 | TACATCTCATACTTGC | 2-12-2 | TAcatctcatacttGC | 101_2 | -17.15 | 60827 |
| 101 | TACATCTCATACTTGC | 2-11-3 | TAcatctcatactTGC | 101_3 | -18.85 | 60827 |
| 101 | TACATCTCATACTTGC | 4-10-2 | TACAtctcatacttGC | 101_4 | -19.71 | 60827 |
| 102 | CCTACATCTCATACTTG | 4-11-2 | CCTAcatctcatactTG | 102_1 | -22.52 | 60828 |
| 102 | CCTACATCTCATACTTG | 2-13-2 | CCtacatctcatactTG | 102_2 | -19.67 | 60828 |
| 102 | CCTACATCTCATACTTG | 3-12-2 | CCTacatctcatactTG | 102_3 | -21.29 | 60828 |
| 102 | CCTACATCTCATACTTG | 3-11-3 | CCTacatctcatacTTG | 102_4 | -22.31 | 60828 |
| 103 | ACCTACATCTCATACTT | 3-11-3 | ACCtacatctcataCTT | 103_1 | -21.93 | 60829 |
| 103 | ACCTACATCTCATACTT | 2-13-2 | ACctacatctcatacTT | 103_2 | -17.76 | 60829 |
| 103 | ACCTACATCTCATACTT | 2-11-4 | ACctacatctcatACTT | 103_3 | -20.03 | 60829 |
| 103 | ACCTACATCTCATACTT | 3-12-2 | ACCtacatctcatacTT | 103_4 | -20.26 | 60829 |
| 104 | CCTACATCTCATACTT | 3-10-3 | CCTacatctcataCTT | 104_1 | -21.50 | 60829 |
| 104 | CCTACATCTCATACTT | 2-12-2 | CCtacatctcatacTT | 104_2 | -18.21 | 60829 |
| 104 | CCTACATCTCATACTT | 2-10-4 | CCtacatctcatACTT | 104_3 | -20.48 | 60829 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 105 | TACCTACATCTCATACTT | 4-12-2 | TACCtacatctcatacTT | 105_1 | -22.49 | 60829 |
| 105 | TACCTACATCTCATACTT | 2-14-2 | TAcctacatctcatacTT | 105_2 | -18.81 | 60829 |
| 105 | TACCTACATCTCATACTT | 2-13-3 | TAcctacatctcataCTT | 105_3 | -20.48 | 60829 |
| 105 | TACCTACATCTCATACTT | 2-12-4 | TAcctacatctcatACTT | 105_4 | -21.08 | 60829 |
| 106 | TTACCTACATCTCATACTT | 3-13-3 | TTAcctacatctcataCTT | 106_1 | -22.30 | 60829 |
| 106 | TTACCTACATCTCATACTT | 2-15-2 | TTacctacatctcatacTT | 106_2 | -19.40 | 60829 |
| 106 | TTACCTACATCTCATACTT | 2-14-3 | TTacctacatctcataCTT | 106_3 | -21.08 | 60829 |
| 106 | TTACCTACATCTCATACTT | 2-13-4 | TTacctacatctcatACTT | 106_4 | -21.67 | 60829 |
| 107 | ACCTACATCTCATACT | 4-10-2 | ACCTacatctcataCT | 107_1 | -21.72 | 60830 |
| 107 | ACCTACATCTCATACT | 2-12-2 | ACctacatctcataCT | 107_2 | -17.61 | 60830 |
| 107 | ACCTACATCTCATACT | 3-11-2 | ACCtacatctcataCT | 107_3 | -20.10 | 60830 |
| 107 | ACCTACATCTCATACT | 2-10-4 | ACctacatctcaTACT | 107_4 | -20.11 | 60830 |
| 108 | TACCTACATCTCATACT | 4-11-2 | TACCtacatctcataCT | 108_1 | -22.34 | 60830 |
| 108 | TACCTACATCTCATACT | 2-13-2 | TAcctacatctcataCT | 108_2 | -18.66 | 60830 |
| 108 | TACCTACATCTCATACT | 3-12-2 | TACctacatctcataCT | 108_3 | -19.85 | 60830 |
| 108 | TACCTACATCTCATACT | 3-11-3 | TACctacatctcatACT | 108_4 | -20.44 | 60830 |
| 109 | TTACCTACATCTCATACT | 2-12-4 | TTacctacatctcaTACT | 109_1 | -21.75 | 60830 |
| 109 | TTACCTACATCTCATACT | 2-14-2 | TTacctacatctcataCT | 109_2 | -19.25 | 60830 |
| 109 | TTACCTACATCTCATACT | 3-13-2 | TTAcctacatctcataCT | 109_3 | -20.48 | 60830 |
| 109 | TTACCTACATCTCATACT | 3-12-3 | TTAcctacatctcatACT | 109_4 | -21.08 | 60830 |
| 110 | TTACCTACATCTCATAC | 3-11-3 | TTAcctacatctcaTAC | 110_1 | -19.50 | 60831 |
| 110 | TTACCTACATCTCATAC | 2-13-2 | TTacctacatctcatAC | 110_2 | -16.37 | 60831 |
| 111 | GTTACCTACATCTCATA | 2-11-4 | GTtacctacatctCATA | 111_1 | -21.69 | 60832 |
| 111 | GTTACCTACATCTCATA | 2-13-2 | GTtacctacatctcaTA | 111_2 | -18.74 | 60832 |
| 111 | GTTACCTACATCTCATA | 3-12-2 | GTTacctacatctcaTA | 111_3 | -19.98 | 60832 |
| 112 | GTTACCTACATCTCAT | 3-10-3 | GTTacctacatctCAT | 112_1 | -20.69 | 60833 |
| 112 | GTTACCTACATCTCAT | 2-12-2 | GTtacctacatctcAT | 112_2 | -17.37 | 60833 |
| 113 | ATATACCCAAAGGCACCT | 3-12-3 | ATAtacccaaaggcaCCT | 113_1 | -25.99 | 62200 |
| 114 | TCTACTCATCCTTTAACTCA | 2-14-4 | TCtactcatcctttaaCTCA | 114_1 | -25.63 | 62251 |
| 115 | CCTTAATCTGTATCACT | 2-13-2 | CCttaatctgtatcaCT | 115_1 | -19.58 | 62286 |
| 116 | CCATACACAGCACATA | 2-12-2 | CCatacacagcacaTA | 116_1 | -19.04 | 62424 |
| 117 | CTCCATACACAGCACAT | 2-13-2 | CTccatacacagcacAT | 117_1 | -20.08 | 62425 |
| 118 | CAGAATAATTCTCCTCC | 2-13-2 | CAgaataattctcctCC | 118_1 | -19.86 | 62441 |
| 119 | GTCCTACATATATACC | 4-10-2 | GTCCtacatatataCC | 119_1 | -22.09 | 66380 |
| 120 | TGCTTCCTTACTAACC | 4-10-2 | TGCTtccttactaaCC | 120_1 | -23.93 | 66701 |
| 120 | TGCTTCCTTACTAACC | 2-12-2 | TGcttccttactaaCC | 120_2 | -20.10 | 66701 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 121 | CCCTTTGTAATCATCT | 4-10-2 | CCCTttgtaatcatCT | 121_1 | -23.44 | 66838 |
| 122 | TCCCTTTGTAATCATCT | 2-13-2 | TCcctttgtaatcatCT | 122_1 | -19.97 | 66838 |
| 123 | CTGCCATCAATACCAT | 2-12-2 | CTgccatcaataccAT | 123_1 | -19.14 | 68918 |
| 124 | TCACTGCCATCAATACC | 2-13-2 | TCactgccatcaataCC | 124_1 | -21.35 | 68920 |
| 125 | ATTCTTACTTTATTCCTCA | 2-15-2 | ATtcttactttattcctCA | 125_1 | -20.16 | 70033 |
| 126 | TCACTTTCCAGATATCA | 4-11-2 | TCACtttccagatatCA | 126_1 | -21.61 | 77567 |
| 126 | TCACTTTCCAGATATCA | 2-13-2 | TCactttccagatatCA | 126_2 | -18.65 | 77567 |
| 127 | TCCTTCAAATTCCACATAC | 3-13-3 | TCCttcaaattccacaTAC | 127_1 | -24.09 | 82053 |
| 128 | ACATGTCCCTTTATATT | 4-11-2 | ACATgtccctttataTT | 128_1 | -20.87 | 92323 |
| 128 | ACATGTCCCTTTATATT | 2-13-2 | ACatgtccctttataTT | 128_2 | -17.66 | 92323 |
| 128 | ACATGTCCCTTTATATT | 3-12-2 | ACAtgtccctttataTT | 128_3 | -19.13 | 92323 |
| 128 | ACATGTCCCTTTATATT | 3-11-3 | ACAtgtccctttatATT | 128_4 | -20.03 | 92323 |
| 129 | ACATGTCCCTTTATAT | 3-10-3 | ACAtgtccctttaTAT | 129_1 | -20.11 | 92324 |
| 129 | ACATGTCCCTTTATAT | 2-12-2 | ACatgtccctttatAT | 129_2 | -16.74 | 92324 |
| 130 | CCAAGAAAGGAGCAAGCT | 3-12-3 | CCAagaaaggagcaaGCT | 130_1 | -25.26 | 97146 |
| 131 | TCCAAGAAAGGAGCAAGC | 3-12-3 | TCCaagaaaggagcaAGC | 131_1 | -24.12 | 97147 |
| 132 | CTCATCCCTCCAAGAAA | 4-11-2 | CTCAtccctccaagaAA | 132_1 | -22.58 | 97156 |
| 132 | CTCATCCCTCCAAGAAA | 2-13-2 | CTcatccctccaagaAA | 132_2 | -19.83 | 97156 |
| 132 | CTCATCCCTCCAAGAAA | 3-12-2 | CTCatccctccaagaAA | 132_3 | -21.11 | 97156 |
| 133 | TCATCCCTCCAAGAAA | 4-10-2 | TCATccctccaagaAA | 133_1 | -20.41 | 97156 |
| 133 | TCATCCCTCCAAGAAA | 2-12-2 | TCatccctccaagaAA | 133_2 | -17.63 | 97156 |
| 133 | TCATCCCTCCAAGAAA | 3-11-2 | TCAtccctccaagaAA | 133_3 | -19.09 | 97156 |
| 133 | TCATCCCTCCAAGAAA | 3-10-3 | TCAtccctccaagAAA | 133_4 | -19.81 | 97156 |
| 134 | CACCTCCCTATTACATAAA | 4-13-2 | CACCtccctattacataAA | 134_1 | -24.18 | 100018 |
| 134 | CACCTCCCTATTACATAAA | 2-15-2 | CAcctccctattacataAA | 134_2 | -20.51 | 100018 |
| 135 | CACCTCCCTATTACATAA | 4-12-2 | CACCtccctattacatAA | 135_1 | -23.75 | 100019 |
| 135 | CACCTCCCTATTACATAA | 2-14-2 | CAcctccctattacatAA | 135_2 | -20.07 | 100019 |
| 136 | CCTCCCTATTACATAA | 2-12-2 | CCtccctattacatAA | 136_1 | -18.40 | 100019 |
| 137 | CTAAATCTTCCAATTCATA | 2-15-2 | CTaaatcttccaattcaTA | 137_1 | -18.12 | 106139 |
| 138 | TATCCCTTGATTATCCT | 2-13-2 | TAtcccttgattatcCT | 138_1 | -20.68 | 109406 |
| 139 | CCTCTTTGTCAAATACT | 2-13-2 | CCtctttgtcaaataCT | 139_1 | -19.30 | 110768 |
| 140 | CAGCTTATTTACCTCTT | 2-13-2 | CAgcttatttacctcTT | 140_1 | -19.30 | 114828 |
| 141 | ACTCTTTACCTCTAACACT | 4-13-2 | ACTCtttacctctaacaCT | 141_1 | -24.26 | 117468 |
| 142 | TTACTCTTTACCTCTAACAC | 3-14-3 | TTActctttacctctaaCAC | 142_1 | -23.23 | 117469 |
| 143 | CCAACCTAATACCTTAATA | 2-15-2 | CCaacctaataccttaaTA | 143_1 | -20.27 | 118639 |
| 144 | TACCAACCTAATACCTTAA | 2-15-2 | TAccaacctaataccttAA | 144_1 | -18.32 | 118641 |

TABLE 3-continued

List of oligonucleotides or contiguous nucleobase sequences complementary to SEQ ID NO: 1
(motif sequences indicated by SEQ ID NO), oligonucleotide designs made from these, as well as
specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 145 | CCAATACCCACAAACC | 3-10-3 | CCAatacccacaaACC | 145_1 | −23.17 | 124162 |
| 145 | CCAATACCCACAAACC | 2-12-2 | CCaatacccacaaaCC | 145_2 | −20.85 | 124162 |
| 146 | CCATTATTCTACTTTGT | 3-11-3 | CCAttattctacttTGT | 146_1 | −21.79 | 125501 |
| 146 | CCATTATTCTACTTTGT | 2-13-2 | CCattattctactttGT | 146_2 | −18.63 | 125501 |
| 147 | CATTTCCTTATCTTCACA | 2-14-2 | CAtttccttatcttcaCA | 147_1 | −20.39 | 125529 |
| 148 | TCATTTCCTTATCTTCACA | 4-13-2 | TCATttccttatcttcaCA | 148_1 | −24.13 | 125529 |
| 149 | AATAATTCCTCATTTCCT | 2-14-2 | AAtaattcctcatttcCT | 149_1 | −18.01 | 125539 |
| 150 | ACAATAATTCCTCATTTCC | 3-13-3 | ACAataattcctcattTCC | 150_1 | −22.71 | 125540 |
| 150 | ACAATAATTCCTCATTTCC | 2-15-2 | ACaataattcctcatttCC | 150_2 | −20.23 | 125540 |
| 151 | TATTGAACCAATTCTA | 3-10-3 | TATtgaaccaattCTA | 151_1 | −16.93 | 4806 |
| 152 | CATATTGAACCAATTC | 4-10-2 | CATAttgaaccaatTC | 152_1 | −16.32 | 4808 |
| 153 | TCATATTGAACCAATT | 4-10-2 | TCATattgaaccaaTT | 153_1 | −16.14 | 4809 |
| 154 | CATCATATTGAACCAA | 2-10-4 | CAtcatattgaaCCAA | 154_1 | −17.65 | 4811 |
| 155 | TCATCATATTGAACCA | 3-10-3 | TCAtcatattgaaCCA | 155_1 | −19.40 | 4812 |
| 156 | CACAATCAACAACAAATA | 4-12-2 | CACAatcaacaacaaaTA | 156_1 | −16.16 | 4972 |
| 157 | TACACAATCAACAACAAAT | 4-13-2 | TACAcaatcaacaacaaAT | 157_1 | −16.76 | 4973 |
| 158 | CTGTACACAATCAACA | 4-10-2 | CTGTacacaatcaaCA | 158_1 | −19.05 | 4979 |
| 159 | CACTAATAATTCACTTT | 4-11-2 | CACTaataattcactTT | 159_1 | −16.39 | 5058 |
| 160 | CAACATTATTGACACT | 2-10-4 | CAacattattgaCACT | 160_1 | −17.17 | 5071 |
| 161 | AAACTTTCCCAACATTAT | 2-12-4 | AAactttcccaacaTTAT | 161_1 | −18.69 | 5078 |
| 162 | TCCTATATTCTCTTAAA | 4-11-2 | TCCTatattctcttaAA | 162_1 | −18.58 | 5094 |
| 163 | TTTCCTATATTCTCTTA | 4-11-2 | TTTCctatattctctTA | 163_1 | −18.69 | 5096 |
| 164 | CAAGTTTCCTATATTCT | 4-11-2 | CAAGtttcctatattCT | 164_1 | −19.97 | 5100 |
| 165 | CAAGTTTCCTATATTC | 4-10-2 | CAAGtttcctatatTC | 165_1 | −17.47 | 5101 |
| 166 | CATTCTATCTGCCAAA | 2-10-4 | CAttctatctgcCAAA | 166_1 | −18.36 | 5218 |
| 167 | CCATTCTATCTGCCAAA | 2-11-4 | CCattctatctgcCAAA | 167_1 | −22.08 | 5218 |
| 168 | TATAGCCATTCTATCT | 4-10-2 | TATAgccattctatCT | 168_1 | −20.63 | 5224 |
| 169 | TTATAGCCATTCTATCT | 4-11-2 | TTATagccattctatCT | 169_1 | −20.82 | 5224 |
| 169 | TTATAGCCATTCTATCT | 1-10-3-1-2 | TtatagccattCTAtCT | 169_2 | −20.51 | 5224 |
| 169 | TTATAGCCATTCTATCT | 2-9-1-2-3 | TTatagccattCtaTCT | 169_3 | −20.12 | 5224 |
| 169 | TTATAGCCATTCTATCT | 1-1-1-8-2-1-3 | TtAtagccattCTaTCT | 169_4 | −20.59 | 5224 |
| 169 | TTATAGCCATTCTATCT | 1-3-1-6-2-2-2 | TtatAgccattCTatCT | 169_5 | −19.97 | 5224 |
| 169 | TTATAGCCATTCTATCT | 3-8-1-3-2 | TTAtagccattCtatCT | 169_6 | −20.13 | 5224 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 169 | TTATAGCCATTCTATCT | 1-10-2-2-2 | TtatagccattCTatCT | 169_7 | -19.37 | 5224 |
| 169 | TTATAGCCATTCTATCT | 2-9-1-1-4 | TTatagccattCtATCT | 169_8 | -21.02 | 5224 |
| 169 | TTATAGCCATTCTATCT | 1-1-1-8-1-1-4 | TtAtagccattCtATCT | 169_9 | -19.88 | 5224 |
| 169 | TTATAGCCATTCTATCT | 1-2-1-7-1-1-4 | Tta_TagccattCtATCT | 169_10 | -20.65 | 5224 |
| 169 | TTATAGCCATTCTATCT | 1-3-1-6-1-1-4 | TtatAgccattCtATCT | 169_11 | -20.38 | 5224 |
| 169 | TTATAGCCATTCTATCT | 1-10-1-1-4 | TtatagccattCtATCT | 169_12 | -19.78 | 5224 |
| 169 | TTATAGCCATTCTATCT | 3-8-1-1-1-1-2 | TTAtagccattCtAtCT | 169_13 | -20.22 | 5224 |
| 169 | TTATAGCCATTCTATCT | 2-1-1-7-1-1-1-1-2 | TTaTagccattCtAtCT | 169_14 | -19.96 | 5224 |
| 169 | TTATAGCCATTCTATCT | 2-2-1-6-1-1-1-1-2 | TTatAgccattCtAtCT | 169_15 | -19.69 | 5224 |
| 169 | TTATAGCCATTCTATCT | 2-9-1-1-1-1-2 | TTatagccattCtAtCT | 169_16 | -19.09 | 5224 |
| 169 | TTATAGCCATTCTATCT | 1-2-2-6-1-1-1-1-2 | TtaTAgccattCtAtCT | 169_17 | -20.35 | 5224 |
| 169 | TTATAGCCATTCTATCT | 1-2-1-7-1-1-1-1-2 | TtaTagccattCtAtCT | 169_18 | -18.72 | 5224 |
| 169 | TTATAGCCATTCTATCT | 1-3-1-6-1-1-1-1-2 | TtatAgccattCtAtCT | 169_19 | -18.45 | 5224 |
| 169 | TTATAGCCATTCTATCT | 2-2-1-6-1-2-3 | TTatAgccattCtaTCT | 169_20 | -20.71 | 5224 |
| 169 | TTATAGCCATTCTATCT | 1-1-2-7-1-2-3 | TtATagccattCtaTCT | 169_21 | -20.65 | 5224 |
| 169 | TTATAGCCATTCTATCT | 1-1-1-1-1-6-1-2-3 | TtAtAgccattCtaTCT | 169_22 | -19.57 | 5224 |
| 169 | TTATAGCCATTCTATCT | 1-1-1-8-1-2-3 | TtAtagccattCtaTCT | 169_23 | -18.98 | 5224 |
| 169 | TTATAGCCATTCTATCT | 4-7-1-3-2 | TTATagccattCtatCT | 169_24 | -21.80 | 5224 |
| 169 | TTATAGCCATTCTATCT | 3-1-1-6-1-3-2 | TTAtAgccattCtatCT | 169_25 | -20.72 | 5224 |
| 169 | TTATAGCCATTCTATCT | 2-1-1-7-1-3-2 | TTaTagccattCtatCT | 169_26 | -19.86 | 5224 |
| 169 | TTATAGCCATTCTATCT | 2-2-1-6-1-3-2 | TTatAgccattCtatCT | 169_27 | -19.59 | 5224 |
| 169 | TTATAGCCATTCTATCT | 2-9-1-3-2 | TTatagccattCtatCT | 169_28 | -18.99 | 5224 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 169 | TTATAGCCATTCTATCT | 1-1-3-6-1-3-2 | TtATAgccattCtatCT | 169_29 | -21.16 | 5224 |
| 169 | TTATAGCCATTCTATCT | 1-1-2-7-1-3-2 | TtATagccattCtatCT | 169_30 | -19.53 | 5224 |
| 169 | TTATAGCCATTCTATCT | 1-1-1-1-1-6-1-3-2 | TtAtAgccattCtatCT | 169_31 | -18.45 | 5224 |
| 169 | TTATAGCCATTCTATCT | 1-2-2-6-1-3-2 | TtaTAgccattCtatCT | 169_32 | -20.25 | 5224 |
| 169 | TTATAGCCATTCTATCT | 1-2-1-7-1-3-2 | TtaTagccattCtatCT | 169_33 | -18.62 | 5224 |
| 169 | TTATAGCCATTCTATCT | 1-3-1-6-1-3-2 | TtatAgccattCtatCT | 169_34 | -18.35 | 5224 |
| 169 | TTATAGCCATTCTATCT | 1-1-1-9-5 | TtAtagccattcTATCT | 169_35 | -20.88 | 5224 |
| 169 | TTATAGCCATTCTATCT | 2-10-2-1-2 | TTatagccattcTAtCT | 169_36 | -20.09 | 5224 |
| 169 | TTATAGCCATTCTATCT | 1-1-1-9-2-1-2 | TtAtagccattcTAtCT | 169_37 | -18.95 | 5224 |
| 169 | TTATAGCCATTCTATCT | 1-2-1-8-2-1-2 | TtaTagccattcTAtCT | 169_38 | -19.72 | 5224 |
| 169 | TTATAGCCATTCTATCT | 1-3-1-7-2-1-2 | TtatAgccattcTAtCT | 169_39 | -19.44 | 5224 |
| 169 | TTATAGCCATTCTATCT | 1-11-2-1-2 | TtatagccattcTAtCT | 169_40 | -18.85 | 5224 |
| 169 | TTATAGCCATTCTATCT | 3-9-1-1-3 | TTAtagccattcTaTCT | 169_41 | -21.21 | 5224 |
| 169 | TTATAGCCATTCTATCT | 1-1-1-9-1-1-3 | TtAtagccattcTaTCT | 169_42 | -18.94 | 5224 |
| 169 | TTATAGCCATTCTATCT | 3-9-1-2-2 | TTAtagccattcTatCT | 169_43 | -20.09 | 5224 |
| 169 | TTATAGCCATTCTATCT | 1-2-1-8-1-2-2 | TtaTagccattcTatCT | 169_44 | -18.58 | 5224 |
| 169 | TTATAGCCATTCTATCT | 1-3-1-7-1-2-2 | TtatAgccattcTatCT | 169_45 | -18.31 | 5224 |
| 169 | TTATAGCCATTCTATCT | 1-1-1-10-4 | TtAtagccattctATCT | 169_46 | -18.90 | 5224 |
| 169 | TTATAGCCATTCTATCT | 3-10-1-1-2 | TTAtagccattctAtCT | 169_47 | -19.24 | 5224 |
| 169 | TTATAGCCATTCTATCT | 2-11-1-1-2 | TTatagccattctAtCT | 169_48 | -18.11 | 5224 |
| 169 | TTATAGCCATTCTATCT | 1-2-2-8-1-1-2 | TtaTAgccattctAtCT | 169_49 | -19.37 | 5224 |
| 169 | TTATAGCCATTCTATCT | 3-1-1-10-2 | TTAtAgccattctatCT | 169_50 | -19.74 | 5224 |
| 169 | TTATAGCCATTCTATCT | 3-12-2 | TTAtagccattctatCT | 169_51 | -19.15 | 5224 |
| 169 | TTATAGCCATTCTATCT | 2-1-2-10-2 | TTaTAgccattctatCT | 169_52 | -20.51 | 5224 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 169 | TTATAGCCATTCTATCT | 2-1-1-11-2 | TTaTagccattctatCT | 169_53 | −18.88 | 5224 |
| 169 | TTATAGCCATTCTATCT | 2-2-1-10-2 | TTatAgccattctatCT | 169_54 | −18.61 | 5224 |
| 169 | TTATAGCCATTCTATCT | 2-13-2 | TTatagccattctatCT | 169_55 | −18.02 | 5224 |
| 169 | TTATAGCCATTCTATCT | 1-1-3-10-2 | TtATAgccattctatCT | 169_56 | −20.18 | 5224 |
| 169 | TTATAGCCATTCTATCT | 1-1-2-11-2 | TtATagccattctatCT | 169_57 | −18.55 | 5224 |
| 169 | TTATAGCCATTCTATCT | 2-9-3-1-2 | TTatagccattCTAtCT | 169_58 | −21.75 | 5224 |
| 169 | TTATAGCCATTCTATCT | 1-1-1-8-2-2-2 | TtAtagccattCTatCT | 169_59 | −19.47 | 5224 |
| 169 | TTATAGCCATTCTATCT | 1-2-2-6-2-2-2 | TtaTAgccattCTatCT | 169_60 | −21.87 | 5224 |
| 169 | TTATAGCCATTCTATCT | 1-1-3-6-1-1-1-1-2 | TtATAgccattCtAtCT | 169_61 | −21.25 | 5224 |
| 169 | TTATAGCCATTCTATCT | 3-8-1-2-3 | TTAtagccattCtaTCT | 169_62 | −21.25 | 5224 |
| 170 | ATTTAAATTTCCAAACATT | 2-13-4 | ATttaaatttccaaaCATT | 170_1 | −16.82 | 5427 |
| 171 | GCTAATTTAAATTTCC | 4-10-2 | GCTAatttaaatttCC | 171_1 | −18.50 | 5434 |
| 172 | ATCAATATCTTCTCAC | 3-10-3 | ATCaatatcttctCAC | 172_1 | −17.10 | 5785 |
| 173 | TATCAATATCTTCTCA | 2-10-4 | TAtcaatatcttCTCA | 173_1 | −17.55 | 5786 |
| 174 | CTACAAATTCAATTTACT | 2-12-4 | CTacaaattcaattTACT | 174_1 | −17.38 | 6341 |
| 175 | TCTTACTCTGACTTTCCA | 2-14-2 | TCttactctgactttcCA | 175_1 | −21.47 | 6694 |
| 176 | TCTTACTCTGACTTTCC | 2-12-3 | TCttactctgactTCC | 176_1 | −21.53 | 6695 |
| 177 | AAATTTCCAAACCTTTC | 2-11-4 | AAatttccaaaccTTTC | 177_1 | −16.30 | 6958 |
| 178 | CTTCTTGTTTATCCCAA | 2-11-4 | CTtcttgtttatcCCAA | 178_1 | −22.77 | 7159 |
| 179 | TTCTTGTTTATCCCAA | 2-10-4 | TTcttgtttatcCCAA | 179_1 | −20.17 | 7159 |
| 180 | ATGCTTCTAACTAACA | 4-10-2 | ATGCttctaactaaCA | 180_1 | −19.21 | 7720 |
| 181 | CTTTAATGCTTCTAACT | 4-11-2 | CTTTaatgcttctaaCT | 181_1 | −18.49 | 7724 |
| 182 | CCTTTAATGCTTCTAAC | 2-11-4 | CCtttaatgcttcTAAC | 182_1 | −20.06 | 7725 |
| 183 | CTTTAATGCTTCTAAC | 2-10-4 | CTttaatgcttcTAAC | 183_1 | −16.07 | 7725 |
| 184 | TTCCTTTAATGCTTCTA | 4-11-2 | TTCCtttaatgcttcTA | 184_1 | −21.59 | 7727 |
| 185 | TATACCTTTCTTTAACCCT | 2-15-2 | TAtacctttctttaaccCT | 185_1 | −22.03 | 8117 |
| 186 | ATACCTTTCTTTAACCC | 4-11-2 | ATACctttctttaacCC | 186_1 | −22.68 | 8118 |
| 187 | TTATACCTTTCTTTAACC | 4-12-2 | TTATacctttctttaaCC | 187_1 | −21.52 | 8119 |
| 188 | TTTATACCTTTCTTTAAC | 2-12-4 | TTtatacctttcttTAAC | 188_1 | −17.01 | 8120 |
| 189 | TCAAGAATTCTCTCCTT | 2-11-4 | TCaagaattctctCCTT | 189_1 | −21.29 | 8571 |
| 190 | TTCAAGAATTCTCTCC | 2-10-4 | TTcaagaattctCTCC | 190_1 | −19.38 | 8573 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 191 | CTTCAAGAATTCTCTC | 2-10-4 | CTtcaagaattcTCTC | 191_1 | -18.00 | 8574 |
| 192 | TCTTCAAGAATTCTCT | 2-10-4 | TCttcaagaattCTCT | 192_1 | -18.46 | 8575 |
| 193 | ATCTTCAAGAATTCTC | 3-10-3 | ATCttcaagaattCTC | 193_1 | -17.04 | 8576 |
| 194 | TTTCTTACTATCTTCA | 4-10-2 | TTTCttactatcttCA | 194_1 | -17.47 | 8585 |
| 195 | CCTTTAGCATTTCTATT | 2-11-4 | CCtttagcatttcTATT | 195_1 | -21.72 | 8819 |
| 196 | TCCTTTAGCATTTCTAT | 3-11-3 | TCCtttagcatttcTAT | 196_1 | -22.39 | 8820 |
| 197 | GTTCTCTTTATTTCTTCT | 2-12-4 | GTtctctttatttcTTCT | 197_1 | -21.76 | 8887 |
| 198 | TTTACTGTCAACTCCT | 2-10-4 | TTtactgtcaacTCCT | 198_1 | -20.83 | 9150 |
| 199 | TTTCCAATGAATCTAT | 2-10-4 | TTtccaatgaatCTAT | 199_1 | -16.61 | 9201 |
| 200 | CCTTTCCAATGAATCTA | 2-11-4 | CCtttccaatgaaTCTA | 200_1 | -22.34 | 9202 |
| 201 | CTTTCCAATGAATCTA | 2-10-4 | CTttccaatgaaTCTA | 201_1 | -18.34 | 9202 |
| 202 | CCTTTCCAATGAATCT | 3-10-3 | CCTttccaatgaaTCT | 202_1 | -21.30 | 9203 |
| 203 | TTATACCCTTTCCAAT | 2-10-4 | TTataccctttcCAAT | 203_1 | -19.61 | 9209 |
| 204 | GTTTATACCCTTTCCAA | 3-11-3 | GTTtataccctttcCAA | 204_1 | -21.88 | 9210 |
| 205 | TTTATACCCTTTCCAA | 2-10-4 | TTtatacccttTCCAA | 205_1 | -20.50 | 9210 |
| 206 | GTTTATACCCTTTCCA | 2-11-3 | GTttatacccttTCCA | 206_1 | -22.69 | 9211 |
| 207 | TGTTTATACCCTTTCCA | 3-12-2 | TGTttatacccttccCA | 207_1 | -22.80 | 9211 |
| 208 | ACTGTTTATACCCTTTCC | 2-14-2 | ACtgtttatacccttcCC | 208_1 | -22.96 | 9212 |
| 208 | ACTGTTTATACCCTTTCC | 1-11-1-3-2 | ActgtttataccCtttCC | 208_2 | -22.45 | 9212 |
| 208 | ACTGTTTATACCCTTTCC | 1-2-1-10-1-1-2 | ActGtttatacccttTtCC | 208_3 | -22.17 | 9212 |
| 208 | ACTGTTTATACCCTTTCC | 1-2-1-1-1-10-2 | ActGtTtatacccttTCC | 208_4 | -22.17 | 9212 |
| 208 | ACTGTTTATACCCTTTCC | 1-2-1-12-2 | ActGtttatacccttTCC | 208_5 | -21.87 | 9212 |
| 208 | ACTGTTTATACCCTTTCC | 1-3-1-11-2 | ActgTttatacccttTCC | 208_6 | -22.22 | 9212 |
| 208 | ACTGTTTATACCCTTTCC | 1-15-2 | ActgtttatacccttTCC | 208_7 | -21.56 | 9212 |
| 209 | ACTGTTTATACCCTTTC | 4-11-2 | ACTGtttatacccttTC | 209_1 | -21.65 | 9213 |
| 209 | ACTGTTTATACCCTTTC | 1-11-1-2-2 | ActgtttataccCttTC | 209_2 | -18.25 | 9213 |
| 209 | ACTGTTTATACCCTTTC | 1-1-1-8-1-1-1-1-2 | AcTgtttatacCcTtTC | 209_3 | -19.56 | 9213 |
| 209 | ACTGTTTATACCCTTTC | 1-2-1-9-4 | ActGtttatacccTTTC | 209_4 | -19.51 | 9213 |
| 209 | ACTGTTTATACCCTTTC | 1-3-1-6-1-2-3 | ActgTttatacCctTTC | 209_5 | -19.51 | 9213 |
| 209 | ACTGTTTATACCCTTTC | 2-9-1-3-2 | ACtgtttatacCcttTC | 209_6 | -19.43 | 9213 |

TABLE 3-continued

List of oligonucleotides or contiguous nucleobase sequences complementary to SEQ ID NO: 1
(motif sequences indicated by SEQ ID NO), oligonucleotide designs made from these, as well as
specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 209 | ACTGTTTATACCCTTTC | 1-2-1-7-1-3-2 | ActGtttatacCcttTC | 209_7 | -18.35 | 9213 |
| 209 | ACTGTTTATACCCTTTC | 1-3-1-8-1-1-2 | ActgTttatacccTtTC | 209_8 | -18.53 | 9213 |
| 209 | ACTGTTTATACCCTTTC | 1-11-1-1-3 | ActgtttataccCtTTC | 209_9 | -19.06 | 9213 |
| 209 | ACTGTTTATACCCTTTC | 2-10-1-2-2 | ACtgtttataccCttTC | 209_10 | -19.64 | 9213 |
| 210 | AACTGTTTATACCCTTT | 4-11-2 | AACTgtttataccctTT | 210_1 | -19.51 | 9214 |
| 211 | TATGACTCCAATAATC | 3-10-3 | TATgactccaataATC | 211_1 | -16.57 | 10832 |
| 212 | CTCCTTTATGACTCCAA | 4-11-2 | CTCCtttatgactccAA | 212_1 | -22.74 | 10837 |
| 213 | CTCCTTTATGACTCCA | 3-11-2 | CTCctttatgactcCA | 213_1 | -21.50 | 10838 |
| 214 | CCATTATTTCTTAAATA | 4-11-2 | CCATtatttcttaaaTA | 214_1 | -17.56 | 10877 |
| 215 | ATTTCATATTACTAACTA | 2-12-4 | ATttcatattactaACTA | 215_1 | -16.64 | 11434 |
| 216 | CATTTCATATTACTAACT | 3-12-3 | CATttcatattactaACT | 216_1 | -17.70 | 11435 |
| 217 | TCATTTCATATTACTAAC | 4-12-2 | TCATttcatattactaAC | 217_1 | -16.72 | 11436 |
| 218 | ATCATTTCATATTACTA | 3-11-3 | ATCatttcatattaCTA | 218_1 | -17.23 | 11438 |
| 219 | TTATCATTTCATATTACT | 4-12-2 | TTATcatttcatattaCT | 219_1 | -17.77 | 11439 |
| 220 | TGTACTTTCCTTTACCA | 2-13-2 | TGtactttcctttacCA | 220_1 | -20.37 | 11464 |
| 221 | TATACACCATCATTATA | 4-11-2 | TATAcaccatcattaTA | 221_1 | -18.48 | 11507 |
| 222 | TTATACACCATCATTAT | 3-11-3 | TTAtacaccatcatTAT | 222_1 | -17.83 | 11508 |
| 223 | TATTTATACACCATCAT | 3-11-3 | TATttatacaccatCAT | 223_1 | -18.54 | 11511 |
| 224 | TTATTTATACACCATC | 2-10-4 | TTatttatacacCATC | 224_1 | -16.60 | 11513 |
| 225 | AATTATTTATACACCAT | 2-11-4 | AAttatttatacaCCAT | 225_1 | -16.82 | 11514 |
| 226 | CATGACACTTACATAA | 3-10-3 | CATgacacttacaTAA | 226_1 | -16.26 | 11736 |
| 227 | AGTTCACTACTATTAC | 3-10-3 | AGTtcactactatTAC | 227_1 | -17.55 | 12361 |
| 228 | ATAAGCTTACCTCATA | 2-10-4 | ATaagcttacctCATA | 228_1 | -19.32 | 12794 |
| 229 | TATAAGCTTACCTCAT | 3-10-3 | TATaagcttacctCAT | 229_1 | -19.32 | 12795 |
| 230 | ATATAAGCTTACCTCA | 4-10-2 | ATATaagcttacctCA | 230_1 | -19.32 | 12796 |
| 231 | CTTCCCTTTGATAACAT | 3-11-3 | CTTccctttgataaCAT | 231_1 | -21.19 | 12894 |
| 232 | TTCCCTTTGATAACAT | 4-10-2 | TTCCctttgataacAT | 232_1 | -19.27 | 12894 |
| 233 | CCTTCCCTTTGATAACA | 2-12-3 | CCttccctttgataACA | 233_1 | -23.06 | 12895 |
| 234 | CTTCCCTTTGATAACA | 4-10-2 | CTTCcctttgataaCA | 234_1 | -20.51 | 12895 |
| 235 | CCTTCCCTTTGATAAC | 3-11-2 | CCTtccctttgataAC | 235_1 | -20.96 | 12896 |
| 236 | TTGATTCAATTCCCTTA | 2-11-4 | TTgattcaattccCTTA | 236_1 | -20.48 | 13223 |
| 236 | TTGATTCAATTCCCTTA | 2-9-1-1-1-1-2 | TTgattcaattCcCtTA | 236_2 | -19.54 | 13223 |
| 236 | TTGATTCAATTCCCTTA | 2-10-1-1-3 | TTgattcaattcCcTTA | 236_3 | -19.59 | 13223 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 236 | TTGATTCAATTCCCTTA | 2-1-1-8-1-2-2 | TTgAttcaattcCctTA | 236_4 | -19.06 | 13223 |
| 236 | TTGATTCAATTCCCTTA | 2-2-1-7-1-2-2 | TTgaTtcaattcCctTA | 236_5 | -19.00 | 13223 |
| 236 | TTGATTCAATTCCCTTA | 2-9-1-3-2 | TTgattcaattCcctTA | 236_6 | -18.65 | 13223 |
| 236 | TTGATTCAATTCCCTTA | 1-2-2-6-2-2-2 | TtgATtcaattCCctTA | 236_7 | -21.37 | 13223 |
| 236 | TTGATTCAATTCCCTTA | 2-1-1-7-1-1-1-1-2 | TTgAttcaattCcCtTA | 236_8 | -20.04 | 13223 |
| 236 | TTGATTCAATTCCCTTA | 1-1-2-7-1-1-1-1-2 | TtGAttcaattCcCtTA | 236_9 | -20.10 | 13223 |
| 236 | TTGATTCAATTCCCTTA | 1-2-1-9-4 | TtgAttcaattccCTTA | 236_10 | -19.67 | 13223 |
| 236 | TTGATTCAATTCCCTTA | 1-3-1-6-1-1-1-1-2 | TtgaTtcaattCcCtTA | 236_11 | -18.67 | 13223 |
| 236 | TTGATTCAATTCCCTTA | 2-10-1-2-2 | TTgattcaattcCctTA | 236_12 | -18.56 | 13223 |
| 236 | TTGATTCAATTCCCTTA | 1-2-2-7-2-1-2 | TtgATtcaattcCCtTA | 236_13 | -21.49 | 13223 |
| 236 | TTGATTCAATTCCCTTA | 1-1-2-8-1-2-2 | TtGAttcaattcCctTA | 236_14 | -19.13 | 13223 |
| 236 | TTGATTCAATTCCCTTA | 2-11-1-1-2 | TTgattcaattccCtTA | 236_15 | -18.77 | 13223 |
| 236 | TTGATTCAATTCCCTTA | 1-1-1-1-1-8-1-1-2 | TtGaTtcaattccCtTA | 236_16 | -18.07 | 13223 |
| 236 | TTGATTCAATTCCCTTA | 1-1-2-7-2-2-2 | TtGAttcaattCCctTA | 236_17 | -21.50 | 13223 |
| 236 | TTGATTCAATTCCCTTA | 1-2-1-7-1-1-4 | TtgAttcaattCcCTTA | 236_18 | -20.44 | 13223 |
| 236 | TTGATTCAATTCCCTTA | 3-8-1-1-1-1-2 | TTGattcaattCcCtTA | 236_19 | -20.60 | 13223 |
| 236 | TTGATTCAATTCCCTTA | 2-2-1-6-1-3-2 | TTgaTtcaattCcctTA | 236_20 | -19.09 | 13223 |
| 236 | TTGATTCAATTCCCTTA | 2-2-1-7-2-1-2 | TTgaTtcaattcCCtTA | 236_21 | -21.49 | 13223 |
| 237 | ATTGATTCAATTCCCTT | 2-11-4 | ATtgattcaattcCCTT | 237_1 | -21.28 | 13224 |
| 237 | ATTGATTCAATTCCCTT | 3-8-3-1-2 | ATTgattcaatTCCcTT | 237_2 | -22.78 | 13224 |
| 237 | ATTGATTCAATTCCCTT | 1-1-1-8-3-1-2 | AtTgattcaatTCCcTT | 237_3 | -21.02 | 13224 |
| 237 | ATTGATTCAATTCCCTT | 1-2-1-8-2-1-2 | AttGattcaattCCcTT | 237_4 | -19.40 | 13224 |
| 237 | ATTGATTCAATTCCCTT | 1-3-1-7-2-1-2 | AttgAttcaattCCcTT | 237_5 | -19.74 | 13224 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 237 | ATTGATTCAATTCCCTT | 1-2-1-7-2-1-3 | AttGattcaatTCcCTT | 237_6 | -19.67 | 13224 |
| 237 | ATTGATTCAATTCCCTT | 2-2-1-7-1-1-3 | ATtgAttcaattCcCTT | 237_7 | -20.27 | 13224 |
| 237 | ATTGATTCAATTCCCTT | 1-1-1-9-1-1-3 | AtTgattcaattCcCTT | 237_8 | -19.32 | 13224 |
| 237 | ATTGATTCAATTCCCTT | 1-3-1-7-1-1-3 | AttgAttcaattCcCTT | 237_9 | -19.02 | 13224 |
| 237 | ATTGATTCAATTCCCTT | 1-1-1-1-1-7-2-1-2 | AtTgAttcaattCCcTT | 237_10 | -20.53 | 13224 |
| 237 | ATTGATTCAATTCCCTT | 1-2-2-7-2-1-2 | AttGAttcaattCCcTT | 237_11 | -21.11 | 13224 |
| 237 | ATTGATTCAATTCCCTT | 1-2-1-8-1-1-3 | AttGattcaattCcCTT | 237_12 | -18.68 | 13224 |
| 237 | ATTGATTCAATTCCCTT | 1-1-2-8-1-2-2 | AtTGattcaattCccTT | 237_13 | -18.81 | 13224 |
| 237 | ATTGATTCAATTCCCTT | 3-10-1-1-2 | ATTgattcaattcCcTT | 237_14 | -19.42 | 13224 |
| 237 | ATTGATTCAATTCCCTT | 1-1-2-9-4 | AtTGattcaattcCCTT | 237_15 | -21.89 | 13224 |
| 237 | ATTGATTCAATTCCCTT | 2-2-1-8-1-1-2 | ATtgAttcaattcCcTT | 237_16 | -18.61 | 13224 |
| 237 | ATTGATTCAATTCCCTT | 1-2-2-6-3-1-2 | AttGAttcaatTCCcTT | 237_17 | -22.09 | 13224 |
| 237 | ATTGATTCAATTCCCTT | 1-1-1-8-2-1-3 | AtTgattcaatTCcCTT | 237_18 | -20.30 | 13224 |
| 237 | ATTGATTCAATTCCCTT | 1-1-1-9-2-1-2 | AtTgattcaattCCcTT | 237_19 | -20.03 | 13224 |
| 237 | ATTGATTCAATTCCCTT | 1-1-1-1-1-7-1-1-3 | AtTgAttcaattCcCTT | 237_20 | -19.82 | 13224 |
| 237 | ATTGATTCAATTCCCTT | 3-1-1-8-1-1-2 | ATTgAttcaattcCcTT | 237_21 | -19.92 | 13224 |
| 238 | TTGATTCAATTCCCTT | 2-10-4 | TTgattcaattcCCTT | 238_1 | -20.52 | 13224 |
| 239 | TATTGATTCAATTCCCT | 2-11-4 | TAttgattcaattCCCT | 239_1 | -22.82 | 13225 |
| 239 | TATTGATTCAATTCCCT | 3-9-2-1-2 | TATtgattcaatTCcCT | 239_2 | -21.17 | 13225 |
| 239 | TATTGATTCAATTCCCT | 2-9-1-1-1-1-2 | TAttgattcaaTtCcCT | 239_3 | -19.37 | 13225 |
| 239 | TATTGATTCAATTCCCT | 1-1-2-7-3-1-2 | TaTTgattcaaTTCcCT | 239_4 | -21.49 | 13225 |
| 239 | TATTGATTCAATTCCCT | 1-3-1-6-3-1-2 | TattGattcaaTTCcCT | 239_5 | -19.90 | 13225 |
| 239 | TATTGATTCAATTCCCT | 2-9-1-2-3 | TAttgattcaaTtcCCT | 239_6 | -20.89 | 13225 |
| 239 | TATTGATTCAATTCCCT | 1-10-1-2-3 | TattgattcaaTtcCCT | 239_7 | -19.76 | 13225 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 239 | TATTGATTCAATTCCCT | 1-1-1-1-1-8-1-1-2 | TaTtGattcaattCcCT | 239_8 | -18.41 | 13225 |
| 239 | TATTGATTCAATTCCCT | 1-2-2-8-1-1-2 | TatTGattcaattCcCT | 239_9 | -19.66 | 13225 |
| 239 | TATTGATTCAATTCCCT | 1-2-1-9-1-1-2 | TatTgattcaattCcCT | 239_10 | -18.60 | 13225 |
| 239 | TATTGATTCAATTCCCT | 2-2-1-10-2 | TAttGattcaattccCT | 239_11 | -18.33 | 13225 |
| 239 | TATTGATTCAATTCCCT | 1-12-4 | TattgattcaattCCCT | 239_12 | -21.69 | 13225 |
| 239 | TATTGATTCAATTCCCT | 2-1-1-9-1-1-2 | TAtTgattcaattCcCT | 239_13 | -19.73 | 13225 |
| 239 | TATTGATTCAATTCCCT | 2-12-3 | TAttgattcaattcCCT | 239_14 | -20.45 | 13225 |
| 239 | TATTGATTCAATTCCCT | 1-2-1-10-3 | TatTgattcaattcCCT | 239_15 | -20.11 | 13225 |
| 239 | TATTGATTCAATTCCCT | 1-1-3-10-2 | TaTTGattcaattccCT | 239_16 | -19.84 | 13225 |
| 239 | TATTGATTCAATTCCCT | 1-1-1-1-1-6-3-1-2 | TaTtGattcaaTTCcCT | 239_17 | -20.34 | 13225 |
| 239 | TATTGATTCAATTCCCT | 2-2-1-6-1-1-1-1-2 | TAttGattcaaTtCcCT | 239_18 | -19.54 | 13225 |
| 239 | TATTGATTCAATTCCCT | 2-1-1-8-2-1-2 | TAtTgattcaatTCcCT | 239_19 | -20.72 | 13225 |
| 239 | TATTGATTCAATTCCCT | 1-1-2-9-1-1-2 | TaTTgattcaattCcCT | 239_20 | -19.55 | 13225 |
| 239 | TATTGATTCAATTCCCT | 2-1-1-10-3 | TAtTgattcaattcCCT | 239_21 | -21.24 | 13225 |
| 240 | TATTGATTCAATTCCC | 3-10-3 | TATtgattcaattCCC | 240_1 | -20.58 | 13226 |
| 241 | GCACATTCTTTCTATAC | 3-11-3 | GCAcattctttctaTAC | 241_1 | -21.17 | 15115 |
| 241 | GCACATTCTTTCTATAC | 1-1-3-6-2-2-2 | GcACAttctttCTatAC | 241_2 | -20.68 | 15115 |
| 241 | GCACATTCTTTCTATAC | 1-1-1-1-1-6-1-2-3 | GcAcAttctttCtaTAC | 241_3 | -18.46 | 15115 |
| 241 | GCACATTCTTTCTATAC | 1-1-2-7-1-2-3 | GcACattctttCtaTAC | 241_4 | -19.49 | 15115 |
| 241 | GCACATTCTTTCTATAC | 2-9-1-3-2 | GCacattctttCtatAC | 241_5 | -18.68 | 15115 |
| 241 | GCACATTCTTTCTATAC | 1-1-3-8-4 | GcACAttctttctATAC | 241_6 | -20.89 | 15115 |
| 241 | GCACATTCTTTCTATAC | 2-2-1-9-3 | GCacAttctttctaTAC | 241_7 | -19.66 | 15115 |
| 241 | GCACATTCTTTCTATAC | 2-1-1-11-2 | GCaCattctttctatAC | 241_8 | -18.39 | 15115 |
| 241 | GCACATTCTTTCTATAC | 1-1-3-9-3 | GcACAttctttctaTAC | 241_9 | -19.98 | 15115 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 241 | GCACATTCTTTCTATAC | 3-12-2 | GCAcattctttctatAC | 241_10 | -19.27 | 15115 |
| 241 | GCACATTCTTTCTATAC | 1-1-1-1-1-6-1-1-4 | GcAcAttctttCtATAC | 241_11 | -19.36 | 15115 |
| 241 | GCACATTCTTTCTATAC | 3-8-1-1-1-1-2 | GCAcattctttCtAtAC | 241_12 | -20.34 | 15115 |
| 241 | GCACATTCTTTCTATAC | 2-1-1-7-1-2-3 | GCaCattctttCtaTAC | 241_13 | -21.27 | 15115 |
| 241 | GCACATTCTTTCTATAC | 1-2-2-8-4 | GcaCAttctttctATAC | 241_14 | -20.33 | 15115 |
| 241 | GCACATTCTTTCTATAC | 1-1-3-10-2 | GcACAttctttctatAC | 241_15 | -18.08 | 15115 |
| 242 | GAATTTCAACTACTAT | 2-10-4 | GAatttcaactaCTAT | 242_1 | -16.13 | 15258 |
| 243 | CCATTTATTTCCATTTAT | 3-12-3 | CCAtttatttccattTAT | 243_1 | -21.92 | 15568 |
| 244 | TTTCCATTTATTTCCATTT | 4-13-2 | TTTCcatttatttccatTT | 244_1 | -20.93 | 15570 |
| 244 | TTTCCATTTATTTCCATTT | 1-4-1-7-1-1-4 | TttccAtttatttCcATTT | 244_2 | -20.48 | 15570 |
| 244 | TTTCCATTTATTTCCATTT | 2-1-1-10-2-1-2 | TTtCcatttatttcCAtTT | 244_3 | -21.47 | 15570 |
| 244 | TTTCCATTTATTTCCATTT | 1-2-1-1-1-7-1-3-2 | TttCcAtttatttCcatTT | 244_4 | -19.43 | 15570 |
| 244 | TTTCCATTTATTTCCATTT | 2-2-2-11-2 | TTtcCAtttatttccatTT | 244_5 | -20.70 | 15570 |
| 245 | CTTTCCATTTATTTCCAT | 3-12-3 | CTTtccatttatttcCAT | 245_1 | -22.31 | 15572 |
| 246 | TCTTTCCATTTATTTCCA | 4-12-2 | TCTTtccatttatttcCA | 246_1 | -22.74 | 15573 |
| 247 | ATCTTTCCATTTATTTCC | 3-12-3 | ATCtttccatttattTCC | 247_1 | -22.85 | 15574 |
| 248 | TTCCATGCAAACTTTA | 4-10-2 | TTCCatgcaaactttTA | 248_1 | -19.01 | 15722 |
| 249 | CAGTTTAAATTCACAC | 3-10-3 | CAGtttaaattcaCAC | 249_1 | -16.68 | 16597 |
| 250 | CTATTCCAGTTTAAAT | 4-10-2 | CTATtccagtttaaAT | 250_1 | -16.86 | 16603 |
| 251 | TGCAAATACCTCTTCA | 4-10-2 | TGCAaatacctcttCA | 251_1 | -21.49 | 16730 |
| 252 | CTAAATAGATTCCACT | 2-10-4 | CTaaatagattcCACT | 252_1 | -17.95 | 16849 |
| 253 | TATTGATATTTACTCT | 2-10-4 | TAttgatatttaCTCT | 253_1 | -16.32 | 17089 |
| 254 | CCTTAGTATTACAATT | 4-10-2 | CCTTagtattacaaTT | 254_1 | -17.43 | 17401 |
| 255 | CTATTCAATAAACTAAACA | 4-13-2 | CTATtcaataaactaaaCA | 255_1 | -16.45 | 24290 |
| 256 | CAGCTATTCAATAAAC | 4-10-2 | CAGCtattcaataaAC | 256_1 | -16.94 | 24296 |
| 257 | TATAGACCCAAACTAT | 3-10-3 | TATagacccaaacTAT | 257_1 | -18.15 | 24811 |
| 258 | TAATCCCATACATCTAT | 2-11-4 | TAatcccatacatCTAT | 258_1 | -20.45 | 25032 |
| 259 | ATAATCCCATACATCTA | 3-11-3 | ATAatcccatacatCTA | 259_1 | -20.45 | 25033 |
| 260 | ATCTCAACTACCATTT | 4-10-2 | ATCTcaactaccatTT | 260_1 | -18.14 | 25250 |
| 261 | AATCTCAACTACCATT | 4-10-2 | AATCtcaactaccaTT | 261_1 | -16.76 | 25251 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 262 | ACAACTTCTATCATAC | 3-10-3 | ACAacttctatcaTAC | 262_1 | −16.33 | 25718 |
| 263 | GAACAACTTCTATCAT | 2-10-4 | GAacaacttctaTCAT | 263_1 | −16.94 | 25720 |
| 264 | TGAACAACTTCTATCA | 3-10-3 | TGAacaacttctaTCA | 264_1 | −17.36 | 25721 |
| 265 | TACACAAATACTTAAATCA | 4-13-2 | TACAcaaatacttaaatCA | 265_1 | −16.93 | 26331 |
| 266 | TTAAGCTTTCACCTAT | 2-10-4 | TTaagctttcacCTAT | 266_1 | −19.36 | 27165 |
| 267 | AAACTCTTGCATCTACT | 2-13-2 | AAactcttgcatctaCT | 267_1 | −16.65 | 27248 |
| 268 | AAATTTCTCAACCTAAATTT | 2-14-4 | AAatttctcaacctaaATTT | 268_1 | −16.78 | 29330 |
| 269 | CCAACATAGATCCTCT | 2-10-4 | CCaacatagatcCTCT | 269_1 | −22.49 | 29635 |
| 270 | TCCAACATAGATCCTCT | 2-11-4 | TCcaacatagatcCTCT | 270_1 | −22.81 | 29635 |
| 271 | CTCCAACATAGATCCTC | 3-11-3 | CTCcaacatagatcCTC | 271_1 | −22.81 | 29636 |
| 272 | TCCAACATAGATCCTC | 2-10-4 | TCcaacatagatCCTC | 272_1 | −21.69 | 29636 |
| 273 | CTCCAACATAGATCCT | 3-10-3 | CTCcaacatagatCCT | 273_1 | −22.68 | 29637 |
| 274 | TCTCCAACATAGATCCT | 4-11-2 | TCTCcaacatagatcCT | 274_1 | −22.81 | 29637 |
| 275 | ATTCTCAATTGCACTT | 4-10-2 | ATTCtcaattgcacTT | 275_1 | −17.90 | 29661 |
| 276 | TATTCTCAATTGCACTT | 4-11-2 | TATTctcaattgcacTT | 276_1 | −18.54 | 29661 |
| 277 | TCACCTAATAGCACCA | 2-10-4 | TCacctaatagcACCA | 277_1 | −21.99 | 29684 |
| 278 | TTCACCTAATAGCACCA | 2-11-4 | TTcacctaatagcACCA | 278_1 | −22.53 | 29684 |
| 279 | CATTATTATTTAACCTT | 2-11-4 | CAttattatttaaCCTT | 279_1 | −17.83 | 30455 |
| 280 | ACATTATTATTTAACCT | 3-11-3 | ACAttattatttaaCCT | 280_1 | −18.05 | 30456 |
| 281 | TACATTATTATTTAACC | 4-11-2 | TACAttattatttaaCC | 281_1 | −16.80 | 30457 |
| 282 | CATTTACATTATTATTTAAC | 2-14-4 | CAtttacattattattTAAC | 282_1 | −16.44 | 30458 |
| 283 | CTCATTTACATTATTATT | 4-12-2 | CTCAtttacattattaTT | 283_1 | −17.33 | 30462 |
| 284 | TATCTCATTTACATTATT | 4-12-2 | TATCtcatttacattaTT | 284_1 | −17.62 | 30465 |
| 285 | ATCATTCTCAACAATTA | 4-11-2 | ATCAttctcaacaatTA | 285_1 | −17.04 | 30601 |
| 285 | ATCATTCTCAACAATTA | 4-7-6 | ATCAttctcaaCAATTA | 285_2 | −21.48 | 30601 |
| 285 | ATCATTCTCAACAATTA | 1-1-3-6-6 | AtCATtctcaaCAATTA | 285_3 | −20.80 | 30601 |
| 285 | ATCATTCTCAACAATTA | 5-6-2-2-2 | ATCATtctcaaCAatTA | 285_4 | −20.46 | 30601 |
| 285 | ATCATTCTCAACAATTA | 4-7-1-1-4 | ATCAttctcaaCaATTA | 285_5 | −19.80 | 30601 |
| 285 | ATCATTCTCAACAATTA | 5-7-1-1-3 | ATCATtctcaacAaTTA | 285_6 | −19.31 | 30601 |
| 285 | ATCATTCTCAACAATTA | 5-6-3-1-2 | ATCATtctcaaCAAtTA | 285_7 | −20.97 | 30601 |
| 285 | ATCATTCTCAACAATTA | 4-7-2-1-3 | ATCAttctcaaCAaTTA | 285_8 | −20.16 | 30601 |
| 285 | ATCATTCTCAACAATTA | 5-6-1-1-4 | ATCATtctcaaCaATTA | 285_9 | −21.05 | 30601 |

TABLE 3-continued

List of oligonucleotides or contiguous nucleobase sequences complementary to SEQ ID NO: 1
(motif sequences indicated by SEQ ID NO), oligonucleotide designs made from these, as well as
specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 285 | ATCATTCTCAACAATTA | 5-6-1-1-1-1-2 | ATCATtctcaaCaAtTA | 285_10 | −19.29 | 30601 |
| 285 | ATCATTCTCAACAATTA | 1-1-3-7-5 | AtCATtctcaacAATTA | 285_11 | −18.70 | 30601 |
| 286 | AAGATCATTCTCAACA | 4-10-2 | AAGAtcattctcaaCA | 286_1 | −17.15 | 30605 |
| 287 | TCTCAAAGATCATTCTC | 3-11-3 | TCTcaaagatcattCTC | 287_1 | −19.02 | 30609 |
| 288 | TCTCAAAGATCATTCT | 4-10-2 | TCTCaaagatcattCT | 288_1 | −17.81 | 30610 |
| 289 | ACTTAATTATACTTCC | 4-10-2 | ACTTaattatacttCC | 289_1 | −17.28 | 30667 |
| 290 | TACACTTAATTATACTTC | 2-12-4 | TAcacttaattataCTTC | 290_1 | −16.87 | 30668 |
| 291 | TTACACTTAATTATACTT | 3-12-3 | TTAcacttaattataCTT | 291_1 | −16.20 | 30669 |
| 292 | TTTACACTTAATTATACT | 2-12-4 | TTtacacttaattaTACT | 292_1 | −16.23 | 30670 |
| 293 | CTATTTAATTTACACTT | 3-11-3 | CTAtttaatttacaCTT | 293_1 | −16.26 | 30679 |
| 294 | TATCTATTTAATTTACAC | 3-12-3 | TATctatttaatttaCAC | 294_1 | −16.06 | 30681 |
| 295 | TTTATCTATTTAATTTACA | 4-13-2 | TTTAtctatttaatttaCA | 295_1 | −16.34 | 30682 |
| 296 | CTCTGCTTATAACTTT | 4-10-2 | CTCTgcttataactTT | 296_1 | −18.51 | 30699 |
| 297 | CCTCTGCTTATAACTT | 3-10-3 | CCTctgcttataaCTT | 297_1 | −21.29 | 30700 |
| 298 | TCCTCTGCTTATAACTT | 3-12-2 | TCCtctgcttataacTT | 298_1 | −20.86 | 30700 |
| 299 | TCCTCTGCTTATAACT | 3-11-2 | TCCtctgcttataaCT | 299_1 | −20.70 | 30701 |
| 300 | TTCCTCTGCTTATAACT | 3-12-2 | TTCctctgcttataaCT | 300_1 | −20.03 | 30701 |
| 301 | TTTCCTCTGCTTATAAC | 4-11-2 | TTTCctctgcttataAC | 301_1 | −19.20 | 30702 |
| 302 | TACTATACTTTCCTCT | 2-10-4 | TActatactttcCTCT | 302_1 | −20.07 | 30711 |
| 303 | TTCTACTATACTTTCC | 4-10-2 | TTCTactatactttCC | 303_1 | −19.55 | 30714 |
| 304 | AGTTCTACTATACTTTC | 4-11-2 | AGTTctactatacttTC | 304_1 | −18.49 | 30715 |
| 304 | AGTTCTACTATACTTTC | 1-10-6 | AgttctactatACTTTC | 304_2 | −18.76 | 30715 |
| 304 | AGTTCTACTATACTTTC | 1-1-2-7-1-1-4 | AgTTctactatAcTTTC | 304_3 | −18.23 | 30715 |
| 304 | AGTTCTACTATACTTTC | 3-8-2-2-2 | AGTtctactatACttTC | 304_4 | −19.19 | 30715 |
| 304 | AGTTCTACTATACTTTC | 2-2-1-6-1-1-4 | AGttCtactatAcTTTC | 304_5 | −19.07 | 30715 |
| 304 | AGTTCTACTATACTTTC | 1-2-2-8-4 | AgtTCtactatacTTTC | 304_6 | −18.46 | 30715 |
| 304 | AGTTCTACTATACTTTC | 3-10-1-1-2 | AGTtctactatacTtTC | 304_7 | −18.12 | 30715 |
| 304 | AGTTCTACTATACTTTC | 3-11-3 | AGTtctactatactTTC | 304_8 | −18.42 | 30715 |
| 304 | AGTTCTACTATACTTTC | 3-1-1-10-2 | AGTtCtactatacttTC | 304_9 | −18.58 | 30715 |
| 304 | AGTTCTACTATACTTTC | 2-1-2-10-2 | AGtTCtactatacttTC | 304_10 | −18.02 | 30715 |
| 304 | AGTTCTACTATACTTTC | 1-2-2-6-2-1-3 | AgtTCtactatACtTTC | 304_11 | −19.02 | 30715 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 304 | AGTTCTACTATACTTTC | 2-1-2-6-1-3-2 | AGtTCtactatActtTC | 304_12 | −18.22 | 30715 |
| 304 | AGTTCTACTATACTTTC | 2-2-1-7-2-1-2 | AGttCtactataCTtTC | 304_13 | −19.22 | 30715 |
| 304 | AGTTCTACTATACTTTC | 3-1-1-7-1-1-3 | AGTtCtactataCtTTC | 304_14 | −20.39 | 30715 |
| 304 | AGTTCTACTATACTTTC | 1-1-1-1-1-8-4 | AgTtCtactatacTTTC | 304_15 | −18.13 | 30715 |
| 305 | GTTCTACTATACTTTC | 4-10-2 | GTTCtactatacttTC | 305_1 | −17.48 | 30715 |
| 306 | CATTATATTTAAACTATCA | 4-13-2 | CATTatatttaaactatCA | 306_1 | −16.93 | 31630 |
| 307 | CACATTATATTTAAACTAT | 2-13-4 | CAcattatatttaaaCTAT | 307_1 | −17.11 | 31632 |
| 308 | ACACATTATATTTAAACTA | 3-13-3 | ACAcattatatttaaaCTA | 308_1 | −17.09 | 31633 |
| 309 | ACCACCTAAGACCTCAA | 2-11-4 | ACcacctaagaccTCAA | 309_1 | −22.49 | 32755 |
| 310 | CCACCTAAGACCTCAA | 2-10-4 | CCacctaagaccTCAA | 310_1 | −22.63 | 32755 |
| 311 | ACCACCTAAGACCTCA | 2-11-3 | ACcacctaagaccTCA | 311_1 | −21.74 | 32756 |
| 312 | ACCTTAAGTAACATTT | 4-10-2 | ACCTtaagtaacatTT | 312_1 | −16.82 | 33366 |
| 313 | CACCTTAAGTAACATT | 4-10-2 | CACCttaagtaacaTT | 313_1 | −18.05 | 33367 |
| 314 | CCACCTTAAGTAACAT | 3-10-3 | CCAccttaagtaaCAT | 314_1 | −20.70 | 33368 |
| 315 | ACCACCTTAAGTAACA | 4-10-2 | ACCAccttaagtaaCA | 315_1 | −20.68 | 33369 |
| 316 | TTATTAACCACCTTAA | 3-10-3 | TTAttaaccaccTAA | 316_1 | −16.19 | 33375 |
| 317 | CATTATTAACCACCTT | 2-10-4 | CAttattaaccaCCTT | 317_1 | −19.92 | 33377 |
| 318 | ACATTATTAACCACCT | 3-10-3 | ACAttattaaccaCCT | 318_1 | −20.14 | 33378 |
| 319 | ACCAATTATACTTACAA | 3-11-3 | ACCaattatacttaCAA | 319_1 | −17.16 | 36606 |
| 320 | AACCAATTATACTTACA | 4-11-2 | AACCaattatacttaCA | 320_1 | −17.16 | 36607 |
| 321 | CAAATACAGATTATCC | 2-10-4 | CAaatacagattATCC | 321_1 | −16.44 | 38092 |
| 322 | TTTACATTCCCATCATC | 2-11-4 | TTtacattcccatCATC | 322_1 | −21.08 | 38297 |
| 323 | CACACCTATTATATAAT | 4-11-2 | CACAcctattatataAT | 323_1 | −17.02 | 39173 |
| 324 | TCACACCTATTATATAA | 3-11-3 | TCAcacctattataTAA | 324_1 | −17.02 | 39174 |
| 325 | CTTCACACCTATTATATA | 2-12-4 | CTtcacacctattaTATA | 325_1 | −20.65 | 39175 |
| 326 | ACTTCACACCTATTATAT | 3-12-3 | ACTtcacacctattaTAT | 326_1 | −20.46 | 39176 |
| 327 | GCTCACACTAATTATT | 2-10-4 | GCtcacactaatTATT | 327_1 | −18.72 | 39228 |
| 328 | ATGCTCACACTAATTA | 4-10-2 | ATGCtcacactaatTA | 328_1 | −19.38 | 39230 |
| 329 | AATGCTCACACTAATT | 4-10-2 | AATGctcacactaaTT | 329_1 | −16.21 | 39231 |
| 330 | AAACTGTACACCTACT | 2-10-4 | AAactgtacaccTACT | 330_1 | −17.99 | 39563 |
| 331 | GTTTCCATCTACTATTA | 2-11-4 | GTttccatctactATTA | 331_1 | −19.78 | 39808 |
| 332 | TTTCCATCTACTATTA | 4-10-2 | TTTCcatctactatTA | 332_1 | −17.25 | 39808 |
| 333 | TGACATAACCATATAC | 3-10-3 | TGAcataaccataTAC | 333_1 | −16.63 | 39931 |
| 334 | GCTCCCAAACAACTAA | 2-12-2 | GCtcccaaacaactAA | 334_1 | −17.55 | 41114 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 335 | CCTCAATACTCTACTT | 4-10-2 | CCTCaatactctacTT | 335_1 | -20.30 | 41444 |
| 336 | GACCTCAATACTCTACT | 3-11-3 | GACctcaatactctACT | 336_1 | -21.01 | 41445 |
| 337 | GACCTCAATACTCTAC | 4-10-2 | GACCtcaatactctAC | 337_1 | -20.02 | 41446 |
| 338 | TACTAAACATACACATA | 4-11-2 | TACTaaacatacacaTA | 338_1 | -16.12 | 41725 |
| 339 | CTACTAAACATACACAT | 3-11-3 | CTActaaacatacaCAT | 339_1 | -17.31 | 41726 |
| 340 | TTCTACTAAACATACAC | 3-11-3 | TTCtactaaacataCAC | 340_1 | -16.07 | 41728 |
| 341 | TACCAATAGTTACCTT | 2-10-4 | TAccaatagttaCCTT | 341_1 | -20.03 | 42167 |
| 342 | CTTACCAATAGTTACCT | 3-11-3 | CTTaccaatagttaCCT | 342_1 | -22.29 | 42168 |
| 343 | TTACCAATAGTTACCT | 3-10-3 | TTAccaatagttaCCT | 343_1 | -20.03 | 42168 |
| 344 | CTTACCAATAGTTACC | 4-10-2 | CTTAccaatagttaCC | 344_1 | -20.03 | 42169 |
| 345 | TCTTACCAATAGTTACC | 4-11-2 | TCTTaccaatagttaCC | 345_1 | -21.30 | 42169 |
| 346 | TCAAAGCACACCACCAC | 2-12-3 | TCaaagcacaccacCAC | 346_1 | -21.69 | 42287 |
| 347 | ATTCAAAGCACACCACC | 2-12-3 | ATtcaaagcacaccACC | 347_1 | -21.00 | 42289 |
| 348 | AGACTAATCCTCTTAA | 3-10-3 | AGActaatcctctTAA | 348_1 | -17.72 | 43452 |
| 349 | TAGACTAATCCTCTTA | 4-10-2 | TAGActaatcctctTA | 349_1 | -19.20 | 43453 |
| 350 | CCCATTTCTAACATTTAC | 3-12-3 | CCCatttctaacattTAC | 350_1 | -22.93 | 43562 |
| 351 | ACCCATTTCTAACATT | 4-10-2 | ACCCatttctaacaTT | 351_1 | -20.64 | 43565 |
| 352 | AACCCATTTCTAACAT | 4-10-2 | AACCcatttctaacAT | 352_1 | -18.25 | 43566 |
| 353 | CCTCAACTTCACCAAT | 2-10-4 | CCtcaacttcacCAAT | 353_1 | -21.73 | 43634 |
| 354 | ACTGATTTCCTTAAAC | 4-10-2 | ACTGatttccttaaAC | 354_1 | -16.67 | 44180 |
| 355 | CACTGATTTCCTTAAAC | 4-11-2 | CACTgatttccttaaAC | 355_1 | -18.91 | 44180 |
| 356 | CCACTGATTTCCTTAAA | 4-11-2 | CCACtgatttccttaAA | 356_1 | -20.91 | 44181 |
| 357 | ACCACTGATTTCCTTA | 2-10-4 | ACcactgatttcCTTA | 357_1 | -20.98 | 44183 |
| 358 | CACCACTGATTTCCTT | 3-10-3 | CACcactgatttcCTT | 358_1 | -22.04 | 44184 |
| 359 | CTCTGCAATACACCAA | 2-10-4 | CTctgcaatacaCCAA | 359_1 | -20.90 | 44439 |
| 360 | ACTCTGCAATACACCA | 3-10-3 | ACTctgcaatacaCCA | 360_1 | -22.19 | 44440 |
| 361 | TACTCTGCAATACACCA | 2-11-4 | TActctgcaatacACCA | 361_1 | -22.32 | 44440 |
| 361 | TACTCTGCAATACACCA | 1-1-1-10-1-1-2 | TaCtctgcaatacAcCA | 361_2 | -19.29 | 44440 |
| 361 | TACTCTGCAATACACCA | 1-3-1-8-1-1-2 | TactCtgcaatacAcCA | 361_3 | -19.28 | 44440 |
| 361 | TACTCTGCAATACACCA | 1-10-1-3-2 | TactctgcaatAcacCA | 361_4 | -18.35 | 44440 |
| 361 | TACTCTGCAATACACCA | 2-10-2-1-2 | TActctgcaataCAcCA | 361_5 | -21.63 | 44440 |
| 361 | TACTCTGCAATACACCA | 1-13-3 | TactctgcaatacaCCA | 361_6 | -20.54 | 44440 |
| 361 | TACTCTGCAATACACCA | 2-10-1-2-2 | TActctgcaataCacCA | 361_7 | -20.06 | 44440 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 361 | TACTCTGCAATACACCA | 1-1-1-12-2 | TaCtctgcaatacacCA | 361_8 | -19.14 | 44440 |
| 361 | TACTCTGCAATACACCA | 1-2-2-10-2 | TacTCtgcaatacacCA | 361_9 | -20.33 | 44440 |
| 361 | TACTCTGCAATACACCA | 1-3-1-10-2 | TactCtgcaatacacCA | 361_10 | -19.13 | 44440 |
| 362 | TACTCTGCAATACACC | 2-10-4 | TActctgcaataCACC | 362_1 | -21.12 | 44441 |
| 362 | TACTCTGCAATACACC | 1-1-1-11-2 | TaCtctgcaatacaCC | 362_2 | -18.23 | 44441 |
| 362 | TACTCTGCAATACACC | 1-1-1-10-3 | TaCtctgcaatacACC | 362_3 | -18.78 | 44441 |
| 362 | TACTCTGCAATACACC | 1-3-1-7-4 | TactCtgcaataCACC | 362_4 | -20.87 | 44441 |
| 362 | TACTCTGCAATACACC | 3-11-2 | TACtctgcaatacaCC | 362_5 | -19.86 | 44441 |
| 362 | TACTCTGCAATACACC | 2-2-1-9-2 | TActCtgcaatacaCC | 362_6 | -19.44 | 44441 |
| 362 | TACTCTGCAATACACC | 2-12-2 | TActctgcaatacaCC | 362_7 | -18.47 | 44441 |
| 362 | TACTCTGCAATACACC | 1-2-2-9-2 | TacTCtgcaatacaCC | 362_8 | -19.42 | 44441 |
| 362 | TACTCTGCAATACACC | 2-1-2-9-2 | TACTCtgcaatacaCC | 362_9 | -20.64 | 44441 |
| 362 | TACTCTGCAATACACC | 1-3-1-9-2 | TactCtgcaatacaCC | 362_10 | -18.22 | 44441 |
| 363 | TTACTCTGCAATACACC | 2-11-4 | TTactctgcaataCACC | 363_1 | -21.71 | 44441 |
| 364 | TTACTCTGCAATACAC | 3-10-3 | TTActctgcaataCAC | 364_1 | -17.75 | 44442 |
| 365 | TTTACTCTGCAATACAC | 3-11-3 | TTTactctgcaataCAC | 365_1 | -18.34 | 44442 |
| 366 | CTTTACTCTGCAATACA | 2-11-4 | CTttactctgcaaTACA | 366_1 | -20.23 | 44443 |
| 367 | TTTACTCTGCAATACA | 2-10-4 | TTtactctgcaaTACA | 367_1 | -17.56 | 44443 |
| 368 | GACCACACTTTCTACCA | 2-13-2 | GAccacactttctacCA | 368_1 | -21.72 | 44477 |
| 369 | GACCACACTTTCTACC | 2-12-2 | GAccacactttctaCC | 369_1 | -20.81 | 44478 |
| 370 | AAGAAACACCCTTCCA | 2-10-4 | AAgaaacaccctTCCA | 370_1 | -21.48 | 44776 |
| 371 | ATCTGCTACATATTCTT | 4-11-2 | ATCTgctacatattcTT | 371_1 | -19.88 | 45216 |
| 372 | ATCTGCTACATATTCT | 4-10-2 | ATCTgctacatattCT | 372_1 | -19.71 | 45217 |
| 373 | CATCTGCTACATATTCT | 4-11-2 | CATCtgctacatattCT | 373_1 | -21.32 | 45217 |
| 374 | CATCTGCTACATATTC | 4-10-2 | CATCtgctacatatTC | 374_1 | -18.82 | 45218 |
| 375 | TTCAACCCTAATCACT | 4-10-2 | TTCAaccctaatcaCT | 375_1 | -19.99 | 45246 |
| 376 | ATTCAACCCTAATCAC | 2-10-4 | ATtcaaccctaaTCAC | 376_1 | -18.67 | 45247 |
| 377 | CATTCAACCCTAATCA | 3-10-3 | CATtcaaccctaaTCA | 377_1 | -19.93 | 45248 |
| 378 | GCATTCAACCCTAATCA | 3-12-2 | GCAttcaaccctaatCA | 378_1 | -22.56 | 45248 |
| 379 | AGCATTCAACCCTAATC | 4-11-2 | AGCAttcaaccctaaTC | 379_1 | -22.98 | 45249 |
| 380 | GCATTCAACCCTAATC | 4-10-2 | GCATtcaaccctaaTC | 380_1 | -21.63 | 45249 |

TABLE 3-continued

List of oligonucleotides or contiguous nucleobase sequences complementary to SEQ ID NO: 1
(motif sequences indicated by SEQ ID NO), oligonucleotide designs made from these, as well as
specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 381 | AGCATTCAACCCTAAT | 4-10-2 | AGCAttcaaccctaAT | 381_1 | −21.62 | 45250 |
| 382 | CAGCATTCAACCCTAAT | 3-12-2 | CAGcattcaaccctaAT | 382_1 | −21.12 | 45250 |
| 383 | TTAAATCCAGCATTCA | 3-10-3 | TTAaatccagcatTCA | 383_1 | −18.08 | 45258 |
| 384 | CTCCATATTTAAATCC | 4-10-2 | CTCCatatttaaatCC | 384_1 | −20.02 | 45266 |
| 385 | GCTCCATATTTAAATCC | 4-11-2 | GCTCcatatttaaatCC | 385_1 | −22.84 | 45266 |
| 386 | GCTCCATATTTAAATC | 4-10-2 | GCTCcatatttaaaTC | 386_1 | −18.78 | 45267 |
| 387 | AGCTCCATATTTAAAT | 4-10-2 | AGCTccatatttaaAT | 387_1 | −18.62 | 45268 |
| 388 | TAAGCTCCATATTTAA | 3-10-3 | TAAgctccatattTAA | 388_1 | −16.08 | 45270 |
| 389 | CCTAAGCTCCATATTTA | 3-11-3 | CCTaagctccatatTTA | 389_1 | −22.65 | 45271 |
| 390 | CTAAGCTCCATATTTA | 4-10-2 | CTAAgctccatattTA | 390_1 | −18.81 | 45271 |
| 391 | CCTAAGCTCCATATTT | 4-10-2 | CCTAagctccatatTT | 391_1 | −21.57 | 45272 |
| 392 | TCTACCCTAAATTCCC | 2-11-3 | TCtaccctaaattCCC | 392_1 | −23.00 | 45560 |
| 393 | CACATCTTGTATACAA | 3-10-3 | CACatcttgtataCAA | 393_1 | −16.65 | 45627 |
| 394 | ACACATCTTGTATACA | 4-10-2 | ACACatcttgtataCA | 394_1 | −17.95 | 45628 |
| 395 | CTACACATCTTGTATAC | 3-11-3 | CTAcacatcttgtaTAC | 395_1 | −19.13 | 45629 |
| 396 | TACACATCTTGTATAC | 3-10-3 | TACacatcttgtaTAC | 396_1 | −16.73 | 45629 |
| 397 | CTTGACTACACATCTT | 3-10-3 | CTTgactacacatCTT | 397_1 | −18.89 | 45635 |
| 398 | CTCTACAACAGTCCCA | 3-11-2 | CTCtacaacagtccCA | 398_1 | −22.06 | 45709 |
| 399 | TCTCTACAACAGTCCCA | 2-13-2 | TCtctacaacagtccCA | 399_1 | −21.70 | 45709 |
| 400 | ATAACATTACTCTTAACA | 3-12-3 | ATAacattactcttaACA | 400_1 | −17.03 | 46215 |
| 401 | TTTGACATTCCATCTCC | 2-12-3 | TTtgacattccatcTCC | 401_1 | −21.62 | 46256 |
| 402 | CTTTGACATTCCATCTC | 2-11-4 | CTttgacattccaTCTC | 402_1 | −21.88 | 46257 |
| 403 | TCTTTGACATTCCATCTC | 4-12-2 | TCTTtgacattccatcTC | 403_1 | −22.41 | 46257 |
| 404 | TTTGACATTCCATCTC | 3-10-3 | TTTgacattccatCTC | 404_1 | −19.40 | 46257 |
| 405 | ATCTTTGACATTCCATC | 2-11-4 | ATctttgacattcCATC | 405_1 | −20.53 | 46259 |
| 406 | TATCTTTGACATTCCAT | 2-11-4 | TAtctttgacattCCAT | 406_1 | −21.32 | 46260 |
| 407 | TACTATCTTTGACATTC | 4-11-2 | TACTatctttgacatTC | 407_1 | −18.39 | 46263 |
| 408 | TACTATCTTTGACATT | 4-10-2 | TACTatctttgacaTT | 408_1 | −16.84 | 46264 |
| 409 | CTGTATACACCATCCC | 2-12-2 | CTgtatacaccatcCC | 409_1 | −21.84 | 46392 |
| 410 | TCTGTATACACCATCC | 4-10-2 | TCTGtatacaccatCC | 410_1 | −22.73 | 46393 |
| 411 | TTTCTGACTCCCTATCC | 2-13-2 | TTtctgactccctatCC | 411_1 | −22.48 | 46420 |
| 412 | CCTATGTTAATACTTTC | 4-11-2 | CCTAtgttaatacttTC | 412_1 | −19.53 | 46505 |
| 413 | CTATGTTAATACTTTC | 4-10-2 | CTATgttaatacttTC | 413_1 | −16.09 | 46505 |
| 414 | CCTATGTTAATACTTT | 4-10-2 | CCTAtgttaatactTT | 414_1 | −17.85 | 46506 |
| 415 | TCCTATGTTAATACTT | 3-10-3 | TCCtatgttaataCTT | 415_1 | −18.47 | 46507 |
| 416 | ATCCTATGTTAATACT | 4-10-2 | ATCCtatgttaataCT | 416_1 | −18.71 | 46508 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 417 | ATTTCATTAAGTCACCC | 3-11-3 | ATTtcattaagtcaCCC | 417_1 | -22.16 | 47364 |
| 418 | ATTTCATTAAGTCACC | 2-10-4 | ATttcattaagtCACC | 418_1 | -18.79 | 47365 |
| 419 | CTCTCCTCAAGATCAAC | 3-11-3 | CTCtcctcaagatcAAC | 419_1 | -20.29 | 48110 |
| 420 | CTCTCCTCAAGATCAA | 3-10-3 | CTCtcctcaagatCAA | 420_1 | -20.33 | 48111 |
| 421 | CCATACAGTATATACA | 4-10-2 | CCATacagtatataCA | 421_1 | -19.53 | 48186 |
| 422 | CAACTATTATCTTCTT | 2-10-4 | CAactattatctTCTT | 422_1 | -16.38 | 48221 |
| 423 | ACAACTATTATCTTCT | 3-10-3 | ACAactattatctTCT | 423_1 | -16.60 | 48222 |
| 424 | TTGCTTCCAATTTATTT | 4-11-2 | TTGCttccaatttatTT | 424_1 | -19.93 | 50282 |
| 425 | ATCTCATGACCACCTAA | 3-11-3 | ATCtcatgaccaccTAA | 425_1 | -21.74 | 51241 |
| 425 | ATCTCATGACCACCTAA | 1-1-1-9-2-1-2 | AtCtcatgaccaCCtAA | 425_2 | -21.11 | 51241 |
| 425 | ATCTCATGACCACCTAA | 1-1-1-8-1-2-3 | AtCtcatgaccAccTAA | 425_3 | -19.96 | 51241 |
| 425 | ATCTCATGACCACCTAA | 1-12-4 | AtctcatgaccacCTAA | 425_4 | -20.40 | 51241 |
| 425 | ATCTCATGACCACCTAA | 3-10-1-1-2 | ATCtcatgaccacCtAA | 425_5 | -20.66 | 51241 |
| 425 | ATCTCATGACCACCTAA | 1-1-1-10-1-1-2 | AtCtcatgaccacCtAA | 425_6 | -18.72 | 51241 |
| 425 | ATCTCATGACCACCTAA | 1-1-1-9-1-1-3 | AtCtcatgaccaCcTAA | 425_7 | -20.59 | 51241 |
| 425 | ATCTCATGACCACCTAA | 1-2-2-7-1-1-3 | AtcTCatgaccaCcTAA | 425_8 | -21.48 | 51241 |
| 425 | ATCTCATGACCACCTAA | 1-3-1-8-4 | AtctCatgaccacCTAA | 425_9 | -21.07 | 51241 |
| 425 | ATCTCATGACCACCTAA | 1-1-3-8-1-1-2 | AtCTCatgaccacCtAA | 425_10 | -21.27 | 51241 |
| 426 | TCTCATGACCACCTAA | 2-10-4 | TCtcatgaccacCTAA | 426_1 | -21.25 | 51241 |
| 427 | ATCTCATGACCACCTA | 3-10-3 | ATCtcatgaccacCTA | 427_1 | -22.56 | 51242 |
| 428 | TATCTCATGACCACCTA | 2-12-3 | TAtctcatgaccacCTA | 428_1 | -21.88 | 51242 |
| 429 | TTTATCTCATGACCACC | 2-11-4 | TTtatctcatgacCACC | 429_1 | -22.37 | 51244 |
| 430 | TTTATCTCATGACCAC | 2-10-4 | TTtatctcatgaCCAC | 430_1 | -19.56 | 51245 |
| 431 | ATTCTTACCGTCTTTA | 4-10-2 | ATTCttaccgtcttTA | 431_1 | -19.52 | 51358 |
| 432 | TATTCTTACCGTCTTTA | 3-11-3 | TATtcttaccgtctTTA | 432_1 | -20.10 | 51358 |
| 433 | TATTCTTACCGTCTTT | 2-10-4 | TAttcttaccgtCTTT | 433_1 | -19.30 | 51359 |
| 434 | TTATTCTTACCGTCTTT | 2-11-4 | TTattcttaccgtCTTT | 434_1 | -19.99 | 51359 |
| 435 | ATCTGATCTCACACAT | 3-10-3 | ATCtgatctcacaCAT | 435_1 | -19.62 | 51438 |
| 436 | CATCTGATCTCACACAT | 4-11-2 | CATCtgatctcacacAT | 436_1 | -20.82 | 51438 |
| 437 | ACTTCCAGATTTCTACA | 2-11-4 | ACttccagatttcTACA | 437_1 | -21.44 | 51953 |
| 438 | TTTATGTTTACTTCAT | 3-10-3 | TTTatgtttacttCAT | 438_1 | -16.05 | 52150 |
| 439 | TAAAGATCCCATCACTC | 3-11-3 | TAAagatcccatcaCTC | 439_1 | -20.31 | 52549 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 440 | TAAAGATCCCATCACT | 4-10-2 | TAAAgatcccatcaCT | 440_1 | -18.82 | 52550 |
| 441 | CCTAAAGATCCCATCAC | 2-12-3 | CCtaaagatcccatCAC | 441_1 | -22.32 | 52551 |
| 442 | ATCATCAGTTACATCA | 4-10-2 | ATCAtcagttacatCA | 442_1 | -18.64 | 52579 |
| 443 | ACTCTCACTGTAACTTT | 4-11-2 | ACTCtcactgtaactTT | 443_1 | -19.76 | 53012 |
| 444 | AACTCTCACTGTAACTT | 3-11-3 | AACtctcactgtaaCTT | 444_1 | -18.53 | 53013 |
| 445 | ACTCTCACTGTAACTT | 3-10-3 | ACTctcactgtaaCTT | 445_1 | -19.04 | 53013 |
| 446 | AACTCTCACTGTAACT | 4-10-2 | AACTctcactgtaaCT | 446_1 | -17.97 | 53014 |
| 447 | CAACTCTCACTGTAACT | 4-11-2 | CAACtctcactgtaaCT | 447_1 | -20.01 | 53014 |
| 448 | CCTTTCATTAACATTTA | 3-11-3 | CCTttcattaacatTTA | 448_1 | -19.03 | 54198 |
| 449 | TTCCTTTCATTAACATTT | 4-12-2 | TTCCtttcattaacatTT | 449_1 | -19.92 | 54199 |
| 450 | TAATCCTATTCCAACT | 3-10-3 | TAAtcctattccaACT | 450_1 | -18.05 | 54232 |
| 451 | CTAATCCTATTCCAAC | 2-10-4 | CTaatcctattcCAAC | 451_1 | -18.65 | 54233 |
| 452 | CTCTAATCCTATTCCA | 3-10-3 | CTCtaatcctattCCA | 452_1 | -22.58 | 54235 |
| 453 | TCTCTAATCCTATTCC | 4-10-2 | TCTCtaatcctattCC | 453_1 | -21.78 | 54236 |
| 454 | TTGTCTCTAATCCTATT | 2-11-4 | TTgtctctaatccTATT | 454_1 | -19.70 | 54238 |
| 455 | TTGTCTCTAATCCTAT | 2-10-4 | TTgtctctaatcCTAT | 455_1 | -19.45 | 54239 |
| 456 | TCTTTAAGCTTCCCAC | 2-10-4 | TCtttaagcttcCCAC | 456_1 | -22.96 | 54609 |
| 457 | AAACTACCCTGCACAA | 3-10-3 | AAActaccctgcaCAA | 457_1 | -18.41 | 54924 |
| 458 | CCATGCTACATAAACC | 4-10-2 | CCATgctacataaaCC | 458_1 | -22.25 | 55337 |
| 459 | TCCATGCTACATAAAC | 4-10-2 | TCCAtgctacataaAC | 459_1 | -18.64 | 55338 |
| 460 | ACTCCTAAGAATTACA | 4-10-2 | ACTCctaagaattaCA | 460_1 | -17.62 | 59565 |
| 461 | GAAACTATTACTCCTA | 2-10-4 | GAaactattactCCTA | 461_1 | -19.06 | 59574 |
| 462 | TGAAACTATTACTCCT | 3-10-3 | TGAaactattactCCT | 462_1 | -19.30 | 59575 |
| 463 | ATGAAACTATTACTCC | 2-10-4 | ATgaaactattaCTCC | 463_1 | -17.96 | 59576 |
| 464 | AACAACTCATGCCACA | 2-10-4 | AAcaactcatgcCACA | 464_1 | -19.72 | 60012 |
| 465 | AAATATTGCCACCATT | 2-10-4 | AAatattgccacCATT | 465_1 | -17.78 | 60298 |
| 466 | GTTACATATTCTTTCAC | 3-11-3 | GTTacatattctttCAC | 466_1 | -18.76 | 60448 |
| 467 | TCATACTTGCTTTAAT | 4-10-2 | TCATacttgctttaAT | 467_1 | -17.29 | 60821 |
| 468 | ATCCTGATAATTAACT | 4-10-2 | ATCCtgataattaaCT | 468_1 | -17.73 | 61925 |
| 469 | CCTTAATCTGTATCAC | 3-10-3 | CCTtaatctgtatCAC | 469_1 | -19.92 | 62287 |
| 470 | ATACACAGCACATATT | 2-10-4 | ATacacagcacaTATT | 470_1 | -17.58 | 62422 |
| 471 | TCAGAATAATTCTCCT | 3-10-3 | TCAgaataattctCCT | 471_1 | -19.81 | 62443 |
| 472 | TCTTCAGCTTTCTAAAT | 4-11-2 | TCTTcagctttctaaAT | 472_1 | -18.58 | 64113 |
| 473 | AGTCCTTCCTTTAACCA | 2-13-2 | AGtccttcctttaacCA | 473_1 | -22.20 | 64461 |
| 474 | TAGTCCTTCCTTTAACC | 2-13-2 | TAgtccttcctttaaCC | 474_1 | -22.12 | 64462 |
| 475 | TTTAACCTTGCTTATA | 2-10-4 | TTtaaccttgctTATA | 475_1 | -17.50 | 65272 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 476 | ATCCCTTTGTAATCAT | 4-10-2 | ATCCctttgtaatcAT | 476_1 | −20.31 | 66840 |
| 477 | CTTGCATTTCTAATTAC | 3-11-3 | CTTgcatttctaatTAC | 477_1 | −18.09 | 67426 |
| 478 | CTTGTCAAATCATTTCT | 4-11-2 | CTTGtcaaatcatttCT | 478_1 | −19.10 | 68194 |
| 479 | CCATCTAATGATTATT | 4-10-2 | CCATctaatgattaTT | 479_1 | −17.28 | 68328 |
| 480 | TATCAGTTATCCAATA | 4-10-2 | TATCagttatccaaTA | 480_1 | −17.39 | 68805 |
| 481 | TCACTGCCATCAATAC | 4-10-2 | TCACtgccatcaatAC | 481_1 | −19.71 | 68921 |
| 482 | TGTCATCTACAAATCA | 4-10-2 | TGTCatctacaaatCA | 482_1 | −18.01 | 70133 |
| 483 | CTCTTTAGATTCATCC | 4-10-2 | CTCTttagattcatCC | 483_1 | −20.94 | 72377 |
| 484 | ACTCTTTAGATTCATC | 2-10-4 | ACtctttagattCATC | 484_1 | −17.81 | 72378 |
| 485 | CAACTCTATGACTACC | 2-10-4 | CAactctatgacTACC | 485_1 | −20.07 | 72826 |
| 486 | ACCTGTAATACTTCTT | 4-10-2 | ACCTgtaatacttcTT | 486_1 | −19.67 | 72861 |
| 487 | GAATTCTTTATTCCTCC | 2-11-4 | GAattctttattcCTCC | 487_1 | −22.53 | 72887 |
| 488 | ATCTGAATCAAACCTT | 2-10-4 | ATctgaatcaaaCCTT | 488_1 | −17.97 | 73474 |
| 489 | ACTTTACTGCCATAATC | 3-11-3 | ACTttactgccataATC | 489_1 | −19.60 | 73992 |
| 490 | TTACTCTTAGCAACCT | 4-10-2 | TTACtcttagcaacCT | 490_1 | −20.19 | 74791 |
| 491 | CACCAGTATTTCTTCTT | 4-11-2 | CACCagtatttcttcTT | 491_1 | −22.15 | 74851 |
| 492 | TTCACCAGTATTTCTTC | 4-11-2 | TTCAccagtatttctTC | 492_1 | −20.43 | 74853 |
| 493 | CCAAATAAGCAAACTC | 3-10-3 | CCAaataagcaaaCTC | 493_1 | −17.54 | 75840 |
| 494 | CCCAAATAAGCAAACT | 4-10-2 | CCCAaataagcaaaCT | 494_1 | −20.23 | 75841 |
| 495 | GACTACATTCTCAATA | 3-10-3 | GACtacattctcaATA | 495_1 | −17.49 | 76238 |
| 496 | TTGTCAATCTTTATTCT | 4-11-2 | TTGTcaatctttattCT | 496_1 | −18.85 | 76254 |
| 497 | AGCTTACCAAATATTC | 4-10-2 | AGCTtaccaaatatTC | 497_1 | −18.68 | 76811 |
| 498 | TTACACATGTATATCC | 3-10-3 | TTAcacatgtataTCC | 498_1 | −18.23 | 77114 |
| 499 | ATCCTGTTAATACCAT | 2-10-4 | ATcctgttaataCCAT | 499_1 | −20.41 | 80468 |
| 500 | TTCTTAGTCACACACA | 4-10-2 | TTCTtagtcacacaCA | 500_1 | −19.37 | 81047 |
| 501 | TTCTGTTTCCATTTACA | 4-11-2 | TTCTgtttccatttaCA | 501_1 | −21.31 | 82233 |
| 502 | TCTATATCAAGTTCCTT | 2-11-4 | TCtatatcaagttCCTT | 502_1 | −20.95 | 84166 |
| 503 | ATTCAGTTACCAACTA | 3-10-3 | ATTcagttaccaaCTA | 503_1 | −18.37 | 85392 |
| 504 | GCTTCTACTTAAATAT | 3-10-3 | GCTtctacttaaaTAT | 504_1 | −17.58 | 86974 |
| 505 | CCCTCAAAGTAATTTC | 4-10-2 | CCCTcaaagtaattTC | 505_1 | −20.53 | 87728 |
| 506 | AACATGTAATTTCCAT | 2-10-4 | AAcatgtaatttCCAT | 506_1 | −17.21 | 87810 |
| 507 | CCAGACTCCAATATTT | 4-10-2 | CCAGactccaatatTT | 507_1 | −20.78 | 88417 |
| 508 | CTTAGACTTCACCTTTC | 2-11-4 | CTtagacttcaccTTTC | 508_1 | −20.56 | 88991 |
| 509 | CTGCTTAATTATATCA | 4-10-2 | CTGCttaattatatCA | 509_1 | −18.85 | 90228 |
| 510 | AAATTGTCTACCTTCCT | 2-12-3 | AAattgtctaccttCCT | 510_1 | −20.62 | 90474 |
| 511 | CACTTAGAATATCCCT | 2-10-4 | CActtagaatatCCCT | 511_1 | −22.28 | 91625 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 512 | ATCCAAAGTTTCTTTC | 4-10-2 | ATCCaaagtttcttTC | 512_1 | -18.64 | 91885 |
| 513 | ATATTTGTCACCTAAC | 4-10-2 | ATATttgtcacctaAC | 513_1 | -17.12 | 92976 |
| 514 | CTATTCTCAGTATTAT | 3-10-3 | CTAttctcagtatTAT | 514_1 | -17.42 | 94304 |
| 515 | CCATTCAATGATCACT | 2-10-4 | CCattcaatgatCACT | 515_1 | -20.55 | 94528 |
| 516 | CACTAGTACTCTTATT | 4-10-2 | CACTagtactcttaTT | 516_1 | -18.01 | 95653 |
| 517 | GCCACAACATCTATTT | 4-10-2 | GCCAcaacatctatTT | 517_1 | -21.53 | 96751 |
| 518 | AGCACATATACCATCA | 4-10-2 | AGCAcatataccatCA | 518_1 | -21.98 | 97636 |
| 519 | GTCATCTAACTTCTTAC | 3-11-3 | GTCatctaacttctTAC | 519_1 | -19.25 | 98480 |
| 520 | TGTCATCTAACTTCTTA | 4-11-2 | TGTCatctaacttctTA | 520_1 | -19.69 | 98481 |
| 521 | CCCTTATAGTTATTAA | 3-10-3 | CCCttatagttatTAA | 521_1 | -19.32 | 99646 |
| 522 | TCCATAGAATTCTTCA | 4-10-2 | TCCAtagaattcttCA | 522_1 | -19.92 | 100334 |
| 523 | TTGATTCCACCATTAA | 3-10-3 | TTGattccaccatTAA | 523_1 | -18.05 | 101110 |
| 524 | CAGCCATAAACTATAT | 4-10-2 | CAGCcataaactatAT | 524_1 | -18.60 | 101898 |
| 525 | TATGACTTATTCCATA | 2-10-4 | TAtgacttattcCATA | 525_1 | -17.88 | 102558 |
| 526 | GTTAACCTATATTTCA | 4-10-2 | GTTAacctatatttCA | 526_1 | -17.69 | 103589 |
| 527 | TGTCTATTCTCTTCATT | 4-11-2 | TGTCtattctcttcaTT | 527_1 | -20.62 | 104309 |
| 528 | TTACTCTTTGATTTCAT | 3-11-3 | TTActctttgatttCAT | 528_1 | -18.39 | 105686 |
| 529 | GATAATTCCAAATCCC | 2-10-4 | GAtaattccaaaTCCC | 529_1 | -20.99 | 107972 |
| 530 | TCTTATCCTTGAATTTC | 4-11-2 | TCTTatccttgaattTC | 530_1 | -18.85 | 108257 |
| 531 | ATATCCCTTGATTATCC | 3-11-3 | ATAtcccttgattaTCC | 531_1 | -22.75 | 109407 |
| 532 | TTAGTATACCCTTTAT | 3-10-3 | TTAgtatacccttTAT | 532_1 | -18.67 | 110210 |
| 533 | CTCTTTGTCAAATACT | 4-10-2 | CTCTttgtcaaataCT | 533_1 | -18.16 | 110768 |
| 534 | CCAAACTGTCTTCTAAT | 2-11-4 | CCaaactgtcttcTAAT | 534_1 | -19.87 | 111811 |
| 535 | TCCAAACTGTCTTCTAA | 3-12-2 | TCCaaactgtcttctAA | 535_1 | -18.33 | 111812 |
| 536 | CCAGCATATTATATAC | 3-10-3 | CCAgcatattataTAC | 536_1 | -18.96 | 112149 |
| 537 | TCCAGCATATTATATA | 4-10-2 | TCCAgcatattataTA | 537_1 | -19.41 | 112150 |
| 538 | TCATTGAACAACTCTTC | 4-11-2 | TCATtgaacaactctTC | 538_1 | -18.01 | 112945 |
| 539 | CTGCCATCTTTATTTAT | 4-11-2 | CTGCcatctttatttAT | 539_1 | -21.89 | 113533 |
| 540 | TGAAACATTCTTCCCAC | 2-12-3 | TGaaacattcttccCAC | 540_1 | -19.76 | 114274 |
| 541 | TTTATTAGATTACTCC | 2-10-4 | TTtattagattaCTCC | 541_1 | -17.38 | 114495 |
| 542 | TTCCAGCTTATTTACCT | 3-12-2 | TTCcagcttatttacCT | 542_1 | -21.28 | 114831 |
| 543 | AGCATCATATAAACCT | 3-10-3 | AGCatcatataaaCCT | 543_1 | -20.62 | 115355 |
| 544 | GTACTTACACATCTAT | 2-10-4 | GTacttacacatCTAT | 544_1 | -18.96 | 116105 |
| 545 | TGTACTTACACATCTA | 3-10-3 | TGTacttacacatCTA | 545_1 | -19.38 | 116106 |
| 546 | ATTTCTCTATGTCACAT | 3-11-3 | ATTtctctatgtcaCAT | 546_1 | -19.28 | 117096 |
| 547 | CAAACCTACGTCTCTC | 2-10-4 | CAaacctacgtcTCTC | 547_1 | -20.87 | 117189 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 548 | GTATTTACTCTTTACCT | 3-11-3 | GTAtttactctttaCCT | 548_1 | -22.15 | 117476 |
| 549 | CTAATGCAATAACCCA | 2-10-4 | CTaatgcaataaCCCA | 549_1 | -21.79 | 118293 |
| 550 | ACTAATGCAATAACCC | 3-10-3 | ACTaatgcaataaCCC | 550_1 | -20.53 | 118294 |
| 551 | AGCTCTAAACCTTCAA | 3-10-3 | AGCtctaaaccttCAA | 551_1 | -20.51 | 118756 |
| 552 | TATTTGTCACCAAACC | 3-10-3 | TATttgtcaccaaACC | 552_1 | -19.63 | 119621 |
| 553 | CTCAGACATCTCAATA | 4-10-2 | CTCAgacatctcaaTA | 553_1 | -19.25 | 120655 |
| 554 | TCTCAGCTTCTTCAAAT | 2-12-3 | TCtcagcttcttcaAAT | 554_1 | -18.33 | 123733 |
| 555 | GCCAATACCCACAAAC | 3-10-3 | GCCaatacccacaAAC | 555_1 | -22.03 | 124163 |
| 556 | CCTCTGACAACCATTA | 4-10-2 | CCTCtgacaaccatTA | 556_1 | -22.57 | 125512 |
| 557 | CAGATAACTCTAAACC | 4-10-2 | CAGAtaactctaaaCC | 557_1 | -18.43 | 126882 |
| 558 | CTAACTGTTTCTCAATT | 3-11-3 | CTAactgtttctcaATT | 558_1 | -18.10 | 127105 |
| 559 | CCAAGATAATCATCAT | 3-10-3 | CCAagataatcatCAT | 559_1 | -18.37 | 127809 |
| 560 | TACATATTGTACTTCT | 4-10-2 | TACAtattgtacttCT | 560_1 | -17.48 | 129020 |
| 561 | TAGCCTACTTTAATAT | 4-10-2 | TAGCctactttaatAT | 561_1 | -18.67 | 129205 |
| 562 | CATTTACAAGCACATA | 2-10-4 | CAtttacaagcaCATA | 562_1 | -17.81 | 129928 |
| 563 | TTATTCTGACACACTT | 3-10-3 | TTAttctgacacaCTT | 563_1 | -17.49 | 130020 |
| 564 | TACATTGACACCTAAT | 4-10-2 | TACAttgacacctaAT | 564_1 | -17.37 | 130884 |
| 565 | TTTACATTGACACCTA | 2-10-4 | TTtacattgacaCCTA | 565_1 | -19.42 | 130886 |
| 566 | TGTATATAACTATTCC | 4-10-2 | TGTAtataactattCC | 566_1 | -17.79 | 131404 |
| 567 | GAATCTTCTAATTCCAC | 2-11-4 | GAatcttctaattCCAC | 567_1 | -20.40 | 132514 |
| 568 | TGCTCACTAACTACAC | 3-10-3 | TGCtcactaactaCAC | 568_1 | -20.66 | 133367 |
| 569 | TGCTACCATCATTACCT | 2-13-2 | TGctaccatcattacCT | 569_1 | -21.32 | 136198 |
| 570 | TTTATCAATATCTTCTCACT | 1-13-1-1-1-1-2 | TttatcaatatcttCtCaCT | 570_1 | -19.69 | 5784 |
| 570 | TTTATCAATATCTTCTCACT | 1-2-1-10-1-2-3 | TttAtcaatatcttCtcACT | 570_2 | -19.67 | 5784 |
| 570 | TTTATCAATATCTTCTCACT | 1-5-1-7-1-2-3 | TttatcAatatcttCtcACT | 570_3 | -19.65 | 5784 |
| 570 | TTTATCAATATCTTCTCACT | 1-1-1-11-1-3-2 | TtTatcaatatcttCtcaCT | 570_4 | -19.75 | 5784 |
| 570 | TTTATCAATATCTTCTCACT | 1-2-1-2-1-11-2 | TttAtcAatatcttctcaCT | 570_5 | -18.21 | 5784 |
| 570 | TTTATCAATATCTTCTCACT | 1-4-1-8-1-3-2 | TttatCaatatcttCtcaCT | 570_6 | -19.69 | 5784 |
| 570 | TTTATCAATATCTTCTCACT | 1-2-1-2-1-9-1-1-2 | TttAtcAatatcttctCaCT | 570_7 | -18.88 | 5784 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 570 | TTTATCAATATCTTCTCACT | 1-2-1-1-1-11-3 | TttAtCaatatcttctcACT | 570_8 | -19.36 | 5784 |
| 570 | TTTATCAATATCTTCTCACT | 1-4-1-10-1-1-2 | TttatCaatatcttctCaCT | 570_9 | -19.38 | 5784 |
| 570 | TTTATCAATATCTTCTCACT | 2-1-1-10-1-1-1-1-2 | TTtAtcaatatcttCtCaCT | 570_10 | -20.60 | 5784 |
| 570 | TTTATCAATATCTTCTCACT | 1-4-1-8-1-1-1-1-2 | TttatCaatatcttCtCaCT | 570_11 | -20.36 | 5784 |
| 570 | TTTATCAATATCTTCTCACT | 1-2-1-1-1-8-1-2-3 | TttAtCaatatcttCtcACT | 570_12 | -20.34 | 5784 |
| 570 | TTTATCAATATCTTCTCACT | 1-2-1-2-1-7-1-3-2 | TttAtcAatatcttCtcaCT | 570_13 | -19.19 | 5784 |
| 570 | TTTATCAATATCTTCTCACT | 1-1-2-1-1-10-1-1-2 | TtTAtCaatatcttctCaCT | 570_14 | -21.24 | 5784 |
| 571 | TTTATCAATATCTTCTCAC | 1-12-2-1-3 | TttatcaatatctTCtCAC | 571_1 | -19.16 | 5785 |
| 571 | TTTATCAATATCTTCTCAC | 2-1-1-1-1-6-2-2-3 | TTtAtCaatatcTTctCAC | 571_2 | -20.17 | 5785 |
| 571 | TTTATCAATATCTTCTCAC | 3-2-1-7-2-2-2 | TTTatCaatatctTCtcAC | 571_3 | -19.79 | 5785 |
| 571 | TTTATCAATATCTTCTCAC | 1-2-3-8-1-2-2 | TttATCaatatcttCtcAC | 571_4 | -18.78 | 5785 |
| 571 | TTTATCAATATCTTCTCAC | 1-4-1-9-4 | TttatCaatatcttcTCAC | 571_5 | -19.06 | 5785 |
| 571 | TTTATCAATATCTTCTCAC | 2-1-1-1-1-8-1-1-3 | TTtAtCaatatcttCtCAC | 571_6 | -19.75 | 5785 |
| 571 | TTTATCAATATCTTCTCAC | 1-1-1-2-1-6-1-3-3 | TtTatCaatatcTtctCAC | 571_7 | -19.11 | 5785 |
| 571 | TTTATCAATATCTTCTCAC | 2-1-3-6-1-4-2 | TTtATCaatatcTtctcAC | 571_8 | -19.13 | 5785 |
| 571 | TTTATCAATATCTTCTCAC | 4-12-3 | TTTAtcaatatcttctCAC | 571_9 | -20.38 | 5785 |
| 571 | TTTATCAATATCTTCTCAC | 1-1-2-1-1-6-1-3-3 | TtTAtCaatatcTtctCAC | 571_10 | -20.24 | 5785 |
| 571 | TTTATCAATATCTTCTCAC | 2-1-1-1-1-7-2-2-2 | TTtAtCaatatctTCtcAC | 571_11 | -18.65 | 5785 |
| 571 | TTTATCAATATCTTCTCAC | 3-2-1-8-1-1-3 | TTTatCaatatcttCtCAC | 571_12 | -20.89 | 5785 |
| 571 | TTTATCAATATCTTCTCAC | 1-3-2-8-1-1-3 | TttaTCaatatcttCtCAC | 571_13 | -19.96 | 5785 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 571 | TTTATCAATATCTTCTCAC | 1-2-1-1-1-9-4 | TttAtCaatatcttcTCAC | 571_14 | -19.16 | 5785 |
| 572 | TTTATCAATATCTTCTCA | 2-1-1-1-1-7-2-1-2 | TTtAtCaatatctTCtCA | 572_1 | -18.69 | 5786 |
| 572 | TTTATCAATATCTTCTCA | 3-2-1-6-1-1-1-1-2 | TTTatCaatatcTtCtCA | 572_2 | -19.36 | 5786 |
| 572 | TTTATCAATATCTTCTCA | 1-4-1-6-1-1-4 | TttatCaatatcTtCTCA | 572_3 | -19.19 | 5786 |
| 572 | TTTATCAATATCTTCTCA | 1-2-3-6-1-2-3 | TttATCaatatcTtcTCA | 572_4 | -19.56 | 5786 |
| 572 | TTTATCAATATCTTCTCA | 4-1-1-7-1-2-2 | TTTAtCaatatctTctCA | 572_5 | -19.37 | 5786 |
| 572 | TTTATCAATATCTTCTCA | 1-2-3-8-1-1-2 | TttATCaatatcttCtCA | 572_6 | -18.83 | 5786 |
| 572 | TTTATCAATATCTTCTCA | 3-2-1-9-3 | TTTatCaatatcttcTCA | 572_7 | -19.07 | 5786 |
| 572 | TTTATCAATATCTTCTCA | 1-2-1-10-4 | TttAtcaatatcttCTCA | 572_8 | -18.10 | 5786 |
| 572 | TTTATCAATATCTTCTCA | 4-10-1-1-2 | TTTAtcaatatcttCtCA | 572_9 | -19.31 | 5786 |
| 572 | TTTATCAATATCTTCTCA | 2-1-3-6-1-1-1-1-2 | TTtATCaatatcTtCtCA | 572_10 | -20.15 | 5786 |
| 572 | TTTATCAATATCTTCTCA | 3-2-1-6-1-2-3 | TTTatCaatatcTtcTCA | 572_11 | -19.59 | 5786 |
| 572 | TTTATCAATATCTTCTCA | 1-1-2-1-1-7-2-1-2 | TtTAtCaatatctTCtCA | 572_12 | -19.64 | 5786 |
| 572 | TTTATCAATATCTTCTCA | 4-9-1-1-3 | TTTAtcaatatctTcTCA | 572_13 | -19.90 | 5786 |
| 572 | TTTATCAATATCTTCTCA | 1-3-2-8-4 | TttaTCaatatcttCTCA | 572_14 | -19.80 | 5786 |
| 573 | TATACCTTTCTTTAACCCTT | 1-4-1-10-1-1-2 | TatacCtttctttaacCcTT | 573_1 | -22.72 | 8116 |
| 573 | TATACCTTTCTTTAACCCTT | 2-4-1-11-2 | TAtaccTttctttaacccTT | 573_2 | -22.80 | 8116 |
| 573 | TATACCTTTCTTTAACCCTT | 1-3-1-10-1-2-2 | TataCctttctttaaCccTT | 573_3 | -22.72 | 8116 |
| 573 | TATACCTTTCTTTAACCCTT | 1-4-1-9-1-2-2 | TatacCtttctttaaCccTT | 573_4 | -22.82 | 8116 |
| 573 | TATACCTTTCTTTAACCCTT | 1-5-1-9-1-1-2 | TataccTttctttaacCcTT | 573_5 | -22.35 | 8116 |
| 573 | TATACCTTTCTTTAACCCTT | 1-15-1-1-2 | TatacctttctttaacCcTT | 573_6 | -21.83 | 8116 |
| 573 | TATACCTTTCTTTAACCCTT | 1-2-1-1-1-10-1-1-2 | TatAcCtttctttaacCcTT | 573_7 | -22.91 | 8116 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 573 | TATACCTTTCTTTAACCCTT | 2-2-1-1-1-11-2 | TAtaCcTttctttaacccTT | 573_8 | -23.58 | 8116 |
| 573 | TATACCTTTCTTTAACCCTT | 2-3-1-12-2 | TAtacCtttctttaacccTT | 573_9 | -23.17 | 8116 |
| 573 | TATACCTTTCTTTAACCCTT | 1-3-1-8-2-1-1-1-2 | TataCctttctttAAcCcTT | 573_10 | -23.35 | 8116 |
| 573 | TATACCTTTCTTTAACCCTT | 2-2-1-1-1-7-1-1-1-1-2 | TAtaCcTttctttaAcCcTT | 573_11 | -24.68 | 8116 |
| 573 | TATACCTTTCTTTAACCCTT | 2-4-1-8-2-1-2 | TAtaccTttctttaaCCcTT | 573_12 | -25.86 | 8116 |
| 573 | TATACCTTTCTTTAACCCTT | 2-3-1-9-1-2-2 | TAtacCtttctttaaCccTT | 573_13 | -23.96 | 8116 |
| 573 | TATACCTTTCTTTAACCCTT | 2-3-1-10-1-1-2 | TAtacCtttctttaacCcTT | 573_14 | -23.85 | 8116 |
| 574 | TTATACCTTTCTTTAACCCT | 1-1-1-10-1-4-2 | TtAtacctttcttTaaccCT | 574_1 | -22.31 | 8117 |
| 574 | TTATACCTTTCTTTAACCCT | 1-13-1-1-1-1-2 | TtatacctttctttAaCcCT | 574_2 | -22.38 | 8117 |
| 574 | TTATACCTTTCTTTAACCCT | 1-1-1-3-1-11-2 | TtAtacCtttctttaaccCT | 574_3 | -22.47 | 8117 |
| 574 | TTATACCTTTCTTTAACCCT | 1-3-1-1-1-7-1-3-2 | TtatAcCtttctttAaccCT | 574_4 | -22.68 | 8117 |
| 574 | TTATACCTTTCTTTAACCCT | 1-4-1-8-1-3-2 | TtataCctttctttAaccCT | 574_5 | -22.38 | 8117 |
| 574 | TTATACCTTTCTTTAACCCT | 1-1-1-13-1-1-2 | TtAtacctttctttaaCcCT | 574_6 | -22.36 | 8117 |
| 574 | TTATACCTTTCTTTAACCCT | 1-3-1-11-1-1-2 | TtatAcctttctttaaCcCT | 574_7 | -22.46 | 8117 |
| 574 | TTATACCTTTCTTTAACCCT | 1-1-1-2-1-12-2 | TtAtaCctttctttaaccCT | 574_8 | -22.36 | 8117 |
| 574 | TTATACCTTTCTTTAACCCT | 1-5-1-11-2 | TtatacCtttctttaaccCT | 574_9 | -22.37 | 8117 |
| 574 | TTATACCTTTCTTTAACCCT | 1-1-1-2-1-10-1-1-2 | TtAtaCctttctttaaCcCT | 574_10 | -23.14 | 8117 |
| 574 | TTATACCTTTCTTTAACCCT | 1-1-1-3-1-9-1-1-2 | TtAtacCtttctttaaCcCT | 574_11 | -23.25 | 8117 |
| 574 | TTATACCTTTCTTTAACCCT | 1-1-1-3-1-10-3 | TtAtacCtttctttaacCCT | 574_12 | -24.75 | 8117 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 574 | TTATACCTTTCTTTAACCCT | 1-1-1-2-2-11-2 | TtAtaCCtttctttaaccCT | 574_13 | -24.85 | 8117 |
| 574 | TTATACCTTTCTTTAACCCT | 1-3-1-1-1-11-2 | TtatAcCtttctttaaccCT | 574_14 | -22.56 | 8117 |
| 575 | TTTATACCTTTCTTTAACCC | 1-2-1-9-1-4-2 | TttAtacctttctTtaacCC | 575_1 | -21.69 | 8118 |
| 575 | TTTATACCTTTCTTTAACCC | 1-12 1-4-2 | TttatacctttctTtaacCC | 575_2 | -21.59 | 8118 |
| 575 | TTTATACCTTTCTTTAACCC | 1-12-1-1-1-2-2 | TttatacctttctTtAacCC | 575_3 | -21.71 | 8118 |
| 575 | TTTATACCTTTCTTTAACCC | 1-4-1-10-1-1-2 | TttatAcctttctttaAcCC | 575_4 | -21.90 | 8118 |
| 575 | TTTATACCTTTCTTTAACCC | 1-13-1-3-2 | TttatacctttcttTaacCC | 575_5 | -22.01 | 8118 |
| 575 | TTTATACCTTTCTTTAACCC | 2-1-1-14-2 | TTtAtacctttctttaacCC | 575_6 | -22.20 | 8118 |
| 575 | TTTATACCTTTCTTTAACCC | 1-14-2-1-2 | TttatacctttctttAAcCC | 575_7 | -22.02 | 8118 |
| 575 | TTTATACCTTTCTTTAACCC | 1-14-1-2-2 | TttatacctttctttAacCC | 575_8 | -21.41 | 8118 |
| 575 | TTTATACCTTTCTTTAACCC | 1-15-1-1-2 | TttatacctttctttaAcCC | 575_9 | -21.71 | 8118 |
| 575 | TTTATACCTTTCTTTAACCC | 2-1-1-9-1-4-2 | TTtAtacctttctTtaacCC | 575_10 | -22.50 | 8118 |
| 575 | TTTATACCTTTCTTTAACCC | 1-2-1-10-1-3-2 | TttAtacctttcttTaacCC | 575_11 | -22.11 | 8118 |
| 575 | TTTATACCTTTCTTTAACCC | 1-4-2-8-2-1-2 | TttatACctttctttAAcCC | 575_12 | -23.40 | 8118 |
| 575 | TTTATACCTTTCTTTAACCC | 1-2-1-2-1-9-1-1-2 | TttAtaCctttctttaAcCC | 575_13 | -22.59 | 8118 |
| 575 | TTTATACCTTTCTTTAACCC | 1-1-2-14-2 | TtTAtacctttctttaacCC | 575_14 | -23.15 | 8118 |
| 576 | TTTTATACCTTTCTTTAACC | 1-1-1-10-2-3-2 | TtTtatacctttcTTtaaCC | 576_1 | -21.12 | 8119 |
| 576 | TTTTATACCTTTCTTTAACC | 1-3-1-8-1-4-2 | TtttAtacctttcTttaaCC | 576_2 | -20.10 | 8119 |
| 576 | TTTTATACCTTTCTTTAACC | 1-1-1-10-1-2-4 | TtTtatacctttcTttAACC | 576_3 | -21.45 | 8119 |
| 576 | TTTTATACCTTTCTTTAACC | 3-11-1-1-1-1-2 | TTTtatacctttctTtAaCC | 576_4 | -21.54 | 8119 |
| 576 | TTTTATACCTTTCTTTAACC | 2-4-1-7-1-3-2 | TTttatAcctttctTtaaCC | 576_5 | -20.80 | 8119 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 576 | TTTTATACCTTTCTTTAACC | 1-14-1-2-2 | TtttataccttttcttTaaCC | 576_6 | −20.22 | 8119 |
| 576 | TTTTATACCTTTCTTTAACC | 1-15-1-1-2 | TtttatacctttctttAaCC | 576_7 | −19.61 | 8119 |
| 576 | TTTTATACCTTTCTTTAACC | 1-5-1-10-3 | TtttatAcctttctttaACC | 576_8 | −20.51 | 8119 |
| 576 | TTTTATACCTTTCTTTAACC | 1-1-2-14-2 | TtTTatacctttctttaaCC | 576_9 | −21.03 | 8119 |
| 576 | TTTTATACCTTTCTTTAACC | 1-1-2-10-1-1-1-1-2 | TtTTatacctttctTtAaCC | 576_10 | −21.46 | 8119 |
| 576 | TTTTATACCTTTCTTTAACC | 2-2-1-9-1-3-2 | TTttAtacctttctTtaaCC | 576_11 | −20.70 | 8119 |
| 576 | TTTTATACCTTTCTTTAACC | 1-5-1-7-1-3-2 | TtttatAcctttctTtaaCC | 576_12 | −19.99 | 8119 |
| 576 | TTTTATACCTTTCTTTAACC | 1-1-1-12-2-1-2 | TtTtatacctttctttTAaCC | 576_13 | −21.68 | 8119 |
| 576 | TTTTATACCTTTCTTTAACC | 1-1-1-1-1-13-2 | TtTtAtacctttctttaaCC | 576_14 | −19.89 | 8119 |
| 577 | TTTTTATACCTTTCTTTAAC | 1-12 1-2-4 | TttttatacctttCttTAAC | 577_1 | −19.19 | 8120 |
| 577 | TTTTTATACCTTTCTTTAAC | 1-2-1-9-1-1-2-1-2 | TttTtatacctttCtTTaAC | 577_2 | −18.96 | 8120 |
| 577 | TTTTTATACCTTTCTTTAAC | 2-12-3-1-2 | TTtttatacctttcTTTaAC | 577_3 | −19.52 | 8120 |
| 577 | TTTTTATACCTTTCTTTAAC | 1-1-1-2-1-7-2-3-2 | TtTttAtacctttCTttaAC | 577_4 | −18.71 | 8120 |
| 577 | TTTTTATACCTTTCTTTAAC | 4-9-1-1-1-2-2 | TTTTtatacctttCtTtaAC | 577_5 | −19.85 | 8120 |
| 577 | TTTTTATACCTTTCTTTAAC | 3-1-1-8-1-1-1-1-3 | TTTtTatacctttCtTtAAC | 577_6 | −20.08 | 8120 |
| 577 | TTTTTATACCTTTCTTTAAC | 2-1-2-8-2-2-3 | TTtTTatacctttCTttAAC | 577_7 | −20.97 | 8120 |
| 577 | TTTTTATACCTTTCTTTAAC | 1-1-2-10-2-1-3 | TtTTtatacctttcTTtAAC | 577_8 | −18.89 | 8120 |
| 577 | TTTTTATACCTTTCTTTAAC | 1-3-2-7-1-4-2 | TtttTAtacctttCtttaAC | 577_9 | −18.97 | 8120 |
| 577 | TTTTTATACCTTTCTTTAAC | 1-2-1-9-2-1-1-1-2 | TttTtatacctttCTtTaAC | 577_10 | −19.34 | 8120 |
| 577 | TTTTTATACCTTTCTTTAAC | 2-3-1-7-2-2-3 | TTtttAtacctttCTttAAC | 577_11 | −19.53 | 8120 |
| 577 | TTTTTATACCTTTCTTTAAC | 1-1-2-9-1-1-1-1-3 | TtTTtatacctttCtTtAAC | 577_12 | −18.84 | 8120 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 577 | TTTTTATACCTTTCTTTAAC | 1-3-2-7-1-1-1-2-2 | TtttTAtacctttCtTtaAC | 577_13 | -19.27 | 8120 |
| 577 | TTTTTATACCTTTCTTTAAC | 3-1-1-8-1-2-1-1-2 | TTTtTatacctttCttTaAC | 577_14 | -20.20 | 8120 |
| 578 | TTTTTTCTTACTATCTTCAA | 1-5-1-7-2-2-2 | TtttttCttactatCTtcAA | 578_1 | -19.02 | 8584 |
| 578 | TTTTTTCTTACTATCTTCAA | 2-2-1-1-1-7-1-1-1-1-2 | TTttTtCttactatCtTcAA | 578_2 | -19.31 | 8584 |
| 578 | TTTTTTCTTACTATCTTCAA | 1-2-2-9-1-2-3 | TttTTtcttactatCttCAA | 578_3 | -20.05 | 8584 |
| 578 | TTTTTTCTTACTATCTTCAA | 1-1-1-1-1-1-1-7-1-3-2 | TtTtTtCttactatCttcAA | 578_4 | -18.43 | 8584 |
| 578 | TTTTTTCTTACTATCTTCAA | 3-3-1-8-1-2-2 | TTTtttCttactatcTtcAA | 578_5 | -18.99 | 8584 |
| 578 | TTTTTTCTTACTATCTTCAA | 2-1-2-1-1-8-1-2-2 | TTtTTtCttactatcTtcAA | 578_6 | -19.29 | 8584 |
| 578 | TTTTTTCTTACTATCTTCAA | 1-1-3-1-1-9-1-1-2 | TtTTTtCttactatctTcAA | 578_7 | -19.15 | 8584 |
| 578 | TTTTTTCTTACTATCTTCAA | 2-1-1-11-1-1-3 | TTtTttcttactatcTtCAA | 578_8 | -19.58 | 8584 |
| 578 | TTTTTTCTTACTATCTTCAA | 1-4-1-10-4 | TttttTcttactatctTCAA | 578_9 | -19.31 | 8584 |
| 579 | TTTTTTTCTTACTATCTTCA | 1-12-1-1-1-2-2 | TttttttcttactAtCttCA | 579_1 | -19.29 | 8585 |
| 579 | TTTTTTTCTTACTATCTTCA | 2-1-1-9-1-4-2 | TTtTtttcttactAtcttCA | 579_2 | -19.42 | 8585 |
| 579 | TTTTTTTCTTACTATCTTCA | 1-1-1-2-1-7-1-4-2 | TtTttTtcttactAtcttCA | 579_3 | -18.91 | 8585 |
| 579 | TTTTTTTCTTACTATCTTCA | 1-1-2-9-1-2-1-1-2 | TtTTtttcttactAtcTtCA | 579_4 | -19.94 | 8585 |
| 579 | TTTTTTTCTTACTATCTTCA | 1-3-2-10-1-1-2 | TtttTTtcttactatcTtCA | 579_5 | -19.84 | 8585 |
| 579 | TTTTTTTCTTACTATCTTCA | 2-3-1-12-2 | TTtttTtcttactatcttCA | 579_6 | -19.33 | 8585 |
| 579 | TTTTTTTCTTACTATCTTCA | 3-15-2 | TTTttttcttactatcttCA | 579_7 | -19.84 | 8585 |
| 579 | TTTTTTTCTTACTATCTTCA | 1-2-2-13-2 | TttTTttcttactatcttCA | 579_8 | -19.33 | 8585 |
| 579 | TTTTTTTCTTACTATCTTCA | 1-14-1-2-2 | TttttttcttactatCttCA | 579_9 | -19.19 | 8585 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 580 | ATTTTTTTCTTACTATCTTC | 1-4-1-8-1-1-1-1-2 | AttttTttcttactAtCtTC | 580_1 | -18.09 | 8586 |
| 580 | ATTTTTTTCTTACTATCTTC | 2-1-1-10-1-2-3 | ATtTttttcttactAtcTTC | 580_2 | -19.39 | 8586 |
| 580 | ATTTTTTTCTTACTATCTTC | 1-3-2-8-1-2-3 | AtttTTttcttactAtcTTC | 580_3 | -18.95 | 8586 |
| 580 | ATTTTTTTCTTACTATCTTC | 1-5-1-6-1-3-3 | AtttttTtcttacTatcTTC | 580_4 | -18.98 | 8586 |
| 580 | ATTTTTTTCTTACTATCTTC | 2-2-1-1-1-7-1-3-2 | ATttTtTtcttactAtctTC | 580_5 | -18.66 | 8586 |
| 580 | ATTTTTTTCTTACTATCTTC | 1-1-3-8-1-4-2 | AtTTTttcttacTatctTC | 580_6 | -19.58 | 8586 |
| 580 | ATTTTTTTCTTACTATCTTC | 2-1-1-12-1-1-2 | ATtTttttcttactatCtTC | 580_7 | -19.24 | 8586 |
| 580 | ATTTTTTTCTTACTATCTTC | 1-1-1-2-1-11-3 | AtTttTttcttactatcTTC | 580_8 | -18.34 | 8586 |
| 580 | ATTTTTTTCTTACTATCTTC | 1-1-2-1-2-11-2 | AtTTtTTtcttactatctTC | 580_9 | -18.94 | 8586 |
| 581 | AATTTTTTTCTTACTATCTT | 1-4-1-7-1-1-1-1-3 | AatttTtttcttaCtAtCTT | 581_1 | -18.53 | 8587 |
| 581 | AATTTTTTTCTTACTATCTT | 1-3-1-1-1-6-2-3-2 | AattTtTttcttaCTatcTT | 581_2 | -18.69 | 8587 |
| 581 | AATTTTTTTCTTACTATCTT | 1-1-2-10-2-2-2 | AaTTtttttcttacTAtcTT | 581_3 | -18.80 | 8587 |
| 581 | AATTTTTTTCTTACTATCTT | 2-1-1-1-1-8-1-2-3 | AAtTtTtttcttacTatCTT | 581_4 | -19.20 | 8587 |
| 581 | AATTTTTTTCTTACTATCTT | 4-2-1-7-1-3-2 | AATTttTttcttacTatcTT | 581_5 | -19.30 | 8587 |
| 581 | AATTTTTTTCTTACTATCTT | 2-2-2-7-1-1-2-1-2 | AAttTTtttcttaCtATcTT | 581_6 | -19.52 | 8587 |
| 581 | AATTTTTTTCTTACTATCTT | 1-12-1-2-4 | AatttttttcttaCtaTCTT | 581_7 | -19.25 | 8587 |
| 581 | AATTTTTTTCTTACTATCTT | 1-1-4-7-1-4-2 | AaTTTTtttcttaCtatcTT | 581_8 | -19.35 | 8587 |
| 581 | AATTTTTTTCTTACTATCTT | 2-1-3-9-1-1-3 | AAtTTTtttcttactAtCTT | 581_9 | -19.68 | 8587 |
| 582 | GTTTATACCCTTTCCAAT | 1-1-1-1-1-7-2-2-2 | GtTtAtaccctttTCcaAT | 582_1 | -21.48 | 9209 |
| 582 | GTTTATACCCTTTCCAAT | 1-12-2-1-2 | GtttatacccttttCCaAT | 582_2 | -22.28 | 9209 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 582 | GTTTATACCCTTTCCAAT | 1-3-1-8-1-1-3 | GtttAtacccttttCcAAT | 582_3 | -20.46 | 9209 |
| 582 | GTTTATACCCTTTCCAAT | 1-1-1-1-1-9-1-1-2 | GtTtAtaccctttcCaAT | 582_4 | -20.30 | 9209 |
| 582 | GTTTATACCCTTTCCAAT | 2-11-1-2-2 | GTttataccctttCcaAT | 582_5 | -21.64 | 9209 |
| 582 | GTTTATACCCTTTCCAAT | 1-1-2-9-1-1-3 | GtTTatacccttttCcAAT | 582_6 | -21.90 | 9209 |
| 582 | GTTTATACCCTTTCCAAT | 1-1-1-13-2 | GtTtataccctttccaAT | 582_7 | -19.63 | 9209 |
| 582 | GTTTATACCCTTTCCAAT | 1-2-1-12-2 | GttTataccctttccaAT | 582_8 | -20.05 | 9209 |
| 582 | GTTTATACCCTTTCCAAT | 1-13-4 | GtttataccctttcCAAT | 582_9 | -21.59 | 9209 |
| 583 | TGTTTATACCCTTTCCAA | 2-1-1-10-1-1-2 | TGtTtataccctttCcAA | 583_1 | -21.08 | 9210 |
| 583 | TGTTTATACCCTTTCCAA | 1-4-1-6-1-1-1-1-2 | TgtttAtaccctTtCcAA | 583_2 | -19.97 | 9210 |
| 583 | TGTTTATACCCTTTCCAA | 1-3-1-9-1-1-2 | TgttTataccctttCcAA | 583_3 | -20.30 | 9210 |
| 583 | TGTTTATACCCTTTCCAA | 2-1-1-1-1-6-1-3-2 | TGtTtAtaccctTtccAA | 583_4 | -20.71 | 9210 |
| 583 | TGTTTATACCCTTTCCAA | 1-2-1-8-1-2-3 | TgtTtataccctTtcCAA | 583_5 | -21.40 | 9210 |
| 583 | TGTTTATACCCTTTCCAA | 1-4-1-9-3 | TgtttAtaccctttcCAA | 583_6 | -20.89 | 9210 |
| 583 | TGTTTATACCCTTTCCAA | 1-1-2-12-2 | TgTTtataccctttccAA | 583_7 | -20.27 | 9210 |
| 583 | TGTTTATACCCTTTCCAA | 1-12-2-1-2 | TgtttatacccttTCcAA | 583_8 | -20.56 | 9210 |
| 583 | TGTTTATACCCTTTCCAA | 2-2-1-11-2 | TGttTataccctttccAA | 583_9 | -20.74 | 9210 |
| 584 | CTGTTTATACCCTTTCCA | 1-1-1-10-1-2-2 | CtGtttataccctTtcCA | 584_1 | -22.45 | 9211 |
| 584 | CTGTTTATACCCTTTCCA | 1-12-1-2-2 | CtgtttataccctTtcCA | 584_2 | -22.14 | 9211 |
| 584 | CTGTTTATACCCTTTCCA | 1-1-1-1-1-11-2 | CtGtTtataccctttcCA | 584_3 | -22.45 | 9211 |
| 584 | CTGTTTATACCCTTTCCA | 1-1-1-13-2 | CtGtttataccctttcCA | 584_4 | -22.15 | 9211 |
| 584 | CTGTTTATACCCTTTCCA | 1-2-1-12-2 | CtgTttataccctttcCA | 584_5 | -22.50 | 9211 |
| 584 | CTGTTTATACCCTTTCCA | 1-3-1-11-2 | CtgtTtataccctttcCA | 584_6 | -22.14 | 9211 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 584 | CTGTTTATACCCTTTCCA | 1-4-1-10-2 | CtgttTatacccttttcCA | 584_7 | −22.57 | 9211 |
| 584 | CTGTTTATACCCTTTCCA | 1-15-2 | CtgtttatacccttttcCA | 584_8 | −21.84 | 9211 |
| 585 | AATTATTTATACACCATCAT | 2-1-1-1-1-8-3-1-2 | AAtTaTttatacacCATcAT | 585_1 | −20.76 | 11511 |
| 585 | AATTATTTATACACCATCAT | 3-2-2-6-1-1-2-1-2 | AATtaTTtatacaCcATcAT | 585_2 | −20.88 | 11511 |
| 585 | AATTATTTATACACCATCAT | 1-4-1-7-2-1-1-1-2 | AattaTttatacaCCaTcAT | 585_3 | −19.62 | 11511 |
| 585 | AATTATTTATACACCATCAT | 1-3-1-1-1-6-1-3-3 | AattAtTtatacaCcatCAT | 585_4 | −18.98 | 11511 |
| 585 | AATTATTTATACACCATCAT | 1-2-3-7-1-1-1-2-2 | AatTATttatacaCcAtcAT | 585_5 | −19.65 | 11511 |
| 585 | AATTATTTATACACCATCAT | 1-1-2-11-1-1-3 | AaTTatttatacaccAtCAT | 585_6 | −19.53 | 11511 |
| 585 | AATTATTTATACACCATCAT | 2-2-1-9-1-1-4 | AAttAtttatacacCaTCAT | 585_7 | −20.11 | 11511 |
| 585 | AATTATTTATACACCATCAT | 3-1-2-8-1-2-3 | AATtATttatacacCatCAT | 585_8 | −21.48 | 11511 |
| 585 | AATTATTTATACACCATCAT | 4-2-1-7-1-3-2 | AATTatTtatacacCatcAT | 585_9 | −19.60 | 11511 |
| 585 | AATTATTTATACACCATCAT | 2-1-1-2-1-6-3-2-2 | AAtTatTtatacaCCAtcAT | 585_10 | −21.69 | 11511 |
| 585 | AATTATTTATACACCATCAT | 1-3-2-7-1-1-1-1-3 | AattATttatacaCcAtCAT | 585_11 | −19.97 | 11511 |
| 585 | AATTATTTATACACCATCAT | 2-1-3-8-1-1-1-1-2 | AAtTATttatacacCaTcAT | 585_12 | −20.42 | 11511 |
| 585 | AATTATTTATACACCATCAT | 1-1-2-1-1-8-1-2-3 | AaTTaTttatacacCatCAT | 585_13 | −20.49 | 11511 |
| 585 | AATTATTTATACACCATCAT | 2-1-1-2-1-9-4 | AAtTatTtatacaccaTCAT | 585_14 | −20.47 | 11511 |
| 586 | AAATTATTTATACACCATCA | 1-12-3-1-3 | AaattatttatacACCaTCA | 586_1 | −20.58 | 11512 |
| 586 | AAATTATTTATACACCATCA | 1-1-1-2-1-7-1-1-2-1-2 | AaAttAtttatacAcCAtCA | 586_2 | −18.56 | 11512 |
| 586 | AAATTATTTATACACCATCA | 3-2-2-6-2-3-2 | AAAttATttatacACcatCA | 586_3 | −19.68 | 11512 |
| 586 | AAATTATTTATACACCATCA | 4-10-1-2-3 | AAATtatttatacaCcaTCA | 586_4 | −20.15 | 11512 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 586 | AAATTATTTATACACCATCA | 1-1-4-8-1-1-1-1-2 | AaATTAtttatacaCcAtCA | 586_5 | -20.72 | 11512 |
| 586 | AAATTATTTATACACCATCA | 2-1-2-1-1-7-1-3-2 | AAaTTaTttatacaCcatCA | 586_6 | -19.39 | 11512 |
| 586 | AAATTATTTATACACCATCA | 1-3-2-7-1-1-1-1-3 | AaatTAtttatacAcCaTCA | 586_7 | -19.65 | 11512 |
| 586 | AAATTATTTATACACCATCA | 1-1-3-8-1-2-4 | AaATTatttatacAccATCA | 586_8 | -20.88 | 11512 |
| 586 | AAATTATTTATACACCATCA | 2-2-1-1-1-9-4 | AAatTaTttatacaccATCA | 586_9 | -19.63 | 11512 |
| 586 | AAATTATTTATACACCATCA | 1-1-1-1-1-1-1-6-3-2-2 | AaAtTaTttatacACCatCA | 586_10 | -20.95 | 11512 |
| 586 | AAATTATTTATACACCATCA | 1-3-2-7-1-1-2-1-2 | AaatTAtttatacAcCAtCA | 586_11 | -20.00 | 11512 |
| 586 | AAATTATTTATACACCATCA | 2-1-2-1-1-7-1-1-1-1-2 | AAaTTaTttatacaCcAtCA | 586_12 | -19.44 | 11512 |
| 586 | AAATTATTTATACACCATCA | 3-2-1-8-1-2-3 | AAAttAtttatacaCcaTCA | 586_13 | -19.00 | 11512 |
| 586 | AAATTATTTATACACCATCA | 1-1-4-9-1-1-3 | AaATTAtttatacacCaTCA | 586_14 | -21.59 | 11512 |
| 587 | AAAATTATTTATACACCATC | 2-3-1-7-1-1-5 | AAaatTatttataCaCCATC | 587_1 | -21.17 | 11513 |
| 587 | AAAATTATTTATACACCATC | 1-2-2-9-6 | AaaATtatttatacACCATC | 587_2 | -21.34 | 11513 |
| 587 | AAAATTATTTATACACCATC | 2-3-2-6-3-1-3 | AAaatTAtttataCACcATC | 587_3 | -20.67 | 11513 |
| 587 | AAAATTATTTATACACCATC | 3-1-1-1-1-7-3-1-2 | AAAaTtAtttatacACCaTC | 587_4 | -19.11 | 11513 |
| 587 | AAAATTATTTATACACCATC | 7-6-1-1-1-2-2 | AAAATTAtttataCaCcaTC | 587_5 | -20.66 | 11513 |
| 587 | AAAATTATTTATACACCATC | 1-1-1-1-2-8-2-1-3 | AaAaTTatttatacACcATC | 587_6 | -18.20 | 11513 |
| 587 | AAAATTATTTATACACCATC | 1-1-5-6-2-3-2 | AaAATTAtttataCAccaTC | 587_7 | -20.71 | 11513 |
| 587 | AAAATTATTTATACACCATC | 2-1-3-7-1-2-4 | AAaATTatttataCacCATC | 587_8 | -20.87 | 11513 |
| 587 | AAAATTATTTATACACCATC | 4-1-1-8-1-1-4 | AAAAtTatttatacAcCATC | 587_9 | -19.30 | 11513 |
| 587 | AAAATTATTTATACACCATC | 1-1-2-1-2-6-3-2-2 | AaAAtTAtttataCACcaTC | 587_10 | -20.13 | 11513 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 587 | AAAATTATTTATACACCATC | 1-2-3-7-1-1-2-1-2 | AaaATTatttataCaCCaTC | 587_11 | -20.44 | 11513 |
| 587 | AAAATTATTTATACACCATC | 3-1-2-7-1-2-4 | AAAaTTatttataCacCATC | 587_12 | -20.27 | 11513 |
| 587 | AAAATTATTTATACACCATC | 3-2-1-8-3-1-2 | AAAatTatttatacACCaTC | 587_13 | -19.30 | 11513 |
| 587 | AAAATTATTTATACACCATC | 2-1-3-8-2-1-3 | AAaATTatttatacACcATC | 587_14 | -19.52 | 11513 |
| 588 | TAAAATTATTTATACACCAT | 2-3-1-7-1-1-5 | TAaaaTtatttatAcACCAT | 588_1 | -20.14 | 11514 |
| 588 | TAAAATTATTTATACACCAT | 1-2-1-2-1-6-2-1-4 | TaaAatTatttatACaCCAT | 588_2 | -20.15 | 11514 |
| 588 | TAAAATTATTTATACACCAT | 1-1-1-1-2-8-1-1-4 | TaAaATtatttataCaCCAT | 588_3 | -20.40 | 11514 |
| 588 | TAAAATTATTTATACACCAT | 4-1-2-6-4-1-2 | TAAAaTTatttatACACcAT | 588_4 | -21.36 | 11514 |
| 588 | TAAAATTATTTATACACCAT | 1-3-3-6-3-1-3 | TaaaATTatttatACAcCAT | 588_5 | -21.07 | 11514 |
| 588 | TAAAATTATTTATACACCAT | 2-1-4-7-3-1-2 | TAaAATTatttataCACcAT | 588_6 | -21.36 | 11514 |
| 588 | TAAAATTATTTATACACCAT | 3-1-1-1-1-7-2-1-3 | TAAaAtTatttataCAcCAT | 588_7 | -20.41 | 11514 |
| 588 | TAAAATTATTTATACACCAT | 7-6-1-3-3 | TAAAATTatttatAcacCAT | 588_8 | -20.85 | 11514 |
| 588 | TAAAATTATTTATACACCAT | 2-1-2-11-4 | TAaAAttatttatacaCCAT | 588_9 | -19.82 | 11514 |
| 588 | TAAAATTATTTATACACCAT | 2-2-3-6-4-1-2 | TAaaATTatttatACACcAT | 588_10 | -21.41 | 11514 |
| 588 | TAAAATTATTTATACACCAT | 1-1-1-1-3-6-1-2-4 | TaAaATTatttatAcaCCAT | 588_11 | -21.15 | 11514 |
| 588 | TAAAATTATTTATACACCAT | 2-1-2-1-1-7-2-1-3 | TAaAAtTatttataCAcCAT | 588_12 | -20.41 | 11514 |
| 588 | TAAAATTATTTATACACCAT | 3-2-2-7-1-1-4 | TAAaaTTatttataCaCCAT | 588_13 | -21.86 | 11514 |
| 588 | TAAAATTATTTATACACCAT | 1-1-2-1-1-9-5 | TaAAaTtatttatacACCAT | 588_14 | -19.68 | 11514 |
| 589 | TAAAATTATTTATACACCA | 1-1-2-1-1-7-6 | TaAAaTtatttatACACCA | 589_1 | -20.31 | 11515 |
| 589 | TAAAATTATTTATACACCA | 1-2-3-6-1-1-5 | TaaAATtatttaTaCACCA | 589_2 | -21.36 | 11515 |
| 589 | TAAAATTATTTATACACCA | 2-3-1-7-6 | TAaaaTtatttatACACCA | 589_3 | -20.58 | 11515 |
| 589 | TAAAATTATTTATACACCA | 3-1-2-6-4-1-2 | TAAaATtatttaTACAcCA | 589_4 | -21.36 | 11515 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 589 | TAAAATTATTTATACACCA | 4-1-1-6-2-2-3 | TAAAaTtatttaTAcaCCA | 589_5 | -20.51 | 11515 |
| 589 | TAAAATTATTTATACACCA | 2-1-2-7-1-1-1-1-3 | TAaAAttatttaTaCaCCA | 589_6 | -19.30 | 11515 |
| 589 | TAAAATTATTTATACACCA | 1-3-2-6-2-2-3 | TaaaATtatttaTAcaCCA | 589_7 | -19.40 | 11515 |
| 589 | TAAAATTATTTATACACCA | 5-8-2-1-3 | TAAAAttatttatACaCCA | 589_8 | -19.77 | 11515 |
| 589 | TAAAATTATTTATACACCA | 3-1-2-9-4 | TAAaATtatttatacACCA | 589_9 | -19.55 | 11515 |
| 589 | TAAAATTATTTATACACCA | 2-1-3-6-4-1-2 | TAaAATtatttaTACAcCA | 589_10 | -21.36 | 11515 |
| 589 | TAAAATTATTTATACACCA | 3-1-2-6-3-1-3 | TAAaATtatttaTACaCCA | 589_11 | -22.18 | 11515 |
| 589 | TAAAATTATTTATACACCA | 1-1-3-7-2-1-4 | TaAAAttatttaTAcACCA | 589_12 | -19.78 | 11515 |
| 589 | TAAAATTATTTATACACCA | 2-2-1-7-1-1-1-1-3 | TAaaAttatttaTaCaCCA | 589_13 | -18.76 | 11515 |
| 589 | TAAAATTATTTATACACCA | 4-1-1-8-5 | TAAAaTtatttataCACCA | 589_14 | -21.06 | 11515 |
| 590 | ATATTGATTCAATTCCC | 2-9-2-1-3 | ATattgattcaATtCCC | 590_1 | -21.84 | 13226 |
| 590 | ATATTGATTCAATTCCC | 1-2-1-7-6 | AtaTtgattcaATTCCC | 590_2 | -22.10 | 13226 |
| 590 | ATATTGATTCAATTCCC | 2-9-1-1-1-1-2 | ATattgattcaAtTcCC | 590_3 | -18.59 | 13226 |
| 590 | ATATTGATTCAATTCCC | 1-1-2-8-5 | AtATtgattcaaTTCCC | 590_4 | -21.87 | 13226 |
| 590 | ATATTGATTCAATTCCC | 1-2-2-7-2-1-2 | AtaTTgattcaaTTcCC | 590_5 | -19.29 | 13226 |
| 590 | ATATTGATTCAATTCCC | 1-3-1-6-2-2-2 | AtatTgattcaATtcCC | 590_6 | -18.59 | 13226 |
| 590 | ATATTGATTCAATTCCC | 1-2-2-6-1-2-3 | AtaTTgattcaAttCCC | 590_7 | -20.66 | 13226 |
| 590 | ATATTGATTCAATTCCC | 1-1-1-1-1-7-1-1-3 | AtAtTgattcaaTtCCC | 590_8 | -19.92 | 13226 |
| 590 | ATATTGATTCAATTCCC | 1-1-1-8-1-2-3 | AtAttgattcaAttCCC | 590_9 | -19.01 | 13226 |
| 590 | ATATTGATTCAATTCCC | 4-7-1-3-2 | ATATtgattcaAttcCC | 590_10 | -20.60 | 13226 |
| 590 | ATATTGATTCAATTCCC | 3-1-1-7-1-2-2 | ATAtTgattcaaTtcCC | 590_11 | -20.26 | 13226 |
| 590 | ATATTGATTCAATTCCC | 1-3-1-8-4 | AtatTgattcaatTCCC | 590_12 | -20.37 | 13226 |
| 590 | ATATTGATTCAATTCCC | 2-1-1-10-3 | ATaTtgattcaattCCC | 590_13 | -20.71 | 13226 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 590 | ATATTGATTCAATTCCC | 2-2-1-9-3 | ATatTgattcaattCCC | 590_14 | -21.06 | 13226 |
| 590 | ATATTGATTCAATTCCC | 1-1-3-10-2 | AtATTgattcaattcCC | 590_15 | -18.87 | 13226 |
| 590 | ATATTGATTCAATTCCC | 2-2-1-6-2-2-2 | ATatTgattcaATtcCC | 590_16 | -20.26 | 13226 |
| 590 | ATATTGATTCAATTCCC | 3-8-1-1-4 | ATAttgattcaAtTCCC | 590_17 | -22.71 | 13226 |
| 590 | ATATTGATTCAATTCCC | 1-1-3-6-1-2-3 | AtATTgattcaAttCCC | 590_18 | -21.57 | 13226 |
| 590 | ATATTGATTCAATTCCC | 1-1-1-1-1-7-5 | AtAtTgattcaaTTCCC | 590_19 | -21.42 | 13226 |
| 590 | ATATTGATTCAATTCCC | 2-1-1-8-1-1-3 | ATaTtgattcaaTtCCC | 590_20 | -21.15 | 13226 |
| 591 | GCACATTCTTTCTATACCT | 1-1-1-1-1-12-2 | GcAcAttctttctatacCT | 591_1 | -21.27 | 15113 |
| 591 | GCACATTCTTTCTATACCT | 1-3-1-12-2 | GcacAttctttctatacCT | 591_2 | -21.12 | 15113 |
| 592 | GCACATTCTTTCTATACC | 1-12-1-2-2 | GcacattctttctAtaCC | 592_1 | -20.07 | 15114 |
| 592 | GCACATTCTTTCTATACC | 1-1-1-1-1-11-2 | GcAcAttctttctataCC | 592_2 | -20.17 | 15114 |
| 592 | GCACATTCTTTCTATACC | 1-3-1-11-2 | GcacAttctttctataCC | 592_3 | -20.02 | 15114 |
| 592 | GCACATTCTTTCTATACC | 1-1-2-11-3 | GcACattctttctatACC | 592_4 | -21.80 | 15114 |
| 592 | GCACATTCTTTCTATACC | 1-1-1-1-2-7-1-1-3 | GcAcATtctttctAtACC | 592_5 | -22.11 | 15114 |
| 592 | GCACATTCTTTCTATACC | 1-1-1-1-2-7-1-2-2 | GcAcATtctttctAtaCC | 592_6 | -21.51 | 15114 |
| 592 | GCACATTCTTTCTATACC | 1-15-2 | GcacattctttctataCC | 592_7 | -19.97 | 15114 |
| 592 | GCACATTCTTTCTATACC | 1-4-1-9-3 | GcacaTtctttctatACC | 592_8 | -21.01 | 15114 |
| 592 | GCACATTCTTTCTATACC | 1-4-1-10-2 | GcacaTtctttctataCC | 592_9 | -20.41 | 15114 |
| 592 | GCACATTCTTTCTATACC | 2-11-1-2-2 | GCacattctttctAtaCC | 592_10 | -22.39 | 15114 |
| 592 | GCACATTCTTTCTATACC | 1-1-1-1-1-8-1-2-2 | GcAcAttctttctAtaCC | 592_11 | -20.27 | 15114 |
| 592 | GCACATTCTTTCTATACC | 1-3-1-9-1-1-2 | GcacAttctttctaTaCC | 592_12 | -20.89 | 15114 |
| 592 | GCACATTCTTTCTATACC | 1-1-1-1-1-10-3 | GcAcAttctttctatACC | 592_13 | -20.77 | 15114 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 592 | GCACATTCTTTCTATACC | 1-1-1-2-1-10-2 | GcAcaTtctttctataCC | 592_14 | -20.56 | 15114 |
| 593 | TTATTTCCATTTATTTTCA | 1-1-1-1-1-8-3-1-2 | TtAtTtccatttaTTTtCA | 593_1 | -19.10 | 15563 |
| 593 | TTATTTCCATTTATTTTCA | 1-2-2-7-1-1-1-1-3 | TtaTTtccatttAtTtTCA | 593_2 | -19.27 | 15563 |
| 593 | TTATTTCCATTTATTTTCA | 2-2-1-8-1-1-1-1-2 | TTatTtccatttaTtTtCA | 593_3 | -18.92 | 15563 |
| 593 | TTATTTCCATTTATTTTCA | 1-1-2-9-1-2-3 | TtATttccatttaTttTCA | 593_4 | -19.41 | 15563 |
| 594 | TTTATTTCCATTTATTTTCA | 1-1-1-11-1-2-3 | TtTatttccatttaTttTCA | 594_1 | -19.80 | 15563 |
| 594 | TTTATTTCCATTTATTTTCA | 1-4-1-7-1-1-1-2-2 | TttatTtccatttAtTttCA | 594_2 | -18.34 | 15563 |
| 594 | TTTATTTCCATTTATTTTCA | 1-3-2-9-2-1-2 | TttaTTtccatttatTTtCA | 594_3 | -20.01 | 15563 |
| 594 | TTTATTTCCATTTATTTTCA | 2-1-1-1-1-8-1-1-1-1-2 | TTtAtTtccatttaTtTtCA | 594_4 | -19.60 | 15563 |
| 595 | ATTTATTTCCATTTATTTTC | 1-1-1-2-1-8-3-1-2 | AtTtaTttccatttATTtTC | 595_1 | -19.05 | 15564 |
| 595 | ATTTATTTCCATTTATTTTC | 1-3-2-7-1-3-3 | AtttATttccattTattTTC | 595_2 | -19.03 | 15564 |
| 595 | ATTTATTTCCATTTATTTTC | 1-1-2-10-1-2-3 | AtTTatttccatttAttTTC | 595_3 | -18.60 | 15564 |
| 595 | ATTTATTTCCATTTATTTTC | 2-1-1-1-1-8-1-1-1-1-2 | ATtTaTttccatttAtTtTC | 595_4 | -18.96 | 15564 |
| 596 | TTTATTTCCATTTATTTTC | 1-1-1-1-1-8-2-1-3 | TtTaTttccatttATtTTC | 596_1 | -18.66 | 15564 |
| 596 | TTTATTTCCATTTATTTTC | 3-2-1-7-3-1-2 | TTTatTtccatttATTtTC | 596_2 | -19.84 | 15564 |
| 596 | TTTATTTCCATTTATTTTC | 2-2-2-7-1-1-4 | TTtaTTtccatttAtTTTC | 596_3 | -19.12 | 15564 |
| 596 | TTTATTTCCATTTATTTTC | 5-7-1-3-3 | TTTATttccattTattTTC | 596_4 | -21.30 | 15564 |
| 597 | CCATTTATTTCCATTTATTT | 1-1-1-11-2-2-2 | CcAtttatttccatTTatTT | 597_1 | -19.89 | 15566 |
| 597 | CCATTTATTTCCATTTATTT | 1-3-1-9-1-1-1-1-2 | CcatTtatttccatTtAtTT | 597_2 | -19.00 | 15566 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 597 | CCATTTATTTCCATTTATTT | 1-1-1-2-1-8-1-2-3 | CcAttTatttccatTtaTTT | 597_3 | -20.33 | 15566 |
| 597 | CCATTTATTTCCATTTATTT | 1-2-2-1-1-11-2 | CcaTTtAtttccatttatTT | 597_4 | -19.64 | 15566 |
| 598 | TCCATTTATTTCCATTTATT | 2-11-2-3-2 | TCcatttatttccATttaTT | 598_1 | -21.22 | 15567 |
| 598 | TCCATTTATTTCCATTTATT | 2-2-1-8-1-1-1-2-2 | TCcaTttatttccAtTtaTT | 598_2 | -20.71 | 15567 |
| 598 | TCCATTTATTTCCATTTATT | 1-1-2-9-1-4-2 | TcCAtttatttccAtttaTT | 598_3 | -20.63 | 15567 |
| 598 | TCCATTTATTTCCATTTATT | 2-1-1-1-1-11-3 | TCcAtTtatttccatttATT | 598_4 | -21.18 | 15567 |
| 599 | TCCATTTATTTCCATTTAT | 2-11-2-2-2 | TCcatttatttccATttAT | 599_1 | -20.30 | 15568 |
| 599 | TCCATTTATTTCCATTTAT | 2-2-1-8-1-1-1-1-2 | TCcaTttatttccAtTtAT | 599_2 | -19.80 | 15568 |
| 599 | TCCATTTATTTCCATTTAT | 1-1-2-9-1-3-2 | TcCAtttatttccAtttAT | 599_3 | -19.72 | 15568 |
| 599 | TCCATTTATTTCCATTTAT | 1-1-1-1-2-7-1-3-2 | TcCaTTtatttccAtttAT | 599_4 | -19.50 | 15568 |
| 600 | TTCCATTTATTTCCATTTAT | 1-1-1-2-1-8-1-1-1-1-2 | TtCcaTttatttccAtTtAT | 600_1 | -20.12 | 15568 |
| 600 | TTCCATTTATTTCCATTTAT | 1-3-1-10-2-1-2 | TtccAtttatttccaTTtAT | 600_2 | -19.86 | 15568 |
| 600 | TTCCATTTATTTCCATTTAT | 1-1-1-3-1-7-1-3-2 | TtCcatTtatttccAtttAT | 600_3 | -19.68 | 15568 |
| 600 | TTCCATTTATTTCCATTTAT | 1-1-1-1-2-8-1-3-2 | TtCcATttatttccAtttAT | 600_4 | -20.68 | 15568 |
| 601 | TTTCCATTTATTTCCATTTA | 1-4-1-7-1-2-1-1-2 | TttccAtttatttCcaTtTA | 601_1 | -20.53 | 15569 |
| 601 | TTTCCATTTATTTCCATTTA | 2-2-1-12-3 | TTtcCatttatttccatTTA | 601_2 | -21.47 | 15569 |
| 601 | TTTCCATTTATTTCCATTTA | 1-2-1-2-1-8-1-2-2 | TttCcaTttatttccAttTA | 601_3 | -20.53 | 15569 |
| 601 | TTTCCATTTATTTCCATTTA | 1-4-1-9-1-2-2 | TttccAtttatttccAttTA | 601_4 | -19.37 | 15569 |
| 602 | CTTTCCATTTATTTCCATT | 1-11-1-1-1-1-3 | CtttccatttatTtCcATT | 602_1 | -21.20 | 15571 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 602 | CTTTCCATTTATTTCCATT | 2-2-1-9-1-2-2 | CTttCcatttatttCcaTT | 602_2 | -22.00 | 15571 |
| 602 | CTTTCCATTTATTTCCATT | 1-4-1-9-1-1-2 | CtttcCatttatttcCaTT | 602_3 | -20.42 | 15571 |
| 602 | CTTTCCATTTATTTCCATT | 1-3-1-11-3 | CtttCcatttatttccATT | 602_4 | -20.89 | 15571 |
| 603 | ATCTTTCCATTTATTTCCAT | 1-2-1-12-1-1-2 | AtcTttccatttatttCcAT | 603_1 | -21.24 | 15572 |
| 603 | ATCTTTCCATTTATTTCCAT | 1-3-1-1-1-7-1-3-2 | AtctTtCcatttatTtccAT | 603_2 | -21.33 | 15572 |
| 603 | ATCTTTCCATTTATTTCCAT | 1-5-1-6-1-4-2 | AtctttCcatttaTttccAT | 603_3 | -21.16 | 15572 |
| 603 | ATCTTTCCATTTATTTCCAT | 1-16-3 | AtctttccatttatttcCAT | 603_4 | -21.95 | 15572 |
| 604 | TCTTTCCATTTATTTCCAT | 2-13-1-1-2 | TCtttccatttatttCcAT | 604_1 | -21.57 | 15572 |
| 604 | TCTTTCCATTTATTTCCAT | 1-2-1-1-1-7-1-1-1-1-2 | TctTtCcatttatTtCcAT | 604_2 | -21.35 | 15572 |
| 604 | TCTTTCCATTTATTTCCAT | 2-14-3 | TCtttccatttatttcCAT | 604_3 | -22.80 | 15572 |
| 604 | TCTTTCCATTTATTTCCAT | 2-3-1-11-2 | TCtttCcatttatttccAT | 604_4 | -21.57 | 15572 |
| 605 | ATCTTTCCATTTATTTCCA | 1-2-1-10-1-2-2 | AtcTttccatttatTtcCA | 605_1 | -20.70 | 15573 |
| 605 | ATCTTTCCATTTATTTCCA | 1-3-1-8-1-3-2 | AtctTccatttaTttcCA | 605_2 | -20.63 | 15573 |
| 605 | ATCTTTCCATTTATTTCCA | 1-1-1-14-2 | AtCtttccatttatttcCA | 605_3 | -20.86 | 15573 |
| 605 | ATCTTTCCATTTATTTCCA | 1-4-1-9-1-1-2 | AtcttTccatttattTcCA | 605_4 | -20.63 | 15573 |
| 606 | TATCTTTCCATTTATTTCCA | 1-4-1-8-2-2-2 | TatctTtccatttaTTtcCA | 606_1 | -22.54 | 15573 |
| 606 | TATCTTTCCATTTATTTCCA | 2-16-2 | TAtctttccatttatttcCA | 606_2 | -22.12 | 15573 |
| 606 | TATCTTTCCATTTATTTCCA | 1-2-1-14-2 | TatCtttccatttatttcCA | 606_3 | -21.97 | 15573 |
| 606 | TATCTTTCCATTTATTTCCA | 1-17-2 | TatctttccatttatttcCA | 606_4 | -20.99 | 15573 |
| 607 | TATCTTTCCATTTATTTCC | 2-12-1-2-2 | TAtctttccatttaTttCC | 607_1 | -21.63 | 15574 |
| 607 | TATCTTTCCATTTATTTCC | 1-2-1-13-2 | TatCtttccatttatttCC | 607_2 | -21.04 | 15574 |
| 607 | TATCTTTCCATTTATTTCC | 1-2-2-12-2 | TatCTttccatttatttCC | 607_3 | -22.23 | 15574 |
| 607 | TATCTTTCCATTTATTTCC | 1-4-1-9-1-1-2 | TatctTtccatttatTtCC | 607_4 | -20.66 | 15574 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 608 | AAATCTCAACTACCATTTTT | 1-1-1-3-1-7-3-1-2 | AaAtctCaactaccATTtTT | 608_1 | -19.53 | 25248 |
| 608 | AAATCTCAACTACCATTTTT | 3-1-1-9-2-1-3 | AAAtCtcaactaccATtTTT | 608_2 | -20.58 | 25248 |
| 608 | AAATCTCAACTACCATTTTT | 1-3-1-8-1-1-5 | AaatCtcaactacCaTTTTT | 608_3 | -20.56 | 25248 |
| 608 | AAATCTCAACTACCATTTTT | 1-1-1-2-1-7-2-2-3 | AaAtcTcaactacCAttTTT | 608_4 | -20.20 | 25248 |
| 608 | AAATCTCAACTACCATTTTT | 1-3-1-1-1-6-1-1-1-2-2 | AaatCtCaactacCaTttTT | 608_5 | -19.10 | 25248 |
| 608 | AAATCTCAACTACCATTTTT | 2-3-2-6-1-2-4 | AAatcTCaactacCatTTTT | 608_6 | -21.04 | 25248 |
| 608 | AAATCTCAACTACCATTTTT | 2-1-2-1-1-7-1-3-2 | AAaTCtCaactaccAtttTT | 608_7 | -19.79 | 25248 |
| 608 | AAATCTCAACTACCATTTTT | 1-1-3-11-1-1-2 | AaATCtcaactaccatTtTT | 608_8 | -19.97 | 25248 |
| 608 | AAATCTCAACTACCATTTTT | 3-1-1-1-1-10-3 | AAAtCtCaactaccattTTT | 608_9 | -19.95 | 25248 |
| 609 | AAAATCTCAACTACCATTTT | 1-12-4-1-2 | AaaatctcaactaCCATtTT | 609_1 | -21.31 | 25249 |
| 609 | AAAATCTCAACTACCATTTT | 3-11-2-1-3 | AAAatctcaactacCAtTTT | 609_2 | -19.57 | 25249 |
| 609 | AAAATCTCAACTACCATTTT | 2-1-1-1-1-8-2-1-3 | AAaAtCtcaactacCAtTTT | 609_3 | -20.33 | 25249 |
| 609 | AAAATCTCAACTACCATTTT | 1-1-4-9-1-2-2 | AaAATCtcaactaccAttTT | 609_4 | -19.46 | 25249 |
| 609 | AAAATCTCAACTACCATTTT | 1-1-2-2-1-7-2-2-2 | AaAAtcTcaactacCAttTT | 609_5 | -19.13 | 25249 |
| 609 | AAAATCTCAACTACCATTTT | 4-1-1-7-1-2-4 | AAAAtCtcaactaCcaTTTT | 609_6 | -20.75 | 25249 |
| 609 | AAAATCTCAACTACCATTTT | 1-1-1-2-1-8-1-1-4 | AaAatCtcaactacCaTTTT | 609_7 | -19.30 | 25249 |
| 609 | AAAATCTCAACTACCATTTT | 1-2-3-7-1-1-1-1-3 | AaaATCtcaactaCcAtTTT | 609_8 | -20.51 | 25249 |
| 609 | AAAATCTCAACTACCATTTT | 2-2-2-10-1-1-2 | AAaaTCtcaactaccaTtTT | 609_9 | -18.72 | 25249 |
| 610 | AAAATCTCAACTACCATTT | 1-4-1-6-4-1-2 | AaaatCtcaactACCAtTT | 610_1 | -20.63 | 25250 |
| 610 | AAAATCTCAACTACCATTT | 3-10-6 | AAAatctcaactaCCATTT | 610_2 | -21.90 | 25250 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 610 | AAAATCTCAACTACCATTT | 6-6-2-2-3 | AAAATCtcaactACcaTTT | 610_3 | -21.46 | 25250 |
| 610 | AAAATCTCAACTACCATTT | 2-2-2-7-2-1-3 | AAaaTCtcaactaCCaTTT | 610_4 | -21.18 | 25250 |
| 610 | AAAATCTCAACTACCATTT | 6-7-2-2-2 | AAAATCtcaactaCCatTT | 610_5 | -22.10 | 25250 |
| 610 | AAAATCTCAACTACCATTT | 2-1-1-1-1-8-5 | AAaAtCtcaactacCATTT | 610_6 | -20.27 | 25250 |
| 610 | AAAATCTCAACTACCATTT | 1-1-1-1-2-8-5 | AaAaTCtcaactacCATTT | 610_7 | -20.88 | 25250 |
| 610 | AAAATCTCAACTACCATTT | 1-1-2-1-1-8-2-1-2 | AaAAtCtcaactacCAtTT | 610_8 | -18.51 | 25250 |
| 610 | AAAATCTCAACTACCATTT | 6-9-4 | AAAATCtcaactaccATTT | 610_9 | -20.94 | 25250 |
| 611 | GAAAATCTCAACTACCATT | 1-1-3-7-1-2-4 | GaAAAtctcaacTacCATT | 611_1 | -20.48 | 25251 |
| 611 | GAAAATCTCAACTACCATT | 1-1-2-8-1-1-1-1-3 | GaAAatctcaacTaCcATT | 611_2 | -18.75 | 25251 |
| 611 | GAAAATCTCAACTACCATT | 3-1-1-10-4 | GAAaAtctcaactacCATT | 611_3 | -20.73 | 25251 |
| 611 | GAAAATCTCAACTACCATT | 2-1-2-10-4 | GAaAAtctcaactacCATT | 611_4 | -20.73 | 25251 |
| 611 | GAAAATCTCAACTACCATT | 2-2-1-7-1-4-2 | GAaaAtctcaacTaccaTT | 611_5 | -18.28 | 25251 |
| 611 | GAAAATCTCAACTACCATT | 2-12-5 | GAaaatctcaactaCCATT | 611_6 | -22.25 | 25251 |
| 611 | GAAAATCTCAACTACCATT | 4-10-2-1-2 | GAAAatctcaactaCCaTT | 611_7 | -21.06 | 25251 |
| 611 | GAAAATCTCAACTACCATT | 4-10-1-1-3 | GAAAatctcaactaCcATT | 611_8 | -19.73 | 25251 |
| 611 | GAAAATCTCAACTACCATT | 5-12-2 | GAAAAtctcaactaccaTT | 611_9 | -18.61 | 25251 |
| 612 | TGAAAATCTCAACTACCAT | 1-4-1-6-1-1-2-1-2 | TgaaaAtctcaaCtACcAT | 612_1 | -18.43 | 25252 |
| 612 | TGAAAATCTCAACTACCAT | 2-1-2-7-1-2-1-1-2 | TGaAAatctcaaCtaCcAT | 612_2 | -19.46 | 25252 |
| 612 | TGAAAATCTCAACTACCAT | 1-1-2-8-1-2-1-1-2 | TgAAaatctcaaCtaCcAT | 612_3 | -18.58 | 25252 |
| 612 | TGAAAATCTCAACTACCAT | 1-2-1-1-1-6-1-3-3 | TgaAaAtctcaaCtacCAT | 612_4 | -19.40 | 25252 |
| 612 | TGAAAATCTCAACTACCAT | 1-3-2-10-3 | TgaaAAtctcaactacCAT | 612_5 | -18.60 | 25252 |
| 612 | TGAAAATCTCAACTACCAT | 1-11-1-2-4 | TgaaaatctcaaCtaCCAT | 612_6 | -21.11 | 25252 |
| 612 | TGAAAATCTCAACTACCAT | 3-1-2-6-1-4-2 | TGAaAAtctcaaCtaccAT | 612_7 | -20.39 | 25252 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 612 | TGAAAATCTCAACTACCAT | 1-1-1-1-1-7-1-3-3 | TgAaAatctcaaCtacCAT | 612_8 | -19.60 | 25252 |
| 612 | TGAAAATCTCAACTACCAT | 4-12-3 | TGAAaatctcaactacCAT | 612_9 | -21.07 | 25252 |
| 613 | ATCATTCTCAACAATTAAA | 4-8-7 | ATCAttctcaacAATTAAA | 613_1 | -20.89 | 30599 |
| 613 | ATCATTCTCAACAATTAAA | 1-1-4-6-7 | AtCATTctcaacAATTAAA | 613_2 | -21.09 | 30599 |
| 613 | ATCATTCTCAACAATTAAA | 5-7-2-1-1-1-2 | ATCATtctcaacAAtTaAA | 613_3 | -19.03 | 30599 |
| 613 | ATCATTCTCAACAATTAAA | 5-8-2-2-2 | ATCATtctcaacaATtaAA | 613_4 | -19.28 | 30599 |
| 613 | ATCATTCTCAACAATTAAA | 4-1-1-8-5 | ATCAtTctcaacaaTTAAA | 613_5 | -19.86 | 30599 |
| 613 | ATCATTCTCAACAATTAAA | 5-7-4-1-2 | ATCATtctcaacAATTaAA | 613_6 | -20.79 | 30599 |
| 613 | ATCATTCTCAACAATTAAA | 4-8-1-1-5 | ATCAttctcaacAaTTAAA | 613_7 | -19.56 | 30599 |
| 613 | ATCATTCTCAACAATTAAA | 1-1-4-6-1-1-5 | AtCATTctcaacAaTTAAA | 613_8 | -19.76 | 30599 |
| 613 | ATCATTCTCAACAATTAAA | 4-1-1-7-3-1-2 | ATCAtTctcaacaATTaAA | 613_9 | -19.64 | 30599 |
| 613 | ATCATTCTCAACAATTAAA | 5-8-1-1-4 | ATCATtctcaacaAtTAAA | 613_10 | -20.11 | 30599 |
| 614 | ATCATTCTCAACAATTAA | 4-8-6 | ATCAttctcaacAATTAA | 614_1 | -20.14 | 30600 |
| 614 | ATCATTCTCAACAATTAA | 1-1-4-6-6 | AtCATTctcaacAATTAA | 614_2 | -20.34 | 30600 |
| 614 | ATCATTCTCAACAATTAA | 5-8-1-1-3 | ATCATtctcaacaAtTAA | 614_3 | -19.36 | 30600 |
| 614 | ATCATTCTCAACAATTAA | 4-8-1-1-4 | ATCAttctcaacAaTTAA | 614_4 | -18.81 | 30600 |
| 614 | ATCATTCTCAACAATTAA | 5-8-5 | ATCATtctcaacaATTAA | 614_5 | -21.12 | 30600 |
| 614 | ATCATTCTCAACAATTAA | 5-7-1-2-3 | ATCATtctcaacAatTAA | 614_6 | -19.11 | 30600 |
| 614 | ATCATTCTCAACAATTAA | 3-10-5 | ATCattctcaacaATTAA | 614_7 | -18.40 | 30600 |
| 614 | ATCATTCTCAACAATTAA | 4-9-1-1-3 | ATCAttctcaacaAtTAA | 614_8 | -18.11 | 30600 |
| 614 | ATCATTCTCAACAATTAA | 4-1-1-8-4 | ATCAtTctcaacaaTTAA | 614_9 | -19.11 | 30600 |
| 614 | ATCATTCTCAACAATTAA | 1-1-3-9-4 | AtCATtctcaacaaTTAA | 614_10 | -18.05 | 30600 |
| 615 | GATCATTCTCAACAATTAA | 2-3-1-6-2-1-4 | GAtcaTtctcaaCAaTTAA | 615_1 | -20.54 | 30600 |
| 615 | GATCATTCTCAACAATTAA | 1-2-2-7-1-2-4 | GatCAttctcaaCaaTTAA | 615_2 | -19.04 | 30600 |
| 615 | GATCATTCTCAACAATTAA | 2-1-3-6-3-2-2 | GAtCATtctcaaCAAttAA | 615_3 | -21.29 | 30600 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 615 | GATCATTCTCAACAATTAA | 2-1-2-8-2-1-3 | GAtCAttctcaacAAtTAA | 615_4 | -19.70 | 30600 |
| 615 | GATCATTCTCAACAATTAA | 5-8-1-1-1-1-2 | GATCAttctcaacAaTtAA | 615_5 | -19.79 | 30600 |
| 615 | GATCATTCTCAACAATTAA | 4-8-3-2-2 | GATCattctcaaCAAttAA | 615_6 | -20.50 | 30600 |
| 615 | GATCATTCTCAACAATTAA | 1-2-3-6-2-2-3 | GatCATtctcaaCAatTAA | 615_7 | -20.82 | 30600 |
| 615 | GATCATTCTCAACAATTAA | 2-2-2-6-1-1-5 | GAtcATtctcaaCaATTAA | 615_8 | -21.04 | 30600 |
| 615 | GATCATTCTCAACAATTAA | 2-1-1-8-1-2-4 | GAtCattctcaaCaaTTAA | 615_9 | -19.28 | 30600 |
| 615 | GATCATTCTCAACAATTAA | 1-1-3-9-1-1-3 | GaTCAttctcaacaAtTAA | 615_10 | -18.85 | 30600 |
| 616 | AGATCATTCTCAACAATTA | 1-1-1-2-1-7-3-1-2 | AgAtcAttctcaaCAAtTA | 616_1 | -19.10 | 30601 |
| 616 | AGATCATTCTCAACAATTA | 1-3-1-8-2-1-3 | AgatCattctcaaCAaTTA | 616_2 | -19.65 | 30601 |
| 616 | AGATCATTCTCAACAATTA | 1-3-2-6-1-1-1-2-2 | AgatCAttctcaAcAatTA | 616_3 | -18.49 | 30601 |
| 616 | AGATCATTCTCAACAATTA | 1-1-1-1-2-11-2 | AgAtCAttctcaacaatTA | 616_4 | -18.49 | 30601 |
| 616 | AGATCATTCTCAACAATTA | 1-1-1-2-1-9-4 | AgAtcAttctcaacaATTA | 616_5 | -18.49 | 30601 |
| 616 | AGATCATTCTCAACAATTA | 1-3-2-6-1-1-5 | AgatCAttctcaAcAATTA | 616_6 | -20.76 | 30601 |
| 616 | AGATCATTCTCAACAATTA | 2-2-1-8-3-1-2 | AGatCattctcaaCAAtTA | 616_7 | -20.47 | 30601 |
| 616 | AGATCATTCTCAACAATTA | 3-2-1-7-1-2-3 | AGAtcAttctcaaCaaTTA | 616_8 | -20.51 | 30601 |
| 616 | AGATCATTCTCAACAATTA | 1-2-3-7-1-3-2 | AgaTCAttctcaaCaatTA | 616_9 | -19.80 | 30601 |
| 616 | AGATCATTCTCAACAATTA | 1-1-1-1-2-8-2-1-2 | AgAtCAttctcaacAAtTA | 616_10 | -19.08 | 30601 |
| 617 | GATCATTCTCAACAATTA | 2-3-1-6-6 | GAtcaTtctcaaCAATTA | 617_1 | -21.11 | 30601 |
| 617 | GATCATTCTCAACAATTA | 2-1-2-8-5 | GAtCAttctcaacAATTA | 617_2 | -20.71 | 30601 |
| 617 | GATCATTCTCAACAATTA | 2-2-2-6-2-2-2 | GAtcATtctcaaCAatTA | 617_3 | -19.70 | 30601 |
| 617 | GATCATTCTCAACAATTA | 1-1-3-7-1-1-1-1-2 | GaTCAttctcaaCaAtTA | 617_4 | -18.78 | 30601 |
| 617 | GATCATTCTCAACAATTA | 2-1-2-10-3 | GAtCAttctcaacaaTTA | 617_5 | -19.31 | 30601 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 617 | GATCATTCTCAACAATTA | 2-1-1-1-1-6-3-1-2 | GAtCaTtctcaaCAAtTA | 617_6 | -20.02 | 30601 |
| 617 | GATCATTCTCAACAATTA | 2-1-2-7-2-2-2 | GAtCAttctcaaCAatTA | 617_7 | -20.53 | 30601 |
| 617 | GATCATTCTCAACAATTA | 2-1-3-6-1-2-3 | GAtCATtctcaaCaaTTA | 617_8 | -21.24 | 30601 |
| 617 | GATCATTCTCAACAATTA | 2-2-1-8-5 | GAtcAttctcaacAATTA | 617_9 | -18.63 | 30601 |
| 617 | GATCATTCTCAACAATTA | 1-1-3-9-1-1-2 | GaTCAttctcaacaAtTA | 617_10 | -18.10 | 30601 |
| 618 | AGATCATTCTCAACAATT | 1-3-2-6-6 | AgatCAttctcaACAATT | 618_1 | -21.03 | 30602 |
| 618 | AGATCATTCTCAACAATT | 1-1-1-1-2-7-5 | AgAtCAttctcaaCAATT | 618_2 | -20.70 | 30602 |
| 618 | AGATCATTCTCAACAATT | 1-1-4-6-1-3-2 | AgATCAttctcaAcaaTT | 618_3 | -19.56 | 30602 |
| 618 | AGATCATTCTCAACAATT | 3-1-1-9-4 | AGAtCattctcaacAATT | 618_4 | -19.61 | 30602 |
| 618 | AGATCATTCTCAACAATT | 2-1-3-10-2 | AGaTCAttctcaacaaTT | 618_5 | -19.09 | 30602 |
| 618 | AGATCATTCTCAACAATT | 1-2-3-6-1-3-2 | AgaTCAttctcaAcaaTT | 618_6 | -18.25 | 30602 |
| 618 | AGATCATTCTCAACAATT | 2-2-2-7-2-1-2 | AGatCAttctcaaCAaTT | 618_7 | -20.14 | 30602 |
| 618 | AGATCATTCTCAACAATT | 1-1-1-1-2-7-1-1-3 | AgAtCAttctcaaCaATT | 618_8 | -19.02 | 30602 |
| 618 | AGATCATTCTCAACAATT | 1-2-3-8-4 | AgaTCAttctcaacAATT | 618_9 | -19.23 | 30602 |
| 618 | AGATCATTCTCAACAATT | 3-1-1-10-3 | AGAtCattctcaacaATT | 618_10 | -19.34 | 30602 |
| 619 | GATCATTCTCAACAATT | 2-1-2-6-6 | GAtCAttctcaACAATT | 619_1 | -21.40 | 30602 |
| 619 | GATCATTCTCAACAATT | 1-1-3-7-5 | GaTCAttctcaaCAATT | 619_2 | -19.99 | 30602 |
| 619 | GATCATTCTCAACAATT | 5-7-1-2-2 | GATCAttctcaaCaaTT | 619_3 | -19.69 | 30602 |
| 619 | GATCATTCTCAACAATT | 5-6-1-1-4 | GATCAttctcaAcAATT | 619_4 | -20.83 | 30602 |
| 619 | GATCATTCTCAACAATT | 2-1-2-7-5 | GAtCAttctcaaCAATT | 619_5 | -20.57 | 30602 |
| 619 | GATCATTCTCAACAATT | 5-6-1-3-2 | GATCAttctcaAcaaTT | 619_6 | -19.43 | 30602 |
| 619 | GATCATTCTCAACAATT | 4-8-5 | GATCattctcaaCAATT | 619_7 | -21.04 | 30602 |
| 619 | GATCATTCTCAACAATT | 1-1-3-7-2-1-2 | GaTCAttctcaaCAaTT | 619_8 | -18.67 | 30602 |
| 619 | GATCATTCTCAACAATT | 5-7-1-1-3 | GATCAttctcaaCaATT | 619_9 | -20.82 | 30602 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 619 | GATCATTCTCAACAATT | 2-1-2-8-4 | GAtCAttctcaacAATT | 619_10 | -18.48 | 30602 |
| 620 | AAGATCATTCTCAACAAT | 4-1-1-6-1-1-4 | AAGAtCattctcAaCAAT | 620_1 | -20.71 | 30603 |
| 620 | AAGATCATTCTCAACAAT | 4-9-5 | AAGAtcattctcaACAAT | 620_2 | -20.79 | 30603 |
| 620 | AAGATCATTCTCAACAAT | 2-2-2-6-6 | AAgaTCattctcAACAAT | 620_3 | -19.88 | 30603 |
| 620 | AAGATCATTCTCAACAAT | 4-1-1-7-2-1-2 | AAGAtCattctcaACaAT | 620_4 | -19.77 | 30603 |
| 620 | AAGATCATTCTCAACAAT | 2-1-3-8-4 | AAgATCattctcaaCAAT | 620_5 | -20.10 | 30603 |
| 620 | AAGATCATTCTCAACAAT | 4-1-1-6-2-2-2 | AAGAtCattctcAAcaAT | 620_6 | -18.96 | 30603 |
| 620 | AAGATCATTCTCAACAAT | 3-1-2-6-1-1-4 | AAGaTCattctcAaCAAT | 620_7 | -20.12 | 30603 |
| 620 | AAGATCATTCTCAACAAT | 2-1-3-6-1-1-4 | AAgATCattctcAaCAAT | 620_8 | -20.17 | 30603 |
| 620 | AAGATCATTCTCAACAAT | 1-1-1-2-1-7-5 | AaGatCattctcaACAAT | 620_9 | -18.21 | 30603 |
| 620 | AAGATCATTCTCAACAAT | 4-1-1-8-4 | AAGAtCattctcaaCAAT | 620_10 | -20.63 | 30603 |
| 621 | AAAGATCATTCTCAACAA | 1-1-1-9-6 | AaAgatcattctCAACAA | 621_1 | -18.13 | 30604 |
| 621 | AAAGATCATTCTCAACAA | 1-1-3-7-2-1-3 | AaAGAtcattctCAaCAA | 621_2 | -20.08 | 30604 |
| 621 | AAAGATCATTCTCAACAA | 1-3-2-6-2-1-3 | AaagATcattctCAaCAA | 621_3 | -18.11 | 30604 |
| 621 | AAAGATCATTCTCAACAA | 1-2-2-7-1-1-4 | AaaGAtcattctCaACAA | 621_4 | -18.07 | 30604 |
| 621 | AAAGATCATTCTCAACAA | 5-10-3 | AAAGAtcattctcaaCAA | 621_5 | -18.65 | 30604 |
| 621 | AAAGATCATTCTCAACAA | 1-1-3-7-3-1-2 | AaAGAtcattctCAAcAA | 621_6 | -18.59 | 30604 |
| 621 | AAAGATCATTCTCAACAA | 4-8-2-1-3 | AAAGatcattctCAaCAA | 621_7 | -19.10 | 30604 |
| 621 | AAAGATCATTCTCAACAA | 3-1-1-7-2-1-3 | AAAgAtcattctCAaCAA | 621_8 | -18.35 | 30604 |
| 621 | AAAGATCATTCTCAACAA | 1-1-2-8-2-1-3 | AaAGatcattctCAaCAA | 621_9 | -18.37 | 30604 |
| 621 | AAAGATCATTCTCAACAA | 1-2-2-7-2-1-3 | AaaGAtcattctCAaCAA | 621_10 | -18.74 | 30604 |
| 621 | AAAGATCATTCTCAACAA | 5-7-1-2-3 | AAAGAtcattctCaaCAA | 621_11 | -19.32 | 30604 |
| 622 | CAAAGATCATTCTCAACA | 1-1-2-8-6 | CaAAgatcattcTCAACA | 622_1 | -20.93 | 30605 |
| 622 | CAAAGATCATTCTCAACA | 2-1-1-9-5 | CAaAgatcattctCAACA | 622_2 | -20.68 | 30605 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 622 | CAAAGATCATTCTCAACA | 1-4-1-7-5 | CaaagAtcattctCAACA | 622_3 | −18.86 | 30605 |
| 622 | CAAAGATCATTCTCAACA | 4-1-1-7-1-2-2 | CAAAgAtcattctCaaCA | 622_4 | −19.40 | 30605 |
| 622 | CAAAGATCATTCTCAACA | 3-1-2-10-2 | CAAaGAtcattctcaaCA | 622_5 | −19.67 | 30605 |
| 622 | CAAAGATCATTCTCAACA | 4-8-2-2-2 | CAAAgatcattcTCaaCA | 622_6 | −20.10 | 30605 |
| 622 | CAAAGATCATTCTCAACA | 1-1-2-1-1-7-5 | CaAAgAtcattctCAACA | 622_7 | −20.23 | 30605 |
| 622 | CAAAGATCATTCTCAACA | 2-1-1-9-2-1-2 | CAaAgatcattctCAaCA | 622_8 | −19.66 | 30605 |
| 622 | CAAAGATCATTCTCAACA | 3-2-1-7-1-1-3 | CAAagAtcattctCaACA | 622_9 | −19.21 | 30605 |
| 622 | CAAAGATCATTCTCAACA | 1-3-2-7-1-2-2 | CaaaGAtcattctCaaCA | 622_10 | −18.30 | 30605 |
| 623 | CAAAGATCATTCTCAAC | 3-8-6 | CAAagatcattCTCAAC | 623_1 | −19.95 | 30606 |
| 623 | CAAAGATCATTCTCAAC | 2-1-1-7-6 | CAaAgatcattCTCAAC | 623_2 | −20.23 | 30606 |
| 623 | CAAAGATCATTCTCAAC | 2-2-1-6-6 | CAaaGatcattCTCAAC | 623_3 | −20.15 | 30606 |
| 623 | CAAAGATCATTCTCAAC | 1-2-2-6-6 | CaaAGatcattCTCAAC | 623_4 | −20.00 | 30606 |
| 623 | CAAAGATCATTCTCAAC | 5-6-1-1-4 | CAAAGatcattCtCAAC | 623_5 | −20.35 | 30606 |
| 623 | CAAAGATCATTCTCAAC | 4-7-3-1-2 | CAAAgatcattCTCaAC | 623_6 | −19.28 | 30606 |
| 623 | CAAAGATCATTCTCAAC | 3-1-1-6-1-1-4 | CAAaGatcattCtCAAC | 623_7 | −18.81 | 30606 |
| 623 | CAAAGATCATTCTCAAC | 2-1-1-7-1-1-4 | CAaAgatcattCtCAAC | 623_8 | −18.36 | 30606 |
| 623 | CAAAGATCATTCTCAAC | 1-2-2-6-1-1-4 | CaaAGatcattCtCAAC | 623_9 | −18.12 | 30606 |
| 623 | CAAAGATCATTCTCAAC | 4-8-5 | CAAAgatcattcTCAAC | 623_10 | −19.31 | 30606 |
| 624 | CTCAAAGATCATTCTCA | 1-2-1-7-6 | CtcAaagatcaTTCTCA | 624_1 | −20.57 | 30608 |
| 624 | CTCAAAGATCATTCTCA | 1-1-1-1-1-7-2-1-2 | CtCaAagatcatTCtCA | 624_2 | −18.69 | 30608 |
| 624 | CTCAAAGATCATTCTCA | 1-1-2-7-1-2-3 | CtCAaagatcaTtcTCA | 624_3 | −19.51 | 30608 |
| 624 | CTCAAAGATCATTCTCA | 3-10-1-1-2 | CTCaaagatcattCtCA | 624_4 | −19.23 | 30608 |
| 624 | CTCAAAGATCATTCTCA | 1-1-3-8-4 | CtCAAagatcattCTCA | 624_5 | −21.26 | 30608 |
| 624 | CTCAAAGATCATTCTCA | 1-1-3-6-1-1-1-1-2 | CtCAAagatcaTtCtCA | 624_6 | −19.82 | 30608 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 624 | CTCAAAGATCATTCTCA | 4-7-1-3-2 | CTCAaagatcaTtctCA | 624_7 | -20.18 | 30608 |
| 624 | CTCAAAGATCATTCTCA | 1-2-2-7-5 | CtcAAagatcatTCTCA | 624_8 | -20.16 | 30608 |
| 624 | CTCAAAGATCATTCTCA | 1-1-2-8-2-1-2 | CtCAaagatcatTCtCA | 624_9 | -19.83 | 30608 |
| 624 | CTCAAAGATCATTCTCA | 3-10-4 | CTCaaagatcattCTCA | 624_10 | -21.11 | 30608 |
| 625 | TACACTTAATTATACTTCCA | 1-2-1-1-1-7-2-3-2 | TacAcTtaattatACttcCA | 625_1 | -20.33 | 30666 |
| 625 | TACACTTAATTATACTTCCA | 1-2-1-2-1-6-1-4-2 | TacActTaattatActtcCA | 625_2 | -19.15 | 30666 |
| 625 | TACACTTAATTATACTTCCA | 1-4-1-7-1-1-1-2-2 | TacacTtaattatAcTtcCA | 625_3 | -19.30 | 30666 |
| 625 | TACACTTAATTATACTTCCA | 1-1-1-2-2-6-1-4-2 | TaCacTTaattatActtcCA | 625_4 | -20.71 | 30666 |
| 625 | TACACTTAATTATACTTCCA | 1-1-1-3-1-8-1-2-2 | TaCactTaattatacTtcCA | 625_5 | -20.00 | 30666 |
| 625 | TACACTTAATTATACTTCCA | 1-2-1-1-2-8-1-2-2 | TacAcTTaattatacTtcCA | 625_6 | -20.50 | 30666 |
| 625 | TACACTTAATTATACTTCCA | 1-2-1-13-3 | TacActtaattatacttCCA | 625_7 | -20.60 | 30666 |
| 625 | TACACTTAATTATACTTCCA | 1-4-1-11-3 | TacacTtaattatacttCCA | 625_8 | -20.96 | 30666 |
| 625 | TACACTTAATTATACTTCCA | 2-1-1-1-1-12-2 | TAcAcTtaattatacttcCA | 625_9 | -19.97 | 30666 |
| 625 | TACACTTAATTATACTTCCA | 1-1-1-2-1-7-2-3-2 | TaCacTtaattatACttcCA | 625_10 | -20.87 | 30666 |
| 625 | TACACTTAATTATACTTCCA | 1-2-1-1-2-6-1-1-1-2-2 | TacAcTTaattatAcTtcCA | 625_11 | -20.69 | 30666 |
| 625 | TACACTTAATTATACTTCCA | 1-2-1-1-1-9-1-1-3 | TacAcTtaattatacTtCCA | 625_12 | -21.63 | 30666 |
| 625 | TACACTTAATTATACTTCCA | 1-1-1-3-1-10-3 | TaCactTaattatacttCCA | 625_13 | -21.86 | 30666 |
| 625 | TACACTTAATTATACTTCCA | 2-1-2-1-1-11-2 | TACACtTaattatacttcCA | 625_14 | -21.58 | 30666 |
| 626 | TTACACTTAATTATACTTCC | 1-3-1-1-1-7-2-2-2 | TtacAcTtaattatACttCC | 626_1 | -19.98 | 30667 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 626 | TTACACTTAATTATACTTCC | 1-5-1-7-1-1-1-1-2 | TtacacTtaattatAcTtCC | 626_2 | -18.96 | 30667 |
| 626 | TTACACTTAATTATACTTCC | 2-4-1-11-2 | TTacacTtaattatacttCC | 626_3 | -19.49 | 30667 |
| 626 | TTACACTTAATTATACTTCC | 1-5-1-9-4 | TtacacTtaattatacTTCC | 626_4 | -20.26 | 30667 |
| 626 | TTACACTTAATTATACTTCC | 1-1-1-3-1-8-1-2-2 | TtAcacTtaattataCttCC | 626_5 | -19.43 | 30667 |
| 626 | TTACACTTAATTATACTTCC | 1-1-2-2-1-7-1-3-2 | TtACacTtaattatActtCC | 626_6 | -19.72 | 30667 |
| 626 | TTACACTTAATTATACTTCC | 3-1-1-12-3 | TTAcActtaattatactTCC | 626_7 | -21.33 | 30667 |
| 626 | TTACACTTAATTATACTTCC | 1-1-1-1-1-1-1-9-1-1-2 | TtAcAcTtaattatacTtCC | 626_8 | -19.10 | 30667 |
| 626 | TTACACTTAATTATACTTCC | 1-2-2-1-1-11-2 | TtaCAcTtaattatacttCC | 626_9 | -20.49 | 30667 |
| 626 | TTACACTTAATTATACTTCC | 1-5-1-7-2-1-3 | TtacacTtaattatACtTCC | 626_10 | -20.82 | 30667 |
| 626 | TTACACTTAATTATACTTCC | 4-2-1-7-1-3-2 | TTACacTtaattatActtCC | 626_11 | -21.99 | 30667 |
| 626 | TTACACTTAATTATACTTCC | 1-1-1-1-3-8-1-2-2 | TtAcACTtaattataCttCC | 626_12 | -21.65 | 30667 |
| 626 | TTACACTTAATTATACTTCC | 2-1-2-11-4 | TTaCActtaattatacTTCC | 626_13 | -23.23 | 30667 |
| 626 | TTACACTTAATTATACTTCC | 2-2-1-1-1-9-1-1-2 | TTacAcTtaattatacTtCC | 626_14 | -20.15 | 30667 |
| 627 | TTTACACTTAATTATACTTC | 2-1-2-8-1-1-5 | TTtACacttaattAtACTTC | 627_1 | -20.02 | 30668 |
| 627 | TTTACACTTAATTATACTTC | 2-3-1-7-4-1-2 | TTtacActtaattATACtTC | 627_2 | -19.89 | 30668 |
| 627 | TTTACACTTAATTATACTTC | 1-2-1-1-1-7-2-1-4 | TttAcActtaattATaCTTC | 627_3 | -19.35 | 30668 |
| 627 | TTTACACTTAATTATACTTC | 1-1-3-8-3-2-2 | TtTACacttaattATActTC | 627_4 | -20.58 | 30668 |
| 627 | TTTACACTTAATTATACTTC | 3-2-1-7-3-1-3 | TTTacActtaattATAcTTC | 627_5 | -20.76 | 30668 |
| 627 | TTTACACTTAATTATACTTC | 1-3-2-7-2-2-3 | TttaCActtaattATacTTC | 627_6 | -19.58 | 30668 |
| 627 | TTTACACTTAATTATACTTC | 3-2-1-7-2-1-4 | TTTacActtaattATaCTTC | 627_7 | -21.21 | 30668 |
| 627 | TTTACACTTAATTATACTTC | 3-1-1-8-1-2-4 | TTTaCacttaattAtaCTTC | 627_8 | -20.07 | 30668 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 627 | TTTACACTTAATTATACTTC | 6-7-1-4-2 | TTTACActtaattAtactTC | 627_9 | -20.56 | 30668 |
| 627 | TTTACACTTAATTATACTTC | 4-1-1-7-4-1-2 | TTTAcActtaattATACtTC | 627_10 | -22.36 | 30668 |
| 627 | TTTACACTTAATTATACTTC | 3-1-1-1-1-6-3-1-3 | TTTaCaCttaattATAcTTC | 627_11 | -22.29 | 30668 |
| 627 | TTTACACTTAATTATACTTC | 2-1-3-7-3-2-2 | TTtACActtaattATActTC | 627_12 | -21.19 | 30668 |
| 627 | TTTACACTTAATTATACTTC | 3-1-2-7-2-1-4 | TTTaCActtaattATaCTTC | 627_13 | -23.30 | 30668 |
| 627 | TTTACACTTAATTATACTTC | 1-1-4-7-1-2-4 | TtTACActtaattAtaCTTC | 627_14 | -21.94 | 30668 |
| 628 | ATTTACACTTAATTATACTT | 2-1-1-2-1-6-3-1-3 | ATtTacActtaatTATaCTT | 628_1 | -21.21 | 30669 |
| 628 | ATTTACACTTAATTATACTT | 3-1-1-8-2-1-4 | ATTtAcacttaatTAtACTT | 628_2 | -20.27 | 30669 |
| 628 | ATTTACACTTAATTATACTT | 1-1-2-2-1-6-4-1-2 | AtTTacActtaatTATAcTT | 628_3 | -20.33 | 30669 |
| 628 | ATTTACACTTAATTATACTT | 1-3-1-1-1-7-6 | AtttAcActtaattATACTT | 628_4 | -19.30 | 30669 |
| 628 | ATTTACACTTAATTATACTT | 2-2-2-7-3-2-2 | ATttACacttaatTATacTT | 628_5 | -19.94 | 30669 |
| 628 | ATTTACACTTAATTATACTT | 4-1-2-6-2-3-2 | ATTTaCActtaatTAtacTT | 628_6 | -21.29 | 30669 |
| 628 | ATTTACACTTAATTATACTT | 1-1-4-7-1-1-1-2-2 | AtTTACacttaatTaTacTT | 628_7 | -19.33 | 30669 |
| 628 | ATTTACACTTAATTATACTT | 2-2-3-6-1-2-4 | ATttACActtaatTatACTT | 628_8 | -20.97 | 30669 |
| 628 | ATTTACACTTAATTATACTT | 4-2-1-6-1-3-3 | ATTTacActtaatTataCTT | 628_9 | -19.73 | 30669 |
| 628 | ATTTACACTTAATTATACTT | 1-1-2-1-2-6-4-1-2 | AtTTaCActtaatTATAcTT | 628_10 | -22.43 | 30669 |
| 628 | ATTTACACTTAATTATACTT | 3-2-2-6-2-2-3 | ATTtaCActtaatTAtaCTT | 628_11 | -21.72 | 30669 |
| 628 | ATTTACACTTAATTATACTT | 1-2-4-6-2-2-3 | AttTACActtaatTAtaCTT | 628_12 | -22.02 | 30669 |
| 628 | ATTTACACTTAATTATACTT | 2-1-1-1-2-6-1-1-5 | ATtTaCActtaatTaTACTT | 628_13 | -23.00 | 30669 |
| 628 | ATTTACACTTAATTATACTT | 5-8-1-1-1-1-3 | ATTTAcacttaatTaTaCTT | 628_14 | -21.68 | 30669 |
| 629 | TTCTACTATACTTTCCTCT | 1-3-1-7-1-1-1-2-2 | TtctActatactTtCctCT | 629_1 | -21.04 | 30711 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 629 | TTCTACTATACTTTCCTCT | 1-11-1-1-1-2-2 | TtctactatactTtCctCT | 629_2 | -20.85 | 30711 |
| 629 | TTCTACTATACTTTCCTCT | 1-11-1-2-1-1-2 | TtctactatactTtcCtCT | 629_3 | -20.97 | 30711 |
| 629 | TTCTACTATACTTTCCTCT | 1-1-1-9-1-4-2 | TtCtactatactTtcctCT | 629_4 | -21.06 | 30711 |
| 629 | TTCTACTATACTTTCCTCT | 1-1-1-11-1-2-2 | TtCtactatactttCctCT | 629_5 | -21.53 | 30711 |
| 629 | TTCTACTATACTTTCCTCT | 1-3-1-9-1-2-2 | TtctActatactttCctCT | 629_6 | -20.74 | 30711 |
| 629 | TTCTACTATACTTTCCTCT | 1-4-1-8-1-2-2 | TtctaCtatactttCctCT | 629_7 | -21.54 | 30711 |
| 629 | TTCTACTATACTTTCCTCT | 1-13-1-2-2 | TtctactatactttCctCT | 629_8 | -20.55 | 30711 |
| 629 | TTCTACTATACTTTCCTCT | 1-1-1-12-1-1-2 | TtCtactatactttcCtCT | 629_9 | -21.65 | 30711 |
| 629 | TTCTACTATACTTTCCTCT | 1-3-1-10-1-1-2 | TtctActatactttcCtCT | 629_10 | -20.86 | 30711 |
| 629 | TTCTACTATACTTTCCTCT | 1-14-1-1-2 | TtctactatactttcCtCT | 629_11 | -20.67 | 30711 |
| 629 | TTCTACTATACTTTCCTCT | 1-1-1-1-1-7-1-1-1-2-2 | TtCtActatactTtCctCT | 629_12 | -22.02 | 30711 |
| 629 | TTCTACTATACTTTCCTCT | 1-1-1-2-1-8-1-2-2 | TtCtaCtatactttCctCT | 629_13 | -22.52 | 30711 |
| 629 | TTCTACTATACTTTCCTCT | 1-3-2-8-1-2-2 | TtctACtatactttCctCT | 629_14 | -22.14 | 30711 |
| 629 | TTCTACTATACTTTCCTCT | 1-1-1-1-1-10-1-1-2 | TtCtActatactttcCtCT | 629_15 | -21.84 | 30711 |
| 629 | TTCTACTATACTTTCCTCT | 1-1-1-2-1-9-1-1-2 | TtCtaCtatactttcCtCT | 629_16 | -22.64 | 30711 |
| 630 | GTTCTACTATACTTTCCTC | 1-12-1-1-1-1-2 | GttctactatactTtCcTC | 630_1 | -20.78 | 30712 |
| 630 | GTTCTACTATACTTTCCTC | 1-4-1-9-1-1-2 | GttctActatactttCcTC | 630_2 | -20.67 | 30712 |
| 630 | GTTCTACTATACTTTCCTC | 1-14-1-1-2 | GttctactatactttCcTC | 630_3 | -20.48 | 30712 |
| 631 | GTTCTACTATACTTTCCT | 1-2-1-1-1-7-1-2-2 | GttCtActatactTtcCT | 631_1 | -20.25 | 30713 |
| 631 | GTTCTACTATACTTTCCT | 1-2-1-9-1-2-2 | GttCtactatactTtcCT | 631_2 | -20.06 | 30713 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 631 | GTTCTACTATACTTTCCT | 1-2-1-11-3 | GttCtactatactttCCT | 631_3 | -22.13 | 30713 |
| 631 | GTTCTACTATACTTTCCT | 1-4-1-9-3 | GttctActatactttCCT | 631_4 | -21.34 | 30713 |
| 631 | GTTCTACTATACTTTCCT | 1-14-3 | GttctactatactttCCT | 631_5 | -21.15 | 30713 |
| 631 | GTTCTACTATACTTTCCT | 2-1-1-1-1-10-2 | GTtCtActatactttcCT | 631_6 | -21.50 | 30713 |
| 631 | GTTCTACTATACTTTCCT | 2-1-1-12-2 | GTtCtactatactttcCT | 631_7 | -21.30 | 30713 |
| 631 | GTTCTACTATACTTTCCT | 1-2-1-1-1-10-2 | GttCtActatactttcCT | 631_8 | -19.95 | 30713 |
| 631 | GTTCTACTATACTTTCCT | 1-2-1-12-2 | GttCtactatactttcCT | 631_9 | -19.76 | 30713 |
| 631 | GTTCTACTATACTTTCCT | 1-15-2 | GttctactatactttcCT | 631_10 | -18.78 | 30713 |
| 631 | GTTCTACTATACTTTCCT | 1-2-1-9-1-1-3 | GttCtactatactTtCCT | 631_11 | -22.43 | 30713 |
| 631 | GTTCTACTATACTTTCCT | 2-1-1-1-1-7-1-2-2 | GTtCtActatactTtcCT | 631_12 | -21.80 | 30713 |
| 631 | GTTCTACTATACTTTCCT | 1-2-2-8-1-2-2 | GttCTactatactTtcCT | 631_13 | -21.68 | 30713 |
| 631 | GTTCTACTATACTTTCCT | 1-2-1-1-1-9-3 | GttCtActatactttCCT | 631_14 | -22.32 | 30713 |
| 631 | GTTCTACTATACTTTCCT | 1-2-3-10-2 | GttCTActatactttcCT | 631_15 | -22.60 | 30713 |
| 632 | AGTTCTACTATACTTTCC | 1-12-1-2-2 | AgttctactatacTttCC | 632_1 | -19.37 | 30714 |
| 632 | AGTTCTACTATACTTTCC | 1-13-1-1-2 | AgttctactatactTtCC | 632_2 | -19.16 | 30714 |
| 632 | AGTTCTACTATACTTTCC | 1-1-1-13-2 | AgTtctactatactttCC | 632_3 | -19.51 | 30714 |
| 632 | AGTTCTACTATACTTTCC | 1-15-2 | AgttctactatactttCC | 632_4 | -18.86 | 30714 |
| 632 | AGTTCTACTATACTTTCC | 1-1-1-10-1-2-2 | AgTtctactatacTttCC | 632_5 | -20.03 | 30714 |
| 632 | AGTTCTACTATACTTTCC | 1-4-1-7-1-2-2 | AgttcTactatacTttCC | 632_6 | -20.31 | 30714 |
| 632 | AGTTCTACTATACTTTCC | 2-14-2 | AGttctactatactttCC | 632_7 | -20.26 | 30714 |
| 632 | AGTTCTACTATACTTTCC | 1-2-1-12-2 | AgtTctactatactttCC | 632_8 | -19.23 | 30714 |
| 632 | AGTTCTACTATACTTTCC | 1-4-1-10-2 | AgttcTactatactttCC | 632_9 | -19.80 | 30714 |
| 632 | AGTTCTACTATACTTTCC | 2-10-1-3-2 | AGttctactataCtttCC | 632_10 | -21.25 | 30714 |
| 632 | AGTTCTACTATACTTTCC | 1-4-1-6-1-3-2 | AgttcTactataCtttCC | 632_11 | -20.79 | 30714 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 632 | AGTTCTACTATACTTTCC | 1-4-1-7-2-1-2 | AgttcTactatacTTtCC | 632_12 | -21.13 | 30714 |
| 632 | AGTTCTACTATACTTTCC | 1-1-1-11-1-1-2 | AgTtctactatactTtCC | 632_13 | -19.82 | 30714 |
| 632 | AGTTCTACTATACTTTCC | 1-3-1-11-2 | AgttCtactatactttCC | 632_14 | -19.83 | 30714 |
| 633 | CAACATTATTAACCACCTTA | 1-13-3-1-2 | CaacattattaaccACCtTA | 633_1 | -22.44 | 33376 |
| 633 | CAACATTATTAACCACCTTA | 4-10-1-2-3 | CAACattattaaccAccTTA | 633_2 | -22.98 | 33376 |
| 633 | CAACATTATTAACCACCTTA | 2-2-1-10-1-1-3 | CAacAttattaaccaCcTTA | 633_3 | -21.97 | 33376 |
| 633 | CAACATTATTAACCACCTTA | 1-4-2-8-1-2-2 | CaacaTTattaaccaCctTA | 633_4 | -21.08 | 33376 |
| 633 | CAACATTATTAACCACCTTA | 1-1-2-11-1-2-2 | CaACattattaaccaCctTA | 633_5 | -20.90 | 33376 |
| 633 | CAACATTATTAACCACCTTA | 1-2-2-13-2 | CaaCAttattaaccacctTA | 633_6 | -20.76 | 33376 |
| 633 | CAACATTATTAACCACCTTA | 1-1-1-1-1-11-1-1-2 | CaAcAttattaaccacCtTA | 633_7 | -19.97 | 33376 |
| 633 | CAACATTATTAACCACCTTA | 1-15-4 | CaacattattaaccacCTTA | 633_8 | -21.21 | 33376 |
| 633 | CAACATTATTAACCACCTTA | 2-4-1-11-2 | CAacatTattaaccacctTA | 633_9 | -20.83 | 33376 |
| 634 | CAACATTATTAACCACCTT | 2-10-2-3-2 | CAacattattaaCCaccTT | 634_1 | -21.86 | 33377 |
| 634 | CAACATTATTAACCACCTT | 1-14-4 | CaacattattaaccaCCTT | 634_2 | -21.36 | 33377 |
| 634 | CAACATTATTAACCACCTT | 1-1-1-11-1-1-3 | CaAcattattaaccAcCTT | 634_3 | -19.54 | 33377 |
| 634 | CAACATTATTAACCACCTT | 3-1-1-11-3 | CAAcAttattaaccacCTT | 634_4 | -21.13 | 33377 |
| 634 | CAACATTATTAACCACCTT | 3-11-2-1-2 | CAAcattattaaccACcTT | 634_5 | -20.84 | 33377 |
| 634 | CAACATTATTAACCACCTT | 2-1-2-9-1-1-3 | CAaCAttattaaccAcCTT | 634_6 | -22.76 | 33377 |
| 634 | CAACATTATTAACCACCTT | 2-1-2-10-1-1-2 | CAaCAttattaaccaCcTT | 634_7 | -21.83 | 33377 |
| 634 | CAACATTATTAACCACCTT | 1-1-2-11-1-1-2 | CaACattattaaccaCcTT | 634_8 | -19.70 | 33377 |
| 634 | CAACATTATTAACCACCTT | 1-2-1-12-3 | CaaCattattaaccacCTT | 634_9 | -19.66 | 33377 |
| 635 | GCAACATTATTAACCACCT | 1-1-1-2-1-6-2-3-2 | GcAacAttattaACcacCT | 635_1 | -21.56 | 33378 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 635 | GCAACATTATTAACCACCT | 1-1-2-1-1-6-1-2-1-1-2 | GcAAcAttattaAccAcCT | 635_2 | -21.14 | 33378 |
| 635 | GCAACATTATTAACCACCT | 1-11-2-1-1-1-2 | GcaacattattaACcAcCT | 635_3 | -21.59 | 33378 |
| 635 | GCAACATTATTAACCACCT | 1-4-1-6-1-3-3 | GcaacAttattaAccaCCT | 635_4 | -22.69 | 33378 |
| 635 | GCAACATTATTAACCACCT | 1-1-1-1-1-7-1-4-2 | GcAaCattattaAccacCT | 635_5 | -21.01 | 33378 |
| 635 | GCAACATTATTAACCACCT | 1-11-1-1-1-2-2 | GcaacattattaAcCacCT | 635_6 | -20.83 | 33378 |
| 635 | GCAACATTATTAACCACCT | 2-3-1-6-1-4-2 | GCaacAttattaAccacCT | 635_7 | -22.63 | 33378 |
| 635 | GCAACATTATTAACCACCT | 1-1-1-12-1-1-2 | GcAacattattaaccAcCT | 635_8 | -20.05 | 33378 |
| 635 | GCAACATTATTAACCACCT | 1-2-1-1-1-11-2 | GcaAcAttattaaccacCT | 635_9 | -20.30 | 33378 |
| 636 | AGCAACATTATTAACCACC | 1-2-1-9-2-1-3 | AgcAacattattaACcACC | 636_1 | -22.13 | 33379 |
| 636 | AGCAACATTATTAACCACC | 1-11-1-1-1-2-2 | AgcaacattattAaCcaCC | 636_2 | -20.80 | 33379 |
| 636 | AGCAACATTATTAACCACC | 1-4-1-6-2-3-2 | AgcaaCattattAAccaCC | 636_3 | -21.32 | 33379 |
| 636 | AGCAACATTATTAACCACC | 1-2-2-7-1-2-1-1-2 | AgcAAcattattAacCaCC | 636_4 | -21.29 | 33379 |
| 636 | AGCAACATTATTAACCACC | 2-11-1-3-2 | AGcaacattattaAccaCC | 636_5 | -21.75 | 33379 |
| 636 | AGCAACATTATTAACCACC | 1-1-1-1-1-8-1-2-3 | AgCaAcattattaAccACC | 636_6 | -22.16 | 33379 |
| 636 | AGCAACATTATTAACCACC | 1-2-1-1-1-6-1-3-3 | AgcAaCattattAaccACC | 636_7 | -21.33 | 33379 |
| 636 | AGCAACATTATTAACCACC | 2-1-2-12-2 | AGcAAcattattaaccaCC | 636_8 | -22.02 | 33379 |
| 636 | AGCAACATTATTAACCACC | 1-15-3 | AgcaacattattaaccACC | 636_9 | -20.45 | 33379 |
| 637 | AGCAACATTATTAACCAC | 2-1-1-9-5 | AGcAacattattaACCAC | 637_1 | -21.97 | 33380 |
| 637 | AGCAACATTATTAACCAC | 1-3-1-7-6 | AgcaAcattattAACCAC | 637_2 | -21.20 | 33380 |
| 637 | AGCAACATTATTAACCAC | 2-10-2-1-3 | AGcaacattattAAcCAC | 637_3 | -19.42 | 33380 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 637 | AGCAACATTATTAACCAC | 1-2-1-8-1-1-4 | AgcAacattattAaCCAC | 637_4 | −19.84 | 33380 |
| 637 | AGCAACATTATTAACCAC | 3-9-3-1-2 | AGCaacattattAACcAC | 637_5 | −20.94 | 33380 |
| 637 | AGCAACATTATTAACCAC | 1-1-3-7-3-1-2 | AgCAAcattattAACcAC | 637_6 | −20.15 | 33380 |
| 637 | AGCAACATTATTAACCAC | 1-1-3-7-2-1-3 | AgCAAcattattAAcCAC | 637_7 | −20.96 | 33380 |
| 637 | AGCAACATTATTAACCAC | 5-7-1-3-2 | AGCAAcattattAaccAC | 637_8 | −21.24 | 33380 |
| 637 | AGCAACATTATTAACCAC | 3-1-1-8-1-2-2 | AGCaAcattattaAccAC | 637_9 | −19.86 | 33380 |
| 638 | GTTTCCATCTACTATTAAT | 1-3-1-7-1-1-1-1-3 | GtttCcatctacTaTtAAT | 638_1 | −19.59 | 39806 |
| 638 | GTTTCCATCTACTATTAAT | 1-1-1-9-2-3-2 | GtTtccatctacTAttaAT | 638_2 | −19.50 | 39806 |
| 638 | GTTTCCATCTACTATTAAT | 1-4-1-6-2-2-3 | GtttcCatctacTAttAAT | 638_3 | −20.09 | 39806 |
| 638 | GTTTCCATCTACTATTAAT | 1-3-1-8-1-2-3 | GtttCcatctactAttAAT | 638_4 | −18.30 | 39806 |
| 638 | GTTTCCATCTACTATTAAT | 3-1-1-8-1-3-2 | GTTtCcatctactAttaAT | 638_5 | −20.35 | 39806 |
| 638 | GTTTCCATCTACTATTAAT | 1-2-2-12-2 | GttTCcatctactattaAT | 638_6 | −18.88 | 39806 |
| 638 | GTTTCCATCTACTATTAAT | 1-1-1-11-1-1-3 | GtTtccatctactaTtAAT | 638_7 | −18.18 | 39806 |
| 638 | GTTTCCATCTACTATTAAT | 2-2-1-10-1-1-2 | GTttCcatctactatTaAT | 638_8 | −20.16 | 39806 |
| 638 | GTTTCCATCTACTATTAAT | 1-1-1-1-2-10-3 | GtTtCCatctactattAAT | 638_9 | −20.69 | 39806 |
| 638 | GTTTCCATCTACTATTAAT | 2-2-1-7-1-3-3 | GTttCcatctacTattAAT | 638_10 | −20.69 | 39806 |
| 638 | GTTTCCATCTACTATTAAT | 1-1-1-10-2-1-3 | GtTtccatctactATtAAT | 638_11 | −19.08 | 39806 |
| 638 | GTTTCCATCTACTATTAAT | 1-3-1-8-1-1-1-1-2 | GtttCcatctactAtTaAT | 638_12 | −18.72 | 39806 |
| 638 | GTTTCCATCTACTATTAAT | 1-2-3-7-1-2-3 | GttTCCatctactAttAAT | 638_13 | −21.47 | 39806 |
| 638 | GTTTCCATCTACTATTAAT | 1-1-1-1-2-11-2 | GtTtCCatctactattaAT | 638_14 | −20.37 | 39806 |
| 639 | GTTTCCATCTACTATTAA | 1-11-2-1-3 | GtttccatctacTAtTAA | 639_1 | −19.21 | 39807 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 639 | GTTTCCATCTACTATTAA | 1-3-1-7-1-1-4 | GtttCcatctacTaTTAA | 639_2 | -19.80 | 39807 |
| 639 | GTTTCCATCTACTATTAA | 3-1-1-7-2-2-2 | GTTtCcatctacTAttAA | 639_3 | -20.57 | 39807 |
| 639 | GTTTCCATCTACTATTAA | 2-2-1-7-1-1-1-1-2 | GTttCcatctacTaTtAA | 639_4 | -19.07 | 39807 |
| 639 | GTTTCCATCTACTATTAA | 1-3-2-7-2-1-2 | GtttCCatctactATtAA | 639_5 | -19.67 | 39807 |
| 639 | GTTTCCATCTACTATTAA | 3-2-1-6-1-3-2 | GTTtcCatctacTattAA | 639_6 | -19.25 | 39807 |
| 639 | GTTTCCATCTACTATTAA | 1-1-3-8-1-2-2 | GtTTCcatctactAttAA | 639_7 | -18.04 | 39807 |
| 639 | GTTTCCATCTACTATTAA | 1-1-1-1-2-10-2 | GtTtCCatctactattAA | 639_8 | -18.62 | 39807 |
| 639 | GTTTCCATCTACTATTAA | 3-1-1-9-4 | GTTtCcatctactaTTAA | 639_9 | -21.21 | 39807 |
| 639 | GTTTCCATCTACTATTAA | 1-3-2-6-2-2-2 | GtttCCatctacTAttAA | 639_10 | -20.39 | 39807 |
| 639 | GTTTCCATCTACTATTAA | 1-1-3-7-1-1-1-1-2 | GtTTCcatctacTaTtAA | 639_11 | -19.32 | 39807 |
| 639 | GTTTCCATCTACTATTAA | 2-2-1-7-1-2-3 | GTttCcatctacTatTAA | 639_12 | -20.39 | 39807 |
| 639 | GTTTCCATCTACTATTAA | 2-2-1-8-2-1-2 | GTttCcatctactATtAA | 639_13 | -19.03 | 39807 |
| 639 | GTTTCCATCTACTATTAA | 1-1-1-1-2-8-4 | GtTtCCatctactaTTAA | 639_14 | -21.34 | 39807 |
| 640 | TGTTTCCATCTACTATTA | 1-1-1-11-1-1-2 | TgTttccatctactAtTA | 640_1 | -18.41 | 39808 |
| 640 | TGTTTCCATCTACTATTA | 1-2-1-9-2-1-2 | TgtTtccatctacTAtTA | 640_2 | -20.03 | 39808 |
| 640 | TGTTTCCATCTACTATTA | 1-4-1-7-1-2-2 | TgtttCcatctacTatTA | 640_3 | -19.37 | 39808 |
| 640 | TGTTTCCATCTACTATTA | 1-4-1-8-4 | TgtttCcatctactATTA | 640_4 | -20.28 | 39808 |
| 640 | TGTTTCCATCTACTATTA | 1-4-1-8-1-1-2 | TgtttCcatctactAtTA | 640_5 | -18.52 | 39808 |
| 640 | TGTTTCCATCTACTATTA | 1-1-2-1-1-10-2 | TgTTtCcatctactatTA | 640_6 | -19.89 | 39808 |
| 640 | TGTTTCCATCTACTATTA | 1-4-1-9-3 | TgtttCcatctactaTTA | 640_7 | -19.37 | 39808 |
| 640 | TGTTTCCATCTACTATTA | 1-2-1-1-1-10-2 | TgtTtCcatctactatTA | 640_8 | -18.73 | 39808 |
| 640 | TGTTTCCATCTACTATTA | 1-4-1-10-2 | TgtttCcatctactatTA | 640_9 | -18.42 | 39808 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 640 | TGTTTCCATCTACTATTA | 1-4-1-6-1-1-4 | TgtttCcatctaCtATTA | 640_10 | -21.27 | 39808 |
| 640 | TGTTTCCATCTACTATTA | 2-1-1-9-2-1-2 | TGtTtccatctacTAtTA | 640_11 | -21.24 | 39808 |
| 640 | TGTTTCCATCTACTATTA | 1-3-2-8-1-1-2 | TgttTCcatctactAtTA | 640_12 | -19.51 | 39808 |
| 640 | TGTTTCCATCTACTATTA | 2-1-1-1-1-10-2 | TGtTtCcatctactatTA | 640_13 | -19.94 | 39808 |
| 640 | TGTTTCCATCTACTATTA | 1-1-1-2-1-10-2 | TgTttCcatctactatTA | 640_14 | -19.08 | 39808 |
| 641 | ACTCTGCAATACACCAA | 2-1-1-8-2-1-2 | ACtCtgcaatacACcAA | 641_1 | -19.61 | 44439 |
| 641 | ACTCTGCAATACACCAA | 2-2-1-6-1-1-1-1-2 | ACtcTgcaataCaCcAA | 641_2 | -19.77 | 44439 |
| 641 | ACTCTGCAATACACCAA | 1-2-1-7-1-1-1-1-2 | ActCtgcaataCaCcAA | 641_3 | -18.35 | 44439 |
| 641 | ACTCTGCAATACACCAA | 2-1-2-6-2-2-2 | ACtCTgcaataCAccAA | 641_4 | -22.21 | 44439 |
| 641 | ACTCTGCAATACACCAA | 1-3-1-7-1-1-3 | ActcTgcaatacAcCAA | 641_5 | -19.05 | 44439 |
| 641 | ACTCTGCAATACACCAA | 4-8-1-2-2 | ACTCtgcaatacAccAA | 641_6 | -20.30 | 44439 |
| 641 | ACTCTGCAATACACCAA | 2-1-2-9-3 | ACtCTgcaatacacCAA | 641_7 | -21.96 | 44439 |
| 641 | ACTCTGCAATACACCAA | 2-11-4 | ACtctgcaatacaCCAA | 641_8 | -21.68 | 44439 |
| 641 | ACTCTGCAATACACCAA | 1-1-2-10-3 | AcTCtgcaatacacCAA | 641_9 | -20.07 | 44439 |
| 642 | CTGTATACACCATCCCA | 1-10-1-1-1-1-2 | CtgtatacaccAtCcCA | 642_1 | -21.99 | 46391 |
| 642 | CTGTATACACCATCCCA | 1-10-1-3-2 | CtgtatacaccAtccCA | 642_2 | -21.22 | 46391 |
| 642 | CTGTATACACCATCCCA | 1-1-1-8-1-3-2 | CtGtatacaccAtccCA | 642_3 | -21.53 | 46391 |
| 642 | CTGTATACACCATCCCA | 1-2-1-7-1-3-2 | CtgTatacaccAtccCA | 642_4 | -22.31 | 46391 |
| 642 | CTGTATACACCATCCCA | 1-3-1-6-1-3-2 | CtgtAtacaccAtccCA | 642_5 | -21.32 | 46391 |
| 642 | CTGTATACACCATCCCA | 1-11-2-1-2 | CtgtatacaccaTCcCA | 642_6 | -23.06 | 46391 |
| 642 | CTGTATACACCATCCCA | 1-1-1-1-1-8-1-1-2 | CtGtAtacaccatCcCA | 642_7 | -22.35 | 46391 |
| 642 | CTGTATACACCATCCCA | 1-1-1-10-1-1-2 | CtGtatacaccatCcCA | 642_8 | -22.25 | 46391 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 642 | CTGTATACACCATCCCA | 1-2-1-9-1-1-2 | CtgTatacaccatCcCA | 642_9 | -23.02 | 46391 |
| 642 | CTGTATACACCATCCCA | 1-3-1-8-1-1-2 | CtgtAtacaccatCcCA | 642_10 | -22.04 | 46391 |
| 642 | CTGTATACACCATCCCA | 1-12-1-1-2 | CtgtatacaccatCcCA | 642_11 | -21.94 | 46391 |
| 642 | CTGTATACACCATCCCA | 2-2-1-10-2 | CTgtAtacaccatccCA | 642_12 | -22.95 | 46391 |
| 642 | CTGTATACACCATCCCA | 1-1-1-1-1-10-2 | CtGtAtacaccatccCA | 642_13 | -21.58 | 46391 |
| 642 | CTGTATACACCATCCCA | 1-1-1-12-2 | CtGtatacaccatccCA | 642_14 | -21.48 | 46391 |
| 642 | CTGTATACACCATCCCA | 1-2-2-10-2 | CtgTAtacaccatccCA | 642_15 | -23.39 | 46391 |
| 642 | CTGTATACACCATCCCA | 1-3-1-10-2 | CtgtAtacaccatccCA | 642_16 | -21.27 | 46391 |
| 642 | CTGTATACACCATCCCA | 1-14-2 | CtgtatacaccatccCA | 642_17 | -21.17 | 46391 |
| 642 | CTGTATACACCATCCCA | 1-3-1-6-3-1-2 | CtgtAtacaccATCcCA | 642_18 | -24.02 | 46391 |
| 642 | CTGTATACACCATCCCA | 1-1-1-8-1-1-1-1-2 | CtGtatacaccAtCcCA | 642_19 | -22.30 | 46391 |
| 642 | CTGTATACACCATCCCA | 1-1-3-6-1-3-2 | CtGTAtacaccAtccCA | 642_20 | -24.64 | 46391 |
| 642 | CTGTATACACCATCCCA | 2-2-1-8-1-1-2 | CTgtAtacaccatCcCA | 642_21 | -23.72 | 46391 |
| 642 | CTGTATACACCATCCCA | 1-3-1-9-3 | CtgtAtacaccatcCCA | 642_22 | -23.55 | 46391 |
| 643 | TCTGTATACACCATCCCA | 1-4-1-8-1-1-2 | TctgtAtacaccatCcCA | 643_1 | -22.94 | 46391 |
| 644 | TCTGTATACACCATCCC | 2-10-1-2-2 | TCtgtatacaccAtcCC | 644_1 | -22.70 | 46392 |
| 644 | TCTGTATACACCATCCC | 1-11-1-2-2 | TctgtatacaccAtcCC | 644_2 | -21.11 | 46392 |
| 644 | TCTGTATACACCATCCC | 2-1-1-11-2 | TCtGtatacaccatcCC | 644_3 | -22.96 | 46392 |
| 644 | TCTGTATACACCATCCC | 2-13-2 | TCtgtatacaccatcCC | 644_4 | -22.65 | 46392 |
| 644 | TCTGTATACACCATCCC | 3-9-1-2-2 | TCTgtatacaccAtcCC | 644_5 | -24.39 | 46392 |
| 644 | TCTGTATACACCATCCC | 2-1-1-8-1-2-2 | TCtGtatacaccAtcCC | 644_6 | -23.01 | 46392 |
| 645 | TTCTGTATACACCATCCC | 1-11-1-3-2 | TtctgtatacacCatcCC | 645_1 | -22.57 | 46392 |
| 645 | TTCTGTATACACCATCCC | 1-1-1-10-1-2-2 | TtCtgtatacaccAtcCC | 645_2 | -23.02 | 46392 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 645 | TTCTGTATACACCATCCC | 1-3-1-8-1-2-2 | TtctGtatacaccAtcCC | 645_3 | -22.36 | 46392 |
| 645 | TTCTGTATACACCATCCC | 1-12-1-2-2 | TtctgtatacaccAtcCC | 645_4 | -22.05 | 46392 |
| 645 | TTCTGTATACACCATCCC | 1-15-2 | TtctgtatacaccatcCC | 645_5 | -22.00 | 46392 |
| 645 | TTCTGTATACACCATCCC | 1-4-1-6-2-2-2 | TtctgTatacacCAtcCC | 645_6 | -25.12 | 46392 |
| 645 | TTCTGTATACACCATCCC | 1-3-1-8-1-1-3 | TtctGtatacaccAtCCC | 645_7 | -24.73 | 46392 |
| 645 | TTCTGTATACACCATCCC | 3-10-1-2-2 | TTCtgtatacaccAtcCC | 645_8 | -24.52 | 46392 |
| 645 | TTCTGTATACACCATCCC | 1-1-2-9-1-2-2 | TtCTgtatacaccAtcCC | 645_9 | -24.71 | 46392 |
| 645 | TTCTGTATACACCATCCC | 1-1-1-1-1-8-1-2-2 | TtCtGtatacaccAtcCC | 645_10 | -23.34 | 46392 |
| 646 | TTCTGTATACACCATCC | 1-10-1-3-2 | TtctgtatacaCcatCC | 646_1 | -19.96 | 46393 |
| 646 | TTCTGTATACACCATCC | 1-12-4 | TtctgtatacaccATCC | 646_2 | -21.16 | 46393 |
| 646 | TTCTGTATACACCATCC | 2-11-1-1-2 | TTctgtatacaccAtCC | 646_3 | -20.11 | 46393 |
| 646 | TTCTGTATACACCATCC | 1-2-1-9-1-1-2 | TtcTgtatacaccAtCC | 646_4 | -20.24 | 46393 |
| 646 | TTCTGTATACACCATCC | 1-3-1-8-1-1-2 | TtctGtatacaccAtCC | 646_5 | -19.54 | 46393 |
| 646 | TTCTGTATACACCATCC | 1-2-1-8-1-2-2 | TtcTgtatacacCatCC | 646_6 | -20.77 | 46393 |
| 646 | TTCTGTATACACCATCC | 1-12-1-1-2 | TtctgtatacaccAtCC | 646_7 | -19.23 | 46393 |
| 646 | TTCTGTATACACCATCC | 1-3-1-7-1-1-3 | TtctGtatacacCaTCC | 646_8 | -21.19 | 46393 |
| 646 | TTCTGTATACACCATCC | 1-1-1-1-1-10-2 | TtCtGtatacaccatCC | 646_9 | -20.47 | 46393 |
| 646 | TTCTGTATACACCATCC | 1-1-1-12-2 | TtCtgtatacaccatCC | 646_10 | -20.16 | 46393 |
| 646 | TTCTGTATACACCATCC | 1-1-1-11-3 | TtCtgtatacaccaTCC | 646_11 | -21.28 | 46393 |
| 646 | TTCTGTATACACCATCC | 1-3-1-9-3 | TtctGtatacaccaTCC | 646_12 | -20.61 | 46393 |
| 646 | TTCTGTATACACCATCC | 1-13-3 | TtctgtatacaccaTCC | 646_13 | -20.30 | 46393 |
| 646 | TTCTGTATACACCATCC | 3-1-1-10-2 | TTCtGtatacaccatCC | 646_14 | -21.96 | 46393 |
| 646 | TTCTGTATACACCATCC | 3-12-2 | TTCtgtatacaccatCC | 646_15 | -21.65 | 46393 |
| 646 | TTCTGTATACACCATCC | 1-1-2-11-2 | TtCTgtatacaccatCC | 646_16 | -21.84 | 46393 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 646 | TTCTGTATACACCATCC | 1-2-1-11-2 | TtcTgtatacaccatCC | 646_17 | -20.19 | 46393 |
| 646 | TTCTGTATACACCATCC | 1-3-1-10-2 | TtctGtatacaccatCC | 646_18 | -19.49 | 46393 |
| 646 | TTCTGTATACACCATCC | 1-14-2 | TtctgtatacaccatCC | 646_19 | -19.18 | 46393 |
| 646 | TTCTGTATACACCATCC | 3-8-1-3-2 | TTCtgtatacaCcatCC | 646_20 | -22.44 | 46393 |
| 646 | TTCTGTATACACCATCC | 1-3-1-6-1-3-2 | TtctGtatacaCcatCC | 646_21 | -20.27 | 46393 |
| 646 | TTCTGTATACACCATCC | 1-3-1-7-2-1-2 | TtctGtatacacCAtCC | 646_22 | -21.53 | 46393 |
| 646 | TTCTGTATACACCATCC | 1-1-1-9-1-2-2 | TtCtgtatacacCatCC | 646_23 | -20.74 | 46393 |
| 646 | TTCTGTATACACCATCC | 1-1-1-10-1-1-2 | TtCtgtatacaccAtCC | 646_24 | -20.21 | 46393 |
| 647 | AGCTTTTAACCAGAGT | 2-10-4 | AGcttttaaccaGAGT | 647_1 | -21.73 | EX-EX |
| 648 | AGCTTTTAACCAGAGTG | 2-11-4 | AGcttttaaccagAGTG | 648_1 | -22.27 | EX-EX |
| 649 | AGCTTTTAACCAGAGTGG | 1-14-3 | AgcttttaaccagagTGG | 649_1 | -21.63 | EX-EX |
| 650 | AGCTTTTAACCAGAGTGGC | 1-16-2 | AgcttttaaccagagtgGC | 650_1 | -23.20 | EX-EX |
| 651 | AGCTTTTAACCAGAGTGGCA | 1-17-2 | AgcttttaaccagagtggCA | 651_1 | -24.11 | EX-EX |
| 652 | CAGCTTTTAACCAGAGT | 2-12-3 | CAgcttttaaccagAGT | 652_1 | -21.65 | EX-EX |
| 653 | CAGCTTTTAACCAGAGTG | 3-13-2 | CAGcttttaaccagagTG | 653_1 | -22.27 | EX-EX |
| 654 | CAGCTTTTAACCAGAGTGG | 1-15-3 | CagcttttaaccagagTGG | 654_1 | -22.97 | EX-EX |
| 655 | CAGCTTTTAACCAGAGTGGC | 1-17-2 | CagcttttaaccagagtgGC | 655_1 | -24.53 | EX-EX |
| 656 | CTTTTAACCAGAGTG | 4-7-4 | CTTTtaaccagAGTG | 656_1 | -20.12 | EX-EX |
| 657 | CTTTTAACCAGAGTGG | 4-9-3 | CTTTtaaccagagTGG | 657_1 | -20.92 | EX-EX |
| 658 | CTTTTAACCAGAGTGGC | 4-11-2 | CTTTtaaccagagtgGC | 658_1 | -22.48 | EX-EX |
| 659 | CTTTTAACCAGAGTGGCA | 1-14-3 | CttttaaccagagtgGCA | 659_1 | -22.96 | EX-EX |
| 660 | CTTTTAACCAGAGTGGCAT | 3-13-3 | CTTttaaccagagtggCAT | 660_1 | -24.65 | EX-EX |
| 661 | CTTTTAACCAGAGTGGCATC | 2-16-2 | CTtttaaccagagtggcaTC | 661_1 | -23.19 | EX-EX |
| 662 | GCTTTTAACCAGAGT | 3-9-3 | GCTtttaaccagAGT | 662_1 | -21.02 | EX-EX |
| 663 | GCTTTTAACCAGAGTG | 4-10-2 | GCTTttaaccagagTG | 663_1 | -21.02 | EX-EX |
| 664 | GCTTTTAACCAGAGTGG | 1-12-4 | GcttttaaccagaGTGG | 664_1 | -22.24 | EX-EX |
| 665 | GCTTTTAACCAGAGTGGC | 1-14-3 | GcttttaaccagagtGGC | 665_1 | -23.42 | EX-EX |
| 666 | GCTTTTAACCAGAGTGGCA | 1-16-2 | GcttttaaccagagtggCA | 666_1 | -22.94 | EX-EX |
| 667 | GCTTTTAACCAGAGTGGCAT | 1-16-3 | GcttttaaccagagtggCAT | 667_1 | -25.01 | EX-EX |
| 668 | TCAGCTTTTAACCAGAGT | 2-13-3 | TCagcttttaaccagAGT | 668_1 | -22.18 | EX-EX |
| 669 | TCAGCTTTTAACCAGAGTG | 2-14-3 | TCagcttttaaccagaGTG | 669_1 | -23.15 | EX-EX |
| 670 | TCAGCTTTTAACCAGAGTGG | 2-16-2 | TCagcttttaaccagagtGG | 670_1 | -23.41 | EX-EX |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 671 | TTCAGCTTTTAACCAGAGT | 2-14-3 | TTcagcttttaaccagAGT | 671_1 | -22.72 | EX-EX |
| 672 | TTCAGCTTTTAACCAGAGTG | 2-15-3 | TTcagcttttaaccagaGTG | 672_1 | -23.69 | EX-EX |
| 673 | TTTCAGCTTTTAACCAGAGT | 2-15-3 | TTtcagcttttaaccagAGT | 673_1 | -23.66 | EX-EX |
| 674 | TTTTAACCAGAGTGGC | 1-11-4 | TtttaaccagagTGGC | 674_1 | -20.81 | EX-EX |
| 675 | TTTTAACCAGAGTGGCA | 3-11-3 | TTTtaaccagagtgGCA | 675_1 | -22.30 | EX-EX |
| 676 | TTTTAACCAGAGTGGCAT | 4-11-3 | TTTTaaccagagtggCAT | 676_1 | -23.21 | EX-EX |
| 677 | TTTTAACCAGAGTGGCATC | 4-13-2 | TTTTaaccagagtggcaTC | 677_1 | -22.57 | EX-EX |
| 678 | TTTTAACCAGAGTGGCATCC | 2-16-2 | TTttaaccagagtggcatCC | 678_1 | -24.58 | EX-EX |
| 679 | ATCAATATCTTCTCACT | 1-1-2-7-1-1-1-1-2 | AtCAatatcttCtCaCT | 679_1 | -19.16 | 5782 |
| 679 | ATCAATATCTTCTCACT | 5-6-1-2-3 | ATCAAtatcttCtcACT | 679_2 | -21.49 | 5782 |
| 679 | ATCAATATCTTCTCACT | 1-1-1-1-1-7-5 | AtCaAtatcttcTCACT | 679_3 | -20.18 | 5782 |
| 679 | ATCAATATCTTCTCACT | 1-1-3-8-4 | AtCAAtatcttctCACT | 679_4 | -20.66 | 5782 |
| 679 | ATCAATATCTTCTCACT | 3-10-1-1-2 | ATCaatatcttctCaCT | 679_5 | -18.62 | 5782 |
| 680 | TATCAATATCTTCTCACT | 2-2-1-7-1-1-1-1-2 | TAtcAatatcttCtCaCT | 680_1 | -19.31 | 5782 |
| 680 | TATCAATATCTTCTCACT | 1-1-2-8-1-1-1-1-2 | TaTCaatatcttCtCaCT | 680_2 | -19.89 | 5782 |
| 680 | TATCAATATCTTCTCACT | 1-2-3-6-1-2-3 | TatCAAtatcttCtcACT | 680_3 | -20.66 | 5782 |
| 680 | TATCAATATCTTCTCACT | 1-2-3-7-2-1-2 | TatCAAtatcttcTCaCT | 680_4 | -20.99 | 5782 |
| 680 | TATCAATATCTTCTCACT | 2-1-1-10-4 | TAtCaatatcttctCACT | 680_5 | -20.89 | 5782 |
| 681 | TATCAATATCTTCTCAC | 4-7-2-1-3 | TATCaatatctTCtCAC | 681_1 | -21.30 | 5783 |
| 681 | TATCAATATCTTCTCAC | 1-2-2-6-2-1-3 | TatCAatatctTCtCAC | 681_2 | -19.73 | 5783 |
| 681 | TATCAATATCTTCTCAC | 2-1-1-8-5 | TAtCaatatcttCTCAC | 681_3 | -20.26 | 5783 |
| 681 | TATCAATATCTTCTCAC | 1-1-3-7-5 | TaTCAatatcttCTCAC | 681_4 | -21.74 | 5783 |
| 681 | TATCAATATCTTCTCAC | 5-9-3 | TATCAatatcttctCAC | 681_5 | -20.83 | 5783 |
| 682 | TTATCAATATCTTCTCAC | 1-1-1-1-2-6-2-2-2 | TtAtCAatatctTCtcAC | 682_1 | -18.32 | 5783 |
| 682 | TTATCAATATCTTCTCAC | 1-3-1-8-5 | TtatCaatatcttCTCAC | 682_2 | -19.71 | 5783 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 682 | TTATCAATATCTTCTCAC | 3-10-1-1-3 | TTAtcaatatcttCtCAC | 682_3 | -19.53 | 5783 |
| 682 | TTATCAATATCTTCTCAC | 2-1-2-8-1-1-3 | TTaTCaatatcttCtCAC | 682_4 | -20.20 | 5783 |
| 682 | TTATCAATATCTTCTCAC | 1-2-3-9-3 | TtaTCAatatcttctCAC | 682_5 | -19.47 | 5783 |
| 683 | TTATCAATATCTTCTCACT | 1-1-1-1-1-8-1-1-1-1-2 | TtAtCaatatcttCtCaCT | 683_1 | -19.45 | 5782 |
| 683 | TTATCAATATCTTCTCACT | 1-3-1-8-1-1-1-1-2 | TtatCaatatcttCtCaCT | 683_2 | -19.35 | 5782 |
| 683 | TTATCAATATCTTCTCACT | 1-1-1-1-1-8-1-2-3 | TtAtCaatatcttCtcACT | 683_3 | -19.33 | 5782 |
| 683 | TTATCAATATCTTCTCACT | 1-1-1-2-1-7-1-3-2 | TtAtcAatatcttCtcaCT | 683_4 | -18.18 | 5782 |
| 683 | TTATCAATATCTTCTCACT | 1-1-1-2-1-9-4 | TtAtcAatatcttctCACT | 683_5 | -19.84 | 5782 |
| 684 | ACCTTTCTTTAACCCTTT | 2-1-1-8-2-1-3 | ACcTttctttaaCCcTTT | 684_1 | -25.24 | 8113 |
| 684 | ACCTTTCTTTAACCCTTT | 2-10-1-1-1-1-2 | ACctttctttaaCcCtTT | 684_2 | -22.31 | 8113 |
| 684 | ACCTTTCTTTAACCCTTT | 1-1-1-9-1-1-1-1-2 | AcCtttctttaaCcCtTT | 684_3 | -22.01 | 8113 |
| 684 | ACCTTTCTTTAACCCTTT | 1-1-1-1-1-9-1-1-2 | AcCtTtctttaaccCtTT | 684_4 | -21.53 | 8113 |
| 684 | ACCTTTCTTTAACCCTTT | 1-1-1-11-1-1-2 | AcCtttctttaaccCtTT | 684_5 | -21.23 | 8113 |
| 685 | TACCTTTCTTTAACCCTTT | 1-2-1-8-1-1-1-2-2 | TacCtttctttaAcCctTT | 685_1 | -22.44 | 8113 |
| 685 | TACCTTTCTTTAACCCTTT | 1-2-1-1-1-7-1-1-1-1-2 | TacCtTtctttaaCcCtTT | 685_2 | -23.32 | 8113 |
| 685 | TACCTTTCTTTAACCCTTT | 2-1-1-10-1-1-3 | TAcCtttctttaacCcTTT | 685_3 | -24.28 | 8113 |
| 685 | TACCTTTCTTTAACCCTTT | 1-1-1-12-1-1-2 | TaCctttctttaaccCtTT | 685_4 | -22.13 | 8113 |
| 685 | TACCTTTCTTTAACCCTTT | 1-2-1-11-1-1-2 | TacCtttctttaaccCtTT | 685_5 | -22.23 | 8113 |
| 686 | ATACCTTTCTTTAACCC | 1-2-1-7-1-1-1-1-2 | AtaCctttcttTaAcCC | 686_1 | -20.53 | 8116 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 686 | ATACCTTTCTTTAACCC | 1-3-1-6-1-3-2 | AtacCtttcttTaacCC | 686_2 | -20.21 | 8116 |
| 686 | ATACCTTTCTTTAACCC | 2-2-1-7-2-1-2 | ATacCtttctttAAcCC | 686_3 | -21.89 | 8116 |
| 686 | ATACCTTTCTTTAACCC | 1-1-1-1-1-8-1-1-2 | AtAcCtttctttaAcCC | 686_4 | -20.10 | 8116 |
| 686 | ATACCTTTCTTTAACCC | 1-2-1-10-3 | AtaCctttctttaaCCC | 686_5 | -21.76 | 8116 |
| 687 | ATACCTTTCTTTAACCCTT | 1-3-2-6-1-2-4 | AtacCTttctttAacCCTT | 687_1 | -26.10 | 8114 |
| 687 | ATACCTTTCTTTAACCCTT | 1-1-1-1-1-8-1-1-1-1-2 | AtAcCtttctttaAcCcTT | 687_2 | -22.23 | 8114 |
| 687 | ATACCTTTCTTTAACCCTT | 1-2-1-9-1-1-1-1-2 | AtaCctttctttaAcCcTT | 687_3 | -21.93 | 8114 |
| 687 | ATACCTTTCTTTAACCCTT | 1-2-1-1-1-8-2-1-2 | AtaCcTttctttaaCCcTT | 687_4 | -24.41 | 8114 |
| 687 | ATACCTTTCTTTAACCCTT | 1-3-1-11-3 | AtacCtttctttaaccCTT | 687_5 | -22.51 | 8114 |
| 688 | ATACCTTTCTTTAACCCTTT | 1-3-1-8-1-1-1-2-2 | AtacCtttctttaAcCctTT | 688_1 | -22.83 | 8113 |
| 688 | ATACCTTTCTTTAACCCTTT | 1-3-1-9-1-1-1-1-2 | AtacCtttctttaaCcCtTT | 688_2 | -23.41 | 8113 |
| 688 | ATACCTTTCTTTAACCCTTT | 1-4-2-7-1-2-3 | AtaccTTtctttaaCccTTT | 688_3 | -23.98 | 8113 |
| 688 | ATACCTTTCTTTAACCCTTT | 1-1-1-1-1-10-1-1-3 | AtAcCtttctttaacCcTTT | 688_4 | -23.63 | 8113 |
| 688 | ATACCTTTCTTTAACCCTTT | 1-2-1-12-1-1-2 | AtaCctttctttaaccCtTT | 688_5 | -22.52 | 8113 |
| 689 | ATACCTTTCTTTAACCCT | 1-3-2-6-2-2-2 | AtacCTttctttAAccCT | 689_1 | -22.61 | 8115 |
| 689 | ATACCTTTCTTTAACCCT | 1-1-1-1-2-8-1-1-2 | AtAcCTttctttaaCcCT | 689_2 | -22.85 | 8115 |
| 689 | ATACCTTTCTTTAACCCT | 1-2-1-10-1-1-2 | AtaCctttctttaaCcCT | 689_3 | -21.36 | 8115 |
| 689 | ATACCTTTCTTTAACCCT | 1-2-3-10-2 | AtaCCTttctttaaccCT | 689_4 | -24.26 | 8115 |
| 689 | ATACCTTTCTTTAACCCT | 1-3-1-11-2 | AtacCtttctttaaccCT | 689_5 | -20.69 | 8115 |
| 690 | TATACCTTTCTTTAACCCT | 2-2-1-10-1-1-2 | TAtaCctttctttaaCcCT | 690_1 | -23.60 | 8115 |

TABLE 3-continued

List of oligonucleotides or contiguous nucleobase sequences complementary to SEQ ID NO: 1
(motif sequences indicated by SEQ ID NO), oligonucleotide designs made from these, as well as
specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 690 | TATACCTTTCTTTAACCCT | 1-4-1-9-1-1-2 | TatacCtttctttaaCcCT | 690_2 | −22.57 | 8115 |
| 690 | TATACCTTTCTTTAACCCT | 2-3-1-11-2 | TAtacCtttctttaaccCT | 690_3 | −22.92 | 8115 |
| 690 | TATACCTTTCTTTAACCCT | 1-3-1-12-2 | TataCctttctttaaccCT | 690_4 | −21.68 | 8115 |
| 690 | TATACCTTTCTTTAACCCT | 1-4-1-11-2 | TatacCtttctttaaccCT | 690_5 | −21.79 | 8115 |
| 691 | TTATACCTTTCTTTAAC | 4-7-2-2-2 | TTATacctttcTTtaAC | 691_1 | −18.49 | 8118 |
| 691 | TTATACCTTTCTTTAAC | 3-8-1-1-4 | TTAtacctttcTtTAAC | 691_2 | −18.07 | 8118 |
| 692 | TTATACCTTTCTTTAACCC | 2-10-1-1-1-2-2 | TTatacctttctTtAacCC | 692_1 | −21.94 | 8116 |
| 692 | TTATACCTTTCTTTAACCC | 1-1-1-9-1-4-2 | TtAtacctttctTtaacCC | 692_2 | −20.68 | 8116 |
| 692 | TTATACCTTTCTTTAACCC | 1-4-1-7-1-3-2 | TtataCctttcttTaacCC | 692_3 | −21.79 | 8116 |
| 692 | TTATACCTTTCTTTAACCC | 1-3-2-8-2-1-2 | TtatACctttctttAAcCC | 692_4 | −22.39 | 8116 |
| 692 | TTATACCTTTCTTTAACCC | 1-1-1-2-1-9-1-1-2 | TtAtaCctttctttaAcCC | 692_5 | −21.58 | 8116 |
| 693 | TTATACCTTTCTTTAACC | 2-3-1-6-1-3-2 | TTataCctttctTtaaCC | 693_1 | −19.80 | 8117 |
| 693 | TTATACCTTTCTTTAACC | 1-1-1-1-2-6-1-3-2 | TtAtACctttctTtaaCC | 693_2 | −19.25 | 8117 |
| 693 | TTATACCTTTCTTTAACC | 1-3-2-7-2-1-2 | TtatACctttcttTAaCC | 693_3 | −20.74 | 8117 |
| 693 | TTATACCTTTCTTTAACC | 1-1-1-2-1-7-1-2-2 | TtAtaCctttcttTaaCC | 693_4 | −19.08 | 8117 |
| 693 | TTATACCTTTCTTTAACC | 1-2-1-1-1-8-4 | TtaTaCctttctttAACC | 693_5 | −20.26 | 8117 |
| 694 | TTTATACCTTTCTTTAACC | 2-1-1-8-2-3-2 | TTtAtacctttcTTtaaCC | 694_1 | −20.72 | 8117 |
| 694 | TTTATACCTTTCTTTAACC | 1-4-1-6-1-2-4 | TttatAcctttcTttAACC | 694_2 | −20.33 | 8117 |
| 694 | TTTATACCTTTCTTTAACC | 2-11-1-1-1-1-2 | TTtatacctttctTtAaCC | 694_3 | −19.72 | 8117 |
| 694 | TTTATACCTTTCTTTAACC | 1-1-2-9-1-3-2 | TtTAtacctttctTtaaCC | 694_4 | −20.65 | 8117 |
| 694 | TTTATACCTTTCTTTAACC | 1-3-2-7-1-3-2 | TttaTAcctttctTtaaCC | 694_5 | −20.88 | 8117 |
| 695 | TTTATACCTTTCTTTAAC | 3-9-3-1-2 | TTTatacctttcTTTaAC | 695_1 | −18.74 | 8118 |
| 695 | TTTATACCTTTCTTTAAC | 5-7-2-2-2 | TTTATacctttcTTtaAC | 695_2 | −20.31 | 8118 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 695 | TTTATACCTTTCTTTAAC | 1-1-3-7-2-2-2 | TtTATacctttcTTtaAC | 695_3 | −18.98 | 8118 |
| 695 | TTTATACCTTTCTTTAAC | 4-8-1-1-4 | TTTAtacctttcTtTAAC | 695_4 | −19.89 | 8118 |
| 695 | TTTATACCTTTCTTTAAC | 2-3-1-7-5 | TTtatAcctttctTTAAC | 695_5 | −18.02 | 8118 |
| 696 | TTTTATACCTTTCTTTAAC | 2-3-1-6-3-2-2 | TTttaTacctttCTTtaAC | 696_1 | −19.79 | 8118 |
| 696 | TTTTATACCTTTCTTTAAC | 1-1-2-8-2-1-1-1-2 | TtTTatacctttCTtTaAC | 696_2 | −19.57 | 8118 |
| 696 | TTTTATACCTTTCTTTAAC | 2-1-2-7-2-2-3 | TTtTAtacctttCTttAAC | 696_3 | −20.28 | 8118 |
| 696 | TTTTATACCTTTCTTTAAC | 3-9-1-1-5 | TTTtatacctttCtTTAAC | 696_4 | −20.62 | 8118 |
| 696 | TTTTATACCTTTCTTTAAC | 1-1-3-7-1-1-1-2-2 | TtTTAtacctttCtTtaAC | 696_5 | −19.08 | 8118 |
| 697 | TGTACTTTCCTTTACCA | 2-9-1-3-2 | TGtactttcctTtacCA | 697_1 | −20.68 | 11462 |
| 697 | TGTACTTTCCTTTACCA | 1-2-1-7-1-3-2 | TgtActttcctTtacCA | 697_2 | −19.66 | 11462 |
| 697 | TGTACTTTCCTTTACCA | 1-3-1-6-1-3-2 | TgtaCtttcctTtacCA | 697_3 | −20.46 | 11462 |
| 697 | TGTACTTTCCTTTACCA | 2-2-1-8-1-1-2 | TGtaCtttcctttAcCA | 697_4 | −21.56 | 11462 |
| 697 | TGTACTTTCCTTTACCA | 1-3-1-9-3 | TgtaCtttcctttaCCA | 697_5 | −22.54 | 11462 |
| 698 | TTATACACCATCATTAT | 4-7-3-1-2 | TTATacaccatCATtAT | 698_1 | −21.13 | 11506 |
| 698 | TTATACACCATCATTAT | 4-7-2-1-3 | TTATacaccatCAtTAT | 698_2 | −21.64 | 11506 |
| 698 | TTATACACCATCATTAT | 3-8-1-1-4 | TTAtacaccatCaTTAT | 698_3 | −19.45 | 11506 |
| 698 | TTATACACCATCATTAT | 2-1-2-7-5 | TTaTAcaccatcATTAT | 698_4 | −20.61 | 11506 |
| 698 | TTATACACCATCATTAT | 5-9-3 | TTATAcaccatcatTAT | 698_5 | −20.74 | 11506 |
| 699 | TTATACACCATCATTATA | 3-2-1-6-2-2-2 | TTAtaCaccatcATtaTA | 699_1 | −19.38 | 11505 |
| 699 | TTATACACCATCATTATA | 1-2-3-6-1-1-4 | TtaTACaccatcAtTATA | 699_2 | −20.93 | 11505 |
| 699 | TTATACACCATCATTATA | 4-1-1-7-2-1-2 | TTATaCaccatcaTTaTA | 699_3 | −21.44 | 11505 |
| 699 | TTATACACCATCATTATA | 2-1-2-8-1-1-3 | TTaTAcaccatcaTtATA | 699_4 | −19.71 | 11505 |
| 699 | TTATACACCATCATTATA | 3-2-1-8-4 | TTAtaCaccatcatTATA | 699_5 | −20.75 | 11505 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 700 | TTTATACACCATCATTAT | 2-1-2-7-3-1-2 | TTtATacaccatCATtAT | 700_1 | -20.67 | 11506 |
| 700 | TTTATACACCATCATTAT | 3-1-1-7-2-1-3 | TTTaTacaccatCAtTAT | 700_2 | -21.52 | 11506 |
| 700 | TTTATACACCATCATTAT | 1-3-2-6-2-1-3 | TttaTAcaccatCAtTAT | 700_3 | -20.70 | 11506 |
| 700 | TTTATACACCATCATTAT | 1-1-3-8-1-1-3 | TtTATacaccatcAtTAT | 700_4 | -20.05 | 11506 |
| 700 | TTTATACACCATCATTAT | 3-1-1-9-4 | TTTaTacaccatcaTTAT | 700_5 | -20.34 | 11506 |
| 701 | TTTATACACCATCATTATA | 4-8-1-1-2-1-2 | TTTAtacaccatCaTTaTA | 701_1 | -21.57 | 11505 |
| 701 | TTTATACACCATCATTATA | 2-2-1-7-1-2-4 | TTtaTacaccatCatTATA | 701_2 | -21.05 | 11505 |
| 701 | TTTATACACCATCATTATA | 1-1-1-1-1-8-2-1-3 | TtTaTacaccatcATtATA | 701_3 | -19.83 | 11505 |
| 701 | TTTATACACCATCATTATA | 2-2-2-7-2-2-2 | TTtaTAcaccatcATtaTA | 701_4 | -20.24 | 11505 |
| 701 | TTTATACACCATCATTATA | 1-1-3-10-1-1-2 | TtTATacaccatcatTaTA | 701_5 | -20.30 | 11505 |
| 702 | ATTTATACACCATCATTAT | 1-1-1-2-1-7-3-1-2 | AtTtaTacaccatCATtAT | 702_1 | -20.07 | 11506 |
| 702 | ATTTATACACCATCATTAT | 1-1-2-1-1-7-2-2-2 | AtTTaTacaccatCAttAT | 702_2 | -20.07 | 11506 |
| 702 | ATTTATACACCATCATTAT | 2-1-2-8-1-1-1-1-2 | ATTAtacaccatCaTtAT | 702_3 | -19.74 | 11506 |
| 702 | ATTTATACACCATCATTAT | 2-3-1-7-1-2-3 | ATttaTacaccatCatTAT | 702_4 | -20.07 | 11506 |
| 702 | ATTTATACACCATCATTAT | 1-1-1-1-1-10-4 | AtTtAtacaccatcaTTAT | 702_5 | -18.64 | 11506 |
| 703 | ATTTATACACCATCATTATA | 1-4-1-7-1-2-4 | AtttaTacaccatCatTATA | 703_1 | -21.05 | 11505 |
| 703 | ATTTATACACCATCATTATA | 2-1-1-2-1-7-2-2-2 | ATtTatAcaccatcATtaTA | 703_2 | -20.32 | 11505 |
| 703 | ATTTATACACCATCATTATA | 1-1-1-2-1-8-1-1-1-1-2 | AtTtaTacaccatcAtTaTA | 703_3 | -18.80 | 11505 |
| 703 | ATTTATACACCATCATTATA | 1-2-3-8-1-1-1-1-2 | AttTATacaccatcAtTaTA | 703_4 | -21.17 | 11505 |
| 703 | ATTTATACACCATCATTATA | 3-1-1-9-1-2-3 | ATTtAtacaccatcAttATA | 703_5 | -19.97 | 11505 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 704 | TATTTATACACCATCATTA | 1-2-3-6-2-3-2 | TatTTAtacaccATcatTA | 704_1 | -20.37 | 11507 |
| 704 | TATTTATACACCATCATTA | 4-8-1-1-2-1-2 | TATTtatacaccAtCAtTA | 704_2 | -21.70 | 11507 |
| 704 | TATTTATACACCATCATTA | 1-1-1-1-1-7-1-1-1-1-3 | TaTtTatacaccAtCaTTA | 704_3 | -19.16 | 11507 |
| 704 | TATTTATACACCATCATTA | 2-2-1-8-2-2-2 | TAttTatacaccaTCatTA | 704_4 | -19.98 | 11507 |
| 704 | TATTTATACACCATCATTA | 2-2-1-10-4 | TAttTatacaccatcATTA | 704_5 | -19.99 | 11507 |
| 705 | TATTTATACACCATCATTAT | 2-2-1-1-1-7-2-2-2 | TAttTaTacaccatCAttAT | 705_1 | -21.49 | 11506 |
| 705 | TATTTATACACCATCATTAT | 2-1-1-10-1-1-4 | TAtTtatacaccatCaTTAT | 705_2 | -21.44 | 11506 |
| 705 | TATTTATACACCATCATTAT | 1-1-1-2-1-8-1-1-1-1-2 | TaTttAtacaccatCaTtAT | 705_3 | -18.27 | 11506 |
| 705 | TATTTATACACCATCATTAT | 2-1-2-9-1-3-2 | TAtTTatacaccatCattAT | 705_4 | -19.97 | 11506 |
| 705 | TATTTATACACCATCATTAT | 1-2-3-9-1-1-3 | TatTTAtacaccatcAtTAT | 705_5 | -21.11 | 11506 |
| 706 | TTATTTATACACCATCATTA | 2-3-1-7-1-1-1-1-3 | TTattTatacaccAtCaTTA | 706_1 | -20.54 | 11507 |
| 706 | TTATTTATACACCATCATTA | 1-1-2-1-1-7-1-2-4 | TtATtTatacaccAtcATTA | 706_2 | -20.84 | 11507 |
| 706 | TTATTTATACACCATCATTA | 1-1-1-2-1-8-2-2-2 | TtAttTatacaccaTCatTA | 706_3 | -19.52 | 11507 |
| 706 | TTATTTATACACCATCATTA | 1-2-3-8-1-1-1-1-2 | TtaTTTatacaccaTcAtTA | 706_4 | -19.96 | 11507 |
| 706 | TTATTTATACACCATCATTA | 3-1-1-11-1-1-2 | TTAtTtatacaccatcAtTA | 706_5 | -19.63 | 11507 |
| 707 | ATTATTTATACACCATCAT | 2-2-2-6-3-2-2 | ATtaTTtatacaCCAtcAT | 707_1 | -22.41 | 11509 |
| 707 | ATTATTTATACACCATCAT | 2-3-1-6-1-2-4 | ATtatTtatacaCcaTCAT | 707_2 | -21.02 | 11509 |
| 707 | ATTATTTATACACCATCAT | 1-1-1-1-1-8-3-1-2 | AtTaTttatacacCATcAT | 707_3 | -20.01 | 11509 |
| 707 | ATTATTTATACACCATCAT | 1-1-2-1-1-7-1-2-3 | AtTAtTtatacacCatCAT | 707_4 | -20.30 | 11509 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 707 | ATTATTTATACACCATCAT | 2-1-2-9-1-1-3 | ATtATttatacaccAtCAT | 707_5 | -20.20 | 11509 |
| 708 | ATTATTTATACACCATCA | 2-2-2-6-2-2-2 | ATtaTTtatacaCCatCA | 708_1 | -20.96 | 11510 |
| 708 | ATTATTTATACACCATCA | 3-1-1-7-1-1-4 | ATTaTttatacaCcATCA | 708_2 | -21.19 | 11510 |
| 708 | ATTATTTATACACCATCA | 1-1-3-7-1-3-2 | AtTATttatacaCcatCA | 708_3 | -19.39 | 11510 |
| 708 | ATTATTTATACACCATCA | 1-1-1-2-1-7-2-1-2 | AtTatTtatacacCAtCA | 708_4 | -18.57 | 11510 |
| 708 | ATTATTTATACACCATCA | 2-1-2-8-1-1-3 | ATtATttatacacCaTCA | 708_5 | -19.79 | 11510 |
| 709 | ATTATTTATACACCATCATT | 1-2-3-7-1-1-2-1-2 | AttATTtatacacCaTCaTT | 709_1 | -20.97 | 11508 |
| 709 | ATTATTTATACACCATCATT | 1-1-1-2-2-6-1-4-2 | AtTatTTatacacCatcaTT | 709_2 | -19.29 | 11508 |
| 709 | ATTATTTATACACCATCATT | 1-1-1-2-1-8-2-1-3 | AtTatTtatacaccATcATT | 709_3 | -19.70 | 11508 |
| 709 | ATTATTTATACACCATCATT | 3-1-1-9-1-1-1-1-2 | ATTaTttatacaccAtCaTT | 709_4 | -20.09 | 11508 |
| 709 | ATTATTTATACACCATCATT | 2-1-2-1-1-7-1-2-3 | ATtATtTatacaccAtcATT | 709_5 | -20.67 | 11508 |
| 710 | ATTATTTATACACCATC | 5-6-3-1-2 | ATTATttatacACCaTC | 710_1 | -21.70 | 11511 |
| 710 | ATTATTTATACACCATC | 5-6-2-1-3 | ATTATttatacACcATC | 710_2 | -20.38 | 11511 |
| 710 | ATTATTTATACACCATC | 2-2-1-7-5 | ATtaTttatacaCCATC | 710_3 | -20.25 | 11511 |
| 710 | ATTATTTATACACCATC | 1-1-2-8-5 | AtTAtttatacaCCATC | 710_4 | -20.42 | 11511 |
| 710 | ATTATTTATACACCATC | 5-8-4 | ATTATttatacacCATC | 710_5 | -21.04 | 11511 |
| 711 | AATTATTTATACACCATC | 2-2-2-6-3-1-2 | AAttATttatacACCaTC | 711_1 | -18.93 | 11511 |
| 711 | AATTATTTATACACCATC | 2-1-3-6-1-1-4 | AAtTATttatacAcCATC | 711_2 | -20.18 | 11511 |
| 711 | AATTATTTATACACCATC | 4-1-1-7-5 | AATTaTttatacaCCATC | 711_3 | -22.24 | 11511 |
| 711 | AATTATTTATACACCATC | 2-1-2-8-5 | AAtTAtttatacaCCATC | 711_4 | -21.17 | 11511 |
| 711 | AATTATTTATACACCATC | 1-1-4-7-2-1-2 | AaTTATttatacaCCaTC | 711_5 | -20.58 | 11511 |
| 712 | AATTATTTATACACCATCA | 1-2-1-1-1-6-3-2-2 | AatTaTttatacACCatCA | 712_1 | -20.42 | 11510 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 712 | AATTATTTATACACCATCA | 2-2-1-7-1-1-2-1-2 | AAttAtttatacAcCAtCA | 712_2 | −18.54 | 11510 |
| 712 | AATTATTTATACACCATCA | 1-1-3-7-1-2-4 | AaTTAtttatacAccATCA | 712_3 | −20.67 | 11510 |
| 712 | AATTATTTATACACCATCA | 2-1-2-8-2-1-3 | AAtTAtttatacaCCaTCA | 712_4 | −22.20 | 11510 |
| 712 | AATTATTTATACACCATCA | 3-1-1-8-1-2-3 | AATtAtttatacaCcaTCA | 712_5 | −19.50 | 11510 |
| 713 | AAATTATTTATACACCATC | 3-2-1-6-3-1-3 | AAAttAtttataCACcATC | 713_1 | −19.21 | 11511 |
| 713 | AAATTATTTATACACCATC | 1-2-3-6-3-2-2 | AaaTTAtttataCACcaTC | 713_2 | −20.01 | 11511 |
| 713 | AAATTATTTATACACCATC | 1-1-3-7-2-1-4 | AaATTatttataCAcCATC | 713_3 | −21.68 | 11511 |
| 713 | AAATTATTTATACACCATC | 2-1-2-7-1-1-2-1-2 | AAaTTatttataCaCCaTC | 713_4 | −19.63 | 11511 |
| 713 | AAATTATTTATACACCATC | 1-1-2-1-1-8-5 | AaATtAtttatacaCCATC | 713_5 | −20.67 | 11511 |
| 714 | AAATTATTTATACACCAT | 1-1-4-6-2-1-3 | AaATTAtttataCAcCAT | 714_1 | −20.31 | 11512 |
| 714 | AAATTATTTATACACCAT | 2-2-2-6-1-1-4 | AAatTAtttataCaCCAT | 714_2 | −19.59 | 11512 |
| 714 | AAATTATTTATACACCAT | 1-1-3-7-1-1-4 | AaATTatttataCaCCAT | 714_3 | −20.00 | 11512 |
| 714 | AAATTATTTATACACCAT | 4-9-5 | AAATtatttatacACCAT | 714_4 | −19.36 | 11512 |
| 714 | AAATTATTTATACACCAT | 3-1-2-7-5 | AAAtTAtttatacACCAT | 714_5 | −19.98 | 11512 |
| 715 | AAAATTATTTATACACCAT | 2-1-2-7-3-1-3 | AAaATtatttatACAcCAT | 715_1 | −19.29 | 11512 |
| 715 | AAAATTATTTATACACCAT | 1-3-2-6-2-1-4 | AaaaTTatttatACaCCAT | 715_2 | −19.68 | 11512 |
| 715 | AAAATTATTTATACACCAT | 3-2-1-6-1-1-5 | AAAatTatttatAcACCAT | 715_3 | −19.27 | 11512 |
| 715 | AAAATTATTTATACACCAT | 1-1-4-7-1-1-4 | AaAATTatttataCaCCAT | 715_4 | −20.75 | 11512 |
| 715 | AAAATTATTTATACACCAT | 2-1-2-9-5 | AAaATtatttatacACCAT | 715_5 | −19.38 | 11512 |
| 716 | TAAAATTATTTATACACC | 2-1-3-6-3-1-2 | TAaAATtattta TACaCC | 716_1 | −18.88 | 11514 |
| 716 | TAAAATTATTTATACACC | 3-1-2-7-5 | TAAaATtatttatACACC | 716_2 | −18.95 | 11514 |
| 716 | TAAAATTATTTATACACC | 1-1-4-7-5 | TaAAATtatttatACACC | 716_3 | −18.33 | 11514 |
| 716 | TAAAATTATTTATACACC | 3-1-2-8-4 | TAAaATtatttataCACC | 716_4 | −18.35 | 11514 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 716 | TAAAATTATTTATACACC | 2-1-3-8-4 | TAaAATtatttataCACC | 716_5 | -18.35 | 11514 |
| 717 | GTAAAATTATTTATACACC | 2-1-3-6-4-1-2 | GTaAAAttatttATACaCC | 717_1 | -21.68 | 11514 |
| 717 | GTAAAATTATTTATACACC | 3-2-1-6-2-2-3 | GTAaaAttatttATacACC | 717_2 | -20.00 | 11514 |
| 717 | GTAAAATTATTTATACACC | 3-1-2-7-2-1-3 | GTAaAAttatttaTAcACC | 717_3 | -20.86 | 11514 |
| 717 | GTAAAATTATTTATACACC | 2-1-3-7-1-1-4 | GTaAAAttatttaTaCACC | 717_4 | -21.11 | 11514 |
| 717 | GTAAAATTATTTATACACC | 4-1-1-8-5 | GTAAaAttatttatACACC | 717_5 | -21.46 | 11514 |
| 718 | GTAAAATTATTTATACAC | 4-1-1-7-5 | GTAAaAttatttaTACAC | 718_1 | -18.17 | 11515 |
| 718 | GTAAAATTATTTATACAC | 3-1-2-7-5 | GTAaAAttatttaTACAC | 718_2 | -18.17 | 11515 |
| 719 | GAGTATATTACCTCCA | 3-10-3 | GAGtatattacctCCA | 719_1 | -22.56 | 15162 |
| 719 | GAGTATATTACCTCCA | 2-1-1-9-3 | GAgTatattacctCCA | 719_2 | -22.24 | 15162 |
| 719 | GAGTATATTACCTCCA | 2-11-3 | GAgtatattacctCCA | 719_3 | -21.15 | 15162 |
| 719 | GAGTATATTACCTCCA | 1-1-3-8-3 | GaGTAtattacctCCA | 719_4 | -22.93 | 15162 |
| 719 | GAGTATATTACCTCCA | 5-9-2 | GAGTAtattacctcCA | 719_5 | -23.29 | 15162 |
| 720 | CTTTTCTATAATCTCAC | 2-2-1-6-3-1-2 | CTttTctataaTCTcAC | 720_1 | -18.54 | 30553 |
| 720 | CTTTTCTATAATCTCAC | 3-8-2-1-3 | CTTttctataaTCtCAC | 720_2 | -19.80 | 30553 |
| 720 | CTTTTCTATAATCTCAC | 1-1-3-6-1-1-4 | CtTTTctataaTcTCAC | 720_3 | -19.40 | 30553 |
| 720 | CTTTTCTATAATCTCAC | 4-8-5 | CTTTtctataatCTCAC | 720_4 | -21.37 | 30553 |
| 720 | CTTTTCTATAATCTCAC | 1-3-1-7-5 | CtttTctataatCTCAC | 720_5 | -18.92 | 30553 |
| 721 | CTTTTCTATAATCTCACA | 2-3-1-6-1-1-1-1-2 | CTtttCtataatCtCaCA | 721_1 | -20.17 | 30552 |
| 721 | CTTTTCTATAATCTCACA | 1-1-1-1-2-6-1-2-3 | CtTtTCtataatCtcACA | 721_2 | -20.15 | 30552 |
| 721 | CTTTTCTATAATCTCACA | 1-2-1-1-1-7-2-1-2 | CttTtCtataatcTCaCA | 721_3 | -19.50 | 30552 |
| 721 | CTTTTCTATAATCTCACA | 1-1-3-8-1-1-3 | CtTTTctataatcTcACA | 721_4 | -19.49 | 30552 |
| 721 | CTTTTCTATAATCTCACA | 3-2-1-8-4 | CTTttCtataatctCACA | 721_5 | -21.97 | 30552 |
| 722 | TCTTTTCTATAATCTCACA | 1-1-3-7-1-1-1-1-3 | TcTTTtctataaTcTcACA | 722_1 | -21.04 | 30552 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 722 | TCTTTTCTATAATCTCACA | 1-4-1-6-1-2-1-1-2 | TctttTctataaTctCaCA | 722_2 | -18.81 | 30552 |
| 722 | TCTTTTCTATAATCTCACA | 2-2-1-8-1-2-3 | TCttTtctataatCtcACA | 722_3 | -20.68 | 30552 |
| 722 | TCTTTTCTATAATCTCACA | 2-1-1-9-1-3-2 | TCtTttctataatCtcaCA | 722_4 | -20.13 | 30552 |
| 722 | TCTTTTCTATAATCTCACA | 2-13-1-1-2 | TCttttctataatctCaCA | 722_5 | -19.52 | 30552 |
| 723 | TCTTTTCTATAATCTCAC | 2-1-1-8-2-2-2 | TCtTttctataaTCtcAC | 723_1 | -18.51 | 30553 |
| 723 | TCTTTTCTATAATCTCAC | 3-10-1-1-3 | TCTtttctataatCtCAC | 723_2 | -20.36 | 30553 |
| 723 | TCTTTTCTATAATCTCAC | 1-2-3-7-1-1-3 | TctTTTctataatCtCAC | 723_3 | -19.57 | 30553 |
| 723 | TCTTTTCTATAATCTCAC | 2-2-2-8-4 | TCttTTctataatcTCAC | 723_4 | -20.57 | 30553 |
| 723 | TCTTTTCTATAATCTCAC | 1-1-4-8-4 | TcTTTTctataatcTCAC | 723_5 | -20.82 | 30553 |
| 724 | ATCTTTTCTATAATCTCACA | 1-1-1-1-1-9-1-1-1-1-2 | AtCtTttctataatCtCaCA | 724_1 | -20.93 | 30552 |
| 724 | ATCTTTTCTATAATCTCACA | 1-1-1-11-1-2-3 | AtCttttctataatCtcACA | 724_2 | -20.51 | 30552 |
| 724 | ATCTTTTCTATAATCTCACA | 1-2-1-1-1-8-1-2-3 | AtcTtTtctataatCtcACA | 724_3 | -20.35 | 30552 |
| 724 | ATCTTTTCTATAATCTCACA | 1-3-2-8-1-3-2 | AtctTTtctataatCtcaCA | 724_4 | -20.10 | 30552 |
| 724 | ATCTTTTCTATAATCTCACA | 1-1-1-2-1-10-1-1-2 | AtCttTtctataatctCaCA | 724_5 | -19.95 | 30552 |
| 725 | ATCTTTTCTATAATCTCAC | 1-1-1-9-1-1-1-1-3 | AtCttttctataAtCtCAC | 725_1 | -19.62 | 30553 |
| 725 | ATCTTTTCTATAATCTCAC | 1-2-2-7-1-1-1-1-3 | AtcTTttctataAtCtCAC | 725_2 | -19.97 | 30553 |
| 725 | ATCTTTTCTATAATCTCAC | 1-1-2-1-1-7-2-2-2 | AtCTtTtctataaTCtcAC | 725_3 | -19.83 | 30553 |
| 725 | ATCTTTTCTATAATCTCAC | 1-2-1-1-1-9-4 | AtcTtTtctataatcTCAC | 725_4 | -19.36 | 30553 |
| 725 | ATCTTTTCTATAATCTCAC | 3-13-3 | ATCttttctataatctCAC | 725_5 | -20.25 | 30553 |
| 726 | ATCTTTTCTATAATCTCA | 1-1-2-8-1-1-1-1-2 | AtCTtttctataAtCtCA | 726_1 | -18.77 | 30554 |
| 726 | ATCTTTTCTATAATCTCA | 3-1-1-7-1-2-3 | ATCtTttctataAtcTCA | 726_2 | -20.03 | 30554 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 726 | ATCTTTTCTATAATCTCA | 3-10-2-1-2 | ATCttttctataaTCtCA | 726_3 | -20.31 | 30554 |
| 726 | ATCTTTTCTATAATCTCA | 1-1-1-1-2-7-2-1-2 | AtCtTTtctataaTCtCA | 726_4 | -19.49 | 30554 |
| 726 | ATCTTTTCTATAATCTCA | 1-1-3-9-4 | AtCTTttctataatCTCA | 726_5 | -21.14 | 30554 |
| 727 | CATCTTTTCTATAATCTCAC | 2-11-1-1-1-2-2 | CAtcttttctataAtCtcAC | 727_1 | -19.86 | 30553 |
| 727 | CATCTTTTCTATAATCTCAC | 1-1-2-9-1-1-1-2-2 | CaTCttttctataAtCtcAC | 727_2 | -20.49 | 30553 |
| 727 | CATCTTTTCTATAATCTCAC | 1-3-1-1-1-8-1-1-3 | CatcTtTtctataatCtCAC | 727_3 | -20.97 | 30553 |
| 727 | CATCTTTTCTATAATCTCAC | 1-2-1-1-1-9-1-2-2 | CatCtTttctataatCtcAC | 727_4 | -19.35 | 30553 |
| 727 | CATCTTTTCTATAATCTCAC | 2-1-1-2-1-10-3 | CAtCttTtctataatctCAC | 727_5 | -21.92 | 30553 |
| 728 | CATCTTTTCTATAATCTCA | 1-3-1-7-2-1-1-1-2 | CatcTtttctatAAtCtCA | 728_1 | -19.26 | 30554 |
| 728 | CATCTTTTCTATAATCTCA | 2-3-1-6-2-2-3 | CAtctTttctatAAtcTCA | 728_2 | -20.74 | 30554 |
| 728 | CATCTTTTCTATAATCTCA | 1-2-1-8-1-2-1-1-2 | CatCttttctatAatCtCA | 728_3 | -19.21 | 30554 |
| 728 | CATCTTTTCTATAATCTCA | 2-1-1-1-1-9-1-1-2 | CAtCtTttctataatCtCA | 728_4 | -20.86 | 30554 |
| 728 | CATCTTTTCTATAATCTCA | 1-1-2-13-2 | CaTCttttctataatctCA | 728_5 | -19.23 | 30554 |
| 729 | TCATCTTTTCTATAATCTCA | 1-1-1-2-1-7-2-1-1-1-2 | TcAtcTtttctatAAtCtCA | 729_1 | -20.53 | 30554 |
| 729 | TCATCTTTTCTATAATCTCA | 2-4-1-6-2-3-2 | TCatctTttctatAAtctCA | 729_2 | -20.57 | 30554 |
| 729 | TCATCTTTTCTATAATCTCA | 2-2-1-8-1-2-1-1-2 | TCatCttttctatAatCtCA | 729_3 | -21.70 | 30554 |
| 729 | TCATCTTTTCTATAATCTCA | 3-13-1-1-2 | TCAtcttttctataatCtCA | 729_4 | -22.07 | 30554 |
| 729 | TCATCTTTTCTATAATCTCA | 3-1-1-13-2 | TCAtCttttctataatctCA | 729_5 | -22.07 | 30554 |
| 730 | TCATCTTTTCTATAATCTC | 3-2-1-7-2-2-2 | TCAtcTtttctatAAtcTC | 730_1 | -20.15 | 30555 |
| 730 | TCATCTTTTCTATAATCTC | 3-1-1-8-1-3-2 | TCAtCttttctatAatcTC | 730_2 | -20.09 | 30555 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 730 | TCATCTTTTCTATAATCTC | 2-2-1-9-1-2-2 | TCatCttttctataAtcTC | 730_3 | -18.83 | 30555 |
| 730 | TCATCTTTTCTATAATCTC | 3-13-3 | TCAtcttttctataatCTC | 730_4 | -20.65 | 30555 |
| 730 | TCATCTTTTCTATAATCTC | 2-2-2-10-3 | TCatCTtttctataatCTC | 730_5 | -21.35 | 30555 |
| 731 | GTCATCTTTTCTATAATC | 1-1-1-2-1-6-3-1-2 | GtCatCttttctATAaTC | 731_1 | -19.76 | 30557 |
| 731 | GTCATCTTTTCTATAATC | 1-1-1-1-2-6-1-2-3 | GtCaTCttttctAtaATC | 731_2 | -19.19 | 30557 |
| 731 | GTCATCTTTTCTATAATC | 4-9-1-2-2 | GTCAtcttttctaTaaTC | 731_3 | -20.42 | 30557 |
| 731 | GTCATCTTTTCTATAATC | 3-2-1-8-4 | GTCatCttttctatAATC | 731_4 | -20.51 | 30557 |
| 731 | GTCATCTTTTCTATAATC | 1-1-4-10-2 | GtCATCttttctataaTC | 731_5 | -20.23 | 30557 |
| 732 | TGTCATCTTTTCTATAAT | 2-1-1-8-2-1-3 | TGtCatcttttcTAtAAT | 732_1 | -19.36 | 30558 |
| 732 | TGTCATCTTTTCTATAAT | 2-1-2-7-2-2-2 | TGtCAtcttttcTAtaAT | 732_2 | -20.51 | 30558 |
| 732 | TGTCATCTTTTCTATAAT | 1-1-3-7-1-3-2 | TgTCAtcttttcTataAT | 732_3 | -19.51 | 30558 |
| 732 | TGTCATCTTTTCTATAAT | 4-10-4 | TGTCatcttttctaTAAT | 732_4 | -21.42 | 30558 |
| 732 | TGTCATCTTTTCTATAAT | 2-2-1-9-4 | TGtcAtcttttctaTAAT | 732_5 | -18.57 | 30558 |
| 733 | ACTTAATTATACTTCCA | 5-6-2-2-2 | ACTTAattataCTtcCA | 733_1 | -21.55 | 30664 |
| 733 | ACTTAATTATACTTCCA | 2-1-2-6-1-2-3 | ACtTAattataCttCCA | 733_2 | -21.02 | 30664 |
| 733 | ACTTAATTATACTTCCA | 1-2-2-7-5 | ActTAattatacTTCCA | 733_3 | -20.65 | 30664 |
| 733 | ACTTAATTATACTTCCA | 4-8-1-1-3 | ACTTaattatacTtCCA | 733_4 | -21.09 | 30664 |
| 733 | ACTTAATTATACTTCCA | 1-1-1-1-1-8-4 | AcTtAattatactTCCA | 733_5 | -18.37 | 30664 |
| 734 | CACTTAATTATACTTCC | 2-1-2-6-2-2-2 | CACTTaattatACttCC | 734_1 | -20.10 | 30665 |
| 734 | CACTTAATTATACTTCC | 5-6-1-2-3 | CACTTaattatActTCC | 734_2 | -21.76 | 30665 |
| 734 | CACTTAATTATACTTCC | 1-1-1-1-1-7-2-1-2 | CaCtTaattataCTtCC | 734_3 | -19.09 | 30665 |
| 734 | CACTTAATTATACTTCC | 1-1-3-7-1-1-3 | CaCTTaattataCtTCC | 734_4 | -20.59 | 30665 |
| 734 | CACTTAATTATACTTCC | 2-1-2-8-4 | CACTTaattatacTTCC | 734_5 | -20.52 | 30665 |
| 735 | CACTTAATTATACTTCCA | 2-2-1-7-2-1-3 | CActTaattataCTtCCA | 735_1 | -22.96 | 30664 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 735 | CACTTAATTATACTTCCA | 2-1-1-1-1-6-1-3-2 | CAcTtAattataCttcCA | 735_2 | -19.31 | 30664 |
| 735 | CACTTAATTATACTTCCA | 1-1-3-8-1-1-3 | CaCTTaattatacTtCCA | 735_3 | -22.43 | 30664 |
| 735 | CACTTAATTATACTTCCA | 1-1-1-1-2-7-1-2-2 | CaCtTAattatacTtcCA | 735_4 | -19.51 | 30664 |
| 735 | CACTTAATTATACTTCCA | 2-2-1-9-4 | CActTaattatactTCCA | 735_5 | -21.76 | 30664 |
| 736 | ACACTTAATTATACTTCCA | 1-1-2-1-1-6-2-3-2 | AcACtTaattatACttcCA | 736_1 | -20.93 | 30664 |
| 736 | ACACTTAATTATACTTCCA | 2-2-1-7-1-1-1-2-2 | ACacTtaattatAcTtcCA | 736_2 | -19.38 | 30664 |
| 736 | ACACTTAATTATACTTCCA | 1-1-1-1-1-8-1-2-3 | AcAcTtaattataCttCCA | 736_3 | -21.10 | 30664 |
| 736 | ACACTTAATTATACTTCCA | 1-1-1-2-1-9-4 | AcActTaattatactTCCA | 736_4 | -21.31 | 30664 |
| 736 | ACACTTAATTATACTTCCA | 2-2-2-11-2 | ACacTTaattatacttcCA | 736_5 | -19.91 | 30664 |
| 737 | ACACTTAATTATACTTCC | 1-3-1-7-2-1-3 | AcacTtaattatACtTCC | 737_1 | -19.24 | 30665 |
| 737 | ACACTTAATTATACTTCC | 1-1-1-1-2-6-2-2-2 | AcAcTTaattatACttCC | 737_2 | -19.64 | 30665 |
| 737 | ACACTTAATTATACTTCC | 2-1-2-7-1-1-1-1-2 | ACaCTtaattatAcTtCC | 737_3 | -20.12 | 30665 |
| 737 | ACACTTAATTATACTTCC | 3-2-1-8-4 | ACActTaattatacTTCC | 737_4 | -21.53 | 30665 |
| 737 | ACACTTAATTATACTTCC | 1-1-2-1-1-9-3 | AcACtTaattatactTCC | 737_5 | -19.40 | 30665 |
| 738 | ACACTTAATTATACTTC | 5-7-5 | ACACTtaattatACTTC | 738_1 | -20.47 | 30666 |
| 738 | ACACTTAATTATACTTC | 3-1-1-7-5 | ACAcTtaattatACTTC | 738_2 | -18.40 | 30666 |
| 738 | ACACTTAATTATACTTC | 2-1-2-7-5 | ACaCTtaattatACTTC | 738_3 | -18.51 | 30666 |
| 738 | ACACTTAATTATACTTC | 5-7-2-1-2 | ACACTtaattatACtTC | 738_4 | -18.77 | 30666 |
| 738 | ACACTTAATTATACTTC | 5-7-1-1-3 | ACACTtaattatAcTTC | 738_5 | -18.40 | 30666 |
| 738 | ACACTTAATTATACTTC | 5-8-4 | ACACTtaattataCTTC | 738_6 | -19.88 | 30666 |
| 739 | TACACTTAATTATACTTCC | 3-2-1-7-2-2-2 | TACacTtaattatACttCC | 739_1 | -21.57 | 30665 |
| 739 | TACACTTAATTATACTTCC | 1-4-1-7-1-1-4 | TacacTtaattatAcTTCC | 739_2 | -19.87 | 30665 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 739 | TACACTTAATTATACTTCC | 1-2-3-8-1-2-2 | TacACTtaattataCttCC | 739_3 | -20.88 | 30665 |
| 739 | TACACTTAATTATACTTCC | 4-11-4 | TACActtaattatacTTCC | 739_4 | -23.04 | 30665 |
| 739 | TACACTTAATTATACTTCC | 2-1-1-1-1-10-3 | TAcAcTtaattatactTCC | 739_5 | -20.03 | 30665 |
| 740 | TACACTTAATTATACTTC | 4-1-1-7-5 | TACAcTtaattatACTTC | 740_1 | -20.63 | 30666 |
| 740 | TACACTTAATTATACTTC | 3-1-2-7-5 | TACaCTtaattatACTTC | 740_2 | -20.74 | 30666 |
| 740 | TACACTTAATTATACTTC | 2-1-3-7-5 | TAcACTtaattatACTTC | 740_3 | -20.21 | 30666 |
| 740 | TACACTTAATTATACTTC | 3-1-2-8-4 | TACaCTtaattataCTTC | 740_4 | -20.14 | 30666 |
| 740 | TACACTTAATTATACTTC | 1-1-4-8-4 | TaCACTtaattataCTTC | 740_5 | -20.48 | 30666 |
| 741 | TTACACTTAATTATACTTC | 2-1-2-7-4-1-2 | TTaCActtaattATACtTC | 741_1 | -21.41 | 30666 |
| 741 | TTACACTTAATTATACTTC | 5-7-3-1-3 | TTACActtaattATAcTTC | 741_2 | -22.67 | 30666 |
| 741 | TTACACTTAATTATACTTC | 4-1-1-6-2-1-4 | TTACaCttaattATaCTTC | 741_3 | -22.54 | 30666 |
| 741 | TTACACTTAATTATACTTC | 2-1-2-7-2-1-4 | TTaCActtaattATaCTTC | 741_4 | -21.48 | 30666 |
| 741 | TTACACTTAATTATACTTC | 5-7-1-1-5 | TTACActtaattAtACTTC | 741_5 | -22.04 | 30666 |
| 742 | TTACACTTAATTATACTT | 5-7-3-1-2 | TTACActtaattATAcTT | 742_1 | -20.18 | 30667 |
| 742 | TTACACTTAATTATACTT | 5-7-2-1-3 | TTACActtaattATaCTT | 742_2 | -20.62 | 30667 |
| 742 | TTACACTTAATTATACTT | 5-7-1-1-4 | TTACActtaattAtACTT | 742_3 | -19.54 | 30667 |
| 743 | TTTACACTTAATTATACTT | 4-1-1-6-4-1-2 | TTTAcActtaatTATAcTT | 743_1 | -21.26 | 30667 |
| 743 | TTTACACTTAATTATACTT | 3-1-2-6-3-1-3 | TTTaCActtaatTATaCTT | 743_2 | -22.57 | 30667 |
| 743 | TTTACACTTAATTATACTT | 4-8-2-1-4 | TTTAcacttaatTAtACTT | 743_3 | -20.48 | 30667 |
| 743 | TTTACACTTAATTATACTT | 1-1-4-6-2-2-3 | TtTACActtaatTAtaCTT | 743_4 | -21.20 | 30667 |
| 743 | TTTACACTTAATTATACTT | 2-2-2-6-1-1-5 | TTtaCActtaatTaTACTT | 743_5 | -21.02 | 30667 |
| 744 | TTTACACTTAATTATACT | 3-1-2-6-3-1-2 | TTTaCActtaatTATaCT | 744_1 | -20.75 | 30668 |
| 744 | TTTACACTTAATTATACT | 1-1-4-6-3-1-2 | TtTACActtaatTATaCT | 744_2 | -21.06 | 30668 |
| 744 | TTTACACTTAATTATACT | 2-1-3-6-2-1-3 | TTtACActtaatTAtACT | 744_3 | -19.03 | 30668 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 744 | TTTACACTTAATTATACT | 4-8-1-1-4 | TTTAcacttaatTaTACT | 744_4 | -19.42 | 30668 |
| 744 | TTTACACTTAATTATACT | 1-1-1-1-2-6-1-1-4 | TtTaCActtaatTaTACT | 744_5 | -19.12 | 30668 |
| 745 | ATTTACACTTAATTATACT | 4-1-1-6-4-1-2 | ATTTaCacttaaTTATaCT | 745_1 | -22.20 | 30668 |
| 745 | ATTTACACTTAATTATACT | 2-1-3-6-3-1-3 | ATtTACacttaaTTAtACT | 745_2 | -21.43 | 30668 |
| 745 | ATTTACACTTAATTATACT | 5-7-2-1-4 | ATTTAcacttaaTTaTACT | 745_3 | -22.44 | 30668 |
| 745 | ATTTACACTTAATTATACT | 1-2-3-6-2-1-4 | AttTACacttaaTTaTACT | 745_4 | -20.95 | 30668 |
| 745 | ATTTACACTTAATTATACT | 3-1-2-6-1-1-5 | ATTtACacttaaTtATACT | 745_5 | -20.92 | 30668 |
| 746 | ATTTACACTTAATTATAC | 5-8-5 | ATTTAcacttaatTATAC | 746_1 | -19.94 | 30669 |
| 746 | ATTTACACTTAATTATAC | 4-1-1-7-5 | ATTTaCacttaatTATAC | 746_2 | -19.40 | 30669 |
| 746 | ATTTACACTTAATTATAC | 2-1-3-7-5 | ATTACacttaatTATAC | 746_3 | -19.70 | 30669 |
| 747 | AATTTACACTTAATTATAC | 3-1-2-6-3-1-3 | AATtTAcacttaATTaTAC | 747_1 | -19.51 | 30669 |
| 747 | AATTTACACTTAATTATAC | 1-1-4-6-3-1-3 | AaTTTAcacttaATTaTAC | 747_2 | -19.51 | 30669 |
| 747 | AATTTACACTTAATTATAC | 4-8-2-1-4 | AATTtacacttaATtATAC | 747_3 | -18.04 | 30669 |
| 747 | AATTTACACTTAATTATAC | 5-7-1-1-5 | AATTTacacttaAtTATAC | 747_4 | -19.79 | 30669 |
| 747 | AATTTACACTTAATTATAC | 2-1-3-6-1-1-5 | AAtTTAcacttaAtTATAC | 747_5 | -19.26 | 30669 |
| 748 | AATTTACACTTAATTATACT | 3-2-2-6-4-1-2 | AATttACacttaaTTATaCT | 748_1 | -21.50 | 30668 |
| 748 | AATTTACACTTAATTATACT | 5-1-1-6-3-1-3 | AATTTaCacttaaTTAtACT | 748_2 | -21.87 | 30668 |
| 748 | AATTTACACTTAATTATACT | 3-1-3-6-2-1-4 | AATtTACacttaaTTaTACT | 748_3 | -22.95 | 30668 |
| 748 | AATTTACACTTAATTATACT | 1-1-4-7-2-1-1-1-2 | AaTTTAcacttaaTTaTaCT | 748_4 | -20.23 | 30668 |
| 748 | AATTTACACTTAATTATACT | 2-1-2-1-1-6-1-1-5 | AAtTTaCacttaaTtATACT | 748_5 | -20.55 | 30668 |
| 749 | TAATTTACACTTAATTATAC | 2-1-4-6-4-1-2 | TAaTTTAcacttaATTAtAC | 749_1 | -20.98 | 30669 |
| 749 | TAATTTACACTTAATTATAC | 5-8-3-1-3 | TAATTtacacttaATTaTAC | 749_2 | -20.60 | 30669 |
| 749 | TAATTTACACTTAATTATAC | 2-2-3-6-3-1-3 | TAatTTAcacttaATTaTAC | 749_3 | -20.80 | 30669 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 749 | TAATTTACACTTAATTATAC | 4-1-2-6-2-1-4 | TAATtTAcacttaATtATAC | 749_4 | -21.41 | 30669 |
| 749 | TAATTTACACTTAATTATAC | 1-1-1-1-2-7-1-1-5 | TaAtTTacacttaAtTATAC | 749_5 | -18.92 | 30669 |
| 750 | TAATTTACACTTAATTAT | 5-8-5 | TAATTtacacttaATTAT | 750_1 | -18.27 | 30671 |
| 750 | TAATTTACACTTAATTAT | 4-1-1-7-5 | TAATtTacacttaATTAT | 750_2 | -18.18 | 30671 |
| 750 | TAATTTACACTTAATTAT | 2-1-3-7-5 | TAaTTTacacttaATTAT | 750_3 | -18.18 | 30671 |
| 750 | TAATTTACACTTAATTAT | 1-1-4-7-5 | TaATTTacacttaATTAT | 750_4 | -18.16 | 30671 |
| 751 | TAATTTACACTTAATTATA | 5-7-4-1-2 | TAATTtacacttAATTaTA | 751_1 | -18.87 | 30670 |
| 751 | TAATTTACACTTAATTATA | 5-7-2-1-4 | TAATTtacacttAAtTATA | 751_2 | -19.05 | 30670 |
| 751 | TAATTTACACTTAATTATA | 3-1-2-6-2-1-4 | TAAtTTacacttAAtTATA | 751_3 | -18.54 | 30670 |
| 751 | TAATTTACACTTAATTATA | 4-1-1-6-1-1-5 | TAATtTacacttAaTTATA | 751_4 | -19.40 | 30670 |
| 751 | TAATTTACACTTAATTATA | 2-1-3-6-1-1-5 | TAaTTTacacttAaTTATA | 751_5 | -19.41 | 30670 |
| 752 | TTAATTTACACTTAATTATA | 3-1-3-6-4-1-2 | TTAaTTTacacttAATTaTA | 752_1 | -20.61 | 30670 |
| 752 | TTAATTTACACTTAATTATA | 5-1-1-6-3-1-3 | TTAATtTacacttAATtATA | 752_2 | -20.28 | 30670 |
| 752 | TTAATTTACACTTAATTATA | 2-1-4-6-2-1-4 | TTaATTTacacttAAtTATA | 752_3 | -20.77 | 30670 |
| 752 | TTAATTTACACTTAATTATA | 3-2-2-6-1-1-5 | TTAatTTacacttAaTTATA | 752_4 | -20.28 | 30670 |
| 752 | TTAATTTACACTTAATTATA | 4-1-1-8-1-1-4 | TTAAtTtacacttaAtTATA | 752_5 | -18.80 | 30670 |
| 753 | TTAATTTACACTTAATTAT | 4-1-1-6-3-1-3 | TTAAtTtacactTAAtTAT | 753_1 | -18.65 | 30671 |
| 753 | TTAATTTACACTTAATTAT | 3-1-2-6-2-1-4 | TTAaTTtacactTAaTTAT | 753_2 | -19.52 | 30671 |
| 753 | TTAATTTACACTTAATTAT | 2-1-2-7-2-1-4 | TTaATttacactTAaTTAT | 753_3 | -18.68 | 30671 |
| 753 | TTAATTTACACTTAATTAT | 5-7-1-1-5 | TTAATttacactTaATTAT | 753_4 | -20.00 | 30671 |
| 753 | TTAATTTACACTTAATTAT | 2-1-3-6-1-1-5 | TTaATTtacactTaATTAT | 753_5 | -19.47 | 30671 |
| 754 | TTTAATTTACACTTAATTA | 3-1-2-6-3-1-3 | TTTaATttacacTTAaTTA | 754_1 | -19.46 | 30672 |
| 754 | TTTAATTTACACTTAATTA | 5-7-2-1-4 | TTTAAtttacacTTaATTA | 754_2 | -19.54 | 30672 |
| 754 | TTTAATTTACACTTAATTA | 4-1-1-6-2-1-4 | TTTAaTttacacTTaATTA | 754_3 | -19.46 | 30672 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 754 | TTTAATTTACACTTAATTA | 1-1-1-1-2-6-2-1-4 | TtTaATttacacTTaATTA | 754_4 | -18.11 | 30672 |
| 754 | TTTAATTTACACTTAATTA | 1-1-4-7-3-1-2 | TtTAATttacactTAAtTA | 754_5 | -18.02 | 30672 |
| 755 | TTTAATTTACACTTAATTAT | 4-1-2-6-3-1-3 | TTTAaTTtacactTAAtTAT | 755_1 | -20.90 | 30671 |
| 755 | TTTAATTTACACTTAATTAT | 3-1-2-7-2-1-4 | TTTaATttacactTAaTTAT | 755_2 | -20.50 | 30671 |
| 755 | TTTAATTTACACTTAATTAT | 1-1-5-6-2-1-4 | TtTAATTtacactTAaTTAT | 755_3 | -21.34 | 30671 |
| 755 | TTTAATTTACACTTAATTAT | 5-8-1-1-5 | TTTAAtttacactTaATTAT | 755_4 | -20.58 | 30671 |
| 755 | TTTAATTTACACTTAATTAT | 2-2-3-6-1-1-5 | TTtaATTtacactTaATTAT | 755_5 | -20.05 | 30671 |
| 756 | ATTTAATTTACACTTAATTA | 5-1-1-6-4-1-2 | ATTTAaTttacacTTAAtTA | 756_1 | -21.11 | 30672 |
| 756 | ATTTAATTTACACTTAATTA | 3-2-2-6-3-1-3 | ATTtaATttacacTTAaTTA | 756_2 | -20.29 | 30672 |
| 756 | ATTTAATTTACACTTAATTA | 4-1-2-6-2-1-4 | ATTTaATttacacTTaATTA | 756_3 | -21.50 | 30672 |
| 756 | ATTTAATTTACACTTAATTA | 2-1-4-6-2-2-3 | ATtTAATttacacTTaaTTA | 756_4 | -20.39 | 30672 |
| 756 | ATTTAATTTACACTTAATTA | 2-1-4-8-5 | ATtTAATttacacttAATTA | 756_5 | -20.08 | 30672 |
| 757 | ATTTAATTTACACTTAATT | 5-7-3-1-3 | ATTTAatttacaCTTaATT | 757_1 | -20.52 | 30673 |
| 757 | ATTTAATTTACACTTAATT | 4-1-1-7-2-1-3 | ATTTaAtttacacTTaATT | 757_2 | -18.02 | 30673 |
| 757 | ATTTAATTTACACTTAATT | 2-1-3-7-2-1-3 | ATtTAAtttacacTTaATT | 757_3 | -18.04 | 30673 |
| 757 | ATTTAATTTACACTTAATT | 4-1-1-8-5 | ATTTaAtttacactTAATT | 757_4 | -18.34 | 30673 |
| 757 | ATTTAATTTACACTTAATT | 2-1-3-8-5 | ATtTAAtttacactTAATT | 757_5 | -18.37 | 30673 |
| 758 | TATTTAATTTACACTTAAT | 3-1-2-6-4-1-2 | TATtTAatttacACTTaAT | 758_1 | -20.16 | 30674 |
| 758 | TATTTAATTTACACTTAAT | 2-1-3-6-2-1-4 | TAtTTAatttacACtTAAT | 758_2 | -19.37 | 30674 |
| 758 | TATTTAATTTACACTTAAT | 1-1-4-6-2-1-4 | TaTTTAatttacACtTAAT | 758_3 | -19.19 | 30674 |
| 758 | TATTTAATTTACACTTAAT | 3-1-2-6-1-1-5 | TATtTAatttacAcTTAAT | 758_4 | -19.44 | 30674 |
| 758 | TATTTAATTTACACTTAAT | 2-1-3-6-1-1-5 | TAtTTAatttacAcTTAAT | 758_5 | -19.00 | 30674 |
| 759 | TATTTAATTTACACTTAATT | 2-1-4-6-4-1-2 | TAtTTAAtttacaCTTAaTT | 759_1 | -21.54 | 30673 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 759 | TATTTAATTTACACTTAATT | 5-1-1-6-3-1-3 | TATTTaAtttacaCTTaATT | 759_2 | -21.92 | 30673 |
| 759 | TATTTAATTTACACTTAATT | 4-1-2-7-3-1-2 | TATTtAAtttacacTTAaTT | 759_3 | -19.35 | 30673 |
| 759 | TATTTAATTTACACTTAATT | 3-1-3-7-2-1-3 | TATtTAAtttacacTTaATT | 759_4 | -20.28 | 30673 |
| 759 | TATTTAATTTACACTTAATT | 2-1-4-8-5 | TAtTTAAtttacactTAATT | 759_5 | -20.16 | 30673 |
| 760 | CTATTTAATTTACACTT | 5-6-1-1-4 | CTATTtaatttAcACTT | 760_1 | -19.07 | 30677 |
| 760 | CTATTTAATTTACACTT | 5-7-5 | CTATTtaatttaCACTT | 760_2 | -20.97 | 30677 |
| 760 | CTATTTAATTTACACTT | 2-2-1-7-5 | CTatTtaatttaCACTT | 760_3 | -18.08 | 30677 |
| 760 | CTATTTAATTTACACTT | 5-7-2-1-2 | CTATTtaatttaCAcTT | 760_4 | -18.90 | 30677 |
| 760 | CTATTTAATTTACACTT | 5-7-1-1-3 | CTATTtaatttaCaCTT | 760_5 | -19.01 | 30677 |
| 761 | CTATTTAATTTACACTTAA | 2-1-3-6-4-1-2 | CTaTTTaatttaCACTtAA | 761_1 | -20.98 | 30675 |
| 761 | CTATTTAATTTACACTTAA | 3-1-2-6-3-1-3 | CTAtTTaatttaCACtTAA | 761_2 | -21.73 | 30675 |
| 761 | CTATTTAATTTACACTTAA | 4-1-1-6-2-1-4 | CTATtTaatttaCAcTTAA | 761_3 | -21.80 | 30675 |
| 761 | CTATTTAATTTACACTTAA | 5-7-2-2-3 | CTATTtaatttaCActTAA | 761_4 | -20.86 | 30675 |
| 761 | CTATTTAATTTACACTTAA | 2-1-3-6-1-1-5 | CTaTTTaatttaCaCTTAA | 761_5 | -21.29 | 30675 |
| 762 | CTATTTAATTTACACTTA | 5-7-3-1-2 | CTATTtaatttaCACtTA | 762_1 | -21.50 | 30676 |
| 762 | CTATTTAATTTACACTTA | 3-2-1-6-3-1-2 | CTAttTaatttaCACtTA | 762_2 | -20.17 | 30676 |
| 762 | CTATTTAATTTACACTTA | 3-1-1-7-2-1-3 | CTAtTtaatttaCAcTTA | 762_3 | -19.37 | 30676 |
| 762 | CTATTTAATTTACACTTA | 2-1-3-6-2-1-3 | CTaTTTaatttaCAcTTA | 762_4 | -20.43 | 30676 |
| 762 | CTATTTAATTTACACTTA | 2-1-3-6-1-1-4 | CTaTTTaatttaCaCTTA | 762_5 | -20.54 | 30676 |
| 763 | CTATTTAATTTACACTTAAT | 2-1-4-6-3-2-2 | CTaTTTAatttacACTtaAT | 763_1 | -21.79 | 30674 |
| 763 | CTATTTAATTTACACTTAAT | 4-1-2-6-2-1-4 | CTATtTAatttacACtTAAT | 763_2 | -23.29 | 30674 |
| 763 | CTATTTAATTTACACTTAAT | 1-2-4-6-1-1-5 | CtaTTTAatttacAcTTAAT | 763_3 | -20.68 | 30674 |
| 763 | CTATTTAATTTACACTTAAT | 3-1-3-6-1-1-2-1-2 | CTAtTTAatttacAcTTaAT | 763_4 | -21.14 | 30674 |
| 763 | CTATTTAATTTACACTTAAT | 5-1-1-7-3-1-2 | CTATTtAatttacaCTTaAT | 763_5 | -22.14 | 30674 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 764 | TCTATTTAATTTACACTTA | 2-1-3-6-4-1-2 | TCtATTtaatttACACtTA | 764_1 | -21.94 | 30676 |
| 764 | TCTATTTAATTTACACTTA | 4-1-1-6-3-1-3 | TCTAtTtaatttACAcTTA | 764_2 | -22.47 | 30676 |
| 764 | TCTATTTAATTTACACTTA | 3-1-2-7-2-1-3 | TCTaTTtaatttaCAcTTA | 764_3 | -21.69 | 30676 |
| 764 | TCTATTTAATTTACACTTA | 1-1-4-7-2-2-2 | TcTATTtaatttaCActTA | 764_4 | -20.33 | 30676 |
| 764 | TCTATTTAATTTACACTTA | 3-2-1-7-1-1-4 | TCTatTtaatttaCaCTTA | 764_5 | -20.85 | 30676 |
| 765 | TCTATTTAATTTACACTT | 3-2-1-6-2-1-3 | TCTatTtaatttACaCTT | 765_1 | -19.21 | 30677 |
| 765 | TCTATTTAATTTACACTT | 3-1-2-7-5 | TCTaTTtaatttaCACTT | 765_2 | -21.53 | 30677 |
| 765 | TCTATTTAATTTACACTT | 2-1-3-7-5 | TCtATTtaatttaCACTT | 765_3 | -20.81 | 30677 |
| 765 | TCTATTTAATTTACACTT | 4-1-1-7-2-1-2 | TCTAtTtaatttaCAcTT | 765_4 | -19.64 | 30677 |
| 765 | TCTATTTAATTTACACTT | 1-1-4-7-2-1-2 | TcTATTtaatttaCAcTT | 765_5 | -19.12 | 30677 |
| 766 | TCTATTTAATTTACACTTAA | 2-1-2-1-1-6-3-2-2 | TCtATtTaatttaCACttAA | 766_1 | -20.25 | 30675 |
| 766 | TCTATTTAATTTACACTTAA | 4-1-1-7-2-1-4 | TCTAtTtaatttaCAcTTAA | 766_2 | -22.62 | 30675 |
| 766 | TCTATTTAATTTACACTTAA | 1-1-1-1-3-6-2-2-3 | TcTaTTTaatttaCActTAA | 766_3 | -20.38 | 30675 |
| 766 | TCTATTTAATTTACACTTAA | 3-1-2-7-1-1-2-1-2 | TCTaTTtaatttaCaCTtAA | 766_4 | -20.27 | 30675 |
| 766 | TCTATTTAATTTACACTTAA | 2-3-2-6-1-1-1-1-3 | TCtatTTaatttaCaCtTAA | 766_5 | -19.51 | 30675 |
| 767 | ATCTATTTAATTTACACTT | 2-1-2-7-4-1-2 | ATcTAtttaattTACAcTT | 767_1 | -21.49 | 30677 |
| 767 | ATCTATTTAATTTACACTT | 1-1-4-6-3-1-3 | AtCTATttaattTACaCTT | 767_2 | -23.18 | 30677 |
| 767 | ATCTATTTAATTTACACTT | 4-1-1-6-2-1-4 | ATCTaTttaattTAcACTT | 767_3 | -22.64 | 30677 |
| 767 | ATCTATTTAATTTACACTT | 5-7-2-2-3 | ATCTAtttaattTAcaCTT | 767_4 | -22.78 | 30677 |
| 767 | ATCTATTTAATTTACACTT | 1-1-4-6-1-1-5 | AtCTATttaattTaCACTT | 767_5 | -23.52 | 30677 |
| 768 | ATCTATTTAATTTACACTTA | 1-2-4-6-2-1-1-1-2 | AtcTATTtaatttACaCtTA | 768_1 | -21.10 | 30676 |
| 768 | ATCTATTTAATTTACACTTA | 1-1-3-1-1-6-1-1-5 | AtCTAtTtaatttAcACTTA | 768_2 | -22.17 | 30676 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 768 | ATCTATTTAATTTACACTTA | 3-2-2-6-1-1-2-1-2 | ATCtaTTtaatttAcACtTA | 768_3 | −20.60 | 30676 |
| 768 | ATCTATTTAATTTACACTTA | 1-1-2-1-2-7-2-2-2 | AtCTaTTtaatttaCActTA | 768_4 | −20.80 | 30676 |
| 768 | ATCTATTTAATTTACACTTA | 3-1-1-1-1-7-1-2-3 | ATCtAtTtaatttaCacTTA | 768_5 | −19.72 | 30676 |
| 769 | TATCTATTTAATTTACACTT | 1-1-2-1-2-6-4-1-2 | TaTCtATttaattTACAcTT | 769_1 | −22.65 | 30677 |
| 769 | TATCTATTTAATTTACACTT | 2-1-1-1-2-6-2-1-4 | TAtCtATttaattTAcACTT | 769_2 | −22.23 | 30677 |
| 769 | TATCTATTTAATTTACACTT | 2-1-4-6-2-3-2 | TAtCTATttaattTAcacTT | 769_3 | −22.66 | 30677 |
| 769 | TATCTATTTAATTTACACTT | 1-3-3-6-1-1-5 | TatcTATttaattTaCACTT | 769_4 | −22.96 | 30677 |
| 769 | TATCTATTTAATTTACACTT | 1-1-3-1-1-6-1-3-3 | TaTCTaTttaattTacaCTT | 769_5 | −21.15 | 30677 |
| 770 | TATCTATTTAATTTACACT | 2-1-3-6-3-1-3 | TAtCTAtttaatTTAcACT | 770_1 | −22.62 | 30678 |
| 770 | TATCTATTTAATTTACACT | 1-1-4-6-3-1-3 | TaTCTAtttaatTTAcACT | 770_2 | −22.62 | 30678 |
| 770 | TATCTATTTAATTTACACT | 2-2-2-6-2-1-4 | TAtcTAtttaatTTaCACT | 770_3 | −21.84 | 30678 |
| 770 | TATCTATTTAATTTACACT | 1-2-3-6-1-1-5 | TatCTAtttaatTtACACT | 770_4 | −21.72 | 30678 |
| 770 | TATCTATTTAATTTACACT | 4-1-1-7-2-1-3 | TATCtAtttaattTAcACT | 770_5 | −21.09 | 30678 |
| 771 | TTATCTATTTAATTTACACT | 2-4-1-6-4-1-2 | TTatctAtttaatTTACaCT | 771_1 | −20.22 | 30678 |
| 771 | TTATCTATTTAATTTACACT | 2-2-3-6-3-2-2 | TTatCTAtttaatTTAcaCT | 771_2 | −22.76 | 30678 |
| 771 | TTATCTATTTAATTTACACT | 1-1-5-6-2-2-3 | TtATCTAtttaatTTacACT | 771_3 | −22.87 | 30678 |
| 771 | TTATCTATTTAATTTACACT | 2-2-3-6-1-2-4 | TTatCTAtttaatTtaCACT | 771_4 | −22.94 | 30678 |
| 771 | TTATCTATTTAATTTACACT | 5-1-1-7-1-2-3 | TTATCtAtttaattTacACT | 771_5 | −21.68 | 30678 |
| 772 | TTTATCTATTTAATTTACA | 1-1-3-7-4-1-2 | TtTATctatttaATTTaCA | 772_1 | −19.96 | 30680 |
| 772 | TTTATCTATTTAATTTACA | 4-1-1-6-3-2-2 | TTTAtCtatttaATTtaCA | 772_2 | −19.70 | 30680 |
| 772 | TTTATCTATTTAATTTACA | 3-1-2-6-2-1-4 | TTTaTCtatttaATtTACA | 772_3 | −21.24 | 30680 |
| 772 | TTTATCTATTTAATTTACA | 5-7-2-2-3 | TTTATctatttaATttACA | 772_4 | −19.82 | 30680 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 772 | TTTATCTATTTAATTTACA | 1-1-4-6-1-1-5 | TtTATCtatttaAtTTACA | 772_5 | -21.42 | 30680 |
| 773 | TTTTATCTATTTAATTTAC | 2-1-3-6-3-1-3 | TTtTATctatttAATtTAC | 773_1 | -19.10 | 30681 |
| 773 | TTTTATCTATTTAATTTAC | 1-1-4-6-2-1-4 | TtTTATctatttAAtTTAC | 773_2 | -18.66 | 30681 |
| 773 | TTTTATCTATTTAATTTAC | 3-1-2-6-1-1-5 | TTTtATctatttAaTTTAC | 773_3 | -18.15 | 30681 |
| 773 | TTTTATCTATTTAATTTAC | 1-2-3-6-1-1-5 | TttTATctatttAaTTTAC | 773_4 | -18.29 | 30681 |
| 773 | TTTTATCTATTTAATTTAC | 2-1-3-6-1-2-4 | TTtTATctatttAatTTAC | 773_5 | -18.15 | 30681 |
| 774 | TTTTATCTATTTAATTTACA | 1-1-2-1-1-7-4-1-2 | TtTTaTctatttaATTTaCA | 774_1 | -19.84 | 30680 |
| 774 | TTTTATCTATTTAATTTACA | 2-1-1-1-2-6-3-1-3 | TTtTaTCtatttaATTtACA | 774_2 | -20.79 | 30680 |
| 774 | TTTTATCTATTTAATTTACA | 4-2-1-6-2-1-4 | TTTTatCtatttaATtTACA | 774_3 | -21.94 | 30680 |
| 774 | TTTTATCTATTTAATTTACA | 1-1-5-6-2-3-2 | TtTTATCtatttaATttaCA | 774_4 | -21.32 | 30680 |
| 774 | TTTTATCTATTTAATTTACA | 2-2-3-6-1-2-4 | TTttATCtatttaAttTACA | 774_5 | -20.67 | 30680 |
| 775 | CTTTTATCTATTTAATTTA | 5-7-4-1-2 | CTTTTatctattTAATtTA | 775_1 | -21.18 | 30682 |
| 775 | CTTTTATCTATTTAATTTA | 5-7-2-1-4 | CTTTTatctattTAaTTTA | 775_2 | -21.18 | 30682 |
| 775 | CTTTTATCTATTTAATTTA | 5-7-2-2-3 | CTTTTatctattTAatTTA | 775_3 | -20.23 | 30682 |
| 775 | CTTTTATCTATTTAATTTA | 3-1-1-7-1-1-5 | CTTtTatctattTaATTTA | 775_4 | -19.83 | 30682 |
| 775 | CTTTTATCTATTTAATTTA | 2-1-2-7-1-1-1-1-3 | CTtTTatctattTaAtTTA | 775_5 | -18.07 | 30682 |
| 776 | CTTTTATCTATTTAATTTAC | 1-1-5-6-4-1-2 | CtTTTATctatttAATTtAC | 776_1 | -21.25 | 30681 |
| 776 | CTTTTATCTATTTAATTTAC | 3-1-1-8-3-1-3 | CTTtTatctatttAATtTAC | 776_2 | -20.13 | 30681 |
| 776 | CTTTTATCTATTTAATTTAC | 5-8-2-1-4 | CTTTTatctatttAAtTTAC | 776_3 | -21.02 | 30681 |
| 776 | CTTTTATCTATTTAATTTAC | 1-1-2-1-2-6-2-1-4 | CtTTtATctatttAAtTTAC | 776_4 | -19.49 | 30681 |
| 776 | CTTTTATCTATTTAATTTAC | 2-1-4-6-2-2-3 | CTtTTATctatttAAttTAC | 776_5 | -21.33 | 30681 |
| 777 | ACTTTTATCTATTTAATTT | 4-1-1-6-4-1-2 | ACTTtTatctatTTAAtTT | 777_1 | -20.04 | 30683 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 777 | ACTTTTATCTATTTAATTT | 3-1-2-6-3-1-3 | ACTtTTatctatTTAaTTT | 777_2 | −20.48 | 30683 |
| 777 | ACTTTTATCTATTTAATTT | 5-7-2-1-4 | ACTTTtatctatTTaATTT | 777_3 | −20.54 | 30683 |
| 777 | ACTTTTATCTATTTAATTT | 2-2-2-6-2-1-4 | ACttTTatctatTTaATTT | 777_4 | −19.26 | 30683 |
| 777 | ACTTTTATCTATTTAATTT | 4-1-1-6-1-2-4 | ACTTtTatctatTtaATTT | 777_5 | −19.21 | 30683 |
| 778 | ACTTTTATCTATTTAATTTA | 2-3-1-7-4-1-2 | ACtttTatctattTAATtTA | 778_1 | −19.89 | 30682 |
| 778 | ACTTTTATCTATTTAATTTA | 1-1-4-7-2-1-1-1-2 | AcTTTTatctattTAaTtTA | 778_2 | −19.82 | 30682 |
| 778 | ACTTTTATCTATTTAATTTA | 3-2-1-7-2-2-3 | ACTttTatctattTAatTTA | 778_3 | −20.13 | 30682 |
| 778 | ACTTTTATCTATTTAATTTA | 4-9-1-1-5 | ACTTttatctattTaATTTA | 778_4 | −21.14 | 30682 |
| 778 | ACTTTTATCTATTTAATTTA | 2-1-3-7-1-1-5 | ACtTTTatctattTaATTTA | 778_5 | −21.49 | 30682 |
| 779 | ACTTTTATCTATTTAATT | 2-1-3-6-2-1-3 | ACtTTTatctatTTaATT | 779_1 | −18.25 | 30684 |
| 779 | ACTTTTATCTATTTAATT | 4-1-1-7-5 | ACTTtTatctattTAATT | 779_2 | −19.17 | 30684 |
| 779 | ACTTTTATCTATTTAATT | 3-1-2-7-5 | ACTtTTatctattTAATT | 779_3 | −19.17 | 30684 |
| 779 | ACTTTTATCTATTTAATT | 2-1-3-7-5 | ACtTTTatctattTAATT | 779_4 | −18.79 | 30684 |
| 779 | ACTTTTATCTATTTAATT | 1-1-4-7-5 | AcTTTTatctattTAATT | 779_5 | −18.42 | 30684 |
| 780 | AACTTTTATCTATTTAATT | 5-7-3-1-3 | AACTTttatctaTTTaATT | 780_1 | −19.61 | 30684 |
| 780 | AACTTTTATCTATTTAATT | 5-8-3-1-2 | AACTTttatctatTTAaTT | 780_2 | −18.68 | 30684 |
| 780 | AACTTTTATCTATTTAATT | 4-1-1-7-3-1-2 | AACTtTtatctatTTAaTT | 780_3 | −18.17 | 30684 |
| 780 | AACTTTTATCTATTTAATT | 1-1-4-7-2-1-3 | AaCTTTtatctatTTaATT | 780_4 | −18.45 | 30684 |
| 780 | AACTTTTATCTATTTAATT | 5-9-5 | AACTTttatctattTAATT | 780_5 | −19.19 | 30684 |
| 781 | AACTTTTATCTATTTAAT | 5-8-5 | AACTTttatctatTTAAT | 781_1 | −18.18 | 30685 |
| 782 | AACTTTTATCTATTTAATTT | 1-1-1-1-3-6-4-1-2 | AaCtTTTatctatTTAAtTT | 782_1 | −19.40 | 30683 |
| 782 | AACTTTTATCTATTTAATTT | 4-2-1-6-3-1-3 | AACTttTatctatTTAaTTT | 782_2 | −20.41 | 30683 |
| 782 | AACTTTTATCTATTTAATTT | 5-1-1-6-2-1-4 | AACTTtTatctatTTaATTT | 782_3 | −21.20 | 30683 |
| 782 | AACTTTTATCTATTTAATTT | 2-1-4-6-1-2-4 | AAcTTTTatctatTtaATTT | 782_4 | −19.21 | 30683 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 782 | AACTTTTATCTATTTAATTT | 1-1-2-1-2-7-2-1-3 | AaCTtTTatctattTAaTTT | 782_5 | -19.40 | 30683 |
| 783 | TAACTTTTATCTATTTAAT | 2-1-3-6-4-1-2 | TAaCTTttatctATTTaAT | 783_1 | -19.91 | 30685 |
| 783 | TAACTTTTATCTATTTAAT | 2-1-3-6-2-1-4 | TAaCTTttatctATtTAAT | 783_2 | -19.93 | 30685 |
| 783 | TAACTTTTATCTATTTAAT | 5-7-2-1-1-1-2 | TAACTtttatctATtTaAT | 783_3 | -18.79 | 30685 |
| 783 | TAACTTTTATCTATTTAAT | 1-1-4-6-1-1-5 | TaACTTttatctAtTTAAT | 783_4 | -19.16 | 30685 |
| 783 | TAACTTTTATCTATTTAAT | 5-9-5 | TAACTtttatctatTTAAT | 783_5 | -19.60 | 30685 |
| 784 | TAACTTTTATCTATTTAATT | 4-1-1-7-1-1-2-1-2 | TAACtTttatctaTtTAaTT | 784_1 | -18.83 | 30684 |
| 784 | TAACTTTTATCTATTTAATT | 2-1-4-7-3-1-2 | TAaCTTTtatctatTTAaTT | 784_2 | -20.71 | 30684 |
| 784 | TAACTTTTATCTATTTAATT | 2-1-3-8-2-1-3 | TAaCTTttatctatTTaATT | 784_3 | -19.87 | 30684 |
| 784 | TAACTTTTATCTATTTAATT | 1-1-5-7-2-1-3 | TaACTTTtatctatTTaATT | 784_4 | -20.35 | 30684 |
| 784 | TAACTTTTATCTATTTAATT | 5-10-5 | TAACTttatctattTAATT | 784_5 | -20.61 | 30684 |
| 785 | TAACTTTTATCTATTTAA | 5-7-2-1-3 | TAACTtttatctATtTAA | 785_1 | -18.07 | 30686 |
| 786 | ATAACTTTTATCTATTTAA | 3-1-2-6-4-1-2 | ATAaCTttttatcTATTtAA | 786_1 | -20.14 | 30686 |
| 786 | ATAACTTTTATCTATTTAA | 4-1-1-6-3-1-3 | ATAAcTtttatcTATtTAA | 786_2 | -20.03 | 30686 |
| 786 | ATAACTTTTATCTATTTAA | 2-1-3-6-2-1-4 | ATaACTtttatcTAtTTAA | 786_3 | -20.33 | 30686 |
| 786 | ATAACTTTTATCTATTTAA | 3-1-2-6-2-2-3 | ATAaCTtttatcTAttTAA | 786_4 | -19.84 | 30686 |
| 786 | ATAACTTTTATCTATTTAA | 5-7-1-1-5 | ATAACttttatcTaTTTAA | 786_5 | -20.30 | 30686 |
| 787 | ATAACTTTTATCTATTTAAT | 3-1-3-6-3-2-2 | ATAaCTTttatctATTtaAT | 787_1 | -20.73 | 30685 |
| 787 | ATAACTTTTATCTATTTAAT | 2-1-4-6-2-1-4 | ATaACTTttatctATtTAAT | 787_2 | -21.66 | 30685 |
| 787 | ATAACTTTTATCTATTTAAT | 3-1-2-7-1-2-4 | ATAaCTtttatctAttTAAT | 787_3 | -19.93 | 30685 |
| 787 | ATAACTTTTATCTATTTAAT | 4-2-1-7-3-1-2 | ATAActTttatctaTTTaAT | 787_4 | -18.98 | 30685 |
| 787 | ATAACTTTTATCTATTTAAT | 2-1-4-8-5 | ATaACTTttatctatTTAAT | 787_5 | -21.13 | 30685 |
| 788 | TATAACTTTTATCTATTTA | 1-1-2-1-1-6-4-1-2 | TaTAaCttttatCTATtTA | 788_1 | -21.10 | 30687 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 788 | TATAACTTTTATCTATTTA | 2-2-2-6-3-1-3 | TAtaACttttatCTAtTTA | 788_2 | -20.60 | 30687 |
| 788 | TATAACTTTTATCTATTTA | 3-1-2-6-2-1-4 | TATaACttttatCTaTTTA | 788_3 | -22.09 | 30687 |
| 788 | TATAACTTTTATCTATTTA | 5-7-1-1-5 | TATAActtttatCtATTTA | 788_4 | -21.33 | 30687 |
| 788 | TATAACTTTTATCTATTTA | 4-1-1-7-2-2-2 | TATAaCttttatcTAttTA | 788_5 | -20.13 | 30687 |
| 789 | TATAACTTTTATCTATTTAA | 4-1-1-7-4-1-2 | TATAaCttttatcTATTtAA | 789_1 | -21.18 | 30686 |
| 789 | TATAACTTTTATCTATTTAA | 2-2-3-6-3-1-3 | TAtaACTtttatcTATtTAA | 789_2 | -21.32 | 30686 |
| 789 | TATAACTTTTATCTATTTAA | 1-1-5-6-2-1-4 | TaTAACTtttatcTAtTTAA | 789_3 | -21.97 | 30686 |
| 789 | TATAACTTTTATCTATTTAA | 3-1-2-7-1-1-1-1-3 | TATaACttttatcTaTtTAA | 789_4 | -19.86 | 30686 |
| 789 | TATAACTTTTATCTATTTAA | 4-2-1-6-1-2-4 | TATAacTtttatcTatTTAA | 789_5 | -20.09 | 30686 |
| 790 | TTATAACTTTTATCTATTT | 2-1-3-6-4-1-2 | TTaTAActtttaTCTAtTT | 790_1 | -21.00 | 30688 |
| 790 | TTATAACTTTTATCTATTT | 5-7-2-2-3 | TTATAacttttaTCtaTTT | 790_2 | -20.52 | 30688 |
| 790 | TTATAACTTTTATCTATTT | 4-1-1-6-1-1-5 | TTATaActtttaTcTATTT | 790_3 | -21.08 | 30688 |
| 790 | TTATAACTTTTATCTATTT | 4-1-1-7-3-1-2 | TTATaActtttatCTAtTT | 790_4 | -20.46 | 30688 |
| 790 | TTATAACTTTTATCTATTT | 2-1-3-8-5 | TTaTAActtttatcTATTT | 790_5 | -19.98 | 30688 |
| 791 | TTATAACTTTTATCTATT | 5-7-3-1-2 | TTATAacttttaTCTaTT | 791_1 | -20.32 | 30689 |
| 791 | TTATAACTTTTATCTATT | 5-7-1-1-4 | TTATAacttttaTcTATT | 791_2 | -19.99 | 30689 |
| 791 | TTATAACTTTTATCTATT | 4-1-1-7-5 | TTATaActtttatCTATT | 791_3 | -20.40 | 30689 |
| 791 | TTATAACTTTTATCTATT | 4-9-5 | TTATaacttttatCTATT | 791_4 | -19.98 | 30689 |
| 791 | TTATAACTTTTATCTATT | 2-1-3-7-5 | TTaTAActtttatCTATT | 791_5 | -19.81 | 30689 |
| 792 | TTATAACTTTTATCTATTTA | 1-2-1-1-2-6-3-2-2 | TtaTaACttttatCTAttTA | 792_1 | -20.10 | 30687 |
| 792 | TTATAACTTTTATCTATTTA | 3-2-1-7-1-1-2-1-2 | TTAtaActtttatCtATtTA | 792_2 | -18.80 | 30687 |
| 792 | TTATAACTTTTATCTATTTA | 4-1-2-6-1-3-3 | TTATaACttttatCtatTTA | 792_3 | -21.34 | 30687 |
| 792 | TTATAACTTTTATCTATTTA | 2-1-2-1-1-7-2-1-3 | TTaTAaCttttatcTAtTTA | 792_4 | -20.83 | 30687 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 792 | TTATAACTTTTATCTATTTA | 1-1-4-8-1-1-4 | TtATAActtttatcTaTTTA | 792_5 | -19.94 | 30687 |
| 793 | CTTATAACTTTTATCTATT | 1-1-1-1-2-6-3-2-2 | CtTaTAacttttATCtaTT | 793_1 | -19.45 | 30689 |
| 793 | CTTATAACTTTTATCTATT | 1-2-3-6-1-1-5 | CttATAacttttAtCTATT | 793_2 | -21.25 | 30689 |
| 793 | CTTATAACTTTTATCTATT | 3-2-1-8-5 | CTTatAacttttatCTATT | 793_3 | -20.78 | 30689 |
| 793 | CTTATAACTTTTATCTATT | 1-1-3-9-2-1-2 | CtTATaacttttatCTaTT | 793_4 | -19.82 | 30689 |
| 793 | CTTATAACTTTTATCTATT | 5-9-1-1-3 | CTTATaacttttatCtATT | 793_5 | -20.81 | 30689 |
| 794 | CTTATAACTTTTATCTAT | 5-7-3-1-2 | CTTATaacttttATCtAT | 794_1 | -21.02 | 30690 |
| 794 | CTTATAACTTTTATCTAT | 1-1-3-7-1-1-4 | CtTATaacttttAtCTAT | 794_2 | -20.04 | 30690 |
| 794 | CTTATAACTTTTATCTAT | 2-2-1-8-5 | CTtaTaacttttaTCTAT | 794_3 | -19.59 | 30690 |
| 794 | CTTATAACTTTTATCTAT | 3-1-2-8-4 | CTTaTAacttttatCTAT | 794_4 | -20.86 | 30690 |
| 794 | CTTATAACTTTTATCTAT | 5-10-3 | CTTATaacttttatcTAT | 794_5 | -19.99 | 30690 |
| 795 | CTTATAACTTTTATCTATTT | 1-1-1-2-2-6-2-1-1-1-2 | CtTatAActtttaTCtAtTT | 795_1 | -18.22 | 30688 |
| 795 | CTTATAACTTTTATCTATTT | 1-1-1-1-2-8-2-1-3 | CtTaTAacttttatCTaTTT | 795_2 | -20.86 | 30688 |
| 795 | CTTATAACTTTTATCTATTT | 2-1-2-1-1-7-2-2-2 | CTtATaActtttatCTatTT | 795_3 | -20.54 | 30688 |
| 795 | CTTATAACTTTTATCTATTT | 3-2-1-8-1-1-1-1-2 | CTTatAacttttatCtAtTT | 795_4 | -18.19 | 30688 |
| 795 | CTTATAACTTTTATCTATTT | 1-2-2-1-1-9-4 | CttATaActtttatctATTT | 795_5 | -18.61 | 30688 |
| 796 | CTTATAACTTTTATCTA | 5-6-2-1-3 | CTTATaactttTAtCTA | 796_1 | -21.44 | 30691 |
| 796 | CTTATAACTTTTATCTA | 5-6-1-2-3 | CTTATaactttTatCTA | 796_2 | -20.31 | 30691 |
| 796 | CTTATAACTTTTATCTA | 1-1-3-7-5 | CtTATaacttttATCTA | 796_3 | -19.90 | 30691 |
| 796 | CTTATAACTTTTATCTA | 3-1-1-8-4 | CTTaTaacttttaTCTA | 796_4 | -18.77 | 30691 |
| 796 | CTTATAACTTTTATCTA | 2-1-2-8-4 | CTtATaacttttaTCTA | 796_5 | -18.43 | 30691 |
| 797 | GCTTATAACTTTTATCTA | 2-2-2-6-2-2-2 | GCttATaactttTAtcTA | 797_1 | -21.32 | 30691 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 797 | GCTTATAACTTTTATCTA | 4-9-1-1-3 | GCTTataacttttAtCTA | 797_2 | -21.88 | 30691 |
| 797 | GCTTATAACTTTTATCTA | 2-12-4 | GCttataacttttaTCTA | 797_3 | -20.47 | 30691 |
| 797 | GCTTATAACTTTTATCTA | 2-1-1-1-1-9-3 | GCtTaTaacttttatCTA | 797_4 | -20.94 | 30691 |
| 797 | GCTTATAACTTTTATCTA | 1-1-4-10-2 | GcTTATaacttttatcTA | 797_5 | -19.62 | 30691 |
| 798 | GCTTATAACTTTTATCT | 2-9-1-2-3 | GCttataactttTtaTCT | 798_1 | -18.54 | 30692 |
| 798 | GCTTATAACTTTTATCT | 2-10-5 | GCttataactttTATCT | 798_2 | -20.90 | 30692 |
| 798 | GCTTATAACTTTTATCT | 4-8-1-1-3 | GCTTataactttTaTCT | 798_3 | -21.40 | 30692 |
| 798 | GCTTATAACTTTTATCT | 2-1-2-8-4 | GCtTAtaacttttATCT | 798_4 | -21.00 | 30692 |
| 798 | GCTTATAACTTTTATCT | 5-10-2 | GCTTAtaacttttatCT | 798_5 | -20.68 | 30692 |
| 799 | TGCTTATAACTTTTATC | 3-8-3-1-2 | TGCttataactTTTaTC | 799_1 | -19.59 | 30693 |
| 799 | TGCTTATAACTTTTATC | 3-8-2-1-3 | TGCttataactTTtATC | 799_2 | -19.26 | 30693 |
| 799 | TGCTTATAACTTTTATC | 2-10-5 | TGcttataactttTTATC | 799_3 | -18.08 | 30693 |
| 799 | TGCTTATAACTTTTATC | 5-8-4 | TGCTTataactttTATC | 799_4 | -22.34 | 30693 |
| 799 | TGCTTATAACTTTTATC | 3-10-4 | TGCttataactttTATC | 799_5 | -19.90 | 30693 |
| 800 | TGCTTATAACTTTTATCT | 3-9-3-1-2 | TGCttataactttTTAtCT | 800_1 | -22.27 | 30692 |
| 800 | TGCTTATAACTTTTATCT | 2-2-2-7-5 | TGctTAtaactttTATCT | 800_2 | -22.61 | 30692 |
| 800 | TGCTTATAACTTTTATCT | 3-10-1-1-3 | TGCttataactttTaTCT | 800_3 | -21.45 | 30692 |
| 800 | TGCTTATAACTTTTATCT | 1-1-1-1-2-8-4 | TgCtTAtaacttttATCT | 800_4 | -20.79 | 30692 |
| 800 | TGCTTATAACTTTTATCT | 4-1-1-10-2 | TGCTtAtaacttttatCT | 800_5 | -20.89 | 30692 |
| 801 | CTGCTTATAACTTTTATC | 2-1-1-8-2-1-3 | CTgCttataactTTtATC | 801_1 | -20.05 | 30693 |
| 801 | CTGCTTATAACTTTTATC | 4-8-1-3-2 | CTGCttataactTttaTC | 801_2 | -21.02 | 30693 |
| 801 | CTGCTTATAACTTTTATC | 2-1-1-10-4 | CTgCttataactttTATC | 801_3 | -20.69 | 30693 |
| 801 | CTGCTTATAACTTTTATC | 1-1-2-10-1-1-2 | CtGCttataactttTaTC | 801_4 | -18.86 | 30693 |
| 801 | CTGCTTATAACTTTTATC | 1-1-4-9-3 | CtGCTTataacttttATC | 801_5 | -21.47 | 30693 |
| 802 | CTCTGCTTATAACTTTT | 1-1-1-1-1-6-2-1-3 | CtCtGcttataACtTTT | 802_1 | -18.92 | 30696 |

TABLE 3-continued

List of oligonucleotides or contiguous nucleobase sequences complementary to SEQ ID NO: 1
(motif sequences indicated by SEQ ID NO), oligonucleotide designs made from these, as well as
specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 802 | CTCTGCTTATAACTTTT | 1-1-1-1-1-7-2-1-2 | CtCtGcttataaCTtTT | 802_2 | −18.47 | 30696 |
| 802 | CTCTGCTTATAACTTTT | 1-1-2-8-1-1-3 | CtCTgcttataaCtTTT | 802_3 | −19.44 | 30696 |
| 802 | CTCTGCTTATAACTTTT | 1-2-2-7-1-1-3 | CtcTGcttataaCtTTT | 802_4 | −19.02 | 30696 |
| 802 | CTCTGCTTATAACTTTT | 3-1-1-10-2 | CTCtGcttataacttTT | 802_5 | −18.16 | 30696 |
| 803 | CCTCTGCTTATAACTTT | 1-1-2-7-2-1-3 | CcTCtgcttatAAcTTT | 803_1 | −20.60 | 30697 |
| 803 | CCTCTGCTTATAACTTT | 2-9-1-3-2 | CCtctgcttatAactTT | 803_2 | −19.28 | 30697 |
| 803 | CCTCTGCTTATAACTTT | 2-2-1-7-1-2-2 | CCtcTgcttataActTT | 803_3 | −20.58 | 30697 |
| 803 | CCTCTGCTTATAACTTT | 1-2-1-8-1-2-2 | CctCtgcttataActTT | 803_4 | −18.06 | 30697 |
| 803 | CCTCTGCTTATAACTTT | 2-1-1-9-1-1-2 | CCtCtgcttataaCtTT | 803_5 | −21.12 | 30697 |
| 804 | CTACTATACTTTCCTCT | 3-8-2-2-2 | CTActatacttTCctCT | 804_1 | −22.54 | 30709 |
| 804 | CTACTATACTTTCCTCT | 1-1-1-9-2-1-2 | CtActatactttCCtCT | 804_2 | −21.39 | 30709 |
| 804 | CTACTATACTTTCCTCT | 1-2-1-8-1-2-2 | CtaCtatactttCctCT | 804_3 | −19.70 | 30709 |
| 804 | CTACTATACTTTCCTCT | 2-11-1-1-2 | CTactatactttcCtCT | 804_4 | −20.45 | 30709 |
| 804 | CTACTATACTTTCCTCT | 1-3-1-8-1-1-2 | CtacTatactttcCtCT | 804_5 | −19.77 | 30709 |
| 805 | TCTACTATACTTTCCTCT | 2-1-1-9-1-2-2 | TCtActatactttCctCT | 805_1 | −21.40 | 30709 |
| 805 | TCTACTATACTTTCCTCT | 2-2-1-8-1-2-2 | TCtaCtatactttCctCT | 805_2 | −22.20 | 30709 |
| 805 | TCTACTATACTTTCCTCT | 2-11-1-2-2 | TCtactatactttCctCT | 805_3 | −21.20 | 30709 |
| 805 | TCTACTATACTTTCCTCT | 2-1-1-10-1-1-2 | TCtActatactttcCtCT | 805_4 | −21.52 | 30709 |
| 805 | TCTACTATACTTTCCTCT | 2-2-1-9-1-1-2 | TCtaCtatactttcCtCT | 805_5 | −22.32 | 30709 |
| 806 | TTCTACTATACTTTCCT | 1-1-1-8-1-3-2 | TtCtactatacTttcCT | 806_1 | −18.06 | 30711 |
| 806 | TTCTACTATACTTTCCT | 1-2-1-7-1-3-2 | TtcTactatacTttcCT | 806_2 | −18.02 | 30711 |
| 806 | TTCTACTATACTTTCCT | 1-1-1-1-1-7-1-1-3 | TtCtActatactTtCCT | 806_3 | −20.41 | 30711 |
| 806 | TTCTACTATACTTTCCT | 1-1-1-10-4 | TtCtactatacttTCCT | 806_4 | −20.90 | 30711 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 806 | TTCTACTATACTTTCCT | 1-1-1 1-1-9-3 | TtCtActatactttCCT | 806_5 | -20.11 | 30711 |
| 807 | TTCTACTATACTTTCCTC | 1-2-1-8-1-1-1-1-2 | TtcTactatactTtCcTC | 807_1 | -19.51 | 30710 |
| 807 | TTCTACTATACTTTCCTC | 1-1-1-2-1-6-1-3-2 | TtCtaCtatactTtccTC | 807_2 | -19.77 | 30710 |
| 807 | TTCTACTATACTTTCCTC | 1-1-1-1-1-9-1-1-2 | TtCtActatactttCcTC | 807_3 | -19.44 | 30710 |
| 807 | TTCTACTATACTTTCCTC | 1-1-1-12-3 | TtCtactatactttcCTC | 807_4 | -20.04 | 30710 |
| 807 | TTCTACTATACTTTCCTC | 1-2-1-1-1-10-2 | TtcTaCtatactttccTC | 807_5 | -19.43 | 30710 |
| 808 | TTTCCATCTACTATTAAT | 1-1-3-7-3-1-2 | TtTCCatctactATTaAT | 808_1 | -21.43 | 39804 |
| 808 | TTTCCATCTACTATTAAT | 2-1-2-7-1-1-1-1-2 | TTtCCatctactAtTaAT | 808_2 | -19.50 | 39804 |
| 808 | TTTCCATCTACTATTAAT | 1-1-4-6-1-2-3 | TtTCCAtctactAttAAT | 808_3 | -20.72 | 39804 |
| 808 | TTTCCATCTACTATTAAT | 2-1-2-8-1-1-3 | TTtCCatctactaTtAAT | 808_4 | -19.43 | 39804 |
| 808 | TTTCCATCTACTATTAAT | 4-1-1-8-4 | TTTCcAtctactatTAAT | 808_5 | -20.12 | 39804 |
| 809 | TTTCCATCTACTATTAA | 5-6-3-1-2 | TTTCCatctacTATtAA | 809_1 | -21.74 | 39805 |
| 809 | TTTCCATCTACTATTAA | 2-1-2-6-2-1-3 | TTtCCatctacTAtTAA | 809_2 | -20.76 | 39805 |
| 809 | TTTCCATCTACTATTAA | 1-1-3-6-1-1-4 | TtTCCatctacTaTTAA | 809_3 | -20.75 | 39805 |
| 809 | TTTCCATCTACTATTAA | 2-1-2-7-5 | TTtCCatctactATTAA | 809_4 | -20.54 | 39805 |
| 809 | TTTCCATCTACTATTAA | 5-9-3 | TTTCCatctactatTAA | 809_5 | -20.18 | 39805 |
| 810 | GTTTCCATCTACTATTA | 3-9-2-1-2 | GTTtccatctacTAtTA | 810_1 | -20.81 | 39806 |
| 810 | GTTTCCATCTACTATTA | 1-1-1-1-1-7-1-1-3 | GtTtCcatctacTaTTA | 810_2 | -19.35 | 39806 |
| 810 | GTTTCCATCTACTATTA | 2-2-1-7-1-2-2 | GTttCcatctacTatTA | 810_3 | -19.64 | 39806 |
| 810 | GTTTCCATCTACTATTA | 3-1-1-8-4 | GTTtCcatctactATTA | 810_4 | -21.37 | 39806 |
| 810 | GTTTCCATCTACTATTA | 1-2-2-10-2 | GttTCcatctactatTA | 810_5 | -18.14 | 39806 |
| 811 | AATACAAAATCATCTTAC | 3-1-2-6-1-1-4 | AATaCAaaatcaTcTTAC | 811_1 | -18.05 | 39836 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 811 | AATACAAAATCATCTTAC | 4-9-5 | AATAcaaaatcatCTTAC | 811_2 | -18.25 | 39836 |
| 811 | AATACAAAATCATCTTAC | 3-1-2-7-5 | AATaCAaaatcatCTTAC | 811_3 | -19.20 | 39836 |
| 811 | AATACAAAATCATCTTAC | 2-1-3-7-5 | AAtACAaaatcatCTTAC | 811_4 | -18.12 | 39836 |
| 811 | AATACAAAATCATCTTAC | 1-1-4-7-5 | AaTACAaaatcatCTTAC | 811_5 | -19.50 | 39836 |
| 812 | AATACAAAATCATCTTACA | 2-2-2-6-4-1-2 | AAtaCAaaatcaTCTTaCA | 812_1 | -20.31 | 39835 |
| 812 | AATACAAAATCATCTTACA | 4-8-3-2-2 | AATAcaaaatcaTCTtaCA | 812_2 | -19.80 | 39835 |
| 812 | AATACAAAATCATCTTACA | 3-1-2-6-2-1-4 | AATaCAaaatcaTCtTACA | 812_3 | -21.91 | 39835 |
| 812 | AATACAAAATCATCTTACA | 1-1-4-7-2-2-2 | AaTACAaaatcatCTtaCA | 812_4 | -19.93 | 39835 |
| 812 | AATACAAAATCATCTTACA | 5-8-1-1-4 | AATACaaaatcatCtTACA | 812_5 | -20.93 | 39835 |
| 813 | TAATACAAAATCATCTTA | 1-1-4-6-3-1-2 | TaATACaaaatcATCtTA | 813_1 | -18.46 | 39837 |
| 813 | TAATACAAAATCATCTTA | 5-8-5 | TAATAcaaaatcaTCTTA | 813_2 | -19.57 | 39837 |
| 813 | TAATACAAAATCATCTTA | 5-9-4 | TAATAcaaaatcatCTTA | 813_3 | -18.44 | 39837 |
| 813 | TAATACAAAATCATCTTA | 2-1-3-8-4 | TAaTACaaaatcatCTTA | 813_4 | -18.20 | 39837 |
| 813 | TAATACAAAATCATCTTA | 1-1-4-8-4 | TaATACaaaatcatCTTA | 813_5 | -18.18 | 39837 |
| 814 | TAATACAAAATCATCTTAC | 2-1-3-6-4-1-2 | TAaTACaaaatcATCTtAC | 814_1 | -19.95 | 39836 |
| 814 | TAATACAAAATCATCTTAC | 4-1-1-6-3-1-3 | TAATaCaaaatcATCtTAC | 814_2 | -20.22 | 39836 |
| 814 | TAATACAAAATCATCTTAC | 1-2-3-6-1-1-5 | TaaTACaaaatcAtCTTAC | 814_3 | -19.14 | 39836 |
| 814 | TAATACAAAATCATCTTAC | 5-8-2-1-3 | TAATAcaaaatcaTCtTAC | 814_4 | -19.90 | 39836 |
| 814 | TAATACAAAATCATCTTAC | 4-1-1-8-5 | TAATaCaaaatcatCTTAC | 814_5 | -19.94 | 39836 |
| 815 | TAATACAAAATCATCTTACA | 3-2-2-6-2-1-1-1-2 | TAAtaCAaaatcaTCtTaCA | 815_1 | -20.84 | 39835 |
| 815 | TAATACAAAATCATCTTACA | 2-3-1-8-2-1-3 | TAataCaaaatcatCTtACA | 815_2 | -18.77 | 39835 |
| 815 | TAATACAAAATCATCTTACA | 2-1-2-1-1-7-2-2-2 | TAaTAcAaaatcatCTtaCA | 815_3 | -19.66 | 39835 |
| 815 | TAATACAAAATCATCTTACA | 1-1-1-1-2-8-1-1-4 | TaAtACaaaatcatCtTACA | 815_4 | -19.11 | 39835 |
| 815 | TAATACAAAATCATCTTACA | 4-10-1-1-1-1-2 | TAATacaaaatcatCtTaCA | 815_5 | -19.22 | 39835 |

TABLE 3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID NO | ΔG° | Start SEQ ID NO 1 |
|---|---|---|---|---|---|---|
| 816 | TCTGTATACACCATCCCA | 2-10-1-1-1-1-2 | TCtgtatacaccAtCcCA | 816_1 | −24.49 | 46389 |
| 816 | TCTGTATACACCATCCCA | 2-3-1-6-1-3-2 | TCtgtAtacaccAtccCA | 816_2 | −23.81 | 46389 |
| 816 | TCTGTATACACCATCCCA | 2-10-1-3-2 | TCtgtatacaccAtccCA | 816_3 | −23.72 | 46389 |
| 816 | TCTGTATACACCATCCCA | 2-1-1-10-1-1-2 | TCtGtatacaccatCcCA | 816_4 | −24.75 | 46389 |
| 816 | TCTGTATACACCATCCCA | 2-3-1-8-1-1-2 | TCtgtAtacaccatCcCA | 816_5 | −24.53 | 46389 |
| 816 | TCTGTATACACCATCCCA | 2-3-1-10-2 | TCtgtAtacaccatccCA | 816_6 | −23.76 | 46389 |
| 817 | TTCTGACTCCCTATCCA | 1-1-1-12-2 | TtCtgactccctatcCA | 817_1 | −22.56 | 46417 |
| 818 | TTTCTGACTCCCTATCC | 1-2-1-11-2 | TttCtgactccctatCC | 818_1 | −22.64 | 46418 |

Designs refer to the gapmer design, F-G-F', where each number represents the number of consecutive modified nucleosides, e.g 2' modified nucleosides (first number=5' flank), followed by the number of DNA nucleosides (second number=gap region), followed by the number of modified nucleosides, e.g 2' modified nucleosides (third number=3' flank), optionally preceded by or followed by further repeated regions of DNA and LNA, which are not necessarily part of the contiguous sequence that is complementary to the target nucleic acid. For some oligonucleotides in table 3 the flanks are mixed flanks, such flanks start and end with a 2' modified nucleosides, in these cases the gap region is the number above 5 not located at the 5' or 3' terminal in of the design.

For the oligonucleotide compounds capital letters represent beta-D-oxy LNA nucleosides, lowercase letters represent DNA nucleosides, all LNA C are 5-methyl cytosine, and 5-methyl DNA cytosines are presented by "e", all internucleoside linkages are phosphorothioate internucleoside linkages.

Oligonucleotides with an EX-EX indication as Start on SEQ ID NO: 1 are exon-exon spanning oligonucleotides designed to be complementary across exon-exon junctions of SNHG14-023 (ENST00000554726). The oligonucleotides primarily span exon2 and exon3 (i.e. are complementary to a region in exon2 and a region in exon 3)

Oligonucleotide Synthesis

Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on a MerMade12 or an Oligomaker DNA/RNA synthesizer at 1-4 μmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), LNA-T or amino-C6 linker) is performed by using a solution of 0.1 M of the 5'—O-DMT-protected amidite in acetonitrile and DCI (4,5-dicyanoimidazole) in acetonitrile (0.25 M) as activator. For the final cycle a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphordiester linkages can be introduced using 0.02 M iodine in THE/Pyridine/water 7:2:1. The rest of the reagents are the ones typically used for oligonucleotide synthesis.

Purification by RP-HPLC:

The crude compounds are purified by preparative RP-HPLC on a Phenomenex Jupiter C18 10μ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations:

DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography $T_m$ Assay Oligonucleotide and RNA target duplexes are diluted to 3 mM in 500 ml RNase-free water and mixed with 500 ml $2\times T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Preparation of Mouse Primary Cortical Neuron Cell Cultures

Primary cortical neuron cultures were prepared from mouse embryo brains of 15 days of age according to standard procedure. In brief, culture plates were coated with Poly-L-Lysine (50 μg/ml Poly-L-Lysine, 10 mM Na-tetraborate, pH 8 buffer) for 2-3 hrs at room temperature. The plates were washed with 1×PBS before use. Harvested mouse embryo brains were dissected and homogenized by a razor blade and submerged into 38 ml dissection medium (HBSS, 0.01 M Hepes, Penicillin/Streptomycin). Then, 2 ml trypsin was added and cells were incubated for 30 min at 37° C. and centrifuged down. The cells were dissolved in 20 ml DMEM (+10% FBS) and passed through a syringe for further homogenization. This was followed by centrifugation at 500 rpm for 15 mins. The cells were dissolved in DMEM (+10% FBS) and seeded in 96 well plates (0.1×10^6 cells/well in 100 μl). The neuronal cell cultures were ready for use directly after seeding.

Screening Oligonucleotides in Mouse Primary Cortical Neuron Cell Cultures

Cells were cultured in growth medium (Gibco Neurobasal medium, B27 supplement, Glutamax, Pencillin-streptomycin) in 96-well plates and incubated with oligonucleotides for 3 days at the desired concentrations. Total RNA was isolated from the cells and the knock-down efficacy was measured by qPCR analysis using the qScript™ XLT One-Step RT-qPCR ToughMix®, Low ROX™ kit from Quanta Bioscience (95134-500). A commercial taqman assays from Thermo Fisher Scientific was used to measure Ube3a_ATS including GAPDH for normalization.

Generation of Human Primary Neuronal Cell Cultures

Any cell lines at any described time point was incubated at 37° C., 5% CO2 concentration and 95% relative humidity.

Human Induced Pluripotent Stem Cells (hiPSC) Culture

Whole human blood samples were obtained from patients diagnosed with Angelman syndrome. The subsequent cultures of primary Peripheral Blood Mononuclear Cells (PMCSs) were enriched for erythroblasts. Patient-specific iPSC lines were generated by reprogramming erythroblast with CytoTune-iPS Sendai Reprogramming Kit (Thermo Fisher Scientific). Derived iPSC lines were maintained in feeder-free conditions using hESC-qualified Matrigel (Corning) in mTESR1 (STEMCELL Technologies) with daily medium replacement. Upon reaching confluence, colonies were dissociated into cell cluster of 50-200 μm in size using Gentle Cell Dissociation Reagent (STEMCELL Technologies) and subcultured at a ratio of 1:10-1:20 in the presence of 10 μM Y-27632 (Calbiochem).

Differentiation into Neural Progenitor Cells (NPC)

Upon induction of neural differentiation iPSC-derived cells were maintained in basal medium composed of equal volumes of DMEM:F12 Glutamax medium and Neurobasal medium (Gibco, Invitrogen), supplemented with 1×B27 (Gibco, Invitrogen), 1×N2 (Gibco, Invitrogen), 0.1 mM beta-mercaptoethanol (Gibco, Invitrogen) and indicated supplements.

Neural progenitor cells (NPCs) were derived from hiPSCs by dual SMAD inhibition and according to published procedures with slight modifications (Chambers et al. 2009 Nat Biotechnol. Vol. 3 pp. 275-80, Boissart et al., 2013 Transl Psychiatry. 3:e294). HiPSCs were dissociated with Accutase (Innovative Cell Technologies Inc.) into a single cell suspension and resuspended in basic medium further supplemented with 10 μM Y-27632 (Calbiochem), 5 ng/ml FGF (Peprotech), 10 μM SB-431542 (Calbiochem) and 100 nM LDN (Calbiochem). Single cell suspension was transferred to AggreWell800 plates (STEMCELL Technologies) enabling the formation of aggregates consisting of 8000 cells. After 5 days neural aggregates were transferred onto plates coated with poly-L-ornithine (Sigma) and laminin (Roche) and allowed to form neural rosettes under continued dual SMAD inhibition (SB-431542 and LDN) in basic medium supplemented with FGF. Neural rosettes were selectively isolated using STEMdiff™ Neural Rosette Selection Reagent (STEMCELL Technologies), replated onto dishes coated with poly-L-ornithine and Laminin521 (BioLamina) and expanded in basic medium supplemented with 10 ng/ml FGF (Peprotech), 10 ng/ml EGF (RnD), and 20 ng/ml BDNF (Peprotech). When reaching confluency, cells were enzymatically dissociated with 0.05% Trypsin/EDTA (Gibco, Invitrogen) and sub-cultured. Continued passaging in basic medium supplemented with FGF, EGF and BDNF leads to a stable neural progenitor cell line (NPC line) within 10 to 20 passages. A stable neural progenitor cell line is defined by its capacity to self-renew and by the expression of the developmental stage-specific markers Sox2 and Nestin. Upon specific stimuli, NPCs differentiate into neuronal (MAP2+, Tau+, HuC/D+) and astroglial (GFAP+) progenies (Dunkley et al., 2015 Proteomics Clin Appl. Vol. 7-8 pp. 684-94).

NPC Culture

Conditions for NPC culture have been described previously and were used with slight modifications (Boissart et al., 2013 Transl Psychiatry. 3:e294). In brief, cells were maintained in dishes coated with Laminin521 (BioLamina) and cultured in basic medium [composed of equal volumes of DMEM:F12 Glutamax medium and Neurobasal medium (Gibco, Invitrogen), supplemented with 1×B27 (Gibco, Invitrogen), 1×N2 (Gibco, Invitrogen), 0.1 mM beta-mercaptoethanol (Gibco, Invitrogen)] and supplemented with 10 ng/ml FGF (Peprotech), 10 ng/ml EGF (RnD), and 20 ng/ml BDNF (Peprotech).

Differentiation into Neuronal Cell Culture

To induce neuronal differentiation of NPC, cells were dissociated with 0.05% Trypsin/EDTA (Gibco, Invitrogen) into single cell suspension and seeded onto Laminin521 (BioLamina) coated dishes at a density of 12.000 cells/cm2 and maintained in basic medium supplemented with 200 ng/ml Shh (Peprotech), 100 ng/ml FGF8 (Peprotech), and 100 μM ascorbic acid phosphate (Sigma) for a period of 7 days. Subsequently, cells were replated in basal medium supplemented with 20 ng/ml BDNF (Peprotech), 10 ng/ml GDNF (Peprotech), 0.5 mM cAMP (BIOLOG Life Science), and 100 μM ascorbic acid phosphate (Sigma) at a density of 45000 cells/cm2 and differentiated for a period of 21 days. At day 21 of differentiation, differentiated neuronal cultures were replated onto the screening-compatible plate format. Replating was performed by dissociating the cultures with Accutase (Innovative Cell Technologies Inc.) into a single cell suspension. Cells were seeded at a density of 200.000 cells/cm2 in presence of 10 μM Y-27632 (a cell-permeable, reversible, inhibitor of Rho kinases from Calbiochem) into the 384 well microtiter plates for final oligonucleotides screening assay. Neuronal cultures were further differentiated for additional 7 days in basal medium supplemented with 20 ng/ml BDNF (Peprotech), 10 ng/ml GDNF (Peprotech), 0.5 mM cAMP (BIOLOG Life Science), and 100 μM ascorbic acid phosphate (Sigma). Differentiation medium was exchanged twice per week. After a total differentiation period of 35 days neuronal cell cultures were ready for oligonucleotide treatment.

Screening Oligonucleotides in Human Neuronal Cell Cultures—384 Well System

For screening, oligonucleotide stocks were pre-diluted to the indicated concentrations with water into 384 well microtiter plates (compound plate). The plate layout served as a treatment template. Two microliter oligonucleotide dilution from each well was transferred from the compound plate to a respective culture plate. All liquid handling was done under sterile conditions in a laminar flow using a semi-automated laboratory robotic system (Beckmancoulter). Neuronal cell cultures were incubated with oligonucleotides for 5 days without media change. Subsequently, neuronal cultures were lysed and processed for qPCR assay with RealTime ready Cell lysis and RNA Virus Master kit (Roche). Liquid handling was performed using a semi-automated laboratory robotic system (Beckmancoulter). Samples were analyzed by a Lightcycler480 real-time PCR system (Roche).

Activity of the oligonucleotides was assessed by qPCR monitoring transcript abundance of UBE3A using the following primers and probes

```
UBE3a-Sense: Forward primer:
                                    (SEQ ID NO: 837)
ATATGTGGAAGCCGGAATCT,

Reverse primer:
                                    (SEQ ID NO: 838)
TCCCAGAACTCCCTAATCAGAA,

Internal probe labeled with dye FAM:
                                    (SEQ ID NO: 839)
ATGACGGTGGCTATACCAGG
```

The RT-qPCR was multiplexed with PPIA (peptidylprolyl isomerase A) as housekeeping gene for normalization. PPIA primers and probe labeled with the dye VIC were purchased from Thermo Fisher Scientific (assay ID Hs99999904_m1). Each plate includes a non-targeting oligonucleotide (mock) as negative control (TTGaataagtggaTGT (SEQ ID NO: 846)) and a reference oligonucleotide CMP ID NO: 411, resulting in up-regulation of UBE3A mRNA.

Selectivity of oligonucleotides was verified by counter screening for SNORD 115 transcript, which is located upstream of SNORD109B on chromosome 15. Expression of SNORD115 was monitored by qPCR using the following primers and probe

```
Forward primer:
                                    (SEQ ID NO: 840)
GGGTCAATGATGAGAACCTTAT,

Reverse primer
                                    (SEQ ID NO: 841)
GGGCCTCAGCGTAATCCTATT,
```

-continued

```
Internal probe labeled with the dye FAM:
                                    (SEQ ID NO: 842)
TTCTGAAGAGAGGTGATGACTTAAAA
```

The RT-qPCR was multiplexed with PPIA (Thermo Fisher Scientific) upon oligonucleotide treatment.

The reduction of the SNHG14 transcript downstream of SNORD109B (also termed the UBE3A suppressor) was measured by RT-qPCR using the following primers and probe

```
Forward primer:
                                    (SEQ ID NO: 843)
ATCCGAGGCATGAATCTCAC,

Reverse primer:
                                    (SEQ ID NO: 844)
CAGGCCAAAACCCTTGATAA,

Internal probe labeled with dye FAM:
                                    (SEQ ID NO: 845)
TTGCTGAGCATTTTTGCATC
```

The RT-qPCR was multiplexed with PPIA (Thermo Fisher Scientific).

Data are presented as average % expression relative to mock across all plates and normalized to the reference oligonucleotide to account for plate to plate variation.

Screening Oligonucleotides in Human Neuronal Cell Cultures—96 Well System

For screening, oligonucleotide stocks were pre-diluted to the indicated concentrations with water into 96 well microtiter plates (compound plate). The plate layout served as a treatment template. Two microliter oligonucleotide dilution from each well was transferred from the compound plate to a respective culture plate. All liquid handling was done under sterile conditions in a laminar flow using a semi-automated laboratory robotic system (Beckman Coulter). Neuronal cell cultures were incubated with oligonucleotides for 5 days without media change. Subsequently, neuronal cultures were lysed and RNA purified using RNA purification kit Pure Link Pro96 (12173011A) LifeTechnologies. Liquid handling was performed using a semi-automated laboratory robotic system (Beckmancoulter). qPCR analysis of Ube3a and Ube3a-ATS was carried out on a ViiA™ 7 Real-Time PCR System Thermo Fisher Scientific using the qScript™ XLT 1-Step RT-qPCR ToughMix Low ROX, from Quanta (95134-50).

The following primers and probes were used:

qPCR UBE3a-Sense:

```
Forward primer:
                                    (SEQ ID NO: 697)
ATATGTGGAAGCCGGAATCT,

Reverse primer:
                                    (SEQ ID NO: 698)
TCCCAGAACTCCCTAATCAGAA,

Internal probe labeled with dye FAM:
                                    (SEQ ID NO: 699)
ATGACGGTGGCTATACCAGG
```

qPCR SNHG14 Transcript Downstream of SNORD109B (Also Termed the UBE3A Suppressor):

Commercially available primer and probe set from ThermoFisher: Hs01372957_m1. These primers amplifies a 87 bp exon-exon spanning sequence in the Genbank transcript AF400500.1

QPCR GAPDH Transcript:

Commercially available primer and probe set from Thermofisher: Gene Symbol: with following assay details: RefSeq: NM_002046.3, Probe Exon Location:3, Amplicon Size: 122 bp. Corresponding TaqMan Assay ID: Hs99999905_m1.

The RT-qPCR for both Ube3a and Ube3a-ATS was multiplexed with GAPDH as housekeeping gene for normalization. Each plate includes a non-targeting oligonucleotide (mock) as negative control (TTGaataagtggaTGT (SEQ ID NO: 846)) and a reference oligonucleotide CMP ID NO: 211, resulting in up-regulation of UBE3A mRNA. Moreover panel of oligos not targeting Ub3a or SNHG14 transcript downstream of SNORD109B (also termed the UBE3A suppressor) were included to monitor the assay noise and risk of detecting false positives. These were randomly distributed over the plates.

Control Oligonucleotides:

(SEQ ID NO: 819)
CGAaccactgaaCAA (SEQ ID NO: 820)
CGAaccactgaacAAA (SEQ ID NO: 821)
CGAagtgcacaCG (SEQ ID NO: 822)
GCGtaaagagaGGT (SEQ ID NO: 823)
GAGAaggcacagaCGG (SEQ ID NO: 824)
GCGaagtgcacaCGG (SEQ ID NO: 825)
GAGaaggcacagaCGG (SEQ ID NO: 826)
CGAaccactgAACA -continued (SEQ ID NO: 827)
GAAccactgaacAAA (SEQ ID NO: 828)
caGCGtaaagagaGG (SEQ ID NO: 829)
GCgtaaagagAGG (SEQ ID NO: 830)
CGAaccactgaAC (SEQ ID NO: 831)
CGAAccactgaaCAAA (SEQ ID NO: 832)
AGCgaagtgcacaCGG (SEQ ID NO: 833)
AGGtgaagcgaAGTG (SEQ ID NO: 834)
TAGTaaactgagCCA (SEQ ID NO: 835)
AGAaggcacagaCGG (SEQ ID NO: 836)
CCGcagtatggaTCG

Example 1—Oligonucleotide Activity in Mouse Primary Neuronal Cell Cultures

Oligonucleotides targeting the part of SNHG14 long non-coding RNA which is antisense to the UBE3A pre-mRNA (position 55319 to 141053 of SEQ ID NO: 1) were tested for their ability to reduce the SNHG14 long non-coding RNA transcript preventing UBE3A expression (also termed UBE3A suppressor or UBE3A-SUP in the data table) and their ability to induce UBE3A mRNA re-expression in mouse primary cortical neuron cell cultures, obtained as described in the "Materials and methods" section above. The oligonucleotide concentration was 5 microM.

The oligonucleotides were screened according to the protocol for screening in mouse cortical neuron cell cultures described in the section "Materials and methods". The results are shown in table 4.

TABLE 4

Oligonucleotide activity in primary mouse neuronal cell cultures.

| CMP ID NO | oligonucleotide | % of Mock UBE3A_SUP | sd | % of Mock UBE3A | sd |
|---|---|---|---|---|---|
| 95_1 | CTCAtacttgctttaAT | 3.6 | 0.1 | 154.1 | 15.1 |
| 95_2 | CTcatacttgctttaAT | 15.9 | 2.6 | 119.8 | 12.4 |
| 96_1 | ACatctcatacttGCTT | 4.0 | 0.5 | 149.9 | 11.5 |
| 96_2 | ACatctcatacttgcTT | 9.3 | 3.9 | 139.9 | 36.4 |
| 96_3 | ACatctcatacttgCTT | 3.1 | 0.2 | 143.2 | 3.9 |
| 97_1 | ACatctcatactTGCT | 4.0 | 1.5 | 154.5 | 10.0 |
| 97_2 | ACatctcatacttgCT | 6.1 | 1.7 | 141.1 | 14.1 |
| 97_3 | ACatctcatactTGCT | 3.7 | 0.6 | 162.7 | 15.0 |
| 97_4 | ACATctcatacttgCT | 5.2 | 0.4 | 156.7 | 24.4 |
| 98_1 | TAcatctcatactTGCT | 5.0 | 0.9 | 159.0 | 15.6 |
| 98_2 | TAcatctcatacttgCT | 15.5 | 5.3 | 130.4 | 3.4 |

TABLE 4-continued

Oligonucleotide activity in primary mouse neuronal cell cultures.

| CMP ID NO | oligonucleotide | % of Mock UBE3A_SUP | sd | % of Mock UBE3A | sd |
|---|---|---|---|---|---|
| 98_3 | TACAtctcatacttgCT | 4.7 | 0.4 | 140.3 | 38.2 |
| 101_1 | TACatctcatactTGC | 2.6 | 0.5 | 152.6 | 10.2 |
| 101_2 | TAcatctcatacttGC | 19.2 | 6.0 | 112.0 | 15.0 |
| 101_3 | TAcatctcatactTGC | 3.5 | 0.4 | 117.2 | 13.7 |
| 101_4 | TACAtctcatacttGC | 3.0 | 0.7 | 140.5 | 12.4 |
| 100_1 | CTAcatctcatactTGC | 5.4 | 0.8 | 160.4 | 4.1 |
| 100_2 | CTacatctcatacttGC | 9.6 | 3.7 | 159.2 | 14.5 |
| 100_3 | CTacatctcatactTGC | 3.0 | 0.1 | 133.2 | 5.9 |
| 99_2 | CCtacatctcatacttGC | 7.8 | 1.4 | 150.7 | 11.0 |
| 99_3 | CCtacatctcatactTGC | 3.2 | 0.6 | 134.7 | 12.5 |
| 99_4 | CCtacatctcatacTTGC | 2.7 | 0.2 | 145.2 | 4.7 |
| 102_1 | CCTAcatctcatactTG | 5.8 | 1.7 | 127.0 | 24.5 |
| 102_2 | CCtacatctcatactTG | 20.2 | 6.6 | 129.7 | 9.2 |
| 102_4 | CCTacatctcatacTTG | 4.0 | 0.6 | 140.2 | 7.2 |
| 102_3 | CCTacatctcatactTG | 3.9 | 1.0 | 133.3 | 10.0 |
| 104_1 | CCTacatctcataCTT | 6.6 | 1.5 | 136.5 | 8.7 |
| 104_3 | CCtacatctcatACTT | 3.5 | 0.4 | 131.4 | 6.0 |
| 103_1 | ACCtacatctcataCTT | 5.8 | 1.4 | 130.8 | 0.7 |
| 103_2 | ACctacatctcatacTT | 11.4 | 2.2 | 123.6 | 12.4 |
| 103_3 | ACctacatctcatACTT | 5.8 | 0.8 | 132.2 | 4.5 |
| 105_1 | TACCtacatctcatacTT | 5.2 | 0.8 | 152.3 | 7.2 |
| 106_1 | TTAcctacatctcataCTT | 13.3 | 3.0 | 140.1 | 17.5 |
| 106_2 | TTacctacatctcatacTT | 21.0 | 1.4 | 116.9 | 15.0 |
| 107_1 | ACCTacatctcataCT | 6.2 | 0.9 | 119.2 | 3.4 |
| 107_2 | ACctacatctcataCT | 14.3 | 7.4 | 142.9 | 13.7 |
| 108_1 | TACCtacatctcataCT | 5.6 | 1.0 | 127.0 | 10.7 |
| 108_2 | TAcctacatctcataCT | 21.4 | 12.5 | 117.1 | 8.5 |
| 109_1 | TTacctacatctcaTACT | 4.4 | 0.4 | 138.9 | 1.2 |
| 109_2 | TTacctacatctcataCT | 22.9 | 3.3 | 117.1 | 13.0 |
| 110_1 | TTAcctacatctcaTAC | 8.7 | 2.1 | 133.2 | 5.1 |
| 110_2 | TTacctacatctcatAC | 21.0 | 5.1 | 111.4 | 11.1 |
| 111_1 | GTtacctacatctCATA | 8.0 | 2.4 | 143.8 | 14.8 |
| 111_2 | GTtacctacatctcaTA | 19.0 | 2.3 | 115.4 | 4.1 |
| 112_1 | GTTacctacatctCAT | 6.6 | 1.4 | 145.5 | 16.8 |
| 112_2 | GTtacctacatctcAT | 15.8 | 4.5 | 120.3 | 8.1 |
| 126_1 | TCACtttccagatatCA | 8.0 | 1.9 | 133.8 | 5.4 |
| 126_3 | TCactttccagatatCA | 53.4 | 75.9 | 112.0 | 11.4 |

TABLE 4-continued

Oligonucleotide activity in primary mouse neuronal cell cultures.

| CMP ID NO | oligonucleotide | % of Mock UBE3A_SUP | sd | % of Mock UBE3A | sd |
|---|---|---|---|---|---|
| 128_1 | ACATgtccctttataTT | 16.3 | 2.5 | 114.7 | 11.1 |
| 128_2 | ACatgtccctttataTT | 14.8 | 1.1 | 136.9 | 6.2 |
| 129_1 | ACAtgtccctttaTAT | 11.8 | 1.9 | 135.0 | 14.3 |
| 132_1 | CTCAtccctccaagaAA | 9.1 | 1.6 | 131.7 | 8.4 |
| 132_2 | CTcatccctccaagaAA | 11.2 | 3.9 | 159.3 | 17.7 |

Example 2—Oligonucleotide Activity in Human Neuronal Cell Cultures

Oligonucleotides targeting human SNHG14 in the region downstream of SNORD109B corresponding to position 25278410 to 25419462 on chromosome 15 (SEQ ID NO: 1) were tested in patient derived human neuronal cell cultures (see protocol in "Materials and methods" section). The oligonucleotides ability to reduce the SNHG14 transcript in the region downstream of SNORD109B (also termed UBE3A suppressor or UBE3A-SUP in the data table), without affecting expression of SNORD115 was analyzed. Furthermore, the ability to induce UBE3A mRNA re-expression was analyzed.

The oligonucleotides were screened according to the protocol for screening oligonucleotides in human neuronal cell cultures described in the section "Materials and methods" above.

The results are shown in table 5. The expression of UBE3A mRNA has been measured for all compounds, whereas the knock-down of the UBE3A suppressor and the maintenance of SNORD61115 levels have not been analyzed for all compounds.

TABLE 5

Oligonucleotide activity in patient derived human neuronal cell cultures.

| Start SEQ ID NO 1 | CMP ID NO | Target | % of Mock Oligo conc 0.2 µM | sd | % of Mock Oligo conc 1.0 µM | sd | % of Mock Oligo conc 5.0 µM | sd |
|---|---|---|---|---|---|---|---|---|
| 1678 | 10_1 | UBE3A | 107 | 14 | 88 | 10 | 151 | 8 |
| 1679 | 12_2 | UBE3A | 100 | 9 | 87 | 14 | 158 | 16 |
| 1687 | 20_1 | UBE3A | 87 | 7 | 102 | 22 | 213 | 44 |
| 1712 | 21_1 | UBE3A | 127 | 23 | 166 | 6 | 178 | 13 |
| 1712 | 21_1 | UBE3A-SUP | 81 | 3 | 82 | 8 | 72 | 12 |
| 1712 | 21_1 | SNORD115 | 115 | 6 | 142 | 24 | 169 | 26 |
| 4167 | 22_1 | UBE3A | 87 | 5 | 90 | 8 | 146 | 20 |
| 4170 | 27_1 | UBE3A | 94 | 16 | 106 | 11 | 170 | 10 |
| 4171 | 29_2 | UBE3A | 86 | 13 | 100 | 12 | 194 | 35 |
| 4172 | 30_1 | UBE3A | 96 | 6 | 121 | 12 | 209 | 27 |
| 9210 | 35_1 | UBE3A | 88 | 5 | 112 | 23 | 195 | 27 |
| 10838 | 37_1 | UBE3A | 77 | 7 | 85 | 9 | 169 | 24 |
| 15565 | 38_2 | UBE3A | 93 | 11 | 108 | 6 | 167 | 34 |
| 22209 | 42_1 | UBE3A | 125 | 16 | 143 | 14 | 180 | 17 |
| 22209 | 42_1 | UBE3A-SUP | 108 | 14 | 98 | 15 | 85 | 18 |
| 22209 | 42_1 | SNORD115 | 101 | 14 | 93 | 25 | 127 | 21 |
| 30449 | 43_1 | UBE3A | 99 | 5 | 95 | 13 | 115 | 8 |
| 30451 | 44_1 | UBE3A | 99 | 15 | 80 | 20 | 141 | 17 |
| 30451 | 44_2 | UBE3A | 98 | 31 | 104 | 16 | 119 | 7 |
| 30697 | 46_1 | UBE3A | 91 | 8 | 87 | 5 | 167 | 20 |
| 36066 | 49_1 | UBE3A | 95 | 6 | 111 | 10 | 155 | 29 |
| 36066 | 49_1 | UBE3A-SUP | 76 | 7 | 84 | 24 | 110 | 31 |
| 36066 | 49_1 | SNORD115 | 99 | 14 | 111 | 20 | 94 | 6 |

TABLE 5-continued

Oligonucleotide activity in patient derived human neuronal cell cultures.

| Start SEQ ID NO 1 | CMP ID NO | Target | % of Mock Oligo conc 0.2 µM | sd | % of Mock Oligo conc 1.0 µM | sd | % of Mock Oligo conc 5.0 µM | sd |
|---|---|---|---|---|---|---|---|---|
| 36068 | 50_1 | UBE3A | 109 | 15 | 105 | 11 | 92 | 14 |
| 36068 | 50_1 | UBE3A-SUP | 122 | 24 | 93 | 28 | 73 | 7 |
| 36068 | 50_1 | SNORD115 | 120 | 15 | 113 | 12 | 99 | 6 |
| 37206 | 51_1 | UBE3A | 114 | 16 | 101 | 7 | 101 | 3 |
| 37206 | 51_1 | UBE3A-SUP | 128 | 21 | 67 | 9 | 84 | 13 |
| 37206 | 51_1 | SNORD115 | 140 | 26 | 110 | 9 | 100 | 11 |
| 46130 | 52_1 | UBE3A | 139 | 3 | 160 | 1 | 236 | 36 |
| 46130 | 52_1 | UBE3A-SUP | 135 | 16 | 133 | 26 | 160 | 32 |
| 46130 | 52_1 | SNORD115 | 104 | 8 | 119 | 14 | 100 | 8 |
| 48145 | 59_1 | UBE3A | 179 | 3 | 122 | 17 | 115 | NA |
| 48170 | 76_1 | UBE3A | 85 | 16 | 100 | 8 | 155 | 12 |
| 48171 | 80_1 | UBE3A | 120 | 7 | 114 | 10 | 172 | 20 |
| 48171 | 78_1 | UBE3A | 136 | 31 | 103 | 20 | 169 | 11 |
| 48172 | 82_2 | UBE3A | 96 | 11 | 121 | 4 | 186 | 32 |
| 48172 | 84_1 | UBE3A | 95 | 14 | 100 | 8 | 158 | 14 |
| 49343 | 85_1 | UBE3A | 97 | 22 | 121 | 10 | 189 | 17 |
| 49722 | 87_1 | UBE3A | 111 | 9 | 126 | 11 | 177 | 22 |
| 52417 | 92_1 | UBE3A | 133 | 7 | 140 | 30 | 140 | 8 |
| 52417 | 92_1 | UBE3A-SUP | 88 | 14 | 80 | 14 | 82 | 8 |
| 52417 | 92_1 | SNORD115 | 102 | 8 | 114 | 20 | 91 | 9 |
| 52420 | 93_1 | UBE3A | 111 | 14 | 120 | 9 | 126 | 16 |
| 52420 | 93_1 | UBE3A-SUP | 104 | 23 | 82 | 20 | 79 | 8 |
| 52420 | 93_1 | SNORD115 | 110 | 11 | 114 | 17 | 95 | 7 |
| 53953 | 94_1 | UBE3A | 117 | 12 | 147 | 15 | 166 | 15 |
| 53953 | 94_1 | UBE3A-SUP | 92 | 18 | 81 | 5 | 86 | 22 |
| 53953 | 94_1 | SNORD115 | 124 | 33 | 122 | 17 | 106 | 14 |
| 60819 | 95_1 | UBE3A | 103 | 11 | 131 | 14 | 175 | 7 |
| 60819 | 95_1 | UBE3A-SUP | 93 | 13 | 87 | 3 | 74 | 6 |
| 60819 | 95_1 | SNORD115 | 162 | 19 | 158 | 20 | 201 | 11 |
| 60819 | 95_2 | UBE3A | 147 | 10 | 129 | 20 | 117 | 2 |
| 60819 | 95_2 | UBE3A-SUP | 118 | 24 | 87 | 13 | 83 | 8 |
| 60819 | 95_2 | SNORD115 | 104 | 17 | 118 | 10 | 129 | 6 |
| 60823 | 96_1 | UBE3A | 115 | 16 | 135 | 19 | 174 | 17 |
| 60823 | 96_1 | UBE3A-SUP | 104 | 25 | 93 | 32 | 91 | 11 |
| 60823 | 96_2 | UBE3A | 108 | 7 | 114 | 9 | 115 | 13 |
| 60823 | 96_2 | UBE3A-SUP | 99 | 17 | 92 | 19 | 93 | 10 |
| 60824 | 97_1 | UBE3A | 111 | 12 | 134 | 23 | 169 | 14 |
| 60824 | 97_1 | UBE3A-SUP | 110 | 27 | 105 | 33 | 92 | 10 |
| 60824 | 97_2 | UBE3A | 124 | 13 | 126 | 12 | 124 | 11 |
| 60824 | 97_2 | UBE3A-SUP | 113 | 17 | 107 | 33 | 96 | 20 |
| 60824 | 98_1 | UBE3A | 111 | 16 | 119 | 11 | 138 | 14 |
| 60824 | 98_1 | UBE3A-SUP | 118 | 34 | 98 | 23 | 82 | 19 |
| 60824 | 98_1 | SNORD115 | 109 | 11 | 123 | 18 | 114 | 16 |
| 60824 | 98_2 | UBE3A | 128 | 10 | 109 | 7 | 136 | 12 |
| 60824 | 98_2 | UBE3A-SUP | 91 | 15 | 77 | 11 | 110 | 16 |
| 60824 | 98_2 | SNORD115 | 101 | 3 | 110 | 7 | 124 | 11 |
| 60825 | 99_1 | UBE3A | 125 | 6 | 115 | 5 | 131 | 10 |
| 60825 | 99_1 | UBE3A-SUP | 139 | 18 | 121 | 34 | 127 | 45 |
| 60825 | 99_1 | SNORD115 | 110 | 18 | 112 | 12 | 99 | 19 |
| 60825 | 99_2 | UBE3A | 120 | 21 | 111 | 11 | 135 | 22 |
| 60825 | 99_2 | UBE3A-SUP | 96 | 21 | 79 | 15 | 75 | 11 |
| 60825 | 99_2 | SNORD115 | 104 | 34 | 113 | 22 | 131 | 24 |

TABLE 5-continued

Oligonucleotide activity in patient derived human neuronal cell cultures.

| Start SEQ ID NO 1 | CMP ID NO | Target | % of Mock Oligo conc 0.2 μM | sd | % of Mock Oligo conc 1.0 μM | sd | % of Mock Oligo conc 5.0 μM | sd |
|---|---|---|---|---|---|---|---|---|
| 60825 | 100_1 | UBE3A | 123 | 34 | 139 | 34 | 145 | 21 |
| 60825 | 100_1 | UBE3A-SUP | 104 | 37 | 127 | 46 | 99 | 17 |
| 60825 | 100_2 | UBE3A | 124 | 46 | 138 | 37 | 145 | 31 |
| 60825 | 100_2 | UBE3A-SUP | 111 | 36 | 120 | 47 | 92 | 11 |
| 60825 | 101_1 | UBE3A | 112 | 18 | 123 | 15 | 150 | 13 |
| 60825 | 101_1 | UBE3A-SUP | 96 | 18 | 102 | 14 | 88 | 12 |
| 60825 | 101_2 | UBE3A | 118 | 15 | 138 | 24 | 139 | 32 |
| 60825 | 101_2 | UBE3A-SUP | 100 | 29 | 110 | 39 | 92 | 10 |
| 60826 | 102_1 | UBE3A | 132 | 17 | 120 | 7 | 125 | 9 |
| 60826 | 102_1 | UBE3A-SUP | 113 | 16 | 83 | 5 | 88 | 18 |
| 60826 | 102_1 | SNORD115 | 121 | 36 | 131 | 23 | 100 | 9 |
| 60826 | 102_2 | UBE3A | 90 | 6 | 116 | 23 | 103 | 7 |
| 60826 | 102_2 | UBE3A-SUP | 91 | 7 | 90 | 12 | 64 | 18 |
| 60826 | 102_2 | SNORD115 | 116 | 15 | 146 | 27 | 183 | 28 |
| 60827 | 103_1 | UBE3A | 106 | 8 | 112 | 10 | 115 | 9 |
| 60827 | 103_1 | UBE3A-SUP | 99 | 15 | 110 | 28 | 94 | 8 |
| 60827 | 103_2 | UBE3A | 107 | 14 | 120 | 13 | 112 | 14 |
| 60827 | 103_2 | UBE3A-SUP | 97 | 14 | 118 | 38 | 93 | 20 |
| 60827 | 104_1 | UBE3A | 128 | 14 | 111 | 9 | 111 | 6 |
| 60827 | 104_1 | UBE3A-SUP | 111 | 12 | 97 | 9 | 87 | 19 |
| 60827 | 104_1 | SNORD115 | 114 | 10 | 110 | 12 | 109 | 13 |
| 60827 | 104_2 | UBE3A | 108 | 10 | 111 | 16 | 109 | 10 |
| 60827 | 104_2 | UBE3A-SUP | 103 | 13 | 103 | 33 | 89 | 9 |
| 60827 | 105_1 | UBE3A | 122 | 13 | 121 | 12 | 121 | 4 |
| 60827 | 105_1 | UBE3A-SUP | 119 | 7 | 97 | 15 | 93 | 7 |
| 60827 | 105_1 | SNORD115 | 114 | 21 | 128 | 12 | 118 | 9 |
| 60827 | 105_2 | UBE3A | 123 | 5 | 110 | 9 | 114 | 8 |
| 60827 | 105_2 | UBE3A-SUP | 110 | 11 | 89 | 17 | 94 | 21 |
| 60827 | 105_2 | SNORD115 | 102 | 15 | 108 | 16 | 107 | 18 |
| 60827 | 106_1 | UBE3A | 114 | 17 | 133 | 23 | 125 | 9 |
| 60827 | 106_1 | UBE3A-SUP | 112 | 35 | 103 | 15 | 87 | 12 |
| 60827 | 106_2 | UBE3A | 110 | 12 | 130 | 22 | 123 | 14 |
| 60827 | 106_2 | UBE3A-SUP | 105 | 19 | 107 | 27 | 93 | 10 |
| 60828 | 107_1 | UBE3A | 83 | 11 | 117 | 13 | 112 | 6 |
| 60828 | 107_1 | UBE3A-SUP | 86 | 11 | 114 | 16 | 67 | 7 |
| 60828 | 107_1 | SNORD115 | 108 | 17 | 130 | 21 | 137 | 24 |
| 60828 | 107_2 | UBE3A | 143 | 42 | 117 | 10 | 122 | 11 |
| 60828 | 107_2 | UBE3A-SUP | 116 | 12 | 92 | 4 | 100 | 8 |
| 60828 | 107_2 | SNORD115 | 108 | 4 | 127 | 16 | 108 | 14 |
| 60828 | 108_1 | UBE3A | 120 | 7 | 127 | 31 | 132 | 31 |
| 60828 | 108_1 | UBE3A-SUP | 153 | 33 | 118 | 34 | 89 | 17 |
| 60828 | 108_1 | SNORD115 | 114 | 9 | 114 | 9 | 105 | 15 |
| 60828 | 108_2 | UBE3A | 122 | 18 | 133 | 26 | 128 | 9 |
| 60828 | 108_2 | UBE3A-SUP | 101 | 19 | 100 | 28 | 89 | 17 |
| 60828 | 109_1 | UBE3A | 108 | 10 | 129 | 14 | 128 | 5 |
| 60828 | 109_1 | UBE3A-SUP | 106 | 21 | 107 | 24 | 84 | 8 |
| 60828 | 109_2 | UBE3A | 109 | 11 | 110 | 8 | 111 | 13 |
| 60828 | 109_2 | UBE3A-SUP | 95 | 15 | 86 | 14 | 83 | 9 |
| 60829 | 110_1 | UBE3A | 104 | 6 | 83 | 3 | 101 | 15 |
| 60829 | 110_1 | UBE3A-SUP | 100 | 13 | 95 | 12 | 79 | 4 |
| 60829 | 110_1 | SNORD115 | 126 | 21 | 125 | 6 | 182 | 13 |
| 60829 | 110_2 | UBE3A | 92 | 7 | 87 | 8 | 96 | 7 |
| 60829 | 110_2 | UBE3A-SUP | 99 | 7 | 108 | 9 | 81 | 5 |
| 60829 | 110_2 | SNORD115 | 118 | 15 | 139 | 22 | 198 | 39 |
| 60830 | 111_1 | UBE3A | 110 | 6 | 122 | 13 | 124 | 10 |
| 60830 | 111_1 | UBE3A-SUP | 104 | 14 | 90 | 28 | 79 | 11 |
| 60830 | 111_2 | UBE3A | 115 | 10 | 120 | 15 | 121 | 10 |
| 60830 | 111_2 | UBE3A-SUP | 114 | 20 | 89 | 19 | 87 | 9 |
| 60831 | 112_1 | UBE3A | 93 | 8 | 94 | 13 | 106 | 10 |
| 60831 | 112_1 | UBE3A-SUP | 97 | 1 | 68 | 29 | 82 | 7 |
| 60831 | 112_1 | SNORD115 | 116 | 20 | 110 | 13 | 158 | 20 |
| 60831 | 112_2 | UBE3A | 83 | 8 | 78 | 7 | 83 | 6 |
| 60831 | 112_2 | UBE3A-SUP | 106 | 35 | 80 | 23 | 69 | 9 |
| 60831 | 112_2 | SNORD115 | 107 | 6 | 106 | 8 | 159 | 21 |
| 62198 | 113_1 | UBE3A | 110 | 3 | 122 | 6 | 134 | 9 |
| 62198 | 113_1 | UBE3A-SUP | 113 | 20 | 85 | 19 | 79 | 24 |
| 62198 | 113_1 | SNORD115 | 116 | 18 | 123 | 9 | 91 | 9 |
| 62284 | 115_1 | UBE3A | 105 | 14 | 98 | 19 | 141 | 36 |
| 62422 | 116_1 | UBE3A | 130 | 19 | 142 | 29 | 172 | 18 |
| 62423 | 117_1 | UBE3A | 76 | 8 | 93 | 13 | 171 | 17 |
| 62439 | 118_1 | UBE3A | 75 | 7 | 88 | 9 | 150 | 19 |
| 66378 | 119_1 | UBE3A | 96 | 14 | 93 | 5 | 110 | 10 |

TABLE 5-continued

Oligonucleotide activity in patient derived human neuronal cell cultures.

| Start SEQ ID NO 1 | CMP ID NO | Target | % of Mock Oligo conc 0.2 μM | sd | % of Mock Oligo conc 1.0 μM | sd | % of Mock Oligo conc 5.0 μM | sd |
|---|---|---|---|---|---|---|---|---|
| 77565 | 126_1 | UBE3A | 94 | 6 | 113 | 5 | 125 | 14 |
| 77565 | 126_1 | UBE3A-SUP | 83 | 17 | 95 | 33 | 85 | 5 |
| 77565 | 126_1 | SNORD115 | 105 | 11 | 123 | 19 | 152 | 15 |
| 77565 | 126_2 | UBE3A | 95 | 5 | 126 | 9 | 111 | 2 |
| 77565 | 126_2 | UBE3A-SUP | 77 | 27 | 106 | 21 | 83 | 15 |
| 77565 | 126_2 | SNORD115 | 115 | 17 | 157 | 13 | 180 | 15 |
| 92321 | 128_1 | UBE3A | 102 | 7 | 91 | 5 | 111 | 13 |
| 92321 | 128_1 | UBE3A-SUP | 115 | 3 | 104 | 25 | 91 | 13 |
| 92321 | 128_1 | SNORD115 | 135 | 9 | 132 | 12 | 196 | 35 |
| 92321 | 128_2 | UBE3A | 91 | 5 | 96 | 8 | 104 | 8 |
| 92321 | 128_2 | UBE3A-SUP | 112 | 20 | 92 | 20 | 79 | 7 |
| 92321 | 128_2 | SNORD115 | 125 | 7 | 111 | 13 | 169 | 12 |
| 92322 | 129_1 | UBE3A | 101 | 5 | 103 | 2 | 110 | 7 |
| 92322 | 129_1 | UBE3A-SUP | 99 | 39 | 113 | 12 | 94 | 13 |
| 92322 | 129_1 | SNORD115 | 124 | 25 | 114 | 6 | 140 | 13 |
| 92322 | 129_2 | UBE3A | 93 | 2 | 100 | 4 | 113 | 16 |
| 92322 | 129_2 | UBE3A-SUP | 109 | 4 | 102 | 22 | 85 | 7 |
| 92322 | 129_2 | SNORD115 | 103 | 11 | 99 | 9 | 152 | 31 |
| 97154 | 132_1 | UBE3A | 100 | 10 | 128 | 13 | 142 | 13 |
| 97154 | 132_1 | UBE3A-SUP | 103 | 9 | 115 | 8 | 109 | 6 |
| 97154 | 132_1 | SNORD115 | 49 | 7 | 90 | 12 | 143 | 25 |
| 97154 | 132_2 | UBE3A | 111 | 8 | 128 | 17 | 128 | 17 |
| 97154 | 132_2 | UBE3A-SUP | 95 | 7 | 116 | 9 | 105 | 13 |
| 97154 | 133_2 | SNORD115 | 86 | 7 | 106 | 9 | 121 | 9 |
| 97154 | 133_1 | UBE3A | 101 | 3 | 107 | 11 | 124 | 19 |
| 97154 | 133_1 | UBE3A-SUP | 112 | 9 | 117 | 7 | 146 | 25 |
| 97154 | 133_1 | SNORD115 | 60 | 7 | 110 | 15 | 141 | 15 |
| 97154 | 133_2 | UBE3A | 94 | 13 | 116 | 14 | 138 | 12 |
| 97154 | 133_2 | UBE3A-SUP | 116 | 6 | 128 | 13 | 148 | 38 |
| 97154 | 132_2 | SNORD115 | 70 | 5 | 108 | 9 | 160 | 34 |
| 106137 | 137_1 | UBE3A | 83 | 12 | 74 | 11 | 124 | 20 |
| 109404 | 138_1 | UBE3A | 80 | 20 | 92 | 7 | 120 | 21 |
| 110766 | 139_1 | UBE3A | 76 | 5 | 85 | 12 | 121 | 17 |
| 114826 | 140_1 | UBE3A | 87 | 10 | 88 | 11 | 136 | 9 |
| 118637 | 143_1 | UBE3A | 83 | 7 | 104 | 30 | 141 | 28 |
| 118639 | 144_1 | UBE3A | 74 | 17 | 31 | 39 | 106 | 33 |
| 124160 | 145_2 | UBE3A | 89 | 6 | 95 | 10 | 115 | 25 |
| 125499 | 146_1 | UBE3A | 83 | 13 | 76 | 7 | 124 | 16 |
| 125499 | 146_2 | UBE3A | 123 | 30 | 79 | 14 | 102 | 23 |
| 125538 | 150_2 | UBE3A | 82 | 17 | 82 | 7 | 119 | 24 |

Figure 2:
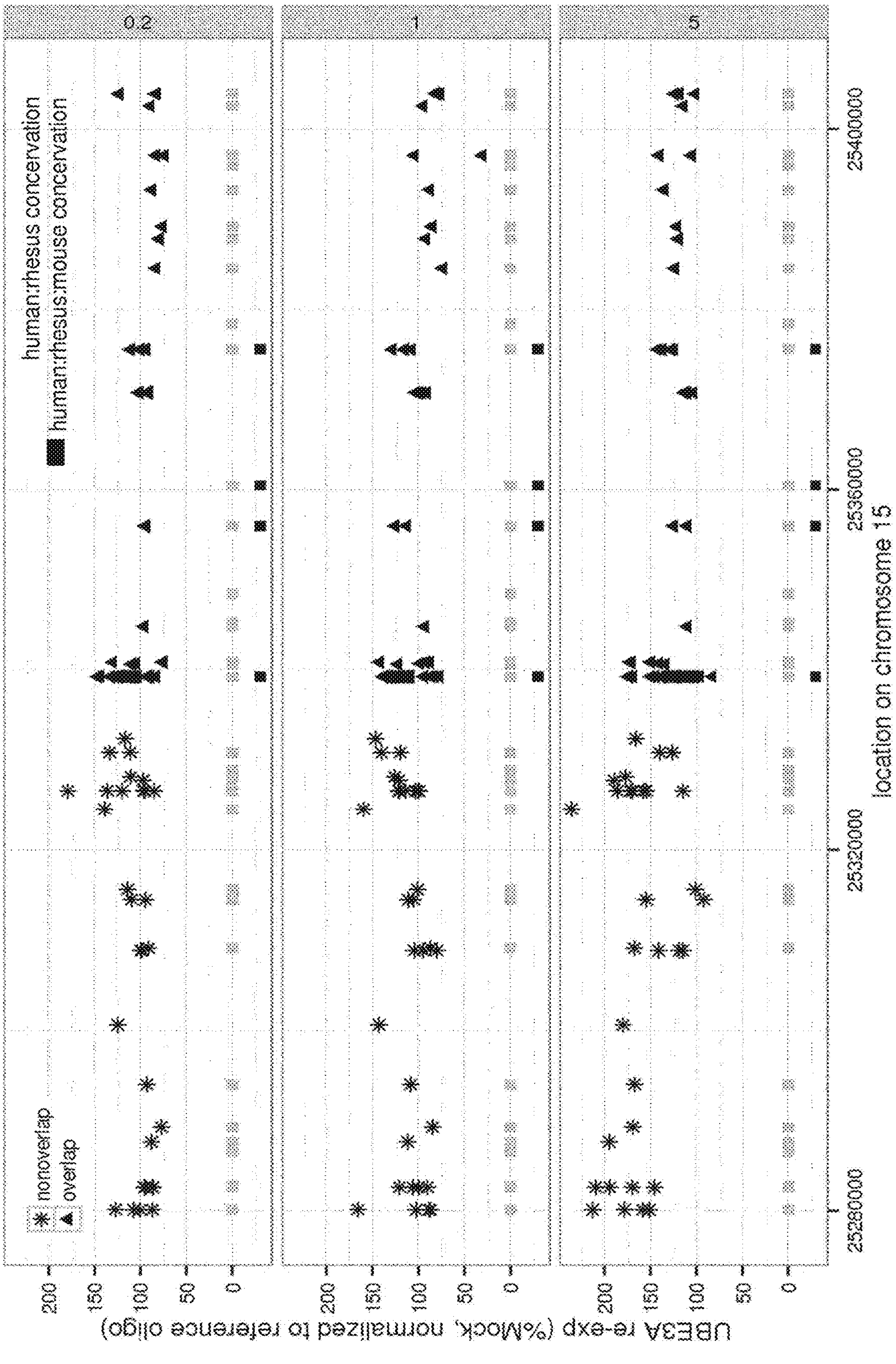
FIG. 2: Representation of the ability of the oligonucleotides, tested in Example 2, to induce re-expression of UBE3A in human neuronal cell cultures. Oligonucleotides complementary to the region of human SNHG14 long non-coding RNA between SNORD109B and the region upstream of the UBE3A coding region (position 1 to 55318 of SEQ ID NO: 1) are indicated with ● nonoverlap. Oligonucleotides complementary to the region of human SNHG14 long non-coding RNA which is antisense to the UBE3A pre-mRNA (position 55319 to 141053 of SEQ ID NO: 1) are indicated with ▲ overlap. Oligonucleotides from Table 3 with conservation to human and rhesus monkey are indicated at the bottom of each plot as ▒. Conservation between human:rhesus:mouse is indicated by ■. The oligonucleotide concentrations were 0.2, 1 and 5 microM as indicated in the right hand side each plot.

Of the 187 compounds tested approximately 90% showed re-expression of UBE3A when compared to the mock oligonucleotide at the 5 micro Molar concentration. The number of oligonucleotides capable of inducing re-expression of UBE3A is higher in the region between position 1 to 55318 of SEQ ID NO: 1 (non-overlapping region) then in the region complementary to UBE3A coding region (overlapping region. FIG. 2 plots the distribution of the oligonucleotides according to their position on chromosome 15 versus the UBE3A mRNA expression relative to the mock oligonucleotide.

For the oligonucleotides where SNORD1115 has been tested there is no significant down regulation when compared to mock at 1 and 5 microM.

Example 3—Activity of Oligonucleotides Targeting the SNHG14 Transcript in the Region Downstream of SNORD19B and Upstream of the Region Antisense to to the UBE3A Pre-mRNA Oligonucleotides targeting position 4806-54939 of SEQ ID NO: 1 were tested in patient derived human neuronal cell cultures (see protocol in "Materials and methods" section). The oligonucleotides ability to reduce the SNHG14 transcript in the region downstream of SNORD109B (also termed UBE3A suppressor or UBE3A-SUP in the data table. Furthermore, the ability to induce UBE3A mRNA re-expression was analyzed.

The oligonucleotides were screened according to the protocol for screening oligonucleotides in human neuronal cell cultures described in the section "Materials and methods"—"Screening oligonucleotides in human neuronal cell cultures—96 well system"

The results are shown in table 6.

TABLE 6

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 4806 | 151_1 | 0.2 | 66 | 2 | 125 | NA |
| 4806 | 151_1 | 1 | 53 | 10 | NA | NA |
| 4808 | 152_1 | 0.2 | 49 | 6 | 167 | NA |
| 4808 | 152_1 | 1 | 33 | 4 | 289 | NA |
| 4809 | 153_1 | 0.2 | 41 | 1 | 208 | NA |
| 4809 | 153_1 | 1 | 29 | 10 | NA | NA |
| 4811 | 154_1 | 0.2 | 48 | 3 | 282 | NA |
| 4811 | 154_1 | 1 | 37 | 5 | 331 | NA |
| 4812 | 155_1 | 0.2 | 35 | 5 | 286 | 64 |
| 4812 | 155_1 | 1 | 32 | 3 | 327 | 21 |
| 4972 | 156_1 | 0.2 | 60 | 6 | 145 | 6 |
| 4972 | 156_1 | 1 | 46 | 14 | 145 | NA |
| 4973 | 157_1 | 0.2 | 75 | 9 | 128 | 6 |
| 4973 | 157_1 | 1 | 59 | NA | 158 | NA |
| 4979 | 158_1 | 0.2 | 46 | 9 | 131 | NA |
| 4979 | 158_1 | 1 | 37 | 5 | 219 | 8 |
| 5058 | 159_1 | 0.2 | 69 | 6 | 133 | 19 |
| 5058 | 159_1 | 1 | 51 | 14 | NA | NA |
| 5071 | 160_1 | 0.2 | 55 | 8 | 98 | NA |
| 5071 | 160_1 | 1 | 39 | 7 | 136 | 34 |
| 5078 | 161_1 | 0.2 | 65 | 7 | 205 | 18 |
| 5078 | 161_1 | 1 | 51 | 10 | 306 | 31 |
| 5094 | 162_1 | 0.2 | 53 | 5 | 154 | 27 |
| 5094 | 162_1 | 1 | 34 | 8 | 300 | 65 |
| 5096 | 163_1 | 0.2 | 44 | 1 | 206 | 49 |
| 5096 | 163_1 | 1 | 36 | 6 | 316 | NA |
| 5100 | 164_1 | 0.2 | 34 | 3 | 220 | NA |
| 5100 | 164_1 | 1 | 30 | 3 | 227 | 32 |
| 5101 | 165_1 | 0.2 | 38 | 7 | 245 | NA |
| 5101 | 165_1 | 1 | 36 | 4 | 246 | 55 |
| 5218 | 166_1 | 0.2 | 45 | 4 | 240 | NA |
| 5218 | 166_1 | 1 | 36 | 6 | 280 | 44 |
| 5218 | 167_1 | 0.2 | 46 | 2 | 261 | NA |
| 5218 | 167_1 | 1 | 31 | 4 | 346 | 30 |
| 5224 | 168_1 | 0.2 | 39 | 3 | 377 | 40 |
| 5224 | 168_1 | 1 | 33 | 5 | 338 | 65 |
| 5224 | 169_1 | 0.2 | 37 | 4 | 313 | NA |
| 5224 | 169_1 | 1 | 31 | 2 | 308 | 3 |
| 5427 | 170_1 | 0.2 | 89 | 13 | 105 | 26 |
| 5427 | 170_1 | 1 | 117 | 35 | 124 | NA |
| 5434 | 171_1 | 0.2 | 51 | 5 | 164 | 10 |
| 5434 | 171_1 | 1 | 33 | 6 | 213 | 46 |
| 5785 | 172_1 | 0.2 | 46 | 5 | 210 | NA |
| 5785 | 172_1 | 1 | 38 | 4 | 342 | NA |
| 5786 | 173_1 | 0.2 | 54 | 4 | 292 | 61 |
| 5786 | 173_1 | 1 | 39 | 6 | 552 | NA |
| 6341 | 174_1 | 0.2 | 97 | 11 | 126 | 3 |
| 6341 | 174_1 | 1 | 90 | 33 | NA | NA |
| 6694 | 175_1 | 0.2 | 44 | 4 | 226 | NA |
| 6694 | 175_1 | 1 | 35 | 4 | 296 | NA |
| 6695 | 176_1 | 0.2 | 32 | 7 | 297 | 87 |
| 6695 | 176_1 | 1 | 29 | 4 | 263 | 9 |
| 6958 | 177_1 | 0.2 | 58 | 7 | 244 | 76 |
| 6958 | 177_1 | 1 | 47 | NA | NA | NA |
| 7159 | 179_1 | 0.2 | 33 | 4 | 282 | NA |
| 7159 | 179_1 | 1 | 29 | 5 | 289 | 7 |
| 7159 | 178_1 | 0.2 | 43 | 5 | 248 | NA |
| 7159 | 178_1 | 1 | 32 | 4 | 258 | NA |
| 7720 | 180_1 | 0.2 | 75 | 6 | 144 | 36 |
| 7720 | 180_1 | 1 | 54 | 7 | 233 | 26 |
| 7724 | 181_1 | 0.2 | 72 | 6 | 177 | 20 |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 7724 | 181_1 | 1 | 45 | 19 | 224 | 62 |
| 7725 | 182_1 | 0.2 | 65 | 5 | 139 | 37 |
| 7725 | 182_1 | 1 | 47 | 4 | 208 | 76 |
| 7725 | 183_1 | 0.2 | 103 | 13 | 140 | 2 |
| 7725 | 183_1 | 1 | 74 | 6 | NA | NA |
| 7727 | 184_1 | 0.2 | 45 | 2 | 300 | 107 |
| 7727 | 184_1 | 1 | 35 | 2 | 272 | 16 |
| 8117 | 185_1 | 0.2 | 87 | 17 | 122 | 13 |
| 8117 | 185_1 | 1 | 63 | 17 | 175 | NA |
| 8118 | 186_1 | 0.2 | 40 | 5 | 368 | 105 |
| 8118 | 186_1 | 1 | 33 | 5 | NA | NA |
| 8119 | 187_1 | 0.2 | 62 | 5 | 197 | NA |
| 8119 | 187_1 | 1 | 43 | 13 | 517 | 143 |
| 8120 | 188_1 | 0.2 | 96 | 10 | 136 | 41 |
| 8120 | 188_1 | 1 | 79 | 22 | 146 | 19 |
| 8571 | 189_1 | 0.2 | 53 | 11 | 204 | NA |
| 8571 | 189_1 | 1 | 49 | 24 | 298 | 15 |
| 8573 | 190_1 | 0.2 | 54 | 9 | 140 | 9 |
| 8573 | 190_1 | 1 | 50 | 10 | 267 | 4 |
| 8574 | 191_1 | 0.2 | 56 | 1 | 117 | NA |
| 8574 | 191_1 | 1 | 57 | 13 | 199 | NA |
| 8575 | 192_1 | 0.2 | 56 | 9 | 165 | 10 |
| 8575 | 192_1 | 1 | 54 | 13 | 246 | NA |
| 8576 | 193_1 | 0.2 | 56 | 6 | 185 | 7 |
| 8576 | 193_1 | 1 | 52 | 8 | 330 | 35 |
| 8585 | 194_1 | 0.2 | 47 | 2 | 302 | NA |
| 8585 | 194_1 | 1 | 39 | 7 | NA | NA |
| 8819 | 195_1 | 0.2 | 62 | 10 | 155 | 10 |
| 8819 | 195_1 | 1 | 41 | 3 | 192 | 7 |
| 8820 | 196_1 | 0.2 | 55 | 12 | 237 | 69 |
| 8820 | 196_1 | 1 | 40 | 3 | 278 | 26 |
| 8887 | 197_1 | 0.2 | 69 | 15 | 301 | 59 |
| 8887 | 197_1 | 1 | 58 | 7 | 383 | 92 |
| 9150 | 198_1 | 0.2 | 49 | 6 | NA | NA |
| 9150 | 198_1 | 1 | 43 | 3 | 365 | 38 |
| 9201 | 199_1 | 0.2 | 79 | 23 | 88 | 42 |
| 9201 | 199_1 | 1 | 64 | 24 | 140 | 22 |
| 9202 | 201_1 | 0.2 | 61 | 10 | NA | NA |
| 9202 | 201_1 | 1 | 45 | 8 | 343 | 27 |
| 9202 | 200_1 | 0.2 | 47 | 3 | 287 | 76 |
| 9202 | 200_1 | 1 | 41 | 4 | 281 | NA |
| 9203 | 202_1 | 0.2 | 55 | 17 | 166 | 92 |
| 9203 | 202_1 | 1 | 40 | 5 | 297 | 54 |
| 9209 | 203_1 | 0.2 | 60 | 1 | 122 | NA |
| 9209 | 203_1 | 1 | 40 | 14 | 204 | 8 |
| 9210 | 204_1 | 0.2 | 43 | 2 | 216 | NA |
| 9210 | 204_1 | 1 | 37 | 3 | 409 | NA |
| 9210 | 205_1 | 0.2 | 45 | 8 | 187 | NA |
| 9210 | 205_1 | 1 | 37 | 22 | 336 | 18 |
| 9211 | 206_1 | 0.2 | 51 | 10 | 384 | 17 |
| 9211 | 206_1 | 1 | 42 | 3 | 381 | 35 |
| 9211 | 207_1 | 0.2 | 65 | 8 | 301 | 28 |
| 9211 | 207_1 | 1 | 50 | 5 | 272 | 53 |
| 9212 | 35_2 | 0.2 | 42 | 11 | 203 | 16 |
| 9212 | 35_2 | 1 | 44 | 18 | 335 | NA |
| 9212 | 208_1 | 0.2 | 64 | 5 | 147 | 58 |
| 9212 | 208_1 | 1 | 50 | 6 | 260 | 73 |
| 9213 | 209_1 | 0.2 | 57 | 7 | NA | NA |
| 9213 | 209_1 | 1 | 49 | 4 | 346 | 31 |
| 9214 | 210_1 | 0.2 | 49 | 7 | 139 | NA |
| 9214 | 210_1 | 1 | 45 | 7 | 223 | 59 |
| 10832 | 211_1 | 0.2 | 70 | 6 | 147 | 10 |
| 10832 | 211_1 | 1 | 56 | 9 | 200 | 38 |
| 10837 | 212_1 | 0.2 | 59 | 9 | 146 | 46 |
| 10837 | 212_1 | 1 | 41 | 6 | 226 | 47 |
| 10838 | 213_1 | 0.2 | 50 | 8 | 247 | 69 |
| 10838 | 213_1 | 1 | 44 | 12 | 307 | NA |
| 10877 | 214_1 | 0.2 | 108 | 21 | 115 | 1 |
| 10877 | 214_1 | 1 | 92 | 37 | 88 | 32 |
| 11434 | 215_1 | 0.2 | 97 | 12 | 81 | 23 |
| 11434 | 215_1 | 1 | 80 | 26 | 111 | 11 |
| 11435 | 216_1 | 0.2 | 90 | 16 | 87 | NA |
| 11435 | 216_1 | 1 | 82 | 29 | 82 | 21 |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 11436 | 217_1 | 0.2 | 87 | 6 | 83 | 11 |
| 11436 | 217_1 | 1 | 68 | 26 | 123 | NA |
| 11438 | 218_1 | 0.2 | 57 | 5 | 133 | NA |
| 11438 | 218_1 | 1 | 44 | 16 | 188 | NA |
| 11439 | 219_1 | 0.2 | 84 | 1 | 93 | NA |
| 11439 | 219_1 | 1 | 66 | 22 | 113 | 29 |
| 11464 | 220_1 | 0.2 | 67 | 9 | 209 | 51 |
| 11464 | 220_1 | 1 | 41 | 6 | 256 | 33 |
| 11507 | 221_1 | 0.2 | 59 | 6 | 237 | NA |
| 11507 | 221_1 | 1 | 40 | 63 | 320 | NA |
| 11508 | 222_1 | 0.2 | 53 | 7 | 195 | NA |
| 11508 | 222_1 | 1 | 48 | 12 | 302 | NA |
| 11511 | 223_1 | 0.2 | 41 | 3 | 210 | 6 |
| 11511 | 223_1 | 1 | 37 | 9 | 273 | NA |
| 11513 | 224_1 | 0.2 | 22 | 8 | 288 | 91 |
| 11513 | 224_1 | 1 | 26 | 5 | 360 | 46 |
| 11514 | 225_1 | 0.2 | 98 | 17 | 98 | 31 |
| 11514 | 225_1 | 1 | 68 | 16 | 129 | 11 |
| 11736 | 226_1 | 0.2 | 69 | 8 | 197 | 80 |
| 11736 | 226_1 | 1 | 55 | 7 | 329 | 66 |
| 12361 | 227_1 | 0.2 | 48 | 8 | 183 | 56 |
| 12361 | 227_1 | 1 | 37 | 4 | 193 | 46 |
| 12794 | 228_1 | 0.2 | 38 | 9 | 201 | 71 |
| 12794 | 228_1 | 1 | 32 | 2 | 362 | 48 |
| 12795 | 229_1 | 0.2 | 50 | 12 | 161 | 30 |
| 12795 | 229_1 | 1 | 34 | 7 | 301 | 35 |
| 12796 | 230_1 | 0.2 | 44 | 12 | 237 | 86 |
| 12796 | 230_1 | 1 | 32 | 3 | 379 | 106 |
| 12894 | 232_1 | 0.2 | 91 | 17 | 79 | 27 |
| 12894 | 232_1 | 1 | 66 | 10 | 99 | 24 |
| 12894 | 231_1 | 0.2 | 80 | 5 | 89 | NA |
| 12894 | 231_1 | 1 | 57 | 14 | 164 | 31 |
| 12895 | 234_1 | 0.2 | 88 | 11 | 75 | 32 |
| 12895 | 234_1 | 1 | 68 | 19 | 91 | 24 |
| 12895 | 233_1 | 0.2 | 57 | 5 | 199 | 37 |
| 12895 | 233_1 | 1 | 38 | 7 | 249 | 57 |
| 12896 | 235_1 | 0.2 | 72 | 3 | 176 | 9 |
| 12896 | 235_1 | 1 | 45 | 3 | 251 | 42 |
| 13223 | 236_1 | 0.2 | 40 | 3 | 267 | 66 |
| 13223 | 236_1 | 1 | 31 | 3 | 270 | 23 |
| 13224 | 238_1 | 0.2 | 33 | 3 | 265 | NA |
| 13224 | 238_1 | 1 | 28 | 4 | 265 | 6 |
| 13224 | 237_1 | 0.2 | 38 | 2 | 212 | NA |
| 13224 | 237_1 | 1 | 31 | 1 | 254 | 31 |
| 13225 | 239_1 | 0.2 | 42 | 5 | 317 | 113 |
| 13225 | 239_1 | 1 | 29 | 7 | 215 | 26 |
| 13226 | 240_1 | 0.2 | 38 | 7 | 223 | NA |
| 13226 | 240_1 | 1 | 32 | 5 | 232 | 16 |
| 15115 | 241_1 | 0.2 | 61 | 8 | 377 | 15 |
| 15115 | 241_1 | 1 | 41 | 3 | 377 | 43 |
| 15258 | 242_1 | 0.2 | 66 | 14 | 133 | 35 |
| 15258 | 242_1 | 1 | 55 | 10 | 170 | 17 |
| 15568 | 243_1 | 0.2 | 62 | 13 | 192 | 58 |
| 15568 | 243_1 | 1 | 41 | 11 | 309 | 5 |
| 15570 | 244_1 | 0.2 | 53 | 17 | 252 | 59 |
| 15570 | 244_1 | 1 | 44 | 5 | 332 | 52 |
| 15572 | 245_1 | 0.2 | 57 | 21 | 321 | 122 |
| 15572 | 245_1 | 1 | 49 | 7 | 407 | 77 |
| 15573 | 246_1 | 0.2 | 47 | 16 | 348 | 129 |
| 15573 | 246_1 | 1 | 40 | 7 | 410 | 69 |
| 15574 | 247_1 | 0.2 | 48 | 14 | 326 | 116 |
| 15574 | 247_1 | 1 | 44 | 8 | 411 | 36 |
| 15722 | 248_1 | 0.2 | 51 | 3 | 258 | 17 |
| 15722 | 248_1 | 1 | 36 | 3 | 230 | NA |
| 16597 | 249_1 | 0.2 | 66 | 19 | 111 | 39 |
| 16597 | 249_1 | 1 | 54 | 14 | 174 | 44 |
| 16603 | 250_1 | 0.2 | 67 | 26 | 89 | 31 |
| 16603 | 250_1 | 1 | 56 | 6 | 172 | 32 |
| 16730 | 251_1 | 0.2 | 36 | 5 | 354 | 41 |
| 16730 | 251_1 | 1 | 31 | 2 | 326 | 75 |
| 16849 | 252_1 | 0.2 | 74 | 17 | 188 | 81 |
| 16849 | 252_1 | 1 | 48 | 17 | 282 | 1 |
| 17089 | 253_1 | 0.2 | 70 | 17 | 98 | 37 |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 17089 | 253_1 | 1 | 62 | 19 | 153 | 13 |
| 17401 | 254_1 | 0.2 | 42 | 6 | 209 | 83 |
| 17401 | 254_1 | 1 | 29 | 3 | 327 | 49 |
| 24290 | 255_1 | 0.2 | 106 | 13 | 105 | 36 |
| 24290 | 255_1 | 1 | 109 | 21 | 136 | NA |
| 24296 | 256_1 | 0.2 | 92 | 20 | 117 | 30 |
| 24296 | 256_1 | 1 | 93 | 15 | 138 | 21 |
| 24811 | 257_1 | 0.2 | 85 | 12 | 126 | 4 |
| 24811 | 257_1 | 1 | 74 | 12 | 137 | 17 |
| 25032 | 258_1 | 0.2 | 50 | 11 | 329 | 131 |
| 25032 | 258_1 | 1 | 39 | 5 | 41 | 53 |
| 25033 | 259_1 | 0.2 | 40 | 10 | 343 | 50 |
| 25033 | 259_1 | 1 | 31 | 3 | 483 | 84 |
| 25250 | 260_1 | 0.2 | 33 | 10 | 279 | 42 |
| 25250 | 260_1 | 1 | 33 | 4 | 338 | 65 |
| 25251 | 261_1 | 0.2 | 40 | 8 | 209 | 97 |
| 25251 | 261_1 | 1 | 34 | 3 | 370 | 57 |
| 25718 | 262_1 | 0.2 | 56 | 20 | 113 | 48 |
| 25718 | 262_1 | 1 | 45 | 8 | 198 | 65 |
| 25720 | 263_1 | 0.2 | 84 | 7 | 121 | 39 |
| 25720 | 263_1 | 1 | 72 | 11 | 88 | 10 |
| 25721 | 264_1 | 0.2 | 83 | 15 | 87 | 40 |
| 25721 | 264_1 | 1 | 84 | 22 | NA | NA |
| 26331 | 265_1 | 0.2 | 93 | 5 | 88 | 38 |
| 26331 | 265_1 | 1 | 81 | 8 | NA | NA |
| 27165 | 266_1 | 0.2 | 63 | 3 | 117 | 39 |
| 27165 | 266_1 | 1 | 46 | 9 | 174 | 15 |
| 27248 | 267_1 | 0.2 | 81 | 10 | 124 | 17 |
| 27248 | 267_1 | 1 | 59 | 10 | 190 | 112 |
| 29330 | 268_1 | 0.2 | 109 | 4 | 124 | 48 |
| 29330 | 268_1 | 1 | 98 | 28 | 114 | 35 |
| 29635 | 269_1 | 0.2 | 45 | 1 | 218 | 50 |
| 29635 | 269_1 | 1 | 33 | 9 | 267 | NA |
| 29635 | 270_1 | 0.2 | 55 | 5 | 225 | 41 |
| 29635 | 270_1 | 1 | 45 | 8 | NA | NA |
| 29636 | 271_1 | 0.2 | 48 | 2 | 285 | 56 |
| 29636 | 271_1 | 1 | 40 | 7 | 359 | 99 |
| 29636 | 272_1 | 0.2 | 48 | 3 | 166 | 5 |
| 29636 | 272_1 | 1 | 35 | 8 | 293 | 40 |
| 29637 | 273_1 | 0.2 | 56 | 5 | 255 | 47 |
| 29637 | 273_1 | 1 | 46 | 4 | 300 | 105 |
| 29637 | 274_1 | 0.2 | 67 | 7 | 134 | 35 |
| 29637 | 274_1 | 1 | 54 | 7 | 234 | 19 |
| 29661 | 275_1 | 0.2 | 51 | 3 | 167 | 15 |
| 29661 | 275_1 | 1 | 42 | 11 | 251 | NA |
| 29661 | 276_1 | 0.2 | 54 | 5 | 127 | 17 |
| 29661 | 276_1 | 1 | 39 | 8 | 229 | NA |
| 29684 | 277_1 | 0.2 | 40 | 3 | 168 | 73 |
| 29684 | 277_1 | 1 | 31 | 13 | NA | NA |
| 29684 | 278_1 | 0.2 | 46 | 7 | 179 | 2 |
| 29684 | 278_1 | 1 | 36 | 8 | NA | NA |
| 30455 | 279_1 | 0.2 | 102 | 20 | 96 | 34 |
| 30455 | 279_1 | 1 | 86 | 22 | 118 | 23 |
| 30456 | 280_1 | 0.2 | 94 | 23 | 91 | 28 |
| 30456 | 280_1 | 1 | 83 | 18 | 134 | 36 |
| 30457 | 281_1 | 0.2 | 89 | 23 | 97 | 37 |
| 30457 | 281_1 | 1 | 94 | 23 | 106 | 39 |
| 30458 | 282_1 | 0.2 | 99 | 14 | 77 | 27 |
| 30458 | 282_1 | 1 | 103 | 17 | 96 | 20 |
| 30462 | 283_1 | 0.2 | 66 | 26 | 98 | 36 |
| 30462 | 283_1 | 1 | 56 | 14 | 129 | 13 |
| 30465 | 284_1 | 0.2 | 73 | 11 | 114 | 47 |
| 30465 | 284_1 | 1 | 57 | 10 | 197 | 63 |
| 30601 | 285_1 | 0.2 | 41 | 31 | 311 | 29 |
| 30601 | 285_1 | 1 | 30 | 16 | 373 | 40 |
| 30605 | 286_1 | 0.2 | 40 | 2 | 221 | 86 |
| 30605 | 286_1 | 1 | 33 | 6 | 375 | NA |
| 30609 | 287_1 | 0.2 | 43 | 3 | 267 | 65 |
| 30609 | 287_1 | 1 | 37 | 5 | 332 | 27 |
| 30610 | 288_1 | 0.2 | 46 | 6 | 253 | 79 |
| 30610 | 288_1 | 1 | 38 | 3 | 338 | NA |
| 30667 | 289_1 | 0.2 | 38 | 15 | 325 | 144 |
| 30667 | 289_1 | 1 | 36 | 3 | 461 | 68 |

TABLE 6-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 30668 | 290_1 | 0.2 | 74 | 19 | 124 | 54 |
| 30668 | 290_1 | 1 | 58 | 14 | 183 | 20 |
| 30669 | 291_1 | 0.2 | 86 | 18 | 98 | 40 |
| 30669 | 291_1 | 1 | 78 | 12 | 133 | 26 |
| 30670 | 292_1 | 0.2 | 93 | 10 | 86 | 31 |
| 30670 | 292_1 | 1 | 94 | 16 | 127 | 22 |
| 30679 | 293_1 | 0.2 | 85 | 19 | 83 | 21 |
| 30679 | 293_1 | 1 | 87 | 21 | 113 | 23 |
| 30681 | 294_1 | 0.2 | 92 | 17 | 78 | 20 |
| 30681 | 294_1 | 1 | 100 | 19 | 86 | 22 |
| 30682 | 295_1 | 0.2 | 93 | 22 | 101 | 40 |
| 30682 | 295_1 | 1 | 94 | 33 | 101 | 8 |
| 30699 | 296_1 | 0.2 | 80 | 24 | 134 | 6 |
| 30699 | 296_1 | 1 | 47 | 21 | 232 | 36 |
| 30700 | 297_1 | 0.2 | 53 | 5 | 146 | 26 |
| 30700 | 297_1 | 1 | 32 | 8 | NA | NA |
| 30700 | 298_1 | 0.2 | 47 | 4 | 221 | NA |
| 30700 | 298_1 | 1 | 38 | 0 | 294 | NA |
| 30701 | 299_1 | 0.2 | 49 | 4 | 140 | NA |
| 30701 | 299_1 | 1 | 23 | NA | NA | NA |
| 30701 | 300_1 | 0.2 | 50 | 9 | 163 | 19 |
| 30701 | 300_1 | 1 | 39 | 11 | 346 | 11 |
| 30702 | 301_1 | 0.2 | 66 | 9 | 116 | 36 |
| 30702 | 301_1 | 1 | 44 | 14 | 230 | 51 |
| 30711 | 302_1 | 0.2 | 41 | 14 | 288 | 120 |
| 30711 | 302_1 | 1 | 40 | 5 | 422 | 132 |
| 30714 | 303_1 | 0.2 | 45 | 9 | 355 | 94 |
| 30714 | 303_1 | 1 | 31 | 5 | 355 | 8 |
| 30715 | 305_1 | 0.2 | 39 | 4 | 292 | 56 |
| 30715 | 305_1 | 1 | 34 | 12 | 253 | 5 |
| 30715 | 304_1 | 0.2 | 50 | 13 | 263 | 87 |
| 30715 | 304_1 | 1 | 43 | 7 | 285 | 12 |
| 31630 | 306_1 | 0.2 | 92 | 32 | 134 | 48 |
| 31630 | 306_1 | 1 | 85 | 25 | 177 | 26 |
| 31632 | 307_1 | 0.2 | 94 | 24 | 92 | 32 |
| 31632 | 307_1 | 1 | 86 | 17 | 109 | 33 |
| 31633 | 308_1 | 0.2 | 92 | 18 | 78 | 13 |
| 31633 | 308_1 | 1 | 102 | 23 | 98 | 7 |
| 32755 | 310_1 | 0.2 | 47 | 12 | 220 | 40 |
| 32755 | 310_1 | 1 | 40 | 16 | 285 | NA |
| 32755 | 309_1 | 0.2 | 62 | 6 | 167 | NA |
| 32755 | 309_1 | 1 | 40 | 10 | 225 | NA |
| 32756 | 311_1 | 0.2 | 55 | 9 | 128 | 9 |
| 32756 | 311_1 | 1 | 56 | NA | 224 | NA |
| 33366 | 312_1 | 0.2 | 64 | 23 | 121 | 4 |
| 33366 | 312_1 | 1 | 56 | 10 | 137 | 1 |
| 33367 | 313_1 | 0.2 | 81 | 7 | 91 | NA |
| 33367 | 313_1 | 1 | 79 | 22 | 115 | 12 |
| 33368 | 314_1 | 0.2 | 70 | 4 | 103 | NA |
| 33368 | 314_1 | 1 | 57 | 15 | 157 | NA |
| 33369 | 315_1 | 0.2 | 73 | 12 | 87 | 20 |
| 33369 | 315_1 | 1 | 67 | 19 | 155 | NA |
| 33375 | 316_1 | 0.2 | 79 | 18 | 100 | 18 |
| 33375 | 316_1 | 1 | 51 | 14 | 159 | 39 |
| 33377 | 317_1 | 0.2 | 46 | 21 | 248 | 72 |
| 33377 | 317_1 | 1 | 41 | 9 | 313 | NA |
| 33378 | 318_1 | 0.2 | 38 | 17 | 273 | 63 |
| 33378 | 318_1 | 1 | 36 | 7 | 321 | 1 |
| 36606 | 319_1 | 0.2 | 79 | 10 | 154 | 21 |
| 36606 | 319_1 | 1 | 48 | 9 | 233 | 65 |
| 36607 | 320_1 | 0.2 | 60 | 9 | 157 | 18 |
| 36607 | 320_1 | 1 | 49 | 9 | 206 | 25 |
| 38092 | 321_1 | 0.2 | 51 | 10 | 22- | 59 |
| 38092 | 321_1 | 1 | 41 | 5 | 328 | 39 |
| 38297 | 322_1 | 0.2 | 43 | 9 | 298 | 31 |
| 38297 | 322_1 | 1 | 34 | 6 | 365 | 91 |
| 39173 | 323_1 | 0.2 | 98 | 8 | 119 | 27 |
| 39173 | 323_1 | 1 | 82 | 20 | 177 | 21 |
| 39174 | 324_1 | 0.2 | 89 | 8 | 139 | 24 |
| 39174 | 324_1 | 1 | 84 | 23 | 192 | 15 |
| 39175 | 325_1 | 0.2 | 93 | 18 | 167 | 13 |
| 39175 | 325_1 | 1 | 68 | 17 | 203 | 33 |
| 39176 | 326_1 | 0.2 | 79 | 12 | 185 | 83 |

TABLE 6-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 39176 | 326_1 | 1 | 55 | 17 | 374 | 107 |
| 39228 | 327_1 | 0.2 | 75 | 12 | 151 | 29 |
| 39228 | 327_1 | 1 | 57 | 8 | 207 | 32 |
| 39230 | 328_1 | 0.2 | 65 | 11 | 176 | 19 |
| 39230 | 328_1 | 1 | 52 | 19 | 357 | NA |
| 39231 | 329_1 | 0.2 | 63 | 19 | 150 | 35 |
| 39231 | 329_1 | 1 | 46 | 6 | 257 | 43 |
| 39563 | 330_1 | 0.2 | 69 | 10 | 116 | 34 |
| 39563 | 330_1 | 1 | 56 | 11 | 196 | NA |
| 39808 | 331_1 | 0.2 | 40 | 8 | 201 | 17 |
| 39808 | 331_1 | 1 | 25 | 5 | 300 | NA |
| 39808 | 332_1 | 0.2 | 40 | 14 | 282 | 109 |
| 39808 | 332_1 | 1 | 33 | 7 | 404 | 81 |
| 39931 | 333_1 | 0.2 | 80 | 11 | 107 | 53 |
| 39931 | 333_1 | 1 | 70 | 16 | 112 | 26 |
| 41114 | 334_1 | 0.2 | 64 | 4 | 113 | NA |
| 41114 | 334_1 | 1 | 28 | NA | 179 | NA |
| 41444 | 335_1 | 0.2 | 57 | 17 | 165 | 39 |
| 41444 | 335_1 | 1 | 46 | 4 | 290 | 40 |
| 41445 | 336_1 | 0.2 | 51 | 2 | 134 | NA |
| 41445 | 336_1 | 1 | 42 | 15 | 238 | NA |
| 41446 | 337_1 | 0.2 | 63 | 1 | 108 | NA |
| 41446 | 337_1 | 1 | 56 | 14 | 151 | 22 |
| 41725 | 338_1 | 0.2 | 91 | 16 | 130 | 50 |
| 41725 | 338_1 | 1 | 75 | 23 | 154 | 27 |
| 41726 | 339_1 | 0.2 | 66 | 20 | 142 | 23 |
| 41726 | 339_1 | 1 | 55 | 14 | 193 | NA |
| 41728 | 340_1 | 0.2 | 60 | 16 | 137 | 23 |
| 41728 | 340_1 | 1 | 51 | 13 | 233 | NA |
| 42167 | 341_1 | 0.2 | 70 | 9 | 138 | 7 |
| 42167 | 341_1 | 1 | 51 | 11 | 182 | 20 |
| 42168 | 343_1 | 0.2 | 67 | 9 | 210 | 92 |
| 42168 | 343_1 | 1 | 52 | 6 | 193 | NA |
| 42168 | 342_1 | 0.2 | 51 | 6 | 183 | NA |
| 42168 | 342_1 | 1 | 46 | 10 | 275 | 14 |
| 42169 | 344_1 | 0.2 | 55 | 1 | 231 | 32 |
| 42169 | 344_1 | 1 | 35 | 3 | NA | NA |
| 42169 | 345_1 | 0.2 | 55 | 7 | 164 | 41 |
| 42169 | 345_1 | 1 | 45 | 5 | 284 | 27 |
| 42287 | 346_1 | 0.2 | 66 | 7 | 144 | 32 |
| 42287 | 346_1 | 1 | 53 | 5 | 279 | 34 |
| 42289 | 347_1 | 0.2 | 75 | 20 | 125 | 10 |
| 42289 | 347_1 | 1 | 68 | 7 | 241 | 69 |
| 43452 | 348_1 | 0.2 | 62 | 12 | 231 | 92 |
| 43452 | 348_1 | 1 | 48 | 23 | 257 | 72 |
| 43453 | 349_1 | 0.2 | 52 | 11 | 142 | 41 |
| 43453 | 349_1 | 1 | 44 | 23 | 257 | 34 |
| 43562 | 350_1 | 0.2 | 50 | 13 | 148 | 35 |
| 43562 | 350_1 | 1 | 36 | 10 | NA | NA |
| 43565 | 351_1 | 0.2 | 71 | 10 | 116 | 43 |
| 43565 | 351_1 | 1 | 60 | 11 | 154 | 37 |
| 43566 | 352_1 | 0.2 | 65 | 19 | 139 | 14 |
| 43566 | 352_1 | 1 | 44 | 8 | 255 | 23 |
| 43634 | 353_1 | 0.2 | 63 | 25 | 172 | 75 |
| 43634 | 353_1 | 1 | 51 | 22 | 214 | NA |
| 44180 | 355_1 | 0.2 | 60 | 6 | 165 | 8 |
| 44180 | 355_1 | 1 | 57 | 25 | 145 | NA |
| 44180 | 354_1 | 0.2 | 76 | 17 | 149 | 55 |
| 44180 | 354_1 | 1 | 48 | 10 | 240 | 29 |
| 44181 | 356_1 | 0.2 | 60 | 5 | 170 | 27 |
| 44181 | 356_1 | 1 | 43 | 15 | 154 | 55 |
| 44183 | 357_1 | 0.2 | 50 | 15 | 214 | 33 |
| 44183 | 357_1 | 1 | 37 | 17 | 196 | 19 |
| 44184 | 358_1 | 0.2 | 57 | 5 | 155 | 31 |
| 44184 | 358_1 | 1 | 47 | 10 | 257 | 94 |
| 44439 | 359_1 | 0.2 | 46 | 4 | 220 | 53 |
| 44439 | 359_1 | 1 | 45 | 2 | 347 | 52 |
| 44440 | 360_1 | 0.2 | 48 | 9 | 261 | 37 |
| 44440 | 360_1 | 1 | 44 | 6 | NA | NA |
| 44440 | 361_1 | 0.2 | 43 | 5 | 218 | 46 |
| 44440 | 361_1 | 1 | 29 | 3 | 291 | 19 |
| 44441 | 362_1 | 0.2 | 50 | 5 | 192 | 60 |
| 44441 | 362_1 | 1 | 45 | 7 | 290 | 58 |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 44441 | 363_1 | 0.2 | 45 | 10 | 185 | 51 |
| 44441 | 363_1 | 1 | 43 | 10 | 247 | NA |
| 44442 | 364_1 | 0.2 | 54 | 8 | 124 | 24 |
| 44442 | 364_1 | 1 | 39 | 5 | 271 | 54 |
| 44442 | 365_1 | 0.2 | 59 | 6 | 166 | 9 |
| 44442 | 365_1 | 1 | 44 | 8 | 313 | 47 |
| 44443 | 367_1 | 0.2 | 55 | 10 | 161 | 29 |
| 44443 | 367_1 | 1 | 40 | 7 | 314 | 67 |
| 44443 | 366_1 | 0.2 | 51 | 5 | 202 | 44 |
| 44443 | 366_1 | 1 | 41 | 10 | 300 | 31 |
| 44477 | 368_1 | 0.2 | 73 | 6 | 155 | 58 |
| 44477 | 368_1 | 1 | 52 | 3 | 362 | 141 |
| 44478 | 369_1 | 0.2 | 82 | 18 | 130 | 35 |
| 44478 | 369_1 | 1 | 58 | 11 | 228 | 66 |
| 44776 | 370_1 | 0.2 | 60 | 7 | 128 | 20 |
| 44776 | 370_1 | 1 | 46 | 5 | 274 | NA |
| 45216 | 371_1 | 0.2 | 50 | 10 | 149 | 33 |
| 45216 | 371_1 | 1 | 41 | 8 | 260 | 59 |
| 45217 | 372_1 | 0.2 | 59 | 7 | 132 | 45 |
| 45217 | 372_1 | 1 | 39 | 4 | 270 | 12 |
| 45217 | 373_1 | 0.2 | 47 | 3 | 167 | 52 |
| 45217 | 373_1 | 1 | 38 | 4 | 330 | 62 |
| 45218 | 374_1 | 0.2 | 51 | 9 | 189 | 27 |
| 45218 | 374_1 | 1 | 42 | 9 | 359 | 93 |
| 45246 | 375_1 | 0.2 | 61 | 8 | 175 | 29 |
| 45246 | 375_1 | 1 | 50 | 7 | 257 | NA |
| 45247 | 376_1 | 0.2 | 84 | 4 | 116 | 40 |
| 45247 | 376_1 | 1 | 74 | 10 | 144 | NA |
| 45248 | 378_1 | 0.2 | 61 | 10 | 226 | 2 |
| 45248 | 378_1 | 1 | 50 | 5 | 367 | 141 |
| 45248 | 377_1 | 0.2 | 74 | 11 | 138 | 29 |
| 45248 | 377_1 | 1 | 62 | 4 | 251 | NA |
| 45249 | 379_1 | 0.2 | 48 | 5 | 232 | NA |
| 45249 | 379_1 | 1 | 50 | NA | 312 | NA |
| 45249 | 380_1 | 0.2 | 54 | 4 | 203 | 16 |
| 45249 | 380_1 | 1 | 53 | 1 | 353 | 12 |
| 45250 | 381_1 | 0.2 | 48 | 6 | 230 | 25 |
| 45250 | 381_1 | 1 | 40 | 7 | 387 | 79 |
| 45250 | 382_1 | 0.2 | 60 | 7 | 153 | 30 |
| 45250 | 382_1 | 1 | 46 | 3 | 288 | 43 |
| 45258 | 383_1 | 0.2 | 46 | 4 | 211 | NA |
| 45258 | 383_1 | 1 | 34 | 6 | 307 | 29 |
| 45266 | 385_1 | 0.2 | 80 | 34 | 85 | 8 |
| 45266 | 385_1 | 1 | 55 | 13 | 128 | 25 |
| 45266 | 384_1 | 0.2 | 92 | 4 | 128 | 50 |
| 45266 | 384_1 | 1 | 79 | 12 | 108 | 23 |
| 45267 | 386_1 | 0.2 | 93 | 23 | 105 | 13 |
| 45267 | 386_1 | 1 | 80 | 23 | 139 | 14 |
| 45268 | 387_1 | 0.2 | 90 | 17 | 111 | 1 |
| 45268 | 387_1 | 1 | 109 | 9 | 122 | 44 |
| 45270 | 388_1 | 0.2 | 97 | 7 | 146 | 47 |
| 45270 | 388_1 | 1 | 88 | 9 | 113 | 22 |
| 45271 | 390_1 | 0.2 | 79 | 12 | 141 | 14 |
| 45271 | 390_1 | 1 | 58 | 14 | 197 | 38 |
| 45271 | 389_1 | 0.2 | 70 | 3 | 97 | 28 |
| 45271 | 389_1 | 1 | 53 | 6 | 150 | 26 |
| 45272 | 391_1 | 0.2 | 61 | 4 | 128 | 24 |
| 45272 | 391_1 | 1 | 55 | 14 | 208 | 39 |
| 45560 | 392_1 | 0.2 | 86 | 22 | 97 | 26 |
| 45560 | 392_1 | 1 | 71 | 19 | 125 | 18 |
| 45627 | 393_1 | 0.2 | 48 | 14 | 150 | 64 |
| 45627 | 393_1 | 1 | 39 | 1 | 209 | 35 |
| 45628 | 394_1 | 0.2 | 51 | 4 | 174 | 34 |
| 45628 | 294_1 | 1 | 44 | | 309 | 30 |
| 45629 | 395_1 | 0.2 | 60 | 5 | 151 | 24 |
| 45629 | 395_1 | 1 | 48 | 7 | 297 | 43 |
| 45629 | 396_1 | 0.2 | 86 | 24 | 139 | 55 |
| 45629 | 396_1 | 1 | 64 | 13 | 203 | 38 |
| 45635 | 397_1 | 0.2 | 50 | 10 | 289 | 61 |
| 45635 | 397_1 | 1 | 46 | 2 | 401 | 56 |
| 45709 | 398_1 | 0.2 | 47 | 6 | 207 | 61 |
| 45709 | 398_1 | 1 | 49 | 6 | 233 | NA |
| 45709 | 399_1 | 0.2 | 56 | 6 | 206 | 13 |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 45709 | 399_1 | 1 | 45 | 4 | 287 | 93 |
| 46215 | 400_1 | 0.2 | 78 | 14 | 122 | 13 |
| 46215 | 400_1 | 1 | 60 | 9 | 114 | 19 |
| 46256 | 401_1 | 0.2 | 62 | 7 | 164 | 56 |
| 46256 | 401_1 | 1 | 45 | 5 | 213 | 20 |
| 46257 | 404_1 | 0.2 | 44 | 4 | 207 | 44 |
| 46257 | 404_1 | 1 | 41 | 3 | 288 | 45 |
| 46257 | 402_1 | 0.2 | 48 | 5 | 197 | 57 |
| 46257 | 402_1 | 1 | 41 | 1 | 300 | 11 |
| 46257 | 403_1 | 0.2 | 51 | 4 | 265 | 50 |
| 46257 | 403_1 | 1 | 44 | 5 | 382 | NA |
| 46259 | 405_1 | 0.2 | 46 | 4 | NA | NA |
| 46259 | 405_1 | 1 | 39 | 10 | 359 | 10 |
| 46260 | 406_1 | 0.2 | 52 | 9 | 153 | 63 |
| 46260 | 406_1 | 1 | 48 | 7 | 262 | 71 |
| 46263 | 407_1 | 0.2 | 52 | 9 | 148 | 9 |
| 46263 | 407_1 | 1 | 41 | 5 | 262 | 45 |
| 46264 | 408_1 | 0.2 | 51 | 17 | 269 | 72 |
| 46264 | 408_1 | 1 | 42 | 8 | 280 | 55 |
| 46392 | 409_1 | 0.2 | 38 | 10 | 359 | 91 |
| 46392 | 409_1 | 1 | 38 | 8 | NA | NA |
| 46393 | 410_1 | 0.2 | 39 | 12 | 295 | 30 |
| 46393 | 410_1 | 1 | 32 | 12 | NA | NA |
| 46420 | 411_1 | 0.2 | 75 | 10 | 69 | 3 |
| 46420 | 411_1 | 1 | 86 | 3 | 101 | 21 |
| 46505 | 412_1 | 0.2 | 65 | 11 | 97 | 7 |
| 46505 | 412_1 | 1 | 53 | 5 | 226 | 59 |
| 46505 | 413_1 | 0.2 | 74 | 16 | 124 | 19 |
| 46505 | 413_1 | 1 | 69 | 13 | 117 | 11 |
| 46506 | 414_1 | 0.2 | 75 | 7 | 149 | 17 |
| 46506 | 414_1 | 1 | 71 | 10 | 169 | 118 |
| 46507 | 415_1 | 0.2 | 86 | 31 | 119 | 36 |
| 46507 | 415_1 | 1 | 66 | 17 | 129 | 28 |
| 46508 | 416_1 | 0.2 | 86 | 22 | 87 | 22 |
| 46508 | 416_1 | 1 | 67 | 10 | 142 | 16 |
| 47364 | 417_1 | 0.2 | 49 | 2 | 166 | 22 |
| 47364 | 417_1 | 1 | 47 | 13 | 295 | NA |
| 47365 | 418_1 | 0.2 | 54 | 3 | 131 | 29 |
| 47365 | 418_1 | 1 | 41 | 3 | 230 | 42 |
| 48110 | 419_1 | 0.2 | 77 | 9 | 101 | 45 |
| 48110 | 419_1 | 1 | 58 | 8 | 178 | 68 |
| 48111 | 420_1 | 0.2 | 63 | 7 | 121 | 32 |
| 48111 | 420_1 | 1 | 51 | 2 | 238 | 59 |
| 48186 | 421_1 | 0.2 | 69 | 5 | 176 | 52 |
| 48186 | 421_1 | 1 | 44 | 12 | 307 | 62 |
| 48221 | 422_1 | 0.2 | 58 | 15 | 149 | 63 |
| 48221 | 422_1 | 1 | 39 | 6 | 235 | 50 |
| 48222 | 423_1 | 0.2 | 60 | 12 | 143 | 9 |
| 48222 | 423_1 | 1 | 43 | 10 | 209 | 57 |
| 49345 | 85_2 | 0.2 | 43 | 14 | 242 | 38 |
| 49345 | 85_2 | 1 | 37 | 5 | 275 | NA |
| 50282 | 424_1 | 0.2 | 75 | 20 | 138 | 19 |
| 50282 | 424_1 | 1 | 56 | 9 | 226 | 62 |
| 51241 | 426_1 | 0.2 | 61 | 6 | 144 | NA |
| 51241 | 426_1 | 1 | 46 | 9 | 264 | 44 |
| 51241 | 425_1 | 0.2 | 46 | 8 | 164 | 22 |
| 51241 | 425_1 | 1 | 44 | 4 | 244 | 35 |
| 51242 | 428_1 | 0.2 | 57 | 6 | 138 | 30 |
| 51242 | 428_1 | 1 | 48 | 7 | 290 | 39 |
| 51242 | 427_1 | 0.2 | 40 | 15 | 341 | NA |
| 51242 | 427_1 | 1 | 30 | 8 | 286 | 63 |
| 51244 | 429_1 | 0.2 | 46 | 5 | 184 | 25 |
| 51244 | 429_1 | 1 | 44 | 6 | 283 | 4 |
| 51245 | 430_1 | 0.2 | 47 | 7 | 203 | 9 |
| 51245 | 430_1 | 1 | 37 | 5 | 271 | 29 |
| 51358 | 431_1 | 0.2 | 51 | 7 | 265 | 10 |
| 51358 | 431_1 | 1 | 40 | 4 | 363 | 70 |
| 51358 | 432_1 | 0.2 | 60 | 4 | 202 | 51 |
| 51358 | 432_1 | 1 | 37 | 7 | 275 | NA |
| 51359 | 433_1 | 0.2 | 40 | 3 | 238 | 20 |
| 51359 | 433_1 | 1 | 32 | 3 | NA | NA |
| 51359 | 434_1 | 0.2 | 39 | 6 | 424 | 83 |
| 51359 | 434_1 | 1 | 35 | 6 | 360 | NA |

TABLE 6-continued

| Oligonucleotide activity in patient derived human neuronal cell cultures. | | | | | | |
|---|---|---|---|---|---|---|
| Start SEQ ID NO 1 | CMP ID NO | Conc μM | % of Mock UBE3A-SUP | sd | % of Mock UBE3A | sd |
| 51438 | 435_1 | 0.2 | 78 | 15 | 144 | 62 |
| 51438 | 435_1 | 1 | 60 | 14 | 201 | 27 |
| 51438 | 436_1 | 0.2 | 71 | 4 | 125 | 32 |
| 51438 | 436_1 | 1 | 54 | 6 | 205 | 71 |
| 51953 | 437_1 | 0.2 | 46 | 6 | 217 | 35 |
| 51953 | 437_1 | 1 | 37 | 4 | 277 | 52 |
| 52150 | 438_1 | 0.2 | 67 | 6 | 131 | 39 |
| 52150 | 438_1 | 1 | 53 | 13 | 177 | NA |
| 52549 | 439_1 | 0.2 | 56 | 5 | 162 | 31 |
| 52549 | 439_1 | 1 | 50 | 10 | 215 | 39 |
| 52550 | 440_1 | 0.2 | 69 | 13 | 137 | 40 |
| 52550 | 440_1 | 1 | 50 | 5 | 156 | 53 |
| 52551 | 441_1 | 0.2 | 66 | 3 | 132 | 8 |
| 52551 | 441_1 | 1 | 49 | 5 | 169 | 27 |
| 52579 | 442_1 | 0.2 | 38 | 7 | 280 | 60 |
| 52579 | 442_1 | 1 | 37 | 5 | 257 | 51 |
| 53012 | 443_1 | 0.2 | 79 | 10 | 197 | 61 |
| 53012 | 443_1 | 1 | 65 | 7 | 212 | 36 |
| 53013 | 445_1 | 0.2 | 64 | 6 | 211 | 13 |
| 53013 | 445_1 | 1 | 56 | 4 | 264 | 42 |
| 53013 | 444_1 | 0.2 | 68 | 11 | 137 | 33 |
| 53013 | 444_1 | 1 | 58 | 9 | 198 | 35 |
| 53014 | 446_1 | 0.2 | 59 | 6 | 125 | NA |
| 53014 | 446_1 | 1 | 47 | 3 | 216 | 22 |
| 53014 | 447_1 | 0.2 | 53 | 2 | 188 | 94 |
| 53014 | 447_1 | 1 | 51 | 10 | 192 | 47 |
| 54198 | 448_1 | 0.2 | 54 | 15 | 161 | 66 |
| 54198 | 448_1 | 1 | 48 | 11 | 243 | NA |
| 54199 | 449_1 | 0.2 | 63 | 12 | 166 | 20 |
| 54199 | 449_1 | 1 | 45 | 8 | 185 | 41 |
| 54232 | 450_1 | 0.2 | 84 | 17 | 112 | 67 |
| 54232 | 450_1 | 1 | 83 | 8 | 157 | 15 |
| 54233 | 451_1 | 0.2 | 67 | 14 | 118 | 44 |
| 54233 | 451_1 | 1 | 51 | 8 | 192 | 34 |
| 54235 | 452_1 | 0.2 | 50 | 3 | 162 | NA |
| 54235 | 452_1 | 1 | 42 | 7 | 190 | NA |
| 54236 | 453_1 | 0.2 | 47 | 21 | 234 | 17 |
| 54236 | 453_1 | 1 | 42 | 5 | 295 | NA |
| 54238 | 454_1 | 0.2 | 76 | 14 | 85 | NA |
| 54238 | 454_1 | 1 | 48 | 12 | 162 | NA |
| 54239 | 455_1 | 0.2 | 62 | 6 | 132 | 69 |
| 54239 | 455_1 | 1 | 46 | 7 | 149 | 57 |
| 54609 | 456_1 | 0.2 | 66 | 10 | 130 | 57 |
| 54609 | 456_1 | 1 | 56 | 11 | 141 | 60 |
| 54924 | 457_1 | 0.2 | 78 | 3 | 137 | 29 |
| 54924 | 457_1 | 1 | 61 | 4 | 178 | 25 |

Example 4—Activity of Oligonucleotides Targeting the SNHG14 Transcript in the Region Antisense to to the UBE3A Pre-mRNA Oligonucleotides targeting position 55337-136214 of SEQ ID NO: 1 were tested in patient derived human neuronal cell cultures (see protocol in "Materials and methods" section). The oligonucleotides ability to reduce the SNHG14 transcript in the region downstream of SNORD109B (also termed UBE3A suppressor or UBE3A-SUP in the data table). Furthermore, the ability to induce UBE3A mRNA re-expression was analyzed.

The oligonucleotides were screened according to the protocol for screening oligonucleotides in human neuronal cell cultures described in the section "Materials and methods"—"Screening oligonucleotides in human neuronal cell cultures—96 well system".

The results are shown in table 7.

TABLE 7

| Oligonucleotide activity in patient derived human neuronal cell cultures. | | | | | | |
|---|---|---|---|---|---|---|
| Start SEQ ID NO 1 | CMP ID NO | Conc μM | % of Mock UBE3A-SUP | sd | % of Mock UBE3A | sd |
| 55337 | 458_1 | 0.2 | 64 | 0 | 177 | 6 |
| 55337 | 458_1 | 1 | 50 | 10 | 233 | 9 |
| 55338 | 459_1 | 0.2 | 48 | 1 | 186 | 6 |
| 55338 | 459_1 | 1 | 44 | 9 | 213 | NA |
| 59565 | 460_1 | 0.2 | 66 | 4 | 110 | 24 |
| 59565 | 460_1 | 1 | 66 | 9 | 131 | 23 |
| 59574 | 461_1 | 0.2 | 56 | 5 | 162 | 19 |
| 59574 | 461_1 | 1 | 45 | 13 | 149 | 6 |
| 59575 | 462_1 | 0.2 | 56 | 7 | 114 | 84 |
| 59575 | 462_1 | 1 | 39 | 11 | 101 | 13 |
| 59576 | 463_1 | 0.2 | 82 | 19 | 52 | NA |
| 59576 | 463_1 | 1 | 65 | 15 | 95 | 18 |
| 60012 | 464_1 | 0.2 | 47 | 5 | 129 | 71 |
| 60012 | 464_1 | 1 | 41 | 3 | 160 | 64 |
| 60298 | 465_1 | 0.2 | 49 | 7 | 206 | 95 |
| 60298 | 465_1 | 1 | 37 | 9 | 222 | 44 |
| 60448 | 466_1 | 0.2 | 47 | 7 | 130 | NA |
| 60448 | 466_1 | 1 | 33 | 8 | 167 | 31 |
| 60821 | 467_1 | 0.2 | 87 | 1 | 73 | NA |
| 60821 | 467_1 | 1 | 62 | 18 | 101 | 3 |
| 61925 | 468_1 | 0.2 | 108 | 19 | 105 | 19 |
| 61925 | 468_1 | 1 | 95 | 17 | 101 | 19 |
| 62287 | 469_1 | 0.2 | 62 | 8 | 180 | 57 |
| 62287 | 469_1 | 1 | 48 | 5 | 196 | 38 |
| 62422 | 470_1 | 0.2 | 71 | 2 | 130 | 20 |
| 62422 | 470_1 | 1 | 57 | 9 | 116 | 18 |
| 62443 | 471_1 | 0.2 | 51 | 2 | NA | NA |
| 62443 | 471_1 | 1 | 43 | 2 | 160 | 34 |
| 64113 | 472_1 | 0.2 | 95 | 4 | 83 | 22 |
| 64113 | 472_1 | 1 | 76 | 14 | 74 | 36 |
| 64461 | 473_1 | 0.2 | 79 | 23 | 141 | 22 |
| 64461 | 473_1 | 1 | 59 | 12 | 279 | 53 |
| 64462 | 474_1 | 0.2 | 80 | 12 | 138 | 3 |
| 64462 | 474_1 | 1 | 84 | 15 | 202 | 3 |
| 65272 | 475_1 | 0.2 | 77 | 3 | 104 | 2 |
| 65272 | 475_1 | 1 | 75 | 23 | 113 | 10 |
| 66840 | 476_1 | 0.2 | 67 | 5 | 86 | 5 |
| 66840 | 476_1 | 1 | 72 | 10 | 100 | 12 |
| 67426 | 477_1 | 0.2 | 62 | 15 | 101 | 8 |
| 67426 | 477_1 | 1 | 65 | 13 | 170 | 52 |
| 68194 | 478_1 | 0.2 | 53 | 10 | 109 | 6 |
| 68194 | 478_1 | 1 | 59 | 4 | 178 | 7 |
| 68328 | 479_1 | 0.2 | 74 | 6 | 94 | 2 |
| 68328 | 479_1 | 1 | 79 | 16 | 111 | 38 |
| 68805 | 480_1 | 0.2 | 58 | 15 | 157 | 63 |
| 68805 | 480_1 | 1 | 49 | 2 | 190 | 26 |
| 68921 | 481_1 | 0.2 | 58 | 7 | 210 | 58 |
| 68921 | 481_1 | 1 | 55 | 10 | 281 | NA |
| 70133 | 482_1 | 0.2 | 50 | 9 | 149 | 6 |
| 70133 | 482_1 | 1 | 54 | 8 | 247 | 41 |
| 72377 | 483_1 | 0.2 | 44 | 2 | 143 | NA |
| 72377 | 483_1 | 1 | 52 | 6 | 195 | 37 |
| 72378 | 484_1 | 0.2 | 47 | 12 | 111 | 8 |
| 72378 | 484_1 | 1 | 56 | 3 | 201 | NA |
| 72826 | 485_1 | 0.2 | 54 | 12 | 116 | 0 |
| 72826 | 485_1 | 1 | 64 | 13 | 172 | 1 |
| 72861 | 486_1 | 0.2 | 52 | 9 | 93 | 6 |
| 72861 | 486_1 | 1 | 54 | 6 | 167 | 16 |
| 72887 | 487_1 | 0.2 | 55 | 3 | 128 | 5 |
| 72887 | 487_1 | 1 | 59 | 4 | 193 | 24 |
| 73474 | 488_1 | 0.2 | 55 | 10 | 132 | 20 |
| 73474 | 488_1 | 1 | 55 | 5 | 202 | 56 |
| 73992 | 489_1 | 0.2 | 60 | 7 | 146 | 17 |
| 73992 | 489_1 | 1 | 67 | 7 | 197 | 31 |
| 74791 | 490_1 | 0.2 | 42 | 5 | 167 | 65 |
| 74791 | 490_1 | 1 | 46 | 6 | 277 | 19 |
| 74851 | 491_1 | 0.2 | 69 | 14 | 78 | 1 |
| 74851 | 491_1 | 1 | 73 | 6 | 114 | 11 |
| 74853 | 492_1 | 0.2 | 64 | 6 | 84 | 1 |

TABLE 7-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 74853 | 492_1 | 1 | 68 | 5 | 136 | 25 |
| 75840 | 493_1 | 0.2 | 40 | 10 | 90 | 6 |
| 75840 | 493_1 | 1 | 61 | 8 | 155 | 32 |
| 75841 | 494_1 | 0.2 | 65 | 10 | 131 | 30 |
| 75841 | 494_1 | 1 | 57 | 4 | 119 | 16 |
| 76238 | 495_1 | 0.2 | 70 | 9 | 109 | 41 |
| 76238 | 495_1 | 1 | 50 | 8 | 156 | 22 |
| 76254 | 496_1 | 0.2 | 67 | 13 | 134 | 34 |
| 76254 | 496_1 | 1 | 55 | 7 | 201 | NA |
| 76811 | 497_1 | 0.2 | 83 | 7 | 134 | 41 |
| 76811 | 497_1 | 1 | 77 | 8 | 148 | 32 |
| 77114 | 498_1 | 0.2 | 59 | 2 | 128 | 13 |
| 77114 | 498_1 | 1 | 64 | 10 | 206 | NA |
| 80468 | 499_1 | 0.2 | 55 | 2 | 105 | 34 |
| 80468 | 499_1 | 1 | 61 | 6 | 151 | 42 |
| 81047 | 500_1 | 0.2 | 103 | 17 | 80 | 6 |
| 81047 | 500_1 | 1 | 143 | 25 | 122 | 7 |
| 82233 | 501_1 | 0.2 | 57 | NA | 104 | NA |
| 82233 | 501_1 | 1 | 61 | 3 | 199 | 39 |
| 84166 | 502_1 | 0.2 | 49 | 6 | 89 | 0 |
| 84166 | 502_1 | 1 | 57 | 5 | 115 | NA |
| 85392 | 503_1 | 0.2 | 61 | 6 | 90 | 14 |
| 85392 | 503_1 | 1 | 62 | 8 | 118 | 15 |
| 86974 | 504_1 | 0.2 | 73 | 7 | 82 | 4 |
| 86974 | 504_1 | 1 | 79 | 3 | 104 | 19 |
| 87728 | 505_1 | 0.2 | 79 | 14 | 76 | 2 |
| 87728 | 505_1 | 1 | 80 | 19 | 97 | 35 |
| 87810 | 506_1 | 0.2 | 69 | 9 | 101 | 20 |
| 87810 | 506_1 | 1 | 73 | 6 | 155 | 2 |
| 88417 | 507_1 | 0.2 | 45 | NA | 116 | 3 |
| 88417 | 507_1 | 1 | 61 | 14 | 168 | 6 |
| 88991 | 508_1 | 0.2 | 51 | 6 | 113 | 20 |
| 88991 | 508_1 | 1 | 59 | 2 | 154 | 31 |
| 90228 | 509_1 | 0.2 | 65 | 6 | 76 | 10 |
| 90228 | 509_1 | 1 | 62 | 7 | 118 | 4 |
| 90474 | 510_1 | 0.2 | 71 | 7 | 83 | 14 |
| 90474 | 510_1 | 1 | 81 | 3 | 125 | NA |
| 91625 | 511_1 | 0.2 | 57 | 17 | 105 | 3 |
| 91625 | 511_1 | 1 | 65 | 11 | 150 | NA |
| 91885 | 512_1 | 0.2 | 57 | 5 | 105 | 1 |
| 91885 | 512_1 | 1 | 66 | 7 | 155 | 30 |
| 92976 | 513_1 | 0.2 | 67 | 6 | 136 | 44 |
| 92976 | 513_1 | 1 | 68 | 11 | 138 | 38 |
| 94304 | 514_1 | 0.2 | 81 | 11 | 110 | 7 |
| 94304 | 514_1 | 1 | 87 | 6 | 153 | 28 |
| 94528 | 515_1 | 0.2 | 48 | 5 | 128 | 6 |
| 94528 | 515_1 | 1 | 55 | 3 | 191 | 25 |
| 95653 | 516_1 | 0.2 | 57 | 3 | 108 | 7 |
| 95653 | 516_1 | 1 | 62 | 3 | 131 | 16 |
| 96751 | 517_1 | 0.2 | 63 | 9 | 90 | 19 |
| 96751 | 517_1 | 1 | 62 | 4 | 106 | NA |
| 97636 | 518_1 | 0.2 | 49 | 5 | 107 | 14 |
| 97636 | 518_1 | 1 | 44 | 9 | 137 | NA |
| 98480 | 519_1 | 0.2 | 55 | 1 | 106 | NA |
| 98480 | 519_1 | 1 | 54 | 5 | 112 | 23 |
| 98481 | 520_1 | 0.2 | 55 | 2 | 116 | 6 |
| 98481 | 520_1 | 1 | 62 | 4 | 129 | 6 |
| 99646 | 521_1 | 0.2 | 74 | 10 | 105 | 1 |
| 99646 | 521_1 | 1 | 87 | 13 | 119 | 27 |
| 100334 | 522_1 | 0.2 | 49 | 7 | 157 | 28 |
| 100334 | 522_1 | 1 | 57 | 2 | 120 | 37 |
| 101110 | 523_1 | 0.2 | 51 | 10 | 96 | 10 |
| 101110 | 523_1 | 1 | 72 | 14 | 114 | 25 |
| 101898 | 524_1 | 0.2 | 85 | 11 | 79 | 3 |
| 101898 | 524_1 | 1 | 93 | 21 | 92 | 46 |
| 102558 | 525_1 | 0.2 | 82 | 9 | 104 | 8 |
| 102558 | 525_1 | 1 | 86 | 18 | 104 | 30 |
| 103589 | 526_1 | 0.2 | 85 | 17 | 114 | 14 |
| 103589 | 526_1 | 1 | 94 | 39 | 126 | 6 |
| 104309 | 527_1 | 0.2 | 63 | 11 | 148 | 2 |
| 104309 | 527_1 | 1 | 70 | 26 | 155 | NA |
| 105686 | 528_1 | 0.2 | 66 | 11 | 91 | 24 |
| 105686 | 528_1 | 1 | 66 | 14 | 140 | 36 |
| 107972 | 529_1 | 0.2 | 84 | 15 | 109 | 15 |

TABLE 7-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 107972 | 529_1 | 1 | 94 | 14 | 127 | 24 |
| 108257 | 530_1 | 0.2 | 63 | 7 | 114 | 19 |
| 108257 | 530_1 | 1 | 67 | 12 | 141 | 40 |
| 109407 | 531_1 | 0.2 | 84 | 24 | 87 | 16 |
| 109407 | 531_1 | 1 | 82 | 11 | 127 | 26 |
| 110210 | 532_1 | 0.2 | 72 | 12 | 91 | 14 |
| 110210 | 532_1 | 1 | 80 | 14 | 122 | 40 |
| 110768 | 533_1 | 0.2 | 67 | 8 | 126 | 16 |
| 110768 | 533_1 | 1 | 87 | 21 | 176 | 45 |
| 111811 | 534_1 | 0.2 | 77 | 2 | 98 | 17 |
| 111811 | 534_1 | 1 | 74 | 6 | 143 | 14 |
| 111812 | 535_1 | 0.2 | 64 | 4 | 97 | 0 |
| 111812 | 535_1 | 1 | 77 | 3 | 136 | 37 |
| 112149 | 536_1 | 0.2 | 73 | 2 | 63 | 2 |
| 112149 | 536_1 | 1 | 77 | 18 | 127 | 36 |
| 112150 | 537_1 | 0.2 | 76 | 6 | 78 | 8 |
| 112150 | 537_1 | 1 | 90 | 29 | 91 | 11 |
| 112945 | 538_1 | 0.2 | 69 | 4 | 121 | 2 |
| 112945 | 538_1 | 1 | 83 | 14 | 102 | 39 |
| 113533 | 539_1 | 0.2 | 95 | 17 | 85 | 2 |
| 113533 | 539_1 | 1 | 91 | 27 | 87 | 17 |
| 114274 | 540_1 | 0.2 | 89 | 11 | 103 | 17 |
| 114274 | 540_1 | 1 | 87 | 26 | 132 | 20 |
| 114495 | 541_1 | 0.2 | 76 | 5 | 88 | 1 |
| 114495 | 541_1 | 1 | 83 | 15 | 120 | 6 |
| 114831 | 542_1 | 0.2 | 59 | 3 | 76 | 4 |
| 114831 | 542_1 | 1 | 74 | 3 | 104 | 4 |
| 115355 | 543_1 | 0.2 | 66 | 8 | 91 | 9 |
| 115355 | 543_1 | 1 | 74 | 16 | 110 | NA |
| 116105 | 544_1 | 0.2 | 55 | 12 | 77 | NA |
| 116105 | 544_1 | 1 | 74 | 6 | 110 | 8 |
| 116106 | 545_1 | 0.2 | 58 | 18 | 96 | 9 |
| 116106 | 545_1 | 1 | 66 | 8 | 130 | 10 |
| 117096 | 546_1 | 0.2 | 69 | 9 | 118 | 20 |
| 117096 | 546_1 | 1 | 65 | 4 | 146 | NA |
| 117189 | 547_1 | 0.2 | 69 | 6 | 98 | 9 |
| 117189 | 547_1 | 1 | 74 | 11 | 146 | 25 |
| 117476 | 548_1 | 0.2 | 59 | 4 | 87 | 5 |
| 117476 | 548_1 | 1 | 65 | 3 | 104 | 10 |
| 118293 | 549_1 | 0.2 | 55 | 8 | 92 | 3 |
| 118293 | 549_1 | 1 | 66 | 10 | 105 | 24 |
| 118294 | 550_1 | 0.2 | 55 | 18 | 90 | 4 |
| 118294 | 550_1 | 1 | 72 | 21 | 119 | 5 |
| 118756 | 551_1 | 0.2 | 60 | 13 | 86 | 18 |
| 118756 | 551_1 | 1 | 88 | 24 | 120 | 26 |
| 119621 | 552_1 | 0.2 | 77 | 21 | 117 | 4 |
| 119621 | 552_1 | 1 | 102 | 19 | 146 | NA |
| 120655 | 553_1 | 0.2 | 55 | 9 | 124 | 19 |
| 120655 | 553_1 | 1 | 57 | 7 | 185 | 14 |
| 123733 | 554_1 | 0.2 | 74 | 6 | 87 | 14 |
| 123733 | 554_1 | 1 | 77 | 4 | 127 | 4 |
| 124163 | 555_1 | 0.2 | 89 | 12 | 117 | 46 |
| 124163 | 555_1 | 1 | 67 | 20 | 152 | 13 |
| 125512 | 556_1 | 0.2 | 70 | 5 | 114 | 26 |
| 125512 | 556_1 | 1 | 69 | 11 | 119 | 47 |
| 126882 | 557_1 | 0.2 | 78 | 15 | 106 | 8 |
| 126882 | 557_1 | 1 | 84 | 10 | 113 | 33 |
| 127105 | 558_1 | 0.2 | 71 | 7 | 91 | 13 |
| 127105 | 558_1 | 1 | 68 | 5 | 108 | 28 |
| 127809 | 559_1 | 0.2 | 59 | 4 | 74 | NA |
| 127809 | 559_1 | 1 | 58 | 7 | 101 | 26 |
| 129020 | 560_1 | 0.2 | 82 | 11 | 103 | 39 |
| 129020 | 560_1 | 1 | 77 | 9 | 103 | 27 |
| 129205 | 561_1 | 0.2 | 75 | 24 | 78 | 16 |
| 129205 | 561_1 | 1 | 89 | 11 | 102 | 23 |
| 129928 | 562_1 | 0.2 | 57 | 0 | 98 | 21 |
| 129928 | 562_1 | 1 | 63 | 9 | 107 | 18 |
| 130020 | 563_1 | 0.2 | 65 | 5 | 85 | 9 |
| 130020 | 563_1 | 1 | 65 | 3 | 145 | 12 |
| 130884 | 564_1 | 0.2 | 81 | 24 | 117 | 31 |
| 130884 | 564_1 | 1 | 83 | 4 | 139 | 17 |
| 130886 | 565_1 | 0.2 | 80 | 8 | 103 | 13 |
| 130886 | 565_1 | 1 | 69 | 7 | 122 | 11 |
| 131404 | 566_1 | 0.2 | 79 | 4 | 85 | 3 |

TABLE 7-continued

| Oligonucleotide activity in patient derived human neuronal cell cultures. | | | | | | |
|---|---|---|---|---|---|---|
| Start SEQ ID NO 1 | CMP ID NO | Conc µM | % of Mock UBE3A-SUP | sd | % of Mock UBE3A | sd |
| 131404 | 566_1 | 1 | 80 | 7 | 116 | 24 |
| 132514 | 567_1 | 0.2 | 71 | 8 | 98 | 28 |
| 132514 | 567_1 | 1 | 69 | 9 | 97 | 29 |
| 133367 | 568_1 | 0.2 | 78 | 9 | 88 | 16 |
| 133367 | 568_1 | 1 | 91 | 17 | 88 | 32 |
| 136198 | 569_1 | 0.2 | 88 | 5 | 87 | 2 |
| 136198 | 569_1 | 1 | 81 | 6 | 109 | 35 |

Example 5—Activity of Oligonucleotides Targeting the SNHG14 Transcript in the Region Downstream of SNORD109B and Upstream of the Region Antisense to to the UBE3A Pre-mRNA Oligonucleotides targeting position 5224-51257 of SEQ ID NO: 1 were tested in patient derived human neuronal cell cultures (see protocol in "Materials and methods" section). The oligonucleotides ability to reduce the SNHG14 transcript in the region downstream of SNORD109B (also termed UBE3A suppressor or UBE3A-SUP in the data table. Furthermore, the ability to induce UBE3A mRNA re-expression was analyzed.

The oligonucleotides were screened according to the protocol for screening oligonucleotides in human neuronal cell cultures described in the section "Materials and methods" "Screening oligonucleotides in human neuronal cell cultures—96 well system" with the following modifications: UBE3a-Sense Primer Using commercially available primers and probe from ThermoFisher: Hs00166580_m1 amplifying a 94 bp sequence in position 838 of refseq ID NM_000462.3.

Each plate include PBS controls (instead on a non-targeting ologinucleotide) and a positive control oligonucleotide CMP ID NO: 2711, resulting in up-regulation of UBE3A mRNA. The additional control oligonucleotides were not included.

Data are presented as average % expression relative to PBS controls across all plates and normalized to the positive control oligonucleotide to manage plate to plate variation in efficacy levels. The results are shown in table 8.

TABLE 8

| Oligonucleotide activity in patient derived human neuronal cell cultures. | | | | | | |
|---|---|---|---|---|---|---|
| Start SEQ ID NO 1 | CMP ID NO | Conc µM | % of Mock UBE3A-SUP | sd | % of Mock UBE3A | sd |
| 5224 | 169_2 | 7.5 µM | 49 | 4 | 209 | 9 |
| 5224 | 169_3 | 7.5 µM | 47 | 5 | 282 | 5 |
| 5224 | 169_4 | 7.5 µM | 57 | 14 | 202 | 12 |
| 5224 | 169_5 | 7.5 µM | 84 | 36 | 148 | 4 |
| 5224 | 169_6 | 7.5 µM | 42 | 1 | 285 | 16 |
| 5224 | 169_7 | 7.5 µM | 52 | 6 | 233 | 27 |
| 5224 | 169_8 | 7.5 µM | 51 | 7 | 278 | 11 |
| 5224 | 169_9 | 7.5 µM | 51 | 4 | 228 | 20 |
| 5224 | 169_10 | 7.5 µM | 78 | 17 | 143 | 5 |
| 5224 | 169_11 | 7.5 µM | 74 | 15 | 146 | 2 |
| 5224 | 169_12 | 7.5 µM | 47 | 1 | 277 | 26 |
| 5224 | 169_13 | 7.5 µM | 56 | 23 | 244 | 42 |
| 5224 | 169_14 | 7.5 µM | 74 | 16 | 141 | 1 |
| 5224 | 169_15 | 7.5 µM | 95 | 32 | 122 | 13 |
| 5224 | 169_16 | 7.5 µM | 44 | 4 | 276 | 23 |
| 5224 | 169_17 | 7.5 µM | 85 | 5 | 118 | 5 |
| 5224 | 169_18 | 7.5 µM | 75 | 18 | 131 | 4 |

TABLE 8-continued

| Oligonucleotide activity in patient derived human neuronal cell cultures. | | | | | | |
|---|---|---|---|---|---|---|
| Start SEQ ID NO 1 | CMP ID NO | Conc µM | % of Mock UBE3A-SUP | sd | % of Mock UBE3A | sd |
| 5224 | 169_19 | 7.5 µM | 95 | 18 | 126 | 11 |
| 5224 | 169_20 | 7.5 µM | 61 | 12 | 169 | 20 |
| 5224 | 169_21 | 7.5 µM | 79 | 18 | 156 | 3 |
| 5224 | 169_22 | 7.5 µM | 63 | 14 | 173 | 16 |
| 5224 | 169_23 | 7.5 µM | 43 | 2 | 233 | 27 |
| 5224 | 169_24 | 7.5 µM | 56 | 1 | 183 | 9 |
| 5224 | 169_25 | 7.5 µM | 48 | 0 | 220 | 24 |
| 5224 | 169_26 | 7.5 µM | 41 | 1 | 244 | 39 |
| 5224 | 169_27 | 7.5 µM | 55 | 16 | 260 | 42 |
| 5224 | 169_28 | 7.5 µM | 48 | 1 | 265 | 65 |
| 5224 | 169_29 | 7.5 µM | 56 | 2 | 197 | 18 |
| 5224 | 169_30 | 7.5 µM | 57 | 12 | 189 | 12 |
| 5224 | 169_31 | 7.5 µM | 53 | 4 | 196 | 9 |
| 5224 | 169_32 | 7.5 µM | 50 | 1 | 220 | 3 |
| 5224 | 169_33 | 7.5 µM | 64 | 19 | 227 | 8 |
| 5224 | 169_34 | 7.5 µM | 58 | 4 | 193 | 10 |
| 5224 | 169_35 | 7.5 µM | 45 | 2 | 229 | 3 |
| 5224 | 169_36 | 7.5 µM | 44 | 6 | 262 | 14 |
| 5224 | 169_37 | 7.5 µM | 55 | 2 | 180 | 21 |
| 5224 | 169_38 | 7.5 µM | 75 | 22 | 158 | 13 |
| 5224 | 169_39 | 7.5 µM | 76 | 15 | 159 | 17 |
| 5224 | 169_40 | 7.5 µM | 60 | 18 | 232 | 31 |
| 5224 | 169_41 | 7.5 µM | 46 | 3 | 230 | 10 |
| 5224 | 169_42 | 7.5 µM | 47 | 3 | 240 | 11 |
| 5224 | 169_43 | 7.5 µM | 48 | 9 | 273 | 30 |
| 5224 | 169_44 | 7.5 µM | 83 | 32 | 196 | 11 |
| 5224 | 169_45 | 7.5 µM | 69 | 4 | 185 | 20 |
| 5224 | 169_46 | 7.5 µM | 45 | 9 | 256 | 3 |
| 5224 | 169_47 | 7.5 µM | 41 | 2 | 304 | 4 |
| 5224 | 169_48 | 7.5 µM | 44 | 1 | 260 | 16 |
| 5224 | 169_49 | 7.5 µM | 38 | 1 | 245 | 32 |
| 5224 | 169_50 | 7.5 µM | 35 | 2 | 314 | 28 |
| 5224 | 169_51 | 7.5 µM | 41 | 5 | 281 | 5 |
| 5224 | 169_52 | 7.5 µM | 36 | 1 | 282 | 1 |
| 5224 | 169_53 | 7.5 µM | 38 | 7 | 301 | 7 |
| 5224 | 169_54 | 7.5 µM | 36 | 3 | 304 | 6 |
| 5224 | 169_55 | 7.5 µM | 52 | 5 | 246 | 23 |
| 5224 | 169_56 | 7.5 µM | 33 | 15 | 302 | 15 |
| 5224 | 169_57 | 7.5 µM | 34 | 16 | 273 | 16 |
| 5784 | 570_1 | 7.5 µM | 47 | 0 | 274 | 7 |
| 5784 | 570_2 | 7.5 µM | 47 | 8 | 232 | 8 |
| 5784 | 570_3 | 7.5 µM | 55 | 25 | 280 | 54 |
| 5784 | 570_4 | 7.5 µM | 61 | 11 | 235 | 54 |
| 5784 | 570_5 | 7.5 µM | 72 | 10 | 198 | 30 |
| 5784 | 570_6 | 7.5 µM | 66 | 8 | 244 | 50 |
| 5784 | 570_7 | 7.5 µM | 42 | 1 | 284 | 13 |
| 5784 | 570_8 | 7.5 µM | 43 | 6 | 257 | 11 |
| 5784 | 570_9 | 7.5 µM | 32 | 9 | 242 | 30 |
| 5785 | 571_1 | 7.5 µM | 40 | 1 | 269 | 35 |
| 5785 | 571_2 | 7.5 µM | 42 | 3 | 187 | 6 |
| 5785 | 571_3 | 7.5 µM | 46 | 6 | 242 | 8 |
| 5785 | 571_4 | 7.5 µM | 37 | 4 | 282 | 19 |
| 5785 | 571_5 | 7.5 µM | 48 | 16 | 296 | 2 |
| 5785 | 571_6 | 7.5 µM | 37 | 6 | 274 | 10 |
| 5785 | 571_7 | 7.5 µM | 39 | 1 | 260 | 8 |
| 5785 | 571_8 | 7.5 µM | 35 | 1 | 252 | 3 |
| 5785 | 571_9 | 7.5 µM | 30 | 5 | 297 | 10 |
| 5786 | 572_1 | 7.5 µM | 34 | 4 | 279 | 29 |
| 5786 | 572_2 | 7.5 µM | 63 | 10 | 152 | 4 |
| 5786 | 572_3 | 7.5 µM | 39 | 0 | 280 | 42 |
| 5786 | 572_4 | 7.5 µM | 40 | 1 | 283 | 14 |
| 5786 | 572_5 | 7.5 µM | 38 | 6 | 310 | 11 |
| 5786 | 572_6 | 7.5 µM | 33 | 1 | 316 | 18 |
| 5786 | 572_7 | 7.5 µM | 35 | 1 | 318 | 11 |
| 5786 | 572_8 | 7.5 µM | 47 | 9 | 310 | 19 |
| 5786 | 572_9 | 7.5 µM | 31 | 7 | 321 | 12 |
| 8116 | 573_1 | 7.5 µM | 39 | 8 | 316 | 28 |
| 8116 | 573_2 | 7.5 µM | 49 | 15 | 305 | 41 |
| 8116 | 573_3 | 7.5 µM | 46 | 13 | 308 | 3 |
| 8116 | 573_4 | 7.5 µM | 39 | 3 | 332 | 6 |
| 8116 | 573_5 | 7.5 µM | 34 | 6 | 278 | 12 |
| 8116 | 573_6 | 7.5 µM | 42 | 1 | 285 | 10 |
| 8116 | 573_7 | 7.5 µM | 38 | 0 | 289 | 33 |
| 8116 | 573_8 | 7.5 µM | 40 | 4 | 311 | 20 |
| 8116 | 573_9 | 7.5 µM | 57 | 9 | 315 | 5 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 8117 | 574_1 | 7.5 µM | 40 | 2 | 291 | 35 |
| 8117 | 574_2 | 7.5 µM | 42 | 3 | 343 | 18 |
| 8117 | 574_3 | 7.5 µM | 36 | 6 | 325 | 8 |
| 8117 | 574_4 | 7.5 µM | 38 | 1 | 279 | 15 |
| 8117 | 574_5 | 7.5 µM | 42 | 6 | 308 | 10 |
| 8117 | 574_6 | 7.5 µM | 47 | 8 | 340 | 11 |
| 8117 | 574_7 | 7.5 µM | 43 | 0 | 308 | 42 |
| 8117 | 574_8 | 7.5 µM | 44 | 6 | 268 | 10 |
| 8117 | 574_9 | 7.5 µM | 41 | 8 | 241 | 22 |
| 8118 | 575_1 | 7.5 µM | 47 | 0 | 198 | 28 |
| 8118 | 575_2 | 7.5 µM | 83 | 26 | 253 | 31 |
| 8118 | 575_3 | 7.5 µM | 48 | 4 | 348 | 5 |
| 8118 | 575_4 | 7.5 µM | 37 | 2 | 269 | 7 |
| 8118 | 575_5 | 7.5 µM | 43 | 6 | 258 | 17 |
| 8118 | 575_6 | 7.5 µM | 50 | 6 | 286 | 3 |
| 8118 | 575_7 | 7.5 µM | 37 | 2 | 331 | 30 |
| 8118 | 575_8 | 7.5 µM | 47 | 7 | 264 | 1 |
| 8118 | 575_9 | 7.5 µM | 64 | 23 | 243 | 3 |
| 8119 | 576_1 | 7.5 µM | 47 | 1 | 272 | 14 |
| 8119 | 576_2 | 7.5 uM | 109 | 31 | 119 | 3 |
| 8119 | 576_3 | 7.5 µM | 36 | 3 | 287 | 6 |
| 8119 | 576_4 | 7.5 µM | 35 | 3 | 285 | 23 |
| 8119 | 576_5 | 7.5 µM | 49 | 10 | 222 | 1 |
| 8119 | 576_6 | 7.5 µM | 79 | 12 | 132 | 10 |
| 8119 | 576_7 | 7.5 µM | 76 | 4 | 132 | 3 |
| 8119 | 576_8 | 7.5 µM | 62 | 1 | 147 | 5 |
| 8119 | 576_9 | 7.5 µM | 43 | 3 | 230 | 5 |
| 8120 | 577_1 | 7.5 µM | 57 | 3 | 158 | 15 |
| 8120 | 577_2 | 7.5 µM | 39 | 4 | 279 | 60 |
| 8120 | 577_3 | 7.5 µM | 38 | 1 | 290 | 68 |
| 8120 | 577_4 | 7.5 µM | 77 | 11 | 148 | 11 |
| 8120 | 577_5 | 7.5 µM | 31 | 6 | 272 | 36 |
| 8120 | 577_6 | 7.5 µM | 38 | 8 | 228 | 32 |
| 8120 | 577_7 | 7.5 µM | 40 | 8 | 246 | 39 |
| 8120 | 577_8 | 7.5 µM | 43 | 11 | 256 | 26 |
| 8120 | 577_9 | 7.5 µM | 85 | 32 | 109 | 6 |
| 8584 | 578_1 | 7.5 µM | 57 | 7 | 199 | 7 |
| 8584 | 578_2 | 7.5 µM | 40 | 5 | 263 | 3 |
| 8584 | 578_3 | 7.5 µM | 40 | 2 | 289 | 23 |
| 8584 | 578_4 | 7.5 µM | 43 | 8 | 199 | 16 |
| 8584 | 578_5 | 7.5 µM | 42 | 1 | 256 | 15 |
| 8584 | 578_6 | 7.5 µM | 42 | 6 | 241 | 10 |
| 8584 | 578_7 | 7.5 µM | 42 | 5 | 329 | 20 |
| 8584 | 578_8 | 7.5 µM | 49 | 7 | 271 | 13 |
| 8584 | 578_9 | 7.5 µM | 45 | 3 | 222 | 3 |
| 8585 | 579_1 | 7.5 µM | 45 | 0 | 208 | 8 |
| 8585 | 579_2 | 7.5 µM | 51 | 4 | 226 | 6 |
| 8585 | 579_3 | 7.5 µM | 54 | 5 | 178 | 8 |
| 8585 | 579_4 | 7.5 µM | 41 | 4 | 328 | 13 |
| 8585 | 579_5 | 7.5 µM | 50 | 5 | 272 | 3 |
| 8585 | 579_6 | 7.5 µM | 86 | 12 | 161 | 0 |
| 8585 | 579_7 | 7.5 µM | 72 | 5 | 155 | 15 |
| 8585 | 579_8 | 7.5 µM | 57 | 3 | 230 | 14 |
| 8585 | 579_9 | 7.5 µM | 83 | 0 | 123 | 1 |
| 8586 | 580_1 | 7.5 µM | 37 | 2 | 313 | 13 |
| 8586 | 580_2 | 7.5 µM | 43 | 1 | 266 | 3 |
| 8586 | 580_3 | 7.5 µM | 42 | 5 | 303 | 5 |
| 8586 | 580_4 | 7.5 µM | 57 | 4 | 225 | 26 |
| 8586 | 580_5 | 7.5 µM | 51 | 4 | 228 | 35 |
| 8586 | 580_6 | 7.5 µM | 44 | 4 | 253 | 15 |
| 8586 | 580_7 | 7.5 µM | 50 | 1 | 241 | 10 |
| 8586 | 580_8 | 7.5 µM | 44 | 0 | 227 | 26 |
| 8586 | 580_9 | 7.5 µM | 31 | 5 | 323 | 31 |
| 8587 | 581_1 | 7.5 µM | 50 | 6 | 223 | 30 |
| 8587 | 581_2 | 7.5 µM | 66 | 7 | 199 | 19 |
| 8587 | 581_3 | 7.5 µM | 56 | 8 | 197 | 9 |
| 8587 | 581_4 | 7.5 µM | 57 | 12 | 270 | 24 |
| 8587 | 581_5 | 7.5 µM | 51 | 12 | 259 | 12 |
| 8587 | 581_6 | 7.5 µM | 39 | 4 | 282 | 2 |
| 8587 | 581 7 | 7.5 µM | 38 | 11 | 263 | 5 |
| 8587 | 581_8 | 7.5 µM | 45 | 10 | 203 | 19 |
| 8587 | 581_9 | 7.5 µM | 43 | 2 | 234 | 10 |
| 9209 | 582_1 | 7.5 µM | 61 | 7 | 225 | 7 |
| 9209 | 582_2 | 7.5 µM | 46 | 9 | 341 | 36 |
| 9209 | 582_3 | 7.5 µM | 44 | 9 | 306 | 38 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 9209 | 582_4 | 7.5 µM | 43 | 1 | 249 | 5 |
| 9209 | 582_5 | 7.5 µM | 33 | 16 | 306 | 6 |
| 9209 | 582_6 | 7.5 µM | 37 | 8 | 329 | 19 |
| 9209 | 582_7 | 7.5 µM | 44 | 9 | 289 | 4 |
| 9209 | 582_8 | 7.5 µM | 39 | 3 | 314 | 20 |
| 9209 | 582_9 | 7.5 µM | 41 | 4 | 299 | 25 |
| 9210 | 583_1 | 7.5 µM | 43 | 5 | 319 | 25 |
| 9210 | 583_2 | 7.5 µM | 53 | 9 | 352 | 5 |
| 9210 | 583_3 | 7.5 µM | 42 | 2 | 362 | 42 |
| 9210 | 583_4 | 7.5 µM | 46 | 5 | 225 | 13 |
| 9210 | 583_5 | 7.5 µM | 39 | 6 | 343 | 21 |
| 9210 | 583_6 | 7.5 µM | 44 | 9 | 298 | 8 |
| 9210 | 583_7 | 7.5 µM | 37 | 5 | 332 | 9 |
| 9210 | 583_8 | 7.5 µM | 42 | 6 | 343 | 25 |
| 9210 | 583_9 | 7.5 µM | 36 | 2 | 341 | 9 |
| 9211 | 584_1 | 7.5 µM | 45 | 5 | 343 | 39 |
| 9211 | 584_2 | 7.5 µM | 42 | 2 | 298 | 22 |
| 9211 | 584_3 | 7.5 µM | 44 | 10 | 321 | 2 |
| 9211 | 584_4 | 7.5 µM | 50 | 1 | 299 | 5 |
| 9211 | 584_5 | 7.5 µM | 44 | 1 | 319 | 25 |
| 9211 | 584_6 | 7.5 µM | 50 | 6 | 323 | 13 |
| 9211 | 584_7 | 7.5 µM | 42 | 4 | 316 | 27 |
| 9211 | 584_8 | 7.5 µM | 53 | 3 | 217 | 11 |
| 9212 | 208_2 | 7.5 µM | 44 | 7 | 312 | 26 |
| 9212 | 208_3 | 7.5 µM | 38 | 2 | 331 | 21 |
| 9212 | 208_4 | 7.5 µM | 47 | 3 | 353 | 11 |
| 9212 | 208_5 | 7.5 µM | 54 | 11 | 348 | 14 |
| 9212 | 208_6 | 7.5 µM | 51 | 12 | 310 | 8 |
| 9212 | 208_7 | 7.5 µM | 60 | 9 | 224 | 11 |
| 9213 | 209_2 | 7.5 µM | 44 | 12 | 242 | 21 |
| 9213 | 209_3 | 7.5 µM | 37 | 12 | 335 | 12 |
| 9213 | 209_4 | 7.5 µM | 55 | 7 | 350 | 2 |
| 9213 | 209_5 | 7.5 µM | 47 | 7 | 337 | 19 |
| 9213 | 209_6 | 7.5 µM | 51 | 8 | 300 | 19 |
| 9213 | 209_7 | 7.5 µM | 47 | 15 | 342 | 23 |
| 9213 | 209_8 | 7.5 µM | 45 | 12 | 289 | 5 |
| 9213 | 209_9 | 7.5 µM | 41 | 1 | 368 | 37 |
| 9213 | 209_10 | 7.5 µM | 40 | 4 | 315 | 1 |
| 11511 | 585_1 | 7.5 µM | 41 | 7 | 350 | 12 |
| 11511 | 585_2 | 7.5 µM | 44 | 4 | 233 | 7 |
| 11511 | 585_3 | 7.5 µM | 40 | 8 | 310 | 31 |
| 11511 | 585_4 | 7.5 µM | 33 | 8 | 324 | 41 |
| 11511 | 585_5 | 7.5 µM | 29 | 3 | 314 | 23 |
| 11511 | 585_6 | 7.5 µM | 38 | 4 | 332 | 15 |
| 11511 | 585_7 | 7.5 µM | 30 | 2 | 315 | 15 |
| 11511 | 585_8 | 7.5 µM | 36 | 11 | 328 | 37 |
| 11511 | 585_9 | 7.5 µM | 39 | 5 | 303 | 49 |
| 11512 | 586_1 | 7.5 µM | 60 | 3 | 236 | 5 |
| 11512 | 586_2 | 7.5 µM | 40 | 9 | 282 | 53 |
| 11512 | 586_3 | 7.5 µM | 36 | 1 | 279 | 11 |
| 11512 | 586_4 | 7.5 µM | 34 | 3 | 288 | 21 |
| 11512 | 586_5 | 7.5 µM | 30 | 1 | 270 | 4 |
| 11512 | 586_6 | 7.5 µM | 29 | 5 | 269 | 24 |
| 11512 | 586_7 | 7.5 µM | 33 | 4 | 263 | 6 |
| 11512 | 586_8 | 7.5 µM | 32 | 4 | 270 | 4 |
| 11512 | 586_9 | 7.5 µM | 33 | 5 | 310 | 48 |
| 11513 | 587_1 | 7.5 µM | 45 | 2 | 237 | 34 |
| 11513 | 587_2 | 7.5 µM | 44 | 3 | 307 | 4 |
| 11513 | 587_3 | 7.5 µM | 37 | 1 | 285 | 24 |
| 11513 | 587_4 | 7.5 µM | 44 | 1 | 252 | 41 |
| 11513 | 587_5 | 7.5 µM | 51 | 7 | 220 | 29 |
| 11513 | 587_6 | 7.5 µM | 41 | 2 | 262 | 35 |
| 11513 | 587_7 | 7.5 µM | 39 | 7 | 280 | 21 |
| 11513 | 587_8 | 7.5 µM | 48 | 9 | 230 | 11 |
| 11513 | 587_9 | 7.5 µM | 41 | 5 | 270 | 9 |
| 11514 | 588_1 | 7.5 µM | 54 | 9 | 204 | 25 |
| 11514 | 588_2 | 7.5 µM | 98 | 5 | 143 | 4 |
| 11514 | 588_3 | 7.5 µM | 55 | 9 | 180 | 1 |
| 11514 | 588_4 | 7.5 µM | 113 | 24 | 109 | 17 |
| 11514 | 588_5 | 7.5 µM | 66 | 26 | 150 | 5 |
| 11514 | 588_6 | 7.5 µM | 74 | 1 | 13 | 1 |
| 11514 | 588_7 | 7.5 µM | 79 | 4 | 140 | 9 |
| 11514 | 588_8 | 7.5 µM | 49 | 2 | 235 | 2 |
| 11514 | 588_9 | 7.5 µM | 51 | 10 | 281 | 2 |
| 11515 | 589_1 | 7.5 µM | 61 | 2 | 154 | 9 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 11515 | 589_2 | 7.5 µM | 70 | 9 | 126 | 12 |
| 11515 | 589_3 | 7.5 µM | 53 | 3 | 212 | 32 |
| 11515 | 589_4 | 7.5 µM | 93 | 14 | 108 | 14 |
| 11515 | 589_5 | 7.5 µM | 69 | 11 | 191 | 7 |
| 11515 | 589_6 | 7.5 µM | 53 | 9 | 183 | 20 |
| 11515 | 589_7 | 7.5 µM | 45 | 8 | 257 | 4 |
| 11515 | 589_8 | 7.5 µM | 35 | 5 | 213 | 5 |
| 11515 | 589_9 | 7.5 µM | 41 | 2 | 290 | 22 |
| 13223 | 236_2 | 7.5 µM | 39 | 6 | 286 | 21 |
| 13223 | 236_3 | 7.5 µM | 32 | 10 | 256 | 29 |
| 13223 | 236_4 | 7.5 µM | 37 | 5 | 285 | 12 |
| 13223 | 236_5 | 7.5 µM | 33 | 8 | 280 | 19 |
| 13223 | 236_6 | 7.5 µM | 40 | 16 | 295 | 7 |
| 13223 | 236_7 | 7.5 µM | 45 | 10 | 254 | 50 |
| 13223 | 236_8 | 7.5 µM | 41 | 22 | 306 | 50 |
| 13223 | 236_9 | 7.5 µM | 32 | 11 | 292 | 47 |
| 13223 | 236_10 | 7.5 µM | 31 | 10 | 307 | 3 |
| 13223 | 236_11 | 7.5 µM | 52 | 32 | 198 | 29 |
| 13223 | 236_12 | 7.5 µM | 31 | 7 | 261 | 18 |
| 13223 | 236_13 | 7.5 µM | 34 | 3 | 279 | 32 |
| 13223 | 236_14 | 7.5 µM | 38 | 0 | 285 | 75 |
| 13223 | 236_15 | 7.5 µM | 40 | 17 | 307 | 53 |
| 13223 | 236_16 | 7.5 µM | 41 | 6 | 321 | 30 |
| 13224 | 237_2 | 7.5 µM | 49 | 18 | 251 | 38 |
| 13224 | 237_3 | 7.5 µM | 53 | 14 | 236 | 33 |
| 13224 | 237_4 | 7.5 µM | 39 | 0 | 283 | 26 |
| 13224 | 237_5 | 7.5 µM | 43 | 2 | 243 | 2 |
| 13224 | 237_6 | 7.5 µM | 39 | 10 | 265 | 48 |
| 13224 | 237_7 | 7.5 µM | 50 | 3 | 302 | 19 |
| 13224 | 237_8 | 7.5 µM | 46 | 7 | 327 | 43 |
| 13224 | 237_9 | 7.5 µM | 38 | 9 | 287 | 12 |
| 13224 | 237_10 | 7.5 µM | 35 | 6 | 248 | 35 |
| 13224 | 237_11 | 7.5 µM | 41 | 1 | 259 | 24 |
| 13224 | 237_12 | 7.5 µM | 33 | 6 | 303 | 35 |
| 13224 | 237_13 | 7.5 µM | 26 | 4 | 265 | 53 |
| 13224 | 237_14 | 7.5 µM | 30 | 8 | 321 | 15 |
| 13224 | 237_15 | 7.5 µM | 33 | 11 | 315 | 24 |
| 13224 | 237_16 | 7.5 µM | 36 | 11 | 292 | 19 |
| 13225 | 239_2 | 7.5 µM | 35 | 16 | 291 | 30 |
| 13225 | 239_3 | 7.5 µM | 40 | 15 | 311 | 42 |
| 13225 | 239_4 | 7.5 µM | 81 | 6 | 144 | 16 |
| 13225 | 239_5 | 7.5 µM | 90 | 16 | 127 | 11 |
| 13225 | 239_6 | 7.5 µM | 49 | 29 | 282 | 3 |
| 13225 | 239_7 | 7.5 µM | 35 | 4 | 296 | 23 |
| 13225 | 239_8 | 7.5 µM | 40 | 1 | 292 | 48 |
| 13225 | 239_9 | 7.5 µM | 36 | 1 | 318 | 44 |
| 13225 | 239_10 | 7.5 µM | 49 | NA | 304 | NA |
| 13225 | 239_11 | 7.5 µM | 45 | NA | 258 | NA |
| 13225 | 239_12 | 7.5 µM | 43 | 1 | 285 | 1 |
| 13225 | 239_13 | 7.5 µM | 31 | 1 | 308 | 31 |
| 13225 | 239_14 | 7.5 µM | 41 | 8 | 253 | 6 |
| 13225 | 239_15 | 7.5 µM | 28 | 3 | 29- | 16 |
| 13225 | 239_16 | 7.5 µM | 29 | 3 | 314 | 14 |
| 13226 | 590_1 | 7.5 µM | 34 | 1 | 283 | 18 |
| 13226 | 590_2 | 7.5 µM | 49 | 7 | 213 | 17 |
| 13226 | 590_3 | 7.5 µM | 40 | 1 | 274 | 51 |
| 13226 | 590_4 | 7.5 µM | 36 | 1 | 300 | 2 |
| 13226 | 590_5 | 7.5 µM | 37 | 3 | 280 | 36 |
| 13226 | 590_6 | 7.5 µM | 38 | 2 | 204 | 17 |
| 13226 | 590_7 | 7.5 µM | 38 | 5 | 245 | 16 |
| 13226 | 590_8 | 7.5 µM | 30 | 6 | 219 | 34 |
| 13226 | 590_9 | 7.5 µM | 33 | 1 | 269 | 2 |
| 13226 | 590_10 | 7.5 µM | 33 | 2 | 258 | 49 |
| 13226 | 590_11 | 7.5 µM | 48 | 17 | 297 | 31 |
| 13226 | 590_12 | 7.5 µM | 33 | 4 | 317 | 65 |
| 13226 | 590_13 | 7.5 µM | 35 | 7 | 337 | 43 |
| 13226 | 590_14 | 7.5 µM | 25 | 1 | 306 | 22 |
| 13226 | 590_15 | 7.5 µM | 30 | 5 | 299 | 2 |
| 15113 | 591_1 | 7.5 µM | 43 | 3 | 313 | 14 |
| 15113 | 591_2 | 7.5 µM | 52 | 2 | 295 | 24 |
| 15114 | 592_1 | 7.5 µM | 53 | 2 | 232 | 17 |
| 15114 | 592_2 | 7.5 µM | 39 | 1 | 309 | 23 |
| 15114 | 592_3 | 7.5 µM | 46 | 1 | 278 | 12 |
| 15114 | 592_4 | 7.5 µM | 36 | 1 | 328 | 13 |
| 15114 | 592_5 | 7.5 µM | 49 | 9 | 295 | 40 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 15114 | 592_6 | 7.5 µM | 46 | 3 | 297 | 10 |
| 15114 | 592_7 | 7.5 µM | 75 | 21 | 160 | 23 |
| 15114 | 592_8 | 7.5 µM | 41 | 10 | 325 | 23 |
| 15114 | 592_9 | 7.5 µM | 55 | 15 | 265 | 3 |
| 15115 | 241_2 | 7.5 µM | 66 | 18 | 168 | 2 |
| 15115 | 241_3 | 7.5 µM | 51 | 15 | 265 | 11 |
| 15115 | 241_4 | 7.5 µM | 49 | 4 | 239 | 7 |
| 15115 | 241_5 | 7.5 µM | 52 | 11 | 314 | 20 |
| 15115 | 241_6 | 7.5 µM | 41 | 13 | 307 | 7 |
| 15115 | 241_7 | 7.5 µM | 38 | 6 | 344 | 33 |
| 15115 | 241_8 | 7.5 µM | 39 | 10 | 329 | 9 |
| 15115 | 241_9 | 7.5 µM | 50 | 11 | 321 | 32 |
| 15115 | 241_10 | 7.5 µM | 48 | 9 | 316 | 1 |
| 15563 | 593_1 | 7.5 µM | 38 | 10 | 282 | 14 |
| 15563 | 593_2 | 7.5 µM | 31 | 5 | 279 | 16 |
| 15563 | 593_3 | 7.5 µM | 34 | 7 | 281 | 16 |
| 15563 | 593_4 | 7.5 µM | 32 | 16 | 318 | 2 |
| 15563 | 594_1 | 7.5 µM | 40 | 2 | 320 | 21 |
| 15563 | 594_2 | 7.5 µM | 54 | 7 | 237 | 14 |
| 15563 | 594_3 | 7.5 µM | 35 | 6 | 300 | 45 |
| 15563 | 594_4 | 7.5 µM | 37 | 7 | 254 | 6 |
| 15564 | 596_1 | 7.5 µM | 47 | 7 | 225 | 35 |
| 15564 | 596_2 | 7.5 µM | 49 | 2 | 184 | 14 |
| 15564 | 596_3 | 7.5 µM | 34 | 8 | 271 | 18 |
| 15564 | 596_4 | 7.5 µM | 45 | 8 | 277 | 29 |
| 15564 | 595_1 | 7.5 µM | 42 | 4 | 254 | 6 |
| 15564 | 595_2 | 7.5 µM | 36 | 9 | 277 | 35 |
| 15564 | 595_3 | 7.5 µM | 40 | 8 | 295 | 31 |
| 15564 | 595_4 | 7.5 µM | 45 | 5 | 173 | 20 |
| 15566 | 597 1 | 7.5 µM | 48 | 6 | 296 | 22 |
| 15566 | 597_2 | 7.5 µM | 44 | 12 | 293 | 8 |
| 15566 | 597_3 | 7.5 µM | 41 | 6 | 318 | 23 |
| 15566 | 597_4 | 7.5 µM | 60 | 9 | 340 | 72 |
| 15567 | 38_3 | 7.5 µM | 41 | 3 | 306 | 14 |
| 15567 | 38_4 | 7.5 µM | 45 | 1 | 303 | 48 |
| 15567 | 38_5 | 7.5 µM | 39 | 15 | 292 | 28 |
| 15567 | 38_6 | 7.5 µM | 46 | 12 | 261 | 40 |
| 15567 | 598_1 | 7.5 µM | 42 | 2 | 257 | 31 |
| 15567 | 598_2 | 7.5 µM | 41 | 12 | 272 | 46 |
| 15567 | 598_3 | 7.5 µM | 54 | 9 | 281 | 29 |
| 15567 | 598_4 | 7.5 µM | 45 | 8 | 307 | 6 |
| 15568 | 599_1 | 7.5 µM | 47 | 3 | 326 | 68 |
| 15568 | 599_2 | 7.5 µM | 60 | 14 | 307 | 30 |
| 15568 | 599_3 | 7.5 µM | 50 | 8 | 274 | 24 |
| 15568 | 599_4 | 7.5 µM | 45 | 6 | 250 | 12 |
| 15568 | 600_1 | 7.5 µM | 37 | 6 | 251 | 1 |
| 15568 | 600_2 | 7.5 µM | 45 | 11 | 267 | 15 |
| 15568 | 600_3 | 7.5 µM | 44 | 5 | 278 | 1 |
| 15568 | 600_4 | 7.5 µM | 41 | 10 | 265 | 5 |
| 15569 | 601_1 | 7.5 µM | 42 | 12 | 271 | 18 |
| 15569 | 601_2 | 7.5 µM | 38 | 6 | 269 | 24 |
| 15569 | 601_3 | 7.5 µM | 39 | 4 | 260 | 34 |
| 15569 | 601_4 | 7.5 µM | 56 | 8 | 146 | 1 |
| 15570 | 244_2 | 7.5 µM | 46 | 1 | 338 | 6 |
| 15570 | 244_3 | 7.5 µM | 47 | 0 | 275 | 47 |
| 15570 | 244_4 | 7.5 µM | 47 | 8 | 281 | 67 |
| 15570 | 244_5 | 7.5 µM | 41 | 8 | 258 | 52 |
| 15570 | 39_2 | 7.5 µM | 53 | 4 | 339 | 25 |
| 15570 | 39_3 | 7.5 µM | 65 | 5 | 200 | 17 |
| 15570 | 39_4 | 7.5 µM | 47 | 7 | 321 | 6 |
| 15570 | 39_5 | 7.5 µM | 46 | 3 | 289 | 20 |
| 15571 | 602_1 | 7.5 µM | 34 | 5 | 278 | 29 |
| 15571 | 602_2 | 7.5 µM | 39 | 8 | 254 | 37 |
| 15571 | 602_3 | 7.5 µM | 41 | 10 | 266 | 23 |
| 15571 | 602_4 | 7.5 µM | 42 | 8 | 256 | 40 |
| 15571 | 40_2 | 7.5 µM | 58 | 0 | 325 | 4 |
| 15571 | 40_3 | 7.5 µM | 58 | 2 | 326 | 35 |
| 15571 | 40_4 | 7.5 µM | 54 | 1 | 306 | 3 |
| 15571 | 40_5 | 7.5 µM | 44 | 2 | 322 | 4 |
| 15571 | 40_6 | 7.5 µM | 43 | 4 | 293 | 17 |
| 15571 | 40_7 | 7.5 µM | 53 | 7 | 343 | 20 |
| 15571 | 40_8 | 7.5 µM | 52 | 1 | 337 | 17 |
| 15572 | 604_1 | 7.5 µM | 58 | 1 | 289 | 3 |
| 15572 | 604_2 | 7.5 µM | 63 | 12 | 230 | 5 |
| 15572 | 604_3 | 7.5 µM | 57 | 3 | 306 | 23 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 15572 | 604_4 | 7.5 µM | 46 | 6 | 324 | 4 |
| 15572 | 603_1 | 7.5 µM | 60 | 7 | 339 | 31 |
| 15572 | 603_2 | 7.5 µM | 70 | 0 | 279 | 19 |
| 15572 | 603_3 | 7.5 µM | 59 | 9 | 290 | 48 |
| 15572 | 603_4 | 7.5 µM | 85 | 11 | 123 | 24 |
| 15573 | 605_1 | 7.5 µM | 56 | 5 | 288 | 3 |
| 15573 | 605_2 | 7.5 µM | 58 | 4 | 286 | 6 |
| 15573 | 605_3 | 7.5 µM | 59 | 3 | 261 | 9 |
| 15573 | 605_4 | 7.5 µM | 69 | 24 | 328 | 17 |
| 15573 | 606_1 | 7.5 µM | 50 | 4 | 282 | 19 |
| 15573 | 606_2 | 7.5 µM | 112 | NA | 133 | NA |
| 15573 | 606_3 | 7.5 µM | 55 | 22 | 254 | 43 |
| 15573 | 606_4 | 7.5 µM | 107 | 59 | 116 | 2 |
| 15574 | 607_1 | 7.5 µM | 56 | 2 | 337 | 31 |
| 15574 | 607_2 | 7.5 µM | 59 | 1 | 254 | 10 |
| 15574 | 607_3 | 7.5 µM | 53 | 0 | 295 | 26 |
| 15574 | 607_4 | 7.5 µM | 48 | 3 | 268 | 15 |
| 25248 | 608_1 | 7.5 µM | 86 | 7 | 189 | 5 |
| 25248 | 608_2 | 7.5 µM | 102 | 13 | 136 | 3 |
| 25248 | 608_3 | 7.5 µM | 54 | 17 | 280 | 12 |
| 25248 | 608_4 | 7.5 µM | 71 | 8 | 219 | 31 |
| 25248 | 608_5 | 7.5 µM | 59 | 20 | 179 | 16 |
| 25248 | 608_6 | 7.5 µM | 71 | 2 | 198 | 0 |
| 25248 | 608_7 | 7.5 µM | 47 | 3 | 230 | 21 |
| 25248 | 608_8 | 7.5 µM | 55 | 12 | 287 | 13 |
| 25248 | 608_9 | 7.5 µM | 66 | 19 | 297 | 18 |
| 25249 | 609_1 | 7.5 µM | 58 | 19 | 264 | 7 |
| 25249 | 609_2 | 7.5 µM | 88 | 6 | 156 | 5 |
| 25249 | 609_3 | 7.5 µM | 76 | 19 | 140 | 13 |
| 25249 | 609_4 | 7.5 µM | 50 | 15 | 185 | 6 |
| 25249 | 609_5 | 7.5 µM | 95 | 29 | 139 | 1 |
| 25249 | 609_6 | 7.5 µM | 86 | 15 | 126 | 7 |
| 25249 | 609_7 | 7.5 µM | 72 | 9 | 174 | 1 |
| 25249 | 609_8 | 7.5 µM | 64 | 3 | 189 | 18 |
| 25249 | 609_9 | 7.5 µM | 77 | 12 | 223 | 35 |
| 25250 | 610_1 | 7.5 µM | 55 | 17 | 233 | 7 |
| 25250 | 610_2 | 7.5 µM | 52 | 15 | 233 | 9 |
| 25250 | 610_3 | 7.5 µM | 77 | 5 | 151 | 11 |
| 25250 | 610_4 | 7.5 µM | 48 | 0 | 242 | 21 |
| 25250 | 610_5 | 7.5 µM | 59 | 8 | 234 | 0 |
| 25250 | 610_6 | 7.5 µM | 59 | 12 | 208 | 23 |
| 25250 | 610_7 | 7.5 µM | 69 | 7 | 216 | 5 |
| 25250 | 610_8 | 7.5 µM | 70 | 16 | 211 | 2 |
| 25250 | 610_9 | 7.5 µM | 77 | 22 | 157 | 19 |
| 25251 | 611_1 | 7.5 µM | 43 | 4 | 306 | 10 |
| 25251 | 611_2 | 7.5 µM | 43 | 1 | 300 | 36 |
| 25251 | 611_3 | 7.5 µM | 43 | 17 | 306 | 6 |
| 25251 | 611_4 | 7.5 µM | 40 | 1 | 320 | 37 |
| 25251 | 611_5 | 7.5 µM | 48 | 9 | 273 | 7 |
| 25251 | 611_6 | 7.5 µM | 51 | 2 | 302 | 26 |
| 25251 | 611_7 | 7.5 µM | 40 | 8 | 326 | 8 |
| 25251 | 611_8 | 7.5 µM | 55 | 10 | 330 | 17 |
| 25251 | 611_9 | 7.5 µM | 40 | 3 | 297 | 11 |
| 25252 | 612_1 | 7.5 µM | 58 | 9 | 219 | 5 |
| 25252 | 612_2 | 7.5 µM | 54 | 9 | 282 | 4 |
| 25252 | 612_3 | 7.5 µM | 56 | 13 | 265 | 35 |
| 25252 | 612_4 | 7.5 µM | 81 | 16 | 239 | 51 |
| 25252 | 612_5 | 7.5 µM | 57 | 2 | 234 | 25 |
| 25252 | 612_6 | 7.5 µM | 76 | 18 | 221 | 8 |
| 25252 | 612_7 | 7.5 µM | 45 | 7 | 285 | 11 |
| 25252 | 612_8 | 7.5 µM | 50 | 8 | 231 | 4 |
| 25252 | 612_9 | 7.5 µM | 51 | 3 | 305 | 17 |
| 29636 | 271_1 | 7.5 µM | 35 | 4 | 345 | 29 |
| 29636 | 271_1 | 7.5 µM | 32 | 6 | 383 | 31 |
| 29636 | 271_1 | 7.5 µM | 42 | 7 | 292 | 13 |
| 29636 | 271_1 | 7.5 µM | 40 | 1 | 309 | 41 |
| 29636 | 271_1 | 7.5 µM | 41 | 10 | 339 | 17 |
| 29636 | 271_1 | 7.5 µM | 35 | 8 | 306 | 40 |
| 29636 | 271_1 | 7.5 µM | 33 | 1 | 320 | 12 |
| 29636 | 271_1 | 7.5 µM | 43 | 1 | 347 | 7 |
| 29636 | 271_1 | 7.5 µM | 36 | 2 | 339 | 19 |
| 29636 | 271_1 | 7.5 µM | 36 | 1 | 315 | 5 |
| 29636 | 271_1 | 7.5 µM | 41 | 1 | 326 | 16 |
| 29636 | 271_1 | 7.5 µM | 38 | 2 | 344 | 1 |
| 29636 | 271_1 | 7.5 µM | 34 | 6 | 341 | 8 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 29636 | 271_1 | 7.5 µM | 42 | 9 | 320 | 1 |
| 29636 | 271_1 | 7.5 µM | 31 | 8 | 344 | 37 |
| 29636 | 271_1 | 7.5 µM | 44 | 2 | 335 | 11 |
| 29636 | 271_1 | 7.5 µM | 32 | 0 | 316 | 17 |
| 29636 | 271_1 | 7.5 µM | 43 | 11 | 323 | 2 |
| 29636 | 271_1 | 7.5 µM | 35 | 7 | 340 | 2 |
| 29636 | 271_1 | 7.5 µM | 43 | 1 | 340 | 8 |
| 29636 | 271_1 | 7.5 µM | 33 | 4 | 296 | 27 |
| 29636 | 271_1 | 7.5 µM | 38 | 5 | 334 | 4 |
| 29636 | 271_1 | 7.5 µM | 36 | 4 | 341 | 22 |
| 29636 | 271_1 | 7.5 µM | 48 | 4 | 334 | 3 |
| 29636 | 271_1 | 7.5 µM | 36 | 8 | 303 | 13 |
| 29636 | 271_1 | 7.5 µM | 36 | 0 | 343 | 7 |
| 29636 | 271_1 | 7.5 µM | 39 | 1 | 326 | 1 |
| 29636 | 271_1 | 7.5 µM | 38 | 2 | 346 | 14 |
| 29636 | 271_1 | 7.5 µM | 32 | 0 | 332 | 11 |
| 29636 | 271_1 | 7.5 µM | 39 | 4 | 330 | 23 |
| 29636 | 271_1 | 7.5 µM | 39 | 7 | 346 | 33 |
| 29636 | 271_1 | 7.5 µM | 40 | 1 | 329 | 14 |
| 29636 | 271_1 | 7.5 µM | 34 | 6 | 316 | 38 |
| 29636 | 271_1 | 7.5 µM | 33 | 4 | 317 | 14 |
| 29636 | 271_1 | 7.5 µM | 41 | 6 | 328 | 11 |
| 29636 | 271_1 | 7.5 µM | 45 | 2 | 345 | 3 |
| 29636 | 271_1 | 7.5 µM | 37 | 1 | 330 | 3 |
| 29636 | 271_1 | 7.5 µM | 45 | 7 | 322 | 18 |
| 29636 | 271_1 | 7.5 µM | 36 | 3 | 334 | 13 |
| 29636 | 271_1 | 7.5 µM | 33 | 8 | 333 | 3 |
| 29636 | 271_1 | 7.5 µM | 35 | 10 | 321 | 43 |
| 29636 | 271_1 | 7.5 µM | 41 | 3 | 323 | 18 |
| 29636 | 271_1 | 7.5 µM | 39 | 8 | 354 | 39 |
| 29636 | 271_1 | 7.5 µM | 35 | 2 | 327 | 23 |
| 30599 | 613_1 | 7.5 µM | 73 | 29 | 172 | 22 |
| 30599 | 613_2 | 7.5 µM | 87 | 40 | 114 | 9 |
| 30599 | 613_3 | 7.5 µM | 59 | 23 | 168 | 23 |
| 30599 | 613_4 | 7.5 µM | 43 | 15 | 281 | 31 |
| 30599 | 613_5 | 7.5 µM | 51 | 3 | 271 | 28 |
| 30600 | 614_1 | 7.5 µM | 56 | 11 | 179 | 22 |
| 30600 | 614_2 | 7.5 µM | 96 | 40 | 100 | 7 |
| 30600 | 614_3 | 7.5 µM | 41 | 7 | 246 | 27 |
| 30600 | 614_4 | 7.5 µM | 47 | 19 | 283 | 14 |
| 30600 | 614_5 | 7.5 µM | 52 | 21 | 209 | 16 |
| 30600 | 615_1 | 7.5 µM | 61 | 19 | 197 | 12 |
| 30600 | 615_2 | 7.5 µM | 45 | 11 | 287 | 25 |
| 30600 | 615_3 | 7.5 µM | 102 | NA | 115 | NA |
| 30600 | 615_4 | 7.5 µM | 72 | NA | 170 | NA |
| 30600 | 615_5 | 7.5 µM | 95 | NA | 138 | NA |
| 30601 | 285_2 | 7.5 µM | 83 | NA | 165 | NA |
| 30601 | 285_3 | 7.5 µM | 124 | NA | 111 | NA |
| 30601 | 285_4 | 7.5 µM | 69 | NA | 183 | NA |
| 30601 | 285_5 | 7.5 µM | 47 | 23 | 211 | 7 |
| 30601 | 285_6 | 7.5 µM | 46 | 12 | 183 | 6 |
| 30601 | 617_1 | 7.5 µM | 67 | 26 | 190 | 19 |
| 30601 | 617_2 | 7.5 µM | 74 | 35 | 137 | 6 |
| 30601 | 617_3 | 7.5 µM | 51 | 16 | 211 | 4 |
| 30601 | 617_4 | 7.5 µM | 65 | 22 | 142 | 11 |
| 30601 | 617_5 | 7.5 µM | 43 | 8 | 298 | 26 |
| 30601 | 616_1 | 7.5 µM | 50 | 22 | 181 | 12 |
| 30601 | 616_2 | 7.5 µM | 37 | 13 | 276 | 33 |
| 30601 | 616_3 | 7.5 µM | 38 | 16 | 264 | 9 |
| 30601 | 616_4 | 7.5 µM | 43 | NA | 304 | NA |
| 30601 | 616_5 | 7.5 µM | 50 | NA | 229 | NA |
| 30602 | 619_1 | 7.5 µM | 90 | 43 | 131 | 22 |
| 30602 | 619_2 | 7.5 µM | 78 | 40 | 138 | 2 |
| 30602 | 619_3 | 7.5 µM | 66 | 22 | 123 | 8 |
| 30602 | 619_4 | 7.5 µM | 100 | 43 | 96 | 5 |
| 30602 | 619_5 | 7.5 µM | 75 | 17 | 157 | 5 |
| 30602 | 618_1 | 7.5 µM | 46 | 16 | 226 | 12 |
| 30602 | 618_2 | 7.5 µM | 68 | NA | 151 | NA |
| 30602 | 618_3 | 7.5 µM | 52 | 4 | 207 | 18 |
| 30602 | 618_4 | 7.5 µM | 57 | 12 | 223 | 2 |
| 30602 | 618_5 | 7.5 µM | 54 | 2 | 211 | 3 |
| 30603 | 620_1 | 7.5 µM | 106 | 23 | 110 | 16 |
| 30603 | 620_2 | 7.5 µM | 48 | 10 | 243 | 18 |
| 30603 | 620_3 | 7.5 µM | 53 | 1 | 174 | 32 |
| 30603 | 620_4 | 7.5 µM | 81 | 0 | 138 | 15 |

TABLE 8-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 30603 | 620_5 | 7.5 μM | 56 | 5 | 218 | 9 |
| 30604 | 621_1 | 7.5 μM | 39 | 4 | 304 | 10 |
| 30604 | 621_2 | 7.5 μM | 35 | 7 | 311 | 3 |
| 30604 | 621_3 | 7.5 μM | 67 | 18 | 142 | 8 |
| 30604 | 621_4 | 7.5 μM | 34 | 6 | 273 | 21 |
| 30604 | 621_5 | 7.5 μM | 36 | 5 | 266 | 18 |
| 30605 | 622_1 | 7.5 μM | 42 | 1 | 242 | 28 |
| 30605 | 622_2 | 7.5 μM | 31 | 10 | 300 | 8 |
| 30605 | 622_3 | 7.5 μM | 35 | 3 | 319 | 11 |
| 30605 | 622_4 | 7.5 μM | 37 | 4 | 281 | 5 |
| 30605 | 622_5 | 7.5 μM | 39 | 5 | 306 | 11 |
| 30606 | 623_1 | 7.5 μM | 47 | 3 | 287 | 1 |
| 30606 | 623_2 | 7.5 μM | 74 | 23 | 166 | 7 |
| 30606 | 623_3 | 7.5 μM | 82 | 1 | 149 | 8 |
| 30606 | 623_4 | 7.5 μM | 66 | 9 | 135 | 8 |
| 30606 | 623_5 | 7.5 μM | 78 | 7 | 128 | 12 |
| 30608 | 624_1 | 7.5 μM | 84 | 13 | 185 | 25 |
| 30608 | 624_2 | 7.5 μM | 35 | 2 | 245 | 9 |
| 30608 | 624_3 | 7.5 μM | 31 | 3 | 267 | 9 |
| 30608 | 624_4 | 7.5 μM | 39 | 16 | 257 | 13 |
| 30608 | 624_5 | 7.5 μM | 34 | 3 | 283 | 4 |
| 30666 | 625_1 | 7.5 μM | 45 | 5 | 286 | 39 |
| 30666 | 625_2 | 7.5 μM | 39 | 3 | 280 | 13 |
| 30666 | 625_3 | 7.5 μM | 40 | 10 | 258 | 9 |
| 30666 | 625_4 | 7.5 μM | 41 | 14 | 234 | 39 |
| 30666 | 625_5 | 7.5 μM | 42 | 5 | 293 | 26 |
| 30666 | 625_6 | 7.5 μM | 44 | 0 | 284 | 25 |
| 30666 | 625_7 | 7.5 μM | 46 | 3 | 271 | 4 |
| 30666 | 625_8 | 7.5 μM | 47 | 5 | 256 | 17 |
| 30666 | 625_9 | 7.5 μM | 40 | 7 | 302 | 2 |
| 30667 | 626_1 | 7.5 μM | 38 | 1 | 279 | 10 |
| 30667 | 626_2 | 7.5 μM | 39 | 21 | 329 | 22 |
| 30667 | 626_3 | 7.5 μM | 59 | 12 | 265 | 65 |
| 30667 | 626_4 | 7.5 μM | 39 | 5 | 318 | 25 |
| 30667 | 626_5 | 7.5 μM | 36 | 2 | 302 | 33 |
| 30667 | 626_6 | 7.5 μM | 36 | 6 | 273 | 34 |
| 30667 | 626_7 | 7.5 μM | 30 | 0 | 299 | 29 |
| 30667 | 626_8 | 7.5 μM | 35 | 4 | 277 | 43 |
| 30667 | 626_9 | 7.5 μM | 32 | 3 | 275 | 22 |
| 30668 | 627_1 | 7.5 μM | 71 | 3 | 131 | 11 |
| 30668 | 627_2 | 7.5 μM | 49 | 4 | 226 | 30 |
| 30668 | 627_3 | 7.5 μM | 64 | 5 | 147 | 8 |
| 30668 | 627_4 | 7.5 μM | 52 | 6 | 176 | 9 |
| 30668 | 627_5 | 7.5 μM | 78 | 14 | 108 | 3 |
| 30668 | 627_6 | 7.5 μM | 40 | 1 | 183 | 23 |
| 30668 | 627_7 | 7.5 μM | 85 | 8 | 116 | 2 |
| 30668 | 627_8 | 7.5 μM | 45 | 1 | 128 | 7 |
| 30668 | 627_9 | 7.5 μM | 42 | 5 | 215 | 36 |
| 30669 | 628_1 | 7.5 μM | 90 | 11 | 120 | 15 |
| 30669 | 628_2 | 7.5 μM | 73 | 12 | 124 | 4 |
| 30669 | 628_3 | 7.5 μM | 88 | 2 | 115 | 4 |
| 30669 | 628_4 | 7.5 μM | 54 | 4 | 190 | 18 |
| 30669 | 628_5 | 7.5 μM | 64 | 1 | 138 | 3 |
| 30669 | 628_6 | 7.5 μM | 62 | 4 | 138 | 11 |
| 30669 | 628_7 | 7.5 μM | 55 | 1 | 138 | 13 |
| 30669 | 628_8 | 7.5 μM | 62 | 1 | 140 | 5 |
| 30669 | 628_9 | 7.5 μM | 79 | 10 | 134 | 22 |
| 30711 | 629_1 | 7.5 μM | 42 | 1 | 252 | 47 |
| 30711 | 629_2 | 7.5 μM | 40 | 2 | 295 | 30 |
| 30711 | 629_3 | 7.5 μM | 46 | 1 | 302 | 78 |
| 30711 | 629_4 | 7.5 μM | 41 | 3 | 260 | 16 |
| 30711 | 629_5 | 7.5 μM | 41 | 1 | 284 | 3 |
| 30711 | 629_6 | 7.5 μM | 43 | 0 | 262 | 1 |
| 30711 | 629_7 | 7.5 μM | 43 | 3 | 278 | 65 |
| 30711 | 629_8 | 7.5 μM | 53 | 5 | 234 | 24 |
| 30711 | 629_9 | 7.5 μM | 37 | 4 | 289 | 1 |
| 30711 | 629_10 | 7.5 μM | 47 | 6 | 292 | 6 |
| 30711 | 629_11 | 7.5 μM | 50 | 5 | 224 | 20 |
| 30712 | 630_1 | 7.5 μM | 44 | 2 | 282 | 22 |
| 30712 | 630_2 | 7.5 μM | 45 | 6 | 297 | 23 |
| 30712 | 630_3 | 7.5 μM | 46 | 2 | 272 | 10 |
| 30713 | 631_1 | 7.5 μM | 45 | 2 | 294 | 10 |
| 30713 | 631_2 | 7.5 μM | 42 | 0 | 285 | 14 |
| 30713 | 631_3 | 7.5 μM | 38 | 3 | 319 | 21 |
| 30713 | 631_4 | 7.5 μM | 43 | 3 | 282 | 4 |
| 30713 | 631_5 | 7.5 μM | 54 | 2 | 173 | 17 |
| 30713 | 631_6 | 7.5 μM | 37 | 0 | 315 | 10 |
| 30713 | 631_7 | 7.5 μM | 40 | 4 | 317 | 2 |
| 30713 | 631_8 | 7.5 μM | 44 | 1 | 275 | 5 |
| 30713 | 631_9 | 7.5 μM | 47 | 2 | 233 | 8 |
| 30713 | 631_10 | 7.5 μM | 108 | 18 | 101 | 3 |
| 30714 | 632_1 | 7.5 μM | 48 | 4 | 210 | 4 |
| 30714 | 632_2 | 7.5 μM | 53 | 5 | 256 | 5 |
| 30714 | 632_3 | 7.5 μM | 60 | 5 | 224 | 19 |
| 30714 | 632_4 | 7.5 μM | 89 | 12 | 117 | 11 |
| 30714 | 632_5 | 7.5 μM | 39 | 6 | 312 | 6 |
| 30714 | 632_6 | 7.5 μM | 40 | 2 | 278 | 31 |
| 30714 | 632_7 | 7.5 μM | 86 | 1 | 160 | 21 |
| 30714 | 632_8 | 7.5 μM | 57 | 17 | 278 | 40 |
| 30714 | 632_9 | 7.5 μM | 51 | 7 | 236 | 13 |
| 30715 | 304_2 | 7.5 μM | 53 | 5 | 206 | 18 |
| 30715 | 304_3 | 7.5 μM | 70 | 11 | 142 | 24 |
| 30715 | 304_4 | 7.5 μM | 88 | 1 | 120 | 10 |
| 30715 | 304_5 | 7.5 μM | 82 | 15 | 123 | 7 |
| 30715 | 304_6 | 7.5 μM | 43 | 4 | 264 | 12 |
| 30715 | 304_7 | 7.5 μM | 41 | 5 | 266 | 49 |
| 30715 | 304_8 | 7.5 μM | 43 | 1 | 291 | 12 |
| 30715 | 304_9 | 7.5 μM | 36 | 3 | 285 | 18 |
| 30715 | 304_10 | 7.5 μM | 42 | 1 | 280 | 40 |
| 33376 | 633_1 | 7.5 μM | 53 | 1 | 234 | 50 |
| 33376 | 633_2 | 7.5 μM | 45 | 5 | 301 | 7 |
| 33376 | 633_3 | 7.5 μM | 53 | 7 | 263 | 17 |
| 33376 | 633_4 | 7.5 μM | 53 | 4 | 229 | 22 |
| 33376 | 633_5 | 7.5 μM | 43 | 3 | 264 | 36 |
| 33376 | 633_6 | 7.5 μM | 53 | 5 | 247 | 12 |
| 33376 | 633_7 | 7.5 μM | 49 | 6 | 289 | 6 |
| 33376 | 633_8 | 7.5 μM | 64 | 11 | 238 | 24 |
| 33376 | 633_9 | 7.5 μM | 63 | 2 | 249 | 28 |
| 33377 | 634_1 | 7.5 μM | 57 | 9 | 250 | 14 |
| 33377 | 634_2 | 7.5 μM | 53 | 10 | 265 | 3 |
| 33377 | 634_3 | 7.5 μM | 48 | 2 | 275 | 10 |
| 33377 | 634_4 | 7.5 μM | 39 | 6 | 287 | 12 |
| 33377 | 634_5 | 7.5 μM | 49 | 1 | 255 | 22 |
| 33377 | 634_6 | 7.5 μM | 51 | 2 | 291 | 15 |
| 33377 | 634_7 | 7.5 μM | 47 | 5 | 297 | 16 |
| 33377 | 634_8 | 7.5 μM | 42 | 9 | 311 | 14 |
| 33377 | 634_9 | 7.5 μM | 47 | 5 | 271 | 23 |
| 33378 | 635_1 | 7.5 μM | 56 | 11 | 257 | 3 |
| 33378 | 635_2 | 7.5 μM | 56 | 5 | 213 | 23 |
| 33378 | 635_3 | 7.5 μM | 61 | 8 | 215 | 8 |
| 33378 | 635_4 | 7.5 μM | 58 | 15 | 232 | 16 |
| 33378 | 635_5 | 7.5 μM | 48 | 3 | 316 | 20 |
| 33378 | 635_6 | 7.5 μM | 59 | 5 | 262 | 30 |
| 33378 | 635_7 | 7.5 μM | 55 | 7 | 287 | 15 |
| 33378 | 635_8 | 7.5 μM | 42 | 1 | 284 | 3 |
| 33378 | 635_9 | 7.5 μM | 40 | 0 | 277 | 23 |
| 33379 | 636_1 | 7.5 μM | 50 | 2 | 239 | 7 |
| 33379 | 636_2 | 7.5 μM | 74 | 16 | 204 | 10 |
| 33379 | 636_3 | 7.5 μM | 55 | 4 | 201 | 3 |
| 33379 | 636_4 | 7.5 μM | 54 | 2 | 238 | 7 |
| 33379 | 636_5 | 7.5 μM | 52 | 5 | 207 | 43 |
| 33379 | 636_6 | 7.5 μM | 47 | 3 | 249 | 6 |
| 33379 | 636_7 | 7.5 μM | 48 | 5 | 241 | 1 |
| 33379 | 636_8 | 7.5 μM | 37 | 7 | 304 | 12 |
| 33379 | 636_9 | 7.5 μM | 62 | 9 | 245 | 5 |
| 33380 | 637_1 | 7.5 μM | 39 | 1 | 219 | 25 |
| 33380 | 637_2 | 7.5 μM | 59 | 1 | 197 | 11 |
| 33380 | 637_3 | 7.5 μM | 56 | 1 | 250 | 19 |
| 33380 | 637_4 | 7.5 μM | 53 | 7 | 244 | 36 |
| 33380 | 637_5 | 7.5 μM | 73 | 13 | 297 | 34 |
| 33380 | 637_6 | 7.5 μM | 65 | 1 | 124 | 17 |
| 33380 | 637_7 | 7.5 μM | 74 | 5 | 133 | 5 |
| 33380 | 637_8 | 7.5 μM | 53 | 2 | 207 | 7 |
| 33380 | 637_9 | 7.5 μM | 54 | 15 | 226 | 26 |
| 39806 | 638_1 | 7.5 μM | 37 | 7 | 283 | 31 |
| 39806 | 638_2 | 7.5 μM | 49 | 11 | 291 | 30 |
| 39806 | 638_3 | 7.5 μM | 41 | 1 | 270 | 20 |
| 39806 | 638_4 | 7.5 μM | 42 | 13 | 267 | 9 |
| 39806 | 638_5 | 7.5 μM | 50 | 1 | 184 | 5 |
| 39806 | 638_6 | 7.5 μM | 38 | 1 | 276 | 15 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 39806 | 638_7 | 7.5 µM | 56 | 1 | 292 | 4 |
| 39806 | 638_8 | 7.5 µM | 41 | 4 | 267 | 11 |
| 39806 | 638_9 | 7.5 µM | 41 | 4 | 218 | 33 |
| 39807 | 639_1 | 7.5 µM | 48 | 15 | 293 | 30 |
| 39807 | 639_2 | 7.5 µM | 38 | 3 | 269 | 2 |
| 39807 | 639_3 | 7.5 µM | 72 | 5 | 167 | 3 |
| 39807 | 639_4 | 7.5 µM | 69 | 38 | 242 | 36 |
| 39807 | 639_5 | 7.5 µM | 47 | 6 | 303 | 36 |
| 39807 | 639_6 | 7.5 µM | 53 | 6 | 179 | 5 |
| 39807 | 639_7 | 7.5 µM | 51 | 3 | 189 | 8 |
| 39807 | 639_8 | 7.5 µM | 42 | 3 | 185 | 19 |
| 39807 | 639_9 | 7.5 µM | 45 | 3 | 202 | 15 |
| 39808 | 640_1 | 7.5 µM | 39 | 5 | 265 | 7 |
| 39808 | 640_2 | 7.5 µM | 37 | 4 | 272 | 56 |
| 39808 | 640_3 | 7.5 µM | 38 | 3 | 260 | 17 |
| 39808 | 640_4 | 7.5 µM | 33 | 4 | 255 | 2 |
| 39808 | 640_5 | 7.5 µM | 38 | 3 | 253 | 3 |
| 39808 | 640_6 | 7.5 µM | 40 | 8 | 216 | 10 |
| 39808 | 640_7 | 7.5 µM | 39 | 8 | 310 | 7 |
| 39808 | 640_8 | 7.5 µM | 41 | 6 | 282 | 21 |
| 39808 | 640_9 | 7.5 µM | 40 | 5 | 269 | 12 |
| 44439 | 641_1 | 7.5 µM | 35 | 6 | 336 | 32 |
| 44439 | 641_2 | 7.5 µM | 67 | 20 | 161 | 6 |
| 44439 | 641_3 | 7.5 µM | 34 | 9 | 317 | 30 |
| 44439 | 641_4 | 7.5 µM | 62 | 18 | 193 | 9 |
| 44439 | 641_5 | 7.5 µM | 34 | 4 | 280 | 3 |
| 44439 | 641_6 | 7.5 µM | 43 | 1 | 315 | 45 |
| 44439 | 641_7 | 7.5 µM | 45 | 17 | 307 | 53 |
| 44439 | 641_8 | 7.5 µM | 41 | 0 | 294 | 41 |
| 44439 | 641_9 | 7.5 µM | 37 | 2 | 334 | 43 |
| 44440 | 361_2 | 7.5 µM | 36 | 1 | 303 | 15 |
| 44440 | 361_3 | 7.5 µM | 32 | 3 | 315 | 12 |
| 44440 | 361_4 | 7.5 µM | 41 | 1 | 299 | 7 |
| 44440 | 361_5 | 7.5 µM | 40 | 5 | 295 | 6 |
| 44440 | 361_6 | 7.5 µM | 40 | 2 | 296 | 30 |
| 44440 | 361_7 | 7.5 µM | 39 | 1 | 300 | 55 |
| 44440 | 361_8 | 7.5 µM | 45 | 6 | 285 | 45 |
| 44440 | 361_9 | 7.5 µM | 44 | 6 | 321 | 26 |
| 44440 | 361_10 | 7.5 µM | 46 | 7 | 290 | 18 |
| 44441 | 362_2 | 7.5 µM | 50 | 4 | 277 | 4 |
| 44441 | 362_3 | 7.5 µM | 40 | 6 | 296 | 8 |
| 44441 | 362_4 | 7.5 µM | 37 | 5 | 340 | 18 |
| 44441 | 362_5 | 7.5 µM | 45 | 2 | 266 | 21 |
| 44441 | 362_6 | 7.5 µM | 39 | 7 | 263 | 0 |
| 44441 | 362_7 | 7.5 µM | 41 | 12 | 262 | 36 |
| 44441 | 362_8 | 7.5 µM | 35 | 13 | 313 | 6 |
| 44441 | 362_9 | 7.5 µM | 36 | 8 | 300 | 20 |
| 44441 | 362_10 | 7.5 µM | 48 | 10 | 293 | 1 |
| 46391 | 642_1 | 7.5 µM | 51 | 25 | 278 | 6 |
| 46391 | 642_2 | 7.5 µM | 46 | 2 | 303 | 4 |
| 46391 | 642_3 | 7.5 µM | 48 | 3 | 297 | 11 |
| 46391 | 642_4 | 7.5 µM | 45 | 11 | 320 | 37 |
| 46391 | 642_5 | 7.5 µM | 71 | 32 | 303 | 40 |
| 46391 | 642_6 | 7.5 µM | 47 | 15 | 298 | 16 |
| 46391 | 642_7 | 7.5 µM | 38 | 6 | 277 | 5 |
| 46391 | 642_8 | 7.5 µM | 38 | 3 | 280 | 20 |
| 46391 | 642_9 | 7.5 µM | 51 | 20 | 285 | 16 |
| 46391 | 642_10 | 7.5 µM | 32 | 7 | 293 | 20 |
| 46391 | 642_11 | 7.5 µM | 42 | 2 | 291 | 2 |
| 46391 | 642_12 | 7.5 µM | 40 | 3 | 317 | 19 |
| 46391 | 642_13 | 7.5 µM | 39 | 11 | 295 | 5 |
| 46391 | 642_14 | 7.5 µM | 52 | 20 | 295 | 16 |
| 46391 | 642_15 | 7.5 µM | 39 | 8 | 316 | 38 |
| 46391 | 642_16 | 7.5 µM | 35 | 2 | 294 | 30 |
| 46391 | 642_17 | 7.5 µM | 51 | 5 | 292 | 8 |
| 46391 | 643_1 | 7.5 µM | 39 | 4 | 276 | 16 |
| 46392 | 644_1 | 7.5 uM | 39 | 0 | 321 | 7 |
| 46392 | 644_2 | 7.5 µM | 46 | 4 | 308 | 4 |
| 46392 | 644_3 | 7.5 µM | 44 | 1 | 317 | 3 |
| 46392 | 644_4 | 7.5 µM | 38 | 6 | 315 | 11 |
| 46392 | 645_1 | 7.5 µM | 46 | 5 | 342 | 42 |
| 46392 | 645_2 | 7.5 µM | 37 | 5 | 292 | 25 |
| 46392 | 645_3 | 7.5 µM | 46 | 16 | 317 | 30 |
| 46392 | 645_4 | 7.5 µM | 47 | 8 | 381 | 102 |
| 46392 | 645_5 | 7.5 µM | 42 | 2 | 269 | 4 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 46393 | 646_1 | 7.5 µM | 49 | 4 | 295 | 2 |
| 46393 | 646_2 | 7.5 µM | 49 | 9 | 304 | 38 |
| 46393 | 646_3 | 7.5 µM | 44 | 6 | 298 | 50 |
| 46393 | 646_4 | 7.5 µM | 43 | 1 | 296 | 41 |
| 46393 | 646_5 | 7.5 µM | 35 | 1 | 260 | 3 |
| 46393 | 646_6 | 7.5 µM | 40 | 2 | 281 | 67 |
| 46393 | 646_7 | 7.5 µM | 38 | 1 | 278 | 44 |
| 46393 | 646_8 | 7.5 µM | 42 | 6 | 262 | 49 |
| 46393 | 646_9 | 7.5 µM | 38 | 3 | 289 | 24 |
| 46393 | 646_10 | 7.5 µM | 38 | 1 | 317 | 4 |
| 46393 | 646_11 | 7.5 µM | 42 | 1 | 320 | 34 |
| 46393 | 646_12 | 7.5 µM | 36 | 5 | 323 | 8 |
| 46393 | 646_13 | 7.5 µM | 41 | 3 | 262 | 27 |
| 46393 | 646_14 | 7.5 µM | 46 | 13 | 315 | 18 |
| 46393 | 646_15 | 7.5 µM | 42 | 4 | 340 | 27 |
| 46393 | 646_16 | 7.5 µM | 45 | 8 | 360 | 14 |
| 46393 | 646 17 | 7.5 µM | 44 | 1 | 303 | 3 |
| 46393 | 646_18 | 7.5 µM | 50 | 2 | 304 | 28 |
| 46393 | 646_19 | 7.5 µM | 54 | 10 | 217 | 25 |
| 51241 | 425_2 | 7.5 µM | 49 | 12 | 296 | 3 |
| 51241 | 425_3 | 7.5 µM | 48 | 6 | 297 | 10 |
| 51241 | 425_4 | 7.5 µM | 52 | 5 | 275 | 25 |
| 51241 | 425_5 | 7.5 µM | 40 | 6 | 284 | 29 |
| 51241 | 425_6 | 7.5 µM | 39 | 5 | 301 | 22 |
| 51241 | 425_7 | 7.5 µM | 39 | 4 | 263 | 13 |
| 51241 | 425_8 | 7.5 µM | 32 | 5 | 188 | 13 |
| 51241 | 425_9 | 7.5 µM | 42 | 5 | 286 | 2 |
| 51241 | 425_10 | 7.5 µM | 34 | 3 | 165 | 17 |

Example 6—Activity of Exon-Exon Spanning Oligonucleotides

Oligonucleotides designed to be complementary across exon-exon junctions of SNHG14-023 (ENST00000554726) were tested for their ability to reduce the SNHG14 transcript in the region downstream of SNORD109B (also termed UBE3A suppressor or UBE3A-SUP in the data table). Furthermore, the ability to induce UBE3A mRNA re-expression was analyzed. The oligonucleotides primarily spar exon2 and exon-3 (i.e. are complementary to a region in exon2 and a region in exon 3).

The oligonucleotides were screened according to the protocol for screening oligonucleotides in human neuronal cell cultures described in the section Example 5.

The results are shown in table 9.

TABLE 9

Oligonucleotide activity in patient derived human neuronal cell cultures.

| CMP ID NO | Conc µM | % of Mock UBE3A-SUP | sd | % of Mock UBE3A | sd |
|---|---|---|---|---|---|
| 674_1 | 7.5 µM | 47 | 2 | 214 | 12 |
| 675_1 | 7.5 µM | 44 | 6 | 265 | 10 |
| 676_1 | 7.5 µM | 44 | 3 | 284 | 16 |
| 677_1 | 7.5 µM | 55 | 19 | 351 | 18 |
| 678_1 | 7.5 µM | 41 | 11 | 257 | 1 |
| 656_1 | 7.5 µM | 46 | 3 | 140 | 19 |
| 657_1 | 7.5 µM | 35 | 7 | 218 | 27 |
| 658_1 | 7.5 µM | 38 | 12 | 253 | 43 |
| 659_1 | 7.5 µM | 39 | 7 | 274 | 6 |
| 660_1 | 7.5 µM | 38 | 8 | 275 | 29 |
| 661_1 | 7.5 µM | 43 | 13 | 246 | 21 |
| 662_1 | 7.5 µM | 27 | 10 | 290 | 5 |
| 663_1 | 7.5 µM | 28 | 0 | 287 | 23 |
| 664_1 | 7.5 µM | 27 | 2 | 288 | 14 |

TABLE 9-continued

| Oligonucleotide activity in patient derived human neuronal cell cultures. | | | | | |
|---|---|---|---|---|---|
| CMP ID NO | Conc µM | % of Mock UBE3A-SUP | sd | % of Mock UBE3A | sd |
| 665_1 | 7.5 µM | 37 | 9 | 321 | 47 |
| 666_1 | 7.5 µM | 54 | 1 | 259 | 10 |
| 667_1 | 7.5 µM | 47 | 8 | 236 | 2 |
| 647_1 | 7.5 µM | 19 | 3 | 300 | 25 |
| 648_1 | 7.5 µM | 22 | 7 | 320 | 3 |
| 649_1 | 7.5 µM | 34 | 8 | 326 | 2 |
| 650_1 | 7.5 µM | 44 | 4 | 292 | 7 |
| 651_1 | 7.5 µM | 36 | 5 | 254 | 9 |
| 652_1 | 7.5 µM | 21 | 2 | 314 | 18 |
| 653_1 | 7.5 µM | 24 | 5 | 299 | 41 |
| 654_1 | 7.5 µM | 31 | 2 | 344 | 41 |
| 655_1 | 7.5 µM | 60 | 9 | 301 | 3 |
| 668_1 | 7.5 µM | 21 | 3 | 297 | 11 |
| 669_1 | 7.5 µM | 24 | 5 | 296 | 27 |
| 670_1 | 7.5 µM | 30 | 3 | 274 | 55 |
| 671_1 | 7.5 µM | 27 | 6 | 263 | 35 |
| 672_1 | 7.5 µM | 27 | 6 | 280 | 50 |
| 673_1 | 7.5 µM | 33 | 2 | 290 | 19 |

Example 7—Testing In Vitro Efficacy and Potency of Selected Oligonucleotides

Based on the screenings in examples 2 to 5 above 52 oligonucleotides were selected for potency and efficacy testing.

The oligonucleotides were screened in human AS patient derived cells as described in the Materials and Method section "Screening oligonucleotides in human neuronal cell cultures—96 well system" with the following modifications:

For UBE3a-Sense primer commercially available primers and probe from ThermoFisher: Hs00166580_m1 amplifying a 94 bp sequence in position 838 of refseq ID NM_000462.3 were used.

Each plate include PBS controls (instead on a non-targeting oligonucleotide) and the positive control oligonucleotides CMP ID NO: 186_1 and 39_1 identified in previous screens were included. The additional control oligonucleotides described in the materials and method section were not included. Oligonucleotide test concentrations were from 31.6 µM to 1 nM using a 10 point half-log dilution. All oligonucleotides were tested in 5 independent experiments in 5 different weeks. In the data QC process some plates were removed from the analysis if these were obvious outliers e.g. no PCR product detected. After this filtration there is a minimum of three independent experiments behind each the reported values.

The EC50 (UBE3A mRNA re-expression) and IC50 (reduction of the SNHG14 transcript in the region downstream of SNORD109B, also termed UBE3A suppressor or UBE3A-SUP in the data table) were determined after curve fitting using a 4 parameter sigmoidal dose-response model. Fitting was executed using the fit engine available inside the Biobook software by IDBS (XLfit). From the curve-fitting the maximum obtainable up-regulation of UBE3A (UBE3A Max Up) and the maximum obtainable knockdown of UBE3A-SUP (UBE3A-SUP max Kd) were determined, Both are shown as % of control (PBS treated cells). The results are shown in table 10, values are reported as geometric means of each biological replicate.

TABLE 10

| Oligonucleotide EC50 and IC 50 values and maximum UBE3A upregulation and UBE3A suppressor knock down. | | | | | | | | |
|---|---|---|---|---|---|---|---|---|
| CMP ID NO | EC50 ↑ UBE3A | Sd | IC50 ↓ UBE3A-SUP | Sd | UBE3A Max Kd | Sd | UBE3A-SUP max Kd | Sd |
| 586_9 | 0.02 | 0.02 | 0.01 | 0.00 | 329.4 | 25.5 | 33.5 | 3.8 |
| 585_1 | 0.03 | 0.01 | 0.03 | 0.02 | 301.6 | 18.3 | 31.0 | 5.3 |
| 572_7 | 0.03 | 0.00 | 0.01 | 0.03 | 294.1 | 30.4 | 31.3 | 3.5 |
| 591_1 | 0.03 | 0.02 | 0.01 | 0.00 | 387.3 | 46.0 | 41.4 | 2.8 |
| 585_8 | 0.04 | 0.02 | 0.02 | 0.01 | 312.3 | 23.1 | 35.2 | 3.3 |
| 626_7 | 0.04 | 0.02 | 0.02 | 0.00 | 362.5 | 44.6 | 38.7 | 3.3 |
| 621_2 | 0.04 | 0.03 | 0.02 | 0.01 | 264.5 | 19.6 | 24.7 | 3.9 |
| 624_3 | 0.04 | 0.03 | 0.04 | 0.03 | 288.1 | 19.2 | 29.7 | 5.2 |
| 169_52 | 0.04 | 0.04 | 0.02 | 0.01 | 303.4 | 23.1 | 27.3 | 1.8 |
| 624_5 | 0.04 | 0.07 | 0.01 | 0.01 | 249.2 | 16.3 | 16.4 | 1.4 |
| 586_5 | 0.04 | 0.01 | 0.01 | 0.00 | 364.4 | 43.9 | 30.4 | 3.3 |
| 626_8 | 0.04 | 0.03 | 0.01 | 0.01 | 338.7 | 24.0 | 39.1 | 2.6 |
| 169_50 | 0.05 | 0.02 | 0.02 | 0.02 | 280.3 | 23.0 | 28.3 | 2.4 |
| 572_6 | 0.05 | 0.01 | 0.01 | 0.02 | 298.5 | 22.4 | 36.3 | 4.0 |
| 639_5 | 0.05 | 0.03 | 0.01 | 0.00 | 327.7 | 22.0 | 38.2 | 3.6 |
| 592_2 | 0.05 | 0.03 | 0.02 | 0.05 | 364.9 | 27.1 | 36.4 | 3.6 |
| 586_8 | 0.05 | 0.03 | 0.02 | 0.01 | 366.6 | 35.1 | 38.0 | 3.9 |
| 625_6 | 0.06 | 0.03 | 0.01 | 0.00 | 335.5 | 34.7 | 32.5 | 1.9 |
| 644_3 | 0.06 | 0.04 | 0.01 | 0.02 | 298.5 | 22.0 | 25.3 | 1.6 |
| 586_4 | 0.06 | 0.03 | 0.01 | 0.01 | 354.3 | 31.5 | 33.0 | 2.3 |
| 642_12 | 0.06 | 0.05 | 0.02 | 0.01 | 289.2 | 14.8 | 24.7 | 3.0 |
| 572_5 | 0.07 | 0.09 | 0.02 | 0.00 | 312.7 | 25.9 | 31.5 | 3.0 |
| 592_4 | 0.07 | 0.06 | 0.03 | 0.01 | 341.1 | 31.9 | 35.7 | 1.8 |
| 622_3 | 0.07 | 0.04 | 0.02 | 0.01 | 300.9 | 21.0 | 27.6 | 3.6 |
| 622_5 | 0.07 | 0.01 | 0.02 | 0.01 | 306.2 | 13.5 | 24.4 | 4.0 |
| 616_4 | 0.07 | 0.04 | 0.03 | 0.02 | 293.8 | 17.9 | 29.1 | 5.0 |
| 304_6 | 0.08 | 0.08 | 0.02 | 0.00 | 318.1 | 39.2 | 43.8 | 3.9 |
| 638_8 | 0.08 | 0.01 | 0.01 | 0.01 | 354.8 | 30.6 | 42.4 | 4.1 |
| 622_4 | 0.08 | 0.07 | 0.02 | 0.01 | 330.3 | 24.8 | 29.5 | 2.4 |
| 642_13 | 0.08 | 0.07 | 0.04 | 0.03 | 268.4 | 21.0 | 26.8 | 2.5 |
| 573_8 | 0.08 | 0.01 | 0.04 | 0.02 | 320.1 | 34.4 | 34.3 | 3.4 |
| 241_9 | 0.09 | 0.04 | 0.04 | 0.03 | 352.6 | 26.4 | 34.1 | 2.3 |
| 304_10 | 0.09 | 0.07 | 0.03 | 0.01 | 289.5 | 19.9 | 28.3 | 2.8 |

TABLE 10-continued

Oligonucleotide EC50 and IC 50 values and maximum UBE3A upregulation and UBE3A suppressor knock down.

| CMP ID NO | EC50 ↑ UBE3A | Sd | IC50 ↓ UBE3A-SUP | Sd | UBE3A Max Kd | Sd | UBE3A-SUP max Kd | Sd |
|---|---|---|---|---|---|---|---|---|
| 636_8 | 0.10 | 0.08 | 0.03 | 0.04 | 330.8 | 34.1 | 53.9 | 13.4 |
| 598_4 | 0.11 | 0.06 | 0.03 | 0.04 | 295.0 | 15.1 | 41.3 | 2.2 |
| 586_6 | 0.11 | 0.10 | 0.02 | 0.02 | 316.2 | 21.2 | 23.8 | 3.5 |
| 621_1 | 0.11 | 0.21 | 0.02 | 0.01 | 311.9 | 19.2 | 27.5 | 5.2 |
| 331_1 | 0.12 | 0.02 | 0.03 | 0.02 | 293.6 | 49.0 | 25.1 | 5.4 |
| 626_9 | 0.13 | 0.12 | 0.02 | 0.03 | 302.2 | 32.6 | 34.4 | 2.2 |
| 169_56 | 0.14 | 0.18 | 0.02 | 0.01 | 356.5 | 22.3 | 26.8 | 2.2 |
| 631_6 | 0.14 | 0.30 | 0.04 | 0.00 | 292.9 | 25.1 | 33.5 | 4.9 |
| 186_1 | 0.16 | 0.02 | 0.04 | 0.05 | 371.7 | 70.1 | 32.5 | 5.5 |
| 611_7 | 0.16 | 0.15 | 0.02 | 0.01 | 369.2 | 29.3 | 37.2 | 3.9 |
| 165_1 | 0.17 | 0.02 | 0.07 | 0.12 | 266.3 | NA | 26.7 | NA |
| 646_16 | 0.18 | 0.15 | 0.03 | 0.02 | 306.0 | 9.0 | 30.6 | 2.9 |
| 640_4 | 0.20 | 0.10 | 0.02 | 0.01 | 328.4 | 31.0 | 40.4 | 7.0 |
| 631_1 | 0.22 | 0.07 | 0.07 | 0.02 | 324.6 | 1.6 | 47.5 | 8.1 |
| 590_13 | 0.23 | 0.59 | 0.02 | 0.02 | 353.4 | 22.3 | 31.8 | 2.2 |
| 172_1 | 0.24 | 0.10 | 0.11 | 0.14 | 254.2 | NA | 34.2 | NA |
| 35_2 | 0.26 | 0.02 | 0.06 | 0.09 | 257.9 | NA | 22.3 | NA |
| 425_5 | 0.26 | 0.14 | 0.08 | 0.08 | 317.3 | 33.9 | 32.9 | 2.4 |
| 359_1 | 0.27 | 0.03 | 0.03 | 0.08 | 260.5 | NA | 31.3 | NA |
| 209_1 | 0.28 | 0.08 | 0.03 | 0.03 | 339.9 | 30.6 | 48.2 | 11.6 |
| 123_1 | 0.28 | 0.13 | 0.26 | 0.08 | 235.9 | NA | 51.8 | NA |
| 361_1 | 0.29 | 0.10 | 0.06 | 0.02 | 331.9 | 17.2 | 30.7 | 6.3 |
| 602_1 | 0.31 | 0.33 | 0.15 | 0.20 | 340.3 | 21.7 | 42.2 | 5.0 |
| NA | 0.44 | 0.12 | 0.15 | 0.18 | 251.3 | NA | 24.6 | NA |
| 287_1 | 0.45 | 0.09 | 0.04 | 0.02 | 318.1 | 45.2 | 28.8 | 9.3 |
| 303_1 | 0.46 | 0.05 | 0.09 | 0.15 | 259.9 | NA | 30.9 | NA |
| 379_1 | 0.47 | 0.02 | 0.08 | 0.16 | 247.2 | NA | 22.5 | NA |
| 405_1 | 0.48 | 0.42 | 0.04 | 0.01 | 323.0 | 56.2 | 32.5 | 11.9 |
| 39_1 | 0.51 | 0.20 | 0.06 | 0.06 | 341.2 | 30.3 | 40.4 | 4.7 |
| 206_1 | 0.52 | 0.07 | 0.14 | 0.31 | 262.9 | NA | 30.5 | NA |
| 155_1 | 0.53 | 0.10 | NA | 0.53 | 260.8 | NA | 26.7 | NA |
| 362_1 | 0.57 | 0.25 | 0.09 | 0.02 | 328.1 | 57.3 | 27.4 | 8.6 |
| 178_1 | 0.58 | 0.35 | 0.11 | 0.04 | 334.3 | 50.8 | 26.6 | 8.0 |
| 48_1 | 0.59 | 0.02 | 0.07 | 0.56 | 262.7 | NA | 27.2 | NA |
| 200_1 | 0.62 | 0.51 | 0.15 | 0.06 | 331.0 | 54.3 | 33.1 | 6.2 |
| 361_5 | 0.67 | 0.18 | 0.07 | 0.00 | 307.1 | 22.9 | 32.1 | 4.5 |
| 597_4 | 0.67 | 0.51 | 0.10 | 0.06 | 325.3 | 17.3 | 35.3 | 2.7 |
| 85_1 | 0.68 | 0.06 | 0.28 | 0.41 | 255.5 | NA | 35.1 | NA |
| 278_1 | 0.69 | 0.67 | 0.08 | 0.09 | 313.8 | 33.4 | 27.2 | 4.6 |
| 271_1 | 0.69 | 0.00 | 0.03 | 0.65 | 247.3 | NA | 24.0 | NA |
| 403_1 | 0.77 | 0.57 | 0.11 | 0.09 | 296.4 | 55.0 | 28.8 | 7.0 |
| 204_1 | 0.78 | 0.59 | 0.05 | 0.05 | 316.1 | 35.5 | 36.3 | 7.9 |
| 116_1 | 0.91 | 0.05 | 0.09 | 0.43 | 240.6 | NA | 31.6 | NA |
| 124_1 | 0.92 | 0.29 | 0.55 | 0.94 | 190.0 | NA | 43.9 | NA |
| 237_8 | 0.93 | 0.66 | 0.05 | 0.03 | 376.2 | 32.8 | 33.6 | 3.7 |
| 378_1 | 0.95 | 0.64 | 0.13 | 0.09 | 317.7 | 30.1 | 48.5 | 6.1 |
| 126_2 | 0.95 | 0.05 | 0.12 | 0.70 | 219.7 | NA | 45.0 | NA |
| 373_1 | 1.03 | 0.63 | 0.13 | 0.08 | 321.7 | 38.6 | 27.5 | 4.8 |
| 641_5 | 1.16 | 1.36 | 0.07 | 0.06 | 335.1 | 28.9 | 26.6 | 5.1 |
| 207_1 | 1.18 | 0.58 | 0.18 | 0.06 | 318.5 | 42.9 | 44.0 | 7.2 |
| 19_1 | 1.50 | 0.19 | 0.24 | 1.07 | 261.7 | NA | 28.4 | NA |
| 175_1 | 1.51 | 0.42 | 0.17 | 0.11 | 333.5 | 23.8 | 29.2 | 5.2 |
| 304_1 | 1.55 | 0.09 | 0.08 | 0.11 | 297.8 | 26.2 | 32.5 | 5.7 |
| 399_1 | 1.86 | 2.50 | 0.44 | 0.26 | 340.1 | 52.2 | 39.6 | 4.3 |
| 38_1 | 2.12 | 0.10 | 0.34 | 0.43 | 257.3 | NA | 45.1 | NA |
| 222_1 | 2.29 | 0.75 | 0.28 | 0.12 | 298.2 | 34.9 | 26.8 | 5.6 |
| 187_1 | 2.30 | 1.39 | 1.00 | 0.91 | 315.3 | 38.4 | 28.6 | 6.2 |
| 272_1 | 2.32 | 1.39 | 0.24 | 0.16 | 330.4 | 41.2 | 37.1 | 6.1 |
| 18_1 | 2.42 | 0.21 | 0.24 | 2.00 | 271.0 | NA | 29.3 | NA |
| 118_1 | 2.78 | 0.30 | 0.31 | 0.07 | 205.4 | NA | 40.4 | NA |
| 35_1 | 2.93 | 4.94 | 3.61 | 1.52 | 258.4 | NA | 48.2 | NA |
| 233_1 | 3.14 | 1.68 | 0.35 | 0.16 | 330.3 | 20.1 | 29.3 | 5.2 |
| 220_1 | 3.47 | 0.99 | 1.02 | 0.48 | 315.5 | 27.4 | 29.6 | 7.6 |
| 33_1 | 3.97 | 0.41 | 1.07 | NA | 265.7 | NA | 32.2 | NA |
| 109_1 | 4.06 | 1.45 | 1.33 | 0.67 | 231.7 | 44.7 | 39.6 | 3.9 |
| 40_1 | 4.17 | 0.05 | 0.12 | 3.74 | 263.6 | NA | 38.3 | NA |
| 115_1 | 4.98 | 0.15 | 0.25 | NA | 184.2 | NA | 47.0 | NA |
| 161_1 | 6.55 | 3.20 | 1.25 | 1.24 | 294.0 | 24.8 | 32.1 | 7.4 |
| 105_4 | 6.61 | 1.62 | 1.38 | 4.20 | NA | NA | 50.6 | NA |
| 19_2 | 6.66 | 1.17 | 3.17 | 1.52 | 201.7 | NA | 57.7 | NA |
| 104_1 | 7.75 | 6.77 | 1.67 | 1.05 | 267.9 | 25.5 | 42.5 | 4.1 |
| 18_2 | 20.00 | 1.67 | 3.50 | NA | 245.9 | NA | 46.4 | NA |
| 108_1 | 20.00 | 0.61 | 1.27 | NA | 219.6 | NA | 51.2 | NA |
| 129_2 | 20.00 | 0.08 | 1.10 | NA | 165.8 | NA | 56.5 | NA |

TABLE 10-continued

Oligonucleotide EC50 and IC 50 values and maximum UBE3A upregulation and UBE3A suppressor knock down.

| CMP ID NO | EC50 ↑ UBE3A | Sd | IC50 ↓ UBE3A-SUP | Sd | UBE3A Max Kd | Sd | UBE3A-SUP max Kd | Sd |
|---|---|---|---|---|---|---|---|---|
| 141_1 | 20.00 | 0.03 | 0.15 | NA | 159.0 | NA | 64.1 | NA |
| 142_1 | 20.00 | 1.04 | 1.12 | NA | 133.1 | NA | 57.6 | NA |
| 145_1 | 20.00 | 1.30 | 1.81 | NA | 139.0 | NA | 56.9 | NA |

SEQUENCE LISTING

The patent contains a lengthy sequence listing. A copy of the sequence listing is available in electronic form from the USPTO web site (https://seqdata.uspto.gov/docdetail?docId=US12596118B2). An electronic copy of the sequence listing will also be available from the USPTO upon request and payment of the fee set forth in 37 CFR 1.19(b)(3).

The invention claimed is:

1. An antisense oligonucleotide comprising a contiguous nucleotide sequence of about 10 to about 30 nucleotides in length with at least 98% complementarity to position 12,179 to 12,256 of SEQ ID NO: 1, wherein the antisense oligonucleotide comprises one or more modified nucleosides.

2. The antisense oligonucleotide of claim 1, wherein the antisense oligonucleotide is about 15 to about 24 nucleotides in length.

3. The antisense oligonucleotide of claim 1, wherein the antisense oligonucleotide is about 17 to about 22 nucleotides in length.

4. The antisense oligonucleotide of claim 1, wherein the antisense oligonucleotide is about 20 nucleotides in length.

5. The antisense oligonucleotide of claim 1, wherein the antisense oligonucleotide comprises a contiguous nucleotide sequence with 100% complementarity to position 12,179 to 12,256 of SEQ ID NO: 1.

6. The antisense oligonucleotide of claim 1, wherein the one or more modified nucleosides comprise one or more 2' sugar modified nucleosides.

7. The antisense oligonucleotide of claim 6, wherein the one or more 2' sugar modified nucleosides are independently selected from the group consisting of 2'-O-alkyl nucleoside, 2'-O-methyl nucleoside, 2'-alkoxy nucleoside, 2'-O-methoxyethyl nucleoside, 2'-amino nucleoside, 2'-fluoro nucleoside, arabino nucleic acid (ANA), 2'-fluoro-ANA, and LNA nucleosides.

8. The antisense oligonucleotide of claim 6, wherein the one or more 2' sugar modified nucleosides are 2'-O-methoxyethyl nucleosides.

9. The antisense oligonucleotide of claim 1, wherein the one or more modified nucleosides comprise modified purines or pyrimidines.

10. The antisense oligonucleotide of claim 9, wherein the modified pyrimidine comprises isocytosine, pseudoisocytosine, 5-methyl cytosine, 5-thiozolo-cytosine, 5-propynyl-cytosine, 5-propynyl-uracil, 5-bromouracil, 5-thiazolo-uracil, 2-thio-uracil, 2'thio-thymine, inosine, diaminopurine, 6-aminopurine, 2-aminopurine, 2,6-diaminopurine, and 2-chloro-6-aminopurine.

11. The antisense oligonucleotide of claim 10, wherein the modified pyrimidine comprises 5-methyl cytosine.

12. The antisense oligonucleotide of claim 1, wherein the antisense oligonucleotide comprises at least one modified internucleoside linkage within the contiguous nucleotide sequence.

13. The antisense oligonucleotide of claim 12, wherein the at least one modified internucleoside linkage within the contiguous nucleotide sequence is at least one phosphorothioate internucleoside linkage.

14. The antisense oligonucleotide of claim 13, wherein at least 50% of internucleoside linkages in the antisense oligonucleotide, or contiguous nucleotide sequence thereof, are phosphorothioate linkages.

15. The antisense oligonucleotide of claim 1, wherein the antisense oligonucleotide is a gapmer.

16. The antisense oligonucleotide of claim 15, wherein the gapmer has a formula of 5'-F-G-F'-3', wherein region F and F' independently comprise between about 1 and about 7 modified nucleosides and G is a region comprising between about 6 and about 16 nucleosides.

17. The antisense oligonucleotide of claim 16, wherein the regions F and F' each comprise 5 modified nucleosides and G is a region comprising 10 nucleosides.

18. The antisense oligonucleotide of claim 16, wherein the modified nucleosides of region F and F' comprise 2'-O-methoxyethyl nucleosides.

19. The antisense oligonucleotide of claim 16, wherein the nucleosides of region G comprise deoxynucleosides.

20. The antisense oligonucleotide of claim 16, wherein the nucleosides of region G comprise phosphorothioate internucleoside linkages.

21. An antisense oligonucleotide gapmer comprising a contiguous nucleotide sequence of about 10 to about 30 nucleotides in length with at least 98% complementarity to position 12,179 to 12,256 of SEQ ID NO: 1, wherein the gapmer has a formula of 5'-F-G-F'-3', wherein region F and F' independently comprise 5 nucleosides and region G comprises 10 nucleosides, wherein the antisense oligonucleotide gapmer comprises at least one modified internucleoside linkage and at least one modified nucleoside, wherein the modified nucleosides comprise 2'-O-methoxyethyl nucleosides, modified pyrimidines, or a combination thereof, wherein the modified pyrimidines comprise 5-methyl cytosine, and wherein at least one modified internucleoside linkage comprises a phosphorothioate internucleoside linkage.

22. The antisense oligonucleotide of claim 21, wherein all nucleosides in region G comprise phosphorothioate internucleoside linkages.

23. A method for treating a disease in a subject comprising administering a therapeutically effective amount of an antisense oligonucleotide comprising a contiguous nucleotide sequence of about 10 to about 30 nucleotides in length with at least 98% complementarity to position 12,179 to 12,256 of SEQ ID NO: 1, wherein the antisense oligonucleotide comprises one or more modified nucleosides.

24. The method of claim 23, wherein the subject suffers from or is susceptible to Angelman syndrome.

25. The method of claim 23, wherein the subject is an infant or a juvenile.

26. The method of claim 23, wherein the one or more modified nucleosides comprise one or more of 2' sugar modified nucleosides, modified purines or pyrimidines, and modified internucleoside linkages.

27. The method of claim 26, wherein the one or more 2' sugar modified nucleosides are 2'-O-methoxyethyl nucleosides.

28. The method of claim 23, wherein the antisense oligonucleotide is a gapmer.

29. The method of claim 28, wherein the gapmer has a formula of 5'-F-G-F'-3', wherein region F and F' independently comprise between about 1 and about 7 modified nucleosides and G is a region comprising between about 6 and about 16 nucleosides.

30. The method of claim 29, wherein the regions F and F' each comprise 5 modified nucleosides and G is a region comprising 10 nucleosides.

* * * * *